(12) United States Patent
Regueiro-Ren et al.

(10) Patent No.: US 8,748,415 B2
(45) Date of Patent: Jun. 10, 2014

(54) C-28 AMINES OF C-3 MODIFIED BETULINIC ACID DERIVATIVES AS HIV MATURATION INHIBITORS

(75) Inventors: Alicia Regueiro-Ren, Middletown, CT (US); Jacob Swidorski, Southington, CT (US); Sing-Yuen Sit, Meriden, CT (US); Yan Chen, Guilford, CT (US); Jie Chen, Madison, CT (US); Nicholas A. Meanwell, East Hampton, CT (US); Zheng Liu, Beacon Falls, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 44 days.

(21) Appl. No.: 13/359,680

(22) Filed: Jan. 27, 2012

(65) Prior Publication Data

US 2013/0029954 A1  Jan. 31, 2013

Related U.S. Application Data

(60) Provisional application No. 61/437,870, filed on Jan. 31, 2011.

(51) Int. Cl.
*A61K 31/58* (2006.01)
*C07J 53/00* (2006.01)

(52) U.S. Cl.
USPC ............ 514/173; 514/172; 514/176; 540/47; 552/510

(58) Field of Classification Search
USPC ............ 514/169, 171, 172, 173, 176; 540/15, 540/47; 552/510
See application file for complete search history.

(56) References Cited

U.S. PATENT DOCUMENTS

| | | | |
|---|---|---|---|
| 5,679,828 | A | 10/1997 | Lee et al. |
| 7,354,924 | B2 | 4/2008 | Wang et al. |
| 7,365,221 | B2 | 4/2008 | Allaway et al. |
| 7,745,625 | B2 | 6/2010 | Ueda et al. |
| 2005/0239748 | A1 | 10/2005 | Power et al. |
| 2008/0207573 | A1 | 8/2008 | Yager et al. |
| 2012/0142653 | A1* | 6/2012 | Regueiro-Ren et al. ...... 514/176 |
| 2013/0035318 | A1* | 2/2013 | Regueiro-Ren et al. ...... 514/171 |

FOREIGN PATENT DOCUMENTS

| | | |
|---|---|---|
| WO | WO 98/51293 | 11/1998 |
| WO | WO 98/51294 | 11/1998 |
| WO | WO 2004/089357 | 10/2004 |
| WO | WO 2006/053255 | 5/2006 |
| WO | WO 2008/127364 | 10/2008 |
| WO | WO 2009/100532 | 8/2009 |
| WO | WO 2011/007230 | 1/2011 |

OTHER PUBLICATIONS

U.S. Appl. No. 61/537,099, filed Sep. 21, 2011, Liu et al.
U.S. Appl. No. 61/599,040, filed Feb. 15, 2012, Swidorski et al.

(Continued)

*Primary Examiner* — My-Chau T Tran
(74) *Attorney, Agent, or Firm* — John F. Levis

(57) ABSTRACT

Compounds having drug and bio-affecting properties, their pharmaceutical compositions and methods of use are set forth. In particular, C-28 amines of C-3 modified betulinic acid derivatives that possess unique antiviral activity are provided as HIV maturation inhibitors. These compounds are useful for the treatment of HIV and AIDS. In particular, the following compounds are provided herein, including pharmaceutically acceptable salts thereof:
a compound of formula I

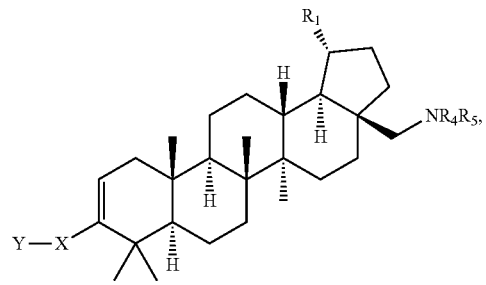

a compound of formula II

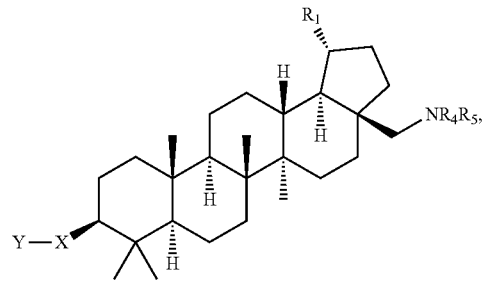

and a compound of formula III

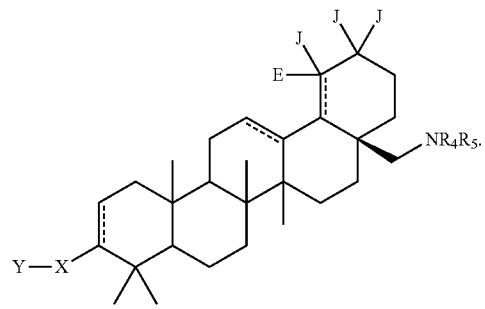

15 Claims, No Drawings

(56) References Cited

OTHER PUBLICATIONS

U.S. Appl. No. 13/151,706, filed Jun. 2, 2011, Regueiro-Ren et al.
U.S. Appl. No. 13/151,722, filed Jun. 2, 2011, Regueiro-Ren et al.
U.S. Appl. No. 13/359,727, filed Jan. 27, 2012, Regueiro-Ren et al.
Blair, W.S. et al., "HIV-1 entry—an expanding portal for drug discovery", Drug Discovery Today, vol. 5, No. 5, pp. 183-194 (2000).
Hotoda, H., "Small-molecule inhibitors of HIV-1 entry via chemokine receptors", Drugs of the Future, vol. 24, No. 12, pp. 1355-1362 (1999).
Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).
Meanwell, N.A. et al., "Inhibitors of the entry of HIV into host cells", Current Opinion in Drug Discovery & Development, vol. 6, No. 4, pp. 451-461 (2003).
Pokrovskii, A.G. et al., "Synthesis of derivatives of plant triterpenes and study of their antiviral and immunostimulating activity", Khimiya y Interesakh Ustoichivogo Razvitiya, vol. 9, No. 3, pp. 485-491 (2001) (English abstract).
Sodroski, J.G., "HIV-1 Entry Inhibitors in the Side Pocket: Minireview", Cell, vol. 99, pp. 243-246 (1999).
Zhu, Y.-M. et al., "Synthesis and Anti-HIV Activity of Oleanolic Acid Derivatives", Bioorganic & Medicinal Chemistry Letters, vol. 11, pp. 3115-3118 (2001).

* cited by examiner

C-28 AMINES OF C-3 MODIFIED BETULINIC ACID DERIVATIVES AS HIV MATURATION INHIBITORS

CROSS REFERENCE TO RELATED APPLICATIONS

This non-provisional application claims the benefit of U.S. Provisional Application Ser. No. 61/437,870 filed Jan. 31, 2011.

FIELD OF THE INVENTION

The present invention relates to novel compounds useful against HIV, and more particularly, to compounds derived from betulinic acid and other structurally related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45 million people infected worldwide at the end of 2007. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), emtricitabine (or FTC— Emtriva®)), Combivir® (contains –3TC plus AZT), Trizivir® (contains abacavir, lamivudine, and zidovudine), Epzicom® (contains abacavir and lamivudine), Truvada® (contains Viread® and Emtriva®); non-nucleoside reverse transcriptase inhibitors: nevirapine (or Viramune®)), delavirdine (or Rescriptor®) and efavirenz (or Sustiva®), Atripla® (Truvada®+Sustiva®), and etravirine, and peptidomimetic protease inhibitors or approved formulations: saquinavir, indinavir, ritonavir, nelfinavir, amprenavir, lopinavir, Kaletra® (lopinavir and Ritonavir), darunavir, atazanavir (Reyataz®) and tipranavir (Aptivus®), and integrase inhibitors such as raltegravir (Isentress®), and entry inhibitors such as enfuvirtide (T-20) (Fuzeon®) and maraviroc (Selzentry®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and US 2005/0209246 are illustrative of HIV attachment inhibitors.

Another emerging class of HIV treatment compounds are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., Gos. Nauchnyi Tsentr Virusol. Biotekhnol. "Vector" 9:485-491 (2001)).

Other references to the use of treating HIV infection with compounds derived from betulinic acid include US 2005/0239748 and US 2008/0207573, as well as WO 2006/053255, WO2009/100532, and WO 2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 Filed on Jun. 2, 2011 and "C-28 AMIDES OF MODIFIED C-3 BETULINIC ACID DERIVATIVES AS HIV MATURATION INHIBITORS" U.S. Ser. No. 13/151,722, filed on Jun. 2, 2011.

What is now needed in the art are new compounds which are useful as HIV maturation inhibitors, as well as new pharmaceutical compositions containing these compounds.

SUMMARY OF THE INVENTION

The present invention provides compounds of Formulas I, II, and III below, including pharmaceutically acceptable salts thereof, their pharmaceutical formulations, and their use in patients suffering from or susceptible to a virus such as HIV. The compounds of Formulas I-III are effective antiviral agents, particularly as inhibitors of HIV. They are useful for the treatment of HIV and AIDS.

One embodiment of the present invention is directed to a compound, including pharmaceutically acceptable salts thereof, which is selected from the group of:

a compound of formula I

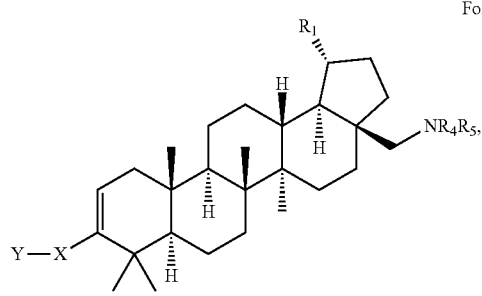

Formula I a compound of formula II

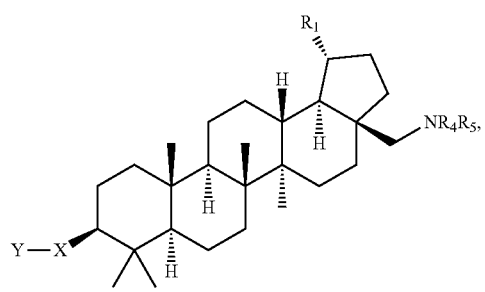

Formula II and
a compound of formula III

Formula III wherein $R_1$ is isopropenyl or isopropyl;
J and E are independently —H or —$CH_3$ and E is absent when the double bond is present;
X is a phenyl or heteroaryl ring substituted with A, wherein A is at least one member selected from the group of —H, -halo, -hydroxyl, —$C_{1-6}$ alkyl, —$C_{1-6}$ alkoxy, and —$COOR_2$;
$R_2$ is —H, —$C_{1-6}$ alkyl, -alkylsubstituted $C_{1-6}$ alkyl or -aryl substituted $C_{1-6}$ alkyl;
Y is selected from the group of —$COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, alkenyl-$COOR_2$, —$C_{1-6}$ alkynyl-$COOR_2$, —$C_{1-6}$ alkyl-$COOR_2$, —NHC(O)($CH_2)_n$—$COOR_2$, —$SO_2NR_2C(O)R_2$, -tetrazole, and —CONHOH, wherein n=1-6;
$R_3$ is —$C_{1-6}$ alkyl or alkylsubstituted $C_{1-6}$ alkyl;
$R_4$ is selected from the group of H, —$C_{1-6}$ alkyl, —$C_{3-6}$ cycloalkyl, —$C_{1-6}$ substituted alkyl, —$C_{1-6}$ alkyl-heteroaryl, —$C_{1-6}$alkyl-substitutedheteroaryl, —$C_{1-6}$ alkyl-$NR_6R_7$, —$C_{1-6}$ alkyl-$CONR_8R_9$, —$C_{3-6}$ cycloalkyl-$CONR_8R_9$, —$C_{3-6}$ cycloalkyl-$(CH_2)_{1-3}$—$NR_6R_7$, —$(CH_2)_{1-3}$—$C_{3-6}$ cycloalkyl-$NR_6R_7$; —$(CH_2)_{1-3}$—$C_{3-6}$ cycloalkyl-$(CH_2)_{1-3}$—$NR_6R_7$, —$C_{1-6}$ alkyl-$Q_1$, $C_{3-6}$ cycloalkyl-$Q_1$, —$COR_{10}$, —$SO_2R_3$ and —$SO_2NR_2R_2$;
$Q_1$=-hydroxy, —$COOR_2$, -halo, —$SO_2R_a$;
$R_a$=$C_{1-6}$ alkyl, $NR_2R_2$,

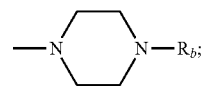

$R_b$=—H, —$C_{1-6}$ alkyl, —$COR_S$, —$SO_2R_3$, —$SONR_3R_3$,
$R_4$ can also be selected from the group of:

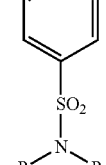

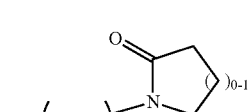

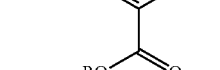

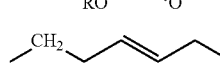

and

$R_5$ is selected from the group of —H, —$C_{1-6}$ alkyl, —$C_{3-6}$ cycloalkyl, —$C_{1-6}$ alkylsubstituted alkyl, —$COR_{10}$, —$SO_2R_3$ and —$SO_2NR_2R_2$;

with the proviso that only one of $R_4$ or $R_5$ can be selected from the group of —$COR_{10}$, —$SO_2R_3$ and —$SO_2NR_2R_2$;

or $R_4$ and $R_5$ are taken together with the adjacent N to form a cycle such as

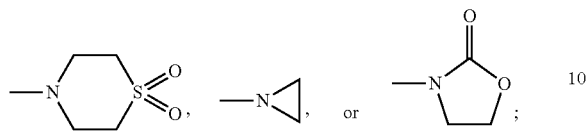

$R_{10}$ is selected from the group of —H, —$C_{1-6}$ alkyl, —$C_{1-6}$ alkyl-$NR_6R_7$, —$NR_{11}R_{12}$, —$OR_{13}$, —$C_{1-6}$ alkyl-$Q_2$, —$C_{3-6}$ cycloalkyl-$Q_2$, aryl-$Q_2$, wherein n=1-6, wherein $Q_2$=hydroxy, —$COOR_2$, -halo, $SO_2R_a$, —$CONHSO_2R_3$, —$CONHSO_2NR_2R_2$;

$R_{10}$ can also be selected from the group of:

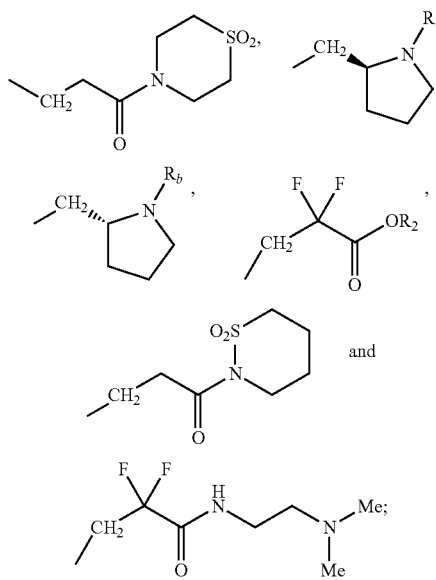

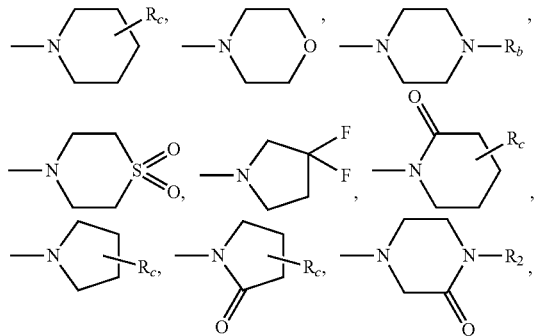

$R_6$ and $R_7$ are independently selected from the group of —H, —$C_{1-6}$ alkyl, —$C_{1-6}$ substituted alkyl, aryl, heteroaryl, substituted aryl, substituted heteroaryl, and —$C_{1-6}$ alkyl-$Q_1$, or $R_6$ and $R_7$ are taken together with the adjacent N to form a cycle selected from the group of

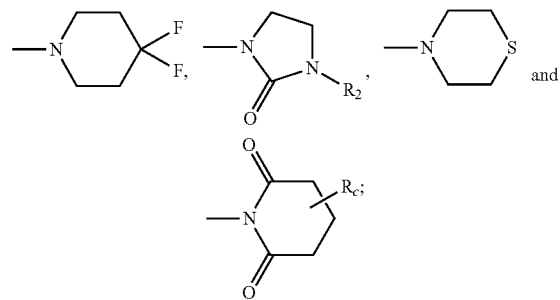

$R_c$=$C_{1-6}$ alkyl, $NR_2R_2$, —$COOR_3$;

$R_8$ and $R_9$ are independently selected from the group of —H, —$C_{1-6}$ alkyl, —$C_{3-6}$ cycloalkyl, —$C_{1-6}$ substituted alkyl, —$C_{1-6}$ alkyl-heteroaryl, —$C_{1-6}$ alkyl-substitutedheteroaryl, —$C_{1-6}$ alkyl-$NR_2R_2$, —$C_{1-6}$ alkyl-$CONR_2R_2$, —$C_{1-6}$ alkyl-$Q_1$, $C_{3-6}$ cycloalkyl-$Q_1$, or $R_8$ and $R_9$ can also be independently selected from the group of

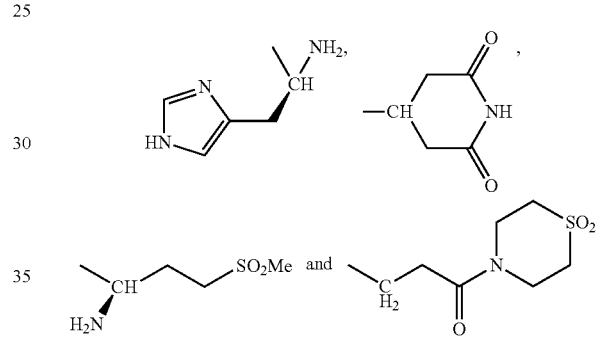

or $R_8$ and $R_9$ are taken together with the adjacent N to form a cycle selected from the group of:

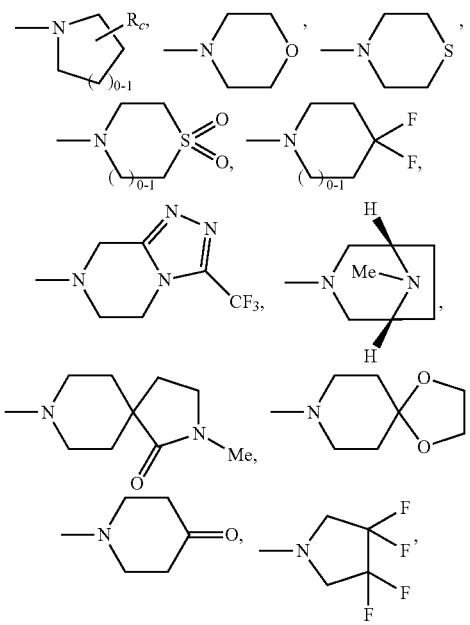

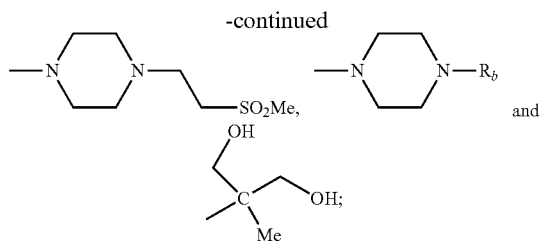

and $R_{11}$ and $R_{12}$ are independently selected from the group of —H, —$C_{1-6}$ alkyl, —$C_{3-6}$ cycloalkyl, and —$C_{1-6}$alkylsubstituted alkyl;
or $R_{11}$ and $R_{12}$ are taken together with the adjacent N to form a cycle selected from the group of

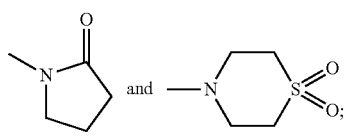

and
$R_{13}$ is selected from the group of —H, —$C_{1-6}$ alkyl, —$C_{1-6}$ alkylsubstituted alkyl, and —$C_{1-6}$ alkyl $NR_{14}R_{15}$, wherein $R_{14}$ and $R_{15}$ are independently selected from the group of —H, —$C_{1-6}$ alkyl, and —$C_{1-6}$ alkylsubstituted alkyl, or $R_{14}$ and $R_{15}$ are taken together with the adjacent N to form a cycle selected from the group of

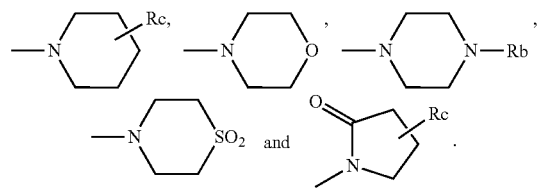

In a further embodiment, there is provided a method for treating mammals infected with a virus, especially wherein said virus is HIV, comprising administering to said mammal an antiviral effective amount of a compound which is selected from the group of compounds of Formulas I, II, III above, and one or more pharmaceutically acceptable carriers, excipients or diluents. Optionally, the compound of Formulas I, II, and/or III can be administered in combination with an antiviral effective amount of another—AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound which is selected from the group of compounds of Formulas I, II, and III, and one or more pharmaceutically acceptable carriers, excipients, and diluents; and optionally in combination with an antiviral effective amount of another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formulas I, II, and III.

Also provided herein are intermediate compounds useful in making the compounds of Formulas I, II, and III.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formulas I, II and III in addition to the mixtures thereof.

DEFINITIONS

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$-fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z as defined above and R$^x$ being H or (C$_{1-6}$)alkyl.

A "sulfinyl" group refers to a —S(=O)—R" group, with R" being (C$_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^X$R$^Y$, with R$^X$ and R$^Y$ independently being H or (C$_{1-6}$)alkyl.

A "N-Sulfonamido" group refers to a R"S(=O)$_2$NR$_x$— group, with R$_x$ being H or (C$_{1-6}$)alkyl.

A "O-carbamyl" group refers to a —OC(=O)NR$^x$R$^y$ group, with R$^X$ and R$^Y$ independently being H or (C$_{1-6}$)alkyl.

A "N-carbamyl" group refers to a R$^x$OC(=O)NR$^y$ group, with R$^x$ and R$^y$ independently being H or (C$_{1-6}$)alkyl.

A "O-thiocarbamyl" group refers to a —OC(=S)NR$^x$R$^y$ group, with R$^x$ and R$^y$ independently being H or (C$_{1-6}$)alkyl.

A "N-thiocarbamyl" group refers to a $R^xOC(=S)NR^y$— group, with $R^x$ and $R^y$ independently being H or $(C_{1-6})$alkyl.

An "amino" group refers to an —$NH_2$ group.

A "C-amido" group refers to a —$C(=O)N^xR^y$ group, with $R^x$ and $R^y$ independently being H or $(C_{1-6})$alkyl.

A "C-thioamido" group refers to a —$C(=S)NR^xR^y$ group, with $R^x$ and $R^y$ independently being H or $(C_{1-6})$alkyl.

A "N-amido" group refers to a $R^xC(=O)NR^y$— group, with $R^x$ and $R^y$ independently being H or $(C_{1-6})$alkyl.

An "ureido" group refers to a —$NR^x(=O)NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "amidino" group refers to a $R^xR^yNC(=N)$— group, with $R^x$ and $R^y$ independently being H or $(C_{1-6})$alkyl.

A "cyano" group refers to a —CN group.

A "silyl" group refers to a —$Si(R'')_3$, with R" being $(C_{1-6})$alkyl or phenyl.

A "phosphonyl" group refers to a $P(=O)(OR^x)_2$ with $R^x$ being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

A "4, 5, or 6 membered ring cyclic N-lactam" group refers to

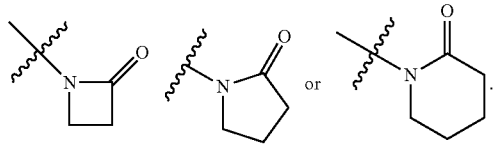

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

Examples of such prodrug esters include

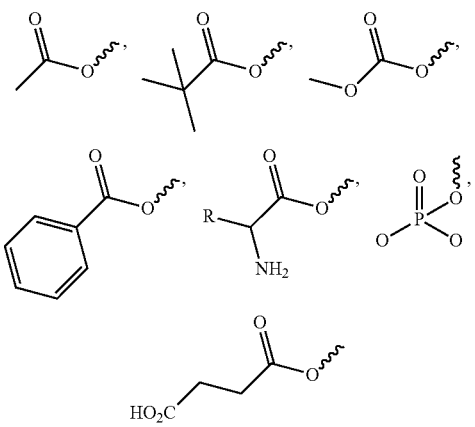

The term "prodrug ethers" include both phosphate acetals and O-glucosides.

Representative examples of such prodrug ethers include

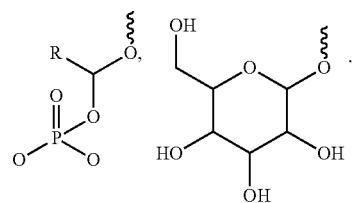

As set forth above, the invention is directed to a compound, including pharmaceutically acceptable salts thereof, which is selected from the group of:

a compound of formula I

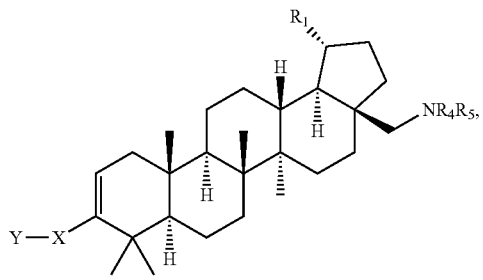

Formula I a compound of formula II

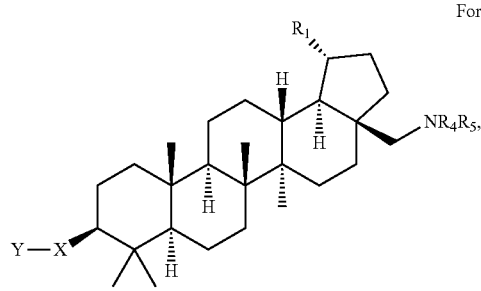

Formula II and
a compound of formula III

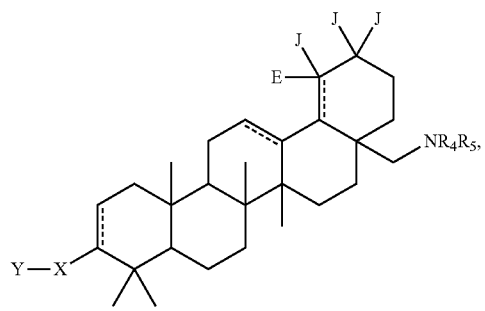

Formula III wherein R₁ is isopropenyl or isopropyl;
J and E are independently —H or —CH₃ and E is absent when the double bond is present;
X is a phenyl or heteroaryl ring substituted with A, wherein A is at least one member selected from the group of —H, -halo, -hydroxyl, —C$_{1-6}$ alkyl, —C$_{1-6}$ alkoxy, and —COOR$_2$;
R$_2$ is —H, —C$_{1-6}$ alkyl or -alkylsubstituted C$_{1-6}$ alkyl or -arylsubstituted C$_{1-6}$ alkyl;
Y is selected from the group of —COOR$_2$, —C(O)NR$_2$SO$_2$R$_3$, —C(O)NHSO$_2$NR$_2$R$_2$, —NR$_2$SO$_2$R$_2$, —SO$_2$NR$_2$R$_2$, —C$_{3-6}$ cycloalkyl-COOR$_2$, —C$_{1-6}$ alkenyl-COOR$_2$, —C$_{1-6}$ alkynyl-COOR$_2$, —C$_{1-6}$alkyl-COOR$_2$, —NHC(O)(CH$_2$)$_n$—COOR$_2$, —SO$_2$NR$_2$C(O)R$_2$, -tetrazole, and —CONHOH, wherein n=1-6;
R$_3$ is —C$_{1-6}$ alkyl or alkylsubstituted C$_{1-6}$ alkyl;
R$_4$ is selected from the group of H, —C$_{1-6}$ alkyl, —C$_{3-6}$cycloalkyl, —C$_{1-6}$ substituted alkyl, —C$_{1-6}$ alkyl-heteroaryl, —C$_{1-6}$ alkyl-substitutedheteroaryl, —C$_{1-6}$ alkyl-NR$_6$R$_7$, —C$_{1-6}$ alkyl-CONR$_8$R$_9$, —C$_{3-6}$ cycloalkyl-CONR$_8$R$_9$, —C$_{3-6}$ cycloalkyl-(CH$_2$)$_{1-3}$—NR$_6$R$_7$, —(CH$_2$)$_{1-3}$—C$_{3-6}$ cycloalkyl-NR$_6$R$_7$, —(CH$_2$)$_{1-3}$—C$_{3-6}$cycloalkyl-(CH$_2$)$_{1-3}$—NR$_6$R$_7$, —C$_{1-6}$ alkyl-Q$_1$, C$_{3-6}$ cycloalkyl-Q$_1$, —COR$_{10}$, —SO$_2$R$_3$ and —SO$_2$NR$_2$R$_2$;
Q$_1$=-hydroxy, —COOR$_2$, -halo, —SO$_2$R$_a$;
R$_a$=C$_{1-6}$ alkyl, NR$_2$R$_2$,

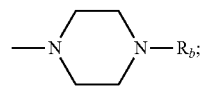

R$_b$=—H, —C$_{1-6}$ alkyl, —COR$_S$, —SO$_2$R$_3$, —SONR$_3$R$_3$,

R$_4$ can also be selected from the group of:

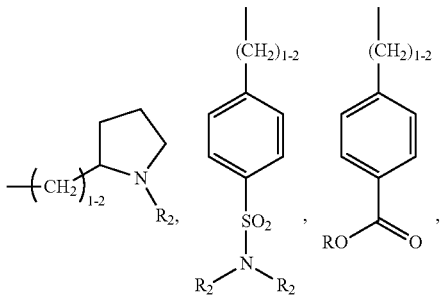

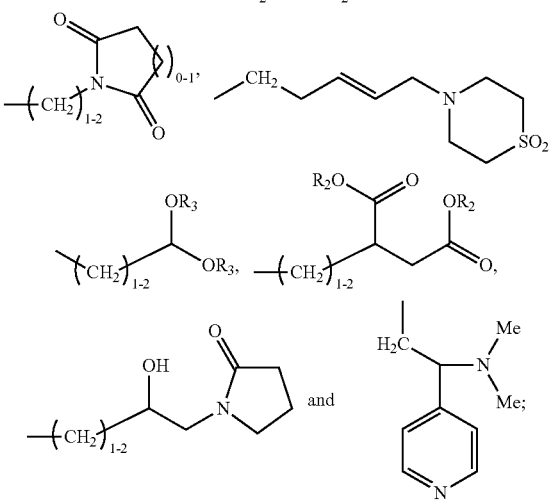

R$_5$ is selected from the group of —H, —C$_{1-6}$ alkyl, —C$_{3-6}$ cycloalkyl, —C$_{1-6}$ alkylsubstituted alkyl, —COR$_{10}$, —SO$_2$R$_3$ and —SO$_2$NR$_2$R$_2$;
with the proviso that only one of R$_4$ or R$_5$ can be selected from the group of —COR$_{10}$, —SO$_2$R$_3$ and —SO$_2$NR$_2$R$_2$;
or R$_4$ and R$_5$ are taken together with the adjacent N to form a cycle such as

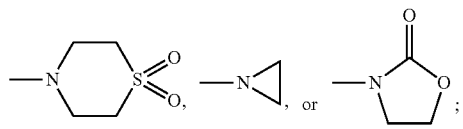

R$_{10}$ is selected from the group of —H, —C$_{1-6}$ alkyl, —C$_{1-6}$ alkyl-NR$_6$R$_7$, —NR$_{11}$R$_{12}$, —OR$_{13}$, —C$_{1-6}$ alkyl-Q$_2$, —C$_{3-6}$ cycloalkyl-Q$_2$, aryl-Q$_2$, wherein n=1-6,
wherein Q$_2$=hydroxy, —COOR$_2$, -halo, SO$_2$R$_a$, —CONHSO$_2$R$_3$, —CONHSO$_2$NR$_2$R$_2$;
R$_{10}$ can also be selected from the group of:

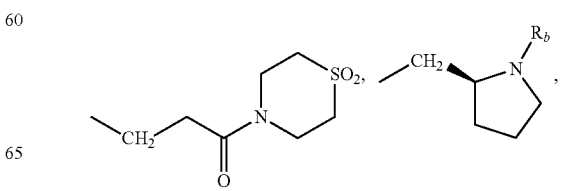

-continued

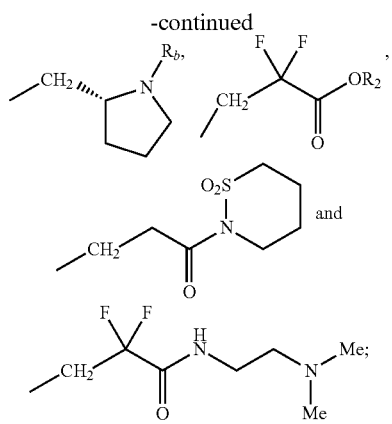

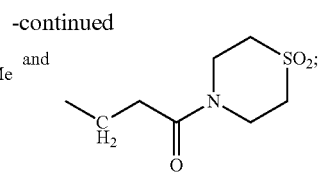

or $R_8$ and $R_9$ are taken together with the adjacent N to form a cycle selected from the group of:

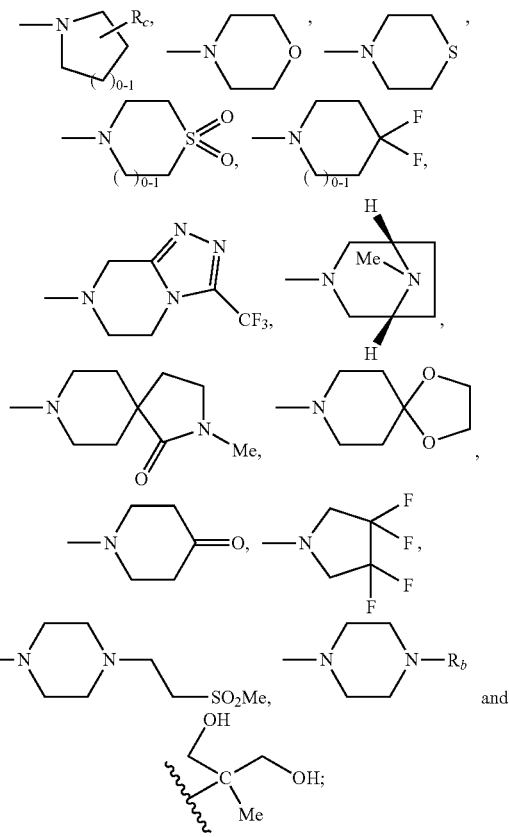

$R_6$ and $R_7$ are independently selected from the group of —H, —$C_{1-6}$ alkyl, —$C_{1-6}$ substituted alkyl, aryl, heteroaryl, substituted aryl, substituted heteroaryl, and —$C_{1-6}$ alkyl-$Q_1$, or $R_6$ and $R_7$ are taken together with the adjacent N to form a cycle selected from the group of

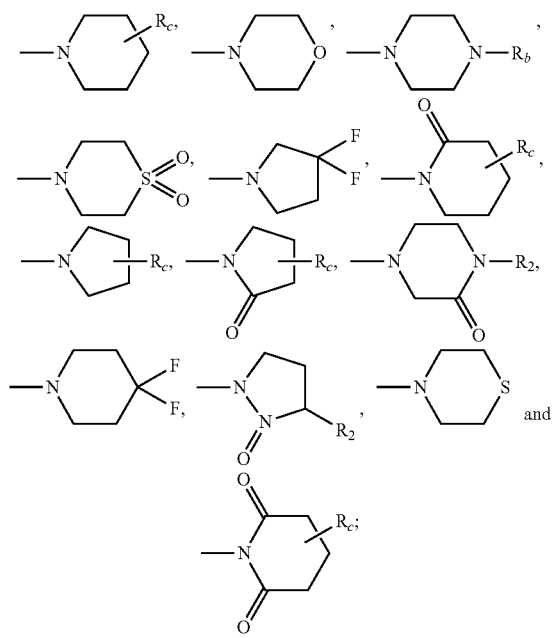

$R_c$=$C_{1-6}$ alkyl, $NR_2R_2$, —$COOR_3$;
$R_8$ and $R_9$ are independently selected from the group of —H, —$C_{1-6}$ alkyl, —$C_{3-6}$ cycloalkyl, —$C_{1-6}$ substituted alkyl, —$C_{1-6}$ alkyl-heteroaryl, —$C_{1-6}$ alkyl-substitutedheteroaryl, —$C_{1-6}$alkyl-$NR_2R_2$, —$C_{1-6}$alkyl-$CONR_2R_2$, —$C_{1-6}$ alkyl-$Q_1$, $C_{3-6}$ cycloalkyl-$Q_1$,
or $R_8$ and $R_9$ can also be independently selected from the group of

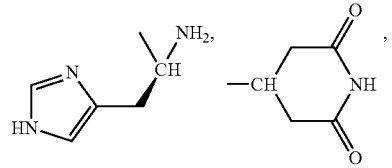

and $R_{11}$ and $R_{12}$ are independently selected from the group of —H, —$C_{1-6}$ alkyl, —$C_{3-6}$ cycloalkyl, and —$C_{1-6}$alkylsubstituted alkyl;

or $R_{11}$ and $R_{12}$ are taken together with the adjacent N to form a cycle selected from the group of

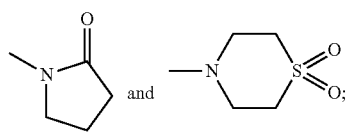

and $R_{13}$ is selected from the group of —H, —$C_{1-6}$ alkyl, —$C_{1-6}$ alkylsubstituted alkyl, and —$C_{1-6}$ alkyl $NR_{14}R_{15}$, wherein $R_{14}$ and $R_{15}$ are independently selected from the group of —H, —$C_{1-6}$ alkyl, and —$C_{1-6}$ alkylsubstituted alkyl, or $R_{14}$ and $R_{15}$ are taken together with the adjacent N to form a cycle selected from the group of

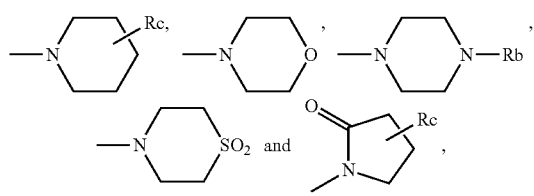

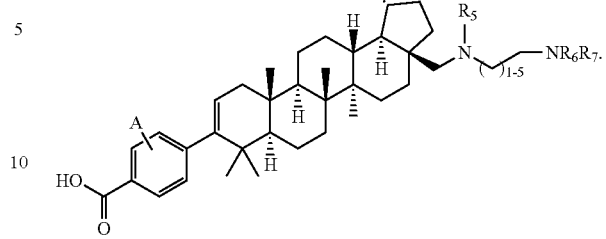

More preferred compounds include those which are encompassed by Formula I. Of these, those wherein X is a phenyl ring are even more preferred. Even more preferred are compounds of Formula I wherein X is a phenyl ring and Y is in the para position.

Also preferred are compounds of Formula I wherein A is at least one member selected from the group of —H, —OH, -halo, —$C_{1-3}$ alkyl, and —$C_{1-3}$ alkoxy, wherein -halo is selected from the group of —Cl, —F and —Br, with —F being more preferred.

Also preferred are compounds of Formula I wherein Y is —$COOR_2$, and more preferably —COOH.

In another preferred embodiment there is provided a compound of Formula Ia below wherein X is a phenyl ring and Y is —COOH in the para position:

Formula Ia

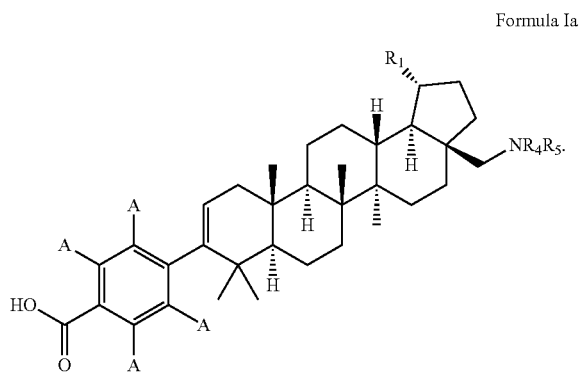

In this embodiment, it is also preferred that A is at least one member selected from the group of —H, -halo, —OH, —$C_{1-3}$ alkyl and —$C_{1-3}$ alkoxy. It is particularly preferred that A is at least one member selected from the group of —H, -fluoro, -chloro, —OH, -methyl and -methoxy.

Other compounds which are preferred as part of the invention include the following:

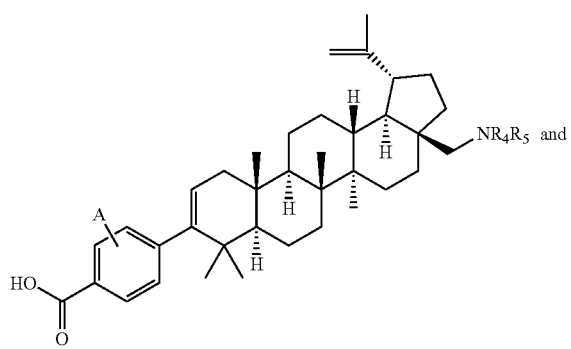

Even more preferred compounds include the following:

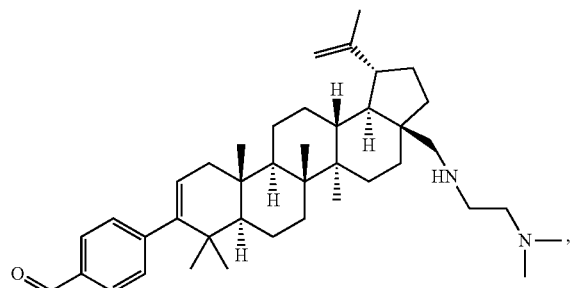

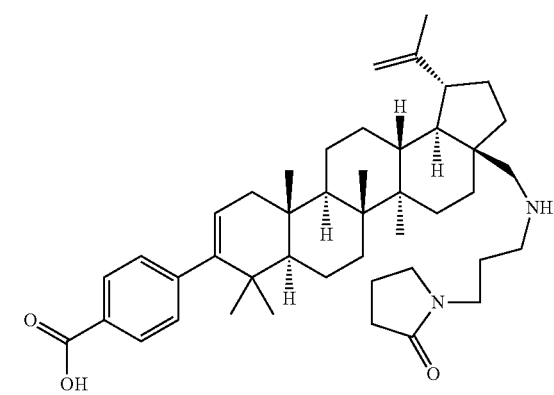

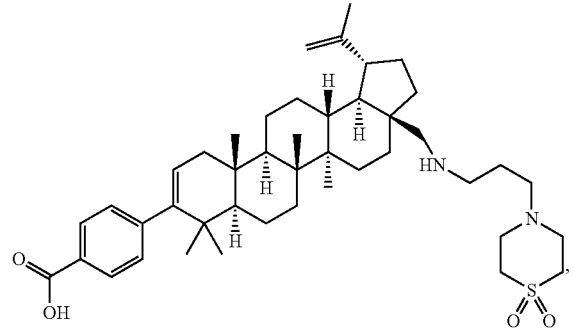

19
-continued
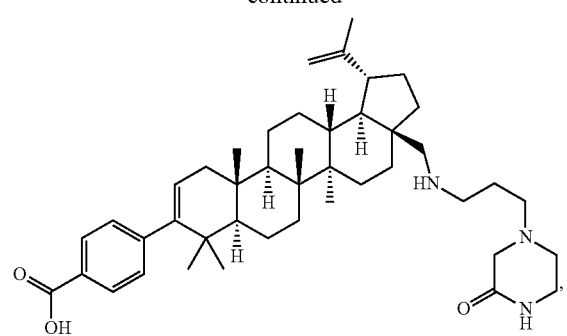
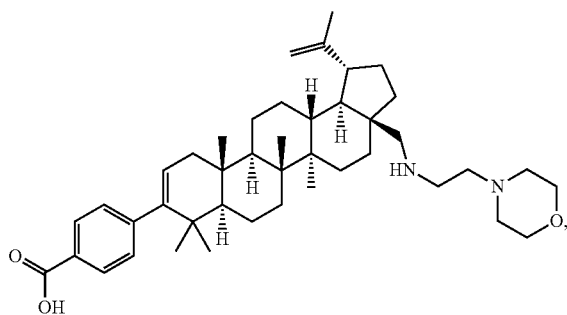
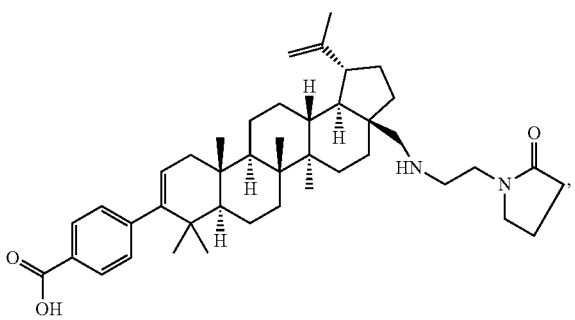
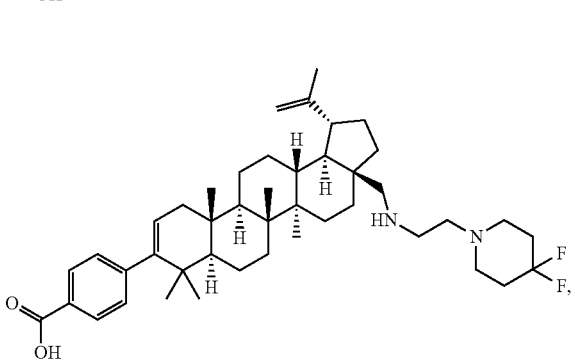
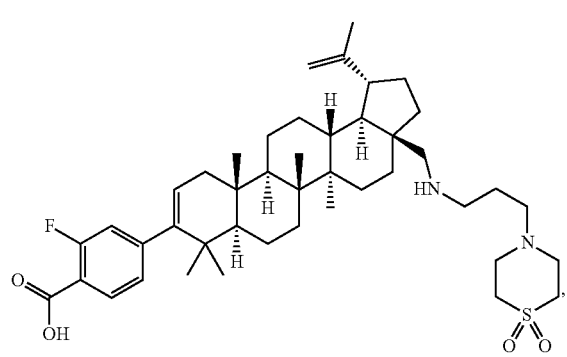
20
-continued
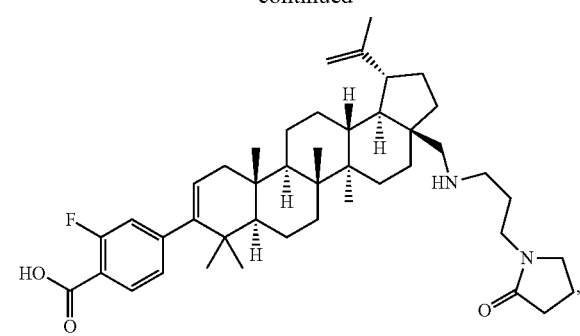
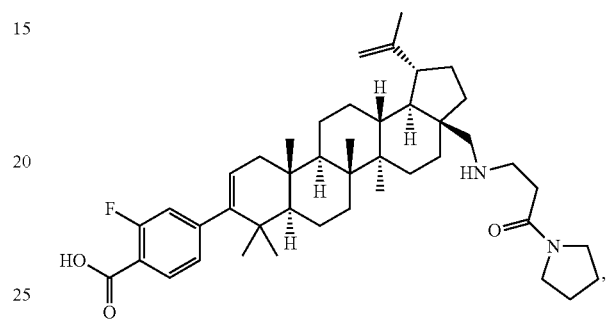
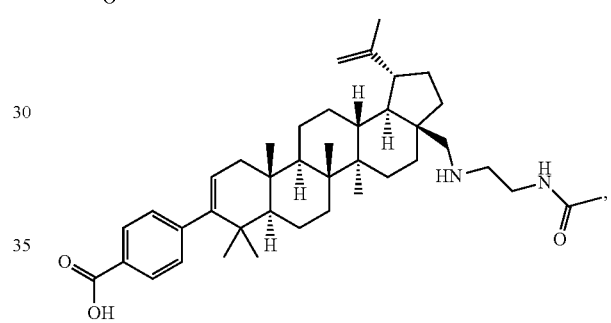
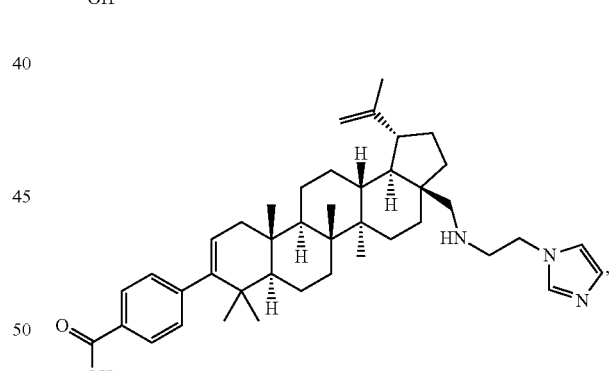
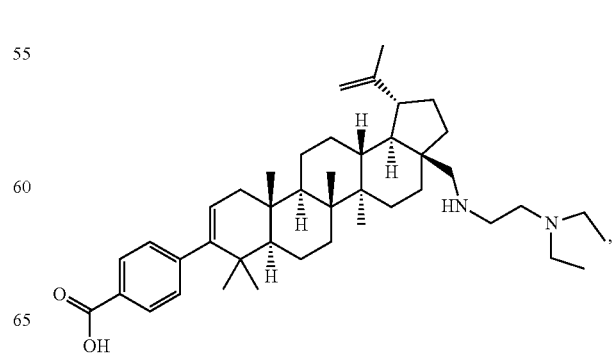

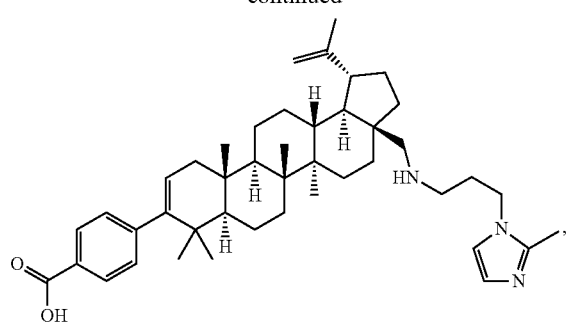
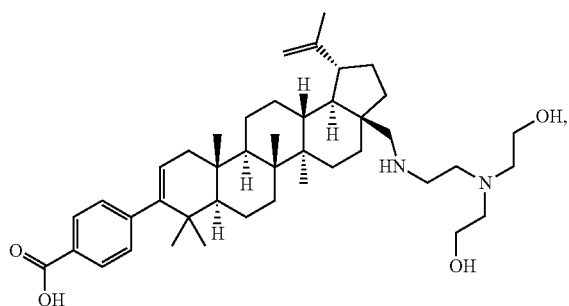
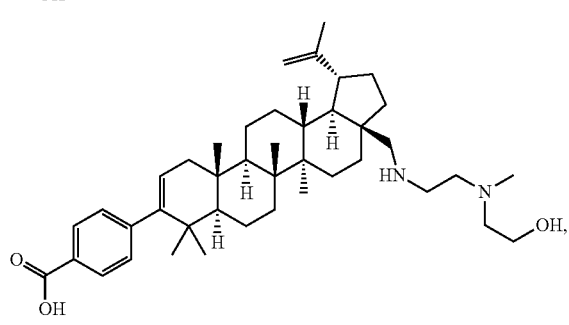
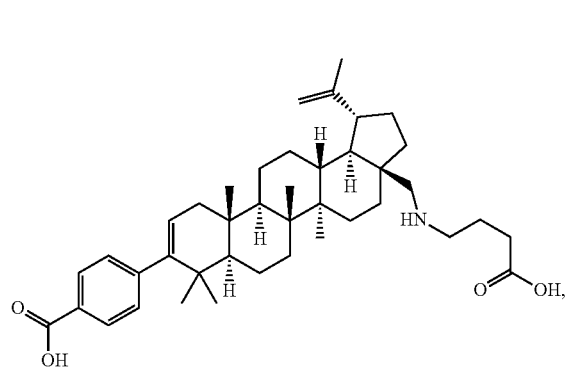
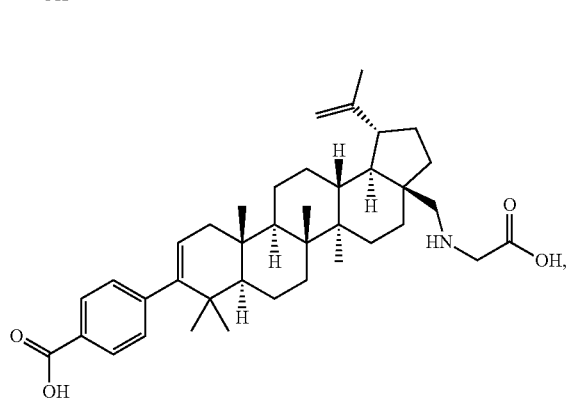
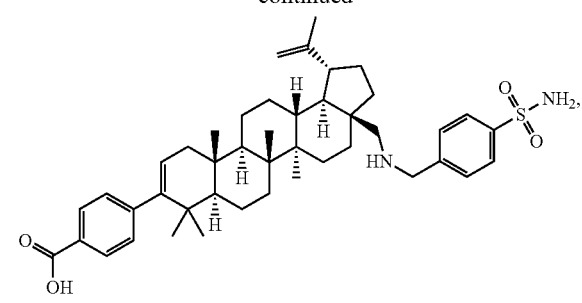
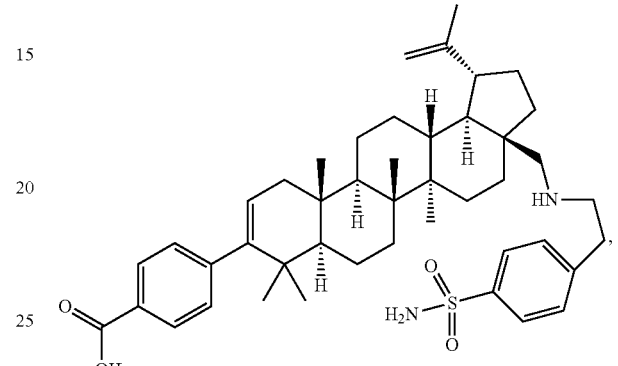
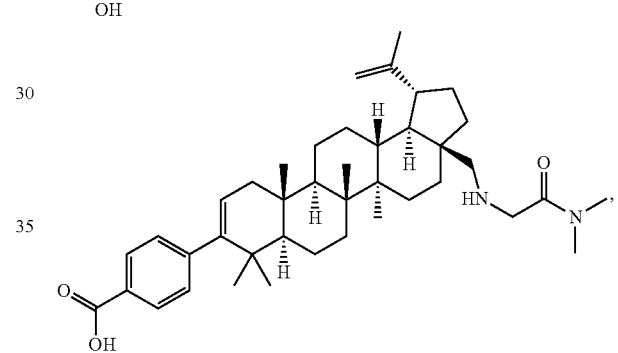
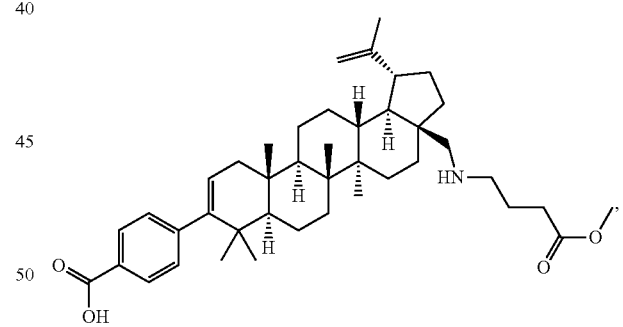
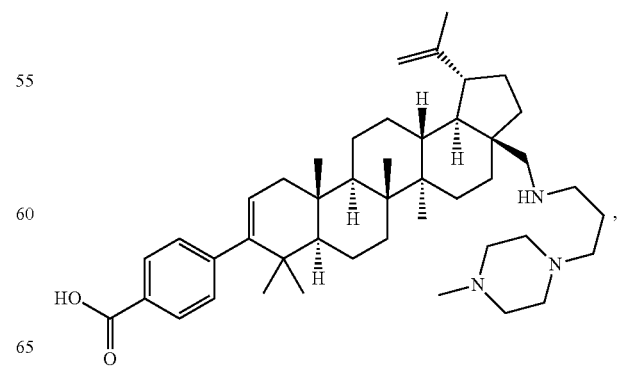

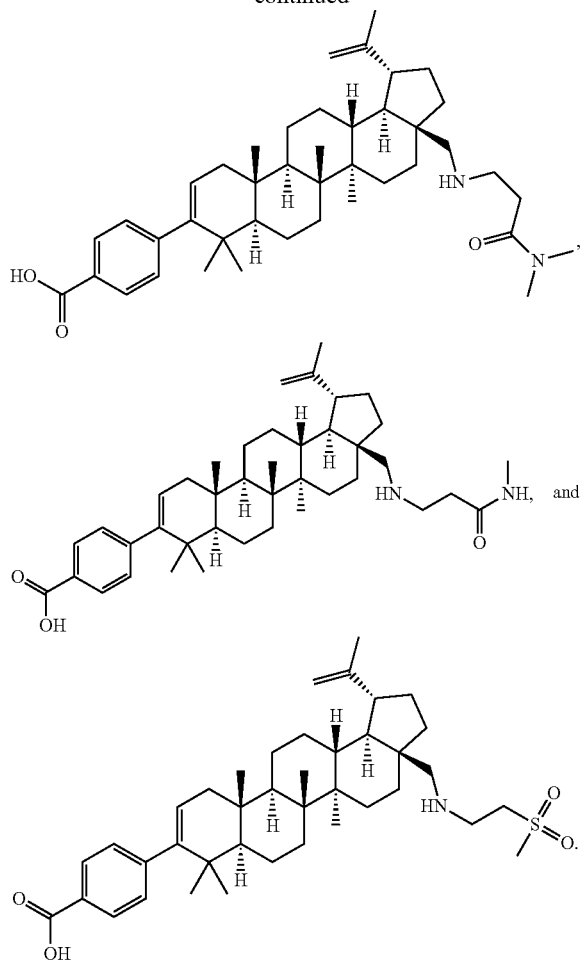

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I, II, and/or III, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I, II, and/or III herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| ANTIVIRALS | | |
|---|---|---|
| Drug Name | Manufacturer | Indication |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) | Glaxo Wellcome | HIV infection, |

ANTIVIRALS

| Drug Name | Manufacturer | Indication |
|---|---|---|
| GW 1592 | | AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, Sustiva ®) (-)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL 10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffman-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Emtriva ® (Emtricitabine) | Gilead | HIV infection, AIDS, |

ANTIVIRALS

| Drug Name | Manufacturer | Indication |
|---|---|---|
| (FTC) | | (reverse transcriptase inhibitor) |
| Combivir ® | GSK | HIV infection, AIDS, (reverse transcriptase inhibitor) |
| Abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (Enfuvirtide or T-20) | Roche/Trimeris | HIV infection AIDs, viral Fusion inhibitor |
| Lexiva ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| Trizivir ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| Truvada ® | Gilead | Combination of Tenofovir disoproxil fumarate salt (Viread ®) and Emtriva ® (Emtricitabine) |
| Integrase Inhibitor GS917/JTK-303 Elvitegravir | Gilead/Japan Tobacco | HIV Infection AIDs in development |
| Triple drug combination Atripla ® | Gilead/Bristol-Myers Squibb | Combination of Tenofovir disoproxil fumarate salt (Viread ®), Emtriva ® (Emtricitabine), and Sustiva ® (Efavirenz) |
| Festinavir ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |

-continued

ANTI-INFECTIVES

| Drug Name | Manufacturer | Indication |
|---|---|---|
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and US 2005/0209246.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is Reyataz® (active ingredient Atazanavir). Typically a dose of 300 to 600 mg is administered once a day. This may be co-administered with a low dose of Ritonavir (50 to 500 mgs). Another preferred inhibitor of HIV protease is Kaletra®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

General Chemistry (Methods of Synthesis)

The present invention comprises compounds of Formulas I, II, and III, their pharmaceutical formulations, and their use in patients suffering from or susceptible to HIV infection. The compounds of Formulas I, II, and III also include pharmaceutically acceptable salts thereof. General procedures to construct compounds of Formulas I, II, and III and intermediates useful for their synthesis are described in the following Schemes (after the Abbreviations).

ABBREVIATIONS

One or more of the following abbreviations, most of which are conventional abbreviations well known to those skilled in the art, may be used throughout the description of the disclosure and the examples:

$Bz_2O$=benzoic anhydride
TBTU=O-(benzotriazol-1-yl)-N,N,N',N'-tetramethyluronium tetrafluoroborate
HATU=2-(1H-7-azabenzotriazol-1-yl)-1,1,3,3-tetramethyluronium hexafluorophosphate methanaminium
DCE=dichloroethane
DCM=dichloromethane
CDI=carbonyl diimidazole
prep. HPLC=preparative high performance liquid chromatography
rt=room temperature
DIPEA=diisopropylethylamine
DMAP=4-dimethylaminopyridine
DMSO=dimethylsulfoxide
THF=tetrahydrofuran
KHMDS=potassium bis(trimethylsilyl)amide
min=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
$Tf_2NPh$=(trifluoromethylsulfonyl)methanesulfonamide
dioxane=1,4-dioxane
PG=protective group
atm=atmosphere(s)
mol=mole(s)
mmol=milimole(s)
mg=milligram(s)

μg=microgram(s)
μl=microliter(s)
μm=micrometer(s)
mm=millimeter(s)
HOAc=acetic acid
MeOH=methanol
DMF=N,N-dimethylformamide
TBAF=tetrabutylammonium fluoride The terms "C-3" and "C-28" refer to certain positions of a triterpene core as numbered in accordance with IUPAC rules (positions depicted below with respect to an illustrative triterpene: betulin):

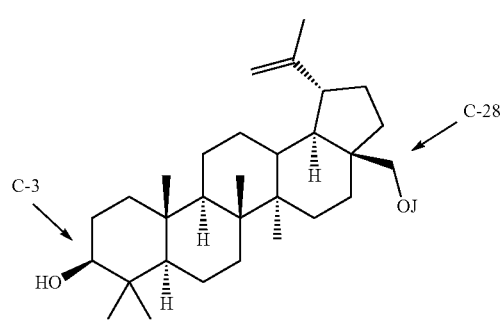

The same numbering is maintained when referring to the compound series in schemes and general descriptions of methods.

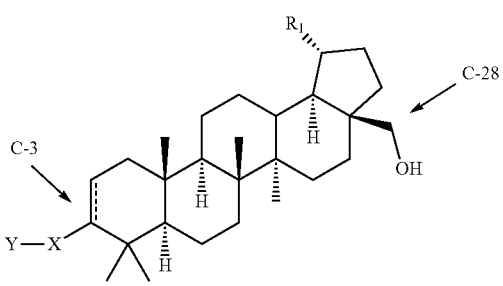

C-28 amines

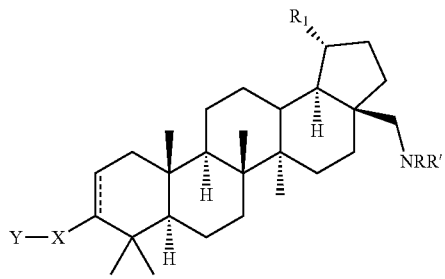

C-28 amides

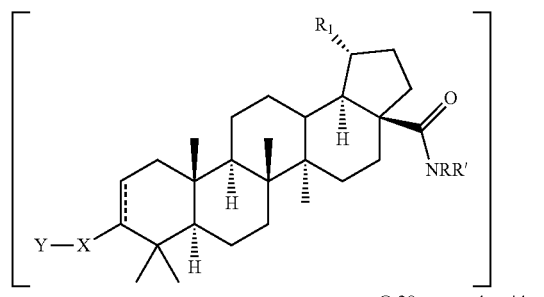

C-28 reversed amides

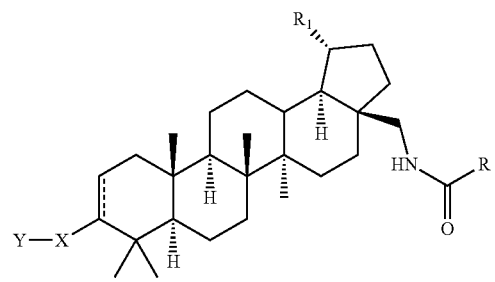

C-28 ureas

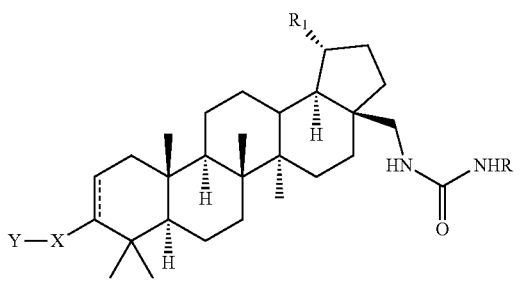

C-28 reversed carbamates

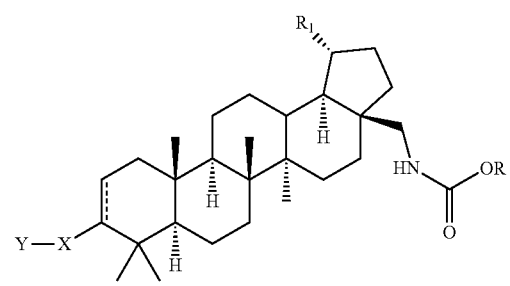

Preparation of Compounds of Formulas I, II, and III
General Chemistry Schemes

Preparation of Compounds of Formulas I, II and III
General Chemistry Schemes

Compounds of Formula I can be prepared from commercially available (Aldrich, others) betulinic acid and betulin by chemistry described in the following schemes. Compounds of Formula II and III are described thereafter.

General Reaction Schemes are Set Forth as Follows:
Scheme 1
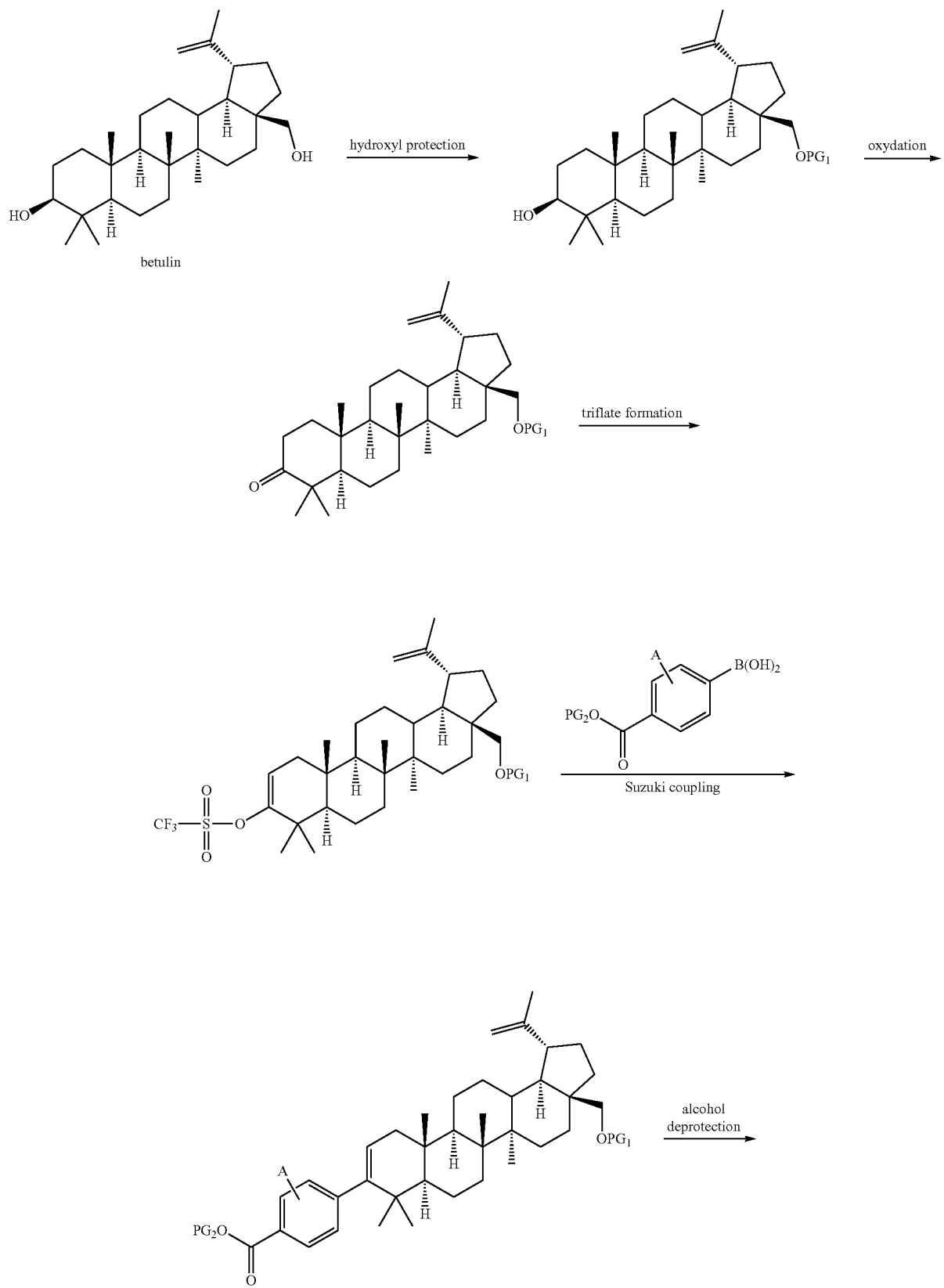

-continued
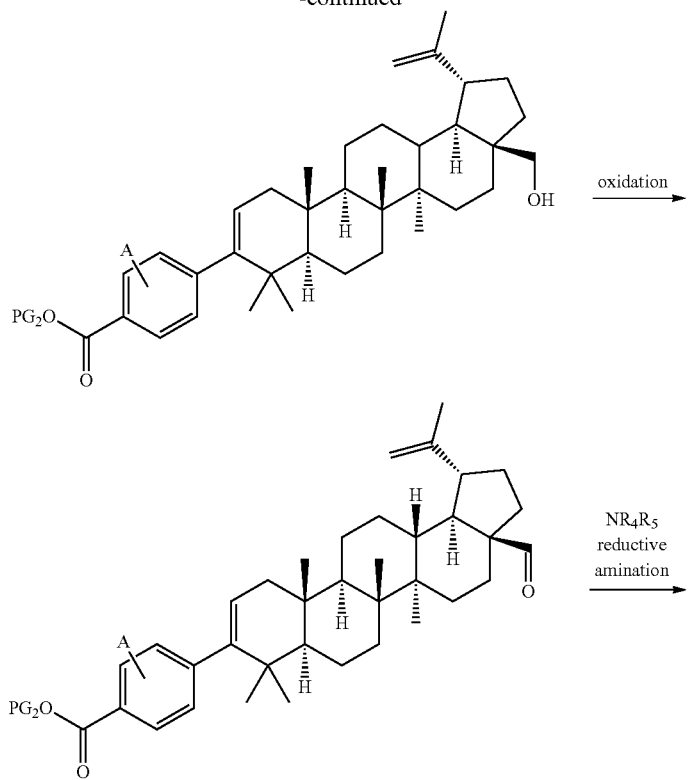
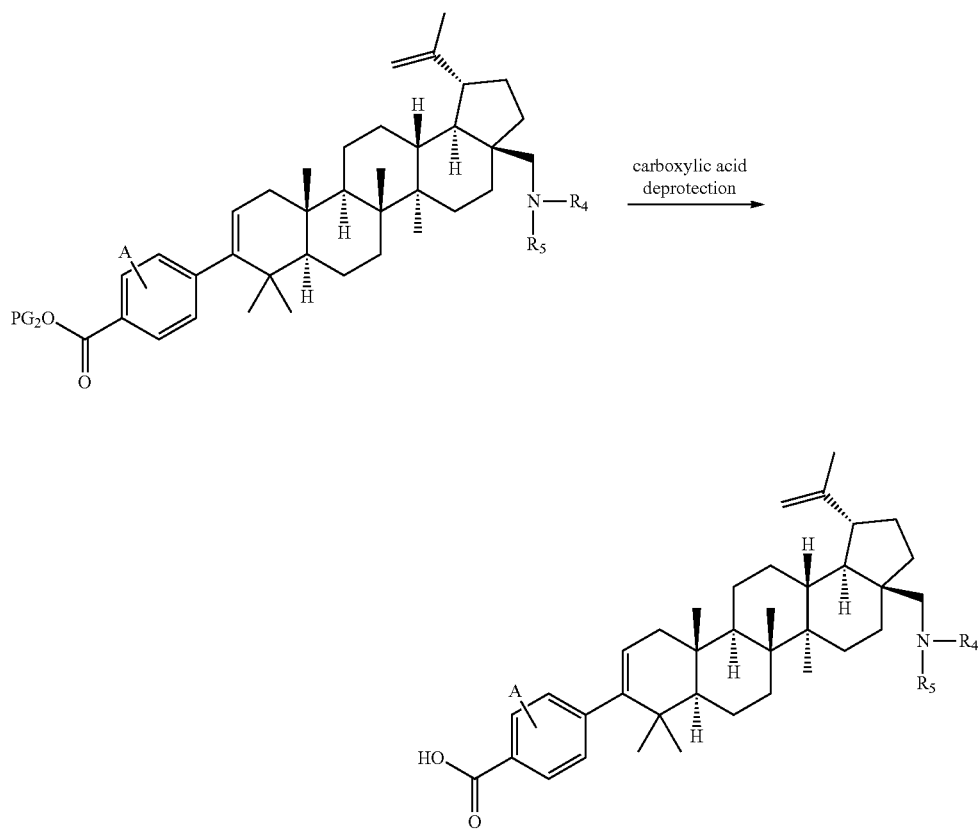

The hydroxyl group in the C-28 position of betulin can be protected with a suitable hydroxyl-protective group. Standard oxidation (i.e. PCC, Dess-Martin) of the C-3 hydroxyl group produces the C-3 ketone which is then converted into the triflate using conditions know to those skilled in the art. Palladium catalyzed cross coupling with boronic acid (Stille coupling using stannanes can also be used) afforded the corresponding C-3 modified betulin derivatives. Deprotection of the hydroxyl group in the C-28 position followed by oxidation under standard conditions (i.e. PCC) affords the corresponding aldehyde. Standard reductive amination of this aldehyde with amines using sodium triacetoxyborohydride (sodium cyanoborohydride can also be used) followed by deprotection of the carboxylic acid affords the desired C-28 amines

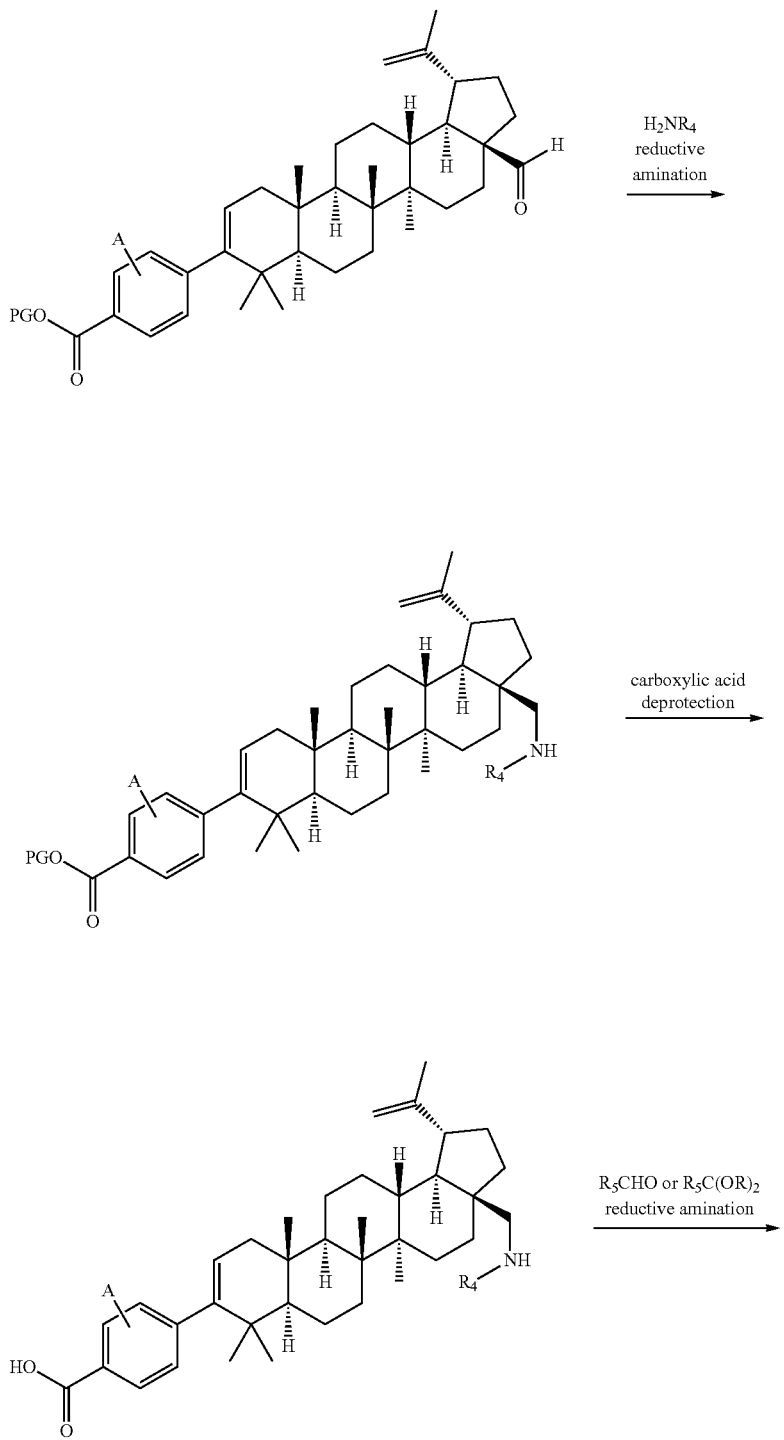

Scheme 2

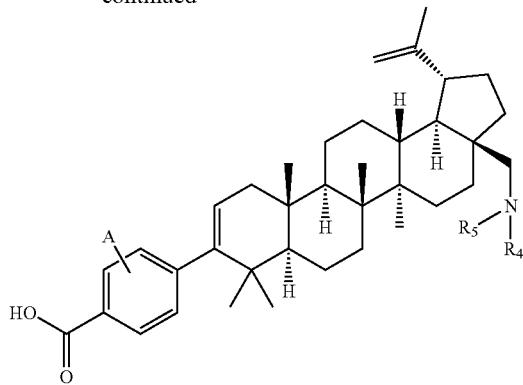

Alternatively, some of the C-28 tertiary amines can be prepared as describe in scheme 2: First, reductive amination of C-28 aldehyde with a primary amine generates a C-28 secondary amine Deprotection of the carboxylic acid followed by reductive amination under standard conditions of the C-28 secondary amine with an aldehyde of a dialkylacetal affords the desired C-28 tertiary amine Scheme 3

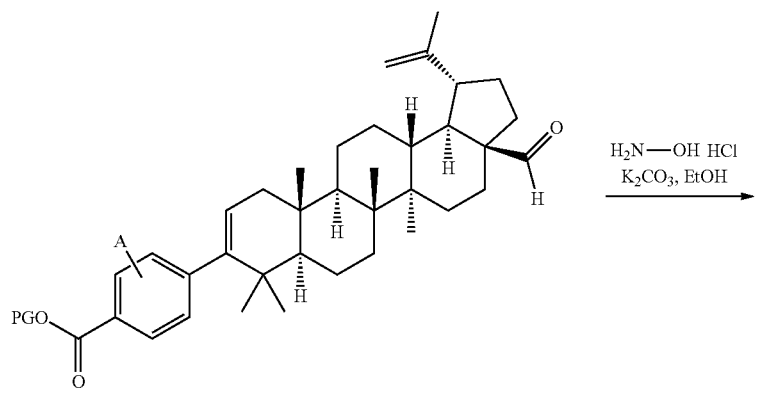

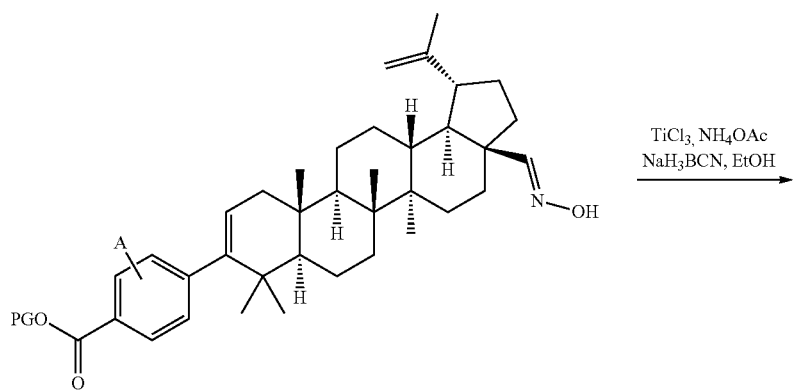

-continued

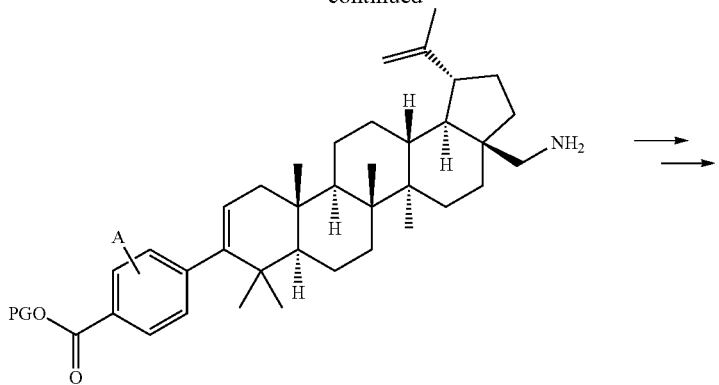

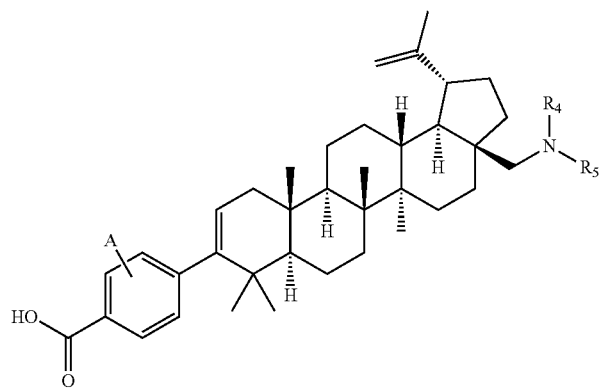
40

Alternatively, the C-28 amines can be prepared by converting the C-28 aldehyde in the corresponding oxime by treatment with hydroxylamine under standard conditions. Reduction of the hydroxylamine using sodium cyanoborohydride in the presence of titanium trichloride afforded the C-28 primary amine which can be further derivatized using methods known to those skilled in the art to provide the desired final products.

Scheme 4

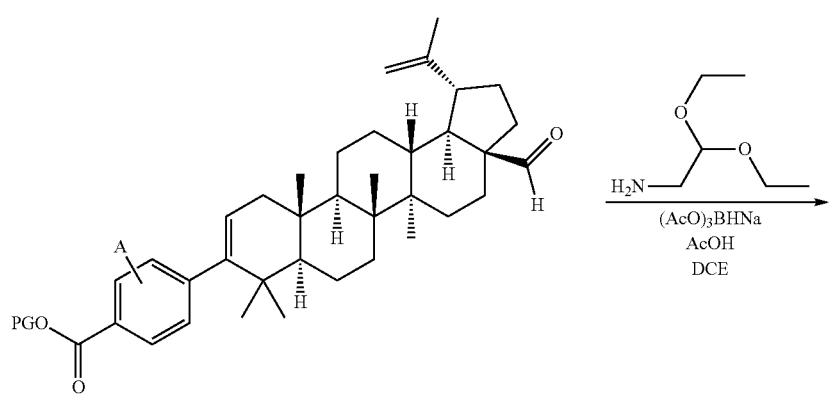

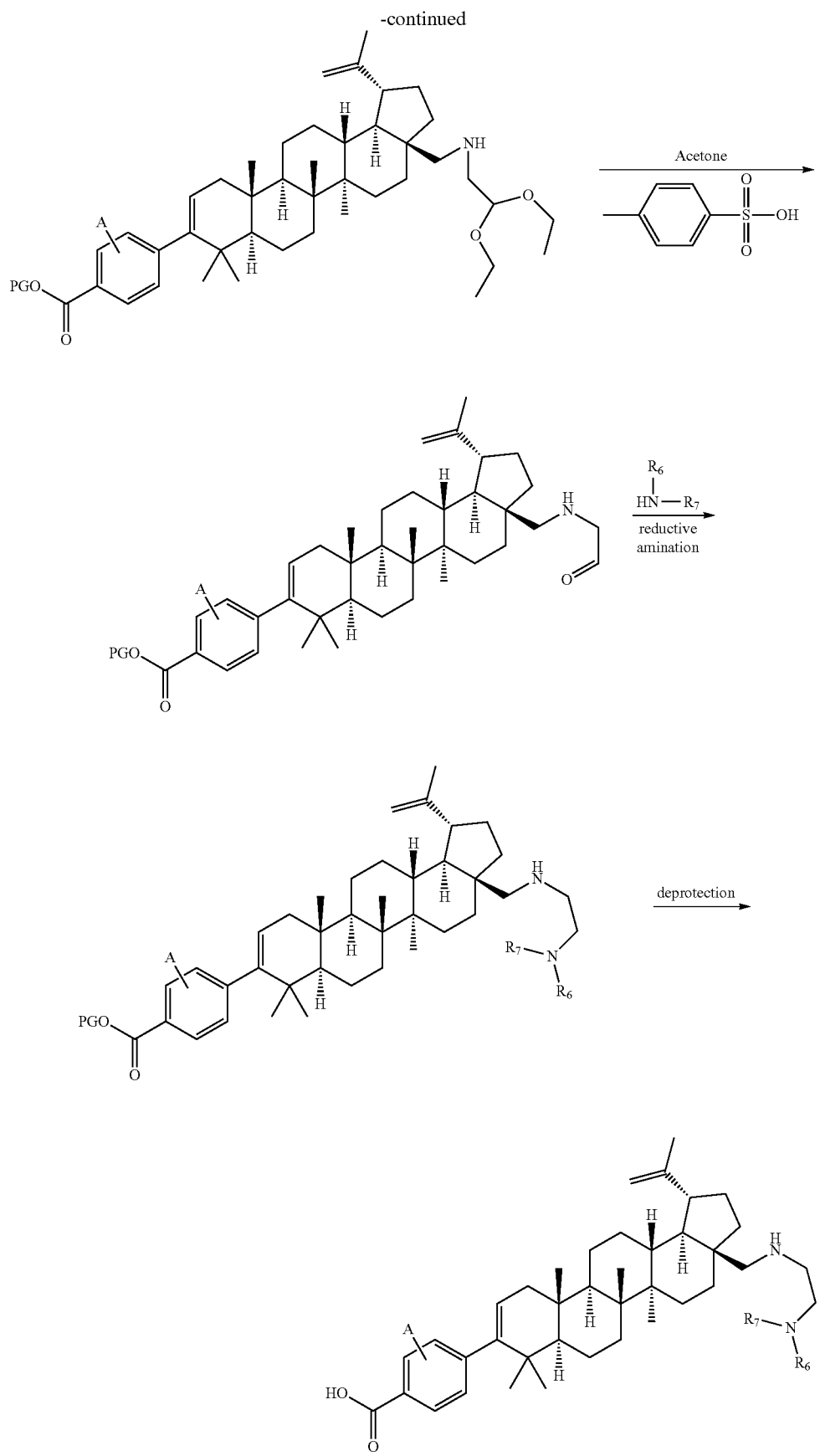

Some of the C-28 amines can be prepared as described in scheme 4: Reductive amination under standard conditions of the C-28 aldehyde in the presence of 2,2-diethoxyethanamine followed by ketal hydrolysis generates a the C-28 amine carrying an aldehyde which can also be submitted to reductive amination under standard conditions. Deprotection of the carboxylic acid produces the desired C-28 amine.

Substituents $R_4$, $R_5$, $R_6$ and $R_7$ may contain functional groups (i.e. COOH, COOR, OH, NHR) that can be further modified by methods know to those skilled in the art.

The modification can be carried out before or after the final deprotection of the carboxylic acid is performed depending on the nature of the functional group Alternatively, when $R_4$, $R_5$, $R_6$ and/or $R_7$ are H, the corresponding amine can be further modified (for example by alkylation, acylation, Michael addition, etc.) by methods known to those skilled in the art. Saturation of the isopropenyl group can be accomplished by hydrogenation under standard conditions of the final products.

Scheme 5

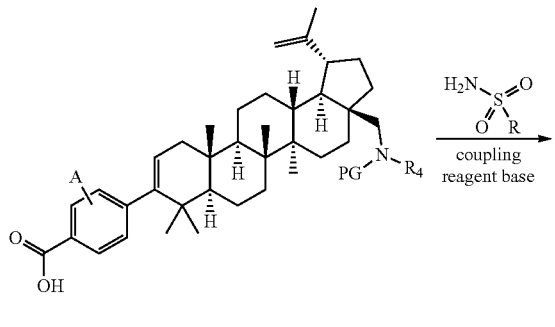

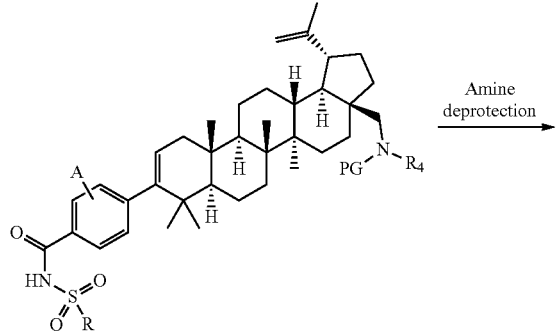

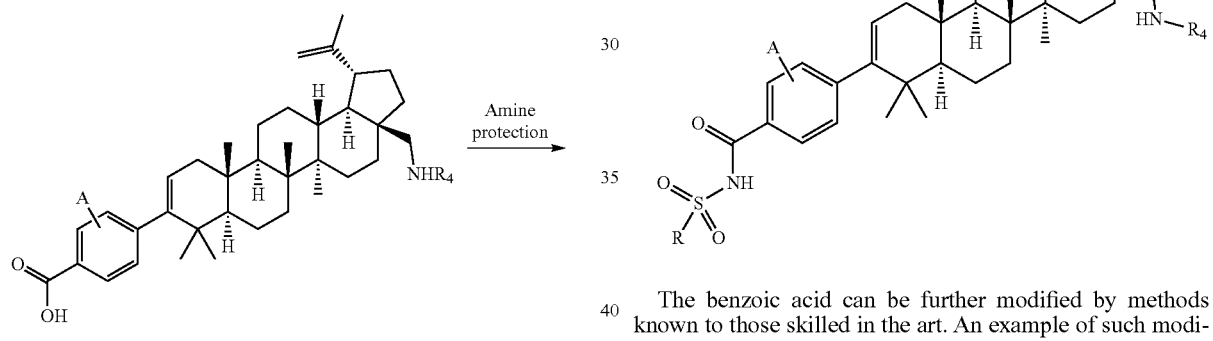

The benzoic acid can be further modified by methods known to those skilled in the art. An example of such modifications is shown in scheme 5: A suitable protective group is installed under standard conditions to mask the free NH in the C-28 position. Then, treatment of the carboxylic acid with the corresponding nucleophile, for example a sulfonyl amide or urea in the presence of a coupling reagent and a base followed by removal of the C-28 amine protective group affords the desired final product.

Compounds of formula I where the modification in the C-3 position is other than benzoic acid can be prepared by selecting the corresponding boronic acid in the palladium cross coupling step shown in scheme 1 (scheme 6) and then using the chemistry methods described in the above schemes.

Scheme 6

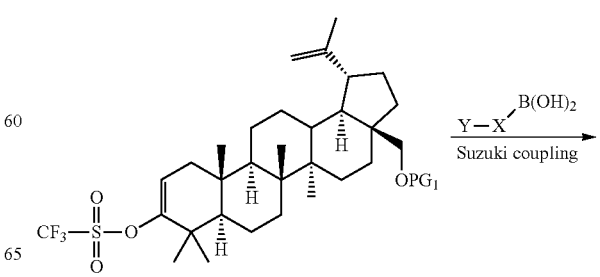

-continued

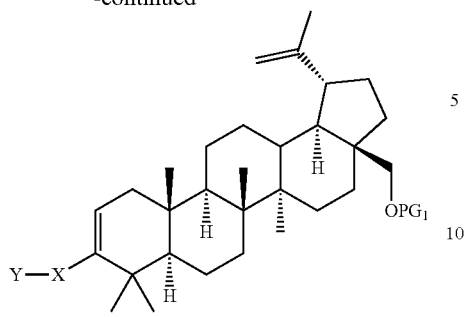

Alternatively, compounds of formula I can be prepared using the method described below in scheme 7. The C-28 primary amine can be treated in the presence of base with 1,2-disubstituted ethane where the substituents are two leaving groups (i.e., tosylate, mesylate, Br, Cl, I), to form the C-28 aziridine. Opening of the aziridine with a nucleophile can be achieve with or without heat to produce the corresponding secondary C-28 amine which can be further modified.

Scheme 7

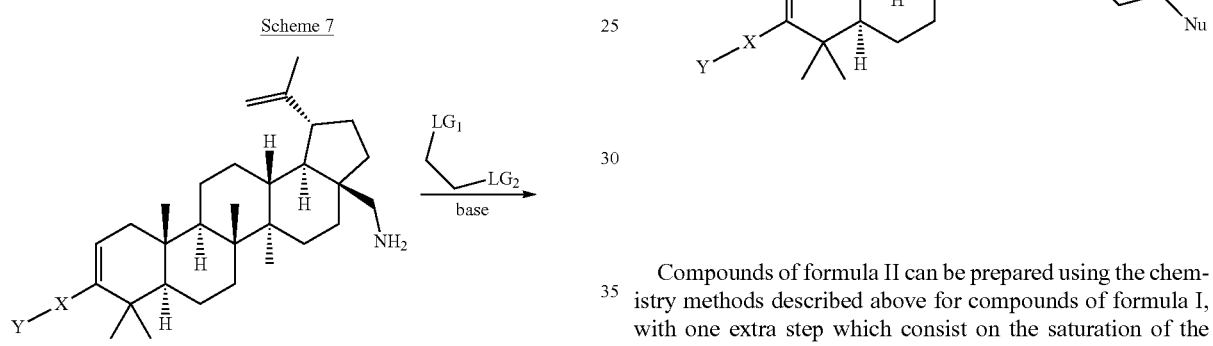

-continued

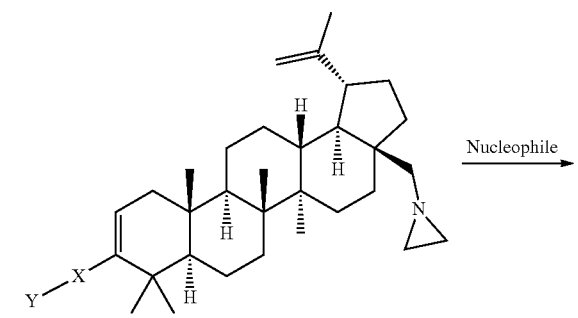

Compounds of formula II can be prepared using the chemistry methods described above for compounds of formula I, with one extra step which consist on the saturation of the double bonds as shown below in scheme 8:

Scheme 8

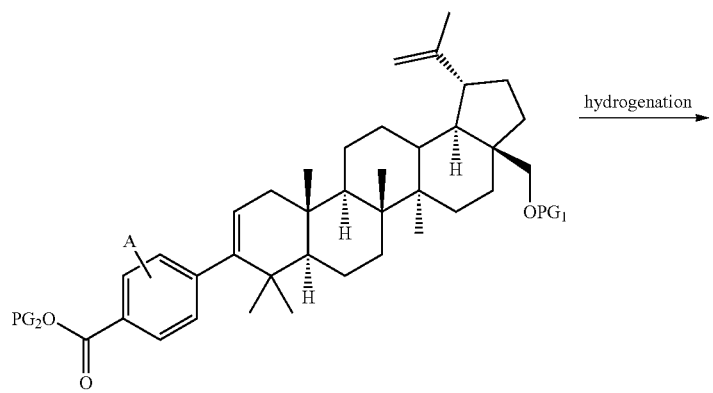

-continued
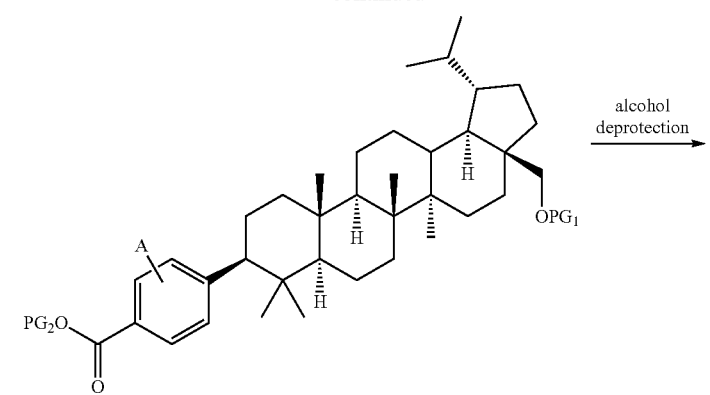
alcohol deprotection →
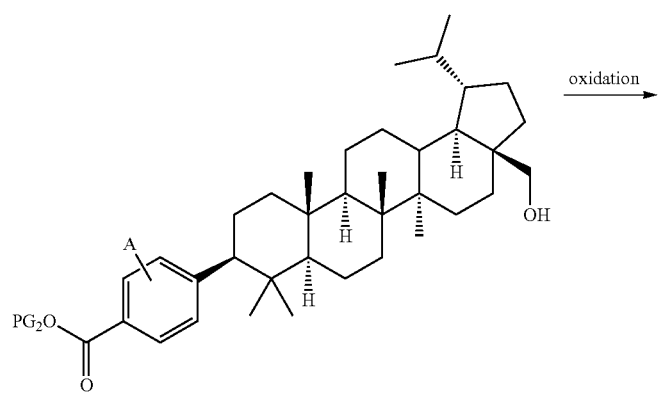
oxidation →
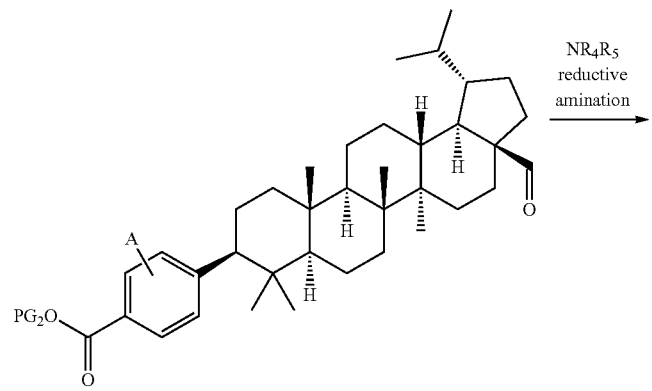
NR₄R₅ reductive amination →
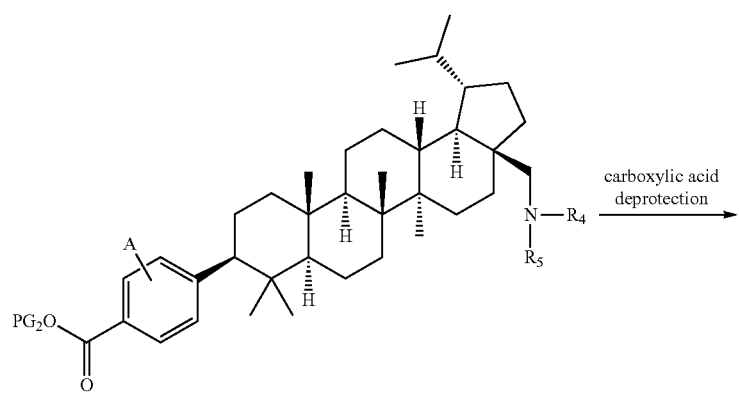
carboxylic acid deprotection →

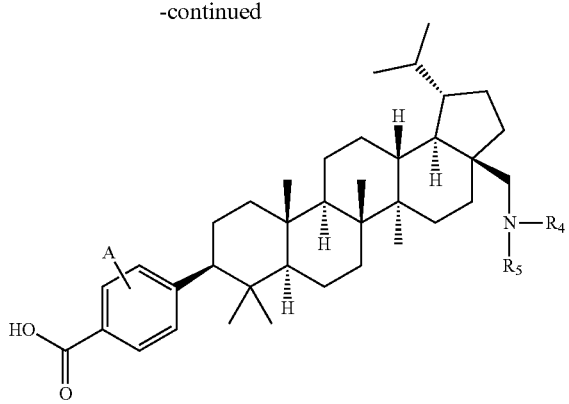

Compound of formula III can be prepared in the same manner described above for compounds of formula I and II using oleanoic or ursolic acid as starting materials instead of betulin.

EXAMPLES

The following examples illustrate typical syntheses of the compounds of Formulas I, II and III as described generally above. These examples are illustrative only and are not intended to limit the disclosure in any way. The reagents and starting materials are readily available to one of ordinary skill in the art.

Chemistry
Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δMS=0. The following internal references were used for the residual protons in the following solvents: CDCl$_3$ ($\delta_H$ 7.26), CD$_3$OD ($\delta_H$ 3.30), Acetic-d$_4$ (Acetic Acid d$_4$) ($\delta_H$ 11.6, 2.07), DMSO mix or DMSO-D6_CDCl$_3$ (($_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS methods
Method 1
Start % B=20, final % B=100 over 1 min gradient
Flow Rate=4 ml/min
Wavelength=254
Solvent A=10% MeOH–90% Water–0.1% TFA
Solvent B=90% MeOH–10% Water–0.1% TFA
Column 3=Xbridge Phenyl 4.6×50 mm S5
Method 2
Start % B=30, final % B=100 over 1 min gradient
Flow Rate=0.8 ml/min
Wavelength=220
Solvent A=10% Methanol/90% Water/0.1% TFA
Solvent B=90% Methanol/10% Water/0.1% TFA
Column 3=Xbridge Phenyl 2.1×50 mm 2.5 μm
Method 3
Start % B=20, final % B=100 over 2 min gradient
Flow Rate=0.8 ml/min
Wavelength=254
Solvent A=10% Methanol/90% Water/0.1% TFA
Solvent B=90% Methanol/10% Water/0.1% TFA
Column 3=Xbridge Phenyl 2.1×50 mm 2.5 μm
Method 4
Start % B=0, final % B=100 over 2 minute gradient
Flow Rate=4 ml/min
Wavelength=220
Solvent A=95% Water/5% Methanol/10 mM Ammonium Acetate
Solvent B=5% Water/95% Methanol/10 mM Ammonium Acetate
Column=PHENOMENEX–LUNA 3.0×50 mm
Method 5
Start % B=0, final % B=100 over 2 minute gradient
Flow Rate=4 ml/min
Wavelength=220
Solvent A=95% Water/5% methanol/10 mM Ammonium Acetate
Solvent B=5% Water/95% methanol/10 mM Ammonium Acetate
Column=Xbridge 4.6×50 mm 5μ C18
Method 6
Start % B=40, final % B=100 over 2 minute gradient
Flow Rate=1 ml/min
Wavelength=220
Solvent A=95% Water/5% methanol/10 mM Ammonium Acetate
Solvent B=5% Water/95% methanol/10 mM Ammonium Acetate
Column=PHENOMENEX–LUNA C18, 2.0×30, μm
Method 7
Start % B=0, final % B=100 over 2 minute gradient
Flow Rate=5 ml/min
Wavelength=220
Solvent A=95% Water/5% methanol/10 mM TFA
Solvent B=5% Water/95% methanol/10 mM TFA
Column=PHENOMENEX–LUNA 3.0×50 mm S10
Method 8
Start % B=0, Final % B=100 over 2 minute gradient, hold at 100% B
Flow Rate=1 mL/min
Wavelength=220 nm Solvent A=95% water, 5% methanol, 10 mM ammonium acetate
Solvent B=5% water, 95% methanol, 10 mM ammonium acetate
Column=Phenomenex LUNA C18, 2.0×30 mm, 3 μm
Method 9
Start % B=0%, Final % B=100 over 2 minute gradient, hold at 100% B
Flow Rate=1.0 mL/min
Wavelength=220 nm
Solvent A=90% water, 10% methanol, 0.1% TFA
Solvent B=10% water, 90% methanol, 0.1% TFA
Column=phenomenex–luna, 2.0×30 mm, 3.0 μm Preparation of Compounds Preparation of tert-butyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

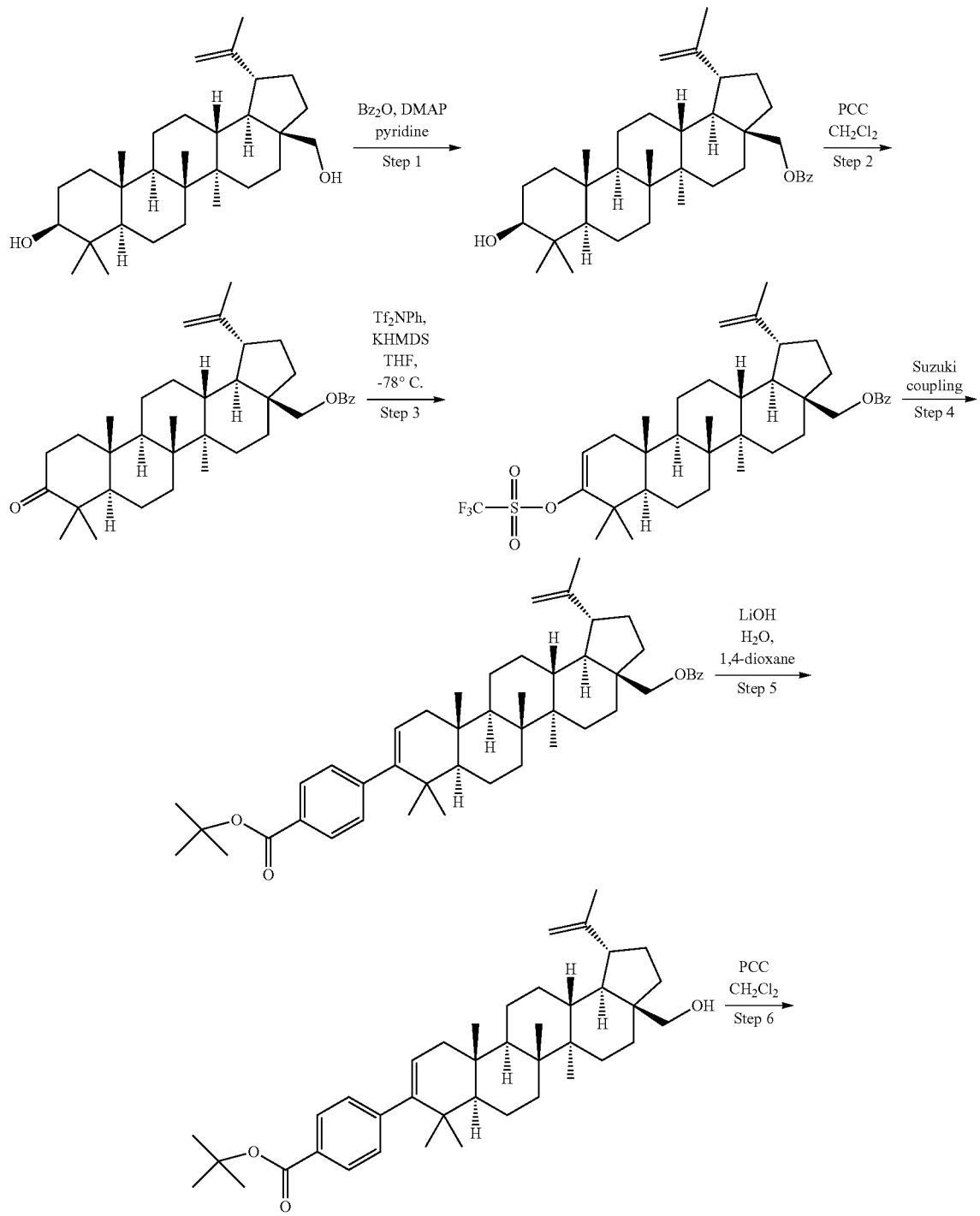

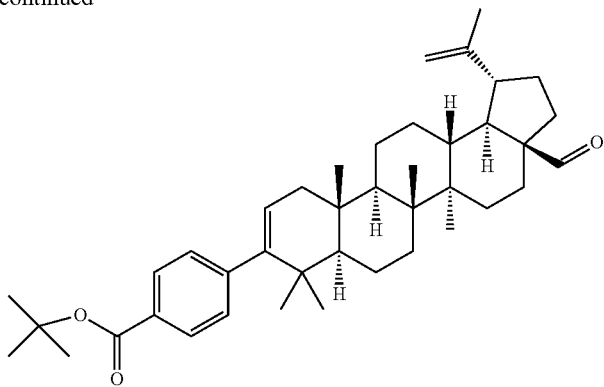

Step 1. Preparation of (((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)methyl benzoate

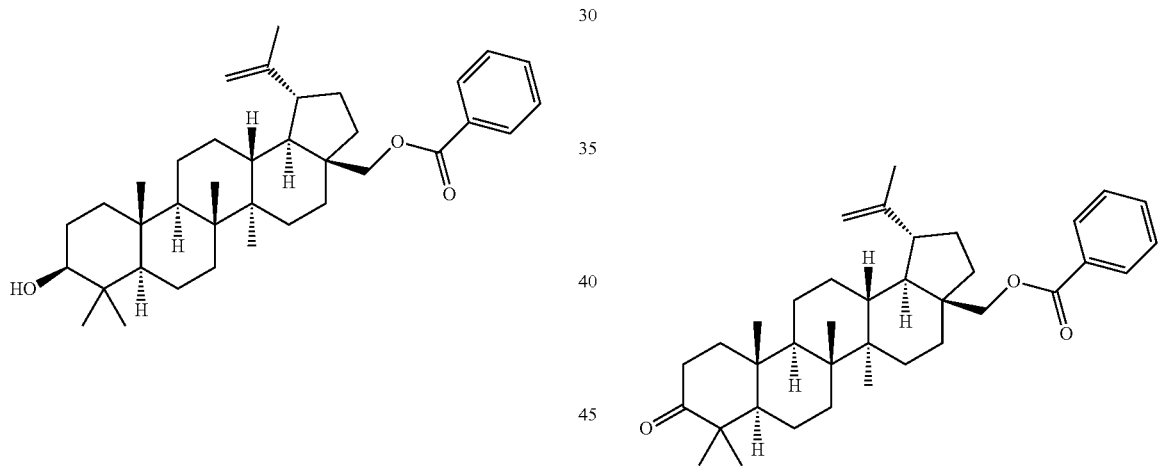

A suspension of (1R,3aS,5aR,5bR,7aR,9S,11aR,11bR,13aR,13bR)-3a-(hydroxymethyl)-5a,5b,8,8,11a-pentamethyl-1-(prop-1-en-2-yl)icosahydro-1H-cyclopenta[a]chrysen-9-ol (10 g, 22.59 mmol) and DMAP (0.552 g, 4.52 mmol) in pyridine (100 ml) was heated to 50° C. Upon heating all solids dissolved. To the solution was added benzoic anhydride (7.66 g, 33.9 mmol) portion wise (4 portions) over 1 h, each time rinsing the sides of the flask with 5 ml of pyridine. The clear, colorless solution was stirred at 50° C. for 4 h then was cooled to rt and concentrated under reduced pressure. The thick amber residue was diluted with sat. NaHCO$_3$ (200 ml) and was extracted with dichloromethane (3×150 ml). The combined organic layers were dried with Na$_2$SO$_4$, the drying agent was removed by filtration and the filtrate was concentrated under reduced pressure. The residue was purified by flash chromatography using a 0-25% EtOAc in hexanes gradient to afford the title compound as a white foam (8.6 g, 15.73 mmol, 69.6% yield). $^1$H NMR (500 MHz, CHLOROFORM-d) δ ppm 8.05 (d, J=7.02 Hz, 2H), 7.55 (t, J=7.32 Hz, 1H), 7.44 (t, J=7.63 Hz, 2H), 4.71 (s, 1H), 4.60 (s, 1H), 4.51 (d, J=10.99 Hz, 1H), 4.09 (d, J=10.99 Hz, 1H), 3.15-3.21 (m, 1H), 2.52 (td, J=10.99, 5.80 Hz, 1H), 1.89-2.08 (m, 3H), 1.70 (s, 3H), 1.06 (s, 3H), 1.00 (s, 3H), 0.96 (s, 3H), 0.83 (s, 3H), 0.75 (s, 3H), 0.63-1.81 (m, 21H).

Step 2. Preparation of (((1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)methyl benzoate To a solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)methyl benzoate (8.6 g, 15.73 mmol) in CH$_2$Cl$_2$ (100 ml) was added PCC (5.09 g, 23.59 mmol). After 7.25 h of stirring at rt, the mixture was filtered through a pad of celite and silica gel and was washed with dichloromethane then with 1:1 EtOAc:hexanes. The filtrate was concentrated under reduced pressure to give the title compound as a white foam (8.26 g, 15.16 mmol, 96% yield). $^1$H NMR (500 MHz, CHLOROFORM-d) δ ppm 8.05 (d, J=7.32 Hz, 2H), 7.56 (t, J=7.48 Hz, 1H), 7.44 (t, J=7.63 Hz, 2H), 4.72 (s, 1H), 4.61 (s, 1H), 4.52 (d, J=10.99 Hz, 1H), 4.09 (d, J=11.29 Hz, 1H), 2.45-2.58 (m, 2H), 2.34-2.43 (m, 1H), 1.86-2.10 (m, 4H), 1.70 (s, 3H), 1.10 (s, 3H), 1.06 (s, 3H), 1.04-1.82 (m, 18H), 1.02 (s, 3H), 1.01 (s, 3H), 0.94 (s, 3H).

Step 3. Preparation of (((1R,3aS,5aR,5bR,7aR,11aR, 11bR,13aR,13bR)-5a,5b,8,8,11a-pentamethyl-1-(prop-1-en-2-yl)-9-(trifluoromethylsulfonyloxy)-2,3, 3a,4,5,5a,5b,6,7,7a,8,11,11a,11b,12,13,13a,13b-octadecahydro-1H-cyclopenta[a]chrysen-3a-yl) methyl benzoate A solution of ((1R,3aS,5aR,5bR,7aR,11aR,11bR,13aR, 13bR)-5a,5b,8,8,11a-pentamethyl-9-oxo-1-(prop-1-en-2-yl) icosahydro-1H-cyclopenta[a]chrysen-3a-yl)methyl benzoate (10.1 g, 18.54 mmol) in THF (100 ml) was cooled to −78° C. To the solution was added KHMDS (0.5M in toluene) (74.2 ml, 37.1 mmol). The mixture was stirred for 15 minutes at −78° C. and a solution of N-Phenyl-bis(trifluoromethanesulfonimide) (7.29 g, 20.4 mmol) in THF (20 ml) and toluene (20 ml) was added via cannula. The mixture was stirred for 3.5 h at −78° C. TLC indicated a trace of starting material was still present so an additional 0.7 g of N-phenyl-bis(trifluoromethanesulfonimide) was added to the mixture and stirring continued at −78° C. for 1 h. TLC indicated the reaction was complete. The mixture was diluted with water (75 ml) and extracted with ethyl acetate (3×75 ml). The combined organic layers were dried with MgSO$_4$. The drying agent was removed by filtration and the filtrate was concentrated under reduced pressure. The residue was purified flash chromatography using 0-20% toluene in hexanes gradient, then 20% toluene in hexanes, followed by a 10-15% EtOAc in hexanes to afford the title compound as a white foam (9.85 g, 14.55 mmol, 78% yield). $^1$H NMR (400 MHz, CHLOROFORM-d) δ ppm 0.94 (s, 3H), 1.03 (s, 3H), 1.04 (s, 3H), 1.10-1.86 (m, 18H), 1.12 (s, 3H), 1.14 (s, 3H), 1.73 (s, 3H), 1.92-2.13 (m, 3H), 2.18 (dd, J=17.07, 6.78 Hz, 1H), 2.55 (td, J=11.11, 5.90 Hz, 1H), 4.12 (d, J=11.04 Hz, 1H), 4.55 (dd, J=11.04, 1.25 Hz, 1H), 4.64 (s, 1H), 4.75 (d, J=2.01 Hz, 1H), 5.58 (dd, J=6.65, 1.88 Hz, 1H), 7.43-7.49 (m, 2H), 7.55-7.60 (m, 1H), 8.05-8.09 (m, 2H).

Step 4. Preparation of tert-butyl 4-((1R,3aS,5aR, 5bR,7aR,11aS,11bR,13aR,13bR)-3a-(benzoyloxymethyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate

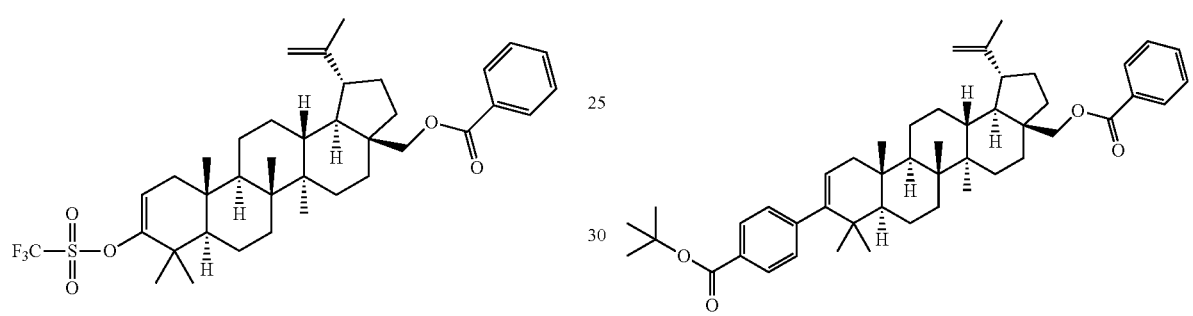

The title compound was prepared via Suzuki coupling as follows:

To a solution of ((1R,3aS,5aR,5bR,7aR,11aR,11bR,13aR, 13bR)-5a,5b,8,8,11a-pentamethyl-1-(prop-1-en-2-yl)-9-(trifluoromethylsulfonyloxy)-2,3,3a,4,5,5a,5b,6,7,7a,8,11,11a, 11b,12,13,13a,13b-octadecahydro-1H-cyclopenta[a] chrysen-3a-yl)methyl benzoate (9.85 g, 14.55 mmol) in 1,4-dioxane (50 ml) was added 2-propanol (50.0 ml), water (20 ml), sodium carbonate monohydrate (5.41 g, 43.7 mmol), 4-tert-butoxycarbonylphenylboronic acid (4.85 g, 21.83 mmol), and tetrakis(triphenylphosphine)palladium(0) (0.504 g, 0.437 mmol). Potassium carbonate and potassium phosphate can also be used instead of sodium carbonate monohydrate. The sides of the flask were rinsed with an additional 20 ml of dioxane and the mixture was attached to a reflux condenser, was flushed with N$_2$ and was heated to reflux. Upon heating, the solids in the mixture dissolved completely. The solution was heated at reflux for 3.5 h, was cooled to rt and was diluted with 200 ml of water. The mixture was extracted with ethyl acetate (3×150 ml) and the combined organic layers were dried with Na$_2$SO$_4$. The drying agent was removed by filtration and the filtrate was concentrated under reduced pressure. The residue purified by flash chromatography using a 0-15% EtOAc in hexanes gradient to afford the title com- Step 5. Preparation of tert-butyl 4-((1R,3aS,5aR, 5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate Step 6. Preparation of tert-butyl 4-((1R,3aS,5aR, 5bR,7aR,11aS,11bR,13aR,13bR)-3a-formyl-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate

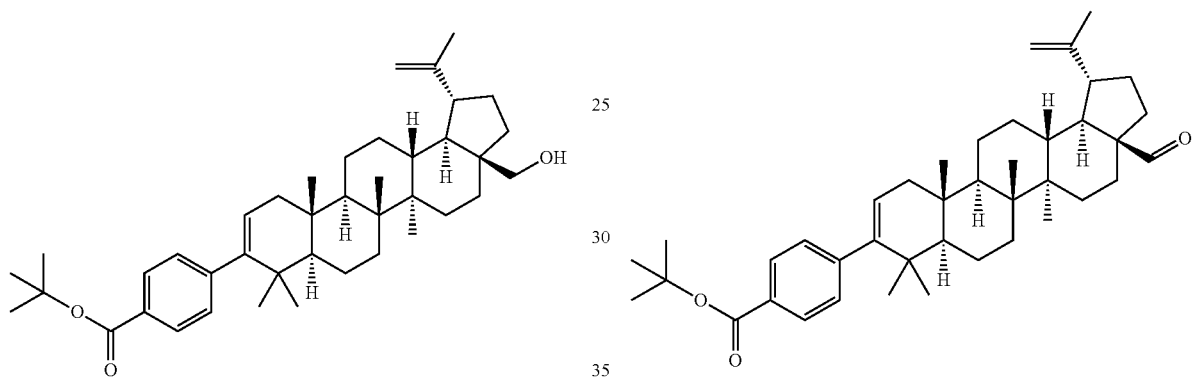

To a solution of tert-butyl 4-((1R,3aS,5aR,5bR,7aR,11aS, 11bR,13aR,13bR)-3a-(benzoyloxymethyl)-5a,5b,8,8,11apentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (9.5 g, 13.47 mmol) in dioxane (200 ml) was added water (25 ml) and lithium hydroxide monohydrate (1.696 g, 40.4 mmol). The mixture was heated to 75° C. Initially solids were apparent in the mixture, but after 2 h of heating, all solids had dissolved. After 23.5 h of heating, solids were again apparent in the mixture. The mixture was cooled to rt and 250 ml of water were added. The solids that had formed were collected by filtration and were washed with water. The solids were dissolved in ether and dichloromethane and were dried with MgSO$_4$. The drying agent was removed by filtration and the filtrate was concentrated under reduced pressure to afford the title compound as a white foam (5.6 g, 9.32 mmol, 64% yield for two steps. $^1$H NMR (500 MHz, CHLOROFORM-d) δ ppm 7.87 (2H, d, J=8.2 Hz), 7.16 (2H, d, J=7.9 Hz), 5.26 (1H, dd, J=6.3, 1.7 Hz), 4.69 (1H, d, J=2.1 Hz), 4.58 (1H, s), 3.82 (1H, d, J=9.8 Hz), 3.35 (1H, d, J=10.7 Hz), 2.40 (1H, td, J=11.0, 5.8 Hz), 2.09 (1H, dd, J=17.1, 6.1 Hz), 1.69 (3H, s), 1.58 (9H, s), 1.08 (3H, s), 1.01 (3H, s), 0.97 (3H, s), 0.91 (6H, s), 0.83-2.03 (21H, m).

To a solution of tert-butyl 4-((1R,3aS,5aR,5bR,7aR,11aS, 11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (5.6 g, 9.32 mmol) in dichloromethane (100 ml) was added PCC (3.01 g, 13.98 mmol). The mixture was stirred at rt for 6.5 h then was filtered through a pad of celite and silica gel which was washed with dichloromethane then 1:1 ethyl acetate:hexanes. The filtrate was concentrated under reduced pressure and the residue was purified by flash chromatography using a 0-10% EtOAc in hexanes gradient to afford the title compound as a white solid (4.49 g, 7.50 mmol, 80% yield). $^1$H NMR (500 MHz, CHLOROFORM-d) δ ppm 9.68 (1H, d, J=1.5 Hz), 7.87 (2H, d, J=8.2 Hz), 7.16 (2H, d, J=8.2 Hz), 5.26 (1H, dd, J=6.4, 1.8 Hz), 4.76 (1H, d, J=1.8 Hz), 4.63 (1H, s), 2.88 (1H, td, J=11.1, 5.8 Hz), 2.02-2.15 (3H, m), 1.70 (3H, s), 1.58 (9H, s), 1.00 (3H, s), 0.97 (3H, s), 0.97 (3H, s), 0.91 (6H, s), 0.83-1.94 (19H, m).

Preparation of tert-butyl 4-((1R,3aS,5aR,5bR,7aR, 11aS,11bR,13aR,13bR)-3a-((2-(dimethylamino) ethylamino)methyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate 1H), 2.48-2.41 (m, 1H), 2.40 (s, 6H), 2.21-1.10 (m, 22H), 1.72 (s, 3H), 1.61 (s, 9H), 1.12 (s, 3H), 1.03 (s, 3H), 1.00 (s, 3H), 0.95 (s, 6H).

Example 1

Preparation of 4-((1R,3aS,5aR,5bR,7aR,11aS,11bR, 13aR,13bR)-3a-((2-(dimethylamino)ethylamino) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

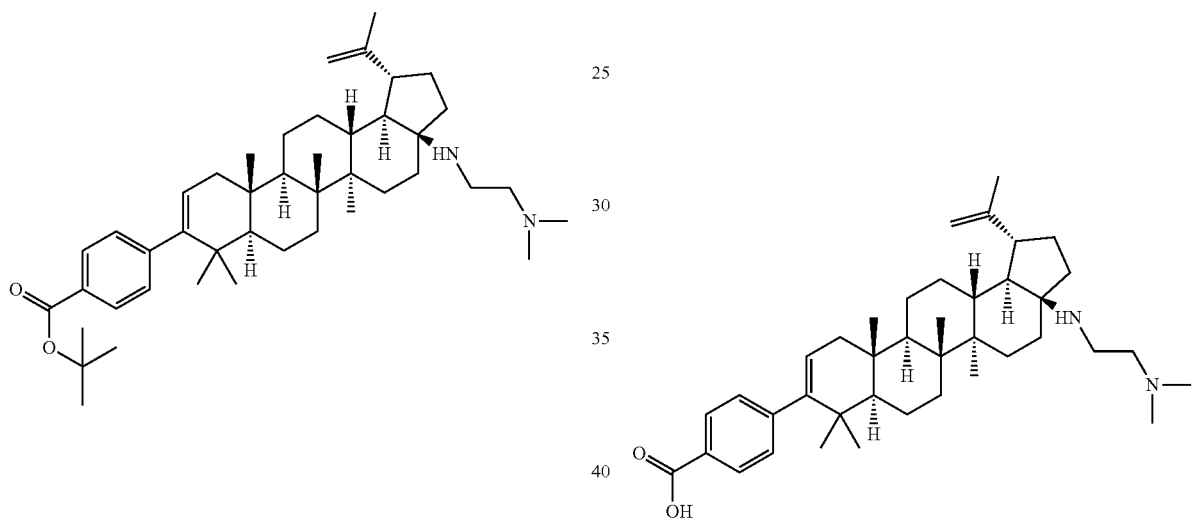

A mixture of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (59 mg, 0.099 mmol), N1,N1-dimethylethane-1,2-diamine (0.13 ml, 1.2 mmol), sodium triacetoxyborohydride (104 mg, 0.493 mmol) and AcOH (0.023 ml, 0.394 mmol) in DCE (3 ml) was stirred at rt for 12 h. The solvent was removed in vacuo. LCMS showed desired product and some imine not reduced yet. The residue was redissolved in DCE (3 ml) and treated again with sodium triacetoxyborohydride (104 mg, 0.493 mmol) and AcOH (0.023 ml, 0.394 mmol) at rt for 48 h. Solvent removed in vacuo and the residue redissolved in methylene chloride and purified by silica gel column (0-10% MeOH/CH$_2$Cl$_2$) to afford the title compound as a white solid (65 mg, 98% yield). $^1$H NMR (400 MHz, CHLOROFORM-d) δ ppm 7.90 (d, J=8.3 Hz, 2H), 7.19 (d, J=8.5 Hz, 2H), 5.30 (dd, J=6.1, 1.6 Hz, 1H), 4.72 (d, J=1.5 Hz, 1H), 4.63 (s, 1H), 3.17-2.95 (m, 3H), 2.72 (t, J=5.9 Hz, 2H), 2.54 (d, J=12.3 Hz, A solution of tert-butyl 4-((1R,3aS,5aR,5bR,7aR,11aS, 11bR,13aR,13bR)-3a-((2-(dimethylamino)ethylamino)methyl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)benzoate (59 mg, 0.088 mmol) in DCM (2 ml) was treated with TFA (0.6 ml, 7.6 mmol) and the mixture was stirred at rt for 12 h. The solvent was removed in vacuo to provide the title compound as a white solid (40 mg, 0.065 mmol, 74.0% yield). LCMS: m/e 615.7 (M+H)$^+$, 2.00 min (method 7). $^1$H NMR (400 MHz, MeOD) δ ppm 7.94 (d, J=8.3 Hz, 2H), 7.24 (d, J=8.0 Hz, 2H), 5.33 (d, J=4.8 Hz, 1H), 4.78 (s, 1H), 4.67 (s, 1H), 3.73-3.42 (m, 4H), 3.33 (m, 1H), 2.99-2.94 (m, 1H), 2.93 (s, 6H), 2.53

(td, J=10.6, 5.6 Hz, 1H), 2.99-1.29 (m, 2H), 1.98-1.22 (m, 20H), 1.76 (s, 3H), 1.20 (s, 3H), 1.10 (s, 3H), 1.06 (s, 3H), 0.99 (s, 3H), 0.98 (s, 3H).

Preparation of tert-butyl 4-((1R,3aS,5aR,5bR,7aR, 11aS,11bR,13aR,13bR)-5a,5b,8,8,11a-pentamethyl-3a-((3-morpholinopropylamino)methyl)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoate

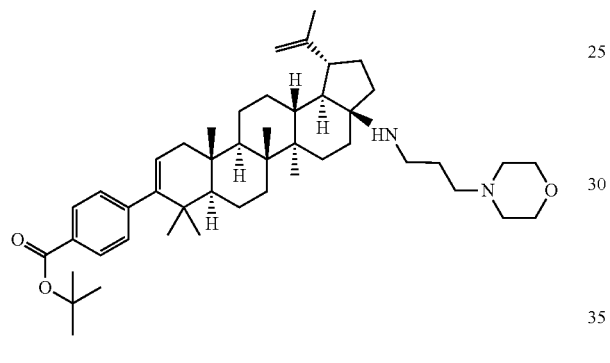

To a solution of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (0.1 g, 0.167 mmol) in DCE (2 ml) was added acetic acid (1M in DCM) (0.167 ml, 0.167 mmol) and N-(3-Aminopropyl)morpholine (0.029 ml, 0.200 mmol). The mixture was stirred for 15 minutes at rt and sodium triacetoxyborohydride (0.071 g, 0.334 mmol) was added. The mixture was stirred at rt for 1.5 h and an additional 0.1 g of sodium triacetoxyborohydride was added. The mixture was stirred overnight at rt then was quenched with 7 ml of sat. NaHCO$_3$. The mixture was extracted with dichloromethane (3×7 ml) and the combined organic layers were dried with Na$_2$SO$_4$. The drying agent was removed by filtration and the filtrate was concentrated under reduced pressure. The mixture was purified by flash chromatography using a 0-10% MeOH in dichloromethane gradient. The fractions containing the expected product were combined and concentrated under reduced pressure to give the title compound as a white foam (69 mg, 0.095 mmol, 56.8% yield). LCMS: m/e 727.5 (M+H)$^+$, 2.81 min (method 6).

Example 2

Preparation of 4-((1R,3aS,5aR,5bR,7aR,11aS,11bR, 13aR,13bR)-5a,5b,8,8,11a-pentamethyl-3a-((3-morpholinopropylamino)methyl)-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid

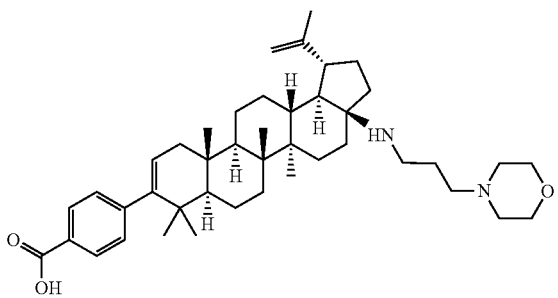

To a solution of tert-butyl 4-((1R,3aS,5aR,5bR,7aR,11aS, 11bR,13aR,13bR)-5a,5b,8,8,11a-pentamethyl-3a-((3-morpholinopropylamino)methyl)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate (69 mg, 0.095 mmol) in DCM (1 ml) was added TFA (0.4 ml, 5.19 mmol). The mixture was stirred at rt for 3 h then was concentrated under reduced pressure. The residue was purified by prep. HPLC. The fractions containing the expected product were combined and concentrated under reduced pressure to afford the title compound (36 mg, 0.054 mmol, 56.5% yield) as a white foam. LCMS: m/e 671.5 (M+H)$^+$, 2.17 min (method 6). $^1$H NMR (400 MHz, CHLOROFORM-d) δ ppm 7.94 (d, J=8.03 Hz, 2H),7.15 (d, J=8.03 Hz, 2H), 5.29 (d, J=4.52 Hz, 1H), 4.71 (br. s., 1H), 4.62 (br. s., 1H), 3.73 (br. s., 4H), 3.09-3.26 (m, 3H), 2.65 (d, J=12.30 Hz, 1H), 2.56 (br. s., 6H), 2.42 (br. s., 1H), 1.69 (s, 3H), 1.07 (s, 3H), 1.05-2.14 (m, 24H), 1.00 (s, 3H), 0.97 (s, 3H), 0.93 (br. s., 3H), 0.93 (br. s., 3H).

Preparation of tert-butyl 4-((1R,3aS,5aR,5bR,7aR, 11aS,11bR,13aR,13bR)-3a-(((1-ethylpyrrolidin-2-yl) methylamino)methyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate

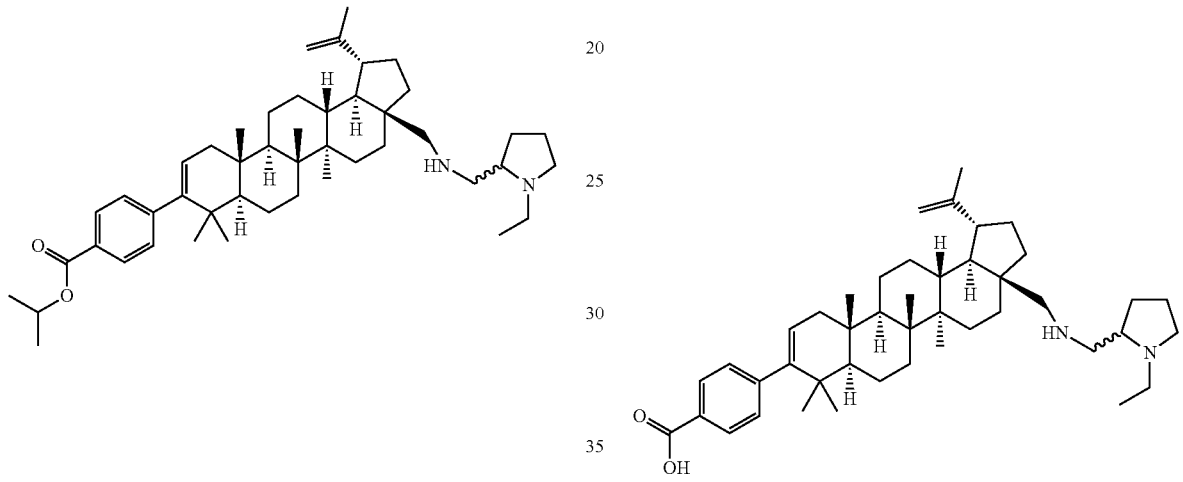

To a solution of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (0.1 g, 0.167 mmol) in DCE (2 ml) was added acetic acid (1M in DCM) (0.167 ml, 0.167 mmol) and 2-(aminomethyl)-1-ethylpyrrolidine (0.029 ml, 0.200 mmol). The mixture was stirred for 15 minutes at rt and sodium triacetoxyborohydride (0.071 g, 0.334 mmol) was added. The mixture was stirred at rt for 1.5 h then an additional 0.1 g of sodium triacetoxyborohydride was added and the mixture was stirred at rt overnight. After 24 h of stirring, some starting material still remained by TLC. To the mixture was added acetic acid (1M in DCM) (0.167 ml, 0.167 mmol), 2-(aminomethyl)-1-ethylpyrrolidine (0.029 ml, 0.200 mmol), and sodium triacetoxyborohydride (0.071 g, 0.334 mmol). The mixture was stirred at rt for an additional 19 h then was diluted with 7 ml of sat. NaHCO₃. The mixture was extracted with dichloromethane (3×7 ml) and the combined organic layers were dried with Na₂SO₄. The drying agent was removed by filtration and the filtrate was concentrated under reduced pressure. The mixture was purified by flash chromatography using a 0-10% MeOH in dichloromethane gradient. Two products were isolated as white foams. LC/MS indicated the same mass for both, with different retention times. ¹H NMR confirmed that two diastereomers were isolated. 44 mg of diastereomer 1 (less polar spot by TLC) was isolated while 55 mg of diastereomer 2 (more polar spot) was isolated. Diastereomer 1: LCMS: m/e 711.4 (M+H)⁺, 3.34 min (method 6). Diastereomer 2: LCMS: m/e 711.6 (M+H)⁺, 3.27 min (method 6).

Example 3 (Diastereomer 1) and Example 4 (Diastereomer 2)

Preparation of 4-((1R,3aS,5aR,5bR,7aR,11aS,11bR, 13aR,13bR)-3a-(((1-ethylpyrrolidin-2-yl)methylamino)methyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid Diasteromer 1   Diasteromer 2
Example 3       Example 4

Two reactions were set up in separate vessels: To a solution of each the diastereomers isolated above (0.044 g of isomer 1 (less polar spot)), (0.044 g of isomer 2 (more polar spot)) in DCM (1 ml) was added TFA (0.4 ml, 5.19 mmol). The mixtures were stirred at rt for 3 h then were concentrated under reduced pressure. The residues were purified by prep. HPLC. The fractions containing the expected products were concentrated under reduced pressure to give diastereomer 1 (31 mg, 0.047 mmol) and diastereomer 2 (37 mg, 0.056 mmol) as off-white foams. Diastereomer 1: LCMS: m/e 653.5 (M−H)⁻, 2.29 min (method 6). ¹H NMR (400 MHz, CHLOROFORM-d) δ ppm 7.96 (d, J=8.03 Hz, 2H), 7.11-7.16 (m, 2H), 5.31 (d, J=6.27 Hz, 1H), 4.71 (br. s., 1H), 4.60 (s, 1H), 3.80-3.90 (m, 1H), 2.32-3.45 (m, 9H), 1.70 (s, 3H), 1.17 (d, J=13.30 Hz, 3H), 1.01 (br. s., 6H), 0.99-2.19 (m, 29H), 0.97 (s, 3H), 0.90 (d, J=5.27 Hz, 3H). Diastereomer 2: LCMS: m/e 653.5 (M−H)⁻, 2.30 min (method 6). ¹H NMR (400 MHz, CHLOROFORM-d) δ ppm 7.96 (d, J=8.03 Hz, 2H). 7.09-7.18 (m, 2H), 5.31 (d, J=6.02 Hz, 1H), 4.71 (br. s., 1H), 4.60 (br. s., 1H), 3.77-3.92 (m, 1H), 2.31-3.44 (m, 9H), 1.70 (s, 3H), 1.17 (d, J=12.05 Hz, 3H), 1.01 (s, 6H), 0.99-2.20 (m, 29H), 0.97 (s, 3H), 0.90 (d, J=5.02 Hz, 3H).

Preparation of 4-((1R,3aS,5aR,5bR,7aR,11aS,11bR, 13aR,13bR)-5a,5b,8,8,11a-pentamethyl-1-(prop-1-en-2-yl)-3a-((2-(pyridin-2-yl)ethylamino)methyl)-2, 3,3a,4,5,5a,5b,6,7,7a,8,11,11a,11b,12,13,13a,13b-octadecahydro-1H-cyclopenta[a]chrysen-9-yl) benzoic acid concentrated under reduced pressure to afford the title compound. LCMS: m/e 705.4 (M+H)$^+$, 2.90 min (method 6).

Example 5

Preparation of 4-((1R,3aS,5aR,5bR,7aR,11aS,11bR, 13aR,13bR)-5a,5b,8,8,11a-pentamethyl-1-(prop-1-en-2-yl)-3a-((2-(pyridin-2-yl)ethylamino)methyl)-2, 3,3a,4,5,5a,5b,6,7,7a,8,11,11a,11b,12,13,13a,13b-octadecahydro-1H-cyclopenta[a]chrysen-9-yl) benzoic acid

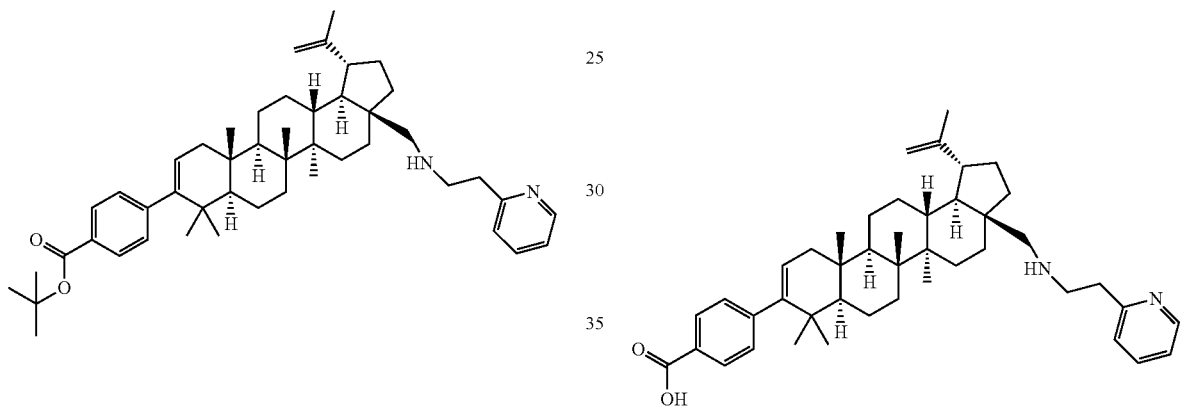

To a solution of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (0.1 g, 0.167 mmol) in DCE (2 ml) was added acetic acid (1M in DCM) (0.167 ml, 0.167 mmol) and 2-(2-pyridyl) ethylamine (0.024 ml, 0.200 mmol). The mixture was stirred for 15 minutes at rt and sodium triacetoxyborohydride (0.071 g, 0.334 mmol) was added. The mixture was stirred at rt for 1.5 h then an additional 0.1 g of sodium triacetoxyborohydride was added to the mixture and it was stirred for 23 h. To the mixture was added additional acetic acid (1M in DCM) (0.167 ml, 0.167 mmol), 2-(2-pyridyl)ethylamine (0.024 ml, 0.200 mmol), and sodium triacetoxyborohydride (0.071 g, 0.334 mmol). The mixture was stirred at rt for an additional 19 h, was diluted with 7 ml of sat. NaHCO$_3$ and was extracted with dichloromethane (3×7 ml). The combined organic layers were dried with Na$_2$SO$_4$, the drying agent was removed by filtration and the filtrate was concentrated under reduced pressure. The mixture was purified by flash chromatography using a 0-10% MeOH in dichloromethane gradient. The fractions containing the expected product were combined and To a solution of tert-butyl 4-((1R,3aS,5aR,5bR,7aR,11aS, 11bR,13aR,13bR)-5a,5b,8,8,11a-pentamethyl-1-(prop-1-en-2-yl)-3a-((2-(pyridin-2-yl)ethylamino)methyl)-2,3,3a,4, 5,5a,5b,6,7,7a,8,11,11a,11b,12,13,13a,13b-octadecahydro-1H-cyclopenta[a]chrysen-9-yl)benzoate (0.119 g, 0.127 mmol) in DCM (1 ml) was added TFA (0.4 ml, 5.19 mmol). The mixture was stirred at rt for 3.5 h and the mixture was concentrated under reduced pressure. The residue was purified by prep. HPLC. The fractions containing the expected product were combined and concentrated under reduced pressure to give the title compound as a light-yellow foam (61 mg, 0.094 mmol, 74.3% yield). LCMS: m/e 647.4 (M−H)$^-$, 2.20 min (method 6). $^1$H NMR (400 MHz, CHLOROFORM-d) δ ppm 8.42-8.48 (m, 1H), 7.95 (d, J=8.28 Hz, 2H), 7.65 (td, J=7.65, 1.76 Hz, 1H), 7.17-7.24 (m, 2H), 7.14 (d, J=8.03 Hz, 2H), 5.29 (d, J=4.52 Hz, 1H), 4.71 (br. s., 1H), 4.61 (br. s., 1H), 3.45-3.59 (m, 2H), 3.18-3.32 (m, 3H), 2.74 (d, J=12.30

Hz, 1H), 2.45 (br. s., 1H), 1.70 (s, 3H), 1.05 (s, 3H), 1.01 (s, 3H), 0.98-2.13 (m, 24H), 0.96 (s, 3H), 0.94 (br. s., 3H), 0.92 (br. s., 3H).

Preparation of tert-butyl 4-((1R,3aS,5aR,5bR,7aR, 11aS,11bR,13aR,13bR)-3a-((2-hydroxyethylamino) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate The crude product was used in the next step with no additional purification. LCMS: m/e 685.6 (M–H)⁻, 2.92 min (method 6).

Example 6

Preparation of 4-((1R,3aS,5aR,5bR,7aR,11aS,11bR, 13aR,13bR)-3a-((3-(dimethylamino)propylamino) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

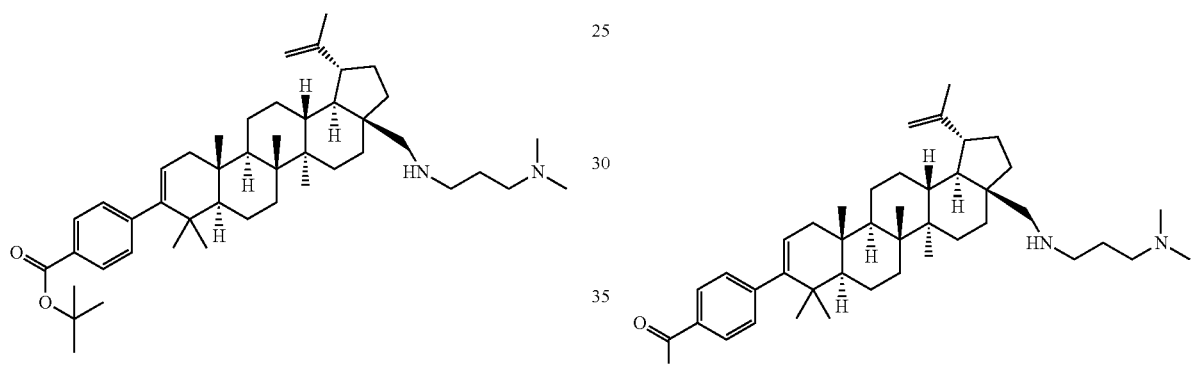

To a solution of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (0.1 g, 0.167 mmol) in DCE (2 ml) was added acetic acid (0.019 ml, 0.334 mmol) and 3-(dimethylamino)propylamine (0.084 ml, 0.668 mmol). To the mixture was added sodium triacetoxyborohydride (0.177 g, 0.835 mmol) and it was stirred at rt for 72 h. After 72 h of stirring, the reaction was diluted with 7 ml of sat. NaHCO₃ was extracted with dichloromethane (3×7 ml) and the combined organic layers were dried with Na₂SO₄. The drying agent was removed by filtration and the filtrate was concentrated under reduced pressure to give the expected product, tert-butyl 4-((1R,3aS,5aR,5bR, 7aR,11aS,11bR,13aR,13bR)-3a-((3-(dimethylamino)propylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate.

To a solution of tert-butyl 4-((1R,3aS,5aR,5bR,7aR,11aS, 11bR,13aR,13bR)-3a-((3-(dimethylamino)propylamino) methyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoate (114 mg, 0.167 mmol) in DCM (1 ml) was added TFA (0.4 ml, 5.19 mmol). The mixture was stirred at rt for 5 h and was concentrated under reduced pressure. The residue was purified by prep HPLC. The fractions containing the expected product were combined and concentrated under reduced pressure to afford the title compound as a white solid (77 mg, 0.122 mmol, 73.3% yield). LCMS: m/e 629.6 (M–H)⁻, 2.22 min (method 6). ¹H NMR (500 MHz, Acetic acid) δ ppm 8.03 (d, J=8.24 Hz, 2H) 7.30 (d, J=8.24 Hz, 2H), 5.37 (d, J=4.58 Hz, 1H), 4.79 (s, 1H), 4.68 (s, 1H), 3.32-3.44 (m, 3H), 3.25-3.32 (m, 2H), 2.96 (d, J=13.12 Hz, 1H), 2.89-2.94 (m, 6H), 2.49-2.58 (m, 1H), 2.30-2.38 (m, J=8.09, 7.86, 7.74, 7.74 Hz, 2H), 1.75 (s, 3H), 1.19 (s, 3H), 1.13-2.23 (m, 22H), 1.09 (s, 3H), 1.08 (s, 3H), 1.02 (s, 3H), 1.00 (s, 3H).

Preparation of tert-butyl 4-((1R,3aS,5aR,5bR,7aR, 11aS,11bR,13aR,13bR)-3a-((2-acetamidoethylamino)methyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoate To a solution of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoate (0.1 g, 0.167 mmol) in DCE (2 ml) was added acetic acid (0.019 ml, 0.334 mmol) and N-acetylethylenediamine (0.048 ml, 0.501 mmol). The mixture was stirred for 2 h at rt then to the mixture was added sodium triacetoxyborohydride (0.177 g, 0.835 mmol). The mixture was stirred at rt for 3 days then was diluted with 7 ml of sat. NaHCO₃ and was extracted with dichloromethane (3×7 ml). The combined organic layers were dried with Na₂SO₄, the drying agent was removed by filtration, and the filtrate was concentrated under reduced pressure. The crude material was used in the next step with no additional purification. LCMS: m/e 685.4 (M+H)⁺, 3.86 min (method 6).

Example 7

Preparation of 4-((1R,3aS,5aR,5bR,7aR,11aS,11bR, 13aR,13bR)-3a-((2-acetamidoethylamino)methyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoic acid

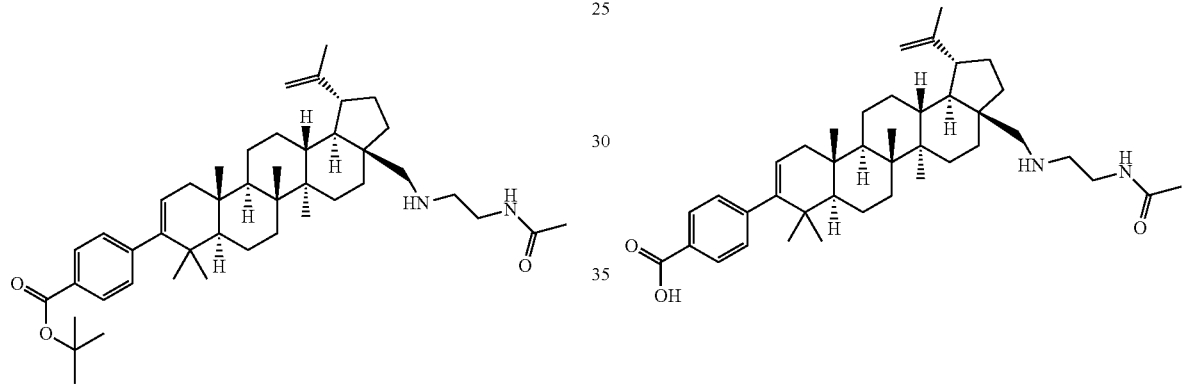

To a solution of tert-butyl 4-((1R,3aS,5aR,5bR,7aR,11aS, 11bR,13aR,13bR)-3a-((2-acetamidoethylamino)methyl)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoate (114 mg, 0.167 mmol) in DCM (1 ml) was added TFA (0.4 ml, 5.19 mmol). The mixture was stirred at rt for 3.5 h then was concentrated under reduced pressure. The residue was dissolved in dioxane and MeOH and was purified by pre. HPLC. The fractions containing the expected product were combined and concentrated under reduced pressure to afford the title compound as an off-white solid (40.7 mg, 0.065 mmol, 38.8% yield). LCMS: m/e 629.5 (M+H)⁺, 2.17 min (method 6). ¹H NMR (500 MHz, Acetic) δ ppm 8.03 (d, J=8.24 Hz, 2H),7.30 (d, J=8.24 Hz, 2H), 5.37 (d, J=4.58 Hz, 1H), 4.79 (s, 1H), 4.68 (s, 1H), 3.61-3.70 (m, 2H), 3.40-3.53 (m, 2H), 3.37 (d, J=13.12 Hz, 1H), 2.98 (d, J=12.82 Hz, 1H), 2.49-2.57 (m, 1H), 2.09 (s, 3H), 1.75 (s, 3H), 1.19 (s, 3H), 1.14-2.24 (m, 22H), 1.10 (s, 3H), 1.07 (s, 3H), 1.02 (s, 3H), 1.00 (s, 3H).

Preparation of tert-butyl 4-(2-(((1R,3aS,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)ethyl)piperazine-1-carboxylate

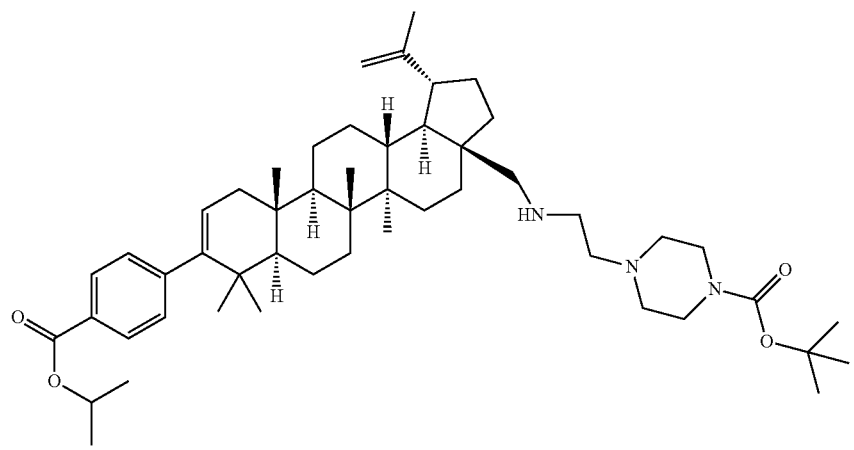

To a solution of tert-butyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.1 g, 0.167 mmol) in DCE (2 ml) was added acetic acid (0.019 ml, 0.334 mmol) and 4-N-(2-Aminoethyl)-1-N-Boc-piperazine (0.077 g, 0.334 mmol). The mixture was stirred at rt for 2 h then to the mixture was added sodium triacetoxyborohydride (0.177 g, 0.835 mmol). The mixture was stirred for 3 days at rt then was diluted with 7 ml of sat. NaHCO$_3$ and was extracted with dichloromethane (3×7 ml). The combined organic layers were dried with Na$_2$SO$_4$. The drying agent was removed by filtration and the filtrate was concentrated under reduced pressure. The crude product was used in the next step without further purification. LCMS: m/e 812.3 (M+H)$^+$, 3.30 min (method 6).

Example 8

Preparation of 4-((1R,3aS,5aR,5bR,7aR,11aS,11bR, 13aR,13bR)-5a,5b,8,8,11a-pentamethyl-3a-((2-(piperazin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

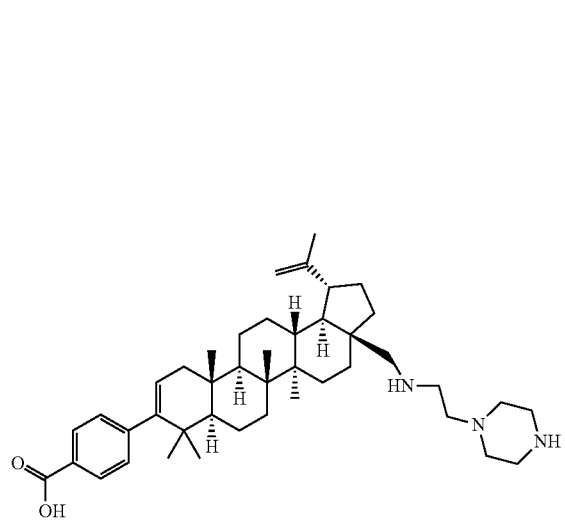

To a solution of tert-butyl 4-(2-(((1R,3aS,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)ethyl)piperazine-1-carboxylate (136 mg, 0.167 mmol) in DCM (1 ml) was added TFA (0.4 ml, 5.19 mmol). The mixture was stirred at rt for 5 h then was concentrated under reduced pressure. The residue was dissolved in dioxane and MeOH and was purified by prep. HPLC. The fractions containing the expected product were combined and concentrated under reduced pressure. HPLC showed some impurities were still present, so the reaction was repurified by prep. HPLC. The fractions were concentrated under reduced pressure to give the title compound as a white solid (18 mg, 0.027 mmol, 16.43% yield). LCMS: m/e 656.6 (M+H)$^+$, 2.24 min (method 6). $^1$H NMR (500 MHz, Acetic) δ ppm 8.03 (d, J=8.24 Hz, 2H), 7.30 (d, J=8.24 Hz, 2H), 5.37 (d, J=4.58 Hz, 1H), 4.79 (s, 1H), 4.68 (s, 1H), 3.50-3.67 (m, 6H), 3.40 (d, J=12.82 Hz, 1H), 3.22-3.29 (m, 6H), 2.99 (d, J=13.12 Hz, 1H), 2.49-2.58 (m, 1H), 1.76 (s, 3H), 1.19 (s, 3H), 1.16-2.23 (m, 22H), 1.10 (s, 3H), 1.08 (s, 3H), 1.02 (s, 3H), 1.00 (s, 3H).

Preparation of tert-butyl 4-((1R,3aS,5aR,5bR,7aR,11aS,11bR,13aR,13bR)-5a,5b,8,8,11a-pentamethyl-3a-((2-(piperidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

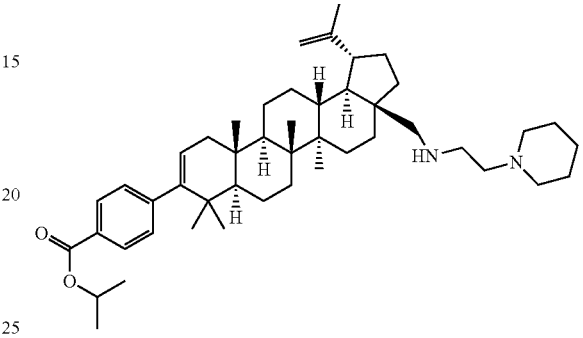

To a solution of tert-butyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.1 g, 0.167 mmol) in DCE (2 ml) was added acetic acid (0.019 ml, 0.334 mmol) and N-(2-aminoethyl)piperidine (0.048 ml, 0.334 mmol). The mixture was stirred at rt for 2 h then sodium triacetoxyborohydride (0.177 g, 0.835 mmol) was added. The mixture was stirred at rt for three days then was diluted with 7 ml of sat. NaHCO$_3$ and was extracted with dichloromethane (3×7 ml). The combined organic layers were dried with Na$_2$SO$_4$. The drying agent was removed by filtration and the filtrate was concentrated under reduced pressure. The crude product was used in the next step with no additional purification. LCMS: m/e 711.2 (M+H)$^+$, 3.32 min (method 6).

Example 9

Preparation of 4-((1R,3aS,5aR,5bR,7aR,11aS,11bR,13aR,13bR)-5a,5b,8,8,11a-pentamethyl-3a-((2-(piperidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

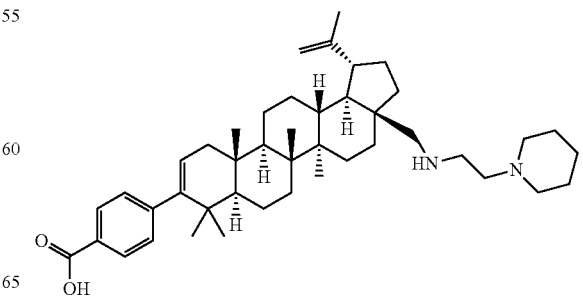

To a solution of tert-butyl 4-((1R,3aS,5aR,5bR,7aR,11aS,11bR,13aR,13bR)-5a,5b,8,8,11a-pentamethyl-3a-((2-(piperidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (119 mg, 0.167 mmol) in DCM (1 ml) was added TFA (0.4 ml, 5.19 mmol). The mixture was stirred at rt for 6 h then was concentrated under reduced pressure. The residue was dissolved in dioxane and MeOH and was purified by prep HPLC. The fractions containing the expected product were combined and concentrated under reduced pressure. The residue was dissolved in dioxane and methanol and the mixture was heated with a heat gun to reflux. Water was slowly added until the mixture was slightly cloudy. The mixture was allowed to cool to rt and then was refrigerated overnight. The solids that formed were collected by filtration and were washed with water to afford the title compound as a light-yellow solid (57 mg, 0.087 mmol, 52.1% yield). LCMS: m/e 655.6 (M+H)$^+$, 2.28 min (method 6). $^1$H NMR (400 MHz, Acetic Acid d4) δ ppm 7.99 (d, J=8.28 Hz, 2H), 7.25 (d, J=8.28 Hz, 2H), 5.32 (d, J=4.52 Hz, 1H), 4.75 (s, 1H), 4.63 (s, 1H), 3.72 (s, 2H), 3.56-3.66 (m, 2H), 3.33 (d, J=12.80 Hz, 1H), 2.98 (d, J=12.80 Hz, 1H), 2.48 (br. s., 1H), 1.71 (s, 3H), 1.14 (s, 3H), 1.09-2.22 (m, 32H), 1.05 (s, 3H), 1.03 (s, 3H), 0.97 (s, 3H), 0.96 (s, 3H).

Preparation of tert-butyl 4-((1R,3aS,5aR,5bR,7aR,11aS,11bR,13aR,13bR)-3a-((2-(dimethylamino)-2-(pyridin-3-yl)ethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

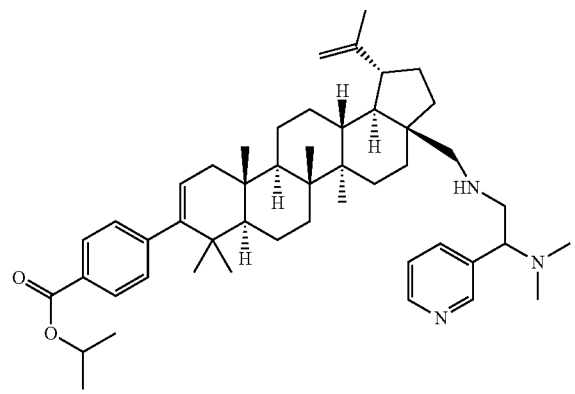

To a solution of tert-butyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.1 g, 0.167 mmol) in DCE (2 ml) was added acetic acid (0.019 ml, 0.334 mmol) and (2-Amino-1-(3-pyridyl)ethyl)dimethylamine (0.055 g, 0.334 mmol). The mixture was stirred at rt for 2 h then sodium triacetoxyborohydride (0.177 g, 0.835 mmol) was added and it was stirred at rt for three days. The mixture was diluted with 7 ml of sat. NaHCO$_3$ and was extracted with dichloromethane (3×7 ml). The combined organic layers were dried with Na$_2$SO$_4$. The drying agent was removed by filtration and the filtrate was concentrated under reduced pressure. The crude product was used in the next step with no additional purification. LCMS: m/e 748.3 (M+H)$^+$, 3.47 min (method 6).

Example 10

Preparation of 4-((1R,3aS,5aR,5bR,7aR,11aS,11bR,13aR,13bR)-3a-((2-(dimethylamino)-2-(pyridin-3-yl)ethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

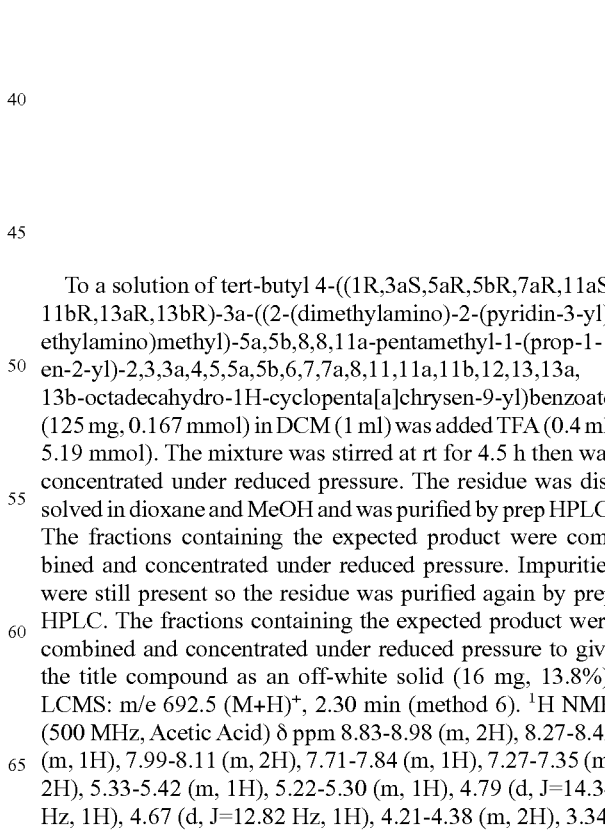

To a solution of tert-butyl 4-((1R,3aS,5aR,5bR,7aR,11aS,11bR,13aR,13bR)-3a-((2-(dimethylamino)-2-(pyridin-3-yl)ethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (125 mg, 0.167 mmol) in DCM (1 ml) was added TFA (0.4 ml, 5.19 mmol). The mixture was stirred at rt for 4.5 h then was concentrated under reduced pressure. The residue was dissolved in dioxane and MeOH and was purified by prep HPLC. The fractions containing the expected product were combined and concentrated under reduced pressure. Impurities were still present so the residue was purified again by prep HPLC. The fractions containing the expected product were combined and concentrated under reduced pressure to give the title compound as an off-white solid (16 mg, 13.8%). LCMS: m/e 692.5 (M+H)$^+$, 2.30 min (method 6). $^1$H NMR (500 MHz, Acetic Acid) δ ppm 8.83-8.98 (m, 2H), 8.27-8.42 (m, 1H), 7.99-8.11 (m, 2H), 7.71-7.84 (m, 1H), 7.27-7.35 (m, 2H), 5.33-5.42 (m, 1H), 5.22-5.30 (m, 1H), 4.79 (d, J=14.34 Hz, 1H), 4.67 (d, J=12.82 Hz, 1H), 4.21-4.38 (m, 2H), 3.34-

3.52 (m, 1H), 2.97-3.15 (m, 1H), 2.83 (br. s., 3H), 2.82 (br. s., 3H), 2.43-2.58 (m, 1H), 0.88-2.23 (m, 40H).

Preparation of tert-butyl 4-((1R,3S,5aR,5bR,7aR, 11aS,11bR,13aR,13bR)-5a,5b,8,8,11a-pentamethyl-3a-((2-(4-methylpiperazin-1-yl)ethylamino)methyl)-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate

Example 11

Preparation of 4-((1R,3aS,5aR,5bR,7aR,11aS,1bR, 13aR,13bR)-5a,5b,8,8,11a-pentamethyl-3a-((2-(4-methylpiperazin-1-yl)ethylamino)methyl)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

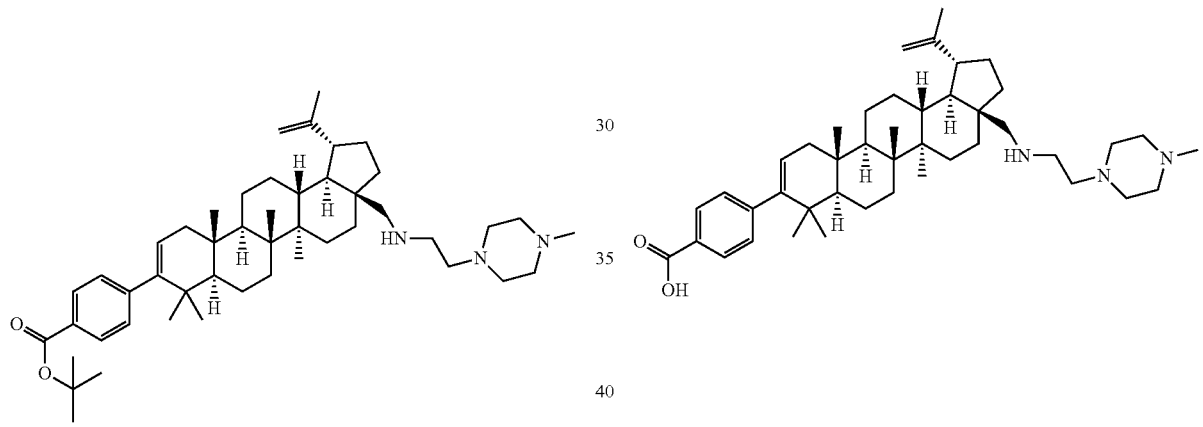

To a solution of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoate (0.1 g, 0.167 mmol) in DCE (2 ml) was added acetic acid (0.019 ml, 0.334 mmol) and 2-(4-methyl-piperazin-1-yl)-ethylamine (0.048 g, 0.334 mmol). The mixture was stirred at rt for 2 h, then sodium triacetoxyborohydride (0.177 g, 0.835 mmol) was added and it was stirred at rt for 3 days. The mixture was diluted with 7 ml of sat. NaHCO₃ and was extracted with dichloromethane (3×7 ml). The combined organic layers were dried with Na₂SO₄. The drying agent was removed by filtration and the filtrate was concentrated under reduced pressure. The crude product was used in the next with no additional purification. LCMS: m/e 726.5 (M+H)⁺, 3.07 min (method 6).

To a solution of tert-butyl 4-((1R,3aS,5aR,5bR,7aR,11aS, 11bR,13aR,13bR)-5a,5b,8,8,11a-pentamethyl-3a-((2-(4-methylpiperazin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.121 g, 0.167 mmol) in DCM (1 ml) was added TFA (0.4 ml, 5.19 mmol). The mixture was stirred at rt for 5.5 h, then was concentrated under reduced pressure. The residue was dissolved in dioxane and MeOH and was purified twice by prep. HPLC to afford the title compound as a white solid (0.044 g, 0.066 mmol, 39.3% yield). LCMS: m/e 670.6 (M+H)⁺, 2.23 min (method 6). ¹H NMR (500 MHz, Acetic acid) δ ppm 8.03 (d, J=8.24 Hz, 2H), 7.30 (d, J=8.55 Hz, 2H), 5.37 (d, J=4.58 Hz, 1H), 4.79 (s, 1H), 4.68 (s, 1H), 3.43-3.66 (m, 6H), 3.40 (d, J=13.43 Hz, 1H), 3.17-3.31 (m, 6H), 2.98 (d, J=12.82 Hz, 1H), 2.92 (s, 3H), 2.47-2.57 (m, 1H), 1.75 (s, 3H), 1.18 (s, 3H), 1.15-2.23 (m, 22H), 1.10 (s, 3H), 1.08 (s, 3H), 1.02 (s, 3H), 1.00 (s, 3H).

Example 12

Preparation of 4-((1R,3aS,5aR,5bR,7aR,11aS,11bR, 13aR,13bR)-3a-((2-carboxy-N-(2-(dimethylamino) ethyl)acetamido)methyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

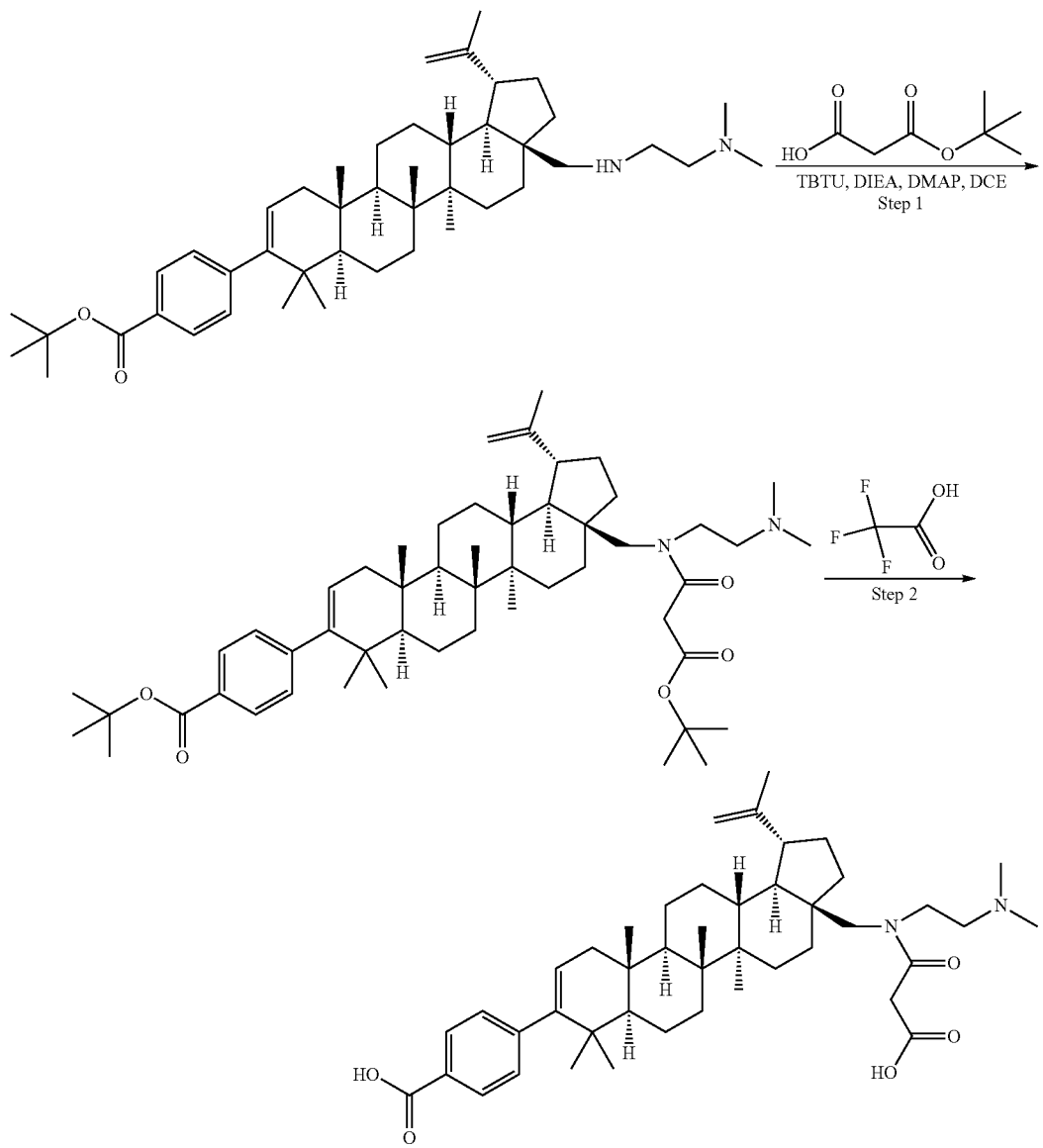

Example 12

Step 1: Preparation of tert-butyl 4-((1R,3aS,5aR, 5bR,7aR,11aS,11bR,13aR,13bR)-3a-((3-tert-butoxy-N-(2-(dimethylamino)ethyl)-3-oxopropanamido) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate To a solution of tert-butyl 4-((1R,3aS,5aR,5bR,7aR,11aS, 11bR,13aR,13bR)-3a-((2-(dimethylamino)ethylamino)me-thyl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)benzoate (27 mg, 0.040 mmol) in DCE (2 ml) was added Hunig's base (0.021 ml, 0.121 mmol), DMAP (1 mg, 8.19 µmol), Mono-tert-butyl malonate (0.012 ml, 0.080 mmol), and O-benzot-riazol-1-yl-N,N,N',N'-tetramethyluronium tetrafluoroborate (19.38 mg, 0.060 mmol). The mixture was stirred at rt. After 5 h of stirring, the mixture was loaded directly onto a silica gel column and was purified using a 0-5% MeOH in dichloromethane gradient to afford tert-butyl 4-((1R,3aS,5aR,5bR,7aR,11aS,11bR,13aR,13bR)-3a-((3-tert-butoxy-N-(2-(dimethylamino)ethyl)-3-oxopropanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as a white foam (31.8 mg, 0.039 mmol, 97% yield). LCMS: m/e 813.4 (M–H)⁻, 3.46 min (method 6).

Step 2: Carboxylic Acids Deprotection

To a solution of tert-butyl 4-((1R,3aS,5aR,5bR,7aR,11aS,11bR,13aR,13bR)-3a-((3-tert-butoxy-N-(2-(dimethylamino)ethyl)-3-oxopropanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (31 mg, 0.038 mmol) in dichloromethane (1 ml) was added TFA (0.25 ml, 3.24 mmol). The mixture was stirred at rt for 3 h then was concentrated under reduced pressure. The residue was purified by prep HPLC. The fractions containing the expected product were combined and concentrated under reduced pressure to afford 4-((1R,3aS,5aR,5bR,7aR,11aS,11bR,13aR,13bR)-3a-((2-carboxy-N-(2-(dimethylamino)ethyl)acetamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid as a white solid (15 mg, 0.021 mmol, 56.1% yield). LCMS: m/e 701.5 (M+H)⁺, 2.11 min (method 6). ¹H NMR (500 MHz, Acetic acid-d₃ acid-d) δ ppm 8.04 (d, J=8.24 Hz, 2H), 7.31 (d, J=8.24 Hz, 2H), 5.38 (d, J=5.19 Hz, 1H), 4.85 (d, J=16.17 Hz, 1H), 4.69 (d, J=15.56 Hz, 1H), 3.86-4.13 (m, 2H), 2.97-3.82 (m, 6H), 2.62-2.73 (m, 1H), 2.13-2.24 (m, 2H), 1.06-1.92 (m, 38H), 1.03 (s, 3H), 1.01 (s, 3H).

Example 13

Preparation of 4-((1R,3aS,5aR,5bR,7aR,11aS,11bR,13aR,13bR)-3a-((3-carboxy-N-(2-(dimethylamino)ethyl)propanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

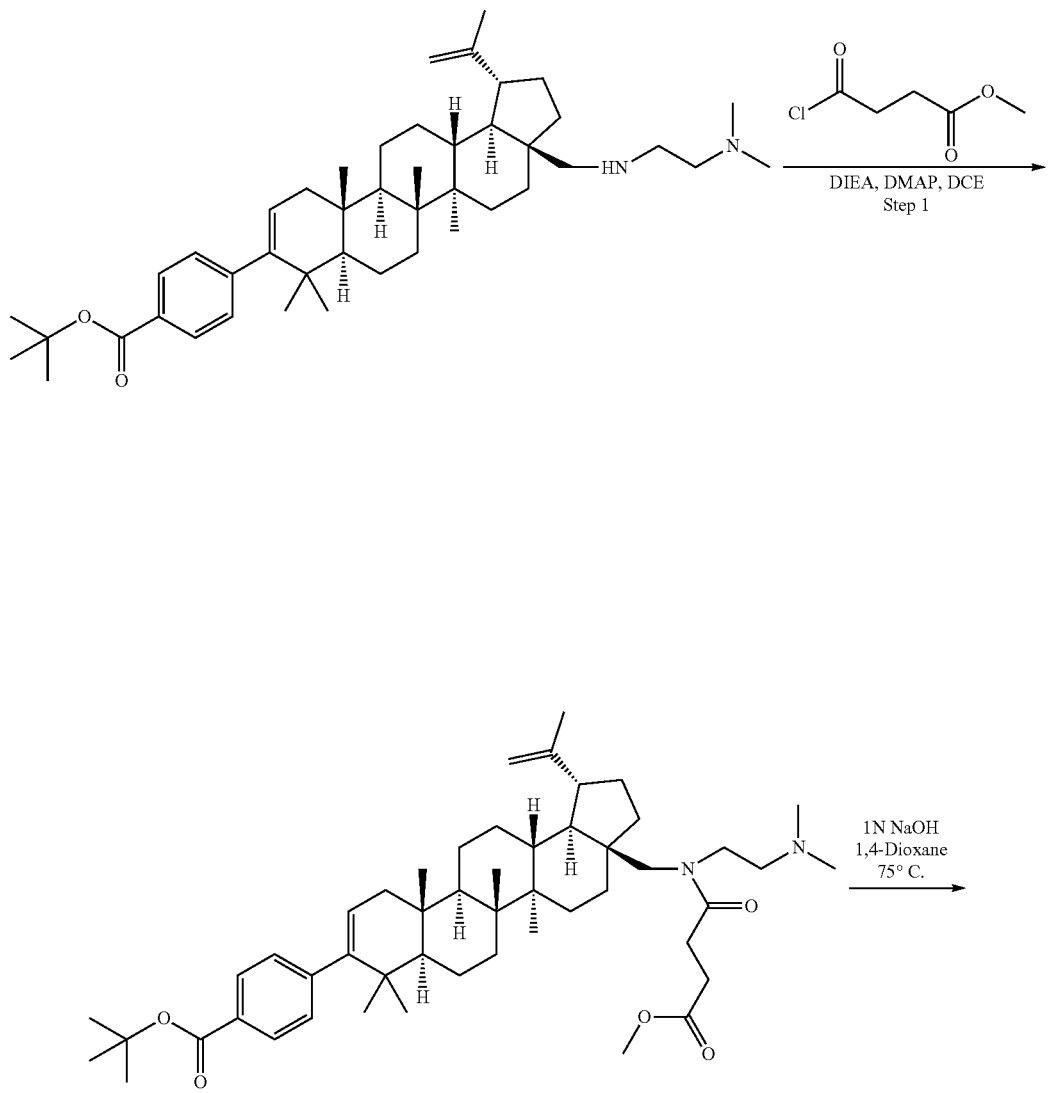

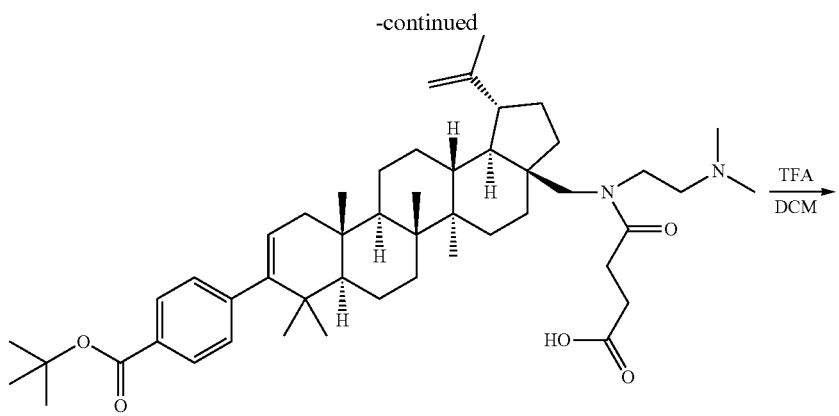

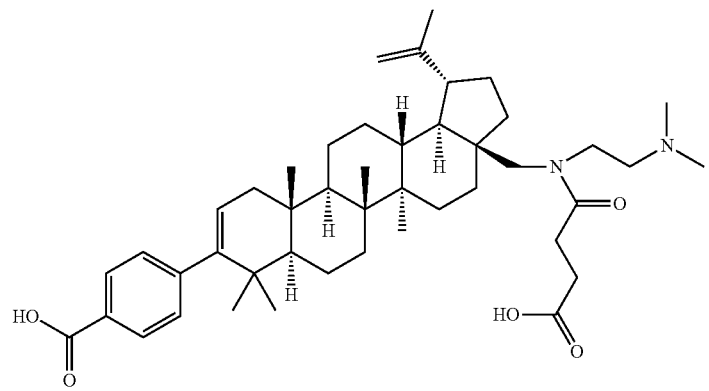

Example 13

Step 1. Preparation of tert-butyl 4-((1R,3aS,5aR, 5bR,7aR,11aS,11bR,13aR,13bR)-3a-((N-(2-(dimethylamino)ethyl)-4-methoxy-4-oxobutanamido) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate To a solution of tert-butyl 4-((1R,3aS,5aR,5bR,7aR,11aS, 11bR,13aR,13bR)-3a-((2-(dimethylamino)ethylamino)methyl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)benzoate (48 mg, 0.072 mmol) in DCE (2 ml) was added Hunig's base (0.037 ml, 0.215 mmol), 3-carboethoxypropionyl chloride (21.54 mg, 0.143 mmol), and DMAP (1 mg, 8.19 mmol). The mixture was stirred at rt for 5 h then was loaded directly onto a silica gel column and was purified using a 0-5% MeOH in dichloromethane gradient to afford tert-butyl 4-((1R,3aS, 5aR,5bR,7aR,11aS,11bR,13aR,13bR)-3a-((N-(2-(dimethylamino)ethyl)-4-methoxy-4-oxobutanamido)methyl)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)benzoate as a white foam (53.8 mg, 0.051 mmol, 71.8% yield). LCMS: m/e 785.6 (M+H)+, 3.21 min (method 6).

Step 2. Preparation of 4-((((1R,3aS,5aR,5bR,7aR, 11aS,11bR,13aR,13bR)-9-(4-(tert-butoxycarbonyl) phenyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-3a-yl) methyl)(2-(dimethylamino)ethyl)amino)-4-oxobutanoic acid To a solution of tert-butyl 4-((1R,3aS,5aR,5bR,7aR,11aS, 11bR,13aR,13bR)-3a-((N-(2-(dimethylamino)ethyl)-4-methoxy-4-oxobutanamido)methyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate (53 mg, 0.068 mmol) in 1,4-dioxane (1 ml) was added NaOH (0.338 ml, 0.338 mmol). The mixture was heated to 75° C. for 3 h. The mixture was cooled to rt and was quenched with 1N HCl (3 ml) and extracted with dichloromethane (3×7 ml). The combined organic layers were dried with $Na_2SO_4$, were filtered, and concentrated under reduced pressure. The crude product was used in the next step with no additional purification. LCMS: m/e 771.6 (M+H)+, 2.70 min (method 6).

Step 3. Deprotection of the Benzoic Acid

To a solution of 4-((((1R,3aS,5aR,5bR,7aR,11aS,11bR, 13aR,13bR)-9-(4-(tert-butoxycarbonyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H- cyclopenta[a]chrysen-3a-yl)methyl)(2-(dimethylamino)ethyl)amino)-4-oxobutanoic acid (47 mg, 0.061 mmol) in DCM (1 ml) was added TFA (0.25 ml, 3.24 mmol). The mixture was stirred at rt. After 1.75 h, The mixture was concentrated under reduced pressure, was diluted with dioxane and MeOH and was purified by prep HPLC to afford 4-((1R,3aS,5aR,5bR,7aR,11aS,11bR,13aR,13bR)-3a-((3-carboxy-N-(2-(dimethylamino)ethyl)propanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid as a white solid (25 mg, 0.035 mmol, 57.4% yield. LCMS: m/e 715.4 (M+H)$^+$, 2.16 min (method 6).

General Procedure for the Preparation of C28 Amines

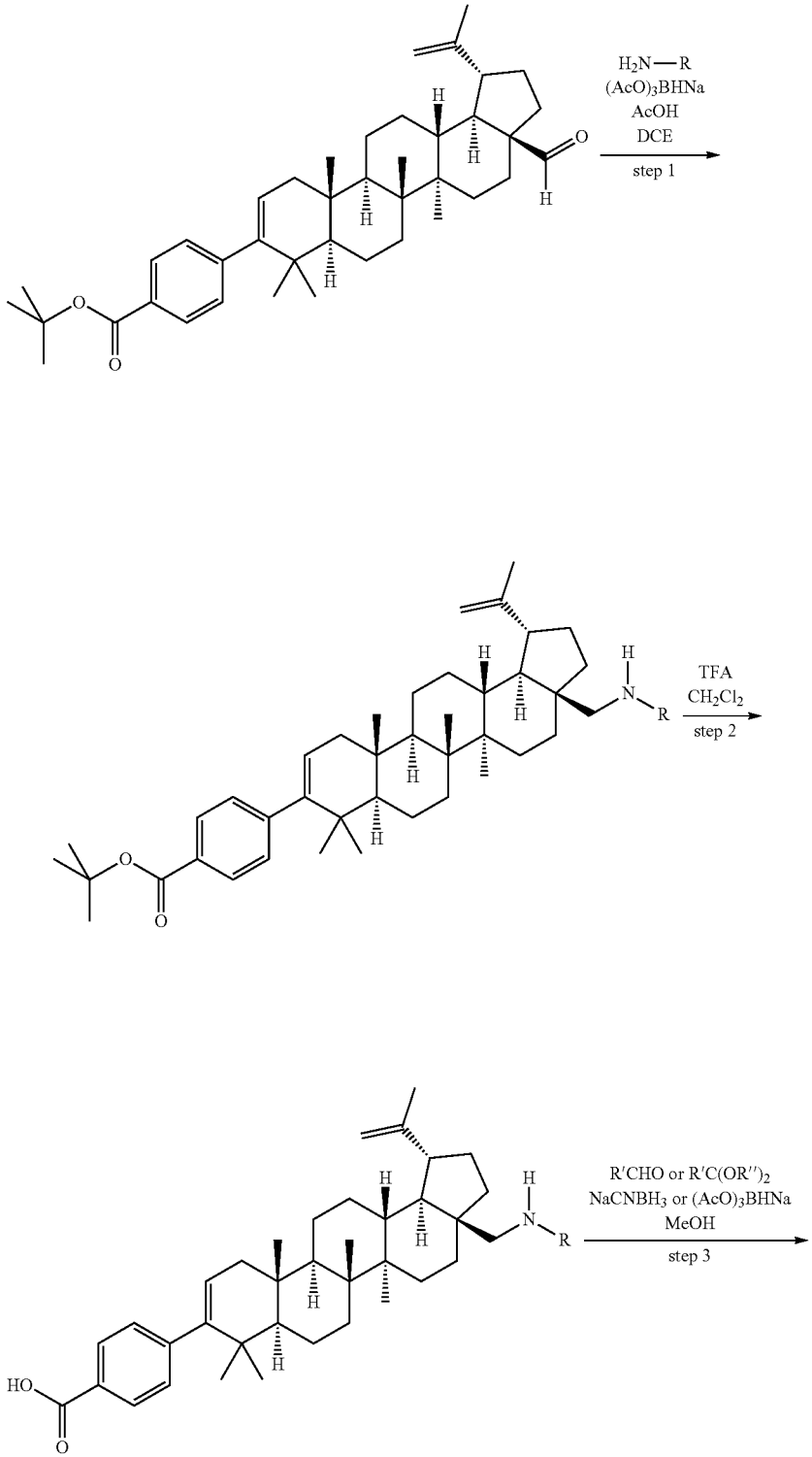

-continued

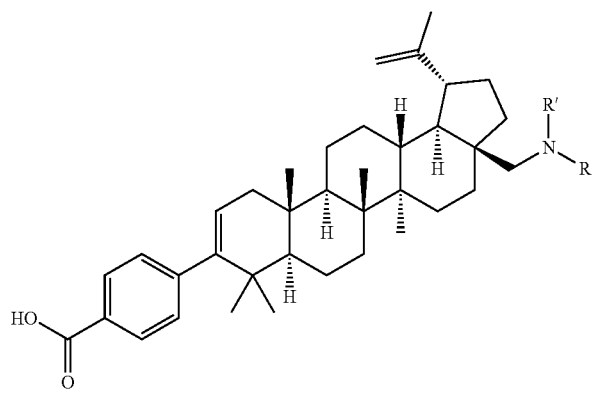

Step 1: Preparation of C28 Amines

A suspension of tert-butyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (1 eq.), the corresponding amine (2 eq.) and acetic acid (2-5 eq.) in DCE (2 ml) was stirred at rt for 30 min. Sodium triacetoxyborohydride (5 eq.) was added. The resulting mixture was stirred at rt for 18-72 h. The reaction mixture was diluted with 5 ml of saturated sodium carbonate and extracted with DCM (3×10 ml). The combined organic layers were dried over sodium sulfate, filtered and concentrated in vacuo. The crude product was purified by Biotage flash chromatography or was used directly in the next step without further purification.

Step 2: Preparation of Benzoic Acids by Hydrolysis of Corresponding tert-butylesters To a solution of the corresponding C28 amine from Step 1 in DCM (2 ml) was added TFA (0.5 ml). The mixture was stirred at rt for 1-2 h. The reaction mixture was concentrated in vacuo. The crude product was purified by prep. HPLC to afford the desired benzoic acid.

Step 3: Reductive Amination to Form Tertiary Amines

To a solution of the material from Step 2 (1 eq.) in methanol (2 ml) was added the corresponding aldehyde or ketal (2 eq.) followed by acetic acid (1 eq). The resulting solution was stirred at rt for 10 min. Sodium triacetoxyhydroborate (3 eq.) was added and the resulting suspension was stirred at rt for 2-48 h. The reaction mixture was quenched by sodium bicarbonate solution and extracted with DCM (3×10 ml). The organic layer were combined and dried over sodium sulfate. The residue was purified by prep. HPLC to afford the desired product.

Example 14

Preparation of 4-((1R,3aS,5aR,5bR,7aR,11aS,11bR,13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b,12,13,13a,13b-octadecahydro-1H-cyclopenta[a]chrysen-9-yl)benzoic acid

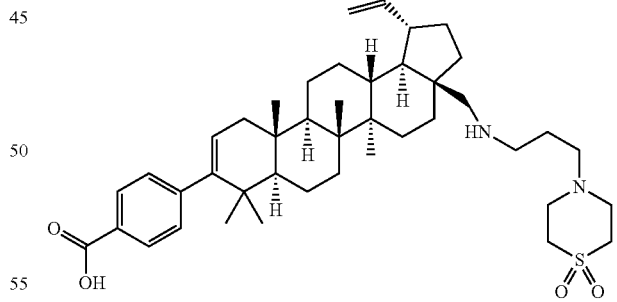

The title compound was prepared following the general procedures described above for the C28 amine formation and hydrolysis using 4-(3-aminopropyl) thiomorpholine 1,1-dioxide as the reactant amine. The product was isolated as a white solid (56 mg, 57.5%). LCMS: m/e 719.5 (MH$^+$), 2.60 min (method 1). $^1$H NMR (400 MHz, MeOD) δ ppm 7.90 (2H, d, J=8.6 Hz), 7.20 (2H, d, J=8.6 Hz), 5.20-5.34 (1H, m), 4.73 (1H, s), 4.62 (1H, s), 3.44-3.58 (4H, m), 3.39 (4H, d, J=4.8 Hz), 3.12-3.26 (3H, m), 3.08 (2H, t, J=7.2 Hz), 2.78-2.91 (1H, m), 2.39-2.58 (1H, m), 2.07-2.19 (3H, m), 1.97-

2.08 (1H, m), 1.64-1.88 (10H, m), 1.39-1.63 (8H, m), 1.18-1.38 (5H, m), 1.15 (3H, s), 1.05 (3H, s), 1.02 (3H, s), 0.95 (3H, s), 0.87-0.94 (3H, s).

Example 15

Preparation of 4-((1R,3aS,5aR,5bR,7aR,11aS,11bR,13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b,12,13,13a,13b-octadecahydro-1H-cyclopenta[a]chrysen-9-yl)benzoic acid The title compound was prepared following the general procedures described above for the C28 amine formation, hydrolysis and tertiary amine formation using 4-(3-aminopropyl) thiomorpholine 1,1-dioxide as the reactant amine and formaldehyde as reactant aldehyde. The product was isolated as a white solid (10 mg, 46.6%). LCMS: m/e 733.6 (MH+), 2.56 min (method 3). $^1$H NMR (400 MHz, MeOD) δ ppm 7.94 (m, J=8.5 Hz, 2H), 7.24 (m, J=8.5 Hz, 2H), 5.26-5.41 (m, 1H), 4.80 (d, J=1.5 Hz, 1H), 4.69 (s, 1H), 3.23-3.46 (m, 12H), 3.03 (s, 3H), 2.91 (t, J=6.9 Hz, 2H), 2.56 (br. s., 1H), 2.08-2.31 (m, 2H), 1.98-2.08 (m, 1H), 1.70-1.95 (m, 10H), 1.47-1.70 (m, 9H), 1.43 (d, J=10.0 Hz, 1H), 1.28-1.41 (m, 3H), 1.15-1.23 (m, 4H), 1.12 (s, 3H), 1.05 (s, 3H), 0.99 (s, 3H), 0.97 (s, 3H).

Example 16

Preparation of 4-((1R,3aS,5aR,5bR,7aR,11aS,11bR,13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b,12,13,13a,13b-octadecahydro-1H-cyclopenta[a]chrysen-9-yl)benzoic acid

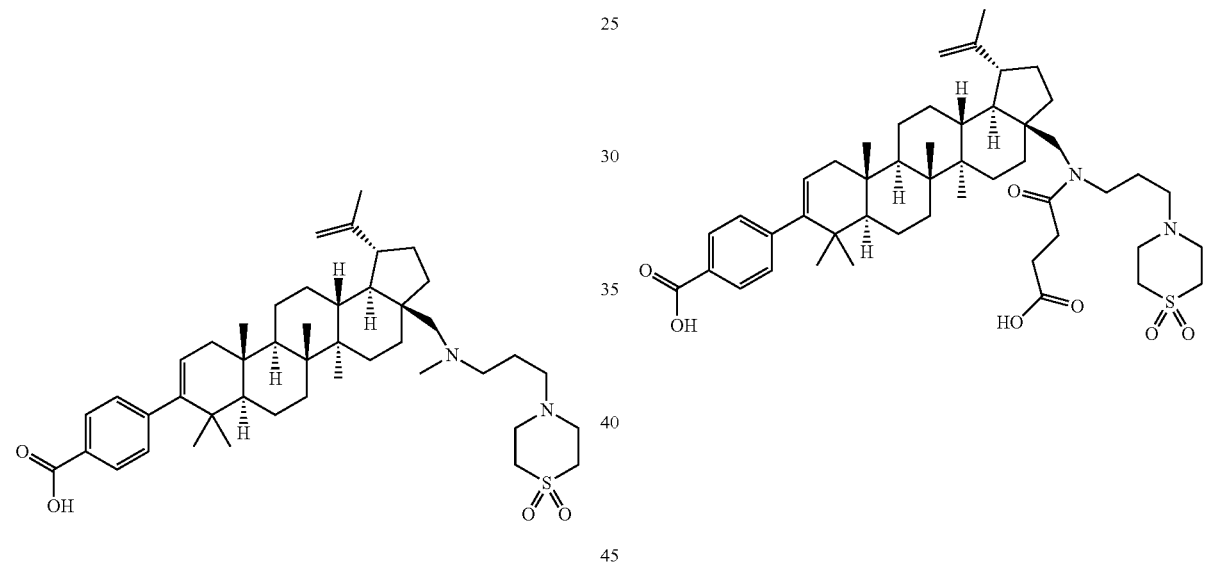

To a solution of 4-((1R,3aS,5aR,5bR,7aR,11aS,11bR,13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b,12,13,13a,13b-octadecahydro-1H-cyclopenta[a]chrysen-9-yl)benzoic acid (10 mg, 0.014 mmole) in CH$_2$Cl$_2$ (0.5 ml) was added dihydrofuran-2,5-dione (4.18 mg, 0.042 mmol) followed by DMAP (1.953 mg, 0.014 mmol) and DIPEA (2.429 mL, 0.014 mmol). The mixture was stirred at rt for 18 hours. The solvent was removed in vacuo and the resulting residue was purified by prep. HPLC to afford the title compound as a white solid (10 mg, 83%). LCMS: m/e 819.3 (MH+), 2.45 min (method 3). $^1$H NMR (400 MHz, MeOD) δ ppm 7.94 (m, J=8.3 Hz, 2H), 7.24 (m, J=8.5 Hz, 2H), 5.33 (d, J=6.3 Hz, 1H), 4.75 (s, 1H), 4.63 (s, 1H), 3.82 (br. s., 2H), 3.48-3.73 (m, 6H), 3.44 (br. s., 3H), 3.20-3.31 (m, 2H), 3.03-3.20 (m, 1H), 2.56-2.80 (m, 5H), 2.08 (br. s., 4H), 1.75 (d, J=11.3 Hz, 8H), 1.57 (d, J=2.0 Hz, 5H), 1.48 (br. s., 2H), 1.24-1.45 (m, 5H), 1.22 (s, 4H), 1.11-1.16 (m, 2H), 1.02-1.11 (m, 6H), 0.88-1.02 (m, 6H).

Example 17

Preparation of 4-(((1R,3aS,5aR,5bR,7aR,11aS,11bR,13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b,12,13,13a,13b-octadecahydro-1H-cyclopenta[a]chrysen-9-yl)benzoic acid

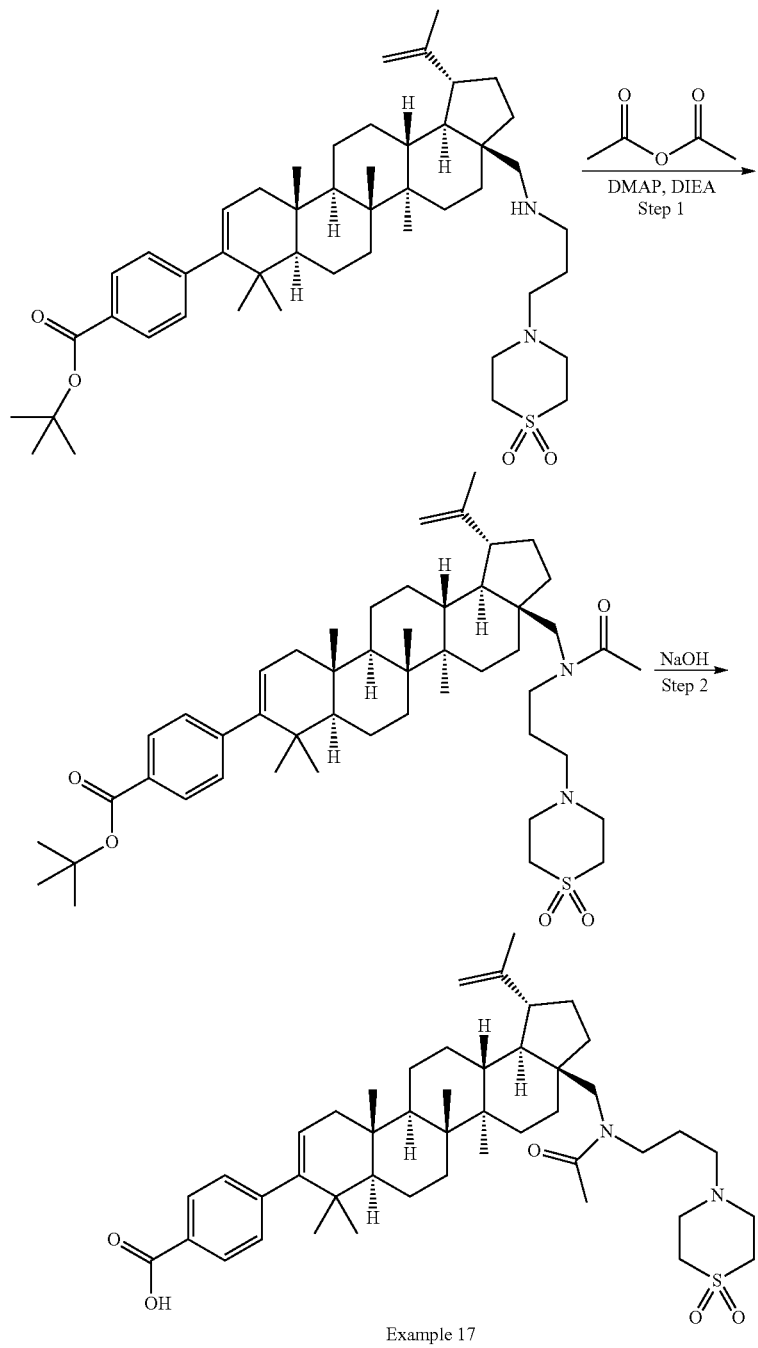

Example 17

Step 1. N-Acetylation

To a solution of tert-butyl 4-(((1R,3aS,5aR,5bR,7aR,11aS,11bR,13aR,13bR)-3a-(((3-(1,1-dioxido-4-thiomorpholinyl)propyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoate (50 mg, 0.065 mmole) in $CH_2Cl_2$ (5 ml) was added acetic anhydride (6.58 mg, 0.065 mmol) followed by DMAP (9.06 mg, 0.065 mmol) and DIPEA (11 µL, 0.065 mmol). The mixture was stirred for 18 hours at room temperature. The solvent was removed in vacuo and the resulting residue was used as it without further purification. LCMS: m/e 817.3 (MH$^+$), 2.75 min (method 3).

Step 2. Saponification of the Benzoate Ester

To a solution of material from Step 1 (6 mg, 7.34 mmol) in dioxane (1 ml) and MeOH (5 ml) sodium hydroxide (5.87 mg, 0.147 mmol) (powder) was added, followed by 5 drops of water. The resulting solution was stirred at 70° C. for 12 h. The solvent was removed in vacuo and the resulting residue was purified by prep. HPLC. The product was isolated as a white solid (6 mg, 100%). LCMS: m/e 761.3 (MH$^+$), 2.51 min (method 3). $^1$H NMR (400 MHz, MeOD) δ ppm 7.94 (m, J=8.3 Hz, 2H), 7.26 (m, 2H), 5.22-5.44 (m, 1H), 4.76 (s, 1H), 4.63 (s, 1H), 3.82 (br. s., 2H), 3.59-3.68 (m, 3H), 3.51-3.59 (m, 2H), 3.40-3.51 (m, 4H), 3.23-3.31 (m, 2H), 3.02-3.16 (m, 1H), 2.57-2.73 (m, 1H), 2.12-2.22 (m, 4H), 1.97-2.12 (m, 3H), 1.85 (d, J=12.3 Hz, 2H), 1.65-1.80 (m, 6H), 1.58 (d, J=16.6 Hz, 4H), 1.45-1.54 (m, 3H), 1.26-1.45 (m, 4H), 1.21 (s, 4H), 1.11-1.19 (m, 3H), 1.01-1.11 (m, 6H), 0.92-1.01 (m, 6H).

Example 18

Preparation of 4-((1R,3aS,5aR,5bR,7aR,11aS,11bR, 13aR,13bR)-5a,5b,8,8,11a-pentamethyl-3a-((3-(methyl(phenyl)amino)propylamino)methyl)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

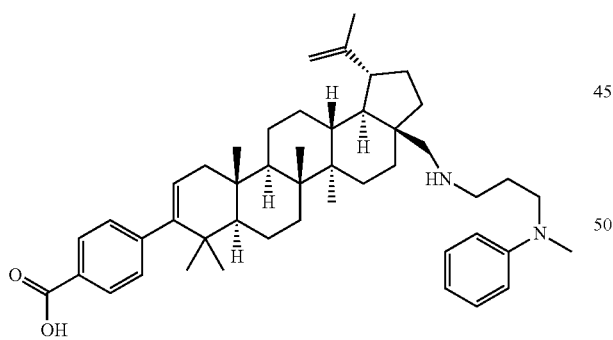

The title compound was prepared following the general procedures described above for the C28 amine formation and hydrolysis using N1-methyl-N1-phenylpropane-1,3-diamine as the reactant amine. The product was isolated as a white solid (7 mg, 14.4%). LCMS: m/e 691.7 (MH$^+$), 2.71 min (method 1). $^1$H NMR (500 MHz, CHLOROFORM-d) δ ppm 7.97 (2H, d, J=7.9 Hz), 7.16-7.27 (4H, m), 6.65-6.84 (3H, m), 5.23-5.37 (1H, m), 4.70 (1H, br. s.), 4.61 (1H, br. s.), 3.30-3.48 (2H, m), 2.95-3.03 (4H, m), 2.93 (3H, s), 2.41-2.53 (1H, m), 2.00-2.14 (2H, m), 1.89-2.00 (4H, m), 1.73-1.89 (7H, m), 1.64-1.73 (2H, m), 1.60 (2H, br. s.), 1.52-1.58 (2H, m), 1.46- 1.52 (2H, m), 1.44 (2H, d, J=10.1 Hz), 1.18-1.33 (2H, m), 1.03-1.12 (3H, m), 1.02 (2H, br. s.), 0.98-1.01 (6H, m), 0.87-0.98 (6H, m).

Example 19

Preparation of 4-((1R,3aS,5aR,5bR,7aR,11aS,11bR, 13aR,13bR)-5a,5b,8,8,11a-pentamethyl-3a-((3-(methylamino)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

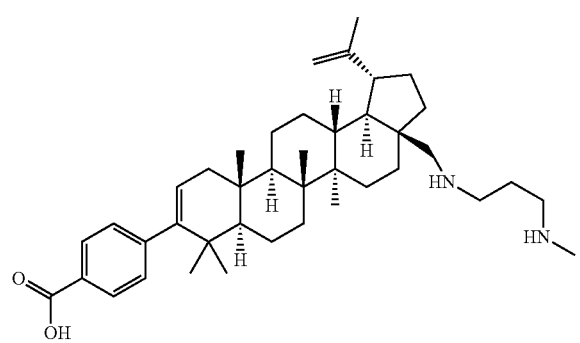

The title compound was prepared following the general procedures described above for the C28 amine formation and hydrolysis using tert-butyl 3-aminopropyl (methyl) carbamate as the reactant amine. The product was isolated as a white solid (26 mg, 51.6%). LCMS: m/e 615.5 (MH$^+$), 2.50 min (method 1). $^1$H NMR (500 MHz, Acetic Acid-d) δ ppm 8.03 (2H, d, J=8.2 Hz), 7.29 (2H, d, J=8.2 Hz), 5.36 (1H, d, J=4.6 Hz), 4.79 (1H, s), 4.67 (1H, s), 3.36-3.43 (1H, m), 3.27-3.36 (2H, m), 3.21 (2H, t, J=7.5 Hz), 2.94 (1H, d, J=12.8 Hz), 2.78 (3H, s), 2.48-2.56 (1H, m), 2.24-2.38 (2H, m), 2.13-2.24 (2H, m), 2.00-2.13 (5H, m), 1.85-2.00 (3H, m), 1.68-1.85 (6H, m), 1.58-1.68 (2H, m), 1.41-1.58 (3H, m), 1.23-1.41 (2H, m), 1.12-1.23 (5H, m), 1.09 (3H, s), 1.07 (3H, s), 1.01 (3H, s), 1.00 (3H, s).

Example 20

Preparation of 4-((1R,3aS,5aR,5bR,7aR,11aS,11bR, 13aR,13bR)-3a-((2-(1H-imidazol-1-yl)ethylamino) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

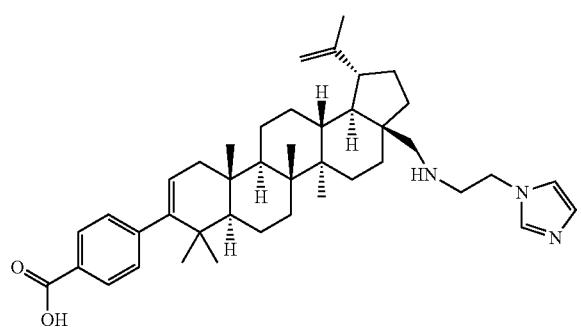

The title compound was prepared following the general procedures described above for the C28 amine formation and hydrolysis using 2-(1H-imidazol-1-yl)ethanamine as the reactant amine. The product was isolated as a white solid (15 mg, 51.7%). LCMS: m/e 638.6 (MH+), 2.49 min (method 1). ¹H NMR (500 MHz, MeOD) δ ppm 9.03 (1H, s), 7.94 (2H, d, J=8.2 Hz), 7.73 (1H, d, J=1.5 Hz), 7.65 (1H, d, J=1.5 Hz), 7.24 (2H, d, J=8.2 Hz), 5.25-5.36 (1H, m), 4.77 (1H, s), 4.74 (2H, t, J=6.7 Hz), 4.66 (1H, s), 3.63-3.79 (2H, m), 3.36 (1H, m), 2.95 (1H, d, J=12.8 Hz), 2.52 (1H, dt, J=10.8, 5.5 Hz), 2.12-2.27 (1H, m), 1.98-2.12 (1H, m), 1.83-1.98 (2H, m), 1.78-1.83 (2H, m), 1.70-1.78 (6H, m), 1.45-1.64 (6H, m), 1.35 (2H, dd, J=11.3, 8.2 Hz), 1.26-1.32 (2H, m), 1.22 (1H, d, J=2.7 Hz), 1.18 (5H, s), 1.09 (3H, s), 1.05 (3H, s), 0.99 (3H, s), 0.97 (3H, s).

Example 21

Preparation of 4-((1R,3aS,5aR,5bR,7aR,11aS,11bR, 13aR,13bR)-3a-((2-(diethylamino)ethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid m), 1.26 (2H, br. s.), 1.22 (6H, t, J=7.2 Hz), 1.16 (5H, br. s.), 1.06 (3H, br. s.), 1.04 (3H, br. s.), 0.88-1.01 (6H, m).

Example 22

Preparation of 4-((1R,3aS,5aR,5bR,7aR,11aS,11bR, 13aR,13bR)-5a,5b,8,8,11a-pentamethyl-3a-((3-(methylamino)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

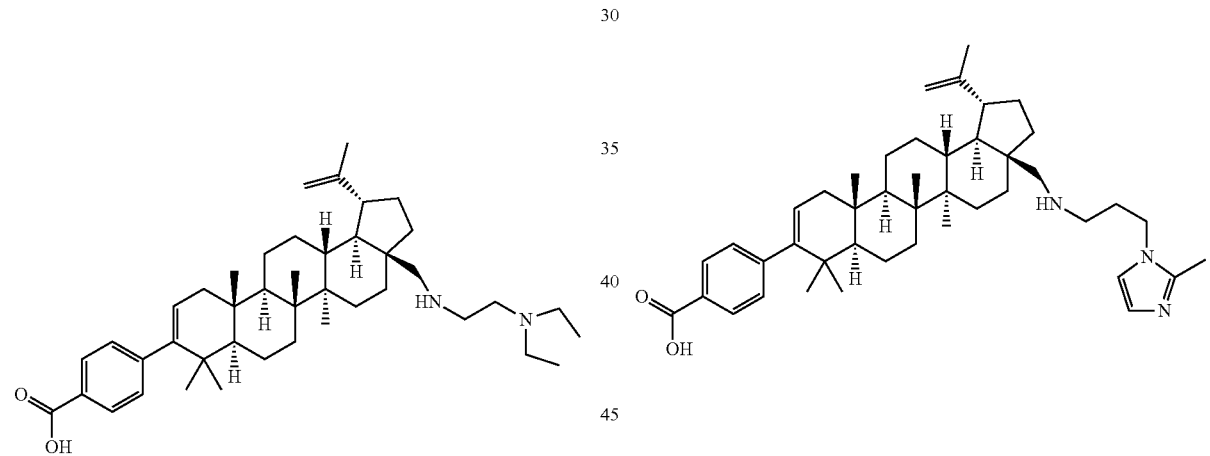

The title compound was prepared following the general procedures described above for the C28 amine formation and hydrolysis using N1,N1-diethylethane-1,2-diamine as the reactant amine. The product was isolated as a white solid (27 mg, 86.0%). LCMS: m/e 643.6 (MH+), 2.52 min (method 1). ¹H NMR (500 MHz, MeOD) δ ppm 7.89 (2H, m, J=7.6 Hz), 7.16 (2H, m, J=7.9 Hz), 5.30 (1H, d, J=4.6 Hz), 4.75 (1H, br. s.), 4.63 (1H, br. s.), 3.04-3.23 (5H, m), 2.88-3.02 (4H, m), 2.69 (1H, d, J=11.9 Hz), 2.51 (1H, d, J=5.5 Hz), 2.15 (1H, dd, J=17.1, 6.1 Hz), 2.09 (1H, br. s.), 1.93-2.00 (6H, m), 1.83-1.93 (2H, m), 1.79 (2H, br. s.), 1.73 (4H, br. s.), 1.42-1.59 (5H, The title compound was prepared following the general procedures described above for the C28 amine formation and hydrolysis using 3-(2-methyl-1H-imidazol-1-yl) propan-1-amine as the reactant amine. The product was isolated as a white solid (40 mg, 66.5%). LCMS: m/e 666.5 (MH+), 2.48 min (method 1). ¹H NMR (400 MHz, MeOD) δ ppm 7.90 (2H, d, J=8.6 Hz), 7.52 (1H, d, J=2.3 Hz), 7.44 (1H, d, J=2.0 Hz), 7.20 (2H, d, J=8.3 Hz), 5.27 (1H, d, J=4.8 Hz), 4.72 (1H, s), 4.61 (1H, s), 4.25 (2H, t, J=7.2 Hz), 3.11-3.26 (3H, m), 2.79-2.92 (1H, m), 2.65 (3H, s), 2.39-2.58 (1H, m), 2.30 (2H, dq, J=7.9, 7.7 Hz), 2.12 (1H, dd, J=17.2, 6.4 Hz), 1.93-2.08 (1H, m), 1.76-1.93 (2H, m), 1.63-1.76 (8H, m), 1.57 (1H, br. s.), 1.54 (1H, d, J=7.6 Hz), 1.38-1.52 (6H, m), 1.29-1.38 (1H, m), 1.22-1.29 (2H, m), 1.19 (1H, br. s.), 1.07-1.16 (4H, m), 1.04 (3H, s), 1.02 (3H, s), 0.96 (3H, s), 0.90 (3H, s).

Example 23

Preparation of 4-((1R,3aS,5aR,5bR,7aR,11aS,11bR, 13aR,13bR)-5a,5b,8,8,11a-pentamethyl-3a-((3-(3-oxopiperazin-1-yl)propylamino)methyl)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

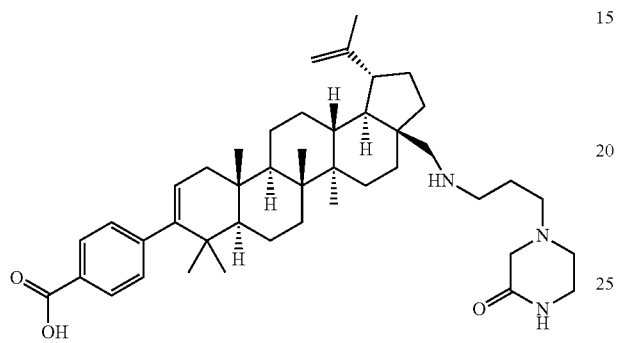

The title compound was prepared following the general procedures described above for the C28 amine formation and hydrolysis using 4-(3-aminopropyl)piperazin-2-one as the reactant amine. The product was isolated as a white solid (55 mg, 80%). LCMS: m/e 684.5 (MH$^+$), 2.53 min (method 1). $^1$H NMR (400 MHz, MeOD) δ ppm 7.91 (2H, d, J=3.3 Hz), 7.21 (2H, d, J=2.8 Hz), 5.28 (1H, br. s.), 4.74 (1H, br. s.), 4.63 (1H, br. s.), 3.93 (2H, br. s.), 3.52-3.69 (4H, m), 3.3 (2 h, m), 3.04-3.27 (3H, m), 2.78-2.97 (1H, m), 2.41-2.63 (1H, m), 2.21-2.38 (2H, m), 1.97-2.21 (2H, m), 1.8 (2H, m), 1.71 (8H, br. s.), 1.51 (8H, br. s.), 1.25 (2H, m), 1.15 (5H, br. s.), 1.03 (7H, d, J=13.8 Hz), 0.85-0.99 (6H, m).

Example 24

Preparation of 4-((1R,3aS,5aR,5bR,7aR,11aS,11bR, 13aR,13bR)-3a-((2-(bis(2-hydroxyethyl)amino)ethylamino)methyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoic acid

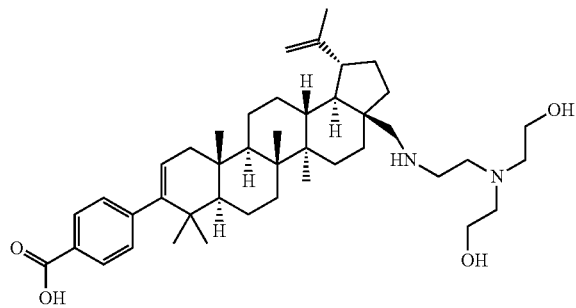

The title compound was prepared following the general procedures described above for the C28 amine formation and hydrolysis using 2,2'-(2-aminoethylazanediyl)diethanol as the reactant amine. The product was isolated as a white solid (19 mg, 40.7%). LCMS: m/e 675.6 (MH$^+$), 2.51 min (Method 1). $^1$H NMR (400 MHz, MeOD) δ ppm 7.90 (d, J=8.3 Hz, 2H), 7.20 (d, J=8.3 Hz, 2H), 5.18-5.37 (m, 1H), 4.74 (s, 1H), 4.62 (s, 1H), 3.79-3.95 (m, 4H), 3.45-3.66 (m, 4H), 3.20-3.35 (m, 5H), 2.78-3.00 (m, 1H), 2.39-2.59 (m, 1H), 2.13 (dd, J=17.0, 6.4 Hz, 1H), 2.04 (d, J=8.6 Hz, 1H), 1.78-1.92 (m, 2H), 1.63-1.78 (m, 8H), 1.55 (d, J=6.5 Hz, 2H), 1.40-1.53 (m, 6H), 1.22-1.40 (m, 4H), 1.09-1.19 (m, 4H), 1.05 (s, 3H), 1.02 (s, 3H), 0.95 (s, 3H), 0.93 (s, 3H).

Example 25

Preparation of 4-((1R,3aS,5aR,5bR,7aR,11aS,11bR, 13aR,13bR)-3a-((2-(1H-imidazol-4-yl)ethylamino) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

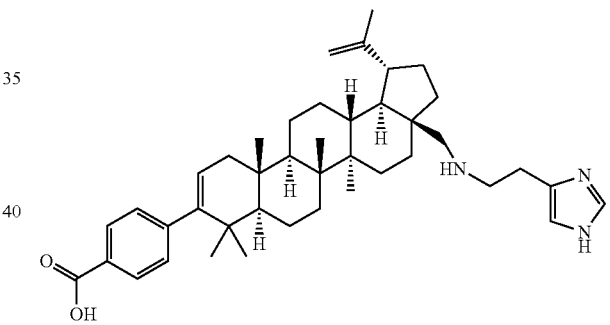

The title compound was prepared following the general procedures described above for the C28 amine formation and hydrolysis using 2-(1H-imidazol-4-yl)ethanamine as the reactant amine. The product was isolated as a white solid (40 mg, 63.4%). LCMS: m/e 638.5 (MH$^+$), 2.48 min (method 1). $^1$H NMR (400 MHz, MeOD) δ ppm 8.86 (d, J=1.3 Hz, 1H), 7.90 (d, J=8.3 Hz, 2H), 7.45 (s, 1H), 7.20 (d, J=8.3 Hz, 2H), 5.16-5.33 (m, 1H), 4.74 (s, 1H), 4.63 (s, 1H), 3.36-3.53 (m, 2H), 3.16-3.26 (m, 3H), 2.90 (d, J=12.8 Hz, 1H), 2.40-2.59 (m, 1H), 2.08-2.20 (m, 1H), 1.98-2.08 (m, 1H), 1.79-1.91 (m, 2H), 1.62-1.79 (m, 7H), 1.53-1.62 (m, 3H), 1.41-1.53 (m, 5H), 1.23-1.41 (m, 4H), 1.09-1.23 (m, 5H), 1.06 (s, 3H), 1.02 (s, 3H), 0.95 (s, 3H), 0.93 (s, 3H).

Example 26

Preparation of 4-((1R,3aS,5aR,5bR,7aR,11aS,11bR, 13aR,13bR)-3a-((2-((2-hydroxyethyl)(methyl) amino)ethylamino)methyl)-5a,5b,8,8,11a-pentam-ethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

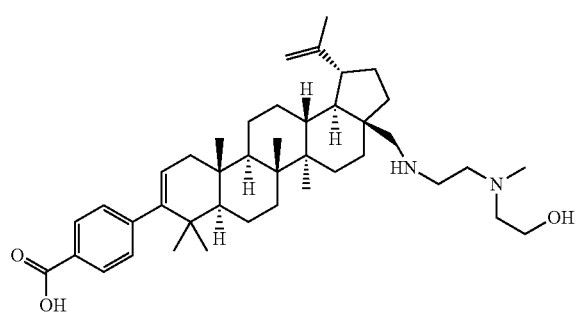

The title compound was prepared following the general procedures described above for the C28 amine formation and hydrolysis using 2-((2-aminoethyl)(methyl)amino)ethanol as the reactant amine. The product was isolated as a white solid (21 mg, 45.7%). LCMS: m/e 645.5 (MH$^+$), 2.49 min (method 1). $^1$H NMR (400 MHz, MeOD) δ ppm 7.90 (m, J=8.3 Hz, 2H), 7.20 (m, J=8.3 Hz, 2H), 5.21-5.34 (m, 1H), 4.74 (s, 1H), 4.63 (s, 1H), 3.82-3.97 (m, 2H), 3.50-3.75 (m, 4H), 3.30-3.43 (m, 3H), 2.98 (s, 3H), 2.93 (d, J=12.8 Hz, 1H), 2.49 (td, J=10.6, 5.8 Hz, 1H), 2.08-2.20 (m, 2H), 1.79-1.93 (m, 2H), 1.64-1.79 (m, 8H), 1.40-1.64 (m, 8H), 1.23-1.40 (m, 4H), 1.13-1.23 (m, 4H), 1.05 (s, 3H), 1.02 (s, 3H), 0.95 (s, 3H), 0.93 (s, 3H).

Example 27

Preparation of 4-((1R,3aS,5aR,5bR,7aR,11aS,11bR, 13aR,13bR)-3a-((4-tert-butoxy-4-oxobutylamino) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

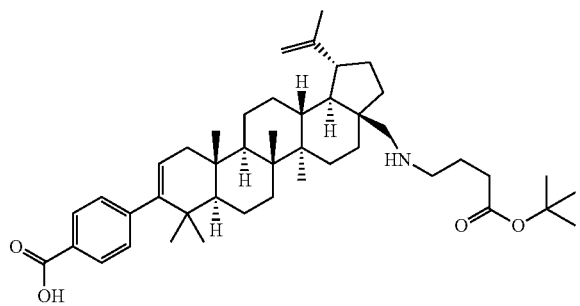

The title compound was prepared following the general procedures described above for the C28 amine formation and hydrolysis using tert-butyl 4-aminobutanoate hydrochloride as the reactant amine. The product was isolated as a white solid (2 mg, 3.62%). LCMS: m/e 689.5 (MH$^+$), 2.96 min (method 1). $^1$H NMR (400 MHz, CHLOROFORM-d) δ ppm 7.90 (m, J=8.3 Hz, 2H), 7.19 (m, J=8.1 Hz, 2H), 5.29 (d, J=4.3 Hz, 1H), 4.65 (s, 1H), 3.21 (s, 2H), 2.85 (d, J=4.5 Hz, 1H), 2.53-2.78 (m, 1H), 2.28-2.45 (m, 1H), 2.02-2.19 (m, 2H), 1.80-2.02 (m, 2H), 1.72 (s, 8H), 1.61 (s, 9H), 1.46-1.54 (m, 4H), 1.43 (d, J=7.1 Hz, 5H), 1.18-1.36 (m, 6H), 1.07-1.18 (m, 6H), 1.03 (s, 3H), 1.00 (s, 3H), 0.76-0.97 (m, 6H).

Example 28

Preparation of 4-((1R,3aS,5aR,5bR,7aR,11aS,11bR, 13aR,13bR)-3a-((3-carboxypropylamino)methyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

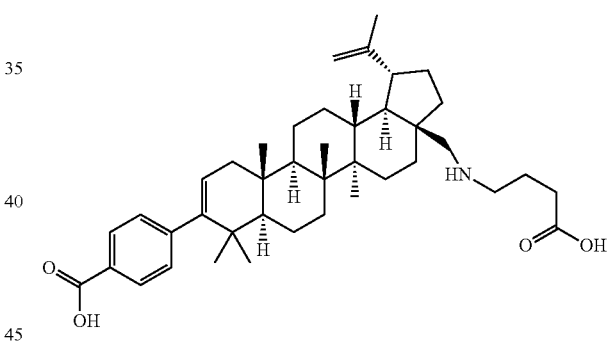

The title compound was prepared following the general procedures described above for the C28 amine formation and hydrolysis using tert-butyl 4-aminobutanoate hydrochloride as the reactant amine. The product was isolated as a white solid (2 mg, 3.62%). LCMS: m/e 630.5 (MH$^+$), 2.59 min (method 1). $^1$H NMR (400 MHz, acetonitrile-d$_3$) δ ppm 7.93 (d, J=8.3 Hz, 2H), 7.23 (d, J=8.3 Hz, 2H), 5.25-5.36 (m, 1H), 4.77 (s, 1H), 4.66 (s, 1H), 3.21-3.49 (m, 1H), 3.16 (t, J=7.7 Hz, 2H), 2.87 (d, J=12.8 Hz, 1H), 2.43-2.60 (m, 3H), 2.12-2.26 (m, 1H), 1.92-2.12 (m, 3H), 1.66-1.90 (m, 8H), 1.59 (d, J=6.0 Hz, 2H), 1.46-1.57 (m, 6H), 1.33-1.34 (m, 2H), 1.28 (d, J=15.4 Hz, 4H), 1.19 (s, 4H), 1.09 (s, 3H), 1.05 (s, 3H), 0.98 (s, 3H), 0.96 (s, 3H).

Example 29

Preparation of 4-((1R,3aS,5aR,5bR,7aR,11aS,11bR, 13aR,13bR)-5a,5b,8,8,11a-pentamethyl-3a-((2-oxopyrrolidin-1-yl)methyl)-1-(prop-1-en-2-yl)-2,3,3a, 4,5,5a,5b,6,7,7a,8,11,11a,11b,12,13,13a,13b-octadecahydro-1H-cyclopenta[a]chrysen-9-ylbenzoic acid

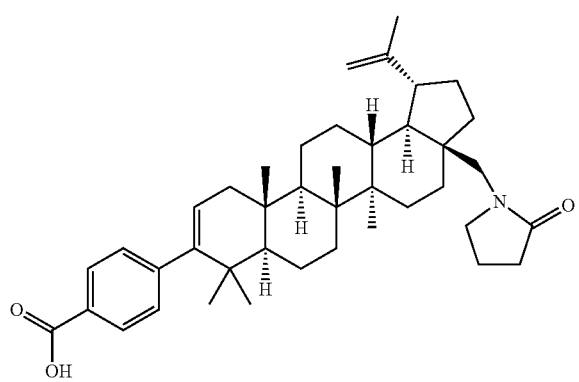

The title compound was prepared following the general procedures described above for the C28 amine formation and hydrolysis using tert-butyl 4-aminobutanoate hydrochloride as the reactant amine. The product was isolated as a white solid (3 mg, 6.28%). LCMS: m/e 612.4 (MH+), 3.18 min (method 1). $^1$H NMR (400 MHz, MeOD) δ ppm 7.88 (m, J=8.3 Hz, 2H), 7.17 (m, J=8.3 Hz, 2H), 5.14-5.31 (m, 1H), 4.69 (s, 1H), 4.56 (s, 1H), 3.36-3.58 (m, 3H), 3.13 (d, J=14.4 Hz, 1H), 2.46-2.61 (m, 1H), 2.34 (t, J=8.2 Hz, 2H), 2.00-2.19 (m, 4H), 1.97 (s, 1H), 1.58-1.75 (m, 8H), 1.47 (br. s., 7H), 1.30 (d, J=7.1 Hz, 3H), 1.24 (s, 4H), 1.14 (s, 3H), 1.00 (s, 3H), 0.98 (s, 3H), 0.92 (s, 3H), 0.91 (s, 3H).

Example 30

Preparation of 4-((1R,3aS,5aR,5bR,7aR,11aS,11bR, 13aR,13bR)-3a-((2-methoxy-2-oxoethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

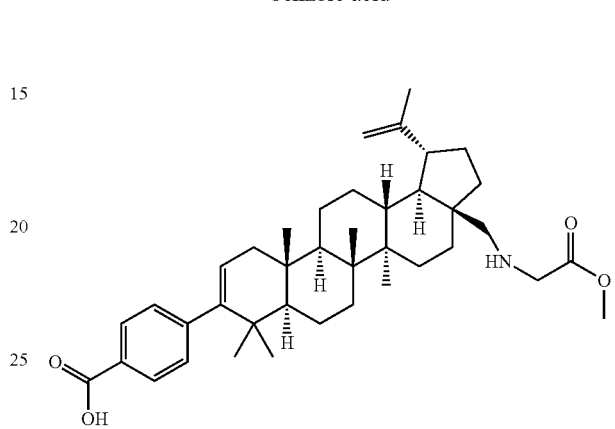

The title compound was prepared following the general procedures described above for the C28 amine formation and hydrolysis using methyl 2-aminoacetate hydrochloride as the reactant amine. The product was isolated as a white solid (27 mg, 45.9%). LCMS: m/e 616.5 (MH+), 2.14 min (method 3). $^1$H NMR (400 MHz, MeOD) δ ppm 7.90 (d, J=8.3 Hz, 2H), 7.20 (d, J=8.3 Hz, 2H), 5.20-5.33 (m, 1H), 4.72 (s, 1H), 4.62 (s, 1H), 4.05 (d, J=3.8 Hz, 2H), 3.86 (s, 3H), 3.33-3.45 (m, 1H), 2.89 (d, J=12.6 Hz, 1H), 2.45 (td, J=10.8, 5.7 Hz, 1H), 1.93-2.18 (m, 2H), 1.77-1.93 (m, 3H), 1.63-1.77 (m, 7H), 1.39-1.63 (m, 8H), 1.18-1.39 (m, 5H), 1.15 (s, 3H), 1.06 (s, 3H), 1.00 (s, 3H), 0.95 (s, 3H), 0.93 (s, 3H).

Example 31

Preparation of 4-((1R,3aS,5aR,5bR,7aR,11aS,11bR, 13aR,13bR)-3a-((carboxymethylamino)methyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

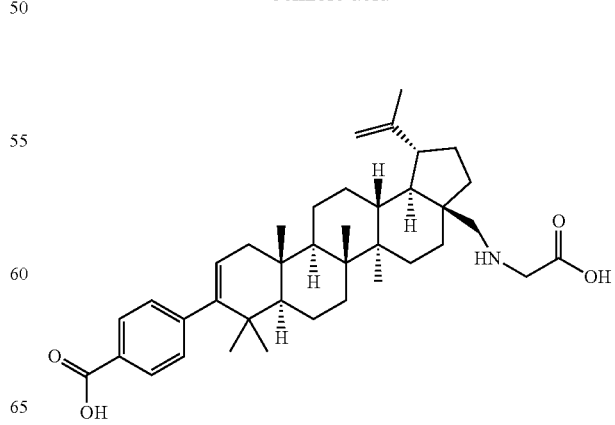

The title compound was prepared following the procedures described below:

To the solution of 4-((1R,3aS,5aR,5bR,7aR,11aS,11bR,13aR,13bR)-3a-((2-methoxy-2-oxoethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (50 mg, 0.081 mmol) in dioxane (2 ml) sodium hydroxide (0.162 ml, 0.162 mmol) was added. The resulting mixture was stirred at 70° C. for 2 h. The solvent was evaporated and the residue was purified by prep. HPLC to afford the title compound as a white solid (18 mg, 35%). LCMS: m/e 602.4 (MH$^+$), 2.32 min (method 3). $^1$H NMR (400 MHz, MeOD) δ ppm 7.90 (d, J=8.3 Hz, 2H), 7.20 (d, J=8.3 Hz, 2H), 5.18-5.40 (m, 1H), 4.73 (s, 1H), 4.62 (br. s., 1H), 3.96 (d, J=5.0 Hz, 2H), 2.78-2.94 (m, 1H), 2.37-2.60 (m, 1H), 2.10 (s, 2H), 1.78-1.92 (m, 3H), 1.62-1.78 (m, 6H), 1.38-1.61 (m, 8H), 1.16-1.38 (m, 6H), 1.11-1.16 (m, 4H), 1.07 (s, 3H), 1.01 (s, 3H), 0.95 (s, 3H), 0.93 (s, 3H).

Example 32

Preparation of 4-((1R,3aS,5aR,5bR,7aR,11aS,11bR,13aR,13bR)-3a-((2-methoxy-2-oxoethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid Example 33

Preparation of 4-((1R,3aS,5aR,5bR,7aR,11aS,11bR,13aR,13bR)-3a-((2-methoxy-2-oxoethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

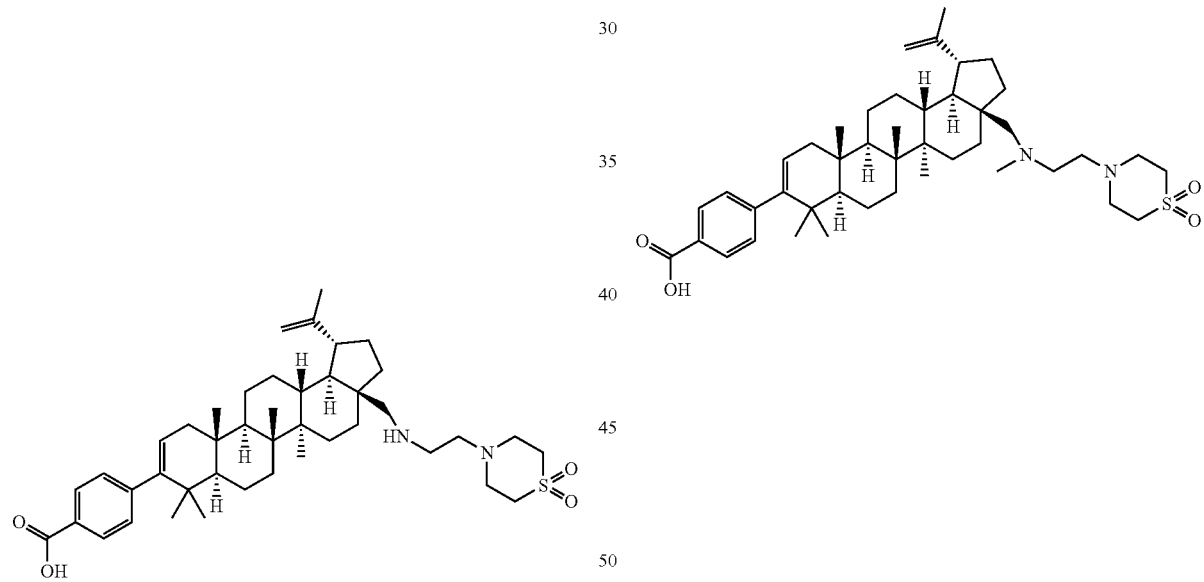

The title compound was prepared following the general procedures described above for the C28 amine formation and hydrolysis using methyl 2-aminoacetate hydrochloride as the reactant amine. The product was isolated as a white solid (34 mg, 58.1%). LCMS: m/e 704.5 (MH$^+$), 2.27 min (method 3). $^1$H NMR (400 MHz, MeOD) δ ppm 7.90 (d, J=8.3 Hz, 2H), 7.20 (d, J=8.1 Hz, 2H), 5.19-5.36 (m, 1H), 4.74 (s, 1H), 4.63 (s, 1H), 3.18-3.35 (m, 5H), 3.12 (br. s., 6H), 2.89-3.01 (m, 2H), 2.86 (d, J=13.8 Hz, 1H), 2.41-2.61 (m, 1H), 2.12 (dd, J=17.1, 6.3 Hz, 1H), 1.93-2.07 (m, 1H), 1.64-1.88 (m, 10H), 1.41-1.62 (m, 8H), 1.18-1.41 (m, 5H), 1.15 (s, 3H), 1.06 (s, 3H), 1.02 (s, 3H), 0.95 (s, 3H), 0.93 (s, 3H).

The title compound was prepared following the general procedures described above for the C28 amine formation, hydrolysis and tertiary amine formation using 4-(3-aminoethyl) thiomorpholine 1,1-dioxide as the reactant amine and formaldehyde as reactant aldehyde. The product was isolated as a white solid (10 mg, 46.6%). LCMS: m/e 719.7 (MH$^+$), 2.56 min (method 3). $^1$H NMR (400 MHz, MeOD) δ ppm 7.94 (m, 2H), 7.25 (m, 2H), 5.24-5.40 (m, 1H), 4.80 (d, J=1.5 Hz, 1H), 4.69 (s, 1H), 3.37-3.56 (m, 3H), 3.16 (d, J=8.3 Hz, 9H), 3.05-3.11 (m, 3H), 2.86-3.05 (m, 2H), 2.56 (td, J=11.1, 5.4 Hz, 1H), 2.17 (dd, J=17.1, 6.3 Hz, 1H), 2.01 (br. s., 2H), 1.69-1.93 (m, 9H), 1.44-1.69 (m, 9H), 1.25-1.42 (m, 3H), 1.13-1.25 (m, 4H), 1.12 (s, 3H), 1.05 (s, 3H), 0.99 (s, 3H), 0.98 (s, 3H).

Example 34

Preparation of 4-((1R,3aS,5aR,5bR,7aR,11aS,11bR, 13aR,13bR)-5a,5b,8,8,11a-pentamethyl-3a-((2-(2-oxopyrrolidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

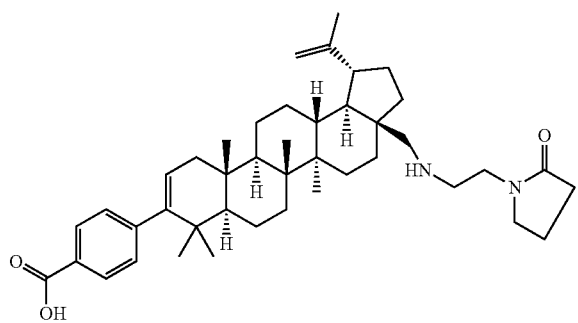

The title compound was prepared following the general procedures described above for the C28 amine formation and hydrolysis using 1-(2-aminoethyl)pyrrolidin-2-one as the reactant amine. The product was isolated as a white solid (34 mg, 63.8%). LCMS: m/e 655.5 (MH+), 2.33 min (method 3). ¹H NMR (400 MHz, MeOD) δ ppm 7.90 (m, J=8.3 Hz, 2H), 7.20 (m, J=8.3 Hz, 2H), 5.22-5.34 (m, 1H), 4.74 (d, J=1.8 Hz, 1H), 4.62 (s, 1H), 3.57-3.71 (m, 2H), 3.53 (t, J=7.2 Hz, 2H), 3.27-3.35 (m, 2H), 3.25 (d, J=12.8 Hz, 1H), 2.92 (d, J=13.1 Hz, 1H), 2.50 (td, J=10.6, 5.7 Hz, 1H), 2.42 (t, J=8.2 Hz, 2H), 1.97-2.18 (m, 4H), 1.62-1.87 (m, 10H), 1.41-1.62 (m, 8H), 1.20-1.41 (m, 4H), 1.13-1.20 (m, 4H), 1.06 (s, 3H), 1.02 (s, 3H), 0.95 (s, 3H), 0.93 (s, 3H).

Example 35

Preparation of 4-((1R,3aS,5aR,5bR,7aR,11aS,11bR, 13aR,13bR)-5a,5b,8,8,11a-pentamethyl-1-(prop-1-en-2-yl)-3a#4-sulfamoylbenzylamino)methyl)-2,3,3a,4,5,5a,5b,6,7,7a,8,11,11a,11b,12,13,13a,13b-octadecahydro-1H-cyclopenta[a]chrysen-9-yl)benzoic acid

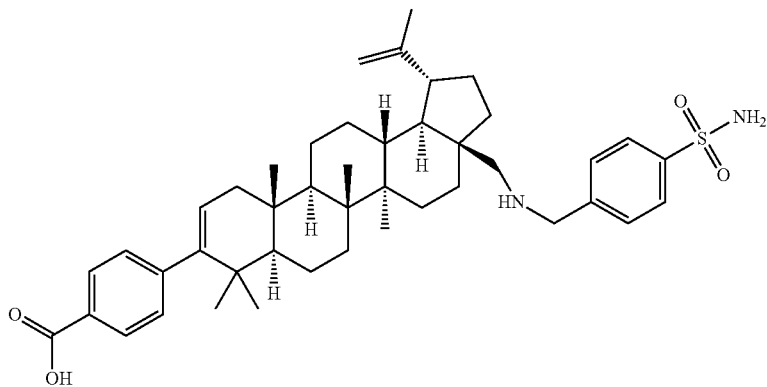

The title compound was prepared following the general procedures described above for the C28 amine formation and hydrolysis using 4-(aminomethyl)benzenesulfonamide as the reactant amine. The product was isolated as a white solid (14 mg, 26.1%). LCMS: m/e 713.4 (MH+), 2.30 min (method 3). ¹H NMR (400 MHz, MeOD) δ ppm 7.97-8.08 (m, 2H), 7.90 (m, J=8.3 Hz, 2H), 7.74 (m, J=8.3 Hz, 2H), 7.19 (d, J=8.3 Hz, 2H), 5.15-5.35 (m, 1H), 4.71 (s, 1H), 4.60 (s, 1H), 4.41-4.54 (m, 1H), 4.29 (d, J=13.3 Hz, 1H), 2.95-3.12 (m, 1H), 2.83 (d, J=12.8 Hz, 1H), 2.41 (td, J=11.1, 5.4 Hz, 1H), 2.09 (dd, J=17.1, 6.3 Hz, 1H), 1.78-1.99 (m, 1H), 1.57-1.77 (m, 8H), 1.30-1.54 (m, 9H), 1.18-1.29 (m, 3H), 1.03-1.16 (m, 2H), 1.01 (br. s., 1H), 0.98 (s, 6H), 0.94 (s, 3H), 0.91 (s, 3H), 0.78 (s, 3H).

Example 36

Preparation of 4-((1R,3aS,5aR,5bR,7aR,11aS,11bR, 13aR,13bR)-5a,5b,8,8,11a-pentamethyl-1-(prop-1-en-2-yl)-3a-((4-sulfamylphenethylamino)methyl)-2, 3,3a,4,5,5a,5b,6,7,7a,8,11,11a,11b,12,13,13a,13b-octadecahydro-1H-cyclopenta[a]chrysen-9-yl) benzoic acid

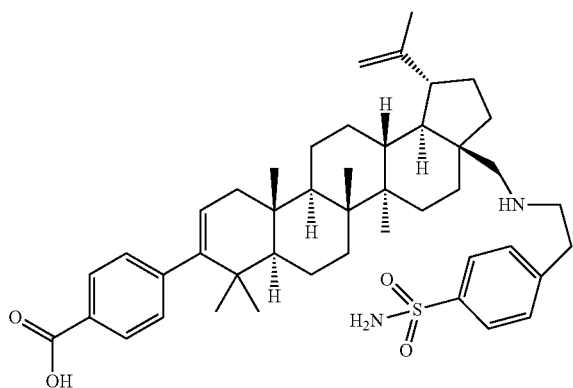

The title compound was prepared following the general procedures described above for the C28 amine formation and hydrolysis using 4-(2-aminoethyl)benzenesulfonamide as the reactant amine. The product was isolated as a white solid (18 mg, 33.5%). LCMS: m/e 727.4 (MH$^+$), 2.30 min (method 3). $^1$H NMR (400 MHz, MeOD) δ ppm 7.82-7.94 (m, 4H), 7.48 (d, J=8.3 Hz, 2H), 7.20 (d, J=8.3 Hz, 2H), 5.28 (d, J=4.8 Hz, 1H), 4.74 (s, 1H), 4.63 (s, 1H), 3.31-3.39 (m, 2H), 3.27-3.29 (m, 1H), 3.09-3.19 (m, 2H), 2.82-2.92 (m, 1H), 2.49 (td, J=10.6, 5.9 Hz, 1H), 2.09-2.20 (m, 1H), 1.97-2.09 (m, 1H), 1.78-1.89 (m, 2H), 1.63-1.78 (m, 8H), 1.40-1.62 (m, 8H), 1.18-1.40 (m, 5H), 1.15 (s, 3H), 1.06 (s, 3H), 1.02 (s, 3H), 0.95 (s, 3H), 0.90 (s, 3H).

Example 37

Preparation of 4-((1R,3aS,5aR,5bR,7aR,11aS,11bR, 13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b, 12,13,13a,13b-octadecahydro-1H-cyclopenta[a] chrysen-9-yl)benzoic acid

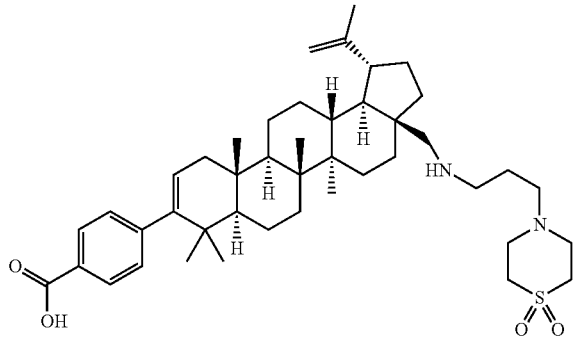

To a solution of 4-((1R,3aS,5aR,5bR,7aR,11aS,11bR, 13aR,13bR)-5a,5b,8,8,11a-pentamethyl-1-(prop-1-en-2-yl)-3a-((3-(1-dioxo-thiomorpholino)propylamino)methyl)-2,3, 3a,4,5,5a,5b,6,7,7a,8,11,11a,11b,12,13,13a,13b-octadecahydro-1H-cyclopenta[a]chrysen-9-yl)benzoic acid (50 mg, 0.070 mmol) in MeOH (15 ml) and acetic acid (5.00 ml) was added palladium on carbon (15 mg, 0.141 mmol). The reaction was conducted in a Parr shaker at 40 psi at rt for 16 h. A 30% conversion was observed. The solvent was removed in vacuo. The residue was purified by prep. HPLC to afford the title compound as a white solid (10 mg, 19.0%). LCMS: m/e 721.2 (MH$^+$), 2.39 min (method 3). $^1$H NMR (400 MHz, MeOD) δ ppm 7.95 (m, J=8.3 Hz, 2H), 7.25 (m, J=8.3 Hz, 2H), 5.34 (dd, J=6.1, 1.6 Hz, 1H), 3.10-3.29 (m, 11H), 2.78-2.92 (m, 3H), 2.20 (dd, J=17.2, 6.4 Hz, 1H), 1.93-2.12 (m, 3H), 1.78 (d, J=12.0 Hz, 2H), 1.75 (d, J=7.8 Hz, 4H), 1.43-1.67 (m, 10H), 1.25-1.41 (m, 4H), 1.18-1.25 (m, 3H), 1.11 (br. s., 2H), 1.08 (d, J=3.0 Hz, 6H), 1.00 (s, 3H), 0.98 (s, 3H), 0.93 (d, J=6.8 Hz, 3H), 0.86 (d, J=6.8 Hz, 3H).

Example 38

Preparation of 4-((1R,3aS,5aR,5bR,7aR,11aS,11bR, 13aR,13bR)-3a-((4-methoxy-4-oxobutylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

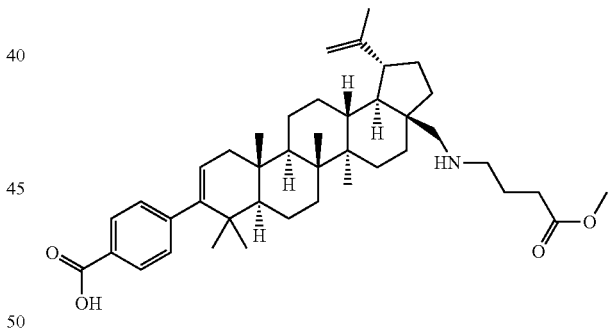

The title compound was prepared following the general procedures described above for the C28 amine formation and hydrolysis using methyl 4-aminobutanoate hydrochloride as the reactant amine. The product was isolated as a white solid (7 mg, 48.2%). LCMS: m/e 644.4 (MH$^+$), 2.21 min (method 3). $^1$H NMR (500 MHz, MeOD) δ ppm 7.82-8.02 (m, 2H), 7.19-7.30 (m, 2H), 5.22-5.39 (m, 1H), 4.78 (s, 1H), 4.67 (br. s., 1H), 3.72 (s, 3H), 3.27 (d, J=13.1 Hz, 1H), 3.08-3.22 (m, 2H), 2.88 (d, J=12.8 Hz, 1H), 2.43-2.62 (m, 3H), 2.12-2.31 (m, 1H), 1.96-2.12 (m, 3H), 1.69-1.88 (m, 10H), 1.47-1.67

(m, 8H), 1.22-1.39 (m, 4H), 1.14-1.22 (m, 4H), 1.11 (s, 3H), 1.06 (s, 3H), 0.99 (s, 3H), 0.97 (s, 3H).

Example 39

Preparation of 4-((1R,3aS,5aR,5bR,7aR,11aS,11bR, 13aR,13bR)-3a-((2-(dimethylamino)-2-oxoethylamino)methyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

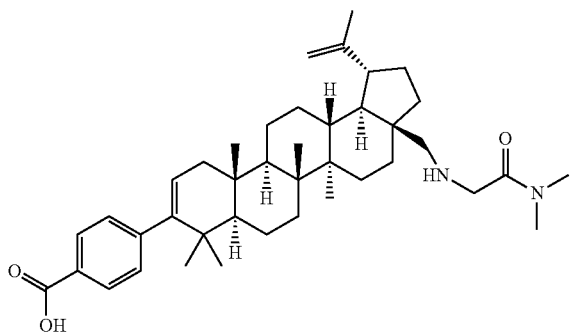

The title compound was prepared following the general procedures described above for the C28 amine formation and hydrolysis using 2-amino-N,N-dimethylacetamide hydrochloride as the reactant amine. The product was isolated as a white solid (34 mg, 87.9%). LCMS: m/e 629.4 (MH$^+$), 2.37 min (method 3). $^1$H NMR (400 MHz, MeOD) δ ppm 7.94 (m, J=8.5 Hz, 2H), 7.24 (m, J=8.3 Hz, 2H), 5.26-5.38 (m, 1H), 4.75 (d, J=1.5 Hz, 1H), 4.65 (s, 1H), 4.00-4.21 (m, 2H), 3.25-3.40 (m, 1H), 2.98-3.12 (m, 6H), 2.86 (d, J=12.5 Hz, 1H), 2.47 (td, J=10.9, 5.6 Hz, 1H), 2.04-2.26 (m, 2H), 1.85-2.04 (m, 3H), 1.67-1.85 (m, 6H), 1.43-1.67 (m, 8H), 1.19-1.42 (m, 5H), 1.13-1.19 (m, 4H), 1.08 (s, 3H), 1.05 (s, 3H), 1.00 (s, 3H), 0.93 (s, 3H).

Example 40

Preparation of 4-((1R,3aS,5aR,5bR,7aR,11aS,11bR, 13aR,13bR)-3a-(((3-(1,1-dioxido-2-isothiazolidinyl) propyl)amino)methyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)benzoic acid

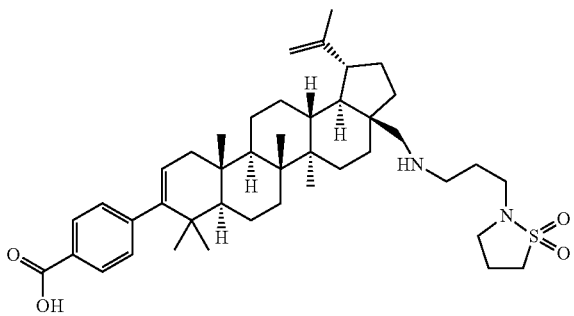

The title compound was prepared following the general procedures described above for the C28 amine formation and hydrolysis using 2-amino-N,N-dimethylacetamide hydrochloride as the reactant amine. The product was isolated as a white solid (34 mg, 77.9%). LCMS: m/e 705.8 (MH$^+$), 2.34 min (method 3). $^1$H NMR (400 MHz, MeOD) δ ppm 7.94 (m, J=8.3 Hz, 2H), 7.24 (m, J=8.3 Hz, 2H), 5.25-5.42 (m, 1H), 4.78 (d, J=1.5 Hz, 1H), 4.66 (s, 1H), 3.31-3.39 (m, 1H), 3.13-3.30 (m, 8H), 2.89 (d, J=13.1 Hz, 1H), 2.45-2.65 (m, 1H), 2.30-2.45 (m, 2H), 1.99-2.21 (m, 4H), 1.67-1.91 (m, 10H), 1.45-1.67 (m, 8H), 1.24-1.45 (m, 4H), 1.12-1.24 (m, 4H), 1.09 (s, 3H), 1.04 (s, 3H), 0.99 (s, 3H), 0.97 (s, 3H).

Example 41

Preparation of 4-((1R,3aS,5aR,5bR,7aR,11aS,11bR, 13aR,13bR)-5a,5b,8,8,11a-pentamethyl-3a-((2-(methylsulfonyl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

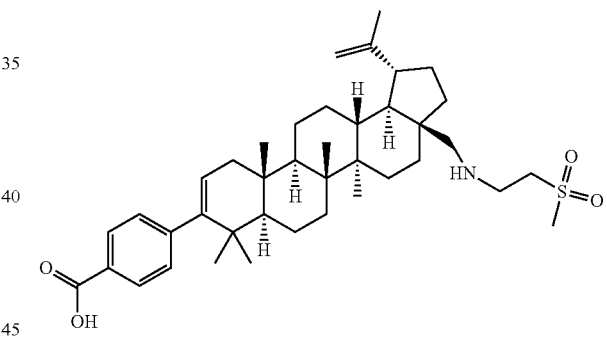

The title compound was prepared following the general procedures described above for the C28 amine formation and hydrolysis using 2-(methylsulfonyl)ethanamine hydrochloride as the reactant amine. The product was isolated as a white solid (22 mg, 47.8%). LCMS: m/e 650.3 (MH$^+$), 2.09 min (method 3). $^1$H NMR (400 MHz, CHLOROFORM-d) δ ppm 8.01 (m, J=8.3 Hz, 2H), 7.25 (m, J=8.3 Hz, 2H), 5.32 (d, J=4.5 Hz, 1H), 4.74 (s, 1H), 4.66 (s, 1H), 3.64-3.88 (m, 4H), 3.34 (br. s., 1H), 3.06-3.22 (m, 3H), 2.84 (d, J=11.8 Hz, 1H), 2.32-2.45 (m, 1H), 2.12 (dd, J=17.2, 6.4 Hz, 1H), 2.05 (m, 1H), 1.79 (br. s., 1H), 1.61-1.76 (m, 8H), 1.56 (d, J=8.3 Hz, 3H), 1.39-1.51 (m, 4H), 1.15-1.39 (m, 5H), 1.07-1.15 (m, 4H), 1.03 (s, 3H), 1.00 (s, 3H), 0.96 (d, J=3.3 Hz, 6H).

Example 42

Preparation of 4-((1R,3aS,5aR,5bR,7aR,11aS,11bR, 13aR,13bR)-3a-((2,2-diethoxyethylamino)methyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid

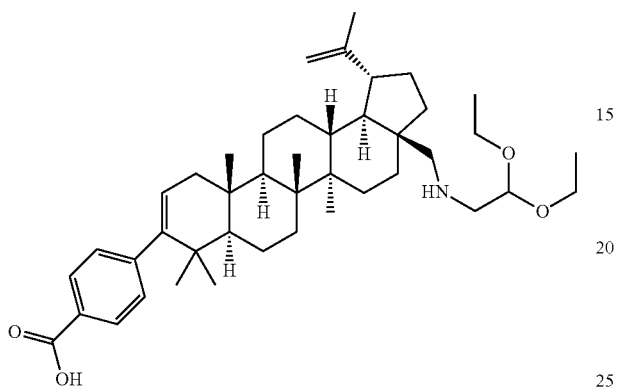

The title compound was prepared following the general procedures described above for the C28 amine formation and hydrolysis using 2,2-diethoxyethanamine as the reactant amine. The product was isolated as a white solid (5 mg, 8.4%). LCMS: m/e 660.4 (MH$^+$), 2.39 min (method 3). $^1$H NMR (400 MHz, MeOD) δ ppm 7.94 (m, J=8.3 Hz, 2H), 7.24 (m, J=8.5 Hz, 2H), 5.27-5.41 (m, 1H), 4.92-4.98 (m, 1H), 4.74-4.81 (m, 1H), 4.67 (d, J=1.8 Hz, 1H), 3.79-3.95 (m, J=9.5, 7.1, 7.1, 7.1, 7.1 Hz, 2H), 3.63-3.79 (m, J=9.6, 7.0, 7.0, 7.0, 2.9 Hz, 2H), 3.48 (d, J=13.8 Hz, 1H), 3.22-3.31 (m, 2H), 2.91-3.08 (m, 1H), 2.47-2.55 (m, 1H), 2.18 (dd, J=17.1, 6.3 Hz, 1H), 2.05 (m, 1H), 1.69-1.93 (m, 9H), 1.62 (br. s., 2H), 1.46-1.61 (m, 6H), 1.24-1.44 (m, 10H), 1.13-1.24 (m, 5H), 1.11 (s, 3H), 1.06 (s, 3H), 0.99 (s, 3H), 0.98 (s, 3H).

Example 43

Preparation of 4-((1R,3aS,5aR,5bR,7aR,11aS,11bR, 13aR,13bR)-5a,5b,8,8,11a-pentamethyl-3a-((2-(piperazin-1-ylsulfonyl)ethylamino)methyl)-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

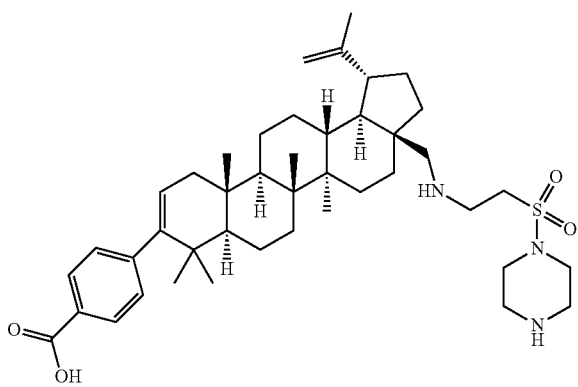

The title compound was prepared following the general procedures described above for the C28 amine formation and hydrolysis using tert-butyl 4-(2-aminoethylsulfonyl)piperazine-1-carboxylate hydrochloride as the reactant amine. The product was isolated as a white solid (47 mg, 91.0%). LCMS: m/e 720.3 (MH$^+$), 2.31 min (method 3). $^1$H NMR (400 MHz, MeOD) δ ppm 7.94 (m, 2H), 7.24 (m, 2H), 5.20-5.41 (m, 1H), 4.78 (d, J=1.8 Hz, 1H), 4.66 (s, 1H), 3.64-3.74 (m, 6H), 3.56-3.64 (m, 2H), 3.35-3.41 (m, 4H), 3.31-3.35 (m, 1H), 2.96 (d, J=13.1 Hz, 1H), 2.47-2.61 (m, 1H), 2.00-2.24 (m, 2H), 1.69-1.92 (m, 10H), 1.60 (br. s., 2H), 1.43-1.59 (m, 6H), 1.26-1.43 (m, 3H), 1.17-1.25 (m, 4H), 1.14 (d, J=2.8 Hz, 1H), 1.09 (s, 3H), 1.04 (s, 3H), 0.99 (s, 3H), 0.95 (s, 3H).

Example 44

Preparation of 4-((1R,3aS,5aR,5bR,7aR,11aS,11bR, 13aR,13bR)-5a,5b,8,8,11a-pentamethyl-3a-((methyl (2-(4-methylpiperazin-1-ylsulfonyl)ethyl)amino) methyl)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

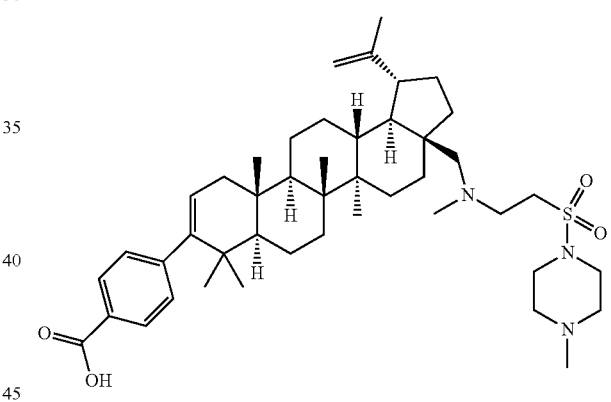

The title compound was prepared following the general procedures described above for the C28 amine formation, hydrolysis and tertiary amine formation using tert-butyl 4-(2-aminoethylsulfonyl)piperazine-1-carboxylate hydrochloride as the reactant amine and formaldehyde as the reactant aldehyde. The product was isolated as a white solid (17 mg, 33.1%). LCMS: m/e 748.5 (MH$^+$), 2.37 min (method 3). $^1$H NMR (400 MHz, MeOD) δ ppm 7.94 (m, J=8.3 Hz, 2H), 7.24 (m, J=8.5 Hz, 2H), 5.23-5.40 (m, 1H), 4.79 (d, J=1.3 Hz, 1H), 4.68 (s, 1H), 4.00 (br. s., 1H), 3.77-3.95 (m, 4H), 3.70 (t, J=7.4 Hz, 4H), 3.38-3.58 (m, 3H), 3.26-3.37 (m, 1H), 3.13-3.25 (m, 1H), 3.07 (s, 3H), 2.98 (s, 3H), 2.56 (dt, J=10.9, 5.5 Hz, 1H), 2.00-2.25 (m, 2H), 1.79-2.00 (m, 3H), 1.69-1.79 (m, 5H), 1.46-1.69 (m, 9H), 1.42 (d, J=10.8 Hz, 1H), 1.24-1.40 (m, 4H), 1.21 (s, 3H), 1.14-1.19 (m, 1H), 1.11 (s, 3H), 1.05 (s, 3H), 1.01 (s, 3H), 0.97 (s, 3H).

Example 45

Preparation of 4-((1R,3aS,5aR,5bR,7aR,11aS,11bR,13aR,13bR)-5a,5b,8,8,11a-pentamethyl-1-(prop-1-en-2-yl)-3a#2-sulfamoylethylamino)methyl)-2,3,3a,4,5,5a,5b,6,7,7a,8,11,11a,11b,12,13,13a,13b-octadecahydro-1H-cyclopenta[a]chrysen-9-yl)benzoic acid

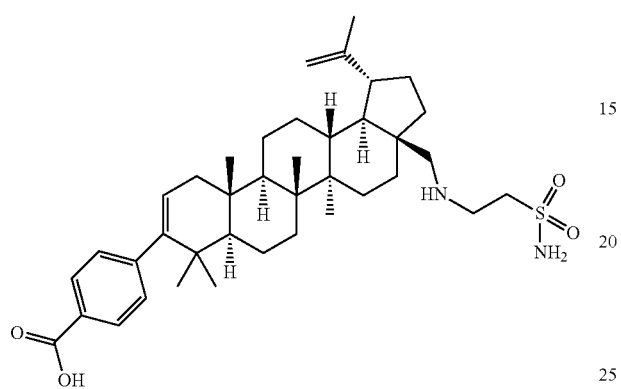

The title compound was prepared following the general procedures described above for the C28 amine formation and hydrolysis using 2-aminoethanesulfonamide as the reactant amine. The product was isolated as a white solid (23 mg, 59.3%). LCMS: m/e 651.3 (MH$^+$), 2.35 min (method 3). $^1$H NMR (400 MHz, MeOD) δ ppm 7.94 (m, J=8.5 Hz, 2H), 7.24 (m, J=8.5 Hz, 2H), 5.18-5.40 (m, 1H), 4.78 (d, J=1.8 Hz, 1H), 4.67 (s, 1H), 3.57-3.65 (m, 2H), 3.42 (m, 1H), 3.33 (dq, J=3.2, 1.5 Hz, 2H), 2.97 (d, J=12.8 Hz, 1H), 2.54 (td, J=10.7, 5.6 Hz, 1H), 1.98-2.22 (m, 2H), 1.67-1.92 (m, 10H), 1.57 (dd, J=19.8, 7.5 Hz, 5H), 1.50 (d, J=13.8 Hz, 3H), 1.24-1.45 (m, 4H), 1.18-1.24 (m, 4H), 1.10 (s, 3H), 1.04 (s, 3H), 0.99 (s, 3H), 0.97 (s, 3H).

Example 46

Preparation of 4-((1R,3aS,5aR,5bR,7aR,11aS,11bR,13aR,13bR)-3a-((4-(methoxycarbonyl)phenethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

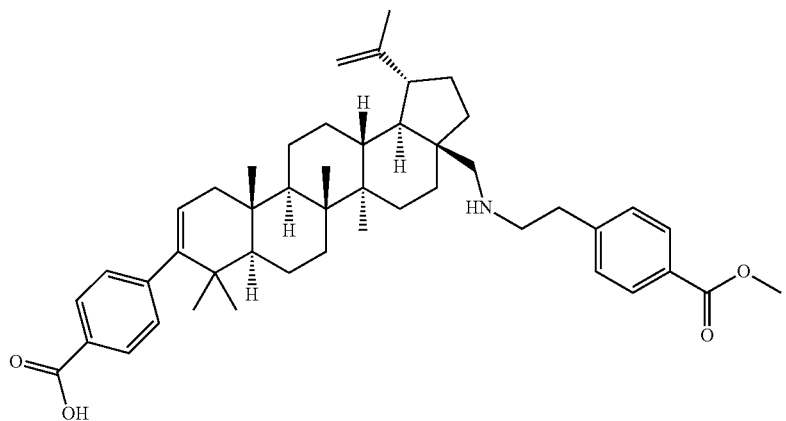

The title compound was prepared following the general procedures described above for the C28 amine formation and hydrolysis using methyl 4-(2-aminoethyl)benzoate as the reactant amine. The product was isolated as a white solid (35 mg, 90.0%). LCMS: m/e 706.3 (MH$^+$), 2.34 min (method 3).

Example 47

Preparation 4-((1R,3aS,5aR,5bR,7aR,11aS,11bR,13aR,13bR)-3a-((4-carboxyphenethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

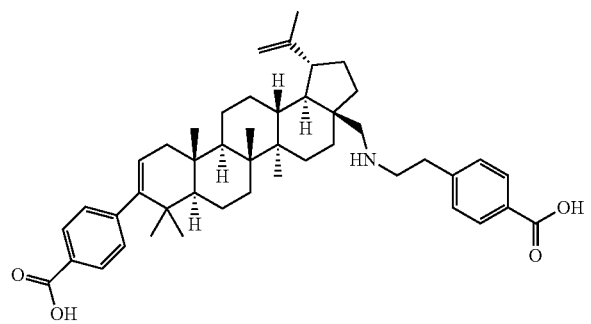

The title compound was prepared following the procedures described below:

To the solution of 4-((1R,3aS,5aR,5bR,7aR,11aS,11bR,13aR,13bR)-3a-((4-(methoxycarbonyl)phenethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (5 mg) in dioxane (2 ml) and MeOH (2 ml), 3 mg of lithium hydroxide was added followed by 0.5 ml of water. The resulting clear solution was stirred at 50° C. for 12 h. The solvent was removed in vacuo and yellow solid was obtained. The crude material was purified by prep. HPLC to afford the title compound as a white solid (1.1 mg, 22.0%). LCMS: m/e 692.5 (MH$^+$), 2.28 min (method 3). $^1$H NMR (400 MHz, MeOD) δ ppm 6.50 (d, J=8.3 Hz, 2H), 6.38 (d, J=8.3 Hz, 2H), 5.91 (d, J=8.3 Hz, 2H), 5.68 (d, J=8.3 Hz, 2H), 3.75-3.81 (m, 1H), 3.22 (s, 1H), 3.11 (s, 1H), 1.79-1.91 (m, 2H), 1.66-1.75 (m, 1H), 1.51-1.66 (m, 2H), 1.33 (s, 1H), 0.84-1.02 (m, 1H), 0.44-0.68 (m, 2H), 0.10-0.33 (m, 8H), 0.12-0.10 (m, 6H), 0.34-0.12 (m, 6H), 0.42-0.34 (m, 6H), 0.46 (s, 3H), 0.49 (s, 3H), 0.57 (s, 3H), 0.59 (s, 3H).

Example 48

Preparation of 4-((1R,3aS,5aR,5bR,7aR,11aS,11bR,13aR,13bR)-3a-((2-(4,4-difluoropiperidin-1-yl)ethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

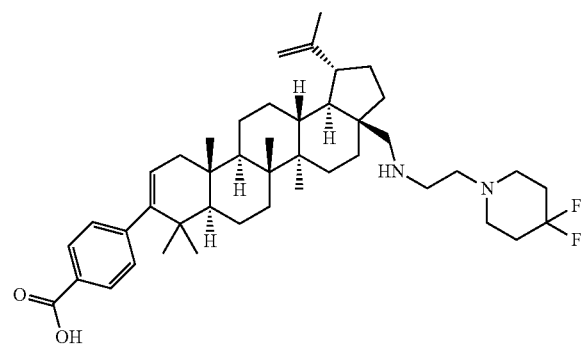

The title compound was prepared following the general procedures described above for the C28 amine formation and hydrolysis using 2-(4,4-difluoropiperidin-1-yl)ethanamine as the reactant amine. The product was isolated as a white solid (45 mg, 62.5%). LCMS: m/e 691.6 (MH$^+$), 2.54 min (method 3). $^1$H NMR (400 MHz, MeOD) δ ppm 7.94 (m, 2H), 7.24 (m, 2H), 5.31 (d, J=4.5 Hz, 1H), 4.72-4.82 (m, 1H), 4.66 (s, 1H), 3.49-3.67 (m, 2H), 3.36-3.49 (m, 2H), 3.31 (d, J=5.0 Hz, 5H), 2.89-3.02 (m, 1H), 2.52 (dt, J=10.6, 5.4 Hz, 1H), 2.23-2.41 (m, 4H), 2.01-2.23 (m, 2H), 1.83-1.95 (m, 2H), 1.67-1.83 (m, 8H), 1.43-1.67 (m, 8H), 1.27-1.43 (m, 3H), 1.24 (br. s., 1H), 1.11-1.21 (m, 4H), 1.09 (s, 3H), 1.05 (s, 3H), 0.99 (s, 3H), 0.94 (s, 3H).

Example 49

Preparation of 4-((1R,3aS,5aR,5bR,7aR,11aS,11bR,13aR,13bR)-3a-(((S)-1,4-dimethoxy-1,4-dioxobutan-2-ylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

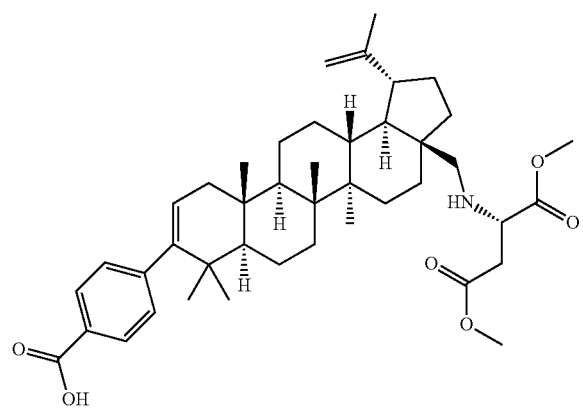

The title compound was prepared following the general procedures described above for the C28 amine formation and hydrolysis using (S)-dimethyl 2-aminosuccinate as the reactant amine. The product was isolated as a white solid (6 mg, 15.7%). LCMS: m/e 688.6 (MH$^+$), 2.73 min (method 3). $^1$H NMR (400 MHz, MeOD) δ ppm 7.96 (m, 2H), 7.24 (m, J=8.5 Hz, 2H), 5.22-5.36 (m, 1H), 4.78 (s, 1H), 4.67 (s, 1H), 4.62 (dd, J=8.4, 4.6 Hz, 1H), 3.92 (s, 3H), 3.83 (s, 3H), 3.44 (m, 1H), 3.22 (m, 1H), 2.93-3.16 (m, 2H), 2.38-2.62 (m, 1H), 2.11-2.26 (m, 2H), 2.07 (br. s., 1H), 1.88-2.03 (m, 2H), 1.67-1.88 (m, 6H), 1.45-1.67 (m, 8H), 1.25-1.45 (m, 4H), 1.15-1.25 (m, 3H), 1.09-1.15 (m, 2H), 1.06 (s, 3H), 1.04 (s, 3H), 1.00 (s, 3H), 0.98 (s, 3H).

Example 50

Preparation of 4-((1R,3aS,5aR,5bR,7aR,11aS,11bR, 13aR,13bR)-3a-((1-carboxycyclopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

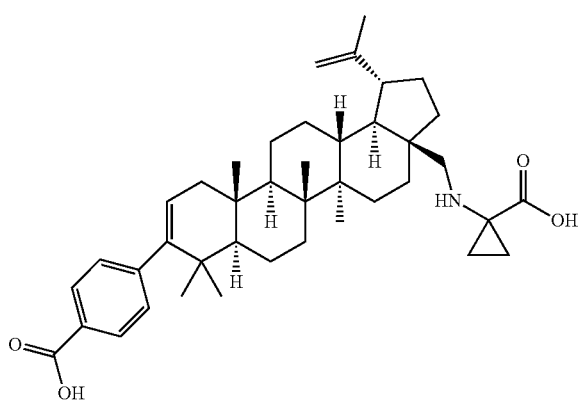

The title compound was prepared following the general procedures described above for the C28 amine formation and hydrolysis using methyl 1-aminocyclopropanecarboxylate hydrochloride as the reactant amine. The product was isolated as a white solid (10 mg, 50%). LCMS: m/e 628.6 (MH$^+$), 2.28 min (method 3). $^1$H NMR (400 MHz, ACETONITRILE-d$_3$) δ ppm 7.91 (m, J=7.8 Hz, 2H), 7.24 (m, J=8.0 Hz, 2H), 5.28 (d, J=5.0 Hz, 1H), 4.72 (s, 1H), 4.62 (br. s., 1H), 3.43 (d, J=12.5 Hz, 1H), 2.94 (d, J=12.5 Hz, 1H), 2.47 (br. s., 1H), 2.12 (dd, J=17.2, 6.7 Hz, 1H), 2.00-2.08 (m, 1H), 1.92 (d, J=2.5 Hz, 1H), 1.85 (br. s., 2H), 1.62-1.77 (m, 8H), 1.57 (br. s., 5H), 1.44 (br. s., 6H), 1.33 (br. s., 1H), 1.28 (br. s., 3H), 1.08-1.19 (m, 4H), 1.04 (s, 3H), 1.01 (s, 3H), 0.86-0.97 (m, 6H).

Example 51

Preparation of 4-((1R,3aS,5aR,5bR,7aR,11aS,11bR, 13aR,13bR)-3a-((1-(methoxycarbonyl)cyclopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

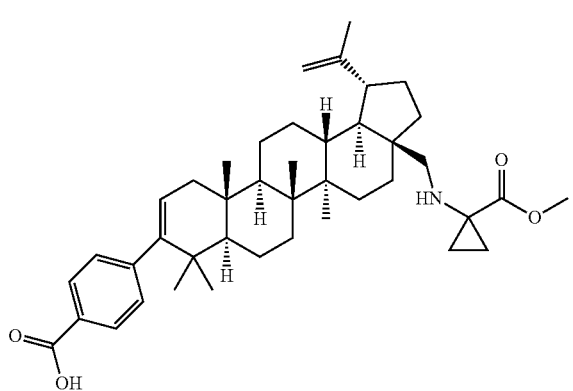

The title compound was prepared following the general procedures described above for the C28 amine formation and hydrolysis using methyl 1-aminocyclopropanecarboxylate hydrochloride as the reactant amine. The product was isolated as a white solid (12 mg, 41.3%). LCMS: m/e 642.6 (MH$^+$), 2.64 min (method 3). $^1$H NMR (400 MHz, MeOD) δ ppm 7.94 (m, 2H), 7.25 (m, 2H), 5.32 (d, J=4.5 Hz, 1H), 4.77 (s, 1H), 4.66 (s, 1H), 3.76-3.87 (m, 3H), 3.53 (d, J=12.5 Hz, 1H), 3.05 (d, J=12.8 Hz, 1H), 2.44-2.62 (m, 1H), 2.02-2.26 (m, 2H), 1.87-2.01 (m, 3H), 1.59-1.80 (m, 13H), 1.48-1.57 (m, 6H), 1.27-1.44 (m, 3H), 1.13-1.27 (m, 5H), 1.10 (s, 3H), 1.06 (s, 3H), 1.01 (s, 3H), 0.95 (s, 3H).

Example 52

Preparation of 4-((1R,3aS,5aR,5bR,7aR,11aS,11bR, 13aR,13bR)-3a-((1-((diethylamino)methyl)cyclopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

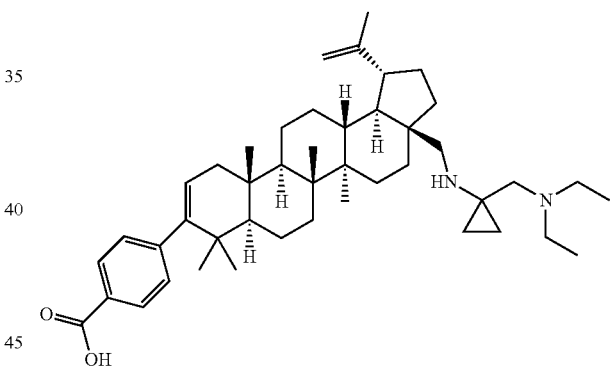

The title compound was prepared following the general procedures described above for the C28 amine formation and hydrolysis using 1-((diethylamino)methyl)cyclopropane amine dihydrochloride as the reactant amine. The product was isolated as a white solid (15 mg, 25.0%). LCMS: m/e 669.6 (MH$^+$), 2.70 min (method 3). $^1$H NMR (400 MHz, MeOD) δ ppm 7.95 (m, 2H), 7.24 (m, 2H), 5.31 (d, J=4.5 Hz, 1H), 4.79 (d, J=1.5 Hz, 1H), 4.67 (s, 1H), 3.83-4.00 (m, 1H), 3.30-3.54 (m, 6H), 3.02 (d, J=12.5 Hz, 1H), 2.48-2.70 (m, 1H), 2.16 (dd, J=17.1, 6.5 Hz, 1H), 1.91-2.10 (m, 1H), 1.64-1.88 (m, 10H), 1.45-1.64 (m, 8H), 1.36-1.45 (m, 7H), 1.21-1.36 (m, 6H), 1.11-1.21 (m, 5H), 1.08 (s, 3H), 1.05 (s, 3H), 0.99 (s, 3H), 0.97 (s, 3H).

Example 53

Preparation of 4-((1R,3aS,5aR,5bR,7aR,11aS,11bR,13aR,13bR)-3a-((furan-3-ylmethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

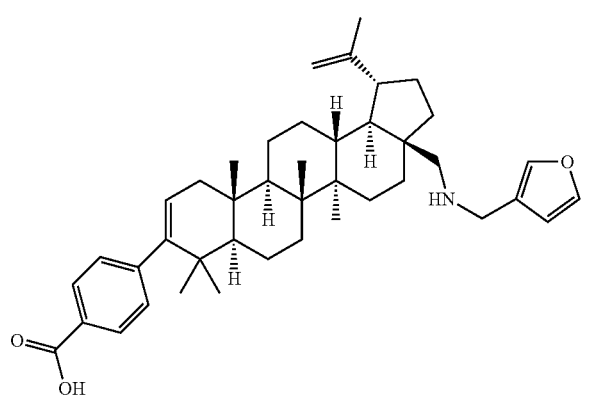

The title compound was prepared following the general procedures described above for the C28 amine formation and hydrolysis using furan-3-ylmethanamine as the reactant amine. The product was isolated as a white solid (60 mg, 41.0%). LCMS: m/e 624.6 (MH$^+$), 2.61 min (method 3). $^1$H NMR (400 MHz, MeOD) δ ppm 6.28-6.44 (m, 2H), 6.17-6.28 (m, 1H), 6.03-6.16 (m, 1H), 5.53-5.73 (m, 2H), 5.06 (d, J=1.3 Hz, 1H), 3.57-3.80 (m, 1H), 3.09-3.20 (m, 1H), 3.03 (s, 1H), 2.47-2.71 (m, 2H), 1.57 (d, J=12.8 Hz, 1H), 1.12-1.32 (m, 1H), 0.85 (td, J=11.1, 5.6 Hz, 1H), 0.52 (dd, J=17.1, 6.3 Hz, 1H), 0.20-0.42 (m, 1H), 0.04-0.19 (m, 8H), 0.25-0.00 (m, 8H), 0.39-0.25 (m, 4H), 0.56-0.39 (m, 3H), 0.58 (s, 6H), 0.63 (s, 3H), 0.64 (s, 3H), 0.66 (s, 3H).

Example 54

Preparation of 4-((1R,3aS,5aR,5bR,7aR,11aS,11bR,13aR,13bR)-3a-(((4-(1,1-dioxido-4-thiomorpholinyl)-4-oxobutyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

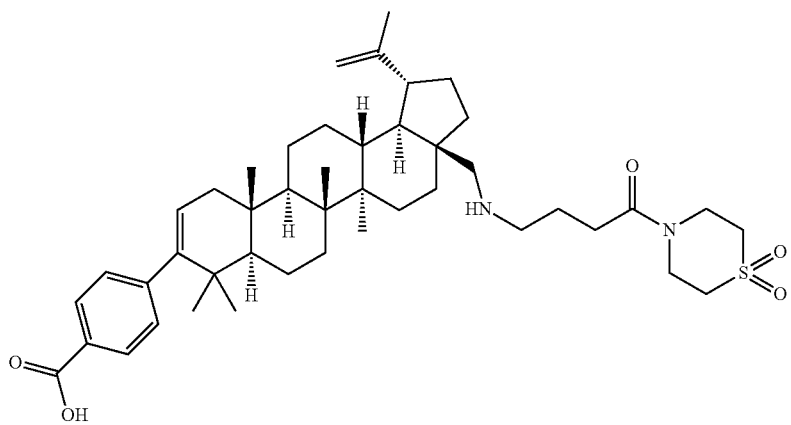

The title compound was prepared following the general procedures described above for the C28 amine formation and hydrolysis using thiomorpholine amide as the reactant amine. The product was isolated as a white solid (12 mg, 41.0%). LCMS: m/e 747.5 (MH$^+$), 2.36 min (method 3). $^1$H NMR (400 MHz, MeOD) δ ppm 7.97 (m, 2H), 7.25 (m, 2H), 5.27-5.34 (m, 1H), 4.78 (d, J=1.5 Hz, 1H), 4.67 (s, 1H), 4.05-4.19 (m, 2H), 3.92-4.05 (m, 2H), 3.20-3.30 (m, 3H), 3.08-3.20 (m, 4H), 2.82-2.97 (m, 1H), 2.75 (t, J=6.4 Hz, 2H), 2.53 (td, J=10.7, 5.4 Hz, 1H), 2.17 (dd, J=17.1, 6.3 Hz, 1H), 1.99-2.13 (m, 3H), 1.83-1.95 (m, 2H), 1.67-1.83 (m, 8H), 1.44-1.67 (m, 8H), 1.25-1.44 (m, 4H), 1.13-1.25 (m, 4H), 1.10 (s, 3H), 1.07 (s, 3H), 1.00 (s, 3H), 0.97 (s, 3H).

Example 55

4-((1R,3aS,5aR,5bR,7aR,11aS,11bR,13aR,13bR)-3a-((3-(1H-imidazol-1-yl)propylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

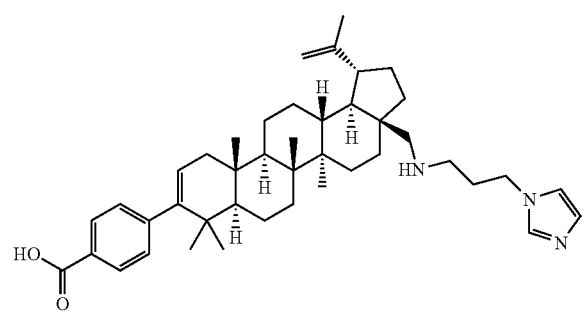

The title compound was prepared in 15% yield following the general procedures described above for the C28 amine formation and hydrolysis using 3-(1H-imidazol-1-yl)propan-1-amine as the reactant amine. MS: m/e 652.6 (MH$^+$), 1.63 min (method 1). $^1$H NMR (400 MHz, CHLOROFORM-d) δ ppm 0.86 (s, 3H) 0.91 (s, 3H) 0.99 (s, 3H) 1.00 (s., 3H) 1.10 (s, 3H) 1.69 (s, 3H) 0.88-2.60 (m, 24H) 2.29 (d, J=11.58 Hz, 1H) 2.61-2.78 (m, 3H) 2.82 (d, J=11.58 Hz, 1H) 4.02-4.10 (m, 1H) 4.12-4.21 (m, 1H) 4.60 (s, 1H) 4.70 (s, 1H) 5.30 (d, J=4.53 Hz, 1H) 6.94 (s, 1H) 7.15 (s, 1H) 7.19 (d, J=8.31 Hz, 2H) 7.63 (s, 1H) 7.99 (d, J=8.31 Hz, 2H).

Example 56

4-((1R,3aS,5aR,5bR,7aR,11aS,11bR,13aR,13bR)-5a,5b,8,8,11a-pentamethyl-3a-((3-(4-methylpiperazin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

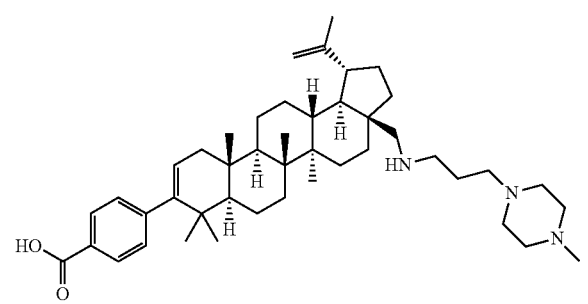

The title compound was prepared in 69% yield following the general procedures described above for the C28 amine formation and hydrolysis using 3-(4-methylpiperazin-1-yl)propan-1-amine as the reactant amine MS: m/e 684.6 (MH$^+$), 1.64 min (method 1). $^1$H NMR (400 MHz, CHLOROFORM-d) δ ppm 0.91 (s, 3H) 0.93 (s, 3H) 0.97 (s, 3H) 1.00 (s, 3H) 1.08 (s, 3H) 1.69 (s, 3H) 2.38 (s, 3H) 0.85-2.13 (m, 31H) 2.55-2.66 (m, 4H) 3.05-3.25 (m, 4H) 4.62 (s, 1H) 4.71 (s, 1H) 5.30 (d, J=4.78 Hz, 1H) 7.17 (d, J=8.31 Hz, 2H) 7.95 (d, J=8.06 Hz, 2H).

Example 57

4-((1R,3aS,5aR,5bR,7aR,11aS,11bR,13aR,13bR)-3a-((2-(diisopropylamino)ethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

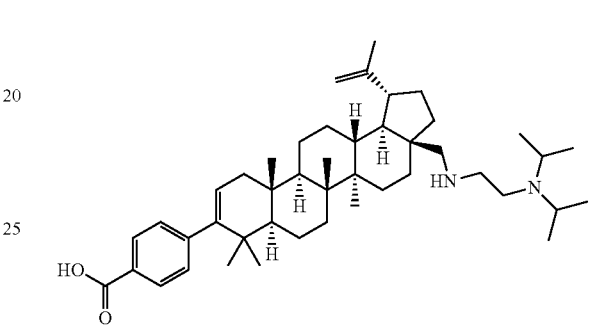

The title compound was prepared in 17% yield following the general procedures described above for the C28 amine formation and hydrolysis using N1,N1-diisopropylethane-1,2-diamine as the reactant amine MS: m/e 671.7 (MH$^+$), 1.65 min (method 1). $^1$H NMR (400 MHz, CHLOROFORM-d) δ ppm 0.94 (s, 3H) 0.94 (s, 3H) 0.97 (s, 3H) 1.00 (s, 3H) 1.07 (s, 3H) 1.69 (s, 3H) 0.85-2.15 (m, 32H) 2.09 (dd, J=15.99, 5.67 Hz, 1H) 2.30-2.39 (m, 1H) 2.76 (d, J=12.09 Hz, 1H) 3.25 (d, J=12.09 Hz, 1H) 3.58-3.70 (m, 6H) 3.70-3.79 (m, 1H) 4.62 (s, 1H) 4.69 (s, 1H) 5.29 (d, J=4.53 Hz, 1H) 7.23 (d, J=8.31 Hz, 2H) 7.98 (d, J=8.31 Hz, 2H).

Example 58

4-((1R,3aS,5aR,5bR,7aR,11aS,11bR,13aR,13bR)-5a,5b,8,8,11a-pentamethyl-3a-((3-(2-oxopyrrolidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

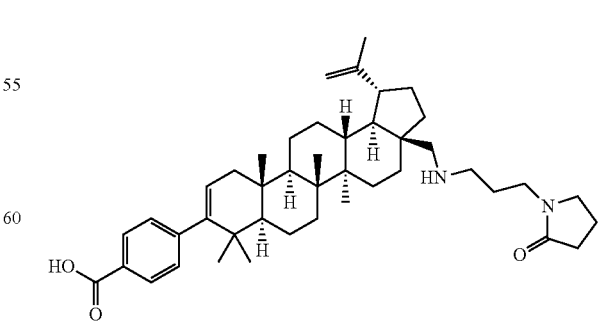

The title compound was prepared in 55% yield following the general procedures described above for the C28 amine formation and hydrolysis using 1-(3-aminopropyl)pyrrolidin-2-one as the reactant amine. MS: m/e 669.6 (MH$^+$), 1.77 min (method 1). $^1$H NMR (400 MHz, CHLOROFORM-d) δ ppm 0.94 (s, 6H) 0.98 (s, 3H) 1.01 (s, 3H) 1.08 (s, 3H) 1.70 (s, 3H) 0.77-1.79 (m, 17H) 1.97-2.18 (m, 8H) 2.38 (td, J=10.14, 5.67 Hz, 1H) 2.49 (t, J=8.18 Hz, 2H) 2.70 (t, J=10.45 Hz, 1H) 2.97-3.08 (m, 1H) 3.08-3.17 (m, 1H) 3.22 (t, J=10.58 Hz, 1H) 3.36-3.54 (m, 3H) 3.48 (t, J=7.05 Hz, 2H) 4.62 (s, 1H) 4.70 (s, 1H) 5.30 (d, J=4.78 Hz, 1H) 7.23 (d, J=8.06 Hz, 2H) 7.99 (d, J=8.06 Hz, 2H).

Example 59

4-((1R,3aS,5aR,5bR,7aR,11aS,11bR,13aR,13bR)-5a,5b,8,8,11a-pentamethyl-3a-((2-(2-methyl-1H-imidazol-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

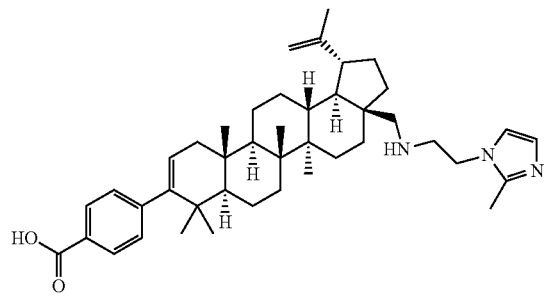

The title compound was prepared in 52% yield following the general procedures described above for the C28 amine formation and hydrolysis using 2-(2-methyl-1H-imidazol-1-yl)ethanamine as the reactant amine MS: m/e 652.6 (MH$^+$), 1.67 min (method 1). $^1$H NMR (400 MHz, MeOD) δ ppm 0.95 (s., 3H) 0.96 (s, 3H) 1.03 (s, 3H) 1.08 (s, 3H) 1.17 (s, 3H) 1.73 (s., 3H) 0.90-1.93 (m, 21H) 2.00-2.10 (m, 1H) 2.14 (dd, J=17.12, 6.55 Hz, 1H) 2.46-2.55 (m, 1H) 2.69 (s, 3H) 2.93 (d, J=12.34 Hz, 1H) 3.53-3.69 (m, 2H) 4.54 (t, J=7.30 Hz, 2H) 4.65 (s., 1H) 4.75 (s., 1H) 5.27-5.33 (m, 1H) 7.21 (d, J=8.31 Hz, 2H) 7.49-7.52 (m, 1H) 7.54 (d, J=2.01 Hz, 1H) 7.91 (d, J=8.31 Hz, 2H).

Example 60

4-((1R,3aS,5aR,5bR,7aR,11aS,11bR,13aR,13bR)-3a-((3-(bis(2-hydroxyethyl)amino)propylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

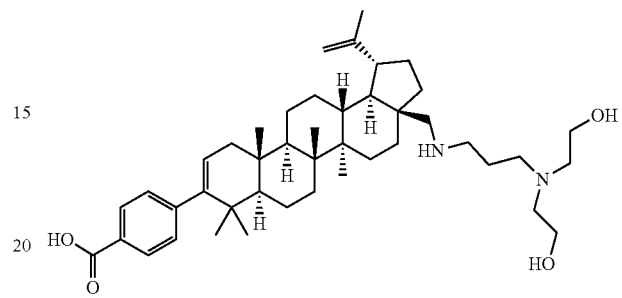

The title compound was prepared in 76% yield following the general procedures described above for the C28 amine formation and hydrolysis using 2,2'-(3-aminopropylazanediyl)diethanol as the reactant amine. MS: m/e 689.6 (MH$^+$), 1.63 min (method 1). $^1$H NMR (400 MHz, MeOD) δ ppm 0.95 (s, 3H) 0.96 (s, 3H) 1.04 (s, 3H) 1.08 (s, 3H) 1.17 (s, 3H) 1.73 (s, 1H) 0.85-1.89 (m. 29H) 2.00-2.11 (m, 1H) 2.15 (dd, J=17.12, 6.04 Hz, 1H) 2.19-2.29 (m, 2H) 2.46-2.56 (m, 1H) 2.87 (d, J=12.34 Hz, 1H) 3.15-3.29 (m, 4H) 3.90 (t, J=4.78 Hz, 4H) 4.65 (s, 1H) 4.76 (s, 1H) 5.28-5.33 (m, 1H) 7.22 (d, J=8.31 Hz, 2H) 7.92 (d, J=8.31 Hz, 2H).

Example 61

4-((1R,3aS,5aR,5bR,7aR,11aS,11bR,13aR,13bR)-3a-((3-(2-hydroxyethylamino)propylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

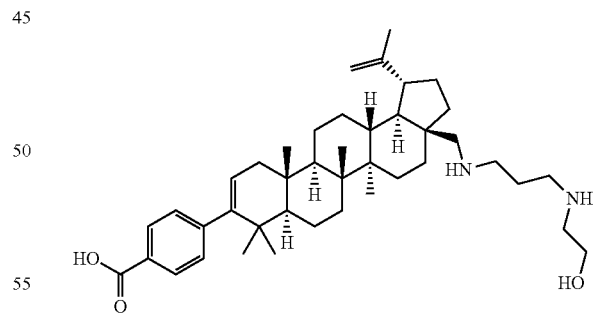

The title compound was prepared in 35% yield following the general procedures described above for the C28 amine formation and hydrolysis using 2-(3-aminopropylamino)ethanol as the reactant amine MS: m/e 645.6 (MH$^+$), 1.65 min (method 1). $^1$H NMR (400 MHz, MeOD) δ ppm 0.94 (s, 3H) 0.96 (s, 3H) 1.03 (s, 3H) 1.07 (s, 3H) 1.16 (s, 3H) 1.72 (s, 3H) 0.85-1.89 (m, 21H) 1.98-2.26 (m, 4H) 2.45-2.55 (m, 1H) 2.85 (d, J=12.84 Hz, 1H) 3.11-3.28 (m, 8H) 3.78-3.84 (m, 2H) 4.64 (s, 1H) 4.75 (s, 1H) 5.29 (d, J=4.53 Hz, 1H) 7.21 (d, J=8.31 Hz, 2H) 7.91 (d, J=8.31 Hz, 2H).

Example 62

4-((1R,3aS,5aR,5bR,7aR,11aS,11bR,13aR,13bR)-3a-((2-(2-hydroxyethylamino)ethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

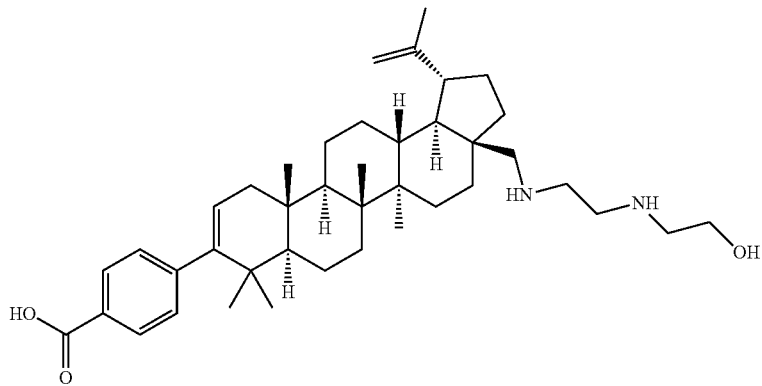

The title compound was prepared in 83% yield following the general procedures described above for the C28 amine formation and hydrolysis using 2-(2-aminoethylamino)ethanol as the reactant amine MS: m/e 631.5 (MH⁺), 1.65 min (method 1). $^1$H NMR (400 MHz, MeOD) δ ppm 0.95 (s, 3H) 0.96 (s, 3H) 1.04 (s, 3H) 1.07 (s, 3H) 1.17 (s, 3H) 1.73 (s, 3H) 0.85-1.93 (m, 22H) 2.00-2.11 (m, 1H) 2.15 (dd, J=17.12, 6.30 Hz, 1H) 2.47-2.56 (m, 1H) 2.93 (d, J=12.84 Hz, 1H) 3.22 (dd, J=5.79, 4.53 Hz, 2H) 3.27-3.29 (m, 1H) 3.46-3.56 (m, 4H) 3.83 (dd, J=5.67, 4.41 Hz, 2H) 4.64 (br. s., 1H) 4.76 (s, 1H) 5.27-5.33 (m, 1H) 7.21 (d, J=8.31 Hz, 2H) 7.91 (d, J=8.31 Hz, 2H).

Example 63

4-((1R,3aS,5aR,5bR,7aR,11aS,11bR,13aR,13bR)-5a,5b,8,8,11a-pentamethyl-3a-((2-morpholinoethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

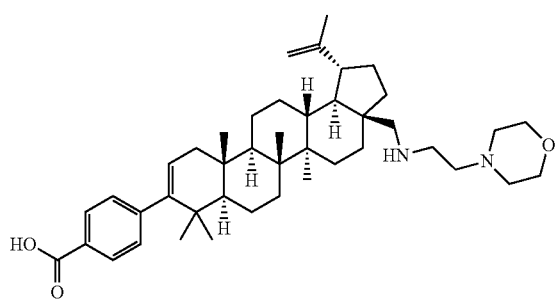

The title compound was prepared in 92% yield following the general procedures described above for the C28 amine formation and hydrolysis using 2-morpholineethanamine as the reactant amine MS: m/e 657.6 (MH⁺), 1.70 min (method 1). $^1$H NMR (400 MHz, MeOD) δ ppm 0.94 (s, 3H) 0.96 (s, 3H) 1.03 (s, 3H) 1.07 (s, 3H) 1.16 (s, 3H) 1.72 (s, 3H) 0.83-1.90 (m, 21H) 1.97-2.09 (m, 1H) 2.14 (dd, J=17.12, 6.30 Hz, 1H) 2.46-2.55 (m, 1H) 2.82-2.95 (m, 5H) 3.02-3.11 (m, 2H) 3.39 (t, J=6.42 Hz, 2H) 3.81 (t, J=4.03 Hz, 4H) 4.64 (s, 1H) 4.74-4.77 (m, 1H) 5.27-5.31 (m, 1H) 7.21 (d, J=8.31 Hz, 2H) 7.91 (d, J=8.31 Hz, 2H).

Example 64

4-((1R,3aS,5aR,5bR,7aR,11aS,11bR,13aR,13bR)-3a-((2-carboxymethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

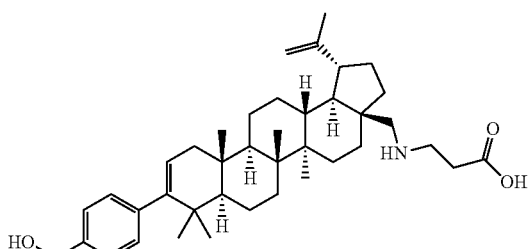

The title compound was prepared in 74% yield following the general procedures described above for the C28 amine formation and hydrolysis using tert-butyl 3-aminopropanoate hydrochloride as the reactant amine. MS: m/e 616.4 (MH⁺), 1.69 min (method 1). $^1$H NMR (400 MHz, MeOD) δ ppm 0.95 (s, 3H) 0.97 (s, 3H) 1.04 (s, 3H) 1.08 (s, 3H) 1.18 (s, 3H) 1.73 (s, 3H) 0.92-1.86 (m, 24H) 1.99-2.10 (m, 1H) 2.15 (dd, J=17.12, 6.30 Hz, 1H) 2.47-2.56 (m, 1H) 2.76 (t, J=6.42 Hz, 2H) 2.88 (d, J=12.34 Hz, 1H) 4.64 (s, 1H) 4.76 (s, 1H) 5.28-5.32 (m, 1H) 7.22 (d, J=8.56 Hz, 2H) 7.91 (d, J=8.31 Hz, 2H).

Example 65

4-((1R,3aS,5aR,5bR,7aR,11aS,11bR,13aR,13bR)-3a-((3-bromopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

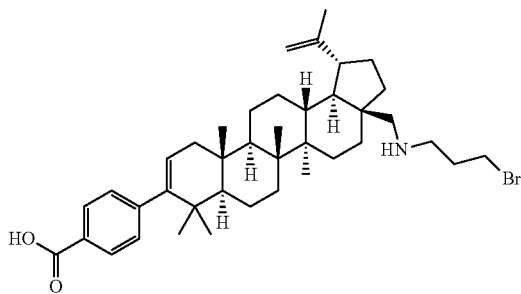

The title compound was prepared in 23% yield following the general procedures described above for the C28 amine formation and hydrolysis using 3-bromopropan-1-amine hydrobromide as the reactant amine MS: m/e 664 (MH+), 1.58 min (method 2). $^1$H NMR (400 MHz, MeOD) δ ppm 0.95 (s, 3H) 0.97 (s, 3H) 1.04 (s, 3H) 1.08 (s, 3H) 1.18 (s, 3H) 1.73 (s, 3H) 0.85-1.85 (m, 19H) 1.99-2.10 (m, 1H) 2.15 (dd, J=17.37, 6.55 Hz, 1H) 2.26-2.36 (m, 2H) 2.47-2.56 (m, 1H) 2.88 (d, J=12.34 Hz, 1H) 3.20-3.28 (m, 4H) 3.56 (t, J=6.30 Hz, 2H) 4.64 (s, 1H) 4.76 (s, 1H) 5.28-5.32 (m, 1H) 7.22 (d, J=8.31 Hz, 2H) 7.92 (d, J=8.56 Hz, 2H).

Example 66

4-((1R,3aS,5aR,5bR,7aR,11aS,11bR,13aR,13bR)-5a,5b,8,8,11a-pentamethyl-1-(prop-1-en-2-yl)-3a-(((1-(pyrrolidin-1-ylmethyl)cyclopropyl)methylamino)methyl)-2,3,3a,4,5,5a,5b,6,7,7a,8,11,11a,11b,12,13,13a,13b-octadecahydro-1H-cyclopenta[a]chrysen-9-yl)benzoic acid

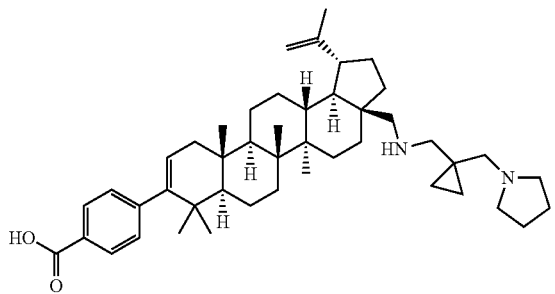

The title compound was prepared in 50% yield following the general procedures described above for the C28 amine formation and hydrolysis using (1-(pyrrolidin-1-ylmethyl)cyclopropyl)methanamine as the reactant amine. MS: m/e 681.3 (MH+), 1.51 min (method 2). $^1$H NMR (400 MHz, MeOD) δ ppm 0.95 (s, 3H) 0.96 (s, 3H) 1.03 (s, 3H) 1.07 (s, 3H) 1.15 (s, 3H) 1.72 (s, 3H) 0.84-1.97 (m, 27H) 2.00-2.19 (m, 6H) 2.48 (td, J=10.95, 5.79 Hz, 1H) 2.89 (d, J=13.09 Hz, 1H) 3.21-3.45 (m, 6H) 4.64 (s, 1H) 4.75 (s, 1H) 5.27-5.32 (m, 1H) 7.22 (d, J=8.31 Hz, 2H) 7.91 (d, J=8.31 Hz, 2H).

Example 67

4-((1R,3aS,5aR,5bR,7aR,11aS,11bR,13aR,13bR)-3a-((3-aminopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

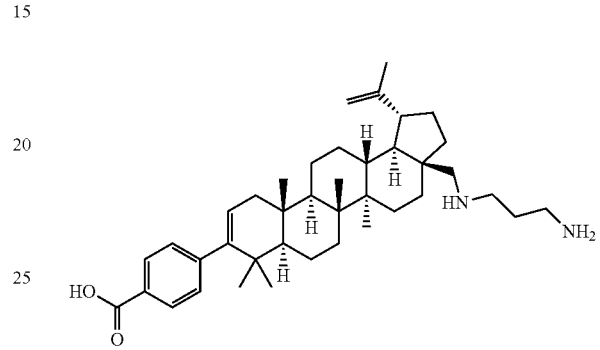

The title compound was prepared in 46% yield following the general procedures described above for the C28 amine formation and hydrolysis using tert-butyl 3-aminopropylcarbamate as the reactant amine MS: m/e 601.4 (MH+), 1.48 min (method 2). $^1$H NMR (400 MHz, MeOD) δ ppm 0.94 (s, 3H) 0.96 (s, 3H) 1.03 (s, 3H) 1.06 (s, 3H) 1.16 (s, 3H) 1.72 (s, 3H) 0.85-1.89 (m, 22H) 1.99-2.20 (m, 4H) 2.50 (td, J=10.45, 5.79 Hz, 1H) 2.85 (d, J=13.09 Hz, 1H) 3.05 (t, J=7.55 Hz, 2H) 3.13-3.28 (m, 3H) 4.63 (s, 1H) 4.73-4.76 (m, 1H) 5.27-5.31 (m, 1H) 7.21 (d, J=8.31 Hz, 2H) 7.91 (d, J=8.31 Hz, 2H).

Example 68

4-((1R,3aS,5aR,5bR,7aR,11aS,11bR,13aR,13bR)-5a,5b,8,8,11a-pentamethyl-1-(prop-1-en-2-yl)-3a-((3-(pyrrolidin-1-yl)propylamino)methyl)-2,3,3a,4,5,5a,5b,6,7,7a,8,11,11a,11b,12,13,13a,13b-octadecahydro-1H-cyclopenta[a]chrysen-9-yl)benzoic acid

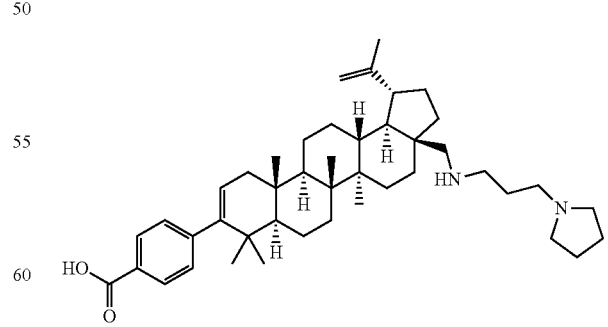

The title compound was prepared in 52% yield following the general procedures described above for the C28 amine formation and hydrolysis using 3-(pyrrolidin-1-yl)propan-1-amine as the reactant amine. MS: m/e 655.4 (MH+), 1.49 min (method 2). ¹H NMR (400 MHz, MeOD) δ ppm 0.94 (s, 3H) 0.96 (s, 3H) 1.03 (s, 3H) 1.07 (s, 3H) 1.16 (s, 3H) 1.72 (s, 3H) 0.85-1.89 (m, 25H) 1.99-2.27 (m, 8H) 2.50 (td, J=10.32, 5.54 Hz, 1H) 2.87 (d, J=13.09 Hz, 1H) 3.19 (dt, J=12.53, 3.56 Hz, 2H) 3.22-3.30 (m, 2H) 4.64 (s, 1H) 4.75 (s, 1H) 5.27-5.31 (m, 1H) 7.21 (d, J=8.31 Hz, 2H) 7.92 (d, J=8.31 Hz, 2H).

Example 69

4-((1R,3aS,5aR,5bR,7aR,11aS,11bR,13aR,13bR)-3a-((3-hydroxypropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

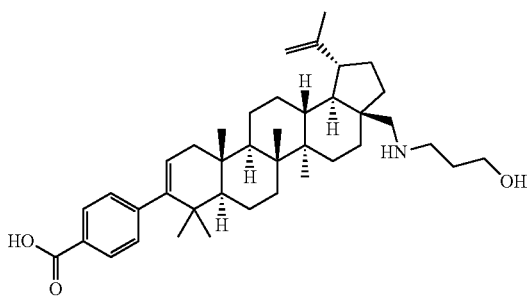

The title compound was prepared in 31% yield following the general procedures described above for the C28 amine formation and hydrolysis using 3-aminopropan-1-ol as the reactant amine. MS: m/e 602.4 (MH⁺), 1.52 min (method 2). ¹H NMR (500 MHz, MeOD) δ ppm 0.95 (s, 3H) 0.96 (s, 3H) 1.04 (s, 3H) 1.08 (s, 3H) 1.18 (s, 3H) 1.73 (s, 3H) 0.87-1.81 (m, 21H) 1.91-1.99 (m, 2H) 1.99-2.09 (m, 1H) 2.15 (dd, J=17.24, 6.26 Hz, 1H) 2.47-2.55 (m, 1H) 2.86 (d, J=12.51 Hz, 1H) 3.21-3.27 (m, 3H) 3.74-3.79 (m, 2H) 4.64 (s, 1H) 4.76 (s, 1H) 5.27-5.32 (m, 1H) 7.22 (d, J=8.24 Hz, 2H) 7.91 (d, J=8.24 Hz, 2H).

Example 70

4-((1R,3aS,5aR,5bR,7aR,11aS,11bR,13aR,13bR)-5a,5b,8,8,11a-pentamethyl-3a-((3-oxo-3-(pyrrolidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

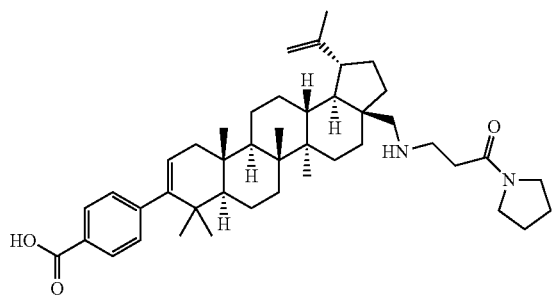

The title compound was prepared in 43% yield following the general procedures described above for the C28 amine formation and hydrolysis using 3-amino-1-(pyrrolidin-1-yl)propan-1-one hydrochloride as the reactant amine MS: m/e 669.4 (MH⁺), 1.58 min (method 2). ¹H NMR (500 MHz, MeOD) δ ppm 0.95 (s, 3H) 0.96 (s, 3H) 1.04 (s, 3H) 1.08 (s, 3H) 1.17 (s, 3H) 1.73 (s, 3H) 0.87-1.86 (m, 20H) 1.88-1.95 (m, 2H) 1.97-2.11 (m, 3H) 2.15 (dd, J=17.09, 6.41 Hz, 1H) 2.48-2.56 (m, 1H) 2.81 (t, J=5.80 Hz, 2H) 2.88 (d, J=13.12 Hz, 1H) 3.25 (d, J=13.43 Hz, 1H) 3.32-3.42 (m, 2H) 3.42-3.52 (m, 4H) 4.64 (s, 1H) 4.76 (s, 1H) 5.27-5.32 (m, 1H) 7.22 (d, J=7.93 Hz, 2H) 7.91 (d, J=8.24 Hz, 2H).

Example 71

4-((1R,3aS,5aR,5bR,7aR,11aS,11bR,13aR,13bR)-3a-((3-(2,5-dioxopyrrolidin-1-yl)propylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

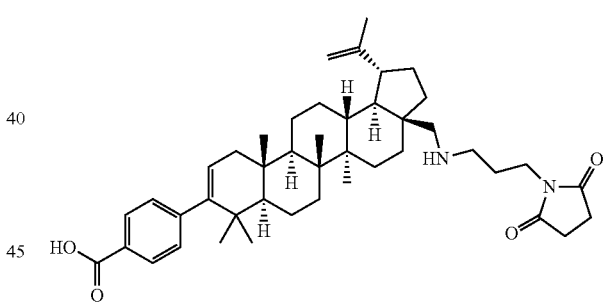

The title compound was prepared in 25% yield following the general procedures described above for the C28 amine formation and hydrolysis using 1-(3-aminopropyl)pyrrolidine-2,5-dione hydrochloride as the reactant amine MS: m/e 683.4 (MH⁺), 1.56 min (method 2). ¹H NMR (500 MHz, MeOD) δ ppm 0.95 (s, 3H) 0.97 (s, 3H) 1.04 (s, 3H) 1.08 (s, 3H) 1.17 (s, 3H) 1.73 (s, 3H) 0.85-2.19 (m, 26H) 2.45-2.53 (m, 1H) 2.71-2.75 (m, 2H) 2.79-2.85 (m, 1H) 3.09 (q, J=6.56

Hz, 2H) 3.18-3.24 (m, 1H) 3.63 (q, J=6.51 Hz, 2H) 4.64 (s, 1H) 4.75 (s, 1H) 5.27-5.31 (m, 1H) 7.22 (d, J=8.24 Hz, 2H) 7.91 (d, J=8.24 Hz, 2H).

Example 72

4-((1R,3aS,5aR,5bR,7aR,11aS,11bR,13aR,13bR)-5a,5b,8,8,11a-pentamethyl-3a-((3-(piperidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

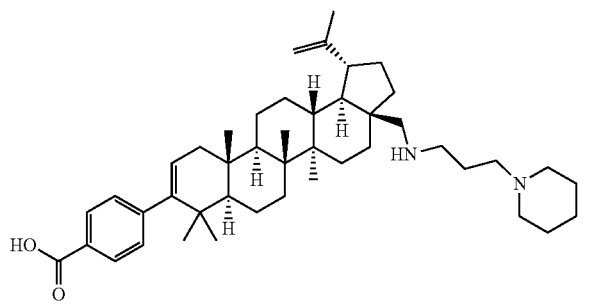

The title compound was prepared in 49% yield following the general procedures described above for the C28 amine formation and hydrolysis using 3-(piperidin-1-yl)propan-1-amine as the reactant amine MS: m/e 683.4 (MH⁺), 1.50 min (method 2). ¹H NMR (500 MHz, MeOD) δ ppm 0.95 (s, 3H) 0.96 (s, 3H) 1.03 (s, 3H) 1.08 (s, 3H) 1.17 (s, 3H) 1.73 (s, 3H) 0.81-2.11 (m, 27H) 2.15 (dd, J=17.24, 6.26 Hz, 1H) 2.22 (dt, J=16.25, 8.20 Hz, 2H) 2.51 (td, J=10.45, 6.26 Hz, 1H) 2.84-3.00 (m, 2H) 3.13-3.28 (m, 6H) 3.50-3.61 (m, 2H) 4.65 (s, 1H) 4.75 (s, 1H) 5.30 (d, J=6.10 Hz, 1H) 7.21 (dd, J=8.24, 1.53 Hz, 2H) 7.91 (dd, J=8.24, 1.53 Hz, 2H).

Example 73

4-((1R,3aS,5aR,5bR,7aR,11aS,11bR,13aR,13bR)-3a-((((2E)-4-(1,1-dioxido-4-thiomorpholinyl)-2-buten-1-yl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

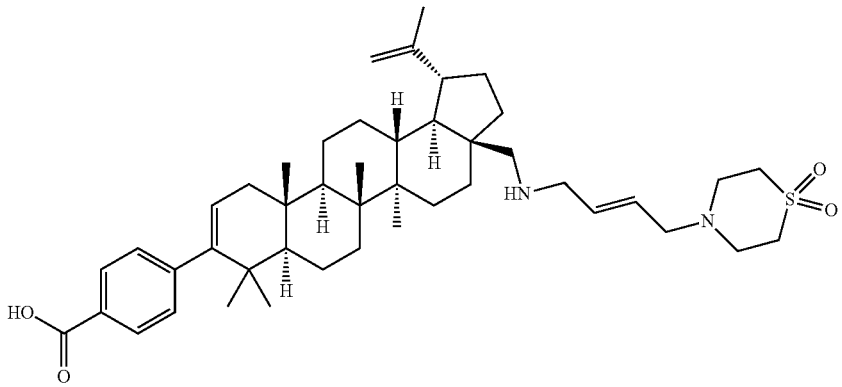

The title compound was prepared in 11% yield following the general procedures described above for the C28 amine formation and hydrolysis using (1,1-dioxido-4-thiomorpholinyl)-2-buten-1-amine as the reactant amine MS: m/e 731.2 (MH⁺), 1.54 min (method 2). ¹H NMR (400 MHz, MeOD) δ ppm 0.95 (s, 3H) 0.97 (s, 3H) 1.04 (s, 3H) 1.08 (s, 3H) 1.16 (s, 3H) 1.72 (s, 3H) 0.85-1.82 (m, 19H) 1.95-2.09 (m, 1H) 2.15 (dd, J=17.07, 6.53 Hz, 1H) 2.49 (td, J=10.67, 5.52 Hz, 1H) 2.81 (d, J=13.05 Hz, 1H) 3.05-3.12 (m, 4H) 3.12-3.18 (m, 4H) 3.19-3.26 (m, 2H) 3.33-3.37 (m, 2H) 3.69-3.82 (m, 2H) 4.65 (s, 1H) 4.76 (d, J=1.51 Hz, 1H) 5.30 (dd, J=6.27, 1.51 Hz, 1H) 5.85 (ddd, J=15.43, 7.15, 7.03 Hz, 1H) 6.11 (dt, J=15.25, 6.31 Hz, 1H) 7.21 (d, J=8.53 Hz, 2H) 7.91 (d, J=8.28 Hz, 2H).

Example 74

4-((1R,3aS,5aR,5bR,7aR,11aS,11bR,13aR,13bR)-3a-((3-(2-(hydroxymethyl)pyrrolidin-1-yl)propylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

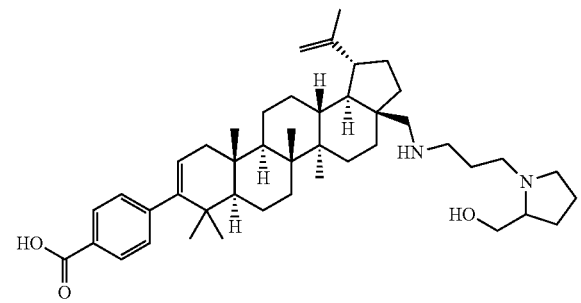

The title compound was prepared in 39% yield following the general procedures described above for the C28 amine formation and hydrolysis using (1-(3-aminopropyl)pyrrolidin-2-yl)methanol as the reactant amine MS: m/e 685.3 (MH⁺), 1.47 min (method 2). ¹H NMR (400 MHz, MeOD) δ ppm 0.95 (s, 3H) 0.96 (s, 3H) 1.04 (s, 3H) 1.08 (s, 3H) 1.17 (s, 3H) 1.73 (s, 3H) 0.86-2.32 (m, 30H) 2.50 (td, J=10.85, 5.65 Hz, 1H) 2.87 (d, J=13.55 Hz, 1H) 3.15-3.23 (m, 4H) 3.49-3.76 (m, 4H) 3.90 (dd, J=12.05, 3.51 Hz, 1H) 4.65 (s, 1H) 4.75

(d, J=1.51 Hz, 1H) 5.30 (dd, J=6.02, 1.51 Hz, 1H) 7.21 (d, J=8.28 Hz, 2H) 7.91 (d, J=8.53 Hz, 2H).

Example 75

4-((1R,3aS,5aR,5bR,7aR,11aS,11bR,13aR,13bR)-3a-((3-(dimethylamino)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

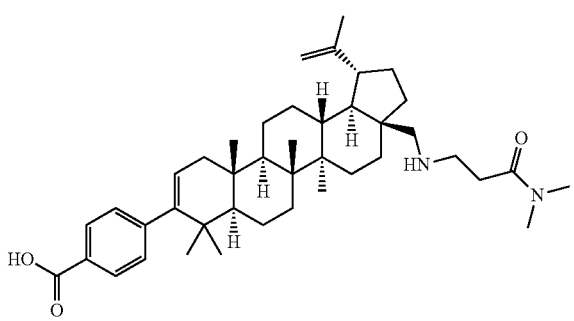

The title compound was prepared in 39% yield following the general procedures described above for the C28 amine formation and hydrolysis using 3-amino-N,N-dimethylpropanamide as the reactant amine MS: m/e 643.3 (MH$^+$), 1.53 min (method 2). $^1$H NMR (400 MHz, MeOD) δ ppm 0.96 (s, 3H) 0.98 (s, 3H) 1.05 (s, 3H) 1.10 (s, 3H) 1.18 (s, 3H) 1.74 (s, 3H) 0.88-1.87 (m, 20H) 2.01-2.11 (m, 1H) 2.16 (dd, J=17.07, 6.53 Hz, 1H) 2.53 (td, J=10.67, 5.52 Hz, 1H) 2.85-2.92 (m, 3H) 2.99 (s, 3H) 3.08 (s, 3H) 3.24-3.29 (m, 1H) 3.34-3.39 (m, 2H) 4.65-4.67 (m, 1H) 4.77 (d, J=1.76 Hz, 1H) 5.31 (dd, J=6.27, 1.76 Hz, 1H) 7.23 (d, J=8.53 Hz, 2H) 7.93 (d, J=8.28 Hz, 2H).

Example 76

4-((1R,3aS,5aR,5bR,7aR,11aS,11bR,13aR,13bR)-3a-(((4-(1,1-dioxido-4-thiomorpholinyl)butyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

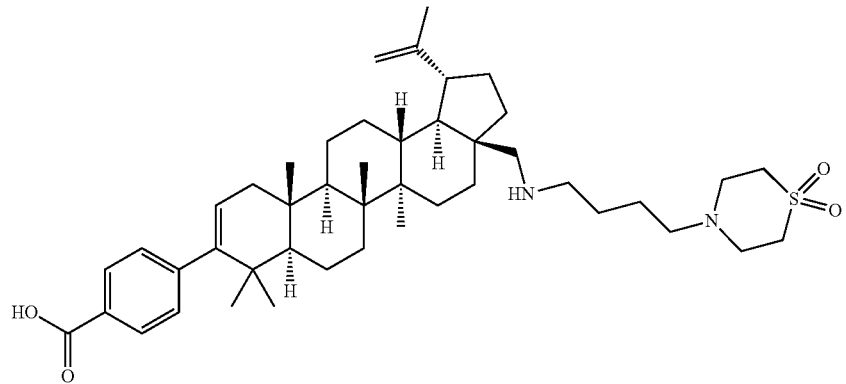

The title compound was prepared in 11% yield following the general procedures described above for the C28 amine formation and hydrolysis using 4-(1,1-dioxido-4-thiomorpholinyl)butyl)amine as the reactant amine. MS: m/e 733.2 (MH$^+$), 1.49 min (method 2). $^1$H NMR (400 MHz, MeOD) δ ppm 0.95 (s, 3H) 0.97 (s, 3H) 1.04 (s, 3H) 1.08 (s, 3H) 1.18 (s, 3H) 1.73 (s, 3H) 0.86-1.91 (m, 27H) 1.98-2.09 (m, 1H) 2.15 (dd, J=17.19, 6.40 Hz, 1H) 2.51 (td, J=10.35, 5.40 Hz, 1H) 2.81-2.87 (m, 1H) 2.94 (t, J=7.15 Hz, 2H) 3.08-3.16 (m, 2H) 3.18-3.27 (m, 2H) 3.36-3.44 (m, 4H) 4.65 (s, 1H) 4.76 (d, J=1.51 Hz, 1H) 5.30 (dd, J=6.02, 1.51 Hz, 1H) 7.21 (d, J=8.28 Hz, 2H) 7.91 (d, J=8.53 Hz, 2H).

Example 77

4-((1R,3aS,5aR,5bR,7aR,11aS,11bR,13aR,13bR)-5a,5b,8,8,11a-pentamethyl-3a-((2-(2-oxoimidazolidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

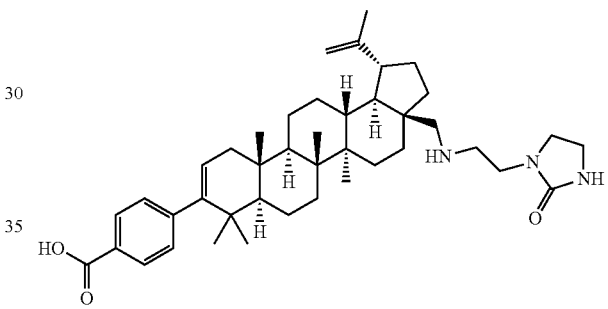

The title compound was prepared in 9% yield following general procedures described above for the C28 amine formation and hydrolysis using 1-(2-aminoethyl)imidazolidin-2-one as the reactant amine. MS: m/e 656.3 (MH$^+$), 1.56 min (method 2). $^1$H NMR (400 MHz, MeOD) δ ppm 0.95 (s, 3H) 0.96 (s, 3H) 1.04 (s, 3H) 1.08 (s, 3H) 1.17 (s, 3H) 1.72 (s, 3H) 0.87-1.87 (m, 20H) 1.99-2.11 (m, 1H) 2.15 (dd, J=17.07, 6.02 Hz, 1H) 2.51 (td, J=10.79, 6.02 Hz, 1H) 2.92 (d, J=13.55 Hz, 1H) 3.21-3.33 (m, 3H) 3.42-3.59 (m, 6H) 4.63-4.65 (m, 1H)

4.76 (d, J=1.76 Hz, 1H) 5.30 (dd, J=6.15, 1.63 Hz, 1H) 7.21 (d, J=8.28 Hz, 2H) 7.91 (d, J=8.28 Hz, 2H).

Example 78

4-((1R,3aS,5aR,5bR,7aR,11aS,11bR,13aR,13bR)-5a,5b,8,8,11a-pentamethyl-3a-((2-(2-oxopiperidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

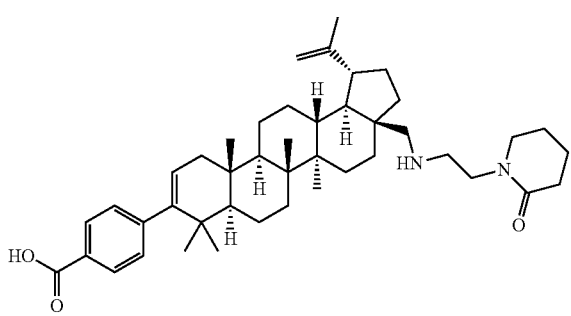

The title compound was prepared in 28% yield following the general procedures described above for the C28 amine formation and hydrolysis using 1-(2-aminoethyl)piperidin-2-one hydrobromide as the reactant amine MS: m/e 669.6 (MH+), 2.13 min (method 2). ¹H NMR (400 MHz, MeOD) δ ppm 0.95 (s, 3H) 0.96 (s, 3H) 1.04 (s, 3H) 1.08 (s, 3H) 1.17 (s, 3H) 1.73 (s, 3H) 0.85-1.92 (26H) 2.00-2.11 (m, 1H) 2.15 (dd, J=17.19, 6.40 Hz, 1H) 2.40 (t, J=6.40 Hz, 2H) 2.51 (td, J=10.60, 4.89 Hz, 1H) 2.91 (d, J=12.80 Hz, 1H) 3.25 (d, J=12.80 Hz, 1H) 3.44 (t, J=5.77 Hz, 2H) 3.60-3.74 (m, 2H) 4.64 (s, 1H) 4.76 (d, J=1.76 Hz, 1H) 5.30 (dd, J=6.15, 1.63 Hz, 1H) 7.21 (d, J=8.28 Hz, 2H) 7.91 (d, J=8.53 Hz, 2H).

Example 79

4-((1R,3aS,5aR,5bR,7aR,11aS,11bR,13aR,13bR)-5a,5b,8,8,11a-pentamethyl-3a-((2-methyl-3-(2-oxopyrrolidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

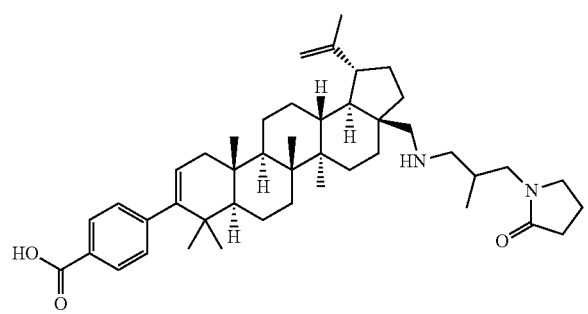

The title compound was prepared in 76% yield following the general procedures described above for the C28 amine formation and hydrolysis using 1-(3-amino-2-methylpropyl)pyrrolidin-2-one as the reactant amine. MS: m/e 683.6 (MH+), 1.62 min (method 2). ¹H NMR (400 MHz, MeOD) δ ppm 0.95 (s, 3H) 0.96 (s, 3H) 1.04 (s, 3H) 1.08 (s, 3H) 1.10 (d, J=7.03 Hz, 3H) 1.17 (s, 3H) 1.73 (s, 3H) 0.91-1.99 (m, 21H) 2.01-2.19 (m, 4H) 2.28-2.55 (m, 4H) 2.76-2.91 (m, 1H) 3.04 (dd, J=12.80, 5.27 Hz, 1H) 3.14 (dt, J=15.00, 3.80 Hz, 1H) 3.18-3.27 (m, 1H) 3.50-3.58 (m, 1H) 3.58-3.67 (m, 2H) 4.64 (s, 1H) 4.75 (s, 1H) 5.30 (dd, J=6.15, 1.63 Hz, 1H) 7.21 (d, J=8.28 Hz, 2H) 7.91 (d, J=8.53 Hz, 2H).

Example 80

4-((1R,3aS,5aR,5bR,7aR,11aS,11bR,13aR,13bR)-3a-((3-(2,6-dioxopiperidin-1-yl)propylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

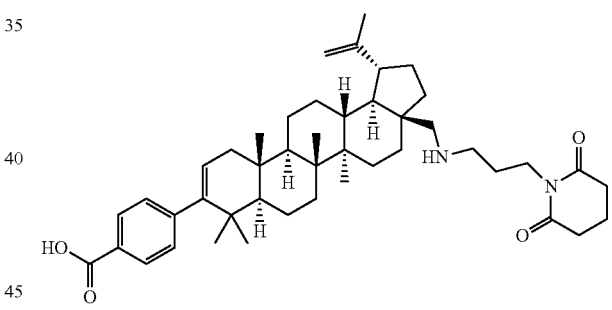

The title compound was prepared in 60% yield following the general procedures described above for the C28 amine formation and hydrolysis using 1-(3-aminopropyl)piperidine-2,6-dione hydrochloride as the reactant amine MS: m/e 697.5 (MH+), 1.63 min (method 2). ¹H NMR (400 MHz, MeOD) δ ppm 0.95 (s, 3H) 0.97 (s, 3H) 1.04 (s, 3H) 1.08 (s, 3H) 1.18 (s, 3H) 1.73 (s, 3H) 0.92-1.91 (m, 20H) 1.92-2.03 (m, 4H) 2.03-2.11 (m, 1H) 2.15 (dd, J=17.07, 6.78 Hz, 1H) 2.45-2.54 (m, 1H) 2.70 (t, J=6.53 Hz, 4H) 2.83 (d, J=13.30 Hz, 1H) 3.05 (t, J=6.78 Hz, 2H) 3.20 (d, J=13.30 Hz, 1H) 3.89

(t, J=6.65 Hz, 2H) 4.62-4.66 (m, 1H) 4.75 (d, J=1.76 Hz, 1H) 5.30 (dd, J=6.15, 1.38 Hz, 1H) 7.22 (d, J=8.53 Hz, 2H) 7.91 (d, J=8.53 Hz, 2H).

Example 81

4-((1R,3aS,5aR,5bR,7aR,11aS,11bR,13aR,13bR)-3a-((2-hydroxy-3-(2-oxopyrrolidin-1-yl)propylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

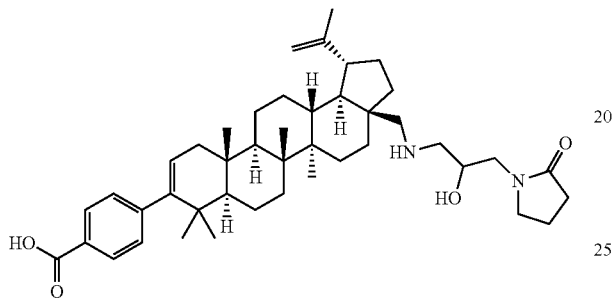

The title compound was prepared in 22% yield following the general procedures described above for the C28 amine formation and hydrolysis using 1-(3-amino-2-hydroxypropyl)pyrrolidin-2-one as the reactant amine MS: m/e 685.5 (MH⁺), 1.72 min (method 2). ¹H NMR (400 MHz, MeOD) δ ppm 0.95 (s, 3H) 0.96 (s, 3H) 1.04 (s, 3H) 1.08 (s, 3H) 1.18 (s, 3H) 1.73 (s, 3H) 0.82-1.91 (m, 20H) 2.02-2.19 (m, 4H) 2.38-2.46 (m, 2H) 2.46-2.56 (m, 1H) 2.89 (d, J=13.05 Hz, 1H) 3.01-3.19 (m, 2H) 3.32-3.50 (m, 4H) 3.53-3.70 (m, 2H) 4.18-4.26 (m, J=9.41, 5.02, 4.71, 4.71 Hz, 1H) 4.64 (s, 1H) 4.75 (d, J=1.76 Hz, 1H) 5.29 (dd, J=6.02, 1.51 Hz, 1H) 7.22 (d, J=8.53 Hz, 2H) 7.91 (d, J=8.28 Hz, 2H).

Example 82

4-((1R,3aS,5aR,5bR,7aR,11aS,11bR,13aR,13bR)-5a,5b,8,8,11a-pentamethyl-3a-((1-(piperidin-1-ylmethyl)cyclopropylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

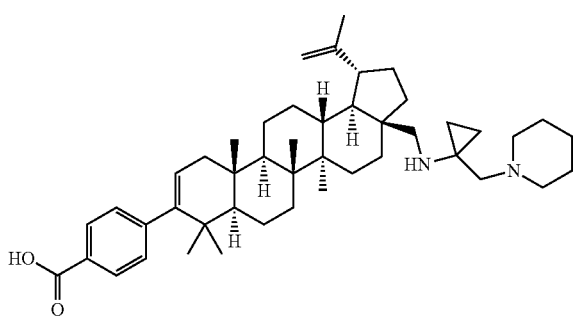

The title compound was prepared in 87% yield following the general procedures described above for the C28 amine formation and hydrolysis using 1-(piperidin-1-ylmethyl)cyclopropanamine hydrochloride as the reactant amine MS: m/e 681.7 (MH⁺), 1.76 min (method 2). ¹H NMR (400 MHz, MeOD) δ ppm 0.95 (s, 3H) 0.97 (s, 3H) 1.04 (s, 3H) 1.07 (s, 3H) 1.17 (s, 3H) 1.72 (s, 3H) 0.87-1.90 (m, 38H) 1.93-2.06 (m, 1H) 2.15 (dd, J=17.19, 6.40 Hz, 1H) 2.56 (td, J=11.23, 5.90 Hz, 1H) 4.63 (s, 1H) 4.75 (s, 1H) 5.30 (dd, J=6.02, 1.51 Hz, 1H) 7.22 (d, J=8.28 Hz, 2H) 7.92 (d, J=8.53 Hz, 2H).

Example 83

Preparation of 4-((1R,3aS,5aR,5bR,7aR,11aS,11bR,13aR,13bR)-3a-((dimethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid The title compound was prepared following the procedure described above in Step 3 using formaldehyde as the reactant aldehyde and 4-((1R,3aS,5aR,5bR,7aR,11aS,11bR,13aR,13bR)-3a-((3-aminopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (example 67) as the starting material amine The product was isolated as a white solid (17 mg, 34.4%). LCMS: m/e 572.5 (MH⁺), 2.21 min (method 3). ¹H NMR (400 MHz, MeOD) δ ppm 6.37 (d, J=8.5 Hz, 2H), 5.67 (d, J=8.3 Hz, 2H), 3.75 (dd, J=6.1, 1.6 Hz, 1H), 3.22 (d, J=1.5 Hz, 1H), 3.11 (s, 1H), 1.79-1.93 (m, 1H), 1.54 (d, J=13.8 Hz, 1H), 1.36-1.48 (m, 6H), 0.97 (td, J=11.0, 5.4 Hz, 1H), 0.60 (dd, J=17.2, 6.4 Hz, 1H), 0.42-0.55 (m, 1H), 0.31-0.38 (m, 1H), 0.10-0.30 (m, 8H), 0.11-0.10 (m, 8H), 0.32-0.11 (m, 5H), 0.44-0.32 (m, 4H), 0.47 (s, 3H), 0.52 (s, 3H), 0.56 (s, 3H), 0.60 (s, 3H).

Example 84

Preparation of 4-((1R,3aS,5aR,5bR,7aR,11aS,11bR,13aR,13bR)-3a-((cyclopropyl(3-(1,1-dioxido-4-thiomorpholinyl)propyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

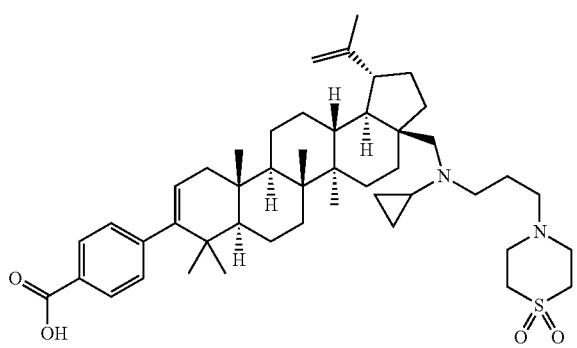

The title compound was prepared following the general procedures described above for the C28 amine formation, hydrolysis and tertiary amine formation using 4-(3-aminopropyl) thiomorpholine 1,1-dioxide as the reactant amine and (1-ethoxycyclopropoxy)trimethylsilane as reactant aldehyde equivalent. The product was isolated as a white solid (5 mg, 22.5%). LCMS: m/e 759.6 (MH$^+$), 2.56 min (method 3). $^1$H NMR (400 MHz, MeOD) δ ppm 6.38 (d, J=8.3 Hz, 2H), 5.68 (d, J=8.3 Hz, 2H), 3.77 (d, J=4.5 Hz, 1H), 3.25 (s, 1H), 3.13 (s, 1H), 1.71-1.76 (m, 2H), 1.56-1.71 (m, 8H), 1.47 (s, 2H), 1.24 (br. s., 2H), 1.01 (br. s., 1H), 0.79 (br. s., 1H), 0.61 (d, J=4.8 Hz, 2H), 0.49 (m, 1H), 0.20 (s, 9H), 0.06 (br. s., 7H), 0.06 (br. s., 4H), 0.29-0.13 (m, 4H), 0.38-0.29 (m, 4H), 0.46-0.38 (m, 5H), 0.54-0.46 (m, 4H), 0.57 (s, 3H), 0.58 (s, 3H).

General Procedures for Preparation of Additional C28 Amines Examples 85-86.

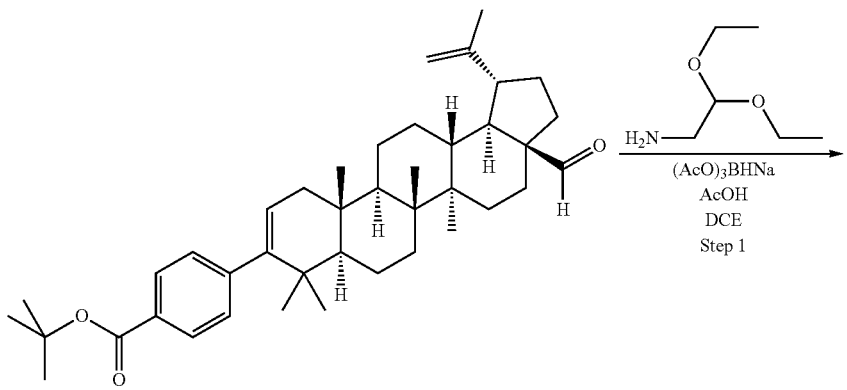

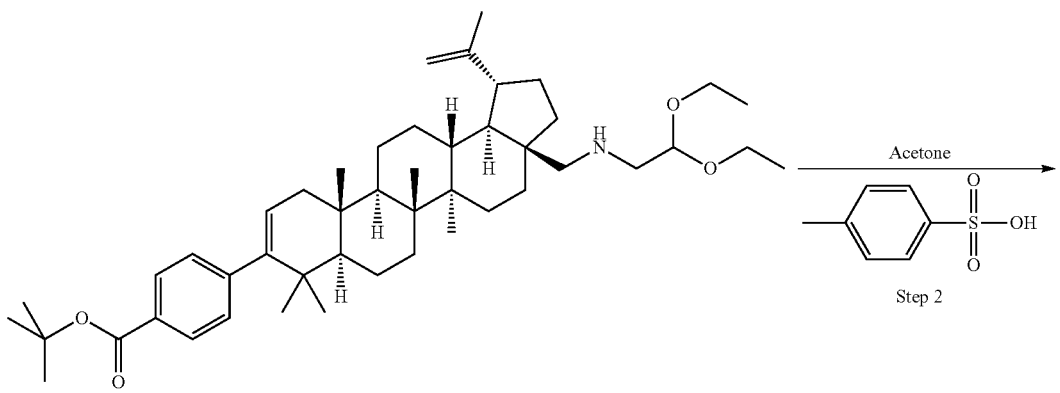

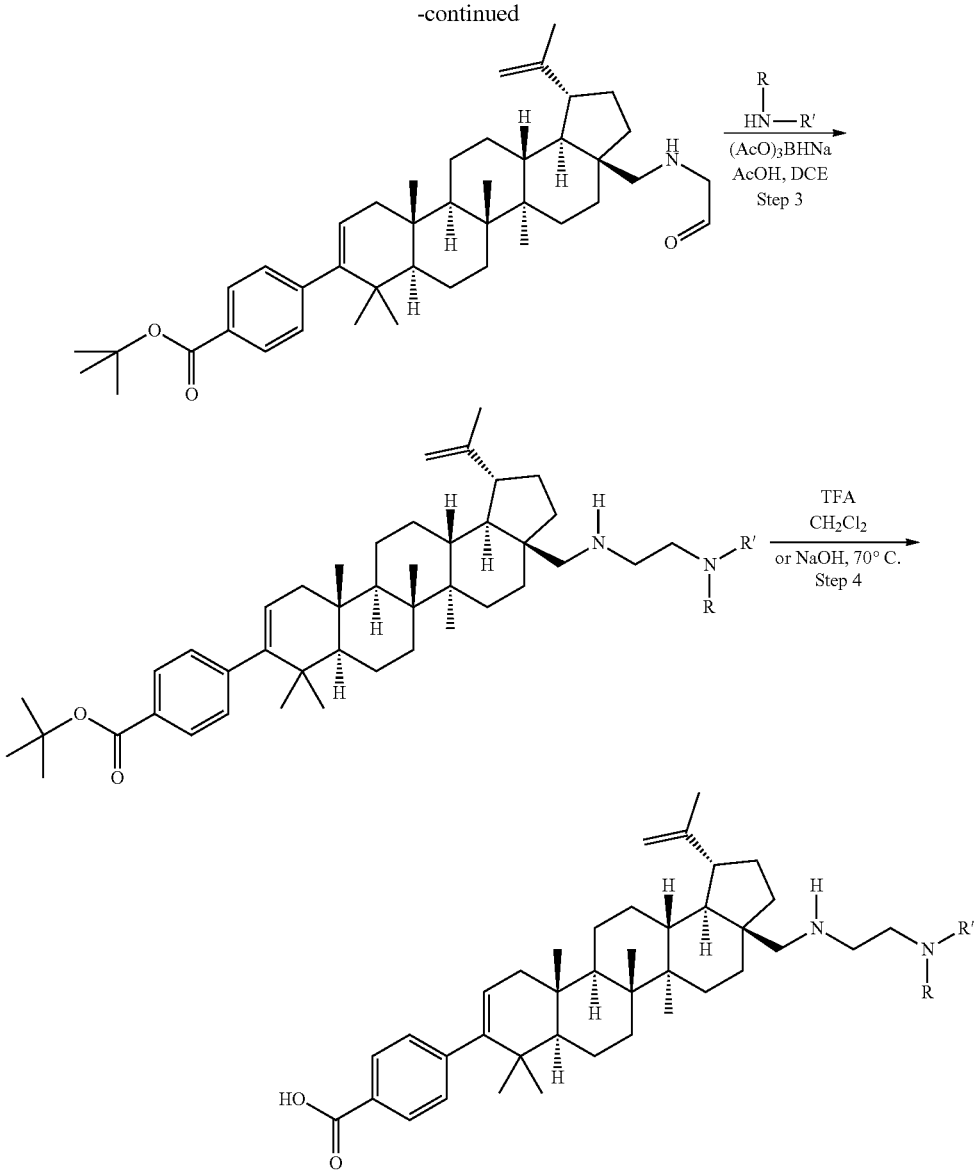

Step 1. Reductive Amination

A suspension of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (1 eq.), 2,2-diethoxyethanamine (2 eq.) and acetic acid (2-5 eq.) in DCE (2 ml) was stirred at rt for 30 min. Sodium triacetoxyborohydride (5 eq.) was added. The resulting mixture was stirred at rt for 18-72 h. The reaction mixture was diluted with 5 ml of saturated sodium carbonate and extracted with DCM (3×10 ml). The combined organic layers were dried over sodium sulfate, filtered and concentrated in vacuo. The crude product was purified by Biotage flash chromatography to afford the desired product was isolated as a white solid (88 mg, 15%). LCMS: m/e 716.6.4 (MH+), 2.96 min (method 3).

Step 2. Conversion of the Acetal to Aldehyde

To a solution of tert-butyl 4-((1R,3aS,5aR,5bR,7aR,11aS, 11bR,13aR,13bR)-3a-((2,2-diethoxyethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate from Step 1 in acetone (10 ml) was added 2 eq. of 4-methylbenzenesulfonic acid. The mixture was stirred and refluxed for 14 h. The solvent was removed in vacuo and the resulting residue was re-dissolved in methylene chloride and washed with sodium bicarbonate solution. The organic layer was separated and dried over sodium sulfate. The yellow solid obtained was used in the next step without further purification. LCMS: m/e 674.6 (M+CH$_3$OH+), 2.78 min (method 3).

Step 3. Reductive Amination

A suspension of tert-butyl 4-((1R,3aS,5aR,5bR,7aR,11aS, 11bR,13aR,13bR)-5a,5b,8,8,11a-pentamethyl-3a-((2-oxoethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (1 eq.), the corresponding amine (2 eq.) and acetic acid (2-5 eq.) in DCE (2 ml) was stirred at rt for 30 min. Sodium triacetoxyborohydride (5 eq.) was added. The resulting mixture was stirred at rt for 18-72 h. The reaction mixture was diluted with 5 ml of saturated sodium carbonate and extracted with DCM (3×10 ml). The combined organic layers were dried over sodium sulfate, filtered and concentrated in vacuo. The crude product was purified by Biotage flash chromatography or was used directly in the next step without further purification.

Step 4

(a) Acidic hydrolysis—To a solution of the material from Step 3 in DCM (4-5 ml) was added TFA (0.4-0.5 ml). The mixture was stirred at rt for 2-6 h. The solvent was evaporated under vacuum. The resulting crude product was purified by prep. HPLC to give the desired benzoic acids.

(b) Basic hydrolysis—To a solution of the material from Step 3 in dioxane (2 ml) and methanol (2 ml) was added NaOH (75 mg, 1.875 mmol) and $H_2O$ (0.5 ml). The resulting solution was stirred at 70° C. for 5-10 h. The solvent was evaporated under vacuum and the resulting crude product was purified by prep. HPLC to give the desired benzoic acids.

Example 85

Preparation of 4-((1R,3aS,5aR,5bR,7aR,11aS,11bR,13aR,13bR)-5a,5b,8,8,11a-pentamethyl-3a-((2-(methyl(2-(methylsulfonyl)ethyl)amino)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

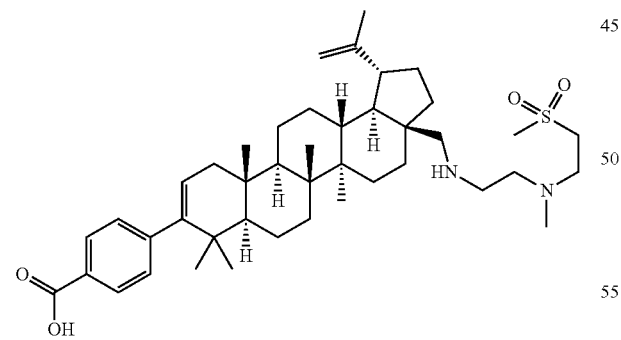

The title compound was prepared following the general procedures described above using N-methyl-2-(methylsulfo-nyl)ethanamine as the reactant amine. The product was isolated as a white solid (10 mg, 18.4%). LCMS: m/e 707.7 (MH$^+$), 2.55 min (method 3).

Example 86

Preparation of 4-((1R,3aS,5aR,5bR,7aR,11aS,11bR,13aR,13bR)-5a,5b,8,8,11a-pentamethyl-1-(prop-1-en-2-yl)-3a#2-thiomorpholinoethylamino)methyl)-2,3,3a,4,5,5a,5b,6,7,7a,8,11,11a,11b,12,13,13a,13b-octadecahydro-1H-cyclopenta[a]chrysen-9-yl) benzoic acid

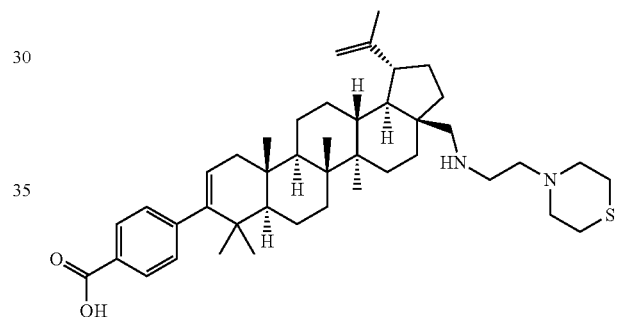

The title compound was prepared following the general procedures described above using thiomorpholine as the reactant amine. The product was isolated as a white solid (6 mg, 20.0%). LCMS: m/e 673.6 (MH$^+$), 2.56 min (method 3). $^1$H NMR (400 MHz, MeOD) δ ppm 7.94 (m, J=8.5 Hz, 2H), 7.24 (m, J=8.3 Hz, 2H), 5.33 (d, J=4.3 Hz, 1H), 4.79 (d, J=2.0 Hz, 1H), 4.68 (s, 1H), 3.42-3.55 (m, 2H), 3.33 (m, 2H), 3.15 (ddd, J=3.4, 1.6, 1.5 Hz, 5H), 2.84-3.01 (m, 5H), 2.53 (br. s., 1H), 2.18 (dd, J=17.2, 6.4 Hz, 2H), 1.67-1.92 (m, 8H), 1.47-1.67 (m, 8H), 1.38 (br. s., 2H), 1.31 (d, J=3.5 Hz, 3H), 1.14-1.26 (m, 5H), 1.11 (s, 3H), 1.07 (s, 3H), 0.99 (s, 3H), 0.98 (s, 3H).

General Procedure for the Preparation of C28 Amines with Fluorinated Benzoic Acids.

Examples 87-95
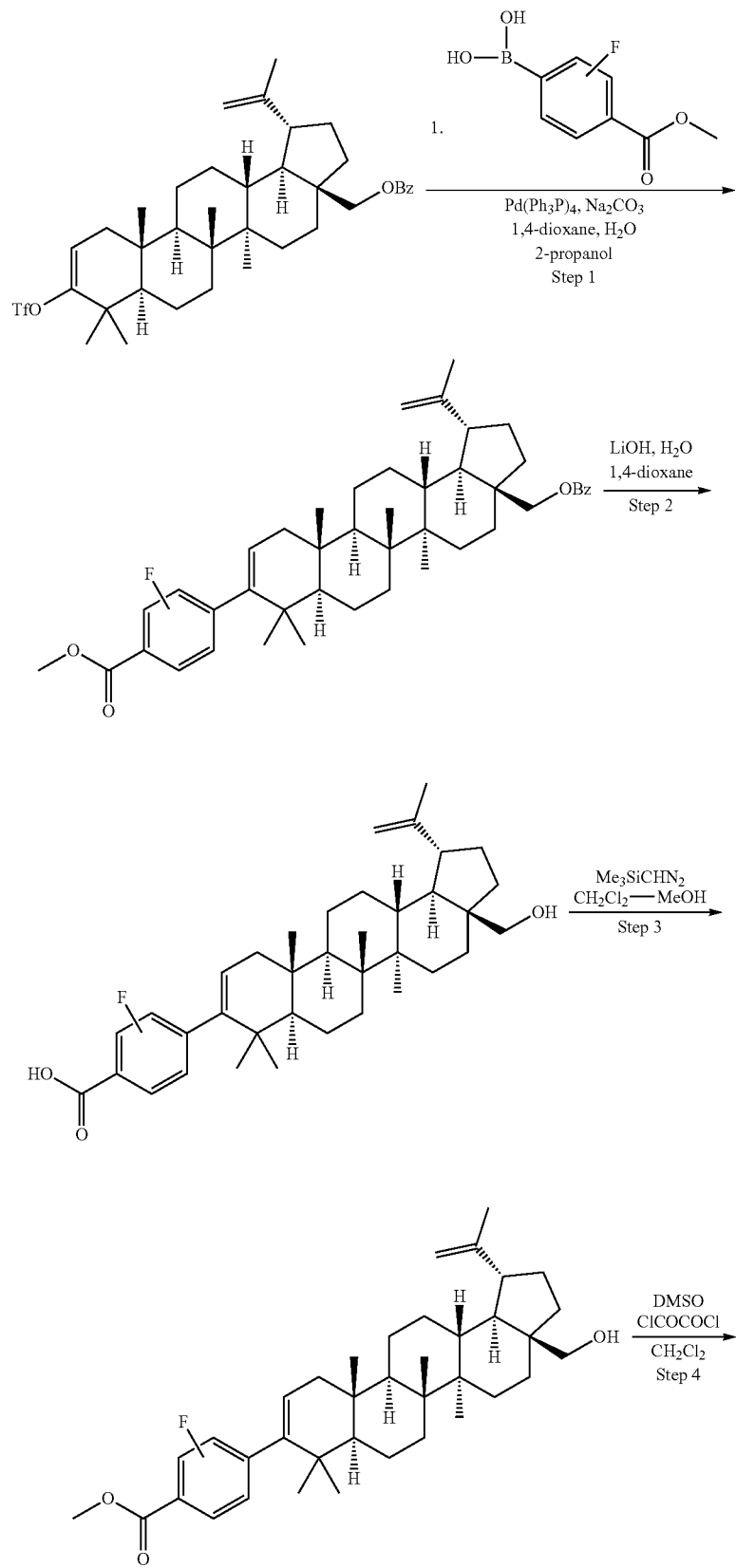

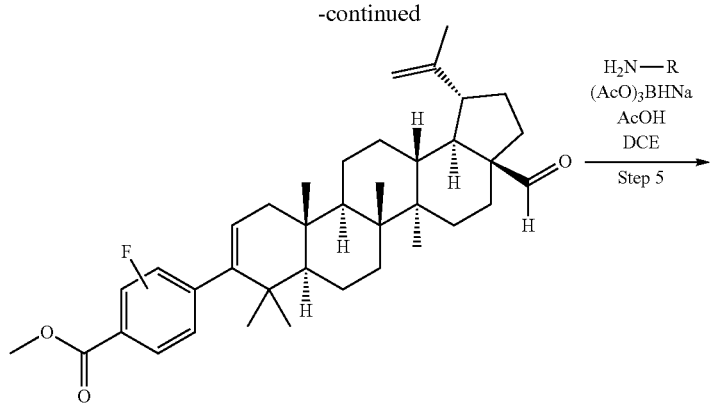

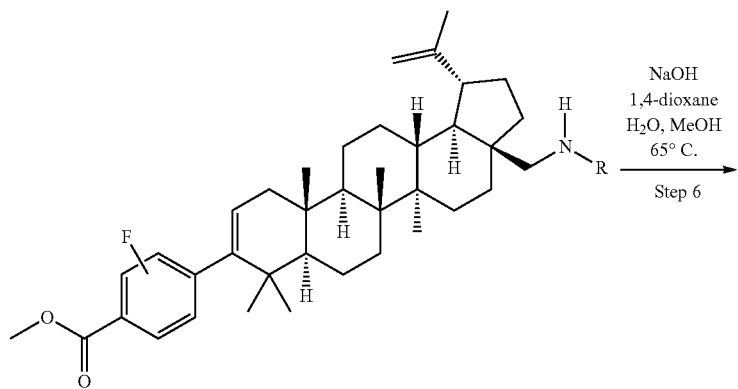

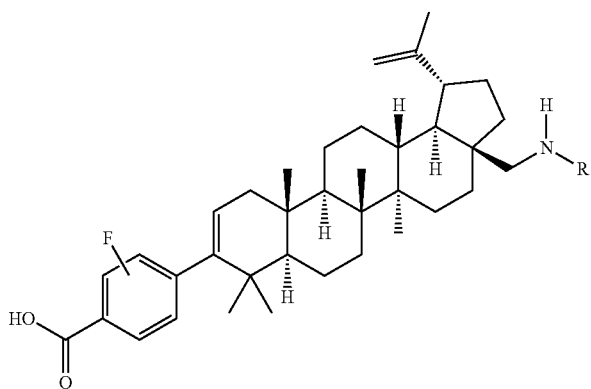

Step 1: Suzuki Coupling

To a solution of (((1R,3aS,5aR,5bR,7aR,11aR,11bR,13aR,13bR)-5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysen-3a-yl)methyl benzoate (675 mg, 1 mmol) in 1,4-dioxane (5 ml) was added 2-propanol (5 ml), H₂O (2 ml), Na₂CO₃ (317 mg, 3 mmol), the corresponding boronic acid (296 mg, 1.5 mmol) and Pd(Ph₃P)₄ (34.6 mg, 0.030 mmol). The mixture was refluxed under nitrogen for 4 h. The reaction mixture was diluted with H₂O (10 ml) and extracted with EtOAc (3×10 ml). The combined organic layers were dried over Na₂SO₄, filtered and concentrated in vacuo. The crude product was purified by Biotage (Thomson 25 g silica gel column; 9:1 Hex/EtOAc). The fractions containing the expected product were combined and concentrated in vacuo to give the corresponding fluorobenzoic methyl esters.

Preparation of methyl 4-((1R,3aS,5aR,5bR,7aR, 11aS,11bR,13aR,13bR)-3a-(benzoyloxymethyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)-3-fluorobenzoate

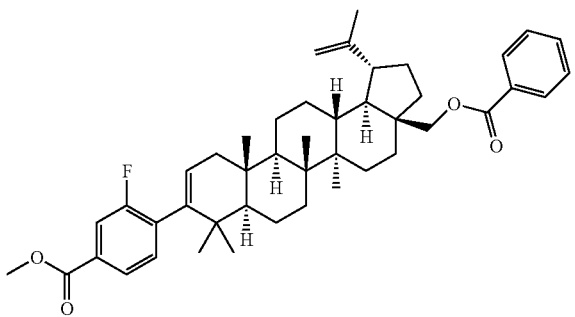

The title compound was prepared in 62% yield following the procedure described for the Suzuki coupling, using 2-fluoro-4-(methoxycarbonyl)phenylboronic acid as the reactant. $^1$H NMR (400 MHz, CHLOROFORM-d) δ 0.90 (3H, s), 0.95 (3H, s), 1.02 (3H, s), 1.05 (3H, s), 1.14 (3H, s), 1.73 (3H, s), 0.84-1.87 (18H, m), 1.91-2.10 (3H, m), 2.14 (1H, dd, J=17.3, 6.5 Hz), 2.56 (1H, td, J=11.0, 5.8 Hz), 3.93 (3H, s), 4.14 (1H, d, J=10.3 Hz), 4.56 (1H, d, J=9.8 Hz), 4.61-4.65 (1H, m), 4.75 (1H, d, J=2.0 Hz), 5.36 (1H, dd, J=6.3, 1.8 Hz), 7.17 (1H, t, J=7.5 Hz), 7.43-7.49 (2H, m), 7.55-7.60 (1H, m), 7.69 (1H, dd, J=9.7, 1.6 Hz), 7.74 (1H, dd, J=7.9, 1.6 Hz), 8.07 (2H, dd, J=8.4, 1.4 Hz).

Preparation of methyl 4-((1R,3aS,5aR,5bR,7aR, 11aS,11bR,13aR,13bR)-3a-(benzoyloxymethyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)-2-fluorobenzoate

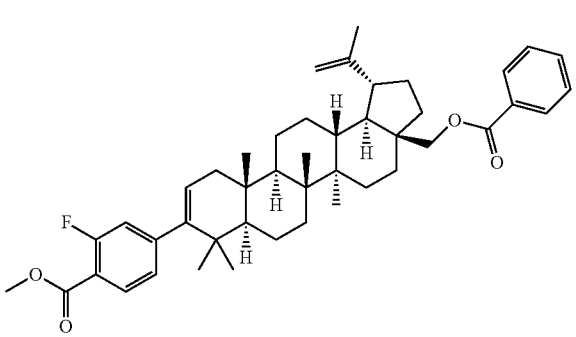

The title compound was prepared in 66% yield following the procedure described for the Suzuki coupling, using 3-fluoro-4-(methoxycarbonyl)phenylboronic acid as the reactant. $^1$H NMR (400 MHz, CHLOROFORM-d) δ 0.94 (3H, s), 0.95 (3H, s), 0.98 (3H, s), 1.05 (3H, s), 1.13 (3H, s), 1.73 (3H, s), 0.87-1.87 (m, 18H), 1.91-2.08 (3H, m), 2.12 (1H, dd, J=17.2, 6.4 Hz), 2.56 (1H, td, J=11.0, 5.8 Hz), 3.93 (3H, s), 4.13 (1H, d, J=10.0 Hz), 4.55 (1H, d, J=10.0 Hz), 4.61-4.65 (1H, m), 4.74 (1H, d, J=2.0 Hz), 5.33 (1H, dd, J=6.3, 1.8 Hz), 6.93 (1H, dd, J=11.8, 1.5 Hz), 6.98 (1H, dd, J=8.0, 1.5 Hz), 7.43-7.49 (2H, m), 7.54-7.60 (1H, m), 7.82 (1H, t, J=7.9 Hz), 8.07 (2H, dd, J=8.4, 1.4 Hz).

Step 2: Deprotection of C28 Alcohols

To a solution of the fluorobenzoic methyl esters from Step 1 in 1,4-dioxane (15 ml) and H$_2$O (2 ml) was added lithium hydroxide hydrate (3.0 eq). The resulting mixture stirred at 75° C. for 48 h. LCMS showed the reaction was incomplete. The mixture was partitioned between H$_2$O (50 ml) and DCM (50 ml) and neutralized with 1N HCl. The organic layer was washed with H$_2$O (2×50 ml), dried over Na$_2$SO$_4$, filtered and concentrated in vacuo. The solid was re-dissolved into 1,4-dioxane (15 ml) and MeOH (15 ml). Lithium hydroxide hydrate (3 eq) and H$_2$O (2 ml) were added. The resulting mixture was stirred at 75° C. for 24 h. LC/MS showed the reaction was complete and that the methyl ester had also been cleaved. The mixture was partitioned between H$_2$O (50 ml) and DCM (50 ml) and neutralized with 1N HCl. The organic layer was washed with H$_2$O (2×50 ml), dried over Na$_2$SO$_4$, filtered and concentrated in vacuo to give the crude C28 alcohols as solids which were used in the next step without further purification.

Preparation of methyl 3-fluoro-4-((1R,3aS,5aR,5bR, 7aR,11aS,11bR,13aR,13bR)-3a-(hydroxymethyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)benzoate

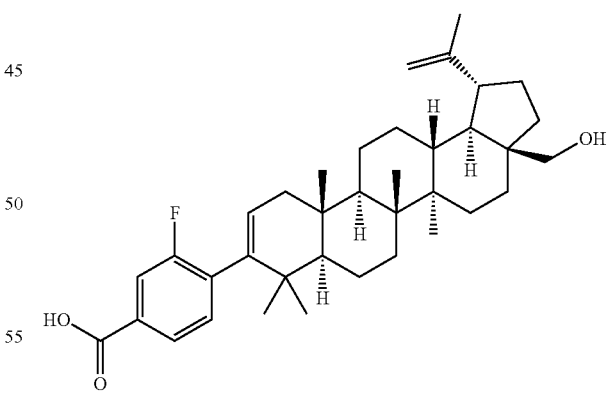

The title compound was prepared following the C28 alcohol deprotection procedure described above. $^1$H NMR (400 MHz, CHLOROFORM-d) δ 0.91 (3H, d, J=1.3 Hz), 0.96 (3H, s), 1.02 (3H, s), 1.03 (3H, s), 1.11 (3H, s), 1.71 (3H, s), 0.82-1.79 (m, 18H), 1.84-2.03 (3H, m), 2.13 (1H, dd, J=17.3, 6.5 Hz), 2.42 (1H, td, J=10.9, 6.1 Hz), 3.37 (1H, d, J=11.0 Hz), 3.84 (1H, d, J=10.5 Hz), 4.60 (1H, dd, J=2.1, 1.4 Hz), 4.71 (1H, d, J=2.0 Hz), 5.37 (1H, dd, J=6.3, 1.8 Hz), 7.21 (1H, t, J=7.4 Hz), 7.73 (1H, dd, J=9.5, 1.5 Hz), 7.79 (1H, dd, J=7.9, 1.6 Hz); MS m/z 561.6 (M−H)⁻, 2.36 min (Method 6).

Preparation of methyl 2-fluoro-4-((1R,3aS,5aR,5bR, 7aR,11aS,11bR,13aR,13bR)-3a-(hydroxymethyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoate Preparation of methyl 3-fluoro-4-((1R,3aS,5aR,5bR, 7aR,11aS,11bR,13aR,13bR)-3a-(hydroxymethyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoate

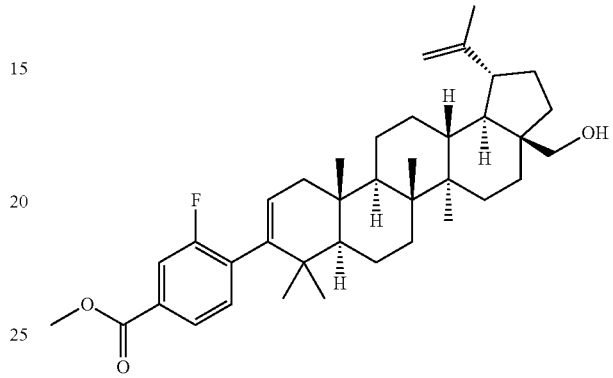

The title compound was prepared following the procedure described above for the methyl ester formation. ¹H NMR (400 MHz, CHLOROFORM-d) δ 0.89 (3H, d, J=1.0 Hz), 0.95 (3H, s), 1.01 (3H, s), 1.02 (3H, s), 1.10 (3H, s), 1.70 (3H, s), 0.81-1.78 (m, 18H), 1.84-2.05 (3H, m), 2.12 (1H, dd, J=17.1, 6.3 Hz), 2.42 (1H, td, J=11.0, 5.9 Hz), 3.36 (1H, dd, J=10.4, 5.6 Hz), 3.84 (1H, dd, J=9.8, 5.3 Hz), 3.93 (3H, s), 4.60 (1H, dd, J=2.3, 1.3 Hz), 4.70 (1H, d, J=2.0 Hz), 5.36 (1H, dd, J=6.3, 1.8 Hz), 7.17 (1H, t, J=7.5 Hz), 7.68 (1H, dd, J=9.5, 1.5 Hz), 7.74 (1H, dd, J=7.9, 1.6 Hz).

Preparation of methyl 2-fluoro-4-((1R,3aS,5aR,5bR, 7aR,11aS,11bR,13aR,13bR)-3a-(hydroxymethyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoate

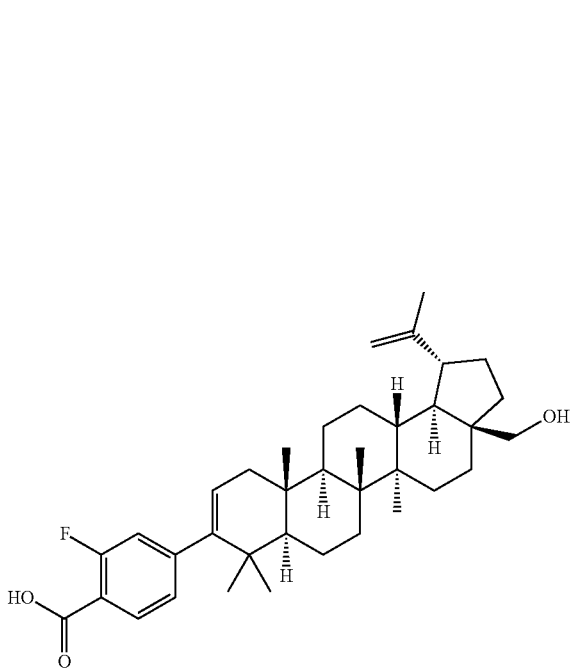

The title compound was prepared following the C28 alcohol deprotection procedure described above. ¹H NMR (400 MHz, CHLOROFORM-d) δ 0.95 (3H, s), 0.96 (3H, s), 0.98 (3H, s), 1.03 (3H, s), 1.10 (3H, s), 1.71 (3H, s), 0.83-1.79 (m, 18H), 1.84-2.06 (3H, m), 2.12 (1H, dd, J=17.4, 6.4 Hz), 2.42 (1H, td, J=10.7, 6.1 Hz), 3.37 (1H, d, J=10.8 Hz), 3.84 (1H, d, J=10.5 Hz), 4.60 (1H, s), 4.71 (1H, d, J=1.5 Hz), 5.34 (1H, dd, J=6.1, 1.6 Hz), 6.97 (1H, dd, J=11.9, 1.1 Hz), 7.02 (1H, dd, J=8.2, 1.4 Hz), 7.91 (1H, t, J=7.9 Hz); MS m/z 561.6 (M−H)⁻, 2.33 min (Method 6).

Step 3: Preparation of Methyl Esters of the Fluorobenzoic Acids

To a suspension of the material from Step 2 in DCM (40 ml) and MeOH (12 ml) was added trimethylsilyldiazomethane (2 M in hexane) (4.8 eq.). The resulting mixture was stirred at rt under nitrogen for 4 days. The reaction mixture was concentrated in vacuo to give crude products as solid which were used in the next step without further purification.

The title compound was prepared following the procedure described above for the methyl ester formation. ¹H NMR (400 MHz, CHLOROFORM-d) δ 0.94 (3H, s), 0.95 (3H, s), 0.97 (3H, s), 1.02 (3H, s), 1.09 (3H, s), 1.70 (3H, s), 0.86-1.78 (m, 18H), 1.84-2.02 (3H, m), 2.11 (1H, dd, J=17.3, 6.3 Hz), 2.42 (1H, td, J=10.5, 5.5 Hz), 3.36 (1H, dd, J=10.3, 6.0 Hz), 3.83 (1H, dd, J=10.4, 6.1 Hz), 3.93 (3H, s), 4.60 (1H, dd, J=2.3, 1.5 Hz), 4.70 (1H, d, J=2.3 Hz), 5.32 (1H, dd, J=6.1, 1.9 Hz), 6.93 (1H, dd, J=11.9, 1.4 Hz), 6.98 (1H, dd, J=8.0, 1.5 Hz), 7.82 (1H, t, J=7.9 Hz).

Step 4: Preparation of C28 aldehydes

To a solution of oxalyl chloride (1.2 eq) in DCM (5 ml) at −70° C. was added drop wise a solution of DMSO (1.5 eq) in DCM (5 ml) under nitrogen. The mixture was warmed to −50° C. A solution of the crude product from Step 3 in DCM (2 ml) was added drop wise. After stirring for 15 min at −50° C., Et₃N (3 eq) was added drop wise and the mixture was warmed to rt. The reaction mixture was diluted with DCM (50 ml) and washed with H₂O (2×50 ml) followed by brine (50 ml), dried over Na₂SO₄, filtered and concentrated in vacuo. The crude product was purified by Biotage (Thomson 25 g silica gel column; 9:1 Hex/EtOAc). The fractions containing the expected product were combined and concentrated in vacuo to give the corresponding aldehyde.

Preparation of methyl 3-fluoro-4-((1R,3aS,5aR,5bR, 7aR,11aS,11bR,13aR,13bR)-3a-formyl-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate

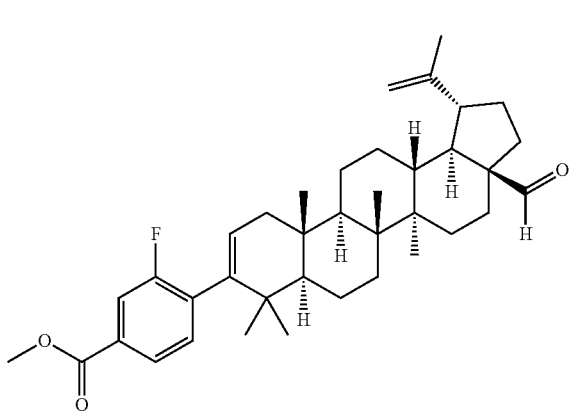

The title compound was prepared in 80% yield in 3 steps (steps 2-4) following the procedure described above for the C28 aldehyde formation. ¹H NMR (400 MHz, CHLOROFORM-d) δ 0.89 (3H, d, J=1.3 Hz), 0.94 (3H, s), 0.99 (3H, s), 1.00 (3H, s), 1.02 (3H, s), 1.72 (3H, s), 1.96-0.81 (m, 19H), 2.04-2.17 (3H, m), 2.90 (1H, td, J=11.1, 5.9 Hz), 3.92 (3H, s), 4.65 (1H, dd, J=2.1, 1.4 Hz), 4.78 (1H, d, J=2.0 Hz), 5.36 (1H, dd, J=6.3, 1.8 Hz), 7.16 (1H, t, J=7.5 Hz), 7.68 (1H, dd, J=9.5, 1.5 Hz), 7.74 (1H, dd, J=7.9, 1.6 Hz), 9.70 (1H, d, J=1.5 Hz). ¹⁹F NMR (376 MHz, MeOD) δ ppm −115.50 (1 F, s)); MS m/z 575.5 (M+H)⁺, 2.93 min (Method 2).

Preparation of methyl 2-fluoro-4-((1R,3aS,5aR,5bR, 7aR,11aS,11bR,13aR,13bR)-3a-formyl-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate

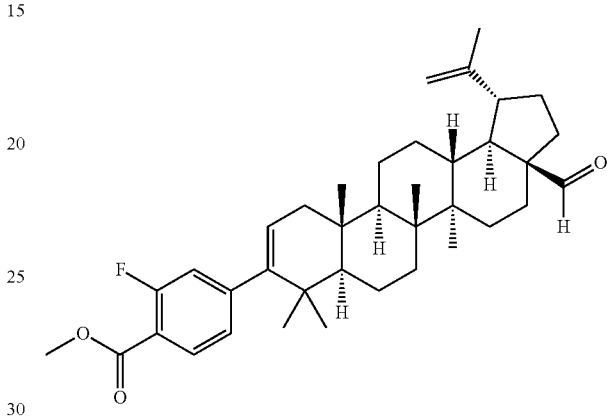

The title compound was prepared in 84% yield in 3 steps (steps 2-4) following the procedure described above for the C28 aldehyde formation. ¹H NMR (400 MHz, CHLOROFORM-d) δ ppm 0.93 (3H, s), 0.94 (3H, s), 0.96 (3H, s), 0.98 (3H, s), 1.01 (3H, s), 1.72 (3H, s), 1.96-0.80 (m, 19H), 2.04-2.16 (3H, m), 2.90 (1H, td, J=11.1, 5.9 Hz), 3.93 (3H, s), 4.65 (1H, dd, J=2.0, 1.5 Hz), 4.78 (1H, d, J=2.0 Hz), 5.32 (1H, dd, J=6.3, 2.0 Hz), 6.93 (1H, dd, J=11.9, 1.4 Hz), 6.97 (1H, dd, J=8.0, 1.5 Hz), 7.82 (1H, t, J=7.8 Hz), 9.70 (1H, d, J=1.5 Hz). ¹⁹F NMR (376 MHz, MeOD) δ ppm −114.87 (1 F, s): MS m/z 575.5 (M+H)⁺, 2.78 min (Method 2).

Step 5: Preparation of C28 Amines

A suspension of the corresponding aldehyde, an amine (2 eq.) and acetic acid (2-5 eq.) in DCE (2-5 ml) was stirred at rt for 0.5-1 h. Sodium triacetoxyborohydride (5 eq.) was added. The resulting mixture was stirred at rt for 18-72 h. The reaction mixture was diluted with 5 ml of saturated sodium carbonate and extracted with DCM (3×10 ml). The combined organic layers were dried over sodium sulfate, filtered and concentrated in vacuo. The crude product was purified by Biotage flash chromatography or was used directly in the next step without further purification.

Step 6: Preparation of Benzoic Acids

To a solution of C28 amine from Step 5 in 1,4-dioxane (1 ml) and methanol (0.5 ml) was added 1N sodium hydroxide (0.5-1 ml). The mixture was stirred at 65° C. for 2-5 h. The crude reaction mixture was purified by prep. HPLC to afford the desired benzoic acids.

Example 87

3-fluoro-4-((1R,3aS,5aR,5bR,7aR,11aS,11bR,13aR,13bR)-5a,5b,8,8,11a-pentamethyl-3a-((3-(2-oxopyrrolidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

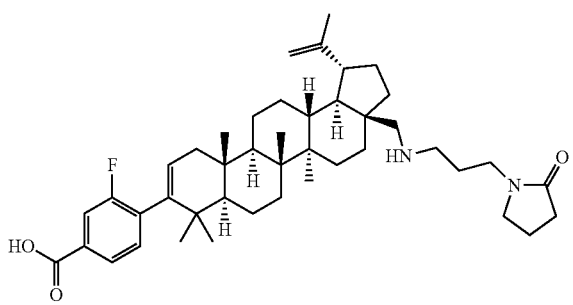

The title compound was prepared in 79% yield following steps 5 and 6 described above, using methyl 3-fluoro-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate and 1-(3-aminopropyl)pyrrolidin-2-one as the reactant amine MS: m/e 687.5 (MH+), 1.71 min (method 2). $^1$H NMR (400 MHz, MeOD) δ ppm 0.91 (s, 3H) 0.96 (s, 3H) 1.05 (s, 3H) 1.08 (s, 3H) 1.17 (s, 3H) 1.73 (s, 3H) 0.85-1.91 (m, 20H) 1.96-2.20 (m, 6H) 2.44 (t, J=8.03 Hz, 2H) 2.47-2.56 (m, 1H) 2.83 (d, J=13.05 Hz, 1H) 3.07 (t, J=7.03 Hz, 2H) 3.21 (d, J=13.05 Hz, 1H) 3.43 (t, J=6.40 Hz, 2H) 3.52 (t, J=7.15 Hz, 2H) 4.62-4.66 (m, 1H) 4.75 (d, J=1.51 Hz, 1H) 5.35 (dd, J=6.02, 1.51 Hz, 1H) 7.22 (t, J=7.65 Hz, 1H) 7.64 (dd, J=9.79, 1.51 Hz, 1H) 7.75 (dd, J=7.91, 1.63 Hz, 1H). $^{19}$F NMR (376 MHz, MeOD) δ ppm −114.92 (s, 1 F).

Example 88

2-fluoro-4-((1R,3aS,5aR,5bR,7aR,11aS,11bR,13aR,13bR)-5a,5b,8,8,11a-pentamethyl-3a-((3-(2-oxopyrrolidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

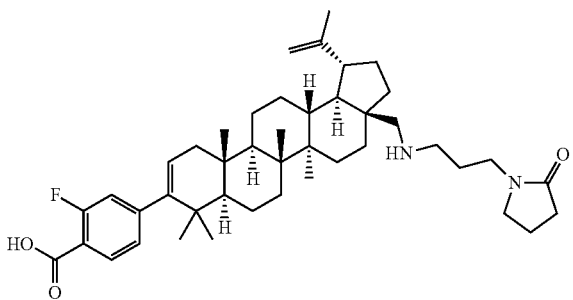

The title compound was prepared in 82% yield following steps 5 and 6 described above, using methyl 2-fluoro-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate and 1-(3-aminopropyl)pyrrolidin-2-one as the reactant amine MS: m/e 687.5 (MH+), 1.71 min (method 2). $^1$H NMR (400 MHz, MeOD) δ ppm 0.96 (s, 3H) 0.98 (s, 3H) 1.02 (s, 3H) 1.08 (s, 3H) 1.17 (s, 3H) 1.73 (s, 3H) 0.90-1.91 (m, 20H) 1.96-2.20 (m, 6H) 2.44 (t, J=8.03 Hz, 2H) 2.47-2.55 (m, 1H) 2.83 (d, J=13.05 Hz, 1H) 3.06 (t, J=7.03 Hz, 2H) 3.20 (d, J=13.55 Hz, 1H) 3.43 (t, J=6.53 Hz, 2H) 3.51 (t, J=7.15 Hz, 2H) 4.62-4.66 (m, 1H) 4.75 (d, J=1.76 Hz, 1H) 5.35 (dd, J=6.15, 1.88 Hz, 1H) 6.94 (dd, J=11.80, 1.25 Hz, 1H) 7.02 (dd, J=8.03, 1.51 Hz, 1H) 7.83 (t, J=7.91 Hz, 1H). $^{19}$F NMR (376 MHz, MeOD) δ ppm −112.76 (s, 1 F).

Example 89

3-fluoro-4-((1R,3aS,5aR,5bR,7aR,11aS,11bR,13aR,13bR)-5a,5b,8,8,11a-pentamethyl-3a-((3-oxo-3-(pyrrolidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

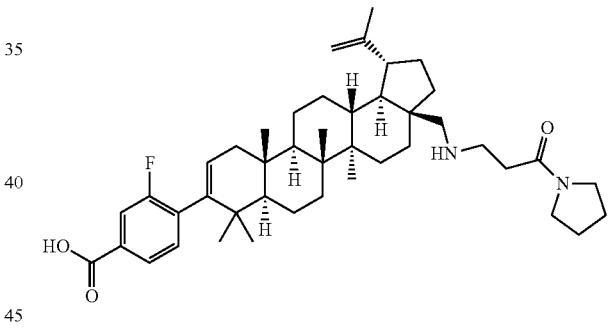

The title compound was prepared in 72% yield following steps 5 and 6, using methyl 3-fluoro-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate and 3-amino-1-(pyrrolidin-1-yl)propan-1-one hydrochloride as the reactant amine MS: m/e 687.5 (MH+), 1.76 min (method 2). $^1$H NMR (400 MHz, MeOD) δ ppm 0.91 (s, 3H) 0.96 (s, 3H) 1.05 (s, 3H) 1.09 (s, 3H) 1.17 (s, 3H) 1.73 (s, 3H) 0.85-1.85 (m, 20H) 1.87-1.96 (m, 2H) 2.01 (dt, J=13.36, 6.74 Hz, 2H) 2.04-2.12 (m, 1H) 2.16 (dd, J=17.07, 6.53 Hz, 1H) 2.48-2.57 (m, 1H) 2.81 (t, J=6.02 Hz, 2H) 2.88 (d, J=12.80 Hz, 1H) 3.33-3.43 (m, 3H) 3.43-3.52 (m, 4H) 4.65 (s, 1H) 4.76 (d, J=1.25 Hz, 1H) 5.35 (dd, J=6.02, 1.51 Hz, 1H) 7.22 (t, J=7.53 Hz, 1H) 7.64 (dd, J=9.79, 1.25 Hz, 1H) 7.75 (dd, J=8.03, 1.51 Hz, 1H). $^{19}$F NMR (376 MHz, MeOD) δ ppm −113.36 (s, 1 F).

Example 90

2-fluoro-4-((1R,3aS,5aR,5bR,7aR,11aS,11bR,13aR,13bR)-5a,5b,8,8,11a-pentamethyl-3a-((3-oxo-3-(pyrrolidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

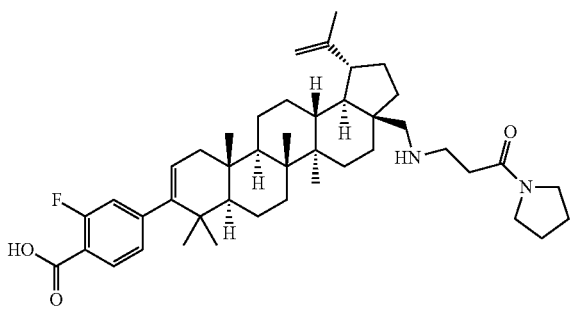

The title compound was prepared in 67% yield following steps 5 and 6, using methyl 2-fluoro-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate and 3-amino-1-(pyrrolidin-1-yl)propan-1-one hydrochloride as the reactant amine MS: m/e 687.5 (MH+), 1.74 min (method 2). $^1$H NMR (400 MHz, MeOD) δ ppm 0.96 (s, 3H) 0.98 (s, 3H) 1.02 (s, 3H) 1.08 (s, 3H) 1.16 (s, 3H) 1.73 (s, 3H) 0.90-1.86 (m, 20H) 1.88-1.96 (m, J=6.78, 6.78, 6.65, 6.40 Hz, 2H) 1.97-2.10 (m, 1H) 2.01 (dt, J=13.74, 6.81 Hz, 2H) 2.16 (dd, J=17.19, 6.40 Hz, 1H) 2.47-2.57 (m, 1H) 2.81 (t, J=6.02 Hz, 2H) 2.88 (d, J=12.55 Hz, 1H) 3.33-3.42 (m, 3H) 3.42-3.52 (m, 4H) 4.65 (s, 1H) 4.76 (d, J=1.76 Hz, 1H) 5.35 (dd, J=5.77, 1.00 Hz, 1H) 6.94 (d, J=11.80 Hz, 1H) 7.02 (dd, J=8.03, 1.25 Hz, 1H) 7.83 (t, J=7.91 Hz, 1H). $^{19}$F NMR (376 MHz, MeOD) δ ppm -112.76 (s, 1 F).

Example 91

2-fluoro-4-((1R,3aS,5aR,5bR,7aR,11aS,11bR,13aR,13bR)-5a,5b,8,8,11a-pentamethyl-3a-((2-(2-oxopyrrolidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

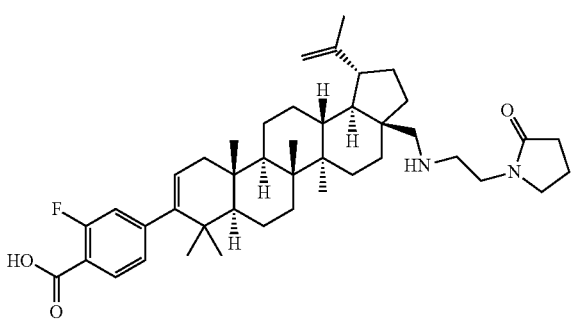

The title compound was prepared in 60% yield following steps 5 and 6, using methyl 2-fluoro-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate and 1-(2-aminoethyl)pyrrolidin-2-one oxalate as the reactant amine MS: m/e 673.6 (MH+), 1.72 min (method 2). $^1$H NMR (400 MHz, MeOD) δ ppm 0.96 (s, 3H) 0.98 (s, 3H) 1.02 (s, 3H) 1.08 (s, 3H) 1.17 (s, 3H) 1.73 (s, 3H) 2.01-2.21 (m, 4H) 2.44 (t, J=8.16 Hz, 2H) 2.51 (td, J=10.79, 5.52 Hz, 1H) 2.94 (d, J=13.05 Hz, 1H) 3.30 (dt, J=3.26, 1.63 Hz, 3H) 3.55 (t, J=7.15 Hz, 2H) 3.58-3.70 (m, 2H) 4.62-4.67 (m, 1H) 4.76 (d, J=1.76 Hz, 1H) 5.35 (dd, J=6.27, 1.76 Hz, 1H) 6.94 (dd, J=11.92, 1.38 Hz, 1H) 7.02 (dd, J=8.03, 1.51 Hz, 1H) 7.83 (t, J=7.91 Hz, 1H). $^{19}$F NMR (376 MHz, MeOD) δ ppm -112.75 (s, 1 F).

Example 92

Preparation of 4-((1R,3aS,5aR,5bR,7aR,11aS,11bR,13aR,13bR)-3a-(((3-(1,1-dioxido-4-thiomorpholinyl)propyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-3-fluorobenzoic acid

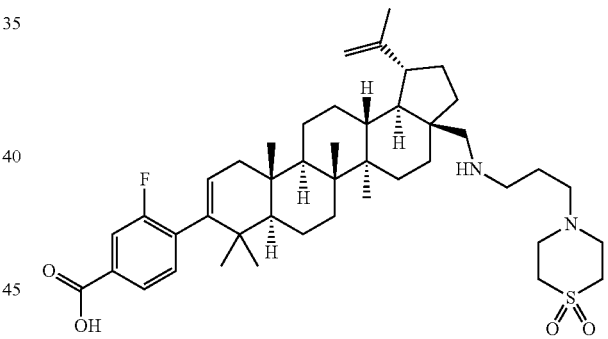

The title compound was prepared following steps 5 and 6 using methyl 3-fluoro-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate and 4-(3-aminopropyl) thiomorpholine 1,1-dioxide as the reactant amine. The product was isolated as a white solid (70 mg, 68.0%). LCMS: m/e 737.5 (MH+), 2.59 min (method 3). $^1$H NMR (400 MHz, MeOD) δ ppm 7.77 (d, J=7.8 Hz, 1H), 7.67 (d, J=9.8 Hz, 1H), 7.19-7.31 (m, 1H), 5.38 (d, J=4.8 Hz, 1H), 4.78 (br. s., 1H), 4.67 (br. s., 1H), 3.41 (br. s., 4H), 3.30-3.38 (m, 4H), 3.27 (d, J=12.5 Hz, 1H), 3.21 (br. s., 2H), 3.00 (t, J=6.4 Hz, 2H), 2.90 (br. s., 1H), 2.53 (br. s., 1H), 2.10 (br. s., 4H), 1.84 (br. s., 3H), 1.75 (br. s., 7H), 1.54 (br. s., 8H), 1.36 (br. s., 3H), 1.20 (br. s., 5H), 1.11 (br. s., 3H), 1.07 (br. s., 3H), 0.98 (br. s., 3H), 0.94 (br. s., 3H). $^{19}$F NMR (376 MHz, MeOD) δ ppm −113.31 (s, 1 F).

Example 93

Preparation of 4-((1R,3aS,5aR,5bR,7aR,11aS,11bR, 13aR,13bR)-3a-(((3-(1,1-dioxido-4-thiomorpholinyl) propyl)amino)methyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)-2-fluorobenzoic acid

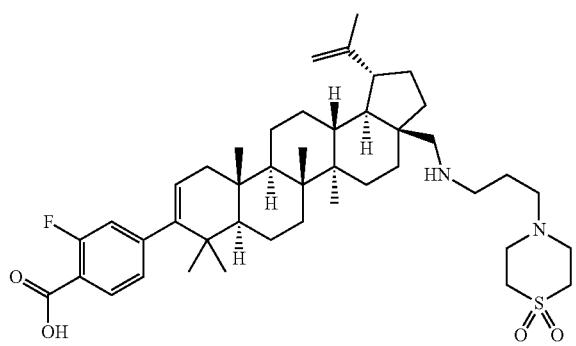

The title compound was prepared following steps 5 and 6 using methyl 2-fluoro-4-((1R,3aS,5aR,5bR,7aR,11aS,11bR, 13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate and 4-(3-aminopropyl) thiomorpholine 1,1-dioxide as the reactant amine. The product was isolated as a white solid (50 mg, 55.0%). LCMS: m/e 737.5 (MH⁺), 2.53 min (method 3). $^1$H NMR (400 MHz, MeOD) δ ppm 7.85 (d, J=3.8 Hz, 1H), 7.01-7.14 (m, 1H), 6.98 (br. s., 1H), 5.37 (br. s., 1H), 4.78 (br. s., 1H), 4.67 (br. s., 1H), 3.56 (br. s., 4H), 3.43 (br. s., 4H), 3.21 (m, 3H), 3.12 (br. s., 2H), 2.90 (br. s., 1H), 2.53 (br. s., 1H), 2.16 (br. s., 4H), 1.75 (br. s., 10H), 1.53 (br. s., 8H), 1.31 (br.

s., 3H), 1.19 (br. s., 5H), 1.10 (br. s., 3H), 1.05 (br. s., 3H), 0.99 (d, J=8.5 Hz, 6H). $^{19}$F NMR (376 MHz, MeOD) δ ppm −112.6 (s, 1 F).

Example 94

Preparation of 4-((1R,3aS,5aR,5bR,7aR,11aS,11bR, 13aR,13bR)-3a-(((2-(1,1-dioxido-4-thiomorpholinyl) ethyl)amino)methyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)-3-fluorobenzoic acid

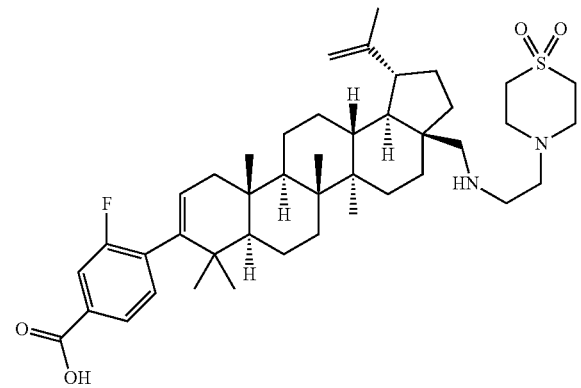

The title compound was prepared following steps 5 and 6 using methyl 3-fluoro-4-((1R,3aS,5aR,5bR,7aR,11aS,11bR, 13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate and 4-(3-aminoethyl) thiomorpholine 1,1-dioxide as the reactant amine. The product was isolated as a white solid (70 mg, 66.4%). LCMS: m/e 723.5 (MH⁺), 2.57 min (method 3). $^1$H NMR (400 MHz, MeOD) δ ppm 7.77 (dd, J=7.9, 1.6 Hz, 1H), 7.67 (dd, J=9.8, 1.5 Hz, 1H), 7.24 (t, J=7.5 Hz, 1H), 5.36 (d, J=4.8 Hz, 1H), 4.78 (d, J=1.5 Hz, 1H), 4.66 (s, 1H), 3.23-3.45 (m, 3H), 3.16 (d, J=2.5 Hz, 8H), 2.94-3.05 (m, 2H), 2.91 (d, J=13.1 Hz, 1H), 2.55 (td, J=10.5, 5.8 Hz, 1H), 2.17 (dd, J=17.1, 6.5 Hz, 1H), 1.96-2.13 (m, 1H), 1.68-1.93 (m, 10H), 1.43-1.66 (m, 8H), 1.28-1.43 (m, 3H), 1.13-1.25 (m, 5H), 1.09 (s, 3H), 1.06 (s, 3H), 0.98 (s, 3H), 0.93 (s, 3H). $^{19}$F NMR (376 MHz, MeOD) δ ppm −113.10 (s, 1 F).

Example 95

Preparation of 4-((1R,3aS,5aR,5bR,7aR,11aS,11bR, 13aR,13bR)-3a-(((2-(1,1-dioxido-4-thiomorpholinyl) ethyl)amino)methyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)-2-fluorobenzoic acid

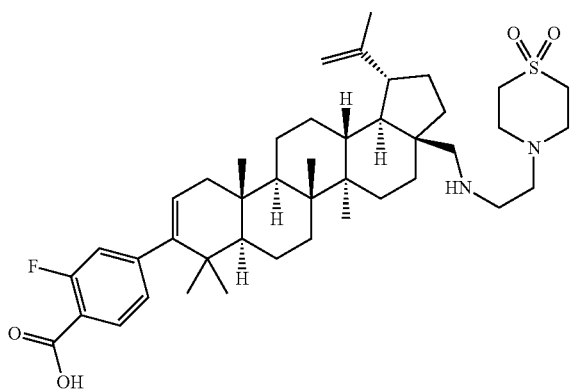

The title compound was prepared following steps 5 and 6 using methyl 2-fluoro-4-((1R,3aS,5aR,5bR,7aR,11aS,11bR, 13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate and 4-(3-aminoethyl) thiomorpholine 1,1-dioxide as the reactant amine. The product was isolated as a white solid (53 mg, 70.7%). LCMS: m/e 723.5 (MH$^+$), 2.56 min (method 3). $^1$H NMR (400 MHz, MeOD) δ ppm 7.74-7.96 (m, 1H), 6.99-7.16 (m, 1H), 6.78-6.99 (m, 1H), 5.25-5.40 (m, 1H), 4.77 (d, J=1.5 Hz, 1H), 4.58-4.70 (m, 1H), 3.24-3.40 (m, 3H), 3.06-3.24 (m, 8H), 2.93-3.05 (m, 2H), 2.81-2.93 (m, 1H), 2.53 (td, J=10.5, 5.5 Hz, 1H), 2.17 (dd, J=17.2, 6.4 Hz, 1H), 1.94-2.12 (m, 1H), 1.67-1.92 (m, 10H), 1.42-1.66 (m, 8H), 1.21-1.42 (m, 5H), 1.18 (s, 3H), 1.09 (s, 3H), 1.04 (s, 3H), 0.92-1.02 (m, 6H). $^{19}$F NMR (376 MHz, MeOD) δ ppm −112.49 (s, 1 F), −112.51 (s, 1 F), −112.54 (s, 1 F).

General procedure for preparation of C28 amines with amide end cap (examples 96-130):

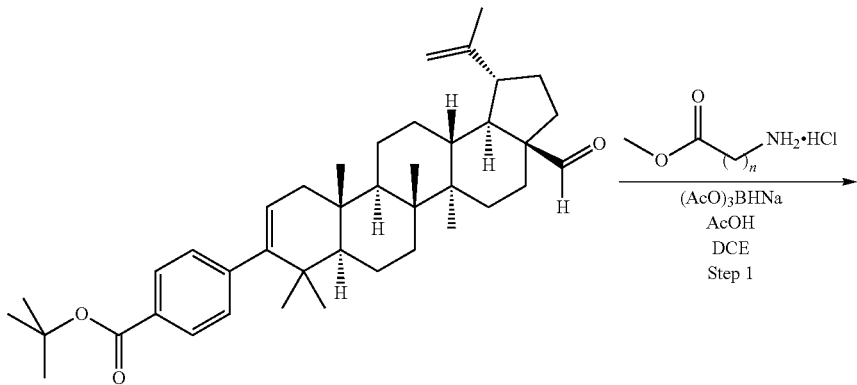

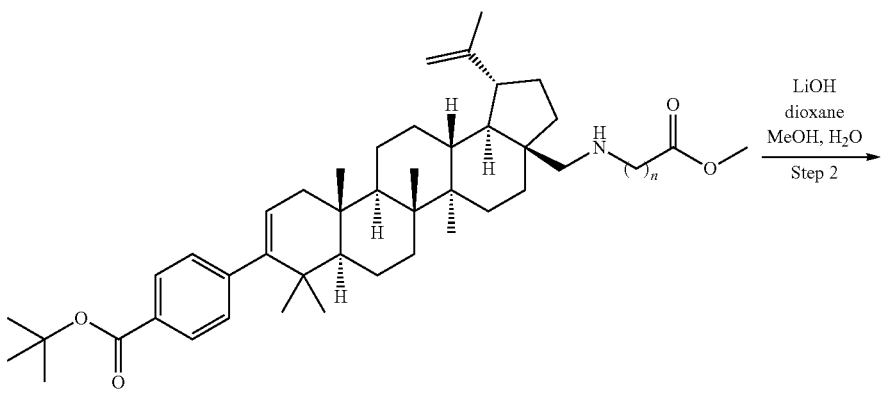

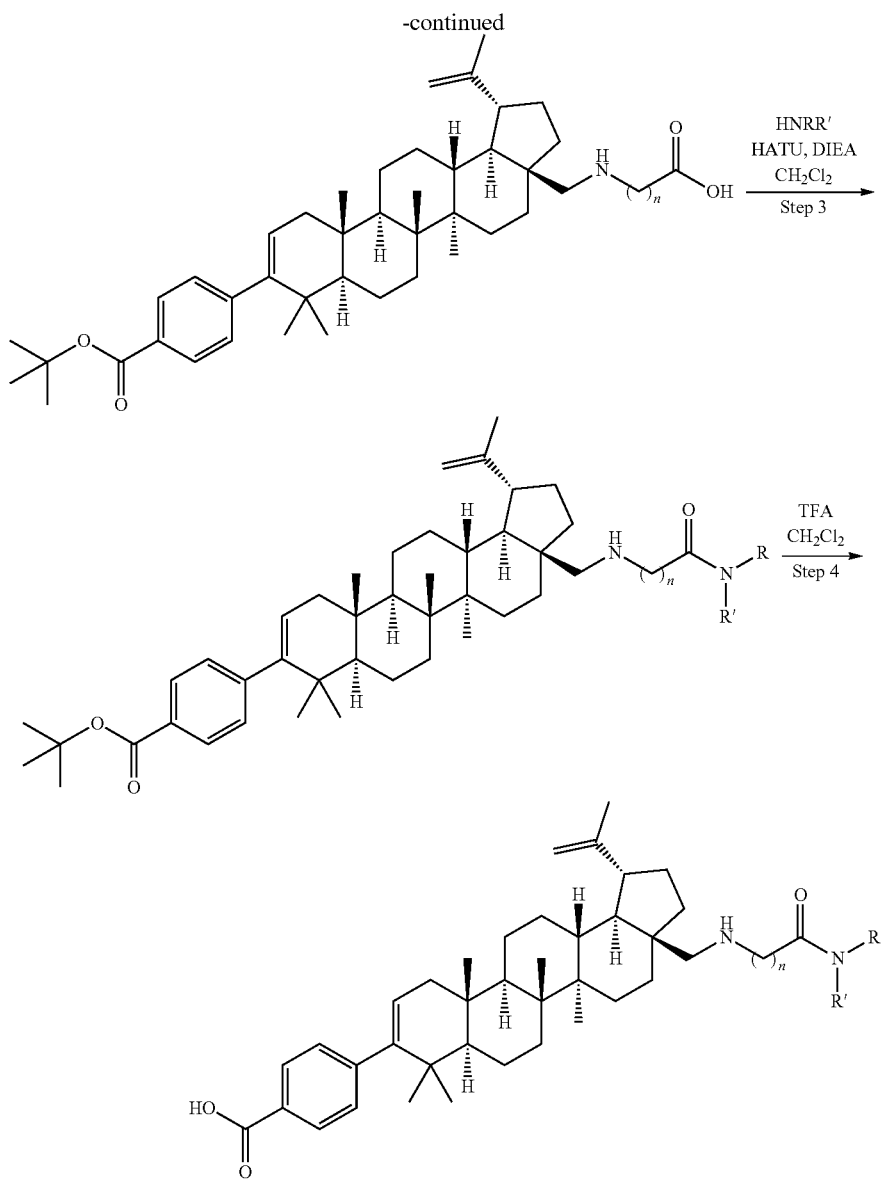

n = 1, methyl 2-aminoacetate hydrochloride
n = 2, methyl 3-aminopropanoate hydrochloride Step 1: Preparation of methyl aminoacetate or methyl 3-aminopropanoate To a solution of the aldehyde (200 mg, 0.334 mmol) in DCE was added potassium carbonate (185 mg, 1.336 mmol). After stirring at rt for 30 min, acetic acid (80 mg, 1.336 mmol) and methyl 2-aminoacetate hydrochloride or methyl 3-aminopropanoate hydrochloride (4 eq. 1.336 mmol) were added. The mixture was stirred at rt for 10 min, then sodium triacetoxyhydroborate (566 mg, 2.67 mmol) was added. The mixture was stirred rt for 48 h. The mixture was diluted with 7 ml of sat. NaHCO$_3$ and was extracted with DCM (3×7 ml). The combined organic layers were dried with sodium sulfate. The drying agent was removed by filtration and the filtrate was concentrated under reduced pressure to give the crude product which was used in the next step with no additional purification.

Step 2: Preparation of aminoacetic acid or 3-aminopropanoic acid

To a solution of the material from Step 1 in dioxane (1 ml) and methanol (5 ml) was added lithium hydroxide (5 eq.) followed by H$_2$O (0.5 ml). The clear solution was stirred at rt for 12 h. The solvent was evaporated and the resulting yellow solid was re-dissolved in dichloromethane and the pH was adjusted to ~4 by adding HCl. The mixture was extracted with DCM (3×10 ml). The combined organic layers were dried with sodium sulfate. The drying agent was removed by filtration and the filtrate was concentrated under reduced pressure to give the crude product which was used in the next step with no additional purification.

Step 3: Preparation of aminoacetic amides or 3-aminopropanoic amides

To the solution of material from Step 2 (1 eq.) in DMC at 0° C. was added the corresponding amine (1.5 eq.), HATU (2 eq.) followed by DIPEA (3 eq.). The resulting suspension was stirred at rt for 18 h. LC/MS was consistent with the expected product. The solvent was removed in vacuo to give the crude product which was used in the next step with no additional purification.

Step 4: Preparation of Benzoic Acids

To the solution of the material from Step 3 in DCM (4-5 ml) was added TFA (0.4-0.5 ml,). The mixture was stirred at rt for 2-16 h. The solvent was removed under reduced pressure. The resulting crude product was purified by prep. HPLC to afford the desired benzoic acids.

Example 96

4-((1R,3aS,5aR,5bR,7aR,11aS,11bR,13aR,13bR)-5a,5b,8,8,11a-pentamethyl-3a-((3-oxo-3-(piperidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

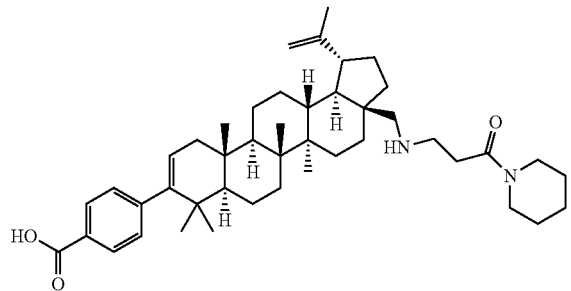

The title compound was prepared in 53% yield following the general procedure described above for the preparation of C28 amines with amide end cap using piperidine as the reactant amine MS: m/e 683.5 (MH$^+$), 1.63 min (method 2). $^1$H NMR (400 MHz, MeOD) δ ppm 0.95 (s, 3H) 0.97 (s, 3H) 1.04 (s, 3H) 1.08 (s, 3H) 1.17 (s, 3H) 1.73 (s, 3H) 0.87-1.85 (m, 26H) 1.99-2.10 (m, 1H) 2.15 (dd, J=16.94, 6.40 Hz, 1H) 2.52 (td, J=10.48, 4.89 Hz, 1H) 2.83-2.90 (m, 3H) 3.26 (d, J=13.80 Hz, 1H) 3.32-3.38 (m, 2H) 3.44-3.50 (m, 2H) 3.54-3.60 (m, 2H) 4.65 (s, 1H) 4.76 (d, J=1.76 Hz, 1H) 5.30 (dd, J=5.90, 1.13 Hz, 1H) 7.21 (d, J=8.28 Hz, 2H) 7.91 (d, J=8.28 Hz, 2H).

Example 97

4-((1R,3aS,5aR,5bR,7aR,11aS,11bR,13aR,13bR)-3a-((3-(4-(N,N-dimethylsulfamoyl)piperazin-1-yl)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

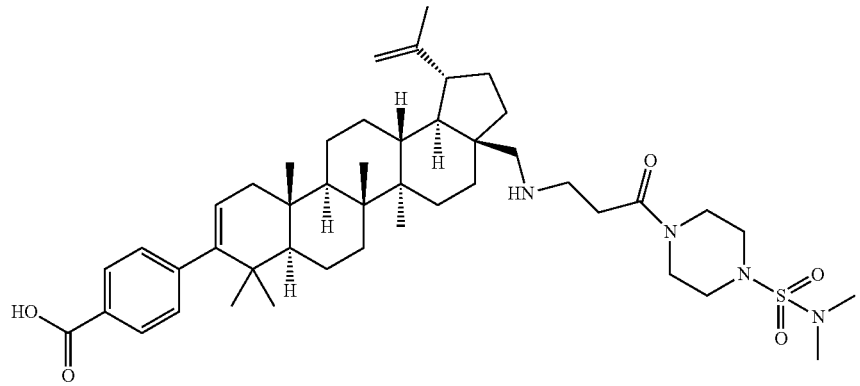

The title compound was prepared in 81% yield following the general procedure described above for the preparation of C28 amines with amide end cap using N,N-dimethylpiperazine-1-sulfonamide as the reactant amine MS: m/e 791.5 (MH+), 1.74 min (method 2). ¹H NMR (400 MHz, MeOD) δ ppm 0.95 (s, 3H) 0.96 (s, 3H) 1.04 (s, 3H) 1.08 (s, 3H) 1.17 (s, 3H) 1.73 (s, 3H) 0.89-1.86 (m, 20H) 1.99-2.10 (m, 1H) 2.15 (dd, J=17.32, 6.53 Hz, 1H) 2.52 (td, J=10.60, 6.15 Hz, 1H) 2.84 (s, 6H) 2.85-2.93 (m, 3H) 3.19-3.28 (m, 4H) 3.33-3.44 (m, 3H) 3.56-3.62 (m, 2H) 3.63-3.76 (m, 2H) 4.65 (s, 1H) 4.76 (d, J=1.51 Hz, 1H) 5.30 (dd, J=6.15, 1.63 Hz, 1H) 7.22 (d, J=8.53 Hz, 2H) 7.92 (d, J=8.53 Hz, 2H).

Example 98

4-((1R,3aS,5aR,5bR,7aR,11aS,11bR,13aR,13bR)-3a-((3-(4-(ethoxycarbonyl)piperidin-1-yl)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

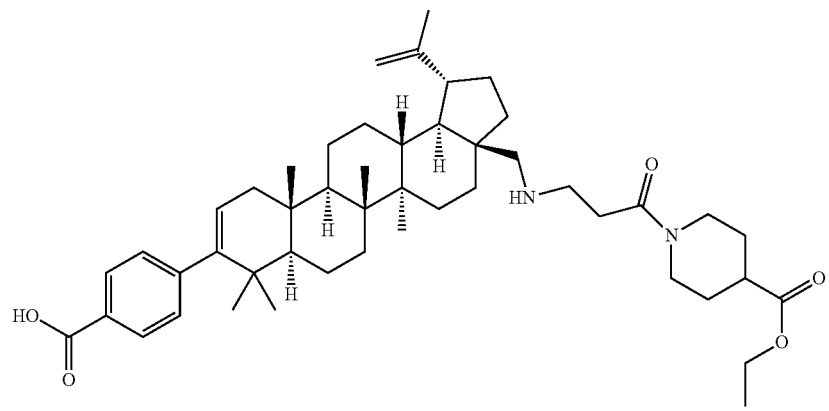

The title compound was prepared in 35% yield following the general procedure described above for the preparation of C28 amines with amide end cap using ethyl piperidine-4-carboxylate as the reactant amine MS: m/e 755.5 (MH+), 1.62 min (method 2). ¹H NMR (400 MHz, MeOD) δ ppm 0.95 (s, 3H) 0.97 (s, 3H) 1.04 (s, 3H) 1.08 (s, 3H) 1.17 (d, J=1.25 Hz, 3H) 1.24 (t, J=7.03 Hz, 3H) 1.73 (s, 3H) 0.87-1.85 (m, 22H) 1.91-2.10 (m, 3H) 2.15 (dd, J=16.94, 6.40 Hz, 1H) 2.46-2.56 (m, 1H) 2.60-2.72 (m, 1H) 2.81-2.95 (m, 4H) 3.16-3.43 (m, 4H) 3.82-3.90 (m, 1H) 4.14 (q, J=7.11 Hz, 2H) 4.35-4.43 (m, 1H) 4.65 (s, 1H) 4.76 (d, J=1.51 Hz, 1H) 5.30 (dd, J=6.02, 1.51 Hz, 1H) 7.21 (d, J=8.28 Hz, 2H) 7.91 (d, J=8.53 Hz, 2H).

Example 99

4-((1R,3aS,5aR,5bR,7aR,11aS,11bR,13aR,13bR)-3a-((3-(3-(dimethylamino)-3-oxopropylamino)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

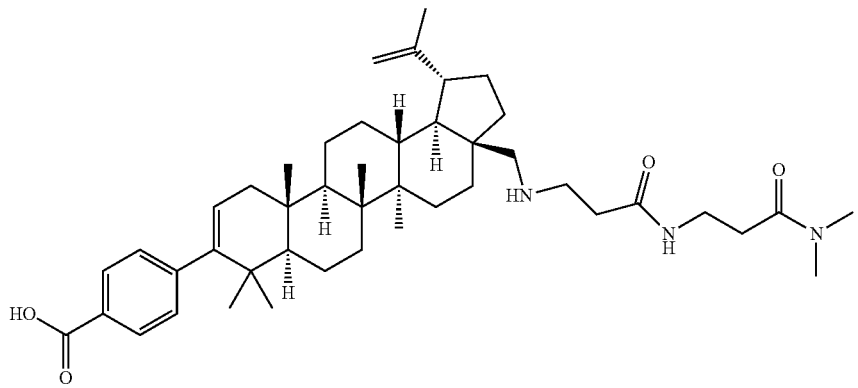

The title compound was prepared in 71 of yield following the general procedure described above for the preparation of C28 amines with amide end cap using 3-amino-N,N-dimethylpropanamide hydrochloride as the reactant amine. MS: m/e 714.6 (MH$^+$), 1.67 min (method 2). $^1$H NMR (400 MHz, MeOD) δ ppm 0.95 (s, 3H) 0.96 (s, 3H) 1.04 (s, 3H) 1.08 (s, 3H) 1.17 (s, 3H) 1.73 (s, 3H) 0.89-1.87 (m, 20H) 1.98-2.10 (m, 1H) 2.15 (dd, J=17.19, 6.40 Hz, 1H) 2.52 (td, J=10.98, 5.65 Hz, 1H) 2.61 (t, J=6.53 Hz, 2H) 2.67 (t, J=6.27 Hz, 2H) 2.87 (d, J=13.05 Hz, 1H) 2.93 (s, 3H) 3.04 (s, 3H) 3.26-3.37 (m, 3H) 3.47 (t, J=6.53 Hz, 2H) 4.64 (s, 1H) 4.76 (d, J=1.76 Hz, 1H) 5.30 (dd, J=6.15, 1.63 Hz, 1H) 7.22 (d, J=8.28 Hz, 2H) 7.92 (d, J=8.53 Hz, 2H).

Example 100

(R)-1-(3-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)propanoyl)pyrrolidine-2-carboxylic acid

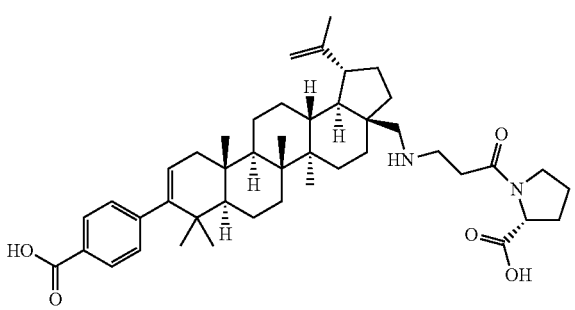

The title compound was prepared in 45% yield following the general procedure described above for the preparation of C28 amines with amide end cap using (R)-tert-butyl pyrrolidine-2-carboxylate as the reactant amine MS: m/e 713.5 (MH$^+$), 1.59 min (method 2). $^1$H NMR (400 MHz, MeOD) δ ppm 0.95 (s, 3H) 0.97 (s, 3H) 1.04 (s, 3H) 1.08 (s, 3H) 1.17 (s, 3H) 1.73 (s, 3H) 0.87-1.86 (m, 20H) 1.99-2.11 (m, 4H) 2.15 (dd, J=17.07, 6.02 Hz, 1H) 2.24-2.32 (m, 1H) 2.47-2.56 (m, 1H) 2.84-2.92 (m, 3H) 3.23-3.28 (m, 1H) 3.38 (t, J=5.90 Hz, 2H) 3.51-3.69 (m, 2H) 4.48 (dd, J=8.41, 3.14 Hz, 1H) 4.64 (s, 1H) 4.76 (d, J=1.25 Hz, 1H) 5.30 (dd, J=6.02, 1.76 Hz, 1H) 7.21 (d, J=8.28 Hz, 2H) 7.91 (d, J=8.28 Hz, 2H).

Example 101

4-((1R,3aS,5aR,5bR,7aR,11aS,11bR,13aR,13bR)-3a-((3-((S)-2-(methoxycarbonyl)pyrrolidin-1-yl)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

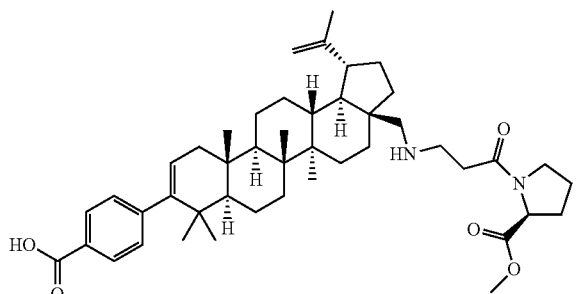

The title compound was prepared in 43% yield following the general procedure described above for the preparation of C28 amines with amide end cap using (S)-methylpyrrolidine-2-carboxylate hydrochloride as the reactant amine MS: m/e 727.5 (MH$^+$), 1.60 min (method 2). $^1$H NMR (400 MHz, MeOD) δ ppm 0.95 (s, 3H) 0.96 (s, 3H) 1.04 (s, 3H) 1.08 (s, 3H) 1.18 (s, 3H) 1.73 (s, 3H) 0.87-1.84 (m, 22H) 1.98-2.10 (m, 4H) 2.15 (dd, J=17.07, 6.27 Hz, 1H) 2.22-2.31 (m, 1H) 2.84-2.91 (m, 3H) 3.38 (ddd, J=6.78, 5.14, 4.89 Hz, 2H) 3.53-3.69 (m, 2H) 3.73 (s, 3H) 4.49 (dd, J=8.66, 3.39 Hz, 1H)

4.64 (s, 1H) 4.76 (d, J=1.76 Hz, 1H) 5.30 (dd, J=6.15, 1.63 Hz, 1H) 7.21 (d, J=8.53 Hz, 2H) 7.91 (d, J=8.28 Hz, 2H).

Example 102

(S)-1-(3-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)propanoyl)pyrrolidine-2-carboxylic acid

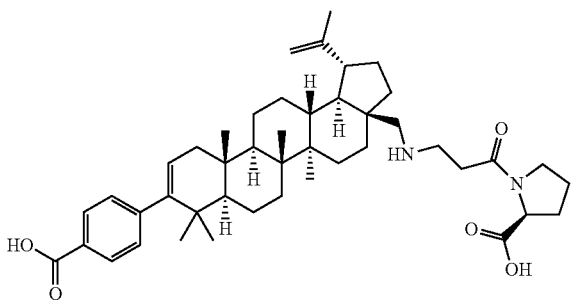

To a solution of 4-((1R,3aS,5aR,5bR,7aR,11aS,11bR,13aR,13bR)-3a-((3-((S)-2-(methoxycarbonyl)pyrrolidin-1-yl)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (10 mg, 0.014 mmol) in dioxane (1 ml) and methanol (2 ml) was added 1N sodium hydroxide (0.08 ml, 0.08 mmol) and $H_2O$ (0.5 ml). The resulting mixture was stirred at rt for 45 h. The reaction mixture was neutralized with 1N HCl and concentrated in vacuo. The residue was purified by prep. HPLC to afford the title compound (8.5 mg, 85%). MS: m/e 713.5 (MH+), 1.68 min (method 2). $^1$H NMR (400 MHz, MeOD) δ ppm 0.95 (s, 3H) 0.97 (s, 3H) 1.04 (s, 3H) 1.08 (s, 3H) 1.18 (s, 3H) 1.73 (s, 3H) 0.87-1.86 (m, 20H) 1.99-2.10 (m, 4H) 2.15 (dd, J=17.32, 6.53 Hz, 1H) 2.24-2.33 (m, 1H) 2.52 (td, J=9.60, 4.14 Hz, 1H) 2.83-2.92 (m, 3H) 3.24-3.28 (m, 1H) 3.38 (t, J=6.15 Hz, 2H) 3.52-3.68 (m, 2H) 4.48 (dd, J=8.41, 3.39 Hz, 1H) 4.64 (s, 1H) 4.76 (d, J=1.76 Hz, 1H) 5.30 (dd, J=6.15, 1.63 Hz, 1H) 7.21 (d, J=8.53 Hz, 2H) 7.91 (d, J=8.28 Hz, 2H).

Example 103

4-((1R,3aS,5aR,5bR,7aR,11aS,11bR,13aR,13bR)-3a-((3-(3,3-difluoropyrrolidin-1-yl)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

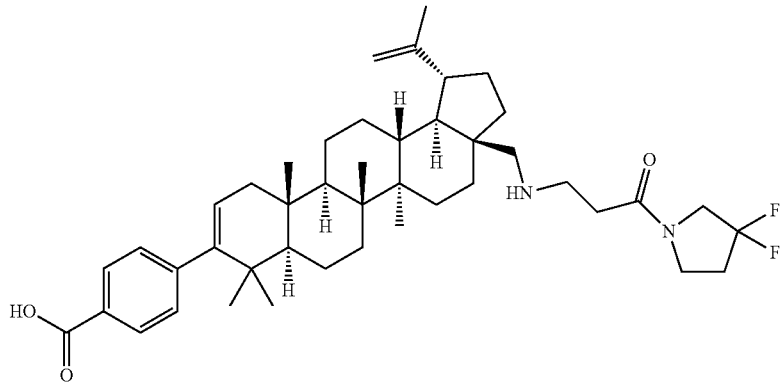

The title compound was prepared in 76% yield following the general procedure described above for the preparation of C28 amines with amide end cap using 3,3-difluoropyrrolidine hydrochloride as the reactant amine MS: m/e 705.5 (MH+), 1.69 min (method 2). $^1$H NMR (400 MHz, MeOD) δ ppm 0.95 (s, 3H) 0.96 (s, 3H) 1.04 (s, 3H) 1.08 (s, 3H) 1.17 (s, 3H) 1.73 (s, 3H) 0.86-1.86 (m, 22H) 1.99-2.10 (m, 1H) 2.15 (dd, J=17.32, 6.53 Hz, 1H) 2.37-2.58 (m, 3H) 2.79 (t, J=6.02 Hz, 1H) 2.84 (t, J=6.02 Hz, 1H) 2.89 (d, J=13.05 Hz, 1H) 3.36-3.41 (m, 1H) 3.70 (t, J=7.65 Hz, 1H) 3.77 (d, J=7.78 Hz, 1H) 3.80 (t, 1H) 3.92 (t, J=12.55 Hz, 1H) 4.65 (s, 1H) 4.76 (d, J=1.76 Hz, 1H) 5.30 (dd, J=6.15, 1.63 Hz, 1H) 7.22 (d, J=8.53 Hz, 2H) 7.92 (d, J=8.53 Hz, 2H). $^{19}$F NMR (376 MHz, MeOD) δ ppm −104.01 (d, J=74.56 Hz, 1 F)-103.19 (d, J=26.01 Hz, 1 F).

Example 104

1-(3-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)propanoyl)piperidine-4-carboxylic acid

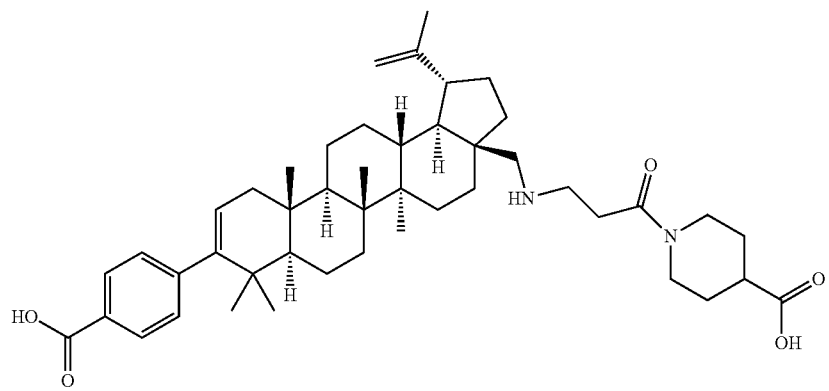

The title compound was prepared in 51% yield following the general procedure described above for the preparation of C28 amines with amide end cap using ethyl piperidine-4-carboxylate as the reactant amine, followed by basic hydrolysis of the ester group as described below:

To a solution of 4-((1R,3aS,5aR,5bR,7aR,11aS,11bR,13aR,13bR)-3a-((3-(4-(ethoxycarbonyl)piperidin-1-yl)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (16 mg, 0.021 mmol) in dioxane (1 ml) and methanol (2 ml) was added 1N sodium hydroxide (0.3 ml, 0.1 mmol) and H$_2$O (0.5 ml). The resulting mixture was stirred at rt for 10 days. The reaction mixture was neutralized with 1N HCl and concentrated in vacuo. The crude product was purified by prep. HPLC to afford the title compound (8 mg). MS: m/e 727.6 (MH$^+$), 1.69 min (method 2). $^1$H NMR (400 MHz, MeOD) δ ppm 0.95 (s, 3H) 0.97 (s, 3H) 1.04 (s, 3H) 1.08 (s, 3H) 1.17 (d, J=2.76 Hz, 3H) 1.73 (s, 3H) 0.87-1.86 (m, 23H) 1.92-2.10 (m, 3H) 2.15 (dd, J=17.32, 6.53 Hz, 1H) 2.47-2.56 (m, 1H) 2.57-2.67 (m, J=7.34, 7.12, 7.12, 3.76 Hz, 1H) 2.83-2.94 (m, 4H) 3.16-3.41 (m, 4H) 3.82-3.91 (m, 1H) 4.35-4.44 (m, 1H) 4.64 (s, 1H) 4.76 (d, J=1.51 Hz, 1H) 5.30 (d, J=5.27 Hz, 1H) 7.22 (d, J=8.28 Hz, 2H) 7.91 (d, J=8.28 Hz, 2H).

Example 105

4-((1R,3aS,5aR,5bR,7aR,11aS,11bR,13aR,13bR)-5a,5b,8,8,11a-pentamethyl-3a-((3-(4-methylpiperazin-1-yl)-3-oxopropylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

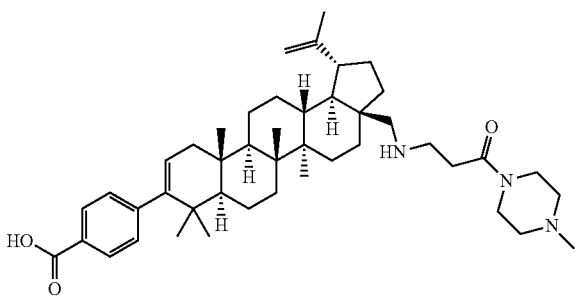

The title compound was prepared in 54% yield following the general procedure described above for the preparation of C28 amines with amide end cap using 1-methylpiperazine as the reactant amine MS: m/e 698.5 (MH$^+$), 1.64 min (method 2). $^1$H NMR (400 MHz, MeOD) δ ppm 0.95 (s, 3H) 0.96 (s, 3H) 1.04 (s, 3H) 1.08 (s, 3H) 1.17 (s, 3H) 1.73 (s, 3H) 0.84-1.88 (m, 22H) 1.99-2.22 (m, 2H) 2.46-2.58 (m, 1H) 2.85-3.02 (m, 6H) 3.15-3.51 (m, 11H) 4.65 (s, 1H) 4.76 (d, J=1.00 Hz, 1H) 5.30 (d, J=3.76 Hz, 1H) 7.21 (d, J=8.03 Hz, 2H) 7.92 (d, J=8.28 Hz, 2H)

Example 106

4-((1R,3aS,5aR,5bR,7aR,11aS,11bR,13aR,13bR)-5a,5b,8,8,11a-pentamethyl-3a-((3-oxo-3-(3,3,4,4-tetrafluoropyrrolidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

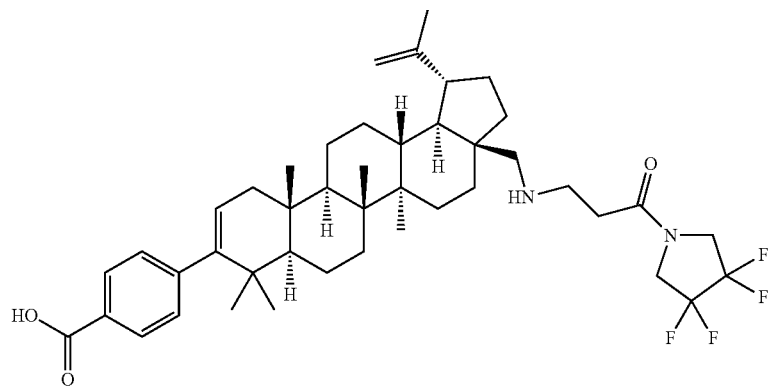

The title compound was prepared in 62% yield following the general procedure described above for the preparation of C28 amines with amide end cap using 3,3,4,4-tetrafluoropyrrolidine hydrochloride as the reactant amine MS: m/e 741.5 (MH$^+$), 1.75 min (method 2). $^1$H NMR (400 MHz, MeOD) δ ppm 0.95 (s, 3H) 0.97 (s, 3H) 1.04 (s, 3H) 1.08 (s, 3H) 1.17 (s, 3H) 1.73 (s, 3H) 0.85-1.85 (m, 20H) 1.99-2.10 (m, 1H) 2.15 (dd, J=17.07, 6.53 Hz, 1H) 2.52 (td, J=10.35, 5.40 Hz, 1H) 2.83 (t, J=6.02 Hz, 2H) 2.90 (d, J=12.80 Hz, 1H) 3.25-3.27 (m, 1H) 3.40 (td, J=5.96, 2.13 Hz, 2H) 4.05 (t, J=13.93 Hz, 2H) 4.21 (t, J=13.43 Hz, 2H) 4.65 (s, 1H) 4.76 (d, J=1.76 Hz, 1H) 5.30 (dd, J=6.15, 1.63 Hz, 1H) 7.22 (d, J=8.53 Hz, 2H)

7.91 (d, J=8.28 Hz, 2H). $^{19}$F NMR (376 MHz, MeOD) δ ppm −125.84 (dd, J=8.67, 3.47 Hz, 2 F)-125.07 (d, J=6.94 Hz, 2 F).

Example 107

4-((1R,3aS,5aR,5bR,7aR,11aS,11bR,13aR,13bR)-5a,5b,8,8,11a-pentamethyl-3a-((3-morpholino-3-oxopropylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

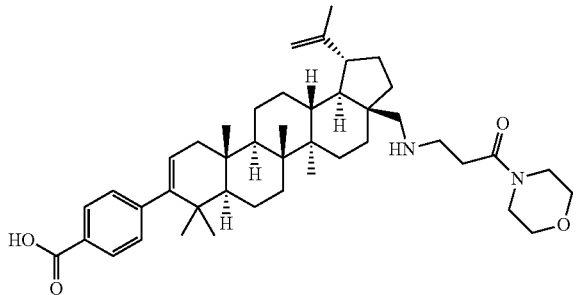

The title compound was prepared in 54% yield following the general procedure described above for the preparation of C28 amines with amide end cap using morpholine as the reactant amine MS: m/e 685.6 (MH$^+$), 1.74 min (method 2). $^1$H NMR (400 MHz, MeOD) δ ppm 0.95 (s, 3H) 0.97 (s, 3H) 1.04 (s, 3H) 1.08 (s, 3H) 1.18 (s, 3H) 1.73 (s, 3H) 0.87-1.86 (m, 20H) 1.99-2.10 (m, 1H) 2.15 (dd, J=17.57, 6.53 Hz, 1H) 2.48-2.56 (m, 1H) 2.84-2.91 (m, 3H) 3.23-3.26 (m, 1H) 3.34-3.41 (m, 2H) 3.49-3.54 (m, 2H) 3.58-3.63 (m, 2H) 3.68 (ddd, J=10.10, 4.96, 4.77 Hz, 4H) 4.65 (s, 1H) 4.76 (d, J=1.51 Hz, 1H) 5.30 (dd, J=6.27, 1.76 Hz, 1H) 7.22 (d, J=8.28 Hz, 2H) 7.92 (d, J=8.28 Hz, 2H).

Example 108

Preparation of 4-((1R,3aS,5aR,5bR,7aR,11aS,11bR,13aR,13bR)-3a-(((2-(1,1-dioxido-4-thiomorpholinyl)-2-oxoethyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

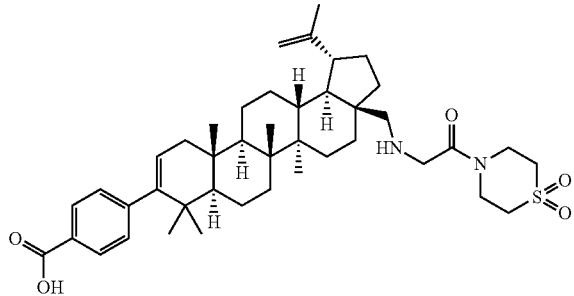

The title compound was prepared following the general procedures described above the general procedure described above for the preparation of C28 amines with amide end cap using methyl 2-aminoacetate hydrochloride and thiomorpholine 1,1-dioxide as the reactant amines. The product was isolated as a white solid (6.5 mg, 33.3%). LCMS: m/e 719.2 (MH$^+$), 2.32 min (method 3). $^1$H NMR (400 MHz, MeOD) δ ppm 7.94 (m, J=8.3 Hz, 2H), 7.24 (m, J=8.5 Hz, 2H), 5.32 (dd, J=6.1, 1.6 Hz, 1H), 4.76 (d, J=1.5 Hz, 1H), 4.66 (s, 1H), 4.22-4.35 (m, 2H), 4.18 (br. s., 2H), 3.92 (br. s., 2H), 3.35-3.41 (m, 1H), 3.25-3.30 (m, 2H), 3.20 (d, J=9.0 Hz, 2H), 2.86-2.94 (m, 1H), 2.48 (d, J=5.5 Hz, 1H), 2.09-2.20 (m, 2H), 1.90-2.04 (m, 3H), 1.69-1.90 (m, 8H), 1.58-1.66 (m, 3H), 1.47-1.58 (m, 5H), 1.25-1.41 (m, 3H), 1.13-1.25 (m, 4H), 1.11 (s, 3H), 1.05 (s, 3H), 0.92-1.02 (m, 6H).

Example 109

Preparation of 4-((1R,3aS,5aR,5bR,7aR,11aS,11bR,13aR,13bR)-5a,5b,8,8,11a-pentamethyl-3a-((2-oxo-2-(pyrrolidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid The title compound was prepared following the general procedure described above for the preparation of C28 amines with amide end cap using methyl 2-aminoacetate hydrochloride and pyrrolidine as the reactant amines. The product was isolated as a white solid (12.9 mg, 53.2%). LCMS: m/e 655.3 (MH$^+$), 2.13 min (method 3). $^1$H NMR (400 MHz, MeOD) δ ppm 7.94 (m, J=8.5 Hz, 2H), 7.24 (m, J=8.5 Hz, 2H), 5.32 (dd, J=6.1, 1.6 Hz, 1H), 4.76 (d, J=1.8 Hz, 1H), 4.66 (s, 1H), 3.99-4.13 (m, 2H), 3.52 (dt, J=13.6, 6.8 Hz, 4H), 3.38 (m, 1H), 2.81-2.99 (m, 1H), 2.47 (dt, J=11.0, 5.5 Hz, 1H), 2.12-2.27 (m, 2H), 2.02-2.12 (m, 2H), 1.84-2.02 (m, J=6.7, 6.7, 6.5, 6.3 Hz, 5H), 1.77-1.84 (m, 1H), 1.67-1.77 (m, 6H), 1.44-1.67 (m, 8H), 1.26-1.39 (m, 3H), 1.19-1.26 (m, 1H), 1.14-1.19 (m, 4H), 1.08-1.14 (m, 3H), 1.04 (s, 3H), 0.99 (s, 3H), 0.95 (s, 3H).

Example 110

Preparation of 4-((1R,3aS,5aR,5bR,7aR,11aS,11bR, 13aR,13bR)-5a,5b,8,8,11a-pentamethyl-3a-((2-oxo-2-(piperidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

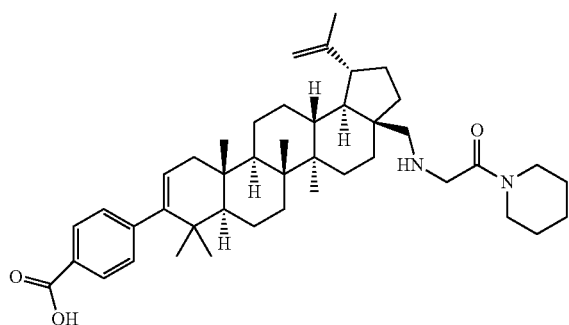

The title compound was prepared following the general procedure described above for the preparation of C28 amines with amide end cap using methyl 2-aminoacetate hydrochloride and piperidine as the reactant amines. The product was isolated as a white solid (10.0 mg, 51.5%). LCMS: m/e 669.4 (MH$^+$), 2.16 min (method 3). $^1$H NMR (400 MHz, MeOD) δ ppm 7.94 (m, J=8.5 Hz, 2H), 7.24 (m, J=8.5 Hz, 2H), 5.32 (dd, J=6.1, 1.6 Hz, 1H), 4.76 (d, J=1.8 Hz, 1H), 4.66 (s, 1H), 4.13 (s, 2H), 3.56-3.72 (m, 2H), 3.35-3.46 (m, 2H), 3.3 (m, 1H), 2.86 (d, J=12.5 Hz, 1H), 2.48 (dt, J=11.1, 5.6 Hz, 1H), 2.03-2.22 (m, 2H), 1.84-2.03 (m, 3H), 1.66-1.78 (m, 10H), 1.48-1.65 (m, 10H), 1.29-1.45 (m, 3H), 1.24 (d, J=10.5 Hz, 2H), 1.14-1.20 (m, 4H), 1.11 (s, 3H), 1.05 (s, 3H), 0.99 (s, 3H), 0.98 (s, 3H).

Example 111

Preparation of 4-((1R,3aS,5aR,5bR,7aR,11aS,11bR, 13aR,13bR)-3a-((2-(4-(ethoxycarbonyl)piperidin-1-yl)-2-oxoethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

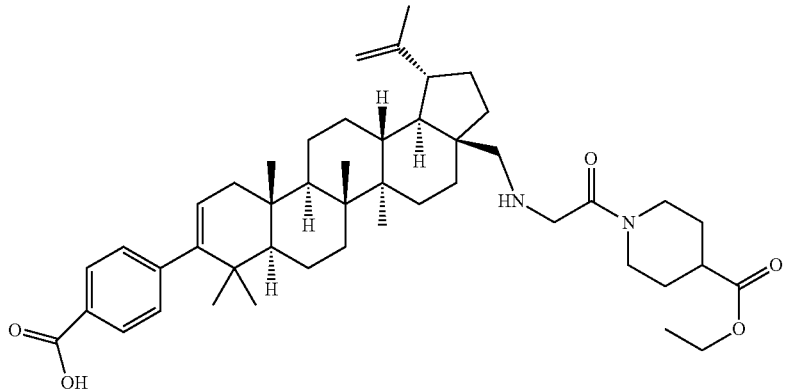

The title compound was prepared following the general procedure described above for the preparation of C28 amines with amide end cap using methyl 2-aminoacetate hydrochloride and ethyl piperidine-4-carboxylate as the reactant amines. The product was isolated as a white solid (10.0 mg, 68.5%). LCMS: m/e 741.6 (MH$^+$), 2.34 min (method 3). $^1$H NMR (400 MHz, MeOD) δ ppm 7.94 (m, J=8.3 Hz, 2H), 7.27 (m, 2H), 5.26-5.40 (m, 1H), 4.76 (d, J=1.8 Hz, 1H), 4.66 (s, 1H), 4.30-4.50 (m, 1H), 4.11-4.24 (m, 4H), 3.64-3.82 (m, 1H), 3.18-3.30 (m, 2H), 2.92-3.10 (m, 1H), 2.87 (dd, J=12.4, 4.6 Hz, 1H), 2.60-2.78 (m, 1H), 2.43-2.55 (m, 1H), 2.08-2.25 (m, 2H), 1.85-2.08 (m, 6H), 1.67-1.85 (m, 6H), 1.46-1.67 (m, 8H), 1.20-1.42 (m, 8H), 1.13-1.19 (m, 3H), 1.11 (s, 3H), 1.04 (s, 3H), 0.99 (s, 3H), 0.96 (s, 3H).

Example 112

Preparation of 1-(2-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)acetyl)piperidine-4-carboxylic acid

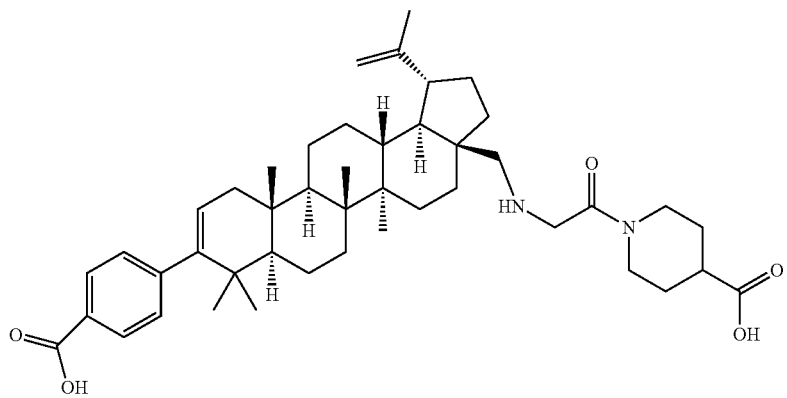

The title compound was prepared following the procedure described below: To the solution of 4-(((1R,3aS,5aR,5bR,7aR,11aS,11bR,13aR,13bR)-3a-((2-(4-(ethoxycarbonyl)piperidin-1-yl)-2-oxoethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (12 mg, 0.016 mmol) in MeOH (3.00 ml) and dioxane (3 ml), sodium hydroxide (10 mg, 0.250 mmol) was added followed by 0.5 ml of water. The resulting suspension was stirred at 25° C. for 4 h. The solvent was removed in vacuo, the product was isolated by prep. HPLC as a white solid (5 mg, 41.4%). LCMS: m/e 713.5 (MH$^+$), 2.37 min (method 3). $^1$H NMR (400 MHz, MeOD) δ ppm 7.95 (m, 2H), 7.27 (m, 2H), 5.32 (d, J=4.5 Hz, 1H), 4.76 (d, J=1.8 Hz, 1H), 4.66 (s, 1H), 4.29-4.46 (m, 1H), 4.09-4.25 (m, 2H), 3.64-3.85 (m, 1H), 3.17-3.32 (m, 2H), 3.05 (m, 1H), 2.87 (dd, J=12.8, 4.8 Hz, 1H), 2.67 (tt, J=10.8, 4.0 Hz, 1H), 2.49 (dt, J=10.9, 5.5 Hz, 1H), 2.07-2.29 (m, 2H), 1.85-2.07 (m, 4H), 1.67-1.85 (m, 8H), 1.43-1.67 (m, 9H), 1.36 (br. s., 2H), 1.32 (d, J=6.5 Hz, 2H), 1.24 (d, J=14.8 Hz, 1H), 1.13-1.20 (m, 4H), 1.11 (s, 3H), 1.04 (s, 3H), 0.99 (s, 3H), 0.98 (s, 3H).

Example 113

Preparation of 4-((1R,3aS,5aR,5bR,7aR,11aS,11bR,13aR,13bR)-3a-((2-(4-(N,N-dimethylsulfamoyl)piperazin-1-yl)-2-oxoethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

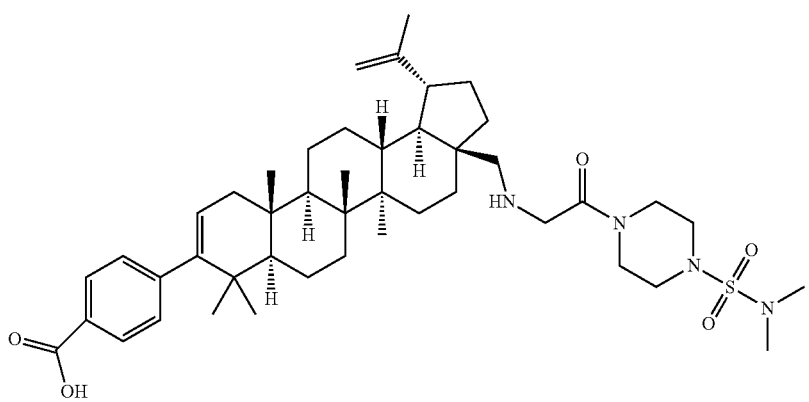

The title compound was prepared the general procedure described above for the preparation of C28 amines with amide end cap using methyl 2-aminoacetate hydrochloride and N,N-dimethylpiperazine-1-sulfonamide as the reactant amines. The product was isolated as a white solid (9.0 mg, 61.1%). LCMS: m/e 777.6 (MH$^+$), 2.39 min (method 3). $^1$H NMR (400 MHz, MeOD) δ ppm 7.96 (m, 2H), 7.24 (m, J=8.5 Hz, 2H), 5.28-5.38 (m, 1H), 4.76 (d, J=1.5 Hz, 1H), 4.66 (s, 1H), 4.19 (s, 2H), 3.75 (t, J=5.0 Hz, 2H), 3.46-3.58 (m, 2H), 3.33-3.38 (m, 3H), 3.26-3.31 (m, 2H), 2.79-2.95 (m, 7H), 2.48 (td, J=10.8, 5.8 Hz, 1H), 2.03-2.24 (m, 2H), 1.90-2.03 (m, 3H), 1.77-1.86 (m, 1H), 1.67-1.77 (m, 6H), 1.44-1.67 (m, 8H), 1.34 (d, J=12.0 Hz, 3H), 1.20-1.28 (m, 1H), 1.13-1.20 (m, 4H), 1.11 (s, 3H), 1.05 (s, 3H), 0.99 (s, 3H), 0.98 (s, 3H).

Example 114

Preparation of (R)-1-(2-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)acetyl)pyrrolidine-2-carboxylic acid

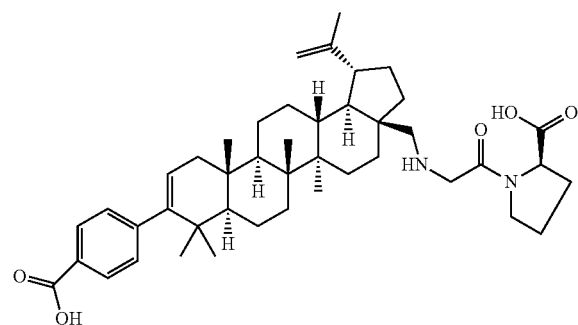

The title compound was prepared following the general procedure described above for the preparation of C28 amines with amide end cap using methyl 2-aminoacetate hydrochloride and (R)-tert-butyl pyrrolidine-2-carboxylate as the reactant amines. The product was isolated as a white solid (9.0 mg, 69.6%). LCMS: m/e 699.3 (MH⁺), 2.34 min (method 3). ¹H NMR (400 MHz, MeOD) δ ppm 7.88-8.01 (m, 2H), 7.17-7.31 (m, 2H), 5.32 (d, J=4.8 Hz, 1H), 4.75 (d, J=1.8 Hz, 1H), 4.61-4.69 (m, 1H), 4.56 (m, 1H), 4.02-4.24 (m, 2H), 3.64-3.73 (m, 1H), 3.51-3.64 (m, 1H), 3.34-3.43 (m, 1H), 2.75-2.97 (m, 1H), 2.43-2.56 (m, 1H), 2.24-2.43 (m, 1H), 2.01-2.22 (m, 5H), 1.86-2.01 (m, 3H), 1.67-1.81 (m, 6H), 1.44-1.67 (m, 8H), 1.27-1.44 (m, 4H), 1.13-1.27 (m, 5H), 1.10 (s, 3H), 1.04 (s, 3H), 0.99 (s, 3H), 0.96 (s, 3H).

Example 115

Preparation of 4-((1R,3aS,5aR,5bR,7aR,11aS,11bR,13aR,13bR)-3a-((2-(4,4-difluoropiperidin-1-yl)-2-oxoethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

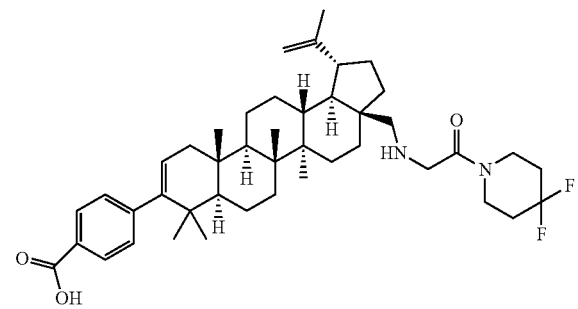

The title compound was prepared the general procedure described above for the preparation of C28 amines with amide end cap using methyl 2-aminoacetate hydrochloride and 4,4-difluoropiperidine as the reactant amines. The product was isolated as a white solid (28 mg, 86.0%). LCMS: m/e 705.5 (MH⁺), 2.36 min (method 3). ¹H NMR (400 MHz, MeOD) δ ppm 7.94 (m, J=8.3 Hz, 2H), 7.24 (m, J=8.5 Hz, 2H), 5.32 (dd, J=6.3, 1.8 Hz, 1H), 4.76 (d, J=1.5 Hz, 1H), 4.66 (s, 1H), 4.22 (s, 2H), 3.73-3.88 (m, 2H), 3.50-3.67 (m, 2H), 3.32-3.41 (m, 1H), 2.88 (d, J=12.5 Hz, 1H), 2.47 (td, J=10.9, 5.5 Hz, 1H), 2.02-2.19 (m, 5H), 1.93-2.00 (m, 2H), 1.68-1.85 (m, 7H), 1.44-1.68 (m, 9H), 1.20-1.42 (m, 5H), 1.13-1.19 (m, 4H), 1.09 (s, 3H), 1.05 (s, 3H), 1.00 (s, 3H), 0.95 (s, 3H). ¹⁹F NMR (376 MHz, MeOD) δ ppm −99.61 (p, J=13.5 Hz, 2F).

Example 116

Preparation of 4-((1R,3aS,5aR,5bR,7aR,11aS,11bR,13aR,13bR)-3a-(((1-((1,1-dioxido-4-thiomorpholinyl)carbonyl)cyclopropyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

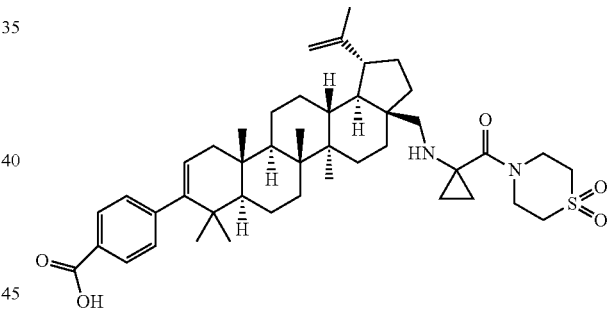

The title compound was prepared following the general procedure described above for the preparation of C28 amines with amide end cap using methyl 1-aminocyclopropanecarboxylate hydrochloride and thiomorpholine-1,1-dioxide as the reactant amines. The product was isolated as a white solid (3 mg, 37.5%). LCMS: m/e 745.6 (MH⁺), 2.76 min (method 3). ¹H NMR (400 MHz, MeOD) δ ppm 6.38 (d, J=8.3 Hz, 2H), 5.68 (d, J=8.5 Hz, 2H), 3.76 (dd, J=6.3, 1.8 Hz, 1H), 3.20 (d, J=2.0 Hz, 1H), 3.08 (s, 1H), 2.63 (br. s., 4H), 1.59-1.69 (m, 4H), 1.45-1.58 (m, 1H), 1.11-1.27 (m, 1H), 0.87-1.07 (m, 1H), 0.61 (d, J=11.0 Hz, 1H), 0.29-0.52 (m, 2H), 0.08-0.25 (m, 9H), 0.11-0.08 (m, 6H), 0.28-0.11 (m, 6H), 0.30 (br. s., 2H), 0.45-0.33 (m, 6H), 0.48 (s, 3H), 0.50 (s, 3H), 0.57 (s, 3H), 0.59 (s, 3H).

Example 117

Preparation of 4-(((1R,3aS,5aR,5bR,7aR,11aS,11bR, 13aR,13bR)-3a-((3-(4,4-difluoropiperidin-1-yl)-3-oxopropylamino)methyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

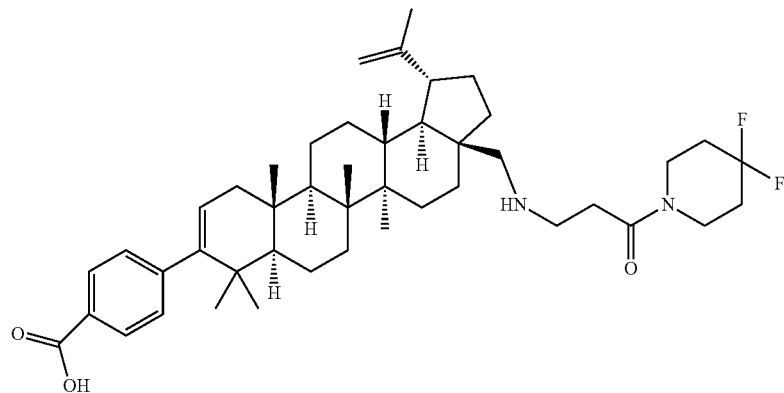

The title compound was prepared following the general procedure described above for the preparation of C28 amines with amide end cap using 3-aminopropanoate hydrochloride and 4,4-difluoropiperidine as the reactant amines. The product was isolated as a white solid (25 mg, 74.0%). LCMS: m/e 719.5 (MH$^+$), 2.63 min (method 3). $^1$H NMR (400 MHz, MeOD) δ ppm 7.95 (m, J=8.5 Hz, 2H), 7.23 (m, 2H), 5.26-5.38 (m, 1H), 4.78 (d, J=1.8 Hz, 1H), 4.67 (s, 1H), 3.70-3.85 (m, 2H), 3.59-3.70 (m, 2H), 3.35-3.45 (m, 2H), 3.30 (d, J=13.3 Hz, 1H), 2.84-3.01 (m, 3H), 2.55 (d, J=5.8 Hz, 1H), 1.95-2.20 (m, 6H), 1.68-1.92 (m, 10H), 1.45-1.68 (m, 8H), 1.38 (d, J=3.5 Hz, 1H), 1.32 (br. s., 2H), 1.13-1.27 (m, 5H), 1.10 (s, 3H), 1.06 (s, 3H), 0.99 (s, 3H), 0.97 (s, 3H). $^{19}$F NMR (376 MHz, MeOD) δ ppm −99.53 (p, J=13.4 Hz, 2F).

Example 118

Preparation of 4-(((1R,3aS,5aR,5bR,7aR,11aS,11bR, 13aR,13bR)-3a-(((3-(1,1-dioxido-4-thiomorpholinyl)-3-oxopropyl)amino)methyl)-1-isopropenyl-5a, 5b,8,8,11a-pentamethyl-2,3,3a,4,5,5a,5b,6,7,7a,8,11, 11a,11b,12,13,13a,13b-octadecahydro-1H-cyclopenta[a]chrysen-9-yl)benzoic acid

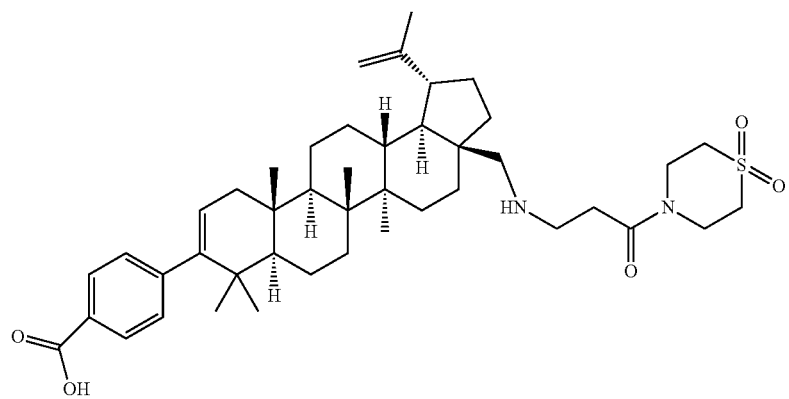

The title compound was prepared following the general procedure described above for the preparation of C28 amines with amide end cap using 3-aminopropanoate hydrochloride and thiomorpholine 1,1-dioxide as the reactant amines. The product was isolated as a white solid (25 mg, 72.6%). LCMS: m/e 733.5 (MH$^+$), 2.55 min (method 3). $^1$H NMR (400 MHz, MeOD) δ ppm 7.97 (m, 2H), 7.25 (m, 2H), 5.26-5.39 (m, 1H), 4.78 (d, J=1.8 Hz, 1H), 4.67 (s, 1H), 4.05-4.19 (m, 2H), 3.92-4.05 (m, 2H), 3.39-3.48 (m, 2H), 3.28-3.32 (m, 1H), 3.20-3.27 (m, 2H), 3.12-3.20 (m, 2H), 2.99 (t, J=5.8 Hz, 2H), 2.93 (d, J=12.8 Hz, 1H), 2.54 (dt, J=10.6, 5.4 Hz, 1H), 2.00-2.24 (m, 2H), 1.68-1.93 (m, 10H), 1.44-1.68 (m, 8H), 1.24-1.44 (m, 4H), 1.13-1.24 (m, 4H), 1.11 (s, 3H), 1.04 (s, 3H), 0.99 (s, 3H), 0.97 (s, 3H).

Example 119

Preparation of 4-((1R,3aS,5aR,5bR,7aR,11aS,11bR,13aR,13bR)-5a,5b,8,8,11a-pentamethyl-3a#3-oxo-3-(3-(trifluoromethyl)-5,6-dihydro-[1,2,4]triazolo[4,3-a]pyrazin-7(8H)-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

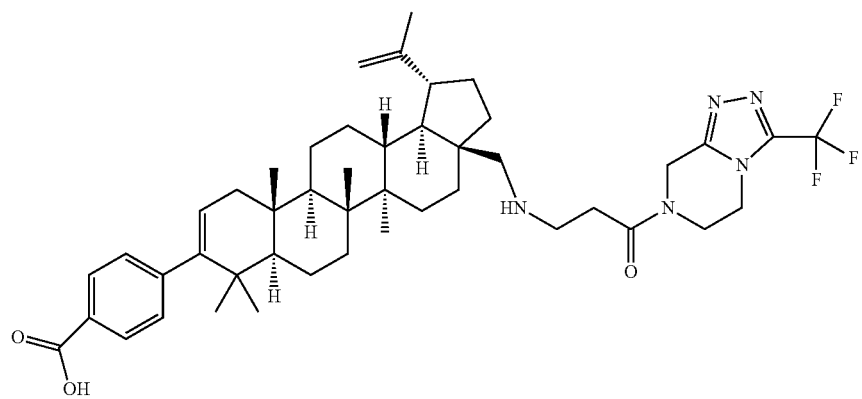

The title compound was prepared following the general procedure described above for the preparation of C28 amines with amide end cap using 3-aminopropanoate hydrochloride and 3-(trifluoromethyl)-5,6,7,8-tetrahydro-[1,2,4]triazolo[4,3-a]pyrazine as the reactant amines. The product was isolated as a white solid (20 mg, 35.7%). LCMS: m/e 790.5 (MH$^+$), 2.48 min (method 3). $^1$H NMR (400 MHz, MeOD) δ ppm 7.94 (m, J=8.5 Hz, 2H), 7.23 (m, 2H), 5.32 (d, J=6.0 Hz, 1H), 4.94-5.19 (m, 2H), 4.78 (s, 1H), 4.67 (s, 1H), 4.32-4.44 (m, 1H), 4.28 (br. s., 1H), 3.96-4.19 (m, 2H), 3.40-3.59 (m, 2H), 3.26-3.33 (m, 1H), 2.99-3.18 (m, 2H), 2.92 (d, J=12.8 Hz, 1H), 2.54 (br. s., 1H), 2.34 (br. s., 1H), 2.14 (br. s., 3H), 1.52 (br. s., 12H), 1.38 (br. s., 2H), 1.31 (br. s., 3H), 1.14-1.18 (m, 2H), 0.94-1.12 (m, 17H).

Example 120

Preparation of 4-((1R,3aS,5aR,5bR,7aR,11aS,11bR,13aR,13bR)-3a-(((3-(1,1-dioxido-1,3-thiazolidin-3-yl)-3-oxopropyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

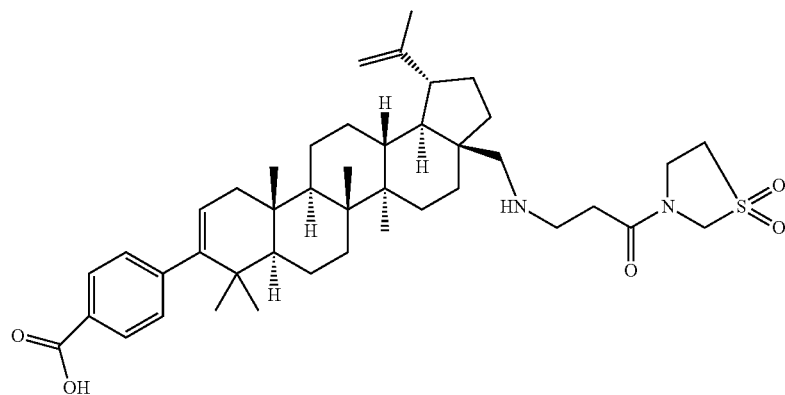

The title compound was prepared following the general procedure described above for the preparation of C28 amines with amide end cap using 3-aminopropanoate hydrochloride and sulfone as the reactant amines. The product was isolated as a white solid (20 mg, 35.7%). LCMS: m/e 719.5 (MH$^+$), 2.56 min (method 3). $^1$H NMR (400 MHz, MeOD) δ ppm 7.94 (d, J=8.5 Hz, 2H), 7.24 (d, J=8.5 Hz, 2H), 5.24-5.43 (m, 1H), 4.8 (s, 1H), 4.61-4.72 (m, 1H), 4.02-4.20 (m, 2H), 3.46-3.63 (m, 1H), 3.43 (t, J=7.3 Hz, 2H), 3.35-3.41 (m, 2H), 3.22-3.31 (m, 2H), 2.95 (br. s., 1H), 2.88 (s, 1H), 2.73 (m, 1H), 2.44-2.64 (m, 1H), 2.05-2.22 (m, 2H), 1.67-1.90 (m, 8H), 1.44-1.67 (m, 8H), 1.39 (br. s., 5H), 1.16-1.27 (m, 5H), 1.11 (s, 3H), 1.07 (s, 3H), 0.99 (s, 3H), 0.98 (s, 3H).

Example 121

Preparation of 4-((1R,3aS,5aR,5bR,7aR,11aS,11bR,13aR,13bR)-5a,5b,8,8,11a-pentamethyl-3a-((3-((1R,5S)-8-methyl-3,8-diazabicyclo[3.2.1]octan-3-yl)-3-oxopropylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

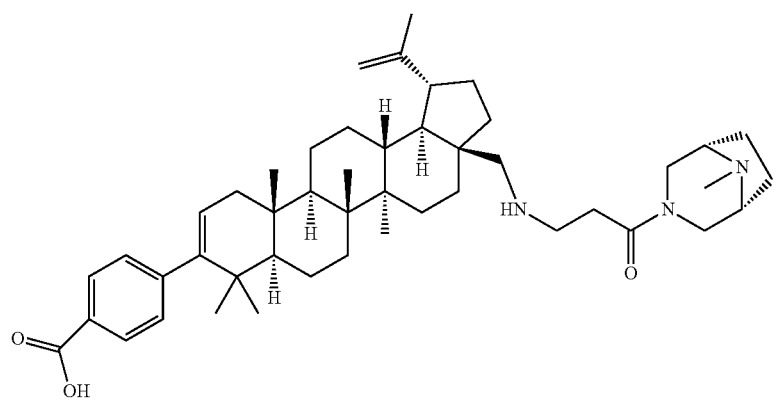

The title compound was prepared following the general procedure described above for the preparation of C28 amines with amide end cap using 3-aminopropanoate hydrochloride and (1R,5S)-8-methyl-3,8-diazabicyclo[3.2.1]octane as the reactant amines. The product was isolated as a white solid (7 mg, 71.7%). LCMS: m/e 724.5 (MH$^+$), 2.41 min (method 3). $^1$H NMR (400 MHz, MeOD) δ ppm 7.92 (m, 2H), 7.23 (m, 2H), 5.25-5.41 (m, 1H), 4.79 (d, J=1.8 Hz, 1H), 4.67 (s, 1H), 4.47-4.61 (m, 1H), 4.03-4.09 (m, 2H), 4.00 (d, J=1.8 Hz, 1H), 3.68 (d, J=14.1 Hz, 1H), 3.39-3.48 (m, 2H), 3.16-3.26 (m, 1H), 2.98-3.13 (m, 1H), 2.78-2.98 (m, 4H), 2.50-2.61 (m, 1H), 2.25-2.47 (m, 2H), 2.13-2.23 (m, 1H), 1.99-2.13 (m, 2H), 1.72-1.91 (m, 10H), 1.50-1.68 (m, 8H), 1.32-1.38 (m, 3H), 1.28-1.32 (m, 2H), 1.24-1.28 (m, 2H), 1.14-1.24 (m, 4H), 1.11 (s, 3H), 1.05 (s, 3H), 0.99 (s, 3H), 0.98 (s, 3H).

Example 122

Preparation of 4-((1R,3aS,5aR,5bR,7aR,11aS,11bR,13aR,13bR)-5a,5b,8,8,11a-pentamethyl-3a-((3-oxo-3-thiomorpholinopropylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

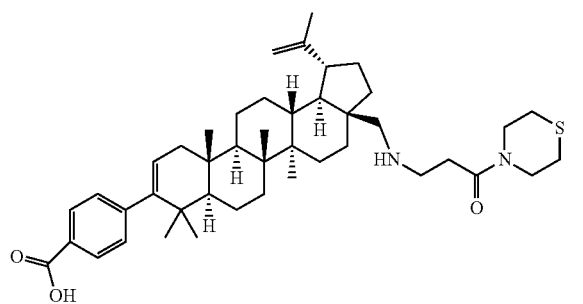

The title compound was prepared following the general procedure described above for the preparation of C28 amines with amide end cap using 3-aminopropanoate hydrochloride and thiomorpholine as the reactant amines. The product was isolated as a white solid (6 mg, 61.6%). LCMS: m/e 701.5 (MH$^+$), 2.67 min (method 3). $^1$H NMR (400 MHz, MeOD) δ ppm 7.81-8.00 (m, 2H), 7.18-7.31 (m, 2H), 5.24-5.47 (m, 1H), 4.79 (d, J=1.5 Hz, 1H), 4.67 (s, 1H), 3.85-3.99 (m, 2H), 3.80 (ddd, J=4.8, 2.9, 2.6 Hz, 2H), 3.36-3.49 (m, 2H), 3.25-3.32 (m, 1H), 2.83-2.92 (m, 3H), 2.61-2.79 (m, 4H), 2.47-2.61 (m, 1H), 1.99-2.23 (m, 2H), 1.67-1.92 (m, 10H), 1.47-1.67 (m, 8H), 1.24-1.45 (m, 4H), 1.20 (s, 4H), 1.11 (s, 3H), 1.05 (s, 3H), 0.99 (s, 3H), 0.96 (s, 3H).

Example 123

Preparation of 4-((1R,3aS,5aR,5bR,7aR,11aS,11bR,13aR,13bR)-5a,5b,8,8,11a-pentamethyl-3a-((3-(2-methyl-1-oxo-2,8-diazaspiro[4.5]decan-8-yl)-3-oxo-propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

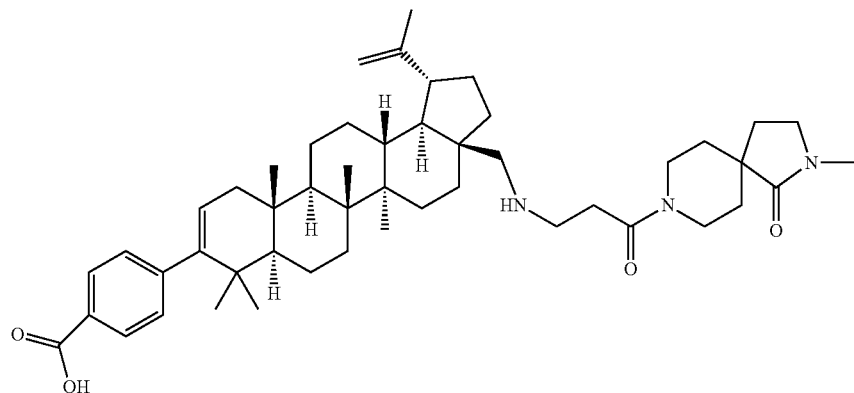

The title compound was prepared following the general procedure described above for the preparation of C28 amines with amide end cap using 3-aminopropanoate hydrochloride and 2-methyl-2,8-diazaspiro[4.5]decan-1-one as the reactant amines. The product was isolated as a white solid (7.6 mg, 77%). LCMS: m/e 766.6 (MH$^+$), 2.63 min (method 3). $^1$H NMR (400 MHz, MeOD) δ ppm 7.94 (m, J=8.3 Hz, 2H), 7.24 (m, J=8.5 Hz, 2H), 5.33 (d, J=4.5 Hz, 1H), 4.79 (s, 1H), 4.67 (s, 1H), 4.38 (d, J=13.6 Hz, 1H), 3.90 (d, J=14.3 Hz, 1H), 3.45 (t, J=6.9 Hz, 2H), 3.34-3.42 (m, 2H), 3.33 (m, 1H), 3.28 (dd, J=5.4, 2.1 Hz, 1H), 3.02-3.15 (m, 1H), 2.91-2.96 (m, 3H), 2.80-2.88 (m, 3H), 2.55 (br. s., 1H), 2.01-2.24 (m, 4H), 1.67-1.92 (m, 12H), 1.46-1.67 (m, 10H), 1.39 (br. s., 1H), 1.23-1.36 (m, 3H), 1.14-1.23 (m, 4H), 1.11 (s, 3H), 1.02-1.09 (s, 3H), 1.00 (s, 3H), 0.98 (s, 3H).

Example 124

Preparation of 4-((1R,3aS,5aR,5bR,7aR,11aS,11bR, 13aR,13bR)-5a,5b,8,8,11a-pentamethyl-3a-((3-(4-(2-(methylsulfonyl)ethyl)piperazin-1-yl)-3-oxopropylamino)methyl)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)benzoic acid

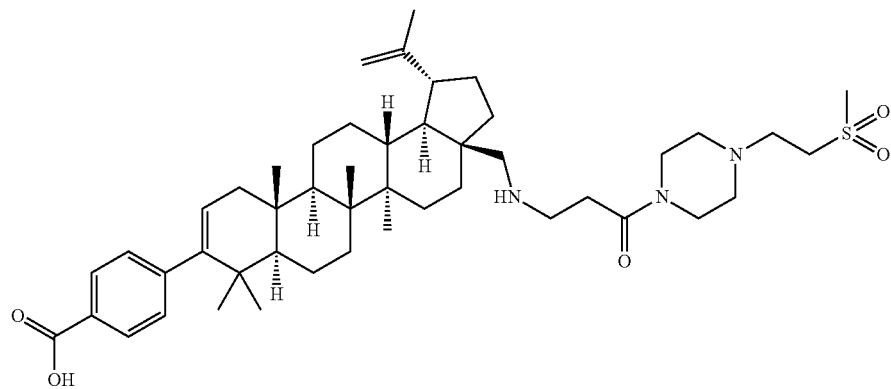

The title compound was prepared following the general procedure described above for the preparation of C28 amines with amide end cap using 3-aminopropanoate hydrochloride and 1-(2-(methylsulfonyl)ethyl)piperazine as the reactant amines. The product was isolated as a white solid (7.0 mg, 71.2%). LCMS: m/e 790.6 (MH$^+$), 2.51 min (method 3). $^1$H NMR (400 MHz, MeOD) δ ppm 7.94 (m, 2H), 7.26 (m, 2H), 5.24-5.42 (m, 1H), 4.79 (d, J=1.8 Hz, 1H), 4.67 (s, 1H), 4.00 (s, 2H), 3.83 (d, J=5.3 Hz, 2H), 3.63-3.75 (m, 2H), 3.53-3.63 (m, 2H), 3.38-3.47 (m, 2H), 3.35-3.38 (m, 2H), 3.28 (dd, J=3.9, 2.1 Hz, 3H), 3.12 (s, 3H), 2.88-3.00 (m, 3H), 2.54 (br. s., 1H), 2.12-2.27 (m, 1H), 2.09 (d, J=2.8 Hz, 1H), 1.67-1.91 (m, 10H), 1.47-1.67 (m, 8H), 1.39 (br. s., 1H), 1.28-1.36 (m, 2H), 1.25 (br. s., 1H), 1.14-1.21 (m, 4H), 1.11 (s, 3H), 1.05 (s, 3H), 1.01 (s, 3H), 0.96 (s, 3H).

Example 125

Preparation of 4-((1R,3aS,5aR,5bR,7aR,11aS,11bR,13aR,13bR)-5a,5b,8,8,11a-pentamethyl-3a-((3-(methyl(2-(methylsulfonyl)ethyl)amino)-3-oxopropylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

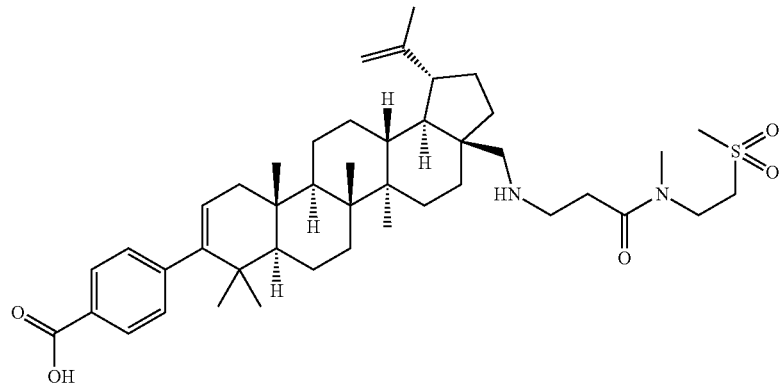

The title compound was prepared following the general procedure described above for the preparation of C28 amines with amide end cap using 3-aminopropanoate hydrochloride and N-methyl-2-(methylsulfonyl)ethanamine as the reactant amines. The product was isolated as a white solid (5.0 mg, 50.0%). LCMS: m/e 735.5 (MH+), 2.24 min (method 3). $^1$H NMR (400 MHz, MeOD) δ ppm 7.94 (m, J=8.5 Hz, 2H), 7.24 (m, J=8.3 Hz, 2H), 5.33 (dd, J=6.3, 1.8 Hz, 1H), 4.79 (s, 1H), 4.67 (d, J=1.5 Hz, 1H), 3.85-4.06 (m, 2H), 3.35-3.48 (m, 4H), 3.25-3.32 (m, 1H), 3.13 (s, 3H), 3.07 (s, 3H), 2.82-2.96 (m, 3H), 2.55 (br. s., 1H), 2.13-2.27 (m, 1H), 2.11 (d, J=12.3 Hz, 1H), 1.66-1.91 (m, 8H), 1.57-1.66 (m, 2H), 1.52 (d, J=13.8 Hz, 3H), 1.29-1.47 (m, 4H), 1.20 (s, 3H), 1.11 (s, 3H), 1.06 (s, 3H), 0.99 (s, 3H), 0.95 (s, 3H).

Example 126

Preparation of 4-((1R,3aS,5aR,5bR,7aR,11aS,11bR,13aR,13bR)-5a,5b,8,8,11a-pentamethyl-3a#3-oxo-3-(1,4-dioxa-8-azaspiro[4.5]decan-8-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

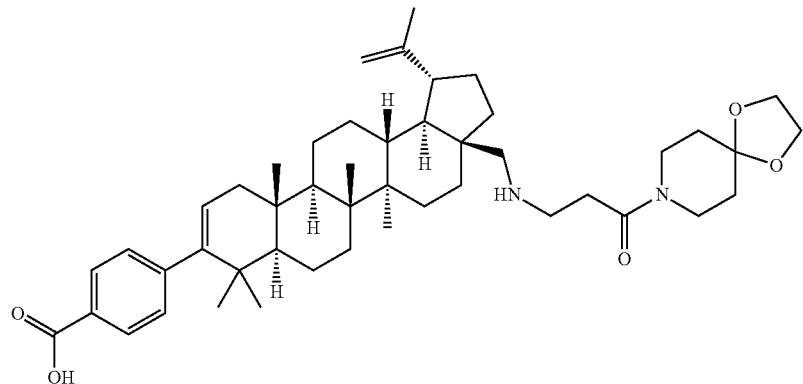

The title compound was prepared following the general procedure described above for the preparation of C28 amines with amide end cap using 3-aminopropanoate hydrochloride and 1,4-dioxa-8-azaspiro[4.5]decane as the reactant amines. The product was isolated as a white solid (3 mg, 30%). LCMS: m/e 741.6 (MH+), 2.65 min (method 3). $^1$H NMR (400 MHz, MeOD) δ ppm 7.94 (m, J=8.3 Hz, 2H), 7.24 (m, J=8.5 Hz, 2H), 5.33 (dd, J=6.3, 1.8 Hz, 1H), 4.79 (d, J=1.5 Hz, 1H), 4.67 (s, 1H), 3.89-4.03 (m, 4H), 3.65-3.81 (m, 2H), 3.61 (dd, J=7.3, 4.5 Hz, 2H), 3.36-3.43 (m, 2H), 3.22-3.31 (m, 1H), 2.85-3.00 (m, 3H), 2.54 (br. s., 1H), 2.18 (dd, J=16.9, 6.4 Hz, 1H), 2.08 (br. s., 1H), 1.67-1.91 (m, 11H), 1.48-1.67 (m, 8H), 1.24-1.48 (m, 6H), 1.13-1.24 (m, 5H), 1.11 (s, 3H), 1.02-1.09 (m, 3H), 1.00 (s, 3H), 0.98 (s, 3H).

Example 127

Preparation of 4-((1R,3aS,5aR,5bR,7aR,11aS,11bR, 13aR,13bR)-5a,5b,8,8,11a-pentamethyl-3a-((3-(methylamino)-3-oxopropylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

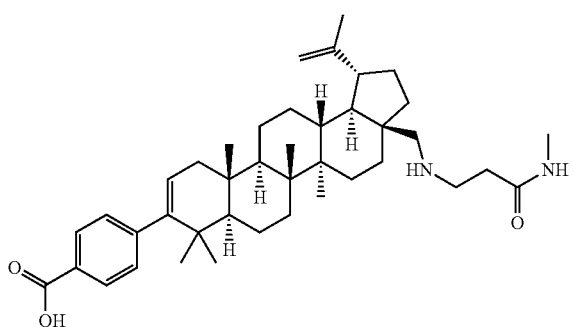

The title compound was prepared following the general procedure described above for the preparation of C28 amines with amide end cap using 3-aminopropanoate hydrochloride and methylamine as the reactant amines. The product was isolated as a white solid (5.0 mg, 50.0%). LCMS: m/e 629.6 (MH⁺), 2.58 min (Method 3).

Example 128

Preparation of 4-((1R,3aS,5aR,5bR,7aR,11aS,11bR, 13aR,13bR)-5a,5b,8,8,11a-pentamethyl-3a-((3-oxo-3-(4-oxopiperidin-1-yl)propylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid The title compound was prepared following the general procedure described above for the preparation of C28 amines with amide end cap using 3-aminopropanoate hydrochloride and piperidin-4-one as the reactant amines. The product was isolated as a white solid (2 mg, 21.6%). LCMS: m/e 697.6 (MH⁺), 2.61 min (method 3). ¹H NMR (400 MHz, MeOD) δ ppm 7.94 (m, J=8.3 Hz, 2H), 7.24 (m, J=8.3 Hz, 2H), 5.25-5.39 (m, 1H), 4.79 (s, 1H), 4.67 (s, 1H), 3.50-3.63 (m, 2H), 3.35-3.47 (m, 6H), 3.28 (dt, J=3.3, 1.6 Hz, 2H), 3.13-3.25 (m, 1H), 2.81-2.97 (m, 3H), 2.44-2.64 (m, 1H), 2.18 (dd, J=17.2, 6.4 Hz, 2H), 1.67-1.91 (m, 8H), 1.60 (br. s., 3H), 1.46-1.57 (m, 4H), 1.24-1.46 (m, 6H), 1.15-1.24 (m, 5H), 1.11 (s, 3H), 1.01-1.09 (m, 3H), 1.00 (s, 3H), 0.98 (s, 3H).

Example 129

Preparation of 4-((1R,3aS,5aR,5bR,7aR,11aS,11bR, 13aR,13bR)-3a-((3-(1,3-dihydroxy-2-methylpropan-2-ylamino)-3-oxopropylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

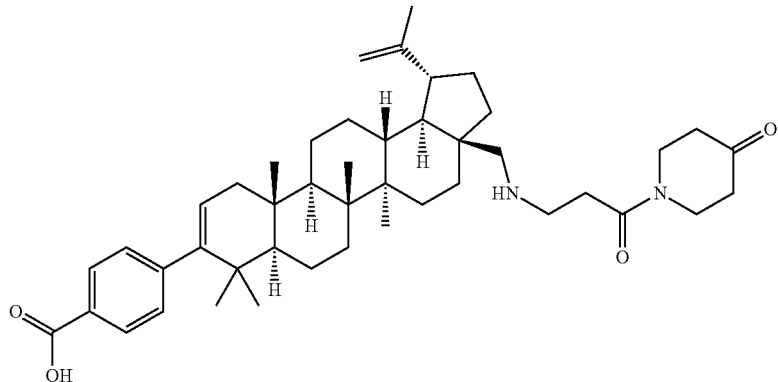

The title compound was prepared following the general procedure described above for the preparation of C28 amines with amide end cap using 3-aminopropanoate hydrochloride and N,3-dimethyloxetane-3-amine as the reactant amines. The product was isolated as a white solid (1 mg, 11.6%). LCMS: m/e 703.7 (MH⁺), 2.47 min (method 3).

Example 130

Preparation of 4-((1R,3aS,5aR,5bR,7aR,11aS,11bR, 13aR,13bR)-5a,5b,8,8,11a-pentamethyl-3a-((2-oxo-2-(piperidin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

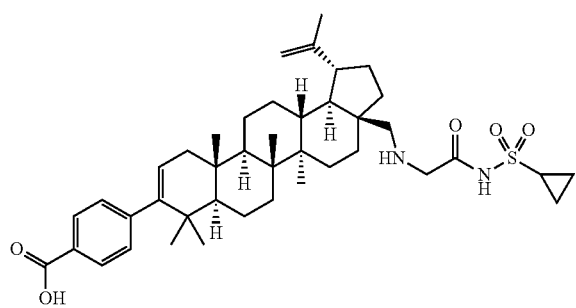

The title compound was prepared following the general procedure described above for the preparation of C28 amines with amide end cap using methyl 2-aminoacetate hydrochloride and piperidine as the reactant amines. The product was isolated as a white solid (10.0 mg, 51.5%). LCMS: m/e 669.4 (MH$^+$), 2.16 min (method 3). $^1$H NMR (400 MHz, MeOD) δ ppm 7.94 (m, J=8.5 Hz, 2H), 7.24 (m, J=8.5 Hz, 2H), 5.32 (dd, J=6.1, 1.6 Hz, 1H), 4.76 (d, J=1.8 Hz, 1H), 4.66 (s, 1H), 4.13 (s, 2H), 3.56-3.72 (m, 2H), 3.35-3.46 (m, 2H), 3.3 (m, 1H), 2.86 (d, J=12.5 Hz, 1H), 2.48 (dt, J=11.1, 5.6 Hz, 1H), 2.03-2.22 (m, 2H), 1.84-2.03 (m, 3H), 1.66-1.78 (m, 10H), 1.48-1.65 (m, 10H), 1.29-1.45 (m, 3H), 1.24 (d, J=10.5 Hz, 2H), 1.14-1.20 (m, 4H), 1.11 (s, 3H), 1.05 (s, 3H), 0.99 (s, 3H), 0.98 (s, 3H).

Example 131

Preparation of 4-((1R,3aS,5aR,5bR,7aR,11aS,11bR, 13aR,13bR)-3a-((3-carboxy-1-(3,3-difluoropyrrolidin-1-yl)-1-oxopropan-2-ylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

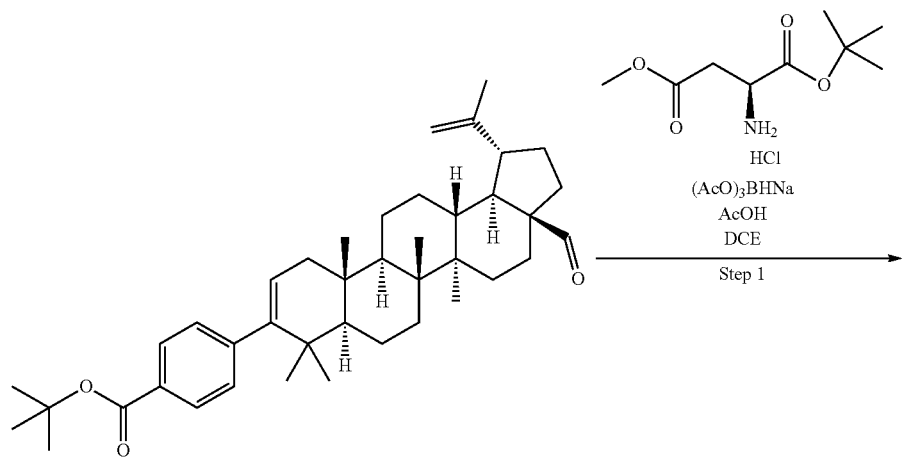

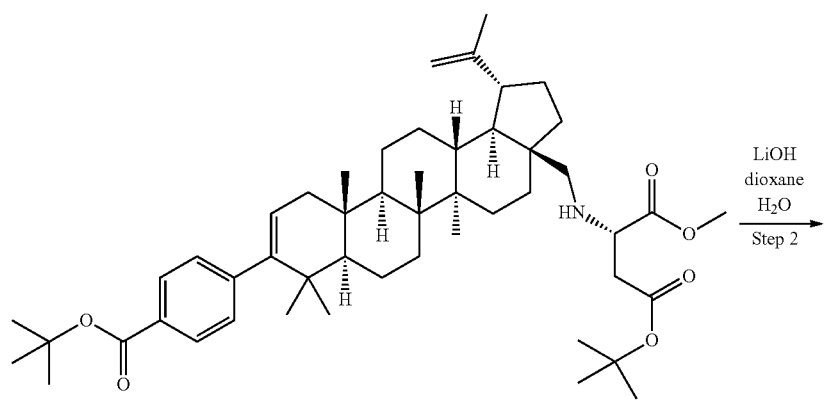

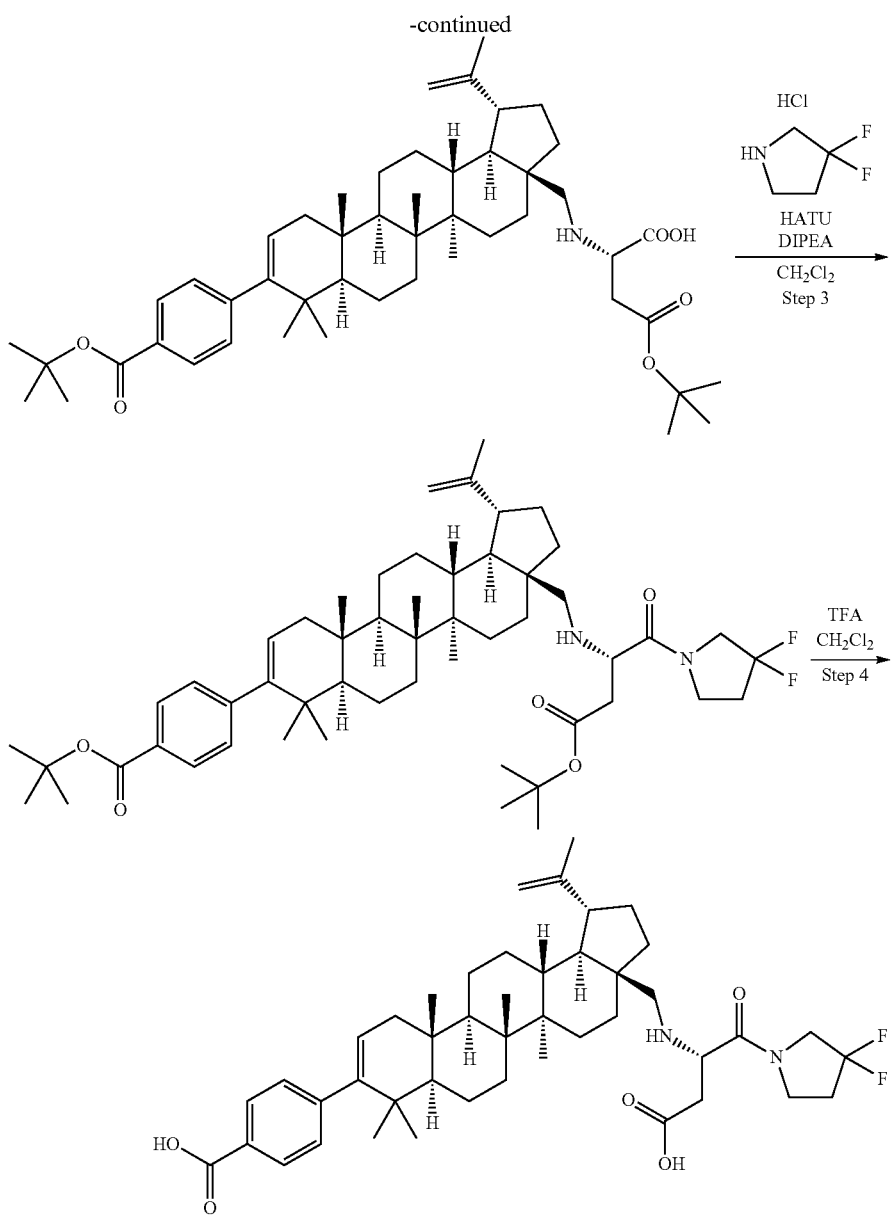

Example 131

Step 1: Preparation of the C28 amine

To a solution of tert-butyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (100 mg, 0.167 mmol)) in DCE was added (S)-1-tert-butyl 4-methyl 2-aminosuccinate hydrochloride (120 mg, 0.501 mmol) and acetic acid (10.03 mg, 0.167 mmol). The mixture was stirred at rt for 10 min. Then sodium triacetoxyhydroborate (106 mg, 0.501 mmol) was added and it was stirred at rt for 48 h. The mixture was diluted with 7 ml of a sat. aqueous solution of sodium carbonate and was extracted with DCM (3×7 ml). The combined organic layers were dried with sodium sulfate. The drying agent was removed by filtration and the filtrate was concentrated under reduced pressure. The crude product was used in the next step with no additional purification. MS: m/e 786.6 (MH$^+$), 3.03 min (method 3). $^1$H NMR (400 MHz, CHLOROFORM-d) δ ppm 0.92 (s, 3H) 0.92 (s, 3H) 0.98 (s, 3H) 0.99 (s, 3H) 1.09 (s, 3H) 1.48 (s, 9H) 1.58 (s, 9H) 1.68 (s, 3H) 0.84-1.78 (m, 20H) 1.86-2.01 (m, 2H) 2.09 (dd, J=17.19, 6.40 Hz, 1H) 2.33 (d, J=11.29 Hz, 1H) 2.40 (td, J=11.04, 5.52 Hz, 1H) 2.53-2.63 (m, 2H) 2.67-2.75 (m, 1H) 3.53 (dd, J=7.28, 6.27 Hz, 1H) 3.68 (s, 3H) 4.57 (s, 1H) 4.68 (d, J=2.01 Hz, 1H) 5.27 (dd, J=6.02, 1.51 Hz, 1H) 7.16 (d, J=8.28 Hz, 2H) 7.88 (d, J=8.28 Hz, 2H).

Step 2: Hydrolysis of the Methyl Ester

To a solution of crude material (0.112 g, 0.142 mmol) from Step 1 in dioxane (1.5 ml) was added lithium hydroxide (6.82 mg, 0.285 mmol). The reaction was heated up to 63° C. for 4 h. Solvent was evaporated and the crude product was purified by prep. HPLC (YMC Combiprep ODS 30×50 mm S5, MeOH/H$_2$O/TFA). MS: m/e 772.6 (MH$^+$), 3.02 min (method 3). The fractions containing the desired product were combined and concentrated under reduce pressure. The residue was taken to the next step without further purification.

Step 3: Preparation of the Amide End Cap

To a mixture of material (30 mg, 0.039 mmol) from Step 2, 3,3-difluoropyrrolidine hydrochloride (6.69 mg, 0.047 mmol) in DCM (1 ml) was added DIPEA (0.034 ml, 0.194 mmol) followed by HATU (22.16 mg, 0.058 mmol). The resulting solution was stirred at rt for 1 h. The reaction mixture was concentrated in vacuo to give crude product which was taken to the next step without further purification. MS: m/e 861.6 (MH$^+$), 2.07 min (method 2).

Step 4: Preparation of the di-acid

To a solution of crude material from Step 3 in DCM (2 ml) was added TFA (0.5 ml, 6.49 mmol). The mixture was stirred at rt for 2 h and then was concentrated in vacuo. The crude product was purified by prep. HPLC (YMC Combiprep ODS 30×50 mm S5, MeOH/H$_2$O/TFA) to afford 4-((1R,3aS,5aR,5bR,7aR,11aS,11bR,13aR,13bR)-3a-((3-carboxy-1-(3,3-difluoropyrrolidin-1-yl)-1-oxopropan-2-ylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (15 mg, 51%). MS: m/e 749.6 (MH$^+$), 1.74 min (method 2). $^1$H NMR (400 MHz, MeOD) δ ppm 0.95 (s, 3H) 0.97 (s, 3H) 1.04 (s, 3H) 1.08 (s, 3H) 1.19 (s, 3H) 1.72 (s, 3H) 0.86-2.02 (m, 24H) 2.15 (dd, J=16.56, 6.27 Hz, 1H) 2.38-2.61 (m, 3H) 2.71 (t, J=11.54 Hz, 1H) 2.78-2.89 (m, 1H) 2.93-3.04 (m, 1H) 3.75-4.03 (m, 3H) 4.61-4.65 (m, 1H) 4.73 (d, J=1.76 Hz, 1H) 5.30 (dd, J=6.40, 1.88 Hz, 1H) 7.22 (d, J=8.28 Hz, 2H) 7.91 (d, J=8.28 Hz, 2H). $^{19}$F NMR (376 MHz, MeOD) δ ppm −105.07−−101.67 (m, 2 F).

Example 132

Preparation of 4-thiomorpholinebutanoic acid, 4-((1R,3aS,5aR,5bR,7aR,11aS,11bR,13aR,13bR)-3a-((((1S)-1-(carboxymethyl)-2-(1,1-dioxido-4-thiomorpholinyl)-2-oxoethyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

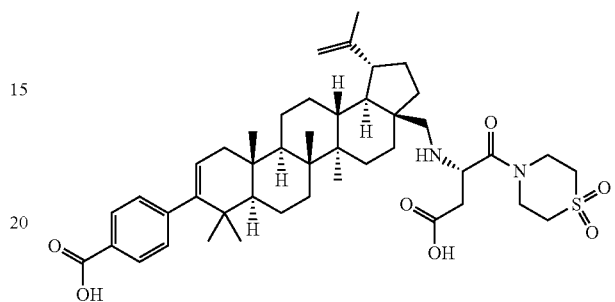

The title compound was prepared following the procedure described above for the preparation of 4-((1R,3aS,5aR,5bR,7aR,11aS,11bR,13aR,13bR)-3a-((3-carboxy-1-(3,3-difluoropyaolidin-1-yl)-1-oxopropan-2-ylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (example 131) using (S)-1-tert-butyl 4-methyl 2-aminosuccinate hydrochloride and thiomorpholine 1,1-dioxide as the reactant amines in steps 1 and 3 respectively. The product was isolated as a white solid (21 mg, 63.8%). LCMS: m/e 777.4 (MH$^+$), 2.60 min (method 3). $^1$H NMR (400 MHz, MeOD) δ ppm 7.78-8.01 (m, 2H), 7.13-7.31 (m, 2H), 5.32 (d, J=4.8 Hz, 1H), 4.77 (d, J=1.0 Hz, 1H), 4.66 (s, 1H), 4.18 (d, J=4.3 Hz, 2H), 3.94-4.15 (m, 2H), 3.37-3.49 (m, 1H), 3.19-3.28 (m, 4H), 2.91-3.15 (m, 3H), 2.71-2.86 (m, 1H), 2.48 (d, J=5.8 Hz, 1H), 2.16 (dd, J=17.1, 6.3 Hz, 1H), 1.95-2.09 (m, 2H), 1.90 (d, J=14.6 Hz, 1H), 1.68-1.87 (m, 8H), 1.60 (br. s., 2H), 1.47-1.60 (m, 6H), 1.36-1.44 (m, 1H), 1.25-1.36 (m, 3H), 1.16-1.25 (m, 4H), 1.10 (s, 3H), 1.05 (s, 3H), 0.99 (s, 3H), 0.96 (s, 3H).

General procedure for the preparation of C28 reversed amides: Examples 133-147.

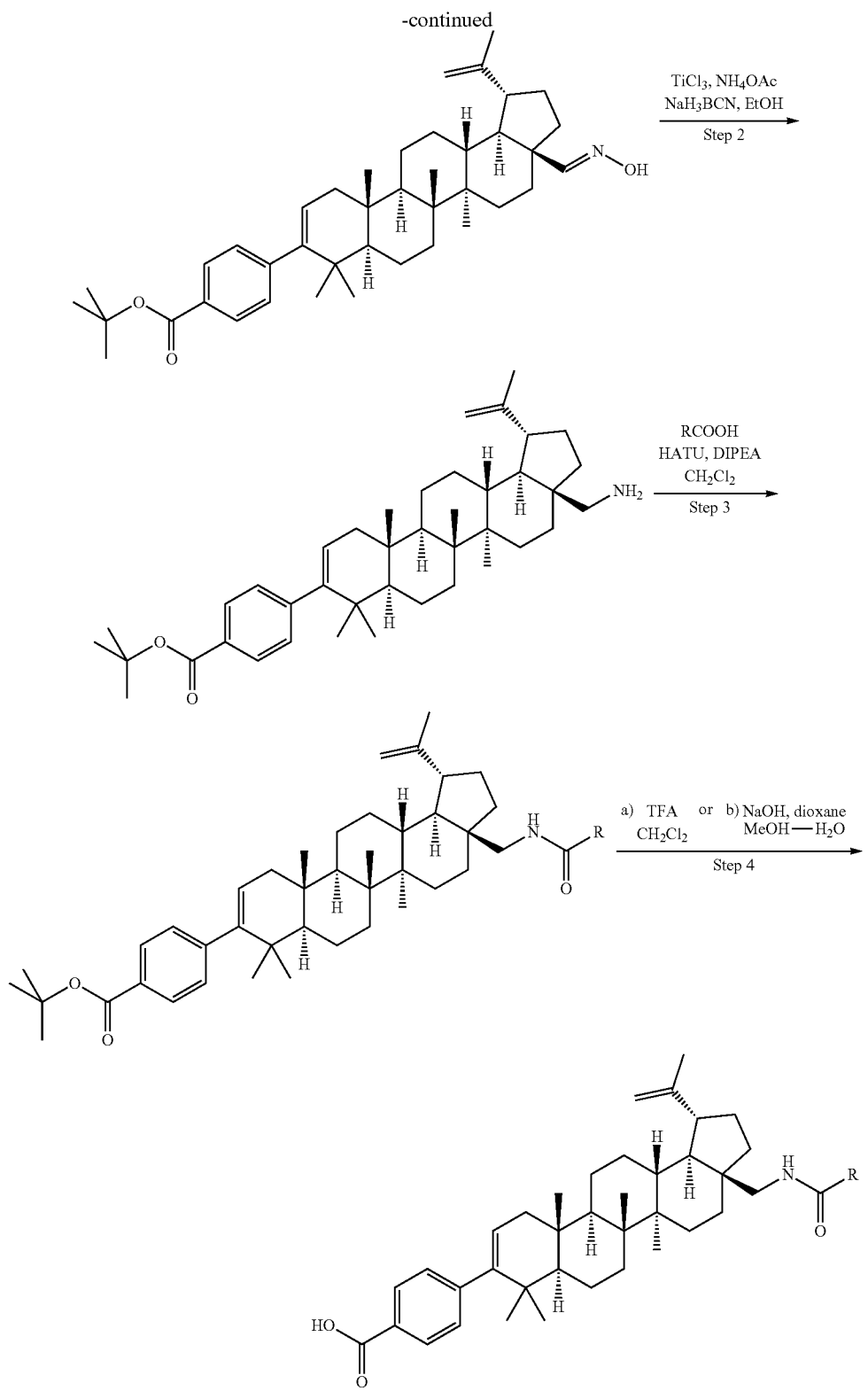

Step 1: Preparation of the C28 Oxime

To a suspension of the tert-butyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (270 mg, 0.451 mmol) in ethanol (20 ml) was added hydroxylamine hydrochloride (433 mg, 6.23 mmol) and potassium carbonate (862 mg, 6.23 mmol). The suspension was stirred at ~50° C. for 2 h. The mixture was diluted with 7 ml of saturated NaHCO₃ solution and was extracted with dichloromethane (3×7 ml). The combined organic layers were dried with sodium sulfate. The drying agent was removed by filtration and the filtrate was concentrated under reduced pressure. The crude product (quantitative) was used in the next step with no further purification. ¹H NMR (400 MHz, CHLOROFORM-d) δ 7.90 (2H, d, J=8.3 Hz), 7.59 (1H, s), 7.19 (2H, d, J=8.3 Hz), 6.96 (1H, s), 5.29 (1H, dd, J=6.2, 1.6 Hz), 4.75 (1H, d, J=1.8 Hz), 4.64 (1H, d, J=2.0 Hz), 2.56 (1H, td, J=11.1, 5.4 Hz), 2.12 (1H, dd, J=16.9, 6.3 Hz), 1.96-2.02 (2H, m), 1.92-1.96 (1H, m), 1.81-1.92 (2H, m), 1.76-1.81 (2H, m), 1.73 (4H, s), 1.63-1.70 (2H, m), 1.61 (9H, s), 1.56 (2H, br. s.), 1.48 (2H, br. s.), 1.31-1.42 (2H, m), 1.27 (3H, s), 1.08-1.20 (2H, m), 1.07 (3H, s), 1.04 (3H, s), 1.00 (3H, s), 0.94 (6H, s).

Step 2: Reduction of the C28 Oxime

To a clear solution of the crude material from Step 1 (1.205 g, 1.963 mmol) in EtOH (40 ml) was added excess of ammonium acetate (1.059 g, 13.74 mmol) and sodium cyanoborohydride (863 mg, 13.74 mmol). The mixture was stirred in an ice bath until it was cold. To this suspension was added titanium (III) chloride (20% solution, 10 ml, 1.963 mmol). The resulting mixture was blanketed under nitrogen, and stirred at rt for an hour. The dark greenish-blue solution was treated with a solution of sodium hydroxide (10N), 3 ml in 25 ml water, along with 30 ml of methylene chloride. The mixture was stirred vigorously in open air until the aqueous phase became light blue.

The suspending titanium residue was removed by a filtration through a short bed of paper cellulose. The clear filtrate was separated, the aqueous phase was extracted with methylene chloride (2×25 ml). The organic layers were combined, evaporated to dryness under high vacuum to obtained tert-butyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (1.3 g, 100%). ¹H NMR (400 MHz, CHLOROFORM-d) δ 0.94 (s, 6H), 1.00 (s, 3H), 1.03 (s, 3H), 1.05-1.09 (m, 1H), 1.10 (s, 3H), 1.19-1.35 (m, 3H), 1.35-1.57 (m, 13H), 1.61 (s, 9H), 1.65-1.69 (m, 1H), 1.72 (s, 3H), 1.75-2.02 (m, 3H), 2.12 (dd, J=17.00, 6.17 Hz, 1H), 2.36 (d, J=13.09 Hz, 1H), 2.44 (td, J=10.89, 5.41 Hz, 1H), 2.89 (d, J=13.09 Hz, 1H), 3.73 (s, 1H), 4.61 (s, 1H), 4.72 (s, 1H), 5.29 (d, J=4.53 Hz, 1H), 7.19 (d, J=8.06 Hz, 2H), 7.90 (d, J=8.31 Hz, 2H).

Step 3: Acylation

To a solution of the material from Step 2 (tert-butyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate) and the corresponding carboxylic acid (2 eq.) in DCM (5-8 ml) at 0° C. was added HATU (2-3 eq.) followed by DIPEA (4 eq.). The mixture was stirred at rt for 2-18 h. The solvent was evaporated under vacuum and the resulting crude product was purified by Biotage flash chromatography or was used directly in the next step without further purification.

Step 4: Preparation of the Benzoic Acids (a) Acidic hydrolysis—To a solution of the material from Step 3 in DCM (4-5 ml) was added TFA (0.4-0.5 ml). The mixture was stirred at room temperature for 2-6 h. The solvent was evaporated under vacuum. The resulting crude product was purified by prep. HPLC to give the desired benzoic acids.

(b) Basic hydrolysis—To a solution of the material from Step 3 in dioxane (2 ml) and methanol (2 ml) was added NaOH (75 mg, 1.875 mmol) and H₂O (0.5 ml). The resulting solution was stirred at 70° C. for 5-10 h. The solvent was evaporated under vacuum and the resulting crude product was purified by prep. HPLC to give the desired benzoic acids.

Example 133

Preparation of 4-((1R,3aS,5aR,5bR,7aR,11aS,11bR,13aR,13bR)-5a,5b,8,8,11a-pentamethyl-3a-((2-(2-oxopyrrolidin-1-yl)acetamido)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

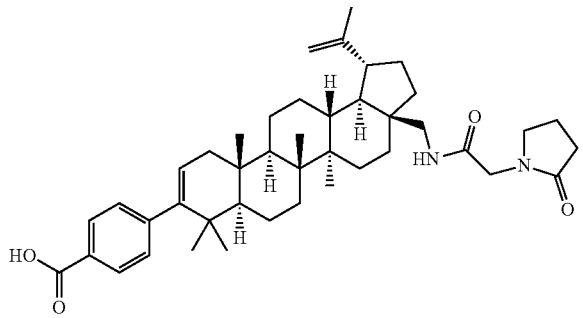

The title compound was prepared in 55% yield following the general procedure described above for the reversed amides preparation, using 2-(2-oxopyrrolidin-1-yl)acetic acid as the reactant acid and acidic hydrolysis. MS: m/e 725.4 (MH⁺), 1.78 min (method 2). ¹H NMR (500 MHz, MeOD) δ ppm 0.94 (s, 3H) 0.96 (s, 3H) 1.03 (s, 3H) 1.04 (s, 3H) 1.18 (s, 3H) 1.70 (s, 3H) 0.89-2.18 (m, 24H) 2.38-2.45 (m, 2H) 2.52 (td, J=10.83, 5.80 Hz, 1H) 2.99-3.06 (m, 1H) 3.45-3.51 (m, 2H) 3.53-3.61 (m, 1H) 3.97 (d, J=2.14 Hz, 2H) 4.59 (s, 1H) 4.72 (s, 1H) 5.27-5.32 (m, 1H) 7.22 (d, J=8.24 Hz, 2H) 7.91 (d, J=8.55 Hz, 2H).

Example 134

Preparation of 4-((1R,3aS,5aR,5bR,7aR,11aS,11bR, 13aR,13bR)-3a-((2,6-dioxopiperidine-4-carboxamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

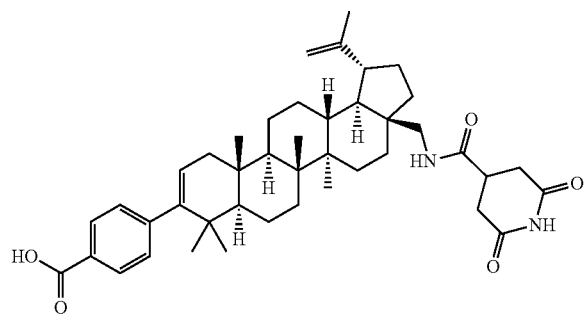

The title compound was prepared in 60% yield following the general procedure described above for the reversed amides preparation, using 2,6-dioxopiperidine-4-carboxylic acid as the reactant acid and acidic hydrolysis. MS: m/e 683.2 (MH$^+$), 1.70 min (method 2). $^1$H NMR (500 MHz, MeOD) δ ppm 0.97 (s, 3H) 0.99 (s, 3H) 1.06 (s, 3H) 1.07 (s, 3H) 1.19 (s, 3H) 1.73 (s, 3H) 0.90-1.79 (m, 18) 1.81-1.96 (m, 2H) 2.03-2.12 (m, 1H) 2.17 (dd, J=16.79, 6.41 Hz, 1H) 2.54 (td, J=11.14, 5.49 Hz, 1H) 2.73 (d, J=6.41 Hz, 4H) 3.05 (dd, J=13.58, 5.95 Hz, 1H) 3.07-3.14 (m, 1H) 3.55 (dd, J=13.28, 5.95 Hz, 1H) 4.62 (s, 1H) 4.74 (s, 1H) 5.32 (d, J=5.80 Hz, 1H) 7.24 (d, J=7.32 Hz, 2H) 7.94 (d, J=7.32 Hz, 2H).

Example 135

Preparation of 4-((1R,3aS,5aR,5bR,7aR,11aS,11bR, 13aR,13bR)-3a-(((R)-2-amino-4-(methylsulfonyl)butanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

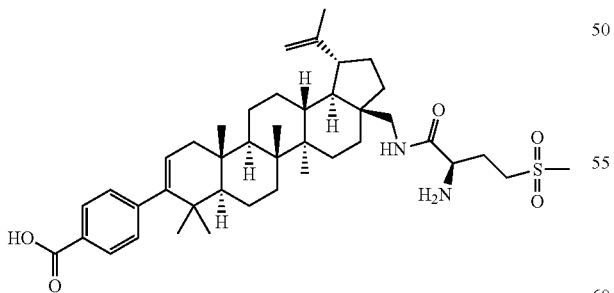

The title compound was prepared in 77% yield following the general procedure described above for the reversed amides preparation, using (R)-2-(tert-butoxycarbonylamino)-4-(methylsulfonyl)butanoic acid as the reactant acid and acidic hydrolysis. MS: m/e 707.2 (MH$^+$), 1.54 min (method 2). $^1$H NMR (400 MHz, MeOD) δ ppm 0.96 (s, 3H) 0.98 (s, 3H) 1.05 (s, 3H) 1.07 (s, 3H) 1.19 (s, 3H) 1.73 (s, 3H) 0.88-1.80 (m, 18H) 1.81-1.96 (m, 2H) 2.04-2.12 (m, 1H) 2.16 (dd, J=17.07, 6.27 Hz, 1H) 2.33-2.42 (m, 2H) 2.54 (td, J=11.04, 5.52 Hz, 1H) 3.04 (s, 3H) 3.08 (d, J=13.80 Hz, 1H) 3.15-3.24 (m, 1H) 3.68 (d, J=13.30 Hz, 1H) 3.99 (s, 1H) 4.08 (t, J=6.27 Hz, 1H) 4.62 (dd, J=2.13, 1.38 Hz, 1H) 4.75 (d, J=1.76 Hz, 1H) 5.31 (dd, J=6.15, 1.63 Hz, 1H) 7.23 (d, J=8.28 Hz, 2H) 7.93 (d, J=8.53 Hz, 2H).

Example 136

Preparation of 4-((1R,3aS,5aR,5bR,7aR,11aS,11bR, 13aR,13bR)-5a,5b,8,8,11a-pentamethyl-1-(prop-1-en-2-yl)-3a-(((S)-pyrrolidine-2-carboxamido)methyl)-2,3,3a,4,5,5a,5b,6,7,7a,8,11,11a,11b,12,13,13a,13b-octadecahydro-1H-cyclopenta[a]chrysen-9-yl)benzoic acid

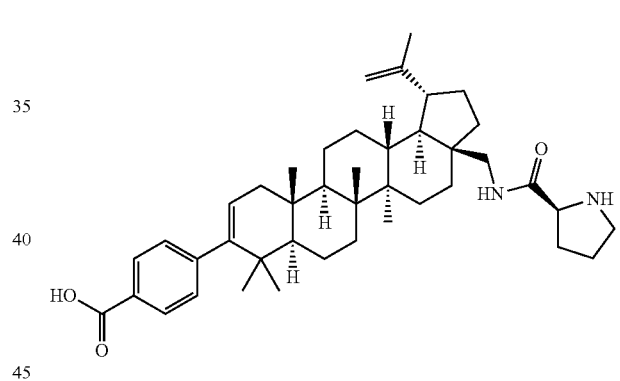

The title compound was prepared in 31% yield following the general procedure described above for the reversed amides preparation, using (S)-1-(tert-butoxycarbonyl)pyrrolidine-2-carboxylic acid as the reactant acid and acidic hydrolysis. MS: m/e 641.7 (MH$^+$), 1.77 min (method 2). $^1$H NMR (400 MHz, MeOD) δ ppm 0.94 (s, 3H) 0.96 (s, 3H) 1.03 (s, 3H) 1.05 (s, 3H) 1.17 (s, 3H) 1.71 (s, 3H) 0.86-2.10 (m, 24H) 2.14 (dd, J=17.19, 6.65 Hz, 1H) 2.39-2.47 (m, 1H) 2.52 (td, J=11.17, 5.52 Hz, 1H) 3.01 (dd, J=13.55, 5.02 Hz, 1H) 3.33-3.36 (m, 1H) 3.38-3.47 (m, 1H) 3.69 (dd, J=13.93, 5.90 Hz, 1H) 4.23 (dd, J=8.03, 7.03 Hz, 1H) 4.61 (s, 1H) 4.73 (d, J=1.76 Hz, 1H) 5.30 (dd, J=6.02, 1.51 Hz, 1H) 7.21 (d, J=8.28 Hz, 2H) 7.91 (d, J=8.28 Hz, 2H) 8.13 (t, J=6.02 Hz, 1H).

Example 137

Preparation of 4-((1R,3aS,5aR,5bR,7aR,11aS,11bR, 13aR,13bR)-5a,5b,8,8,11a-pentamethyl-1-(prop-1-en-2-yl)-3a-(((R)-pyrrolidine-2-carboxamido)methyl)-2,3,3a,4,5,5a,5b,6,7,7a,8,11,11a,11b,12,13,13a,13b-octadecahydro-1H-cyclopenta[a]chrysen-9-yl)benzoic acid

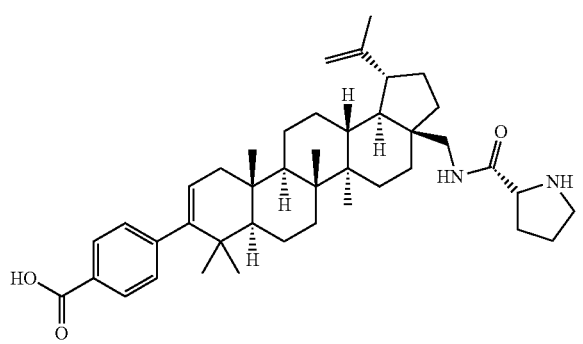

The title compound was prepared in 30% yield following the general procedure described above for the reversed amides preparation, using (R)-1-(tert-butoxycarbonyl)pyrrolidine-2-carboxylic acid as the reactant acid and acidic hydrolysis. MS: m/e 641.7 (MH$^+$), 1.78 min (method 2). $^1$H NMR (400 MHz, MeOD) δ ppm 0.94 (s, 3H) 0.96 (s, 3H) 1.03 (s, 3H) 1.05 (s, 3H) 1.17 (s, 3H) 1.71 (s, 3H) 0.88-2.10 (m, 24H) 2.15 (dd, 1H) 2.38-2.48 (m, 1H) 2.53 (td, J=11.23, 5.14 Hz, 1H) 3.18 (dd, J=12.92, 6.65 Hz, 1H) 3.31-3.33 (m, 1H) 3.38-3.49 (m, 1H) 3.53 (dd, J=12.92, 4.39 Hz, 1H) 4.23 (dd, J=7.78, 6.78 Hz, 1H) 4.60 (s, 1H) 4.73 (d, J=2.01 Hz, 1H) 5.30 (dd, J=6.27, 1.51 Hz, 1H) 7.22 (d, J=8.53 Hz, 2H) 7.91 (d, J=8.28 Hz, 2H) 8.13 (t, J=6.53 Hz, 1H).

Example 138

Preparation of 4-((1R,3aS,5aR,5bR,7aR,11aS,11bR, 13aR,13bR)-3a-(((S)-1-acetylpyrrolidine-2-carboxamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

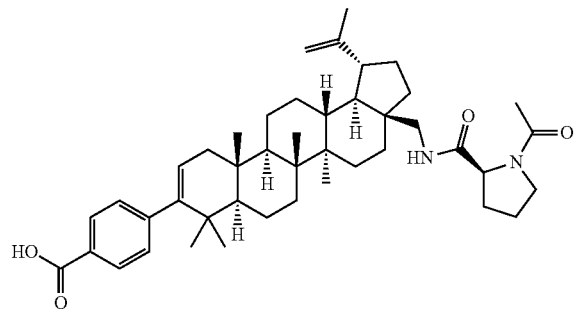

The title compound was prepared in 9% yield following the general procedure described above for the reversed amides preparation, using (S)-1-acetylpyrrolidine-2-carboxylic acid as the reactant acid and acidic hydrolysis. MS: m/e 683.6 (MH$^+$), 2.01 min (method 2). $^1$H NMR (400 MHz, MeOD) δ ppm 0.94 (s, 3H) 0.96 (s, 3H) 1.03 (s, 3H) 1.04 (s, 3H) 1.18 (s, 3H) 1.70 (s, 3H) 2.08 (s, 3H) 0.84-2.23 (m, 26H) 2.47-2.56 (m, 1H) 2.99 (dd, J=12.67, 4.89 Hz, 1H) 3.52-3.70 (m, 3H) 4.39 (dd, J=8.66, 3.89 Hz, 1H) 4.59 (s, 1H) 4.72 (d, J=2.26 Hz, 1H) 5.29 (dd, J=5.90, 1.63 Hz, 1H) 7.22 (d, J=8.53 Hz, 2H) 7.91 (d, J=8.53 Hz, 2H).

Example 139

Preparation of 4-((1R,3aS,5aR,5bR,7aR,11aS,11bR, 13aR,13bR)-5a,5b,8,8,11a-pentamethyl-3a-((2-(methylamino)acetamido)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

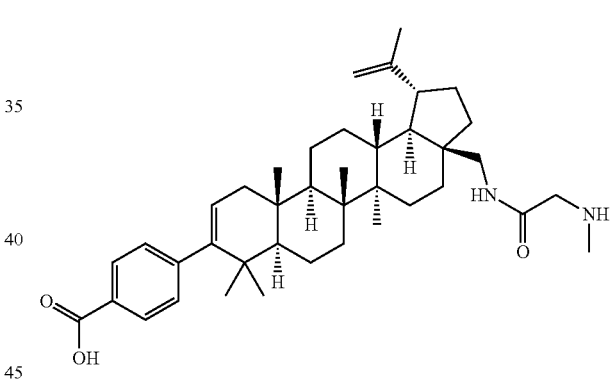

The title compound was prepared following the general procedures described above for the reversed amides preparation, using 2-(tert-butoxycarbonyl(methyl)amino)acetic acid as the reactant carboxylic acid and acidic hydrolysis. The product was isolated as a white solid (14 mg, 76%). LCMS: m/e 615.5 (MH$^+$), 2.68 min (method 3). $^1$H NMR (500 MHz, MeOD) δ ppm 7.94 (2H, d, J=8.5 Hz), 7.24 (2H, d, J=8.2 Hz), 5.23-5.37 (1H, m), 4.75 (1H, br. s.), 4.62 (1H, d, J=1.2 Hz), 3.81 (2H, s), 3.61 (1H, d, J=13.4 Hz), 3.11 (1H, d, J=13.4 Hz), 2.74 (3H, s), 2.45-2.64 (1H, m), 2.17 (1H, dd, J=17.2, 6.3 Hz), 2.02-2.12 (1H, m), 1.81-1.99 (2H, m), 1.65-1.81 (8H, m), 1.58 (2H, dd, J=9.3, 2.6 Hz), 1.45-1.54 (4H, m), 1.34-1.45 (2H, m), 1.30 (3H, s), 1.18 (3H, s), 1.09-1.16 (2H, m), 1.07 (3H, s), 1.05 (3H, s), 1.00 (3H, s), 0.97 (3H, s).

Example 140

Preparation of 4-((1R,3aS,5aR,5bR,7aR,11aS,11bR,13aR,13bR)-3a-(((S)-2-amino-3-(1H-imidazol-4-yl)propanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

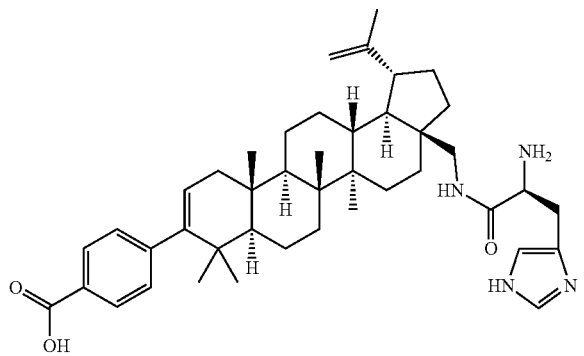

The title compound was prepared following the general procedures described above for the reversed amides preparation, using (S)-2-(tert-butoxycarbonylamino)-3-(1H-imidazol-4-yl) propanoic acid as the reactant carboxylic acid and acidic hydrolysis. The product was isolated as a white solid (11 mg, 64.2%). LCMS: m/e 681.5 (MH$^+$), 2.59 min (method 3). $^1$H NMR (400 MHz, MeOD) δ ppm 8.88 (d, J=1.3 Hz, 1H), 7.90 (d, J=8.6 Hz, 2H), 7.43 (s, 1H), 7.20 (d, J=8.3 Hz, 2H), 5.19-5.36 (m, 1H), 4.70 (s, 2H), 4.58 (s, 1H), 4.25 (t, J=7.1 Hz, 1H), 3.61 (d, J=13.3 Hz, 1H), 3.33-3.42 (m, 1H), 3.26-3.30 (m, 1H), 2.97 (d, J=13.8 Hz, 1H), 2.48 (d, J=5.3 Hz, 1H), 2.13 (dd, J=17.1, 6.0 Hz, 1H), 1.89-2.08 (m, 1H), 1.72-1.87 (m, 2H), 1.63-1.72 (m, 5H), 1.52-1.63 (m, 4H), 1.50 (d, J=7.3 Hz, 1H), 1.46 (d, J=13.6 Hz, 4H), 1.37 (br. s., 2H), 1.31 (d, J=3.3 Hz, 1H), 1.20-1.29 (m, 3H), 1.16 (s, 3H), 0.96-1.07 (m, 6H), 0.95 (s, 3H), 0.92 (s, 3H).

Example 141

Preparation of 4-((1R,3aS,5aR,5bR,7aR,11aS,11bR,13aR,13bR)-5a,5b,8,8,11a-pentamethyl-3a-((3-(piperazin-1-yl)propanamido)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

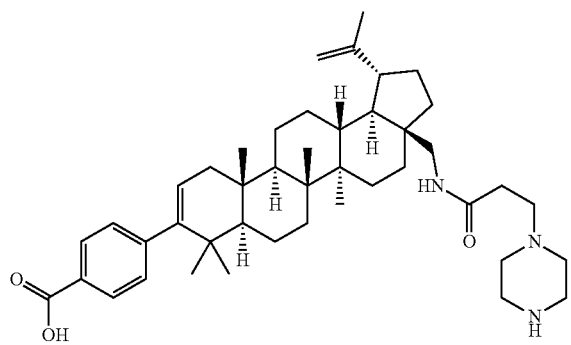

The title compound was prepared following the general procedures described above for the C28 reversed amide preparation and acidic hydrolysis using 3-(4-(tert-butoxycarbonyl)piperazin-1-yl) propanoic acid as the reactant carboxylic acid. The product was isolated as a white solid (17 mg, 77.0%). LCMS: m/e 684.6 (MH$^+$), 2.66 min (method 3). $^1$H NMR (400 MHz, MeOD) δ ppm 7.90 (d, J=8.3 Hz, 2H), 7.20 (d, J=8.3 Hz, 2H), 5.22-5.33 (m, 1H), 4.70 (s, 1H), 4.58 (s, 1H), 3.49-3.62 (m, 1H), 3.38-3.49 (m, 4H), 3.30-3.36 (m, 4H), 3.24-3.27 (m, 2H), 3.02 (d, J=13.6 Hz, 1H), 2.68 (t, J=6.7 Hz, 2H), 2.50 (td, J=11.1, 5.8 Hz, 1H), 2.13 (dd, J=17.1, 6.5 Hz, 1H), 2.05 (d, J=10.3 Hz, 1H), 1.86-1.96 (m, 1H), 1.76-1.86 (m, 1H), 1.60-1.76 (m, 7H), 1.55 (br. s., 2H), 1.45-1.52 (m, 4H), 1.30-1.42 (m, 2H), 1.18-1.30 (m, 4H), 1.14 (s, 3H), 1.06-1.12 (m, 2H), 1.03 (s, 3H), 1.02 (s, 3H), 0.95 (s, 3H), 0.93 (s, 3H).

Example 142

Preparation of 4-((1R,3aS,5aR,5bR,7aR,11aS,11bR,13aR,13bR)-3a-((3-(dimethylamino)propanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

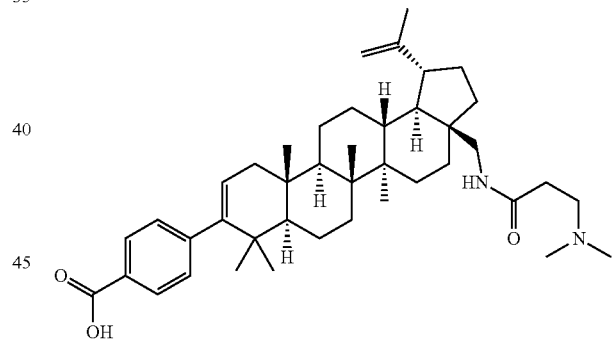

The title compound was prepared following the general procedures described above for the reversed amides preparation, using 3-(dimethylamino)propanoic acid as the reactant carboxylic acid and acidic hydrolysis. The product was isolated as a white solid (12 mg, 24.8%). LCMS: m/e 643.5 (MH$^+$), 2.34 min (method 3). $^1$H NMR (400 MHz, MeOD) δ ppm 7.80-7.99 (m, 2H), 7.20 (d, J=8.3 Hz, 2H), 5.22-5.35 (m, 1H), 4.70 (s, 1H), 4.58 (s, 1H), 3.55 (d, J=13.6 Hz, 1H), 3.37 (t, J=6.5 Hz, 2H), 2.95-3.11 (m, 1H), 2.86 (s, 6H), 2.68-2.81 (m, 2H), 2.50 (td, J=11.1, 5.3 Hz, 1H), 1.99-2.21 (m, 2H), 1.76-1.99 (m, 2H), 1.60-1.76 (m, 7H), 1.54 (d, J=6.8 Hz, 2H), 1.42-1.52 (m, 4H), 1.31-1.42 (m, 2H), 1.20-1.31 (m, 3H), 1.11-1.20 (m, 4H), 1.06-1.11 (m, 2H), 1.03 (s, 3H), 1.01 (s, 3H), 0.95 (s, 3H), 0.93 (s, 3H).

Example 143

Preparation of 3-(((1R,3aS,5aR,5bR,7aR,11aS,11bR, 13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylcarbamoyl)benzoic acid

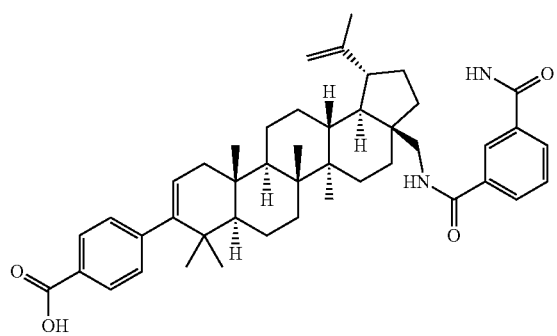

The title compound was prepared following the general procedures described above for the reversed amides preparation using 3-(methoxycarbonyl)benzoic acid as the reactant carboxylic acid and basic hydrolysis. The product was isolated as a white solid (22 mg, 46.0%). LCMS: m/e 692.4 (MH+), 2.68 min (method 3). $^1$H NMR (400 MHz, CHLOROFORM-d) δ ppm 8.43 (s, 1H), 8.27 (d, J=7.6 Hz, 1H), 8.12 (d, J=7.8 Hz, 1H), 8.02 (d, J=8.3 Hz, 2H), 7.62 (t, J=7.8 Hz, 1H), 7.24-7.33 (m, 2H), 6.06-6.25 (m, 1H), 5.26-5.41 (m, 1H), 4.77 (d, J=1.5 Hz, 1H), 4.65 (s, 1H), 4.00 (s, 3H), 3.73-3.88 (m, 1H), 3.28-3.41 (m, 1H), 2.55-2.65 (m, 1H), 2.04-2.25 (m, 2H), 1.83-2.03 (m, 2H), 1.64-1.82 (m, 6H), 1.61 (s, 2H), 1.51 (br. s., 4H), 1.32-1.48 (m, 3H), 1.23-1.32 (m, 2H), 1.19 (s, 3H), 1.12 (br. s., 1H), 1.06 (s, 3H), 1.02 (s, 3H), 0.97 (s, 3H), 0.96 (s, 3H).

Example 144

Preparation of 4-((1R,3aS,5aR,5bR,7aR,11aS,11bR, 13aR,13bR)-5a,5b,8,8,11a-pentamethyl-1-(prop-1-en-2-yl)-3a((4-sulfamoylbenzamido)methyl)-2,3,3a, 4,5,5a,5b,6,7,7a,8,11,11a,11b,12,13,13a,13b-octadecahydro-1H-cyclopenta[a]chrysen-9-yl)benzoic acid

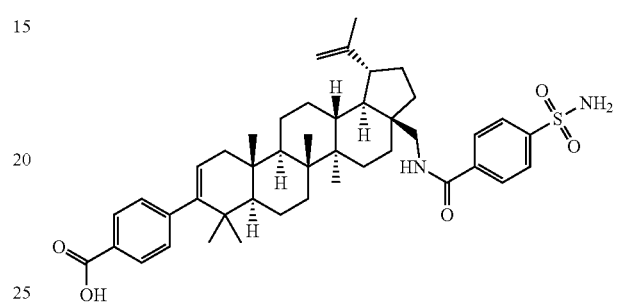

The title compound was prepared following the general procedures described above for the reversed amides preparation using 4-sulfamoylbenzoic acid as the reactant carboxylic acid and basic hydrolysis. The product was isolated as a white solid (35 mg, 53.6%). LCMS: did not match desired product (method 3). $^1$H NMR (400 MHz, MeOD) δ ppm 7.82-7.97 (m, 6H), 7.09-7.28 (m, 2H), 5.29 (d, J=4.5 Hz, 1H), 4.73 (d, J=1.8 Hz, 1H), 4.60 (s, 1H), 3.70-3.81 (m, 1H), 3.12-3.26 (m, 1H), 2.58 (td, J=11.1, 5.7 Hz, 1H), 2.14 (dd, J=17.2, 6.4 Hz, 2H), 1.85-2.00 (m, 1H), 1.61-1.85 (m, 8H), 1.34-1.59 (m, 8H), 1.23-1.33 (m, 3H), 1.21 (s, 3H), 1.07-1.19 (m, 3H), 1.05 (s, 3H), 1.03 (s, 3H), 0.95 (s, 3H), 0.93 (s, 3H).

Example 145

Preparation of 4-((1R,3aS,5aR,5bR,7aR,11aS,11bR, 13aR,13bR)-3a-((((1,1-dioxido-4-thiomorpholinyl) acetyl)amino)methyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)benzoic acid

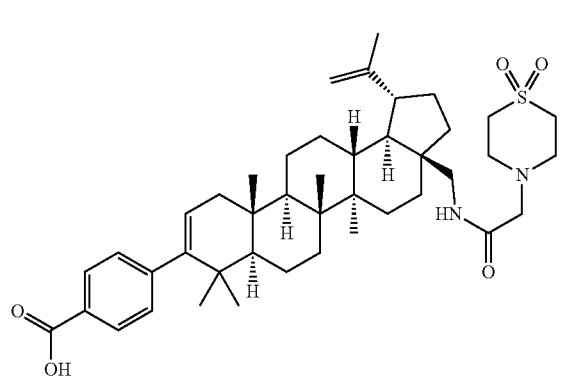

The title compound was prepared following the general procedures described above for the reversed amide preparation, using 4-thiomorpholineacetic acid 1,1-dioxide as the reactant carboxylic acid and basic hydrolysis. The product was isolated as a white solid (14 mg, 35.8%). LCMS: m/e 719.3 (MH⁺), 2.40 min (method 3). ¹H NMR (500 MHz, MeOD) δ ppm 7.86-8.01 (m, 2H), 7.24 (d, J=8.2 Hz, 2H), 5.32 (d, J=6.4 Hz, 1H), 4.75 (s, 1H), 4.63 (s, 1H), 3.58-3.71 (m, 3H), 3.42 (d, J=4.3 Hz, 4H), 3.33-3.38 (m, 4H), 3.04-3.15 (m, 1H), 2.55 (td, J=11.1, 5.6 Hz, 1H), 2.13-2.23 (m, 2H), 1.92-2.04 (m, 1H), 1.81-1.92 (m, 1H), 1.64-1.81 (m, 8H), 1.46-1.64 (m, 6H), 1.35-1.46 (m, 2H), 1.24-1.35 (m, 2H), 1.20 (s, 3H), 1.14-1.19 (m, 1H), 1.11 (d, J=10.4 Hz, 2H), 1.07 (s, 3H), 1.05 (s, 3H), 0.99 (s, 3H), 0.97 (s, 3H).

Example 146

Preparation of 4-((1R,3aS,5aR,5bR,7aR,11aS,11bR,13aR,13bR)-3a-(((3-(1,1-dioxido-4-thiomorpholinyl)propanoyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

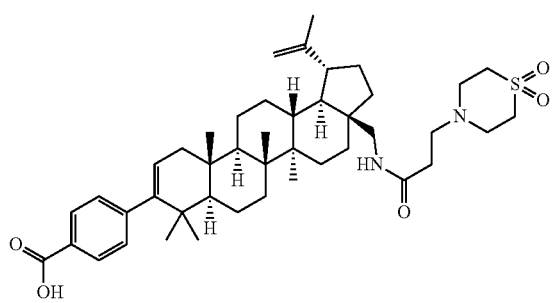

The title compound was prepared following the general procedures described above for the reversed amides preparation, using 3-(1,1-dioxo-λ16,4-thiazinan-4-yl) propanoic acid as the reactant carboxylic acid and basic hydrolysis. The product was isolated as a white solid (14 mg, 35.8%). LCMS: m/e 733.3 (MH⁺), 2.33 min (method 3). ¹H NMR (500 MHz, MeOD) δ ppm 7.94 (d, J=8.2 Hz, 2H), 7.24 (d, J=8.2 Hz, 2H), 5.32 (d, J=4.9 Hz, 1H), 4.74 (d, J=1.5 Hz, 1H), 4.62 (s, 1H), 3.77 (br. s., 1H), 3.76 (d, J=6.1 Hz, 3H), 3.58 (d, J=13.4 Hz, 1H), 3.50-3.54 (m, 4H), 3.48 (t, J=6.7 Hz, 2H), 3.07 (d, J=13.7 Hz, 1H), 2.77 (t, J=6.7 Hz, 2H), 2.53 (td, J=11.2, 5.6 Hz, 1H), 2.17 (dd, J=17.2, 6.3 Hz, 1H), 2.03-2.13 (m, 1H), 1.93 (td, J=13.6, 4.0 Hz, 1H), 1.85 (td, J=12.2, 3.4 Hz, 1H), 1.64-1.81 (m, 8H), 1.46-1.64 (m, 6H), 1.34-1.46 (m, 2H), 1.22-1.34 (m, 3H), 1.19 (s, 3H), 1.10-1.12 (m, 2H), 1.07 (s, 3H), 1.05 (s, 3H), 0.99 (s, 3H), 0.97 (s, 3H).

Example 147

Preparation of 4-((1R,3aS,5aR,5bR,7aR,11aS,11bR,13aR,13bR)-3a-((((1,1-dioxido-1,2-thiazinan-2-yl)acetyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

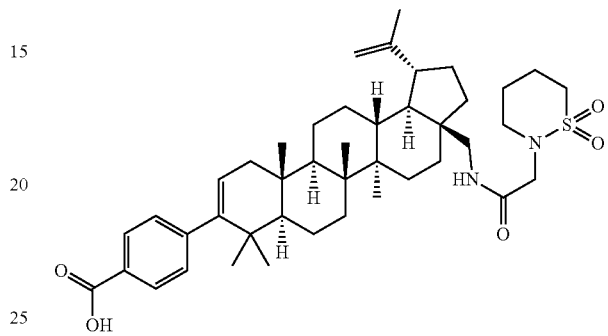

The title compound was prepared following the general procedures described above for the C28 reversed amide preparation using (1,2-dioxo-1,6-[1,2]thiazinan-2-yl)acetic acid as the reactant carboxylic acid and basic hydrolysis. The product was isolated as a white solid (30 mg, 34.8%). LCMS: m/e 719.6 (MH⁺), 2.99 min (method 3). ¹H NMR (400 MHz, CHLOROFORM-d) δ ppm 7.98 (m, J=8.3 Hz, 2H), 7.23 (m, J=8.3 Hz, 2H), 6.60 (t, J=6.0 Hz, 1H), 5.25-5.34 (m, 1H), 4.73 (d, J=2.0 Hz, 1H), 4.62 (s, 1H), 3.85-3.95 (m, 2H), 3.51-3.61 (m, 1H), 3.37-3.51 (m, 2H), 3.06-3.20 (m, 3H), 2.51 (td, J=11.1, 5.6 Hz, 1H), 2.19-2.33 (m, 2H), 2.07-2.18 (m, 1H), 2.04 (d, J=8.8 Hz, 1H), 1.89 (br. s., 4H), 1.81 (td, J=11.8, 4.0 Hz, 2H), 1.60-1.75 (m, 8H), 1.50-1.60 (m, 2H), 1.37-1.50 (m, 4H), 1.16-1.37 (m, 4H), 1.05-1.16 (m, 4H), 1.02 (s, 3H), 1.00 (s, 3H), 0.91-0.97 (m, 6H).

Example 148

Preparation of 4-((1R,3aS,5aR,5bR,7aR,11aS,11bR,13aR,13bR)-3a-((2-(dimethylamino)acetamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

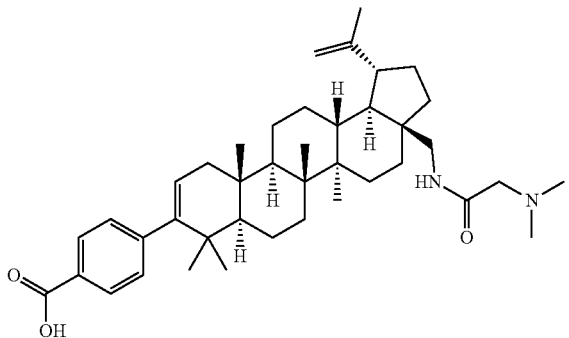

To a solution of 4-((1R,3aS,5aR,5bR,7aR,11aS,11bR, 13aR,13bR)-5a,5b,8,8,11a-pentamethyl-3a-((2-(methylamino)acetamido)methyl)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoic acid, example 139, (10 mg, 0.016 mmol) and formaldehyde (0.488 mg, 0.016 mmol) in MeOH (1 ml) was added acetic acid (1.860 mL, 0.033 mmol) and sodium cyanoborohydride (1.022 mg, 0.016 mmol). A clear solution was formed soon after mixing. The mixture was stirred at rt for 2 h, LC/MS showed the mass of the expected product. The mixture was diluted with 7 ml of sat. NaHCO₃ and was extracted with dichloromethane (3×7 ml). The combined organic layers were dried with Na₂SO₄. The drying agent was removed by filtration and the filtrate was concentrated under reduced pressure to afford the title compound as a white solid (2 mg, 18.6%). LCMS: m/e 629.4 (MH⁺), 2.72 min (method 3). ¹H NMR (400 MHz, MeOD) δ ppm 7.90 (d, J=8.6 Hz, 2H), 7.20 (d, J=8.3 Hz, 2H), 5.19-5.42 (m, 1H), 4.72 (d, J=1.8 Hz, 1H), 4.59 (s, 1H), 3.93 (s, 2H), 3.58 (br. s., 1H), 3.04-3.17 (m, 1H), 2.89 (s, 6H), 2.46-2.60 (m, 1H), 2.10-2.18 (m, 2H), 1.80 (br. s., 2H), 1.65-1.77 (m, 7H), 1.63 (s, 1H), 1.58 (br. s., 2H), 1.38-1.55 (m, 4H), 1.19-1.34 (m, 4H), 1.13-1.19 (m, 4H), 1.06-1.13 (m, 2H), 1.04 (s, 3H), 1.02 (s, 3H), 0.95 (s, 3H), 0.93 (s, 3H).

Example 149

Preparation of 4-((1R,3aS,5aR,5bR,7aR,11aS,11bR, 13aR,13bR)-3a-((dimethylamino)methyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoic acid

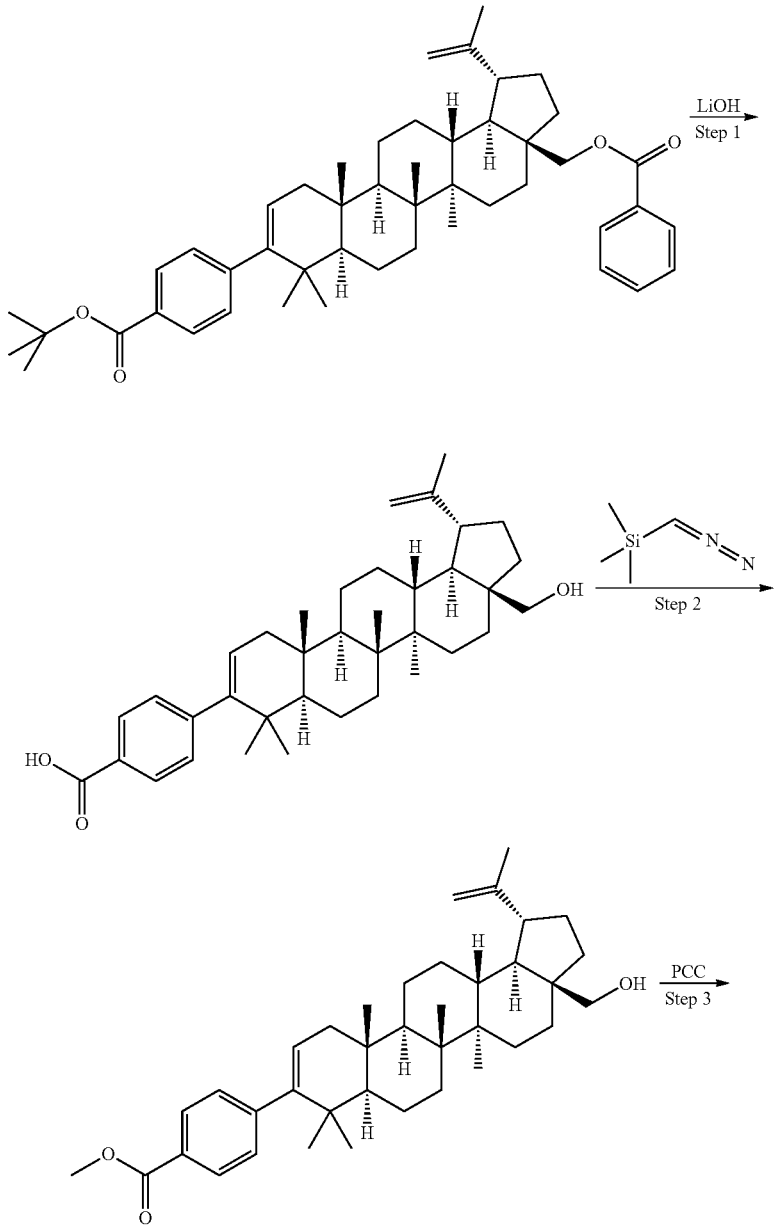

-continued
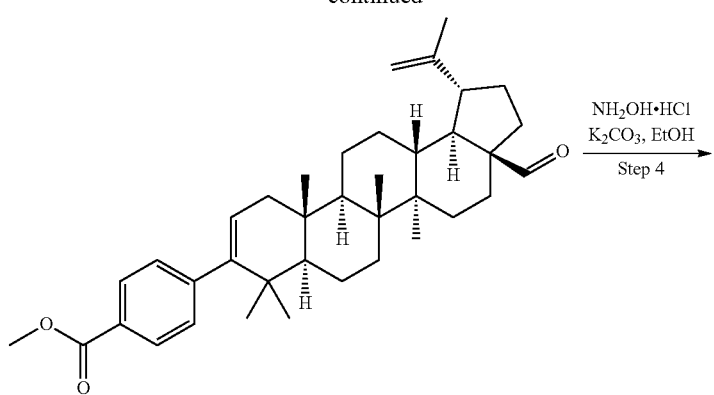
NH$_2$OH·HCl
K$_2$CO$_3$, EtOH
Step 4
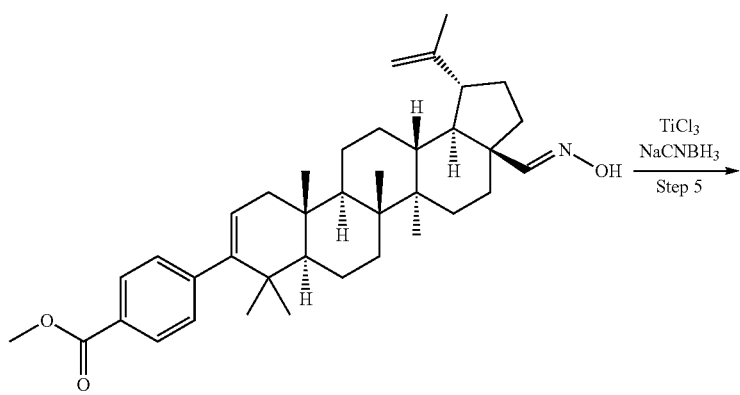
TiCl$_3$
NaCNBH$_3$
Step 5
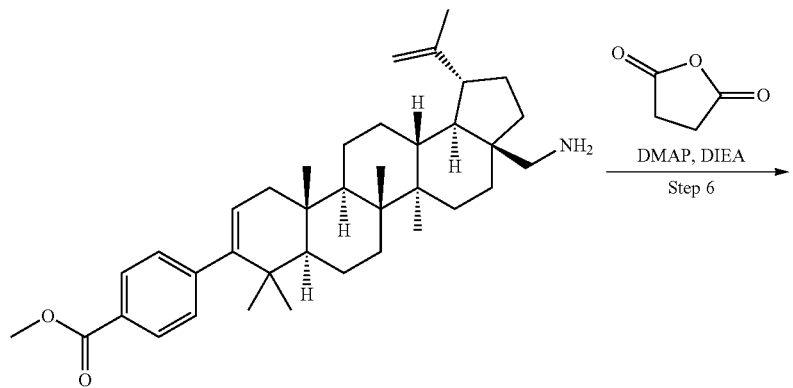
DMAP, DIEA
Step 6
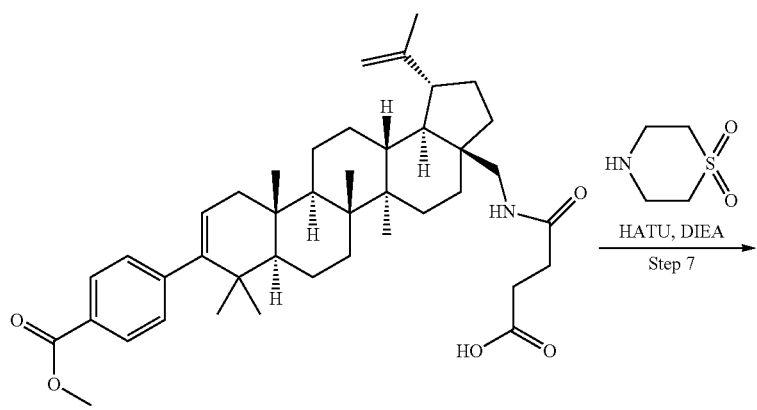
HATU, DIEA
Step 7

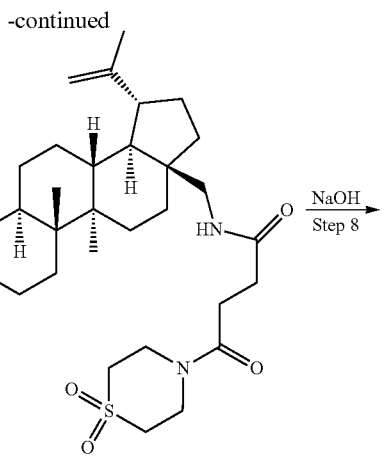

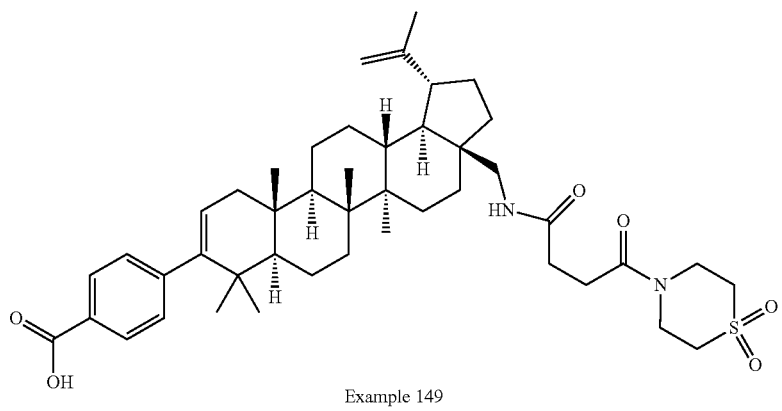

Example 149

Step 1. Ester Hydrolysis

To a solution of tert-butyl 4-((1R,3aS,5aR,5bR,7aR,11aS,11bR,13aR,13bR)-3a-(benzoyloxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (7.2 g, 10.21 mmol) in 1,4-dioxane (75 ml) and water (25 ml) was added lithium hydroxide (1.285 g, 30.6 mmol) and the mixture was stirred at 75° C. Dioxane (50 ml) was added to dissolve all solids and the stirring was continued for 24 h. The solvent was removed and the residue was redissolved into $CH_2Cl_2$, the insoluble white solid was collected to afford 4-((1R,3aS,5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (2.2 g, 39.5%) LCMS: m/e 545.4 (MH+), 2.68 min (method 2).

Step 2. Methyl Ester Formation

To a solution of 4-((1R,3aS,5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (4.23 g, 10 mmol) in a mixture of $CH_2Cl_2$ (50 ml) and MeOH (5 ml) was added (trimethylsilyl)diazomethane (5.00 ml, 10.00 mmol). The solution was stirred at rt for 2 h under nitrogen. LC/MS showed no SM left. The reaction mixture was concentrated to afford methyl 4-((1R,3aS,5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (4.37 g, 100%). The compound was used in the next step without further purification. LCMS: m/e 559.4 (MH+), 3.29 min (method 2). $^1$H NMR (400 MHz, CHLOROFORM-d) δ ppm 7.95 (m, J=8.3 Hz, 2H), 7.22 (m, J=8.6 Hz, 2H), 5.22-5.39 (m, 1H), 4.72 (d, J=2.0 Hz, 1H), 4.49-4.67 (m, 1H), 3.94 (s, 3H), 3.87 (s, 1H), 3.38 (d, J=10.6 Hz, 1H), 2.37-2.60 (m, 1H), 2.05-2.21 (m, 1H), 1.96 (d, J=11.1 Hz, 2H), 1.90 (d, J=13.1 Hz, 1H), 1.61-1.82 (m, 7H), 1.55 (br. s., 8H), 1.37-1.52 (m, 2H), 1.18-1.37 (m, 4H), 1.08-1.18 (m, 3H), 1.04 (s, 3H), 1.00 (s, 3H), 0.95 (s, 6H).

Step 3. Oxidation of C28 alcohol to aldehyde

To a solution of methyl 4-((1R,3aS,5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (1 g, 1.789 mmol) in CH$_2$Cl$_2$ (70 ml) was added PCC (1.157 g, 5.37 mmol). The resulting dark brown mixture was stirred at rt for 4 h. TLC analysis showed the reaction was complete. The mixture was filtered through a short bed of Celite and silica gel, washed with excess of CH$_2$Cl$_2$. The filtrate was concentrated in vacuo. The crude mixture was purified by Biotage on normal phase silica gel. The fractions containing the expected product were combined and concentrated in vacuo to afford methyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as a solid (0.8 g). LCMS: m/e 557.2 (MH$^+$), 3.67 min (method 2).

Step 4. Oxime Formation

To a suspension of methyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (800 mg, 1.437 mmol) in ethanol (60 ml) was added hydroxylamine hydrochloride (1298 mg, 18.68 mmol)) and potassium carbonate (2581 mg, 18.68 mmol). The resulting mixture was stirred at rt for 12 h.

The reaction mixture was diluted with 17 ml of sat. NaHCO$_3$ solution and was extracted with dichloromethane (3×20 ml). The combined organic layers were dried over Na$_2$SO$_4$. The drying agent was removed by filtration and the filtrate was concentrated under reduced pressure. The crude product was used in the next step with no additional purification. LCMS: m/e 572.3 (MH$^+$), 3.26 min (method 2).

Step 5. Oxime Reduction

To the solution of methyl 4-((1R,3aS,5aR,5bR,7aR,11aS,11bR,13aR,13bR)-3a-((hydroxyimino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (800 mg, 1.399 mmol), in ethanol (40 ml) was added excess of ammonium acetate (1078 mg, 13.99 mmol) and sodium cyanoborohydride (879 mg, 13.99 mmol). The mixture was stirred in an ice bath until cold. To this suspension was added an aqueous solution of titanium(III) chloride (Aldrich Chemicals, 20% solution used as supplied, 10 ml, 1.963 mmol). The resulting mixture was blanketed with nitrogen, ice bath was removed and stirring continued at rt for an hour. LCMS showed the reaction was complete. At this point, the mixture was dark greenish-blue. A solution of sodium hydroxide, (3 ml, 10N) in 25 ml water was added into the reaction mixture, along with 30 ml of methylene chloride. The mixture was stirred vigorously until the dark blue phase was floating on top of the organic phase. The mixture was filtered through a plug of paper cellulose, the filtrate was clear. The organic layer was collected and the aqueous layer was extracted with CH$_2$Cl$_2$ (2×20 ml). The combined organic phase was dried over Na$_2$SO$_4$. The solvent was removed in vacuo to afford methyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as an off-white solid (~800 mg). The crude material was used in the next step without further purification. LCMS: m/e 558.5 (MH$^+$), 2.53 min (method 2).

Step 6. Acylation of Amine

To a solution of methyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.054 mmol) in DCM (2 ml) was added dihydrofuran-2,5-dione (16.15 mg, 0.161 mmol) followed by DMAP (6.57 mg, 0.054 mmol) and DIPEA (9.39 µl, 0.054 mmol). The mixture was stirred at rt for 18 hours. The solvent was removed in vacuo and the resulting residue containing 4-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)-4-oxobutanoic acid was used in next step without further purification. LCMS: m/e 658.5 (MH$^+$), 3.27 min (method 3).

Step 7. Amide Coupling

To a solution of 4-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methylamino)-4-oxobutanoic acid (35.4 mg, 0.054 mmol) in DCM (3 ml) at 0° C. was added thiomorpholine-1,1-dioxide (7.27 mg, 0.054 mmol), HATU (40.9 mg, 0.108 mmol) followed by N-ethyl-N-isopropylpropan-2-amine (20.86 mg, 0.161 mmol). The resulting solution was stirred at rt for 18 h. Solvent was removed in vacuo, the resulting solid was used in the next step without further purification. LCMS: m/e 775.5 (MH$^+$), 2.95 min (method 3).

Step 8. Saponification of Benzoate Ester

To a solution of the material from Step 7 (40 mg, 52 mmol) in dioxane (1.5 ml) was added sodium hydroxide (0.5 ml, 1 N, 500 mmol). The resulting solution was stirred at 63° C. for 12 h. The solvent was removed in vacuo and the resulting residue was purified by prep. HPLC. The product was isolated as a white solid (26 mg, 62.9%). LCMS: m/e 761.6 (MH$^+$), 2.57 min (method 3). $^1$H NMR (400 MHz, MeOD) δ ppm 7.94 (m, J=8.3 Hz, 2H), 7.24 (m, J=8.5 Hz, 2H), 5.25-5.38 (m, 1H), 4.74 (d, J=2.0 Hz, 1H), 4.62 (s, 1H), 3.98-4.12 (m, 4H), 3.56 (s, 1H), 3.28 (br. s., 2H), 3.07-3.22 (m, 2H), 3.01 (d, J=13.6 Hz, 1H), 2.69-2.83 (m, 2H), 2.46-2.65 (m, 3H), 2.17 (dd, J=17.2, 6.4 Hz, 2H), 1.84 (d, J=12.5 Hz, 2H), 1.64-1.81 (m, 8H), 1.45-1.64 (m, 6H), 1.39 (br. s., 2H), 1.22-1.33 (m, 4H), 1.12-1.22 (m, 4H), 1.06 (d, J=3.5 Hz, 6H), 0.87-1.04 (m, 6H).

Example 150
Preparation of 4-(((1R,3aS,5aR,5bR,7aR,11aS,11bR,13aR,13bR)-5a,5b,8,8,11a-pentamethyl-3a-(((S)-1-methylpyrrolidine-2-carboxamido)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
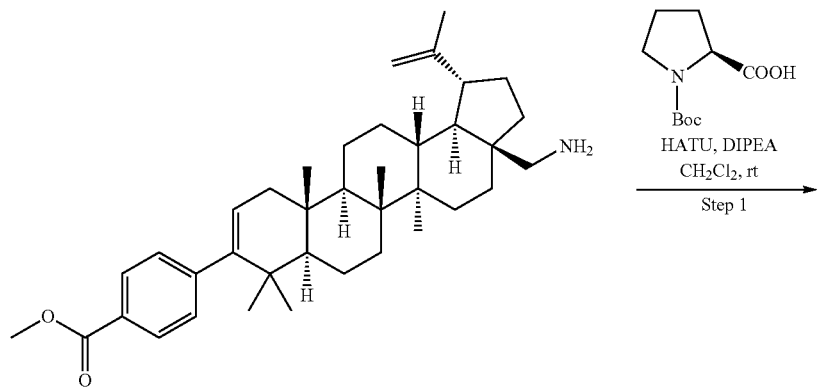
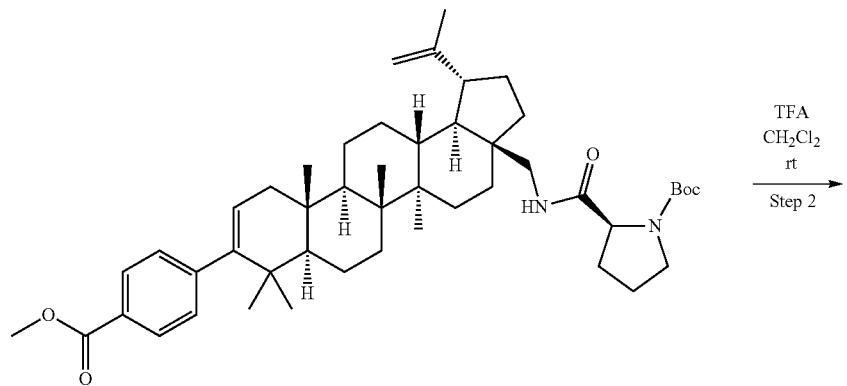
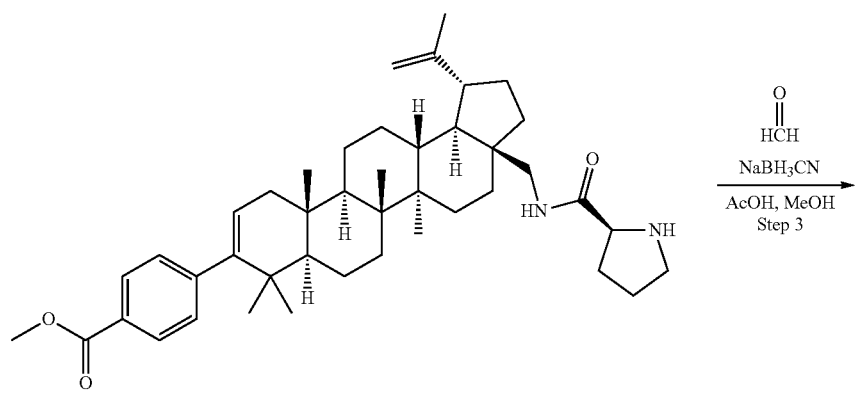

-continued

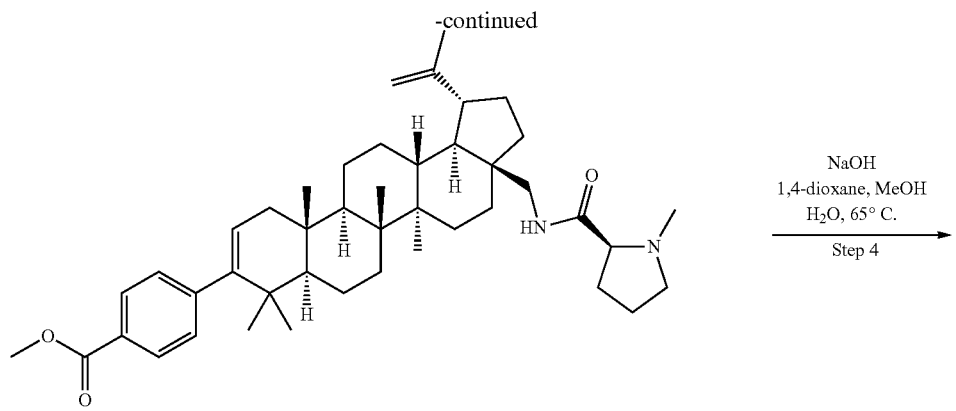

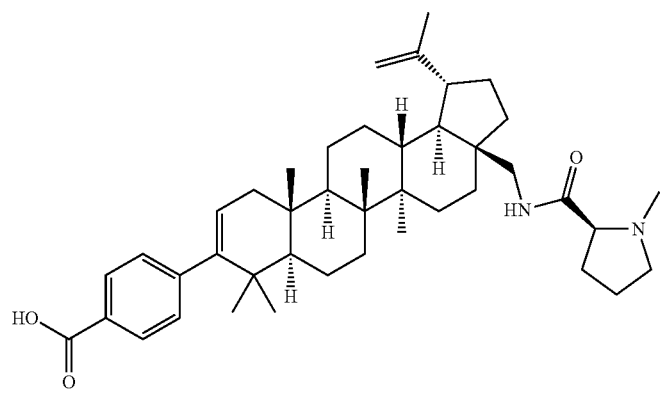

Example 150

Step 1: Preparation of the C28 Amide

To a mixture of methyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (25 mg, 0.045 mmol), (S)-1-(tert-butoxycarbonyl)pyrrolidine-2-carboxylic acid (11.58 mg, 0.054 mmol) in DCM (1 ml) was added DIPEA (29 mg, 0.224 mmol) followed by HATU (25.6 mg, 0.067 mmol). The resulting solution was stirred at rt for 1 h. The reaction mixture was concentrated in vacuo to give crude product without further purification. MS: m/e 755.7 (MH$^+$), 2.84 min (method 2).

Step 2: Deprotection of the Amine

To a solution of crude material from Step 1 in DCM (2 ml) was added TFA (0.3 ml, 3.89 mmol). The mixture was stirred at rt for 2 h. The mixture was concentrated in vacuo to give crude product which was used in the next step without further purification. MS: m/e 655.6 (MH$^+$), 1.96 min (method 2).

Step 3: Alkylation of the Amine

To a solution of crude material from Step 2 in methanol (2 ml) was added formaldehyde (37% in H$_2$O) (6.9 mg, 0.086 mmol) and acetic acid (4.9 µl, 0.086 mmol). The resulting mixture was stirred at rt for 30 min. Sodium cyanoborohydride (5.4 mg, 0.086 mmol) was added and the mixture was stirred at rt for 3 h. The reaction mixture was concentrated in vacuo to give crude product without further purification. MS: m/e 669.7 (MH$^+$), 1.97 min (method 2).

Step 4: Preparation of the Benzoic Acid

To a solution of crude material from Step 3 in 1,4-dioxane (1 ml) and methanol (0.5 ml) was added 1N sodium hydroxide (0.5 ml). The resulting solution was stirred at 65° C. for 2 h. The crude product was purified by prep. HPLC (YMC Combiprep ODS 30×50 mm S5) (MeOH/H$_2$O/TFA) to give 4-((1R,3aS,5aR,5bR,7aR,11aS,11bR,13aR,13bR)-5a,5b,8,8,11a-pentamethyl-3a-(((S)-1-methylpyrrolidine-2-carboxamido)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid as a solid (13 mg, 44%, 4 steps). MS: m/e 655.7 (MH$^+$), 1.73 min (method 2). $^1$H NMR (400 MHz, MeOD) δ ppm 0.94 (s, 3H) 0.96 (s, 3H) 1.03 (s, 3H) 1.04 (s, 3H) 1.18 (s, 3H) 1.71 (s, 3H) 0.86-2.25 (m, 24H) 2.14 (dd, J=17.19, 6.40 Hz, 1H) 2.47-2.63 (m, 2H) 2.91 (s, 3H) 3.03 (dd, J=13.55, 4.77 Hz, 1H) 3.20 (dt, J=11.23, 8.44 Hz, 1H) 3.66-3.76 (m, 2H) 4.04 (t, J=8.16 Hz, 1H) 4.61 (s, 1H)

4.73 (d, J=2.01 Hz, 1H) 5.29 (dd, J=6.15, 1.63 Hz, 1H) 7.21 (d, J=8.53 Hz, 2H) 7.91 (d, J=8.53 Hz, 2H) 8.23 (t, J=6.15 Hz, 1H).

Example 151

Preparation of 4-((1R,3aS,5aR,5bR,7aR,11aS,11bR, 13aR,13bR)-5a,5b,8,8,11a-pentamethyl-3a-(((R)-1-methylpyrrolidine-2-carboxamido)methyl)-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

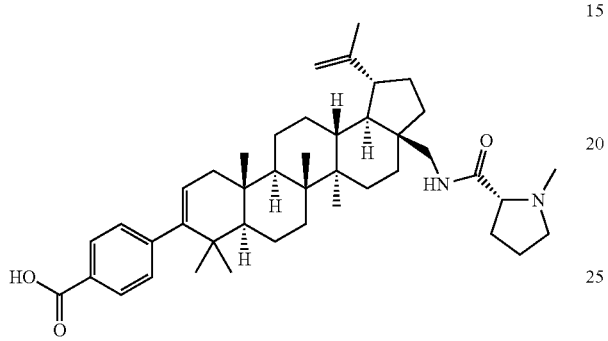

Example 152

Preparation of 4-((1R,3aS,5aR,5bR,7aR,11aS,11bR, 13aR,13bR)-3a-((3-(2-(dimethylamino)ethylamino)-2,2-difluoro-3-oxopropanamido)methyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid The title compound was prepared in 37% yield following the procedure described above in the preparation of 4-((1R, 3aS,5aR,5bR,7aR,11aS,11bR,13aR,13bR)-5a,5b,8,8,11a-pentamethyl-3a-(((S)-1-methylpyrrolidine-2-carboxamido) methyl)-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoic acid, example 150, using (R)-1-methylpyrrolidine-2-carboxylic acid as the reactant acid. MS: m/e 655.7 (MH$^+$), 1.73 min (method 2). $^1$H NMR (400 MHz, MeOD) δ ppm 0.94 (s, 3H) 0.96 (s, 3H) 1.03 (s, 3H) 1.05 (s, 3H) 1.17 (s, 3H) 1.71 (s, 3H) 0.85-2.25 (m, 24H) 2.14 (dd, J=17.07, 6.27 Hz, 1H) 2.48-2.62 (m, 2H) 2.90 (s, 3H) 3.15-3.25 (m, 2H) 3.50-3.57 (m, 1H) 3.67-3.76 (m, 1H) 4.04 (t, J=8.16 Hz, 1H) 4.61 (s, 1H) 4.73 (d, J=2.01 Hz, 1H) 5.29 (dd, J=6.15, 1.63 Hz, 1H) 7.21 (d, J=8.28 Hz, 2H) 7.91 (d, J=8.28 Hz, 2H) 8.24 (t, J=5.90 Hz, 1H).

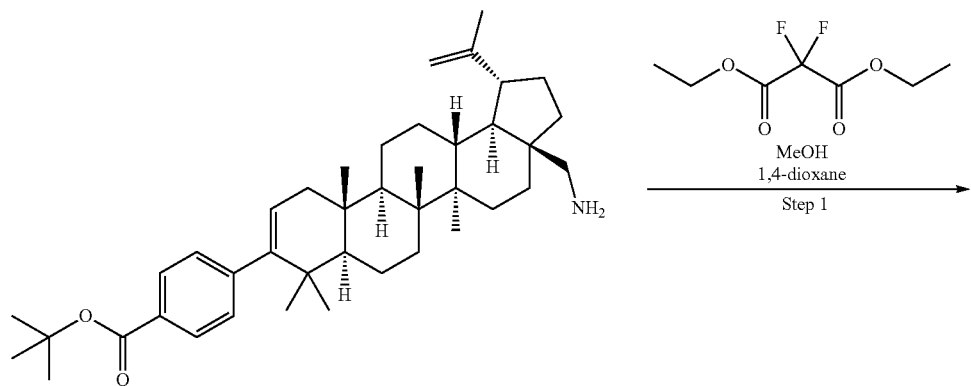

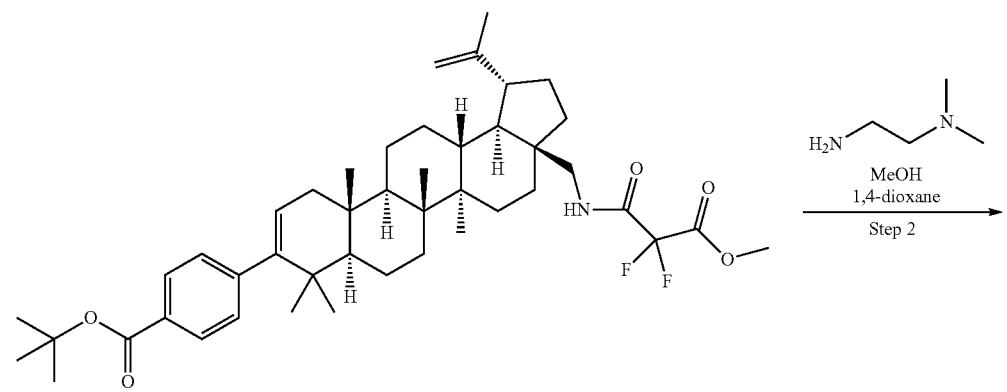

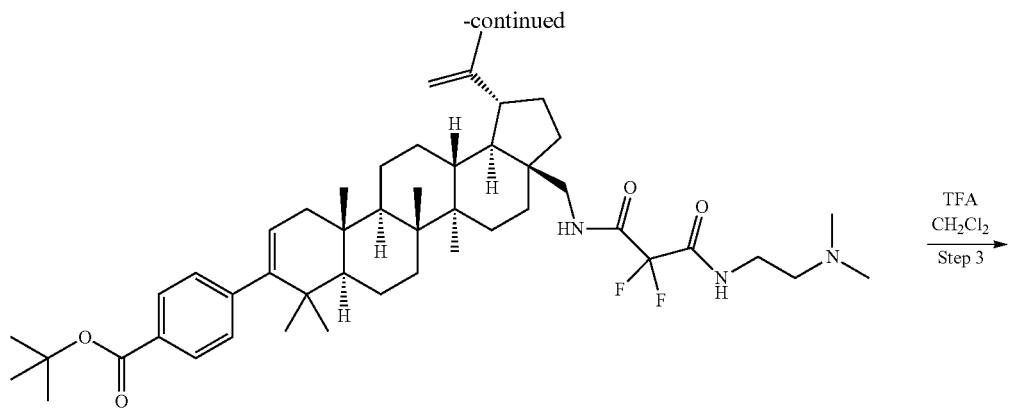

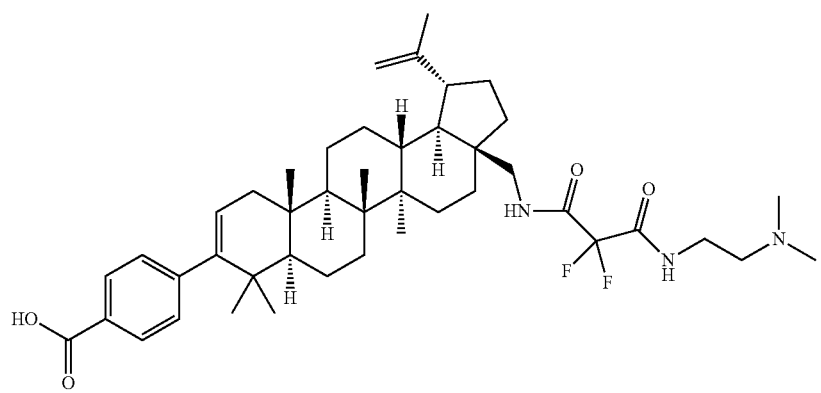

Example 152

Step 1: Preparation of the C28 Reversed Amide

To a solution of tert-butyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (200 mg, 0.333 mmol) in methanol (5 ml) and 1,4-dioxane (5 ml) was added diethyl 2,2-difluoromalonate (654 mg, 3.33 mmol). The resulting solution was stirred at rt for 6 days. The reaction mixture was concentrated in vacuo. The crude product was purified by Biotage (Thomson 25 g silica gel column; 4:1 Hex/EtOAc) to give 116 mg (47%) of product. MS: m/e 736.6 (MH+), 2.86 min (method 2). $^1$H NMR (400 MHz, CHLOROFORM-d) δ ppm 0.93 (s, 6H) 0.99 (s, 3H) 1.02 (s, 3H) 1.13 (s, 3H) 1.60 (s, 9H) 1.71 (s, 3H) 0.85-1.83 (20H) 1.98-2.10 (m, 1H) 2.10 (dd, J=17.07, 6.27 Hz, 1H) 2.49 (td, J=11.04, 5.27 Hz, 1H) 3.16 (dd, J=13.55, 6.27 Hz, 1H) 3.65 (dd, J=14.43, 7.15 Hz, 1H) 3.95 (s, 3H) 4.61-4.65 (m, 1H) 4.73 (d, J=1.76 Hz, 1H) 5.28 (dd, J=6.15, 1.63 Hz, 1H) 6.28 (t, J=7.03 Hz, 1H) 7.18 (d, J=8.53 Hz, 2H) 7.89 (d, J=8.28 Hz, 2H). $^{19}$F NMR (376 MHz, CHLOROFORM-d) δ ppm −112.49 (s, 2 F).

Step 2: Preparation of the Amide End Cap

To a solution of the amide from Step 1 (30 mg, 0.041 mmol) in methanol (1 ml) and 1,4-dioxane (1 ml) was added N1,N1-dimethylethane-1,2-diamine (17.97 mg, 0.204 mmol). The resulting solution was stirred at rt for 3 days. The reaction mixture was concentrated in vacuo to give crude product without further purification. MS: m/e 792.7 (MH+), 2.06 min (method 2).

Step 3: Preparation of the benzoic acid

To a solution of crude material from Step 2 (20 mg, 0.025 mmol) in DCM (5 ml) was added TFA (0.5 ml, 6.49 mmol). The mixture was stirred at rt for 2 h. The mixture was concentrated in vacuo and the crude product was purified by prep. HPLC (YMC Combiprep ODS 30×50 mm S5, MeOH/H$_2$O/TFA) to afford 4-((1R,3aS,5aR,5bR,7aR,11aS,11bR,13aR,13bR)-3a-((3-(2-(dimethylamino)ethylamino)-2,2-difluoro-3-oxopropanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (18 mg, 96%). MS: m/e 736.6 (MH+), 1.79 min (Method 2). $^1$H NMR (400 MHz, MeOD) δ ppm 0.94 (s, 3H) 0.96 (s, 3H) 1.03 (s, 3H) 1.05 (s, 3H) 1.18 (s, 3H) 1.71 (s, 3H) 0.84-1.88 (m, 20H) 1.97-2.20 (m, 2H) 2.15 (dd, J=17.44, 6.65 Hz, 1H) 2.53 (td, J=10.98, 5.40 Hz, 1H) 2.96 (s, 6H) 3.09 (d, J=13.05 Hz, 1H) 3.32-3.36 (m, 1H) 3.61-3.71 (m, 3H) 4.59-4.62 (m, 1H) 4.73 (d, J=2.01 Hz, 1H) 5.30 (dd, J=6.15, 1.63

Hz, 1H) 7.22 (d, J=8.53 Hz, 2H) 7.91 (d, J=8.53 Hz, 2H). $^{19}$F NMR (376 MHz, MeOD) δ ppm −114.91 (d, J=17.34 Hz, 2 F).

Example 153

Preparation of 4-((1R,3aS,5aR,5bR,7aR,11aS,11bR, 13aR,13bR)-3a-((2-carboxy-2,2-difluoroacetamido) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

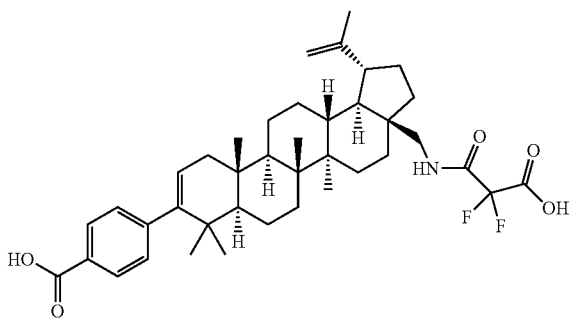

To a solution of the product resulting from Step 1 in example 152, tert-butyl 4-((1R,3aS,5aR,5bR,7aR,11aS, 11bR,13aR,13bR)-3a-((2,2-difluoro-3-methoxy-3-oxopropanamido)methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate (20 mg, 0.027 mmol) in 1,4-dioxane (1 ml) and methanol (0.5 ml) was added 1N sodium hydroxide (0.5 ml, 0.500 mmol). The resulting solution was stirred at 65° C. for 2 h. The crude product was purified by prep. HPLC (YMC Combiprep ODS 30×50 mm S5) (MeOH/H$_2$O/TFA) to give the title compound as a solid (2 mg, 9%). MS: m/e 666.5 (MH$^+$), 1.96 min (method 2). $^1$H NMR (400 MHz, MeOD) δ ppm 0.94 (s, 3H) 0.96 (s, 3H) 1.03 (s, 3H) 1.04 (s, 3H) 1.18 (s, 3H) 1.71 (s, 3H) 0.86-1.89 (m, 20H) 1.93-2.05 (m, 1H) 2.14 (dd, J=17.07, 6.27 Hz, 1H) 2.53 (td, J=11.29, 5.52 Hz, 1H) 3.09 (d, J=13.55 Hz, 1H) 3.62 (d, J=14.05 Hz, 1H) 4.58-4.61 (m, 1H) 4.73 (d, J=1.76 Hz, 1H) 5.29 (dd, J=6.02, 1.51 Hz, 1H) 7.22 (d, J=8.53 Hz, 2H) 7.91 (d, J=8.28 Hz, 2H). $^{19}$F NMR (376 MHz, MeOD) δ ppm −112.65 (s, 2 F).

General Procedures for the Preparation of C28 Urea Derivatives

Synthetic Route 1:

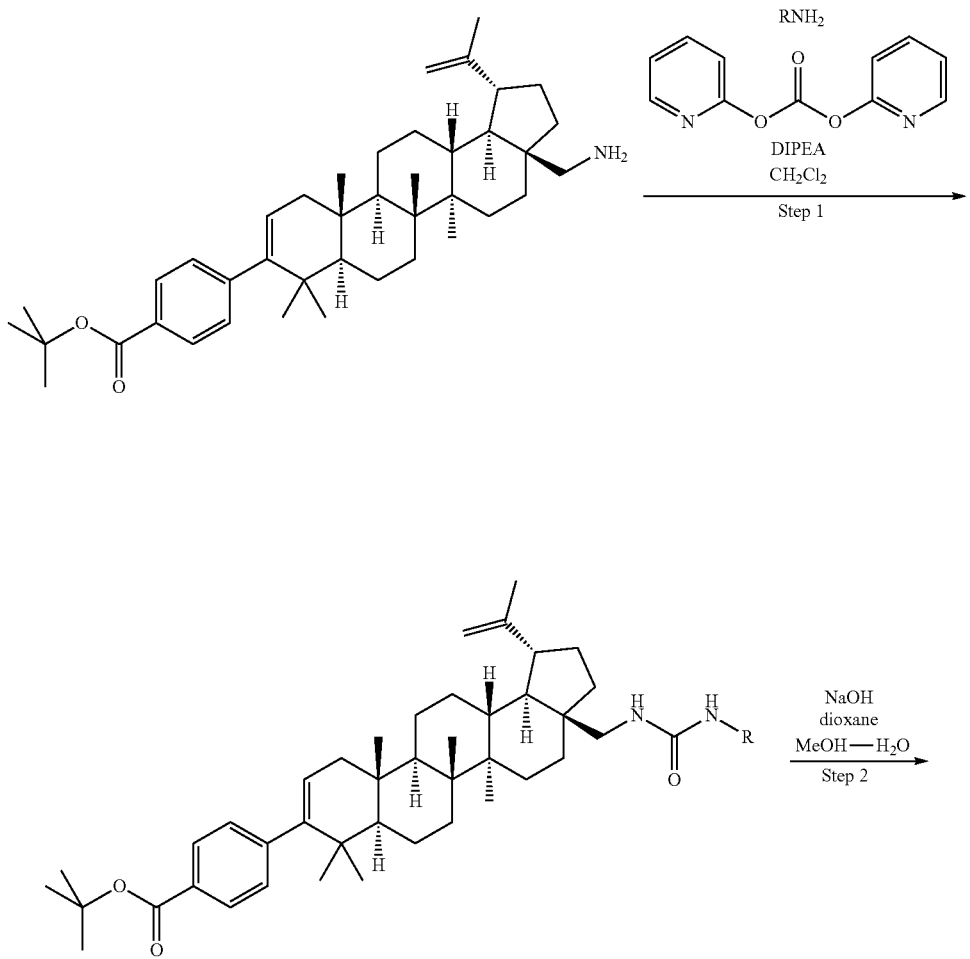

-continued

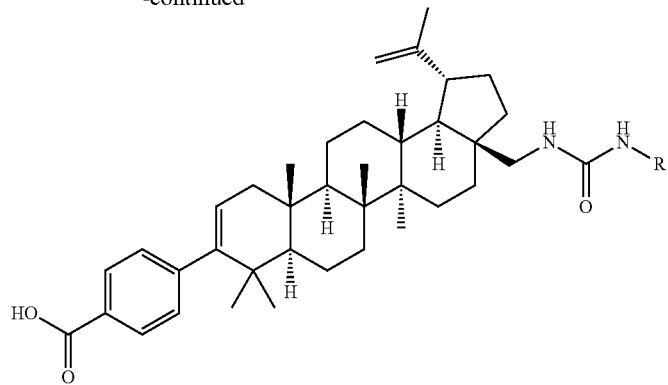

Step 1: Preparation of Ureas

To a solution of tert-butyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (100 mg, 0.167 mmol) in DCM (5 ml) at 0° C. was added dipyridin-2-yl carbonate (43.2 mg, 0.200 mmol) followed by DIPEA (0.070 ml, 0.400 mmol). The resulting solution was stirred at rt for 2 h. The corresponding amine (1.2 eq.) was added followed by DIPEA (3 eq.). The mixture was stirred for 18 h. The solvent was removed in vacuo and the resulting crude product was used without further purification.

Step 2. Preparation of Benzoic Acids

To the solution of the urea resulting from Step 1 in dioxane (2.0 ml) and methanol (2.0 ml) was added sodium hydroxide (5 eq.) and $H_2O$ (0.5 ml). The resulting solution was stirred at 70° C. for 5-10 h. The solvent was removed in vacuo and the crude product was purified by prep. HPLC to give the desired benzoic acids.

Synthetic Route 2:

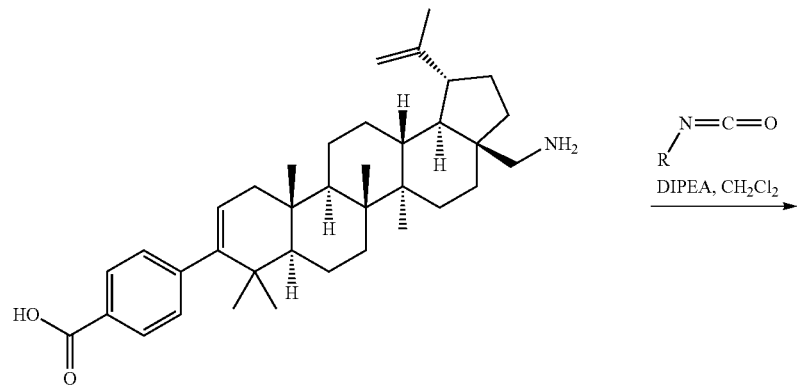

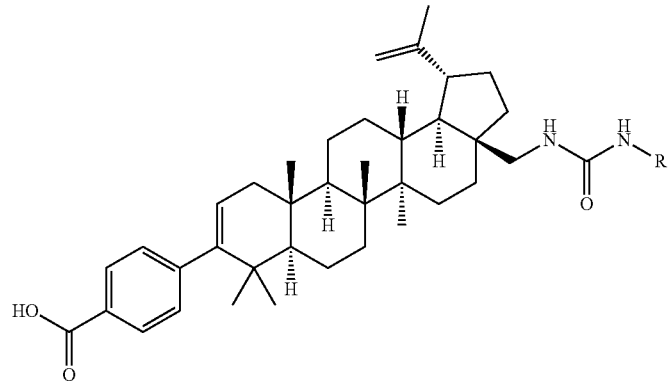

To a solution of 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (1 eq.) and the corresponding isocyanate (2 eq.) in DCM (8 ml) at 0° C. was added DIPEA (3 eq.). The resulting mixture was stirred at rt for 18 h. The solvent was evaporated and the crude product was purified by prep. HPLC to give the desired benzoic acids.

Example 154

4-((1R,3aS,5aR,5bR,7aR,11aS,11bR,13aR,13bR)-5a,5b,8,8,11a-pentamethyl-3a-((3-(2-(2-oxopyrrolidin-1-yl)ethyl)ureido)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

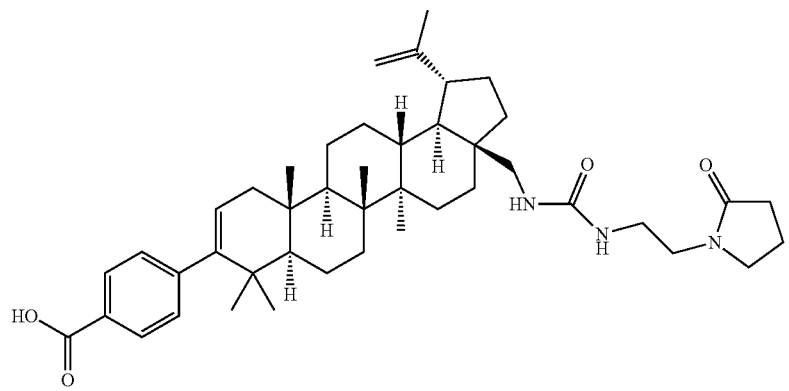

The title compound was prepared in 19% yield following the synthetic route 1 described above, using 1-(2-aminoethyl)pyrrolidin-2-one oxalate as the reactant amine MS: m/e 698.3 (MH$^+$), 1.77 min (method 2). $^1$H NMR (400 MHz, MeOD) δ ppm 0.94 (s, 3H) 0.96 (s, 3H) 1.03 (s, 3H) 1.04 (s, 3H) 1.17 (s, 3H) 1.70 (s, 3H) 0.86-1.92 (m, 20H) 2.03 (quin, J=7.59 Hz, 3H) 2.14 (dd, J=17.19, 6.40 Hz, 1H) 2.35 (t, J=8.16 Hz, 2H) 2.51 (td, J=10.98, 5.40 Hz, 1H) 2.93 (d, J=13.05 Hz, 1H) 3.31-3.37 (m, 4H) 3.43 (d, J=13.05 Hz, 1H) 3.51 (t, J=7.03 Hz, 2H) 4.56-4.62 (m, 1H) 4.71 (d, J=2.26 Hz, 1H) 5.29 (dd, J=6.27, 1.76 Hz, 1H) 7.22 (d, J=8.53 Hz, 2H) 7.91 (d, J=8.53 Hz, 2H).

Example 155

4-((1R,3aS,5aR,5bR,7aR,11aS,11bR,13aR,13bR)-5a,5b,8,8,11a-pentamethyl-3a-((3-(3-(2-oxopyrrolidin-1-yl)propyl)ureido)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

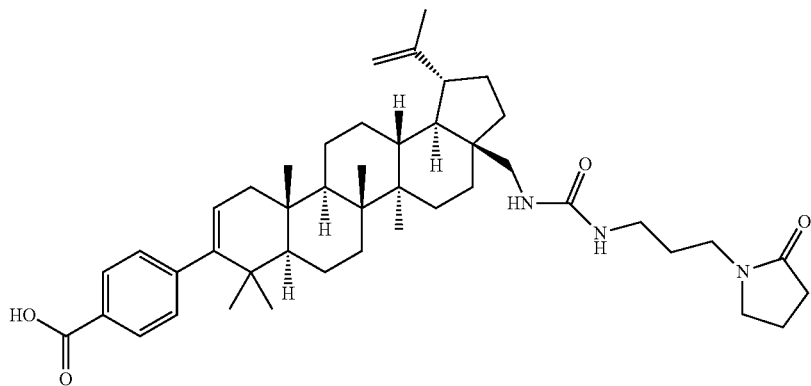

The title compound was prepared in 32% yield following the synthetic route 1 described above, using 1-(3-aminopropyl)pyrrolidin-2-one as the reactant amine MS: m/e 712.3 (MH$^+$), 1.85 min (method 2). $^1$H NMR (400 MHz, MeOD) δ ppm 0.94 (s, 3H) 0.96 (s, 3H) 1.03 (s, 3H) 1.04 (s, 3H) 1.18 (s, 3H) 1.67-1.72 (m, 3H) 0.87-1.93 (m, 22H) 2.04 (quin, J=7.65 Hz, 3H) 2.14 (dd, J=16.94, 6.40 Hz, 1H) 2.38 (t, J=8.03 Hz, 2H) 2.51 (td, J=11.04, 5.02 Hz, 1H) 2.95 (d, J=13.55 Hz, 1H) 3.11 (t, J=6.65 Hz, 2H) 3.32-3.44 (m, 3H) 3.46 (t, J=7.03 Hz, 2H) 4.57-4.61 (m, 1H) 4.71 (d, J=2.01 Hz, 1H) 5.29 (dd, J=6.27, 1.51 Hz, 1H) 7.21 (d, J=8.28 Hz, 2H) 7.91 (d, J=8.28 Hz, 2H).

Example 156

Preparation of 4-((1R,3aS,5aR,5bR,7aR,11aS,11bR,13aR,13bR)-3a-((3-(2-ethoxy-2-oxoethyl)ureido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

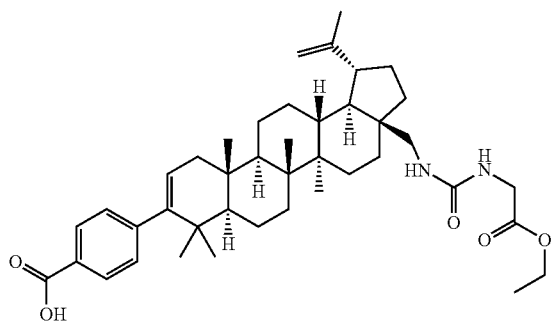

The title compound was prepared following the synthetic route 2 described above using ethyl 2-isocyanatoacetate as the reactant isocyanate, the product was isolated as a white solid (5 mg, 40.4%). LCMS: m/e 673.5 (MH$^+$), 2.90 min (method 3). $^1$H NMR (400 MHz, MeOD) δ ppm 7.90 (d, J=8.3 Hz, 2H), 7.20 (d, J=8.3 Hz, 2H), 5.15-5.36 (m, 1H), 4.70 (s, 1H), 4.57 (s, 1H), 4.16 (q, J=7.1 Hz, 2H), 3.44 (d, J=13.6 Hz, 1H), 3.29 (dt, J=3.3, 1.6 Hz, 2H), 2.95 (d, J=13.6 Hz, 1H), 2.50 (td, J=11.1, 5.5 Hz, 1H), 2.12 (dd, J=17.2, 6.4 Hz, 1H), 1.94-2.08 (m, 1H), 1.76-1.94 (m, 3H), 1.60-1.76 (m, 8H), 1.41-1.60 (m, 6H), 1.28-1.41 (m, 2H), 1.20-1.28 (m, 5H), 1.10-1.20 (m, 4H), 1.05-1.10 (m, 1H), 1.02 (s, 3H), 1.01 (s, 3H), 0.94 (s, 3H), 0.89 (s, 3H).

Example 157

Preparation of 4-((1R,3aS,5aR,5bR,7aR,11aS,11bR,13aR,13bR)-3a-((3-(carboxymethyl)ureido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid 4-((1R,3aS,5aR,5bR,7aR,11aS,11bR,13aR,13bR)-3a-((3-(2-ethoxy-2-oxoethyl)ureido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (7 mg, 10.40 mmol) was dissolved in dioxane (2 ml). Sodium hydroxide solution, 1N (0.021 ml, 0.021 mmol) was added. The mixture was stirred at 70° C. for 2 h. The solvent was evaporated and the residue was purified by prep. HPLC to afford the title compound as a white solid (4 mg, 32.8%). LCMS: m/e 645.3 (MH$^+$), 2.58 min (method 3). $^1$H NMR (400 MHz, MeOD) δ ppm 7.90 (m, J=8.3 Hz, 2H), 7.20 (m, J=8.3 Hz, 2H), 5.21-5.36 (m, 1H), 4.70 (d, J=1.8 Hz, 1H), 4.57 (s, 1H), 3.83 (s, 2H), 3.44 (d, J=13.8 Hz, 1H), 2.95 (d, J=13.6 Hz, 1H), 2.38-2.60 (m, 1H), 2.13 (dd, J=17.1, 6.5 Hz, 1H), 1.93-2.08 (m, 1H), 1.76-1.93 (m, 2H), 1.60-1.76 (m, 8H), 1.40-1.60 (m, 6H), 1.35-1.40 (m, 1H), 1.29-1.35 (m, 1H), 1.18-1.29 (m, 3H), 1.16 (s, 3H), 1.05-1.13 (m, 2H), 1.03 (s, 3H), 1.02 (s, 3H), 0.97 (s, 3H), 0.92 (s, 3H).

Example 158

Preparation of 4-((1R,3aS,5aR,5bR,7aR,11aS,11bR,13aR,13bR)-3a-((3-(2-methoxy-2-oxoethyl)ureido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

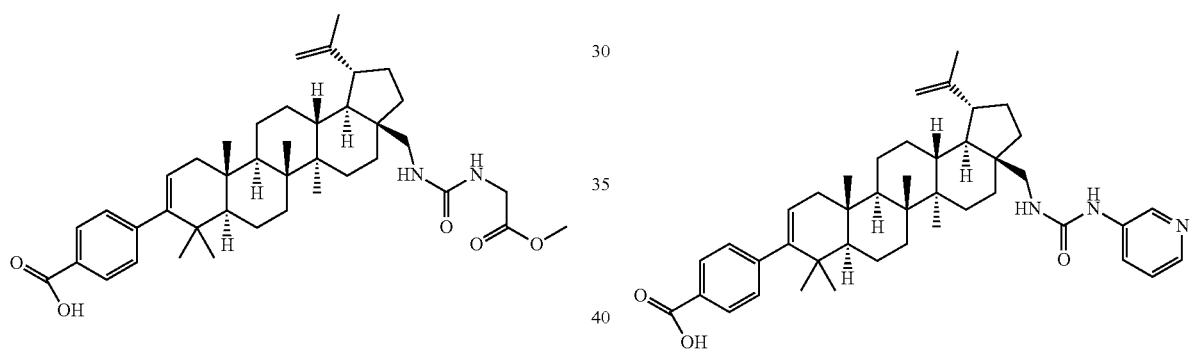

4-((1R,3aS,5aR,5bR,7aR,11aS,11bR,13aR,13bR)-3a-((3-(2-ethoxy-2-oxoethyl)ureido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (7 mg, 10.40 mmol) was dissolved in dioxane (2 ml) and methanol (1 ml). A solution of sodium hydroxide (1N, 0.021 ml, 0.021 mmol) was added. The mixture was stirred at 70° C. for 2 h. The solvent was removed under reduced pressure and the residue was purified by prep. HPLC to afford the title compound as a white solid (2 mg, 29.2%). LCMS: m/e 659.4 (MH$^+$), 2.84 min (method 3). $^1$H NMR (500 MHz, MeOD) δ ppm 7.86 (d, J=8.2 Hz, 2H), 7.14 (d, J=7.9 Hz, 2H), 5.23-5.38 (m, 1H), 4.74 (s, 1H), 4.62 (s, 1H), 3.91 (s, 2H), 3.71-3.78 (m, 3H), 2.95-3.10 (m, 1H), 2.46-2.62 (m, 1H), 2.12-2.25 (m, 1H), 2.05 (s, 1H), 1.99-2.03 (m, 1H), 1.91-1.99 (m, 6H), 1.89 (br. s., 2H), 1.76-1.83 (m, 2H), 1.71-1.76 (m, 4H), 1.69 (br. s., 1H), 1.48 (br. s., 4H), 1.31 (br. s., 4H), 1.19 (s, 3H), 1.07 (br. s., 3H), 1.05 (s, 3H), 0.97 (s, 3H), 0.96 (s, 3H).

Example 159

Preparation of 4-((1R,3aS,5aR,5bR,7aR,11aS,11bR,13aR,13bR)-5a,5b,8,8,11a-pentamethyl-1-(prop-1-en-2-yl)-3a-((3-pyridin-3-ylureido)methyl)-2,3,3a,4,5,5a,5b,6,7,7a,8,11,11a,11b,12,13,13a,13b-octadecahydro-1H-cyclopenta[a]chrysen-9-yl)benzoic acid The title compound was prepared following the synthetic route 2 described above using 3-isocyanatopyridine as the reactant isocyanate. The product was isolated as a white solid (5 mg, 38.9%). LCMS: m/e 664.5 (MH$^+$), 2.80 min (method 3). $^1$H NMR (400 MHz, MeOD) δ ppm 9.22 (d, J=2.5 Hz, 1H), 8.35 (d, J=5.3 Hz, 1H), 8.13-8.28 (m, 1H), 7.76-7.99 (m, 3H), 7.20 (d, J=8.3 Hz, 2H), 5.23-5.37 (m, 1H), 4.72 (d, J=2.0 Hz, 1H), 4.60 (s, 1H), 3.56 (s, 1H), 3.04 (d, J=13.3 Hz, 1H), 2.45-2.64 (m, 1H), 2.10-2.20 (m, 2H), 1.84 (br. s., 2H), 1.62-1.79 (m, 8H), 1.56 (br. s., 2H), 1.47 (d, J=10.6 Hz, 4H), 1.39 (d, J=13.6 Hz, 1H), 1.21-1.34 (m, 3H), 1.18 (s, 3H), 1.10 (d, J=11.3 Hz, 3H), 1.05 (s, 3H), 1.03 (s, 3H), 0.95 (s, 3H), 0.93 (s, 3H).

Example 160

Preparation of 4-((1R,3aS,5aR,5bR,7aR,11aS,11bR, 13aR,13bR)-3a-((3-(4-(methoxycarbonyl)phenyl) ureido)methyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

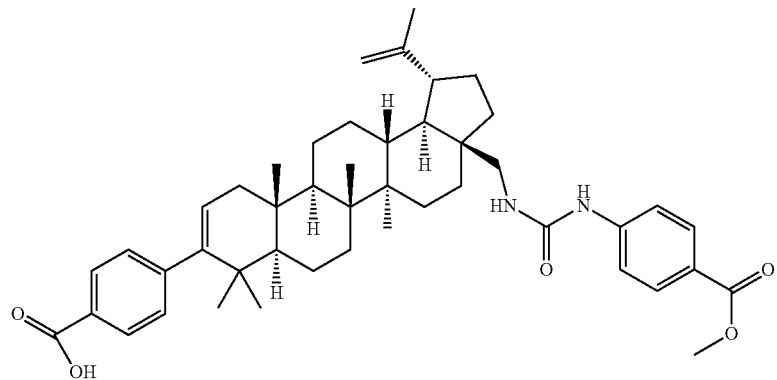

The title compound was prepared following the synthetic route 2 described above using methyl 4-isocyanatobenzoate as the reactant isocyanate. The product was isolated as a white solid (5 mg, 37.7%). LCMS: m/e 721.5 (MH⁺), 3.07 min (method 3). ¹H NMR (400 MHz, MeOD) δ ppm 7.86-7.94 (m, 4H), 7.39-7.51 (m, 2H), 7.15-7.26 (m, 2H), 5.21-5.33 (m, 1H), 4.72 (s, 1H), 4.59 (s, 1H), 3.86 (s, 3H), 3.51 (s, 1H), 3.03 (d, J=13.8 Hz, 1H), 2.42-2.60 (m, 1H), 2.14 (dd, J=17.0, 6.7 Hz, 2H), 1.61-1.76 (m, 8H), 1.48 (br. s., 6H), 1.22-1.35 (m, 5H), 1.15-1.22 (m, 4H), 1.14 (br. s., 3H), 1.04 (s, 3H), 1.03 (s, 3H), 0.96 (s, 3H), 0.93 (s, 3H).

Example 161

Preparation of 4-((1R,3aS,5aR,5bR,7aR,11aS,11bR, 13aR,13bR)-3a-(((((2-(1,1-dioxido-4-thiomorpholi-nyl)ethyl)carbamoyl)amino)methyl)-1-isopropenyl-5a,5b,8,8,11a-pentamethyl-2,3,3a,4,5,5a,5b,6,7,7a,8, 11,11a,11b,12,13,13a,13b-octadecahydro-1H-cyclopenta[a]chrysen-9-yl)benzoic acid

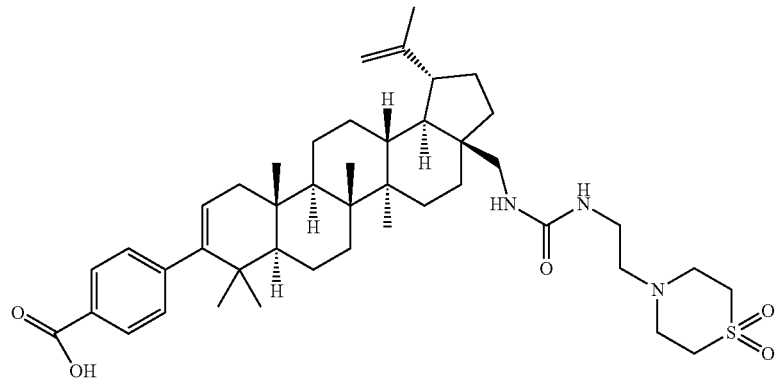

The title compound was prepared following the route 1 described above using N-(2-aminoethyl) thiomorpholine 1,1-dioxide as the reactant amine. The product was isolated as a white solid (8 mg, 20.4%). LCMS: m/e 748.3 (MH+), 2.33 min (method 3). $^1$H NMR (400 MHz, MeOD) δ ppm 7.90 (m, J=8.3 Hz, 2H), 7.20 (m, J=8.3 Hz, 2H), 5.28 (d, J=4.8 Hz, 1H), 4.70 (s, 1H), 4.59 (s, 1H), 3.71 (br. s., 4H), 3.35-3.56 (m, 7H), 3.20 (t, J=5.3 Hz, 2H), 2.94 (d, J=13.6 Hz, 1H), 2.37-2.57 (m, 1H), 2.13 (dd, J=17.1, 6.3 Hz, 1H), 1.94-2.08 (m, 1H), 1.80 (br. s., 2H), 1.61-1.77 (m, 8H), 1.55 (br. s., 2H), 1.48 (br. s., 4H), 1.39 (br. s., 2H), 1.31 (br. s., 1H), 1.19-1.29 (m, 2H), 1.17 (s, 3H), 1.06-1.12 (m, 2H), 1.04 (s, 3H), 1.02 (s, 3H), 0.95 (s, 3H), 0.93 (s, 3H).

General Procedure for the Preparation of C28 Reversed Carbamate Derivatives

Synthetic Route 1:

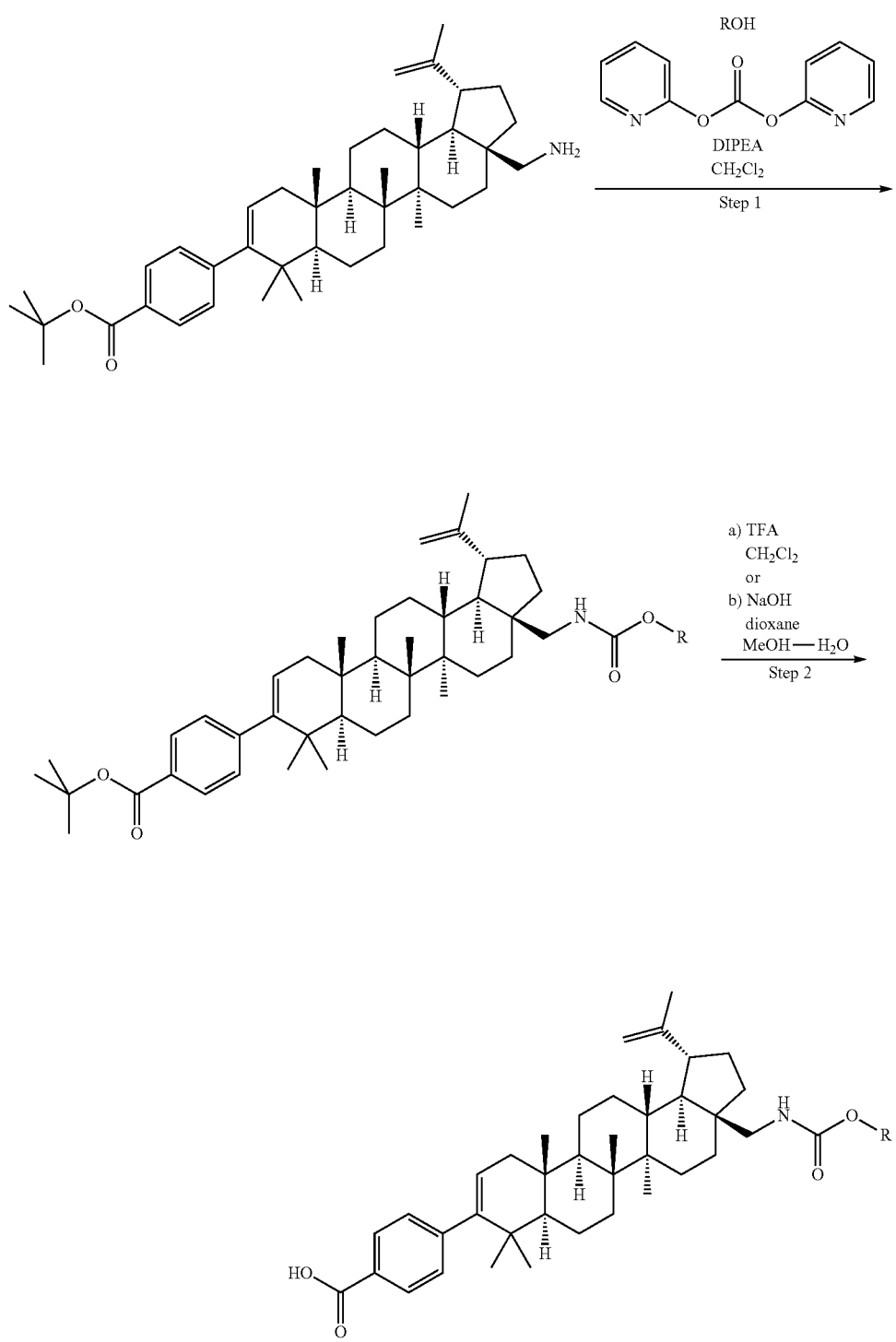

Step 1: Preparation of Carbamates

To the solution of tert-butyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (100 mg, 0.167 mmol) in DCM (5 ml) at 0° C. was added dipyridin-2-yl carbonate (43.2 mg, 0.200 mmol) followed by DIPEA (0.070 ml, 0.400 mmol). The reaction mixture was stirred for 2 h. To the resulting solution was added 2-5 eq. of corresponding alcohol and 3-6 eq. of DIPEA at 0° C. The mixture was stirred for another 18 h. The solvent was removed in vacuo and the resulting crude product was used without further purification.

Step 2: Preparation of benzoic acids a) Acidic hydrolysis—To a solution of the material from Step 1 in DCM (4-5 ml) was added TFA (0.4-0.5 ml). The mixture was stirred at rt for 2-6 h. The solvent was evaporated under vacuum. The resulting crude product was purified by prep. HPLC to give the desired benzoic acid.

b) Basic hydrolysis—To a solution of the material from Step 1 in dioxane (2 ml) and methanol (2 ml) was added sodium hydroxide (75 mg, 1.875 mmol) and H$_2$O (0.5 ml). The resulting solution was stirred at 70° C. for 5-10 h. The solvent was evaporated under vacuum and the resulting crude product was purified by prep. HPLC to give the desired benzoic acid.

Synthetic Route 2:

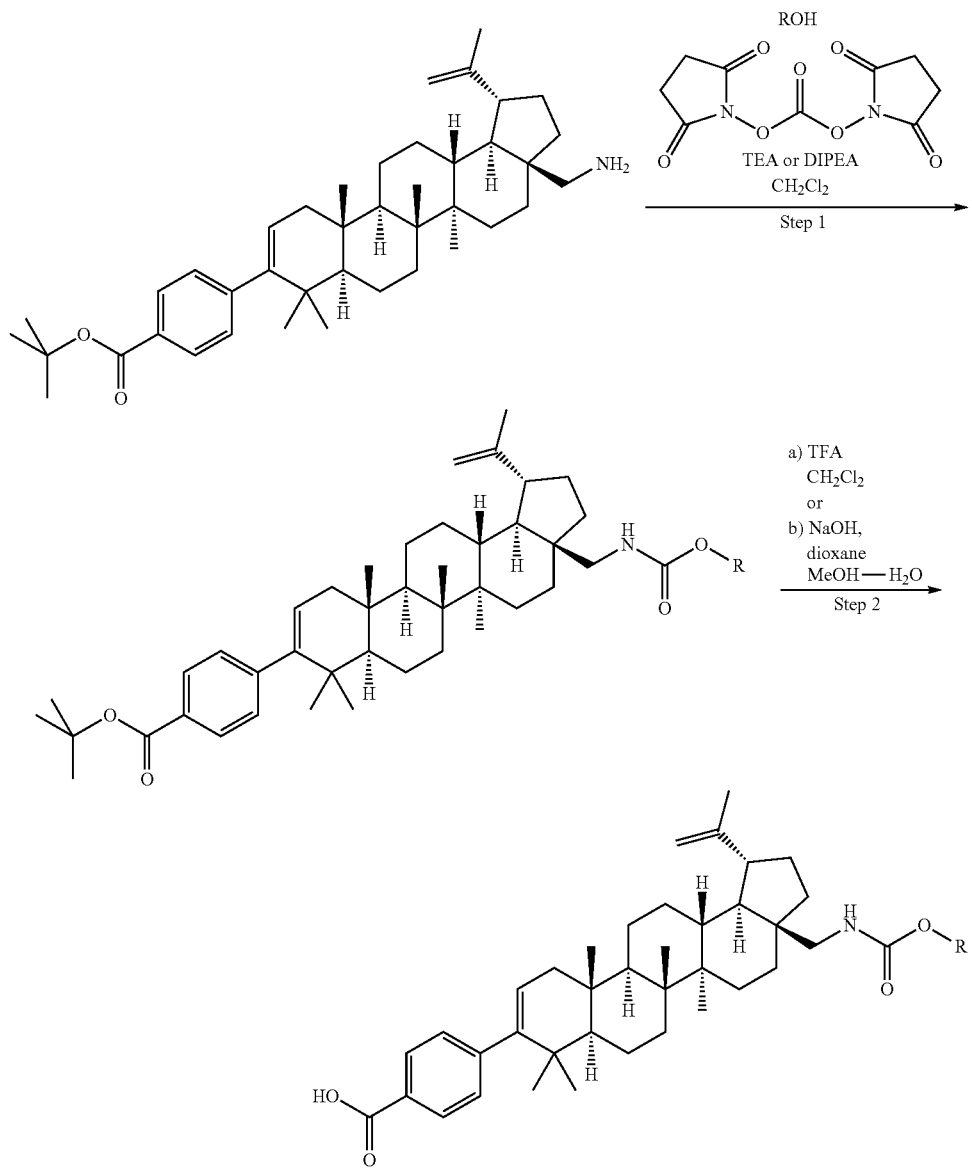

Step 1. Preparation of the Carbamates

To a suspension of bis(2,5-dioxopyrrolidin-1-yl) carbonate (75 mg, 0.293 mmol) and the corresponding alcohol (0.322 mmol) in DCM (2 ml) was added TEA (0.041 ml, 0.293 mmol). The reaction mixture was stirred at rt for 2-4 h. To the intermediate solution was added tert-butyl 4-((1R,3aS,5aR, 5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (1 eq.) in DCM (5 ml) followed by DIPEA (2 eq.). The resulting solution was stirred for two hours. The solvent was evaporated and the resulting crude product was purified by Biotage to give desired carbamates.

Step 2: Preparation of the benzoic acids

To a solution of the material from Step 3 in dioxane (2 ml) and methanol (2 ml) was added sodium hydroxide (75 mg, 1.875 mmol) and $H_2O$ (0.5 ml). The resulting solution was stirred at 70° C. for 5-10 h. The solvent was evaporated under vacuum and the resulting crude product was purified by prep. HPLC to give the desired benzoic acids.

Example 162

4-((1R,3aS,5aR,5bR,7aR,11aS,11bR,13aR,13bR)-5a,5b,8,8,11a-pentamethyl-3a-(((2-(2-oxopyrrolidin-1-yl)ethoxy)carbonylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

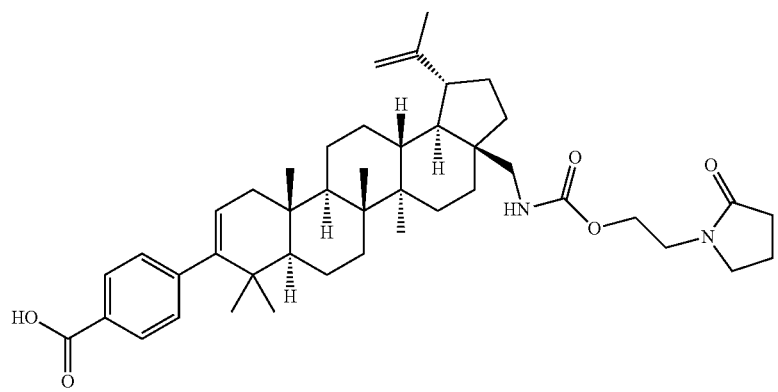

The title compound was prepared in 23% yield following the synthetic route 2 described above for the preparation of the C28 reversed carbamates, using 1-(2-hydroxyethyl)pyrrolidin-2-one as the reactant alcohol. MS: m/e 699.3 ($MH^+$), 1.79 min (method 2). $^1H$ NMR (400 MHz, MeOD) δ ppm 0.94 (s, 3H) 0.96 (s, 3H) 1.03 (s, 3H) 1.04 (s, 3H) 1.17 (s, 3H) 1.70 (s, 3H) 0.87-1.96 (m, 20H) 2.03 (dq, J=7.91, 7.65 Hz, 3H) 2.14 (dd, J=17.19, 6.40 Hz, 1H) 2.36 (t, J=8.16 Hz, 2H) 2.49 (td, J=11.04, 5.27 Hz, 1H) 2.91 (d, J=13.05 Hz, 1H) 3.39-3.46 (m, 1H) 3.48-3.57 (m, 4H) 4.17 (ddd, J=5.02, 2.89, 2.64 Hz, 2H) 4.59 (s, 1H) 4.71 (d, J=2.01 Hz, 1H) 5.29 (dd, J=6.40, 1.88 Hz, 1H) 7.22 (d, J=8.28 Hz, 2H) 7.91 (d, J=8.28 Hz, 2H).

Example 163

Preparation of 4-((1R,3aS,5aR,5bR,7aR,11aS,11bR, 13aR,13bR)-5a,5b,8,8,11a-pentamethyl-3a-(((2-(piperazin-1-yl)ethoxy)carbonylamino)methyl)-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

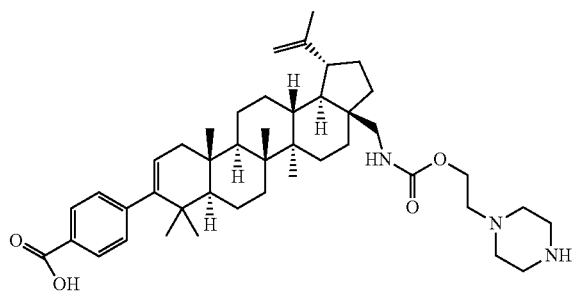

The title compound was prepared following synthetic route 1 described above for the preparation of the C28 reversed carbamates using tert-butyl 4-(2-hydroxyethyl)piperazine-1-carboxylate as the reactant alcohol and acid hydrolysis. The product was isolated as a white solid (1.5 mg, 3.82%). LCMS: m/e 700.4 (MH$^+$), 2.69 min (method 3). $^1$H NMR (400 MHz, MeOD) δ ppm 7.90 (d, J=8.3 Hz, 2H), 7.20 (d, J=8.3 Hz, 2H), 5.19-5.37 (m, 1H), 4.70 (s, 1H), 4.58 (s, 1H), 4.18 (t, J=5.4 Hz, 2H), 3.77-4.02 (m, 2H), 3.49-3.66 (m, 2H), 3.38 (m, 1H), 3.13-3.24 (m, 3H), 3.03 (s, 1H), 2.80-2.86 (m, 2H), 2.76 (t, J=5.3 Hz, 1H), 2.43-2.55 (m, 1H), 2.04-2.23 (m, 2H), 1.97 (br. s., 1H), 1.61-1.76 (m, 8H), 1.52-1.61 (m, 2H), 1.41-1.52 (m, 4H), 1.20-1.41 (m, 8H), 1.16 (s, 3H), 1.02 (d, J=4.0 Hz, 6H), 0.95 (s, 3H), 0.93 (s, 3H).

Example 164

Preparation of 4-((1R,3aS,5aR,5bR,7aR,11aS,11bR, 13aR,13bR)-3a-((((3-(1,1-dioxido-4-thiomorpholinyl)propoxy)carbonyl)amino)methyl)-1-isopropenyl-5a,5b,8,8,11a-pentamethyl-2,3,3a,4,5,5a,5b,6,7,7a,8, 11,11a,11b,12,13,13a,13b-octadecahydro-1H-cyclopenta[a]chrysen-9-yl)benzoic acid

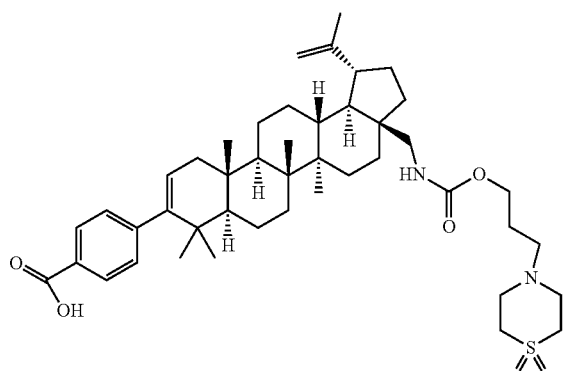

The title compound was prepared following synthetic route 2 described above for the preparation of the C28 reversed carbamates using 4-(3-hydroxypropyl)thiomorpholine 1,1-dioxide as the reactant alcohol. The product was isolated as a white solid (15 mg, 38.2%). LCMS: m/e 763.3 (MH$^+$), 2.32 min (method 3). $^1$H NMR (500 MHz, MeOD) δ ppm 7.88-7.99 (m, 2H), 7.14-7.32 (m, 2H), 5.25-5.40 (m, 1H), 4.74 (s, 1H), 4.62 (br. s., 1H), 4.16 (t, J=6.1 Hz, 2H), 3.67 (br. s., 4H), 3.38-3.53 (m, 5H), 3.14-3.28 (m, 2H), 2.95 (d, J=13.7 Hz, 1H), 2.51 (t, J=6.3 Hz, 1H), 2.17 (dd, J=17.2, 6.3 Hz, 1H), 2.01-2.12 (m, 3H), 1.83 (d, J=11.9 Hz, 1H), 1.64-1.80 (m, 8H), 1.44-1.64 (m, 6H), 1.32-1.44 (m, 3H), 1.22-1.32 (m, 3H), 1.12-1.22 (m, 5H), 1.03-1.09 (m, 6H), 0.99 (s, 3H), 0.97 (s, 3H).

Example 165

Preparation of 4-((1R,3aS,5aR,5bR,7aR,11aS,11bR, 13aR,13bR)-3a-((((2-(1,1-dioxido-4-thiomorpholinyl)ethoxy)carbonyl)amino)methyl)-1-isopropenyl-5a,5b,8,8,11a-pentamethyl-2,3,3a,4,5,5a,5b,6,7,7a,8, 11,11a,11b,12,13,13a,13b-octadecahydro-1H-cyclopenta[a]chrysen-9-yl)benzoic acid

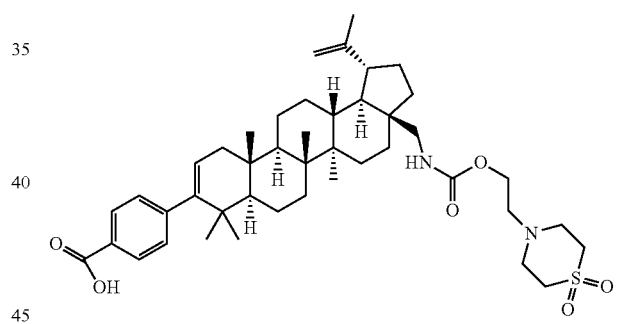

The title compound was prepared following synthetic route 2 described above for the preparation of the C28 reversed carbamates using 4-(2-hydroxyethyl)thiomorpholine 1,2-dioxide as the reactant alcohol. The product was isolated as a white solid (22 mg, 44.9%). LCMS: m/e 749.3 (MH$^+$), 2.54 min (method 3). $^1$H NMR (400 MHz, MeOD) δ ppm 7.94 (m, J=8.3 Hz, 2H), 7.24 (m, J=8.5 Hz, 2H), 5.32 (dd, J=6.1, 1.6 Hz, 1H), 4.74 (d, J=2.0 Hz, 1H), 4.62 (s, 1H), 4.18-4.40 (m, 2H), 3.52 (dd, J=6.5, 3.8 Hz, 4H), 3.40-3.49 (m, 1H), 3.25-3.38 (m, 6H), 3.22 (t, J=5.0 Hz, 2H), 2.97 (d, J=13.8 Hz, 1H), 2.53 (td, J=11.1, 5.6 Hz, 1H), 2.17 (dd, J=17.2, 6.4 Hz, 1H), 2.00-2.13 (m, 1H), 1.84 (dd, J=12.2, 3.4 Hz, 2H), 1.65-1.81 (m, 8H), 1.53-1.65 (m, 4H), 1.50 (d, J=11.0 Hz, 3H), 1.34-

1.46 (m, 2H), 1.22-1.34 (m, 2H), 1.19-1.22 (m, 2H), 1.10-1.15 (m, 1H), 1.03-1.10 (m, 6H), 0.99 (s, 3H), 0.97 (s, 3H).

Example 166

Preparation of 4-((1R,3aS,5aR,5bR,7aR,11aS,11bR,13aR,13bR)-5a,5b,8,8,11a-pentamethyl-3a-(((3-(2-oxopyrrolidin-1-yl)propoxy)carbonylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

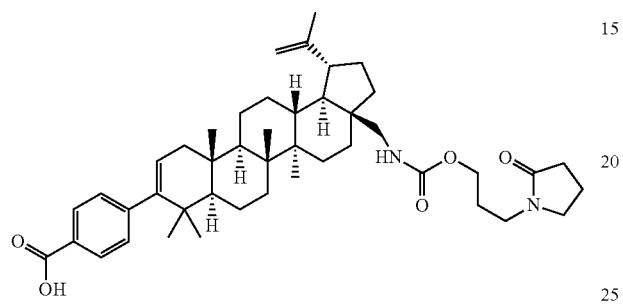

The title compound was prepared following synthetic route 2 described above for the preparation of the C28 reversed carbamates using 1-(3-hydroxypropyl)pyrrolidin-2-one as the reactant alcohol. The product was isolated as a white solid (12 mg, 32.4%). LCMS: m/e 713.3 (MH$^+$), 2.43 min (method 3). $^1$H NMR (400 MHz, MeOD) δ ppm 7.93 (m, 2H), 7.24 (m, 2H), 5.32 (dd, J=6.3, 1.8 Hz, 1H), 4.74 (d, J=2.0 Hz, 1H), 4.62 (s, 1H), 3.94-4.12 (m, 2H), 3.45-3.56 (m, 2H), 3.34-3.45 (m, 3H), 2.95 (d, J=13.8 Hz, 1H), 2.52 (td, J=11.2, 5.6 Hz, 1H), 2.32-2.45 (m, 2H), 2.17 (dd, J=17.2, 6.4 Hz, 1H), 2.01-2.13 (m, 3H), 1.81-2.01 (m, 4H), 1.64-1.81 (m, 8H), 1.45-1.64 (m, 6H), 1.34-1.45 (m, 2H), 1.23-1.34 (m, 2H), 1.20 (s, 3H), 1.15 (dt, J=8.6, 4.4 Hz, 1H), 1.09-1.12 (m, 1H), 1.02-1.09 (m, 7H), 0.99 (s, 3H), 0.97 (s, 3H).

Example 167

Preparation of 4-(N—(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methyl)sulfamoyl)benzoic acid

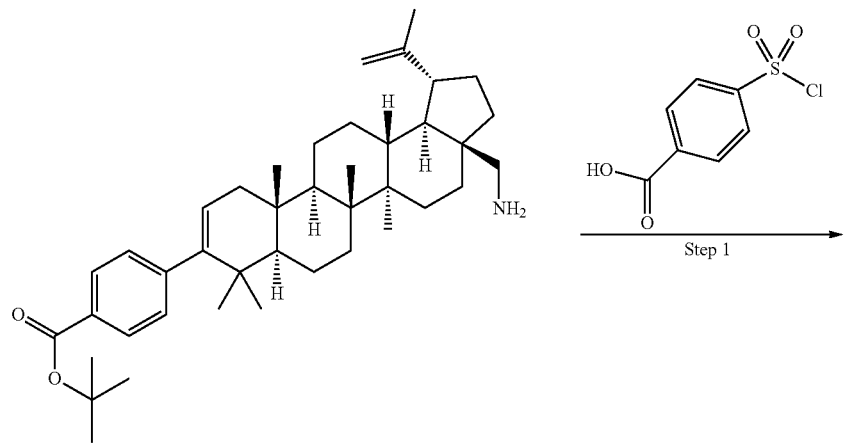

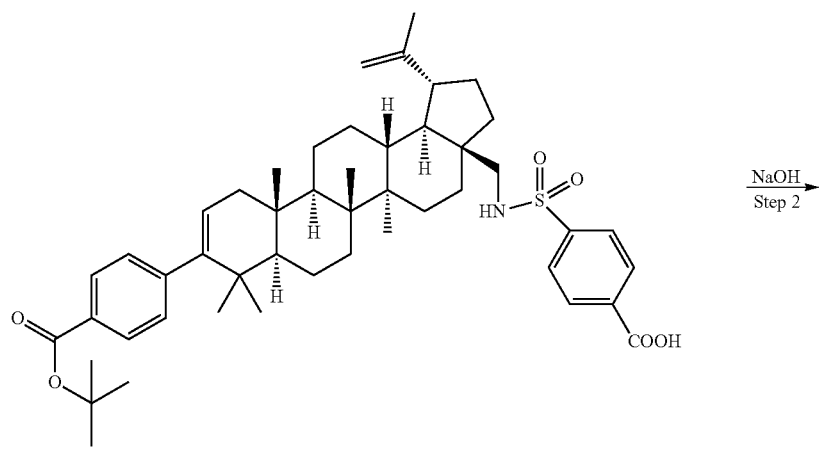

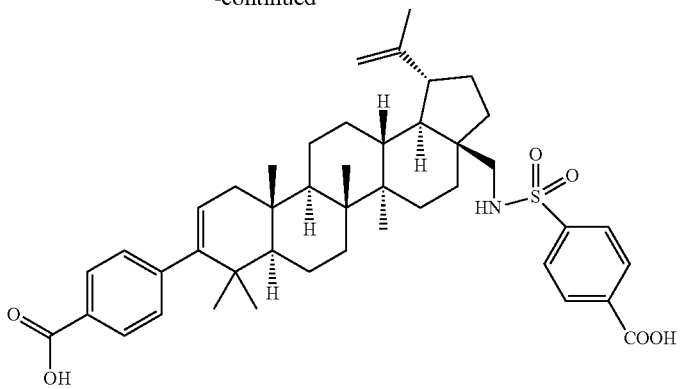

Example 167

Step 1. Preparation of 4-(N—(((1R,3aS,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methyl)sulfamoyl)benzoic acid To a solution of tert-butyl 4-((1R,3aS,5aR,5bR,7aR,11aS,11bR,13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (25 mg, 0.042 mmol) in DCM (2 ml) was added 4-(chlorosulfonyl)benzoic acid (9.19 mg, 0.042 mmol) and DIPEA (7.28 μl, 0.042 mmol). The resulting mixture was stirred for 48 h at rt. The mixture was diluted with 7 ml of sat. NaHCO$_3$ and was extracted with dichloromethane (3×7 ml). The combined organic layers were dried with Na$_2$SO$_4$. The drying agent was removed by filtration and the filtrate was concentrated under reduced pressure. The crude product was used in the next step with no additional purification.

Step 2: Benzoic Acid Deprotection 4-(N—(((1R,3aS,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methyl)sulfamoyl)benzoic acid (10 mg, 0.013 mmol) from Step 1 was dissolved in dioxane (1 ml) and MeOH (5 ml) sodium hydroxide (10.20 mg, 0.255 mmol) (powder) was added followed by 5 drops of water. The resulting suspension was stirred at 70° C. for 6 h. After the reaction was completed, all volatile material was removed in vacuo. The residue was re-dissolved in MeOH and purified by prep. HPLC to afford 4-(N—(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)methyl)sulfamoyl)benzoic acid as a white solid (1.8 mg, 18.4%). LCMS: m/e 728.2 (MH$^+$), 2.11 min (method 3). $^1$H NMR (400 MHz, MeOD) δ ppm 8.24 (m, J=8.5 Hz, 2H), 8.01 (m, J=8.5 Hz, 2H), 7.94 (m, J=8.3 Hz, 2H), 7.24 (m, J=8.3 Hz, 2H), 5.31 (d, J=4.3 Hz, 1H), 4.70 (d, J=2.3 Hz, 1H), 4.59 (s, 1H), 3.05 (s, 1H), 2.62 (d, J=13.1 Hz, 1H), 2.37 (br. s., 1H), 2.11 (m, 1H), 1.76-2.01 (m, 4H), 1.65-1.76 (m, 6H), 1.53-1.65 (m, 4H), 1.44 (br. s., 5H), 1.31 (d, J=2.8 Hz, 6H), 1.03 (s, 6H), 1.01 (s, 3H), 0.99 (s, 3H), 0.96 (s, 3H).

Example 168

Preparation of 4-((1R,3aS,5aR,5bR,7aR,11aS,11bR,13aR,13bR)-3a-((1,1-dioxido-4-thiomorpholinyl)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

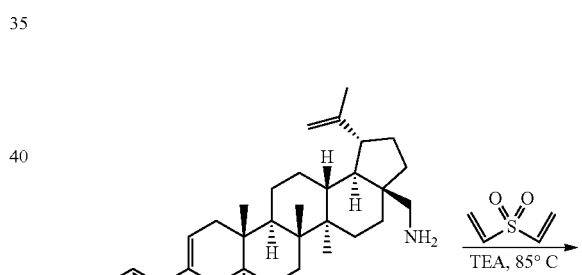

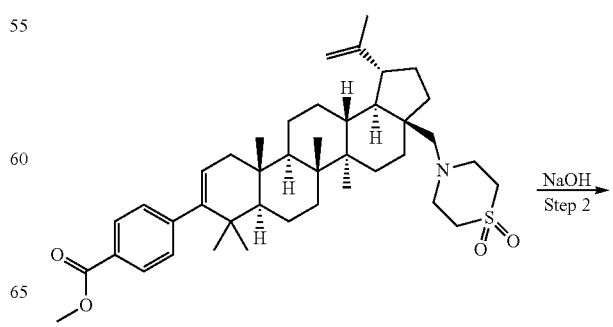

261
-continued

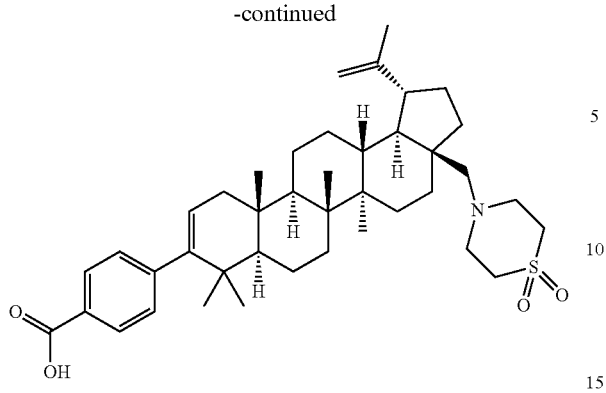

Example 168

Step 1. Tandem Double Michael Addition

To a solution of methyl 4-((1R,3aS,5aR,5bR,7aR,11aS, 11bR,13aR,13bR)-3a-(aminomethyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoate (120 mg, 0.215 mmol) in dioxane (0.5 ml) and ethanol (0.5 ml) was added TEA (0.09 ml, 0.645 mmol) and vinylsulfonylethene (50.8 mg, 0.430 mmol), the reaction mixture was heated at 85° C. for 3 h. The solvent was removed in vacuo, and the crude solid was used in next step without further purification. LCMS: m/e 676.6 (MH⁺), 3.28 min (method 3).

Step 2. Hydrolysis of Methyl Ester

To the solution of the crude material from Step 1 (88 mg, 0.130 mmol) in dioxane (1.5 ml) was added a solution of sodium hydroxide (0.5 ml, 1N, 0.500 mmol). The reaction mixture was heated to 55° C. for 4 h. The solvent was removed in vacuo, the resulting solid was purified by prep. HPLC to afford 4-((1R,3aS,5aR,5bR,7aR,11aS,11bR,13aR,13bR)-3a((1,1-dioxido-4-thiomorpholinyl)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid as a white solid (30 mg, 33.1%). LCMS: m/e 662.5 (MH⁺), 2.98 min (method 3). $^1$H NMR (400 MHz, MeOD) δ ppm 7.94 (m, J=8.3 Hz, 2H), 7.23 (m, J=8.3 Hz, 2H), 5.24-5.39 (m, 1H), 4.75 (s, 1H), 4.65 (s, 1H), 3.64 (br. s., 4H), 3.42 (br. s., 4H), 3.17-3.25 (m, 1H), 2.86 (m, 1H), 2.55 (m, 1H), 2.08-2.23 (m, 1H), 1.94 (br. s., 2H), 1.74 (s, 6H), 1.61 (br. s., 2H), 1.55 (br. s., 6H), 1.21-1.41 (m, 6H), 1.15-1.21 (m, 4H), 1.07-1.15 (m, 4H), 1.05 (s, 3H), 0.98 (s, 3H), 0.96 (s, 3H).

262

Example 169

Preparation of 4-((1R,3aS,5aR,5bR,7aR,11aS,11bR, 13aR,13bR)-3a-((3-carboxypropanamido)methyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid

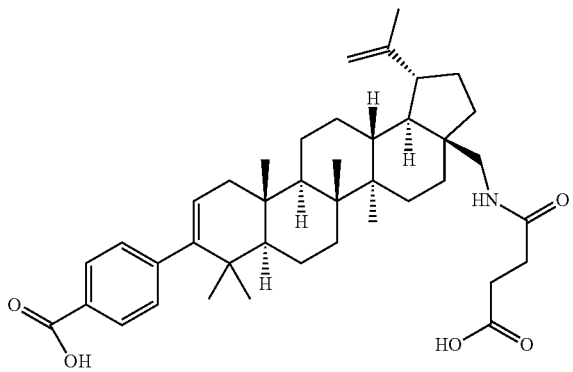

To a solution of 4-((1R,3aS,5aR,5bR,7aR,11aS,11bR, 13aR,13bR)-3a-(aminomethyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid (20 mg, 0.037 mmol) in DCM (2 ml) was added dihydrofuran-2,5-dione (11.04 mg, 0.110 mmol) followed by DMAP (4.49 mg, 0.037 mmol) and DIPEA (6.42 μl, 0.037 mmol). The mixture was stirred at rt for 18 h. The solvent was removed in vacuo and the resulting residue was purified by prep. HPLC. The product was isolated as a white solid (5 mg, 21.1%). LCMS: m/e 644.5 (MH⁺), 2.80 min (method 3). $^1$H NMR (400 MHz, MeOD) δ ppm 7.94 (d, J=8.5 Hz, 2H), 7.16-7.34 (m, 2H), 5.32 (dd, J=6.4, 1.6 Hz, 1H), 4.74 (d, J=2.0 Hz, 1H), 4.62 (s, 1H), 3.54 (d, J=13.6 Hz, 1H), 3.04 (d, J=13.8 Hz, 1H), 2.57-2.71 (m, 2H), 2.44-2.57 (m, 2H), 2.17 (dd, J=17.2, 6.4 Hz, 1H), 2.09 (dd, J=13.1, 1.8 Hz, 1H), 1.85 (dd, J=12.2, 3.4 Hz, 2H), 1.65-1.82 (m, 8H), 1.61 (br. s., 2H), 1.53 (d, J=10.5 Hz, 3H), 1.48 (d, J=2.0 Hz, 1H), 1.35-1.45 (m, 3H), 1.24-1.35 (m, 3H), 1.16-1.24 (m, 4H), 1.02-1.16 (m, 8H), 0.99 (s, 3H), 0.95 (s, 3H).

Example 170

Preparation of 4-((1R,3aS,5aR,5bR,7aR,11aS,11bR, 13aR,13bR)-3a-(((4-methoxy-4-oxobutanamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

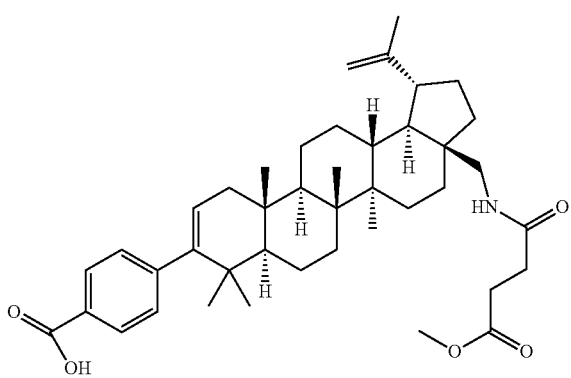

To a solution of 4-((1R,3aS,5aR,5bR,7aR,11aS,11bR, 13aR,13bR)-3a-((3-carboxypropanamido)methyl)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid (20 mg, 0.037 mmol) in methanol (2 ml) was added TFA to form a 0.1% v/v TFA-methanol solution. The mixture was stirred at rt for 28 h. The solvent was removed in vacuo and the resulting residue was purified by prep. HPLC. The product was isolated as a white solid (1.1 mg, 4.55%). LCMS: m/e 658.5 (MH+), 2.90 min (method 3). $^1$H NMR (400 MHz, MeOD) δ ppm 7.94 (d, J=8.5 Hz, 2H), 7.16-7.34 (m, 2H), 5.32 (dd, J=6.4, 1.6 Hz, 1H), 4.74 (d, J=2.0 Hz, 1H), 4.62 (s, 1H), 3.68 (s, 3H), 3.54 (d, J=13.6 Hz, 1H), 3.04 (d, J=13.8 Hz, 1H), 2.57-2.71 (m, 2H), 2.44-2.57 (m, 2H), 2.17 (dd, J=17.2, 6.4 Hz, 1H), 2.09 (dd, J=13.1, 1.8 Hz, 1H), 1.85 (dd, J=12.2, 3.4 Hz, 2H), 1.65-1.82 (m, 8H), 1.61 (br. s., 2H), 1.53 (d, J=10.5 Hz, 3H), 1.48 (d, J=2.0 Hz, 1H), 1.35-1.45 (m, 3H), 1.24-1.35 (m, 3H), 1.16-1.24 (m, 4H), 1.02-1.16 (m, 8H), 0.99 (s, 3H), 0.95 (s, 3H).

Example 171

Preparation of N-(dimethylsulfamoyl)-4-((1R,3aS, 5aR,5bR,7aR,11aS,11bR,13aR,13bR)-3a-(((3-(1,1-dioxido-4-thiomorpholinyl)propyl)amino)methyl)-1-isopropenyl-5a,5b,8,8,11a-pentamethyl-2,3,3a,4,5, 5a,5b,6,7,7a,8,11,11a,11b,12,13,13a,13b-octadecahydro-1H-cyclopenta[a]chrysen-9-yl)benzamide

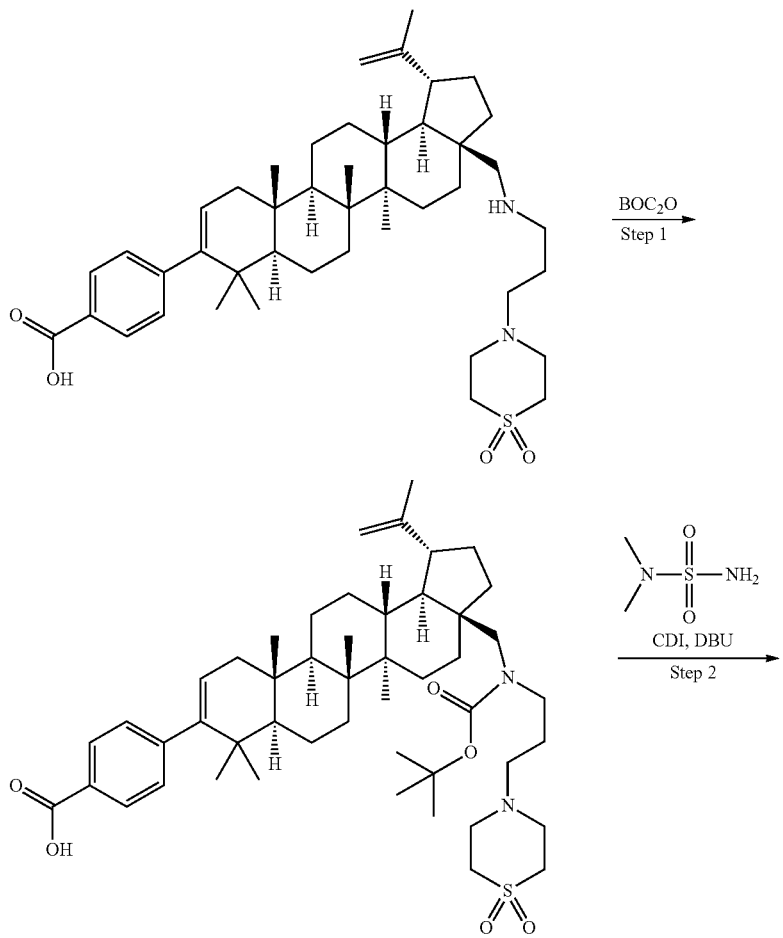

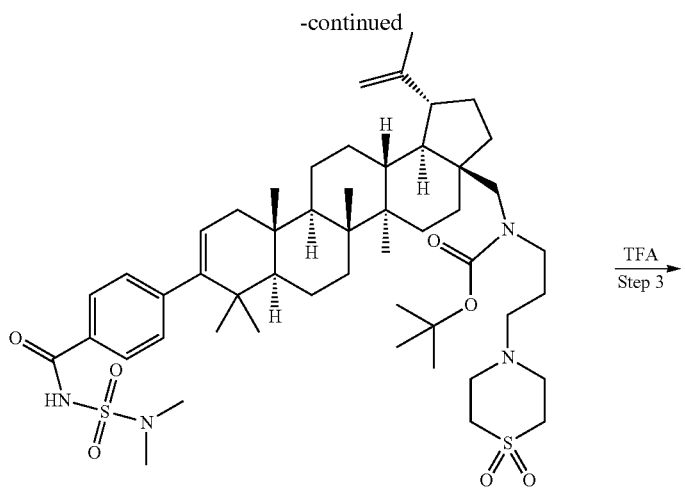

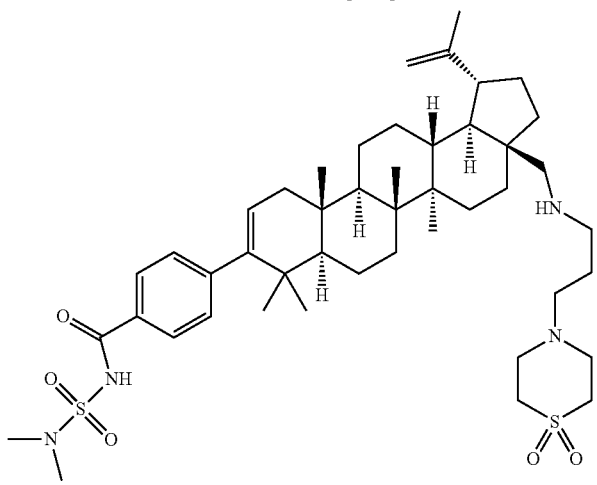

Example 171

Step 1. BOC Protection of the Secondary Amine

To a solution of 4-((1R,3aS,5aR,5bR,7aR,11aS,11bR,13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b,12,13,13a,13b-octadecahydro-1H-cyclopenta[a]chrysen-9-yl)benzoic acid (57 mg, 0.079 mmol) in DCM (2 ml) was added di-tert-butyl dicarbonate (26.0 mg, 0.119 mmol) followed by DMAP (9.68 mg, 0.079 mmol) and DIPEA (0.014 ml, 0.079 mmol). The mixture was stirred at rt for 18 h. The solvent was removed in vacuo, and the resulting solid was carried to the next step without further purification. LCMS: m/e 819.3 (MH$^+$), 2.65 min (method 3).

Step 2. Coupling

To a solution of the material from Step 1 (57 mg, 0.070 mmol) in THF (2 ml) was added carbonyl diimidazole (19.36 mg, 0.119 mmol). The mixture was stirred at rt for 2 h. N,N-dimethylsulfamide (24.11 mg, 0.199 mmol) was added followed by DBU (0.030 ml, 0.199 mmol). The resulting mixture was stirred for 12 h at rt. The reaction was quenched by 1N HCl, and extracted with ethyl acetate (3×10 ml). The organic layers were collected and dried over sodium sulfate. The material obtained was used in next step without further purification. LCMS: m/e 925.6 (MH$^+$), 2.56 min (method 3).

Step 3. De-BOC hydrolysis

To a solution of the material from Step 2 (5 mg, 0.0054 mmol) in DCM (5 ml) was added TFA (0.5 ml, 6.49 mmol). The mixture was stirred at room temperature for 16 h. The mixture was concentrated under reduced pressure. The residue was dissolved in dioxane and MeOH and was purified by prep. HPLC to afford N-(dimethylsulfamoyl)-4-((1R,3aS,5aR,5bR,7aR,11aS,11bR,13aR,13bR)-3a-(((3-(1,1-dioxido-4-thiomorpholinyl)propyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzamide as a white solid (1.3 mg, 29.2%). LCMS: m/e 825.5 (MH$^+$), 2.41 min (method 3). $^1$H NMR (400 MHz, MeOD) δ ppm 7.81 (m, J=8.3 Hz, 2H), 7.28 (m, J=8.5 Hz, 2H), 5.27-5.40 (m, 1H), 4.78 (s, 1H), 4.68 (s, 1H), 3.23-3.31 (m, 1H), 3.13-3.23 (m, 6H), 3.09 (br. s., 4H), 3.00 (s, 6H), 2.88 (s, 1H), 2.74 (t, J=6.7 Hz, 2H), 2.54 (br. s., 1H), 2.17 (s, 1H), 1.96 (d, J=8.5 Hz, 2H), 1.76 (s, 8H), 1.54 (br. s., 8H), 1.39 (d, J=3.5 Hz, 3H), 1.31 (br. s., 4H), 1.17-1.23 (m, 4H), 1.11 (s, 3H), 1.07 (s, 3H), 1.00 (s, 3H), 0.98 (s, 3H)

Example 172

Preparation of benzamide, N-(cyclopropylsulfonyl)-4-((1R,3aS,5aR,5bR,7aR,11aS,11bR,13aR,13bR)-3a-(((3-(1,1-dioxido-4-thiomorpholinyl)propyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzamide

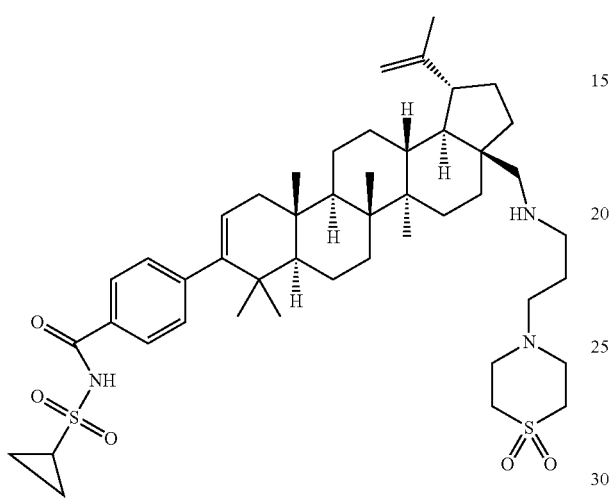

The title compound was prepared following the procedure described above for the preparation of N-(dimethylsulfamoyl)-4-((1R,3aS,5aR,5bR,7aR,11aS,11bR,13aR,13bR)-3a-(((3-(1,1-dioxido-4-thiomorpholinyl)propyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzamide, example 181, using cyclopropanesulfonamide as the reactant amine. The product was isolated as a white solid (32 mg, 68.5%). LCMS: m/e 822.5 (MH$^+$), 2.38 min (method 3). $^1$H NMR (400 MHz, MeOD) δ ppm 7.84 (m, 2H), 7.29 (m, 2H), 5.22-5.38 (m, 1H), 4.78 (d, J=1.5 Hz, 1H), 4.66 (s, 1H), 3.49-3.65 (m, 4H), 3.36-3.46 (m, 4H), 3.19-3.31 (m, 3H), 3.14-3.19 (m, 1H), 3.11 (t, J=7.4 Hz, 2H), 2.89 (d, J=13.1 Hz, 1H), 2.53 (td, J=10.5, 5.6 Hz, 1H), 2.00-2.24 (m, 4H), 1.66-1.91 (m, 10H), 1.43-1.66 (m, 8H), 1.28-1.43 (m, 5H), 1.12-1.28 (m, 7H), 1.09 (s, 3H), 1.05 (s, 3H), 0.99 (s, 3H), 0.97 (s, 3H).

Example 173

Preparation of 4-((1R,3aS,5aR,5bR,7aR,11aS,11bR,13aR,13bR)-3a-(((4-(((cyclopropylsulfonyl)amino)-4-oxobutanoyl)(3-(1,1-dioxido-4-thiomorpholinyl)propyl)amino)methyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

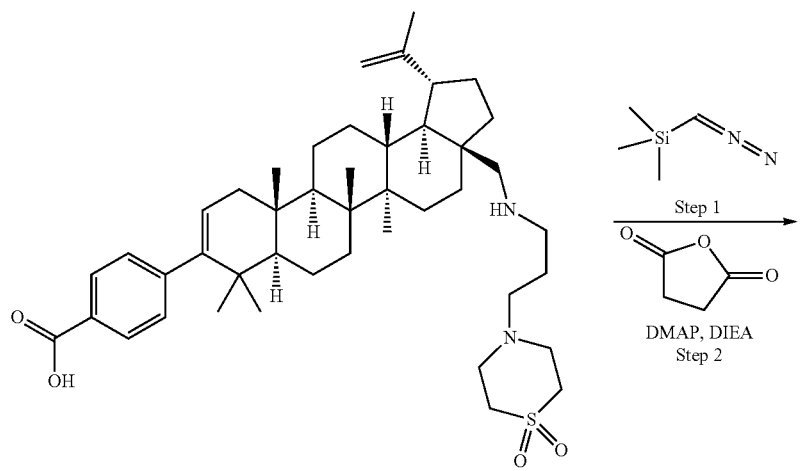

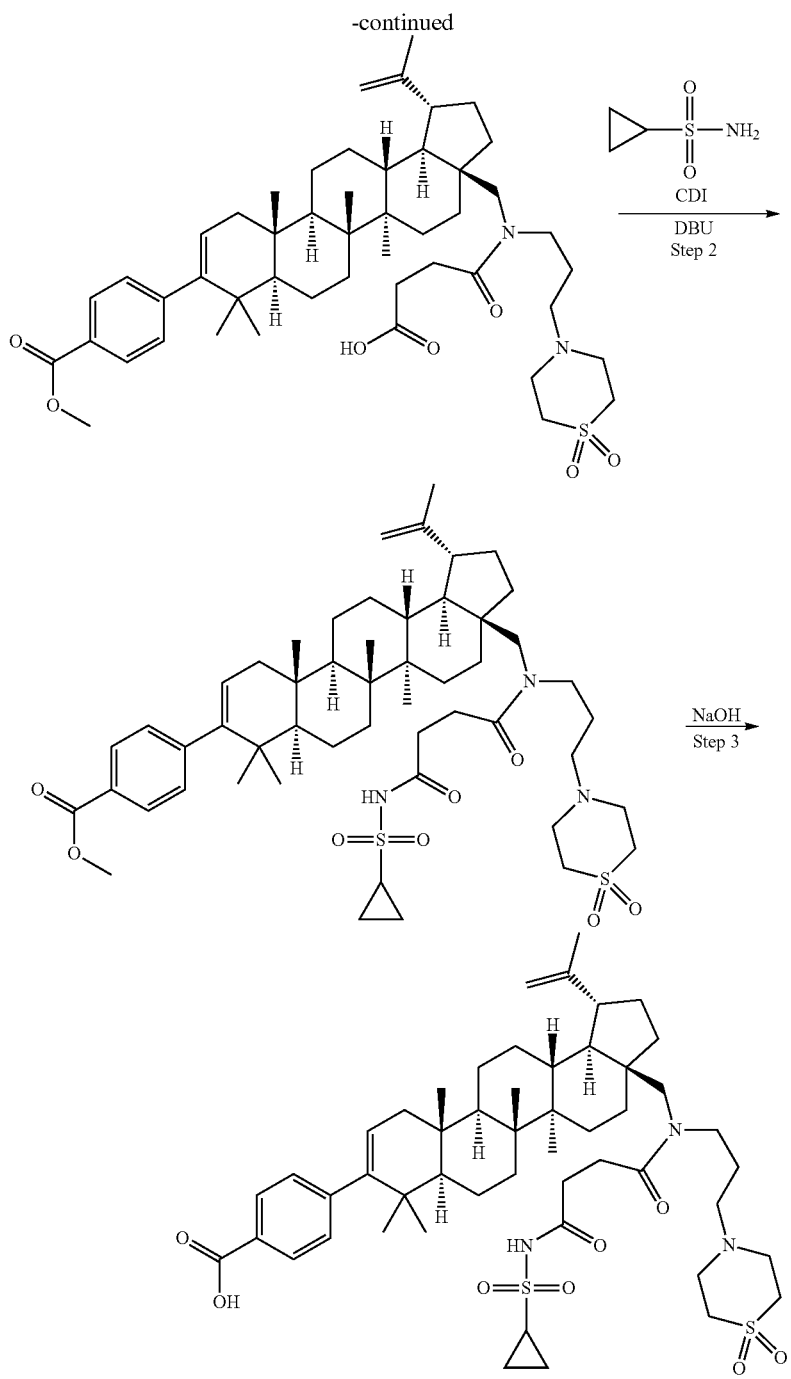

Example 173

Step 1. Methyl ester formation

To a solution of 4-((1R,3aS,5aR,5bR,7aR,11aS,11bR,13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b,12,13,13a,13b-octadecahydro-1H-cyclopenta[a]chrysen-9-yl)benzoic acid (300 mg, 0.42 mmol) in $CH_2Cl_2$ (50 ml)/MeOH (5 ml) was added (diazomethyl)trimethylsilane (2.053 ml, 4.11 mmol). The resulting solution was stirred at rt for 2 h under nitrogen. LC/MS showed no SM remaining. The reaction mixture was concentrated to give (100%) crude product. LCMS: m/e 733.3 ($MH^+$), 2.52 min (method 2).

Step 2. Acylation

To a solution of methyl, 4-((1R,3aS,5aR,5bR,7aR,11aS,11bR,13aR,13bR)-5a,5b,8,8,11a-pentamethyl-1-(prop-1-en-2-yl)-3a-((3-(1-dioxo-thiomorpholino)propylamino)methyl)-2,3,3a,4,5,5a,5b,6,7,7a,8,11,11a,11b,12,13,13a,13b-octadecahydro-1H-cyclopenta[a]chrysen-9-yl)benzoate (16 mg, 0.022 mmole) in $CH_2Cl_2$ (0.5 ml) was added dihydrofuran-2,5-dione (3.28 mg, 0.033 mmol) followed by DMAP (3.07 mg, 0.022 mmol) and DIPEA (0.011 ml, 0.065 mmol). The mixture was stirred at rt for 18 h. The solvent was removed in vacuo and the resulting residue was used in next step without further purification. LCMS: m/e 833.3 (MH+), 2.45 min (method 3).

Step 3. Sulfonamide Formation

To a solution of material from Step 2 (20 mg, 0.024 mmol) in THF (2 ml) was added CDI (4.67 mg, 0.029 mmol). The mixture was stirred at rt for two hours. To the resulting solution was added cyclopropanesulfonamide (5.82 mg, 0.048 mmol), followed by DBU (7.24 µl, 0.048 mmol). The reaction mixture was stirred for 6 h at rt. The solvent was removed under reduced pressure, the residue was redissolved into CH$_2$Cl$_2$ and the solution was washed with aqueous sodium bicarbonate. The organic layer was collected and dried over sodium sulfate. The material obtained was used in the next saponification step without further purification. LCMS: m/e 936.6 (MH+), 2.60 min (Method 3).

Step 4. Alkaline Hydrolysis of Methyl Ester

To a solution of material from Step 3 (18 mg, 0.019 mmol) in dioxane (1.5 ml) was added sodium hydroxide (0.5 ml, 1 N, 500 mmol). The resulting solution was stirred at 63° C. for 12 h the solvent was removed in vacuo and the resulting residue was purified by prep. HPLC to afford the title compound as a white solid (8 mg, 42%). LCMS: m/e 922.5 (MH+), 2.42 min (method 3), $^1$H NMR (400 MHz, MeOD) δ ppm 7.94 (m, J=8.0 Hz, 2H), 7.24 (m, J=8.0 Hz, 2H), 5.33 (d, J=6.3 Hz, 1H), 4.76 (s, 1H), 4.68 (s, 1H), 3.84 (br. s., 2H), 3.59-3.75 (m, 4H), 3.48-3.59 (m, 3H), 3.40-3.48 (m, 2H), 3.06-3.21 (m, 1H), 2.84-3.06 (m, 2H), 2.75-2.84 (m, 2H), 2.54-2.75 (m, 3H), 2.03-2.27 (m, 4H), 1.91 (d, J=16.6 Hz, 2H), 1.81 (br. s., 2H), 1.65-1.79 (m, 6H), 1.52-1.65 (m, 5H), 1.48 (br. s., 2H), 1.35-1.45 (m, 2H), 1.17-1.35 (m, 8H), 1.10-1.17 (m, 4H), 1.02-1.10 (m, 6H), 0.91-1.02 (m, 6H).

The title compound was prepared using the procedure described previously for the preparation of intermediate 3, using ketone intermediate B2 as starting material (29%). $^1$H NMR (400 MHz, CHLOROFORM-d) δ ppm 0.65 (s, 3H), 0.91 (s, 3H), 0.94 (s, 3H), 0.97 (s, 3H), 1.04 (s, 3H), 1.05-1.12 (m, 1H), 1.14 (s, 6H), 1.16-1.28 (m, 3H), 1.28-1.42 (m, 2H), 1.42-1.54 (m, 2H), 1.57-1.65 (m, 2H), 1.68 (d, J=14.56 Hz, 2H), 1.73 (d, J=4.52 Hz, 1H), 1.78-1.84 (m, 2H), 1.86 (dd, J=5.90, 4.14 Hz, 1H), 1.90-1.97 (m, 1H), 1.98-2.04 (m, 1H), 2.12 (dd, J=17.07, 6.78 Hz, 1H), 2.93 (dd, J=13.93, 4.14 Hz, 1H), 5.03-5.14 (m, 3H), 5.33 (t, J=3.51 Hz, 1H), 5.58 (dd, J=6.78, 2.01 Hz, 1H), 7.34-7.38 (m, 5H); $^{19}$F NMR (376.46 MHz, CHLOROFORM-d) δ ppm −74.84.

Example 174

Preparation of 4-((1R,3aS,5aR,5bR,7aR,11aS,11bR, 13aR,13bR)-3a-(aminomethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoic acid

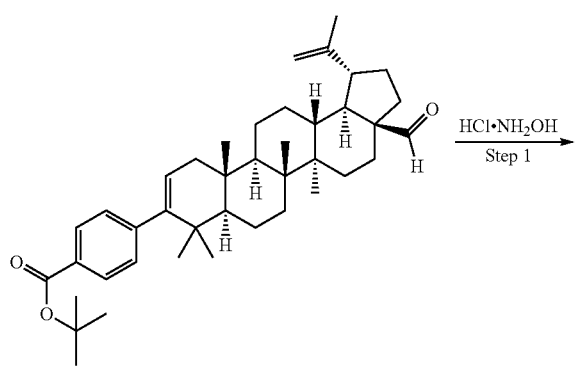

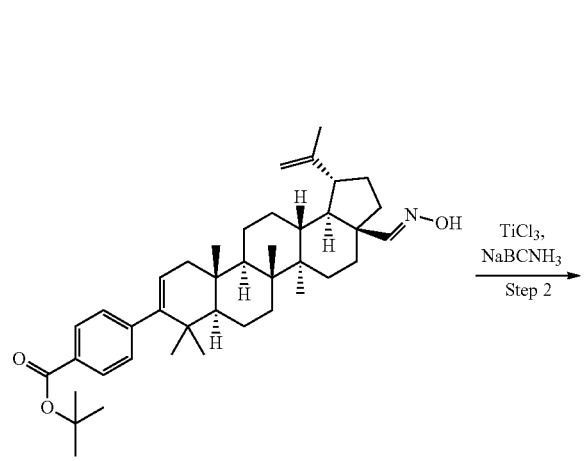

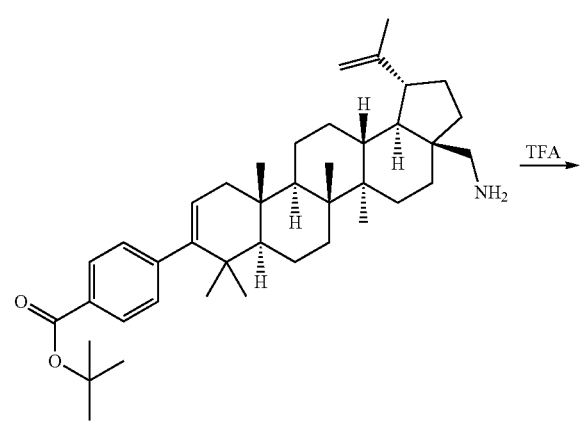

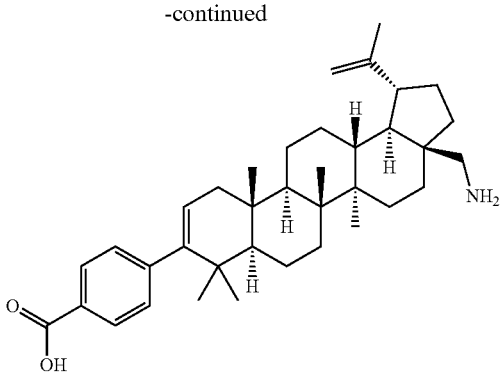

Step 1. Preparation of tert-butyl 4-((1R,3aS,5aR, 5bR,7aR,11aS,11bR,13aR,13bR)-3a-((E)-(hydroxyimino)methyl)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoate To a suspension of tert-butyl 4-((1R,3aS,5aR,5bR,7aR, 11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate (200 mg, 0.334 mmol) in EtOH (20 mL) was added hydroxylamine hydrochloride (186 mg, 2.67 mmol) and potassium carbonate (369 mg, 2.67 mmol) and the mixture was stirred overnight at room temperature. LC/MS showed the mass of the expected product. The mixture was diluted with 7 mL of sat. NaHCO$_3$ and was extracted with dichloromethane (3×7 mL). The combined organic layers were dried with Na$_2$SO$_4$. The drying agent was removed by filtration and the filtrate was concentrated under reduced pressure. The crude product as an off white foam (~100%) was used in the next step with no additional purification. LCMS: m/e 614.53 (MH$^+$), 3.82 min (method 3). $^1$H NMR (400 MHz, CHLOROFORM-d) δ ppm 7.90 (2H, m, J=8.3 Hz), 7.60 (1H, s), 7.19 (2H, m, J=8.3 Hz), 5.23-5.35 (1H, m), 4.76 (1H, d, J=1.8 Hz), 4.64 (1H, s), 2.56 (1H, td, J=11.0, 5.4 Hz), 2.05-2.19 (1H, m), 1.92-2.05 (2H, m), 1.83-1.92 (2H, m), 1.64-1.82 (7H, m), 1.58-1.64 (9H, m), 1.38-1.57 (9H, m), 1.22-1.31 (2H, m), 1.10-1.20 (2H, m), 1.07 (3H, s), 1.04 (3H, s), 0.97-1.01 (3H, m), 0.85-0.97 (6H, m)

Step 2. Preparation of tert-butyl 4-((1R,3aS,5aR, 5bR,7aR,11aS,11bR,13aR,13bR)-3a-(aminomethyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoate To the crude product from above containing tert-butyl 4-((1R,3aS,5aR,5bR,7aR,11aS,11bR,13aR,13bR)-3a-((hydroxyimino)methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate (100 mg, 0.163 mmol) in a 100 mL pear shape flask was added EtOH (12 mL) to form a clear solution. To this was added excess of NH$_4$Cl (400 mg, 5.19 mmol) and sodium cyanoborohydre (300 mg, 4.77 mmol). The mixture was stirred in an ice bath until cold. To this suspension was added titanium(III) chloride (4 mL, 0.163 mmol) 20% solution. The resulting mixture was blanketed with nitrogen. The ice bath was removed and the stirring was continued at rt for an hour. LCMS show the reaction was complete. At this point, the mixture was dark greenish-blue-purple. A solution of sodium hydroxide (3 mL, 10N in 25 mL water) was added into the reaction mixture, along with methylene chloride (30 mL).

The mixture was stirred vigorously until the dark blue phase was floating on top of the organic phase. The mixture was filtered through a plug of paper to afford a clear filtrate. The two-phase filtrate was tested for pH of the top phase (pH), and LCMS of the bottom phase was taken. The organic layer was collected and the aqueous layer was extracted with CH$_2$Cl$_2$ (2×20 mL). The organic layers were combined and dried over NaSO$_4$ to afford an off white solid (95 mg, 97.0%) which was used without further purification in the next step). LCMS: m/e 600.58 (MH$^+$), 3.03 min (method 3). $^1$H NMR (400 MHz, CHLOROFORM-d) δ ppm 7.90 (2H, m, J=8.3 Hz), 7.19 (2H, m, J=8.3 Hz), 5.29 (1H, dd, J=6.2, 1.6 Hz), 4.71 (1H, d, J=2.3 Hz), 4.61 (1H, s), 2.89 (1H, d, J=12.8 Hz), 2.44 (1H, td, J=11.0, 5.7 Hz), 2.36 (1H, d, J=13.3 Hz), 2.11 (1H, dd, J=17.1, 6.5 Hz), 1.75-1.99 (2H, m), 1.71 (5H, s), 1.57-1.70 (9H, m), 1.36-1.57 (9H, m), 1.18-1.32 (5H, m), 1.06-1.18 (6H, m), 1.01-1.06 (3H, m), 1.00 (3H, s), 0.90-0.97 (6H, m).

Step 3. Preparation of 4-((1R,3aS,5aR,5bR,7aR, 11aS,11bR,13aR,13bR)-3a-(aminomethyl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid To a solution of tert-butyl 4-((1R,3aS,5aR,5bR,7aR,11aS, 11bR,13aR,13bR)-3a-(aminomethyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoate (15 mg, 0.025 mmol) in DCM (4 mL) was added TFA (0.4 ml, 5.19 mmol) and the mixture was stirred at room temperature. The color of the solution turned pinkish. After 6 h, the solvent was removed in vacuo and the crude was purified by reverse phase prep. HPLC to afford the title compound as a white foam (12 mg, 80%). LCMS: m/e 544.49 (MH$^+$), 2.60 min (method 3). $^1$H NMR (500 MHz, MeOD) δ ppm 7.94 (2H, d, J=8.5 Hz), 7.24 (2H, d, J=8.5 Hz), 5.32 (1H, dd, J=6.3, 1.7 Hz), 4.77 (1H, d, J=1.8 Hz), 4.66 (1H, s), 3.10-3.24 (1H, m), 2.73-2.84 (1H, m), 2.50 (1H, td, J=10.6, 5.6 Hz), 2.17 (1H, dd, J=17.1, 6.4 Hz), 1.98-2.11 (1H, m), 1.67-1.89 (8H, m), 1.54-1.66 (3H, m), 1.44-1.56 (5H, m), 1.33-1.45 (2H, m), 1.27-1.34 (3H, m), 1.23-1.28 (1H, m), 1.15-1.24 (4H, m), 1.11 (3H, s), 1.06 (3H, s), 0.92-1.02 (6H, m).

Example 175

Preparation of 4-((1R,3aS,5aR,5bR,7aR,11aS,11bR, 13aR,13bR)-3a-((isopropylamino)methyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

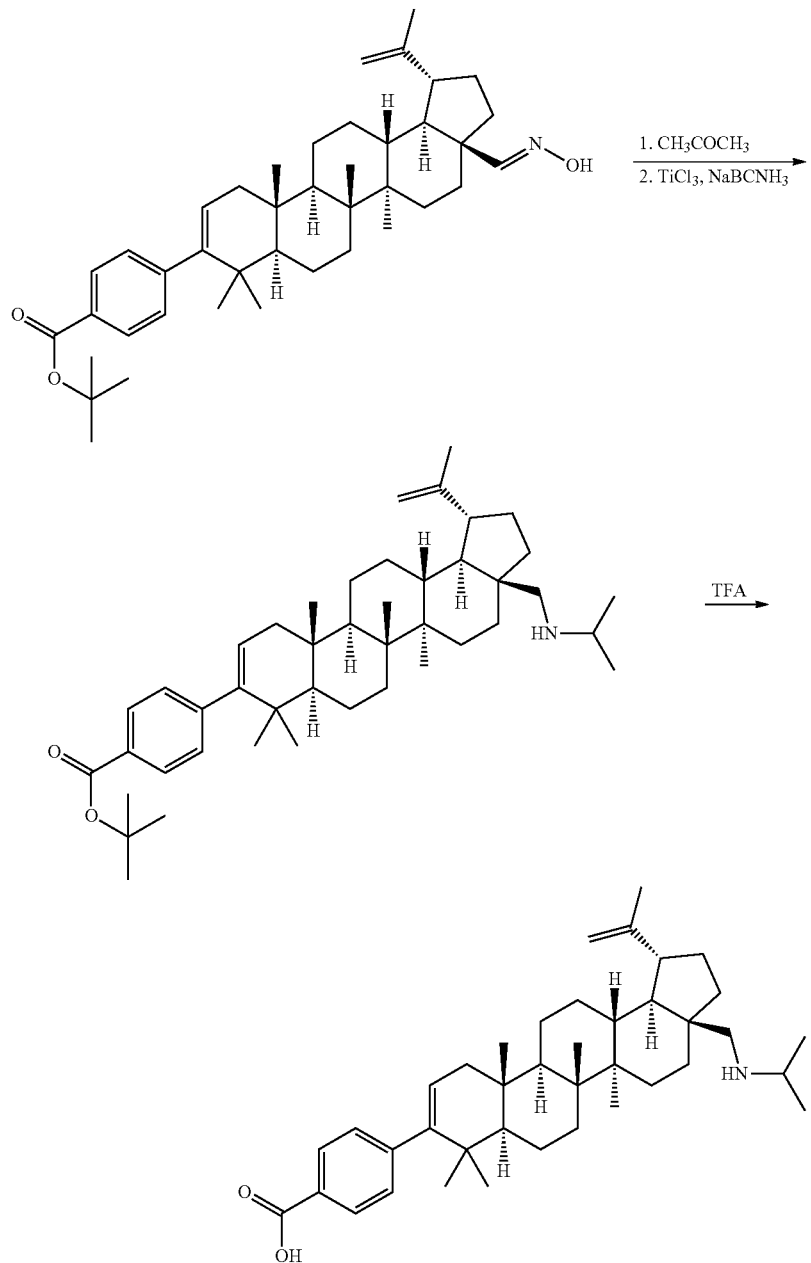

This compound was treated with TiCl$_3$, NaBCNH$_3$ as described above to afford (tert-butyl 4-((1R,3aS,5aR,5bR, 7aR,11aS,11bR,13aR,13bR)-3a-((isopropylamino)methyl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate). LCMS: m/e 642.69 (M+H)$^+$, 2.611 min (method 9 Start % B=75%). $^1$H NMR (400 MHz, CHLOROFORM-d) δ 7.90 (d, J=8.3 Hz, 2H), 7.19 (d, J=8.3 Hz, 2H), 5.30 (dd, J=6.3, 1.8 Hz, 1H), 4.72

During the purification in silica gel chromatography of tert-butyl 4-((1R,3aS,5aR,5bR,7aR,11aS,11bR,13aR, 13bR)-3a-((E)-(hydroxyimino)methyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate, acetone was used. As a result, a small amount of the corresponding acetone aldimine was formed.

(d, J=2.3 Hz, 1H), 4.61 (dd, J=2.1, 1.4 Hz, 1H), 2.82-2.75 (m, J=12.8 Hz, 1H), 2.79-2.71 (m, 1H), 2.79-2.71 (m, 1H), 2.48 (td, J=11.0, 5.8 Hz, 1H), 2.21 (d, J=11.5 Hz, 1H), 2.12 (dd, J=17.2, 6.4 Hz, 1H), 2.02-1.75 (m, 5H), 1.75-1.63 (m, 7H), 1.72 (s, 3H), 1.61 (s, 9H), 1.60-1.53 (m, 3H), 1.51-1.35 (m, 6H), 1.12 (s, 3H), 1.11 (d, J=6.3 Hz, 3H), 1.10 (d, J=6.3 Hz, 3H), 1.02 (s, 3H), 1.00 (s, 3H), 0.94 (s, 6H). $^{13}$C NMR (101

MHz, CHLOROFORM-d) δ 165.6, 159.8, 150.3, 147.9, 145.9, 129.55, 129.37, 128.0, 123.6, 109.2, 80.4, 52.4, 49.0, 48.6, 47.0, 42.3, 41.3, 40.4, 38.9, 37.1, 36.8, 35.9, 33.7, 33.1, 29.4, 29.1, 28.9, 27.9, 26.7, 24.9, 20.9, 20.7, 19.4, 18.9, 16.1, 15.3, 14.4.

Subsequent treatment with TFA to remove the protective group as described above rendered the title compound. LCMS: m/e 586.64 (M+H)+, 2.14 min (method 9). Partial $^1$H NMR (400 MHz, CHLOROFORM-d) δ 7.99 (d, J=8.3 Hz, 2H), 7.23 (d, J=8.3 Hz, 2H), 5.35-5.28 (m, 1H), 4.73 (d, J=1.5 Hz, 1H), 4.66-4.62 (m, 1H), 1.72 (s, 3H), 1.51 (s, 3H), 1.49 (s, 3H), 1.12 (s, 3H), 1.03 (s, 3H), 1.00 (s, 3H), 0.95 (s, 6H).

Example 176

Preparation of 4-((1R,3aS,5aR,5bR,7aR,11aS,11bR, 13aR,13bR)-3a-((3-methoxy-3-oxopropylamino) methyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

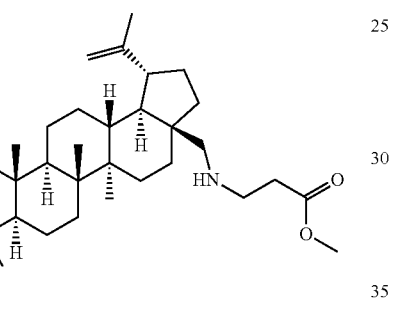

The title compound was prepared following the general procedures described above for the C-28 amine formation and hydrolysis using methyl 3-aminopropanoate as the reactant amine. The product was isolated as a white solid (26 mg, 27.5%). LCMS: m/e 630.3 (MH+), 2.39 min (method 9). $^1$H NMR (400 MHz, CHLOROFORM-d) δ 8.00 (d, J=8.0 Hz, 2H), 7.24 (d, J=8.3 Hz, 2H), 5.31 (d, J=4.5 Hz, 1H), 4.73 (s, 1H), 4.65 (s, 1H), 3.76 (s, 3H), 3.52-3.27 (m, 3H), 2.90 (m, 2H), 2.81 (br. s., 1H), 2.47-2.33 (m, 1H), 2.18-1.95 (m, 2H), 1.93-1.79 (m, 2H), 1.77-1.61 (m, 2H), 1.59-1.38 (m, 7H), 1.37-1.17 (m, 7H), 1.10 (s, 4H), 1.02 (s, 3H), 0.99 (s, 3H), 0.96 (s, 3H), 0.87-0.95 (s, 3H)

Example 177

Preparation of 4-((1R,3aS,5aR,5bR,7aR,11aS,11bR, 13aR,13bR)-3a-(aziridin-1-ylmethyl)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid

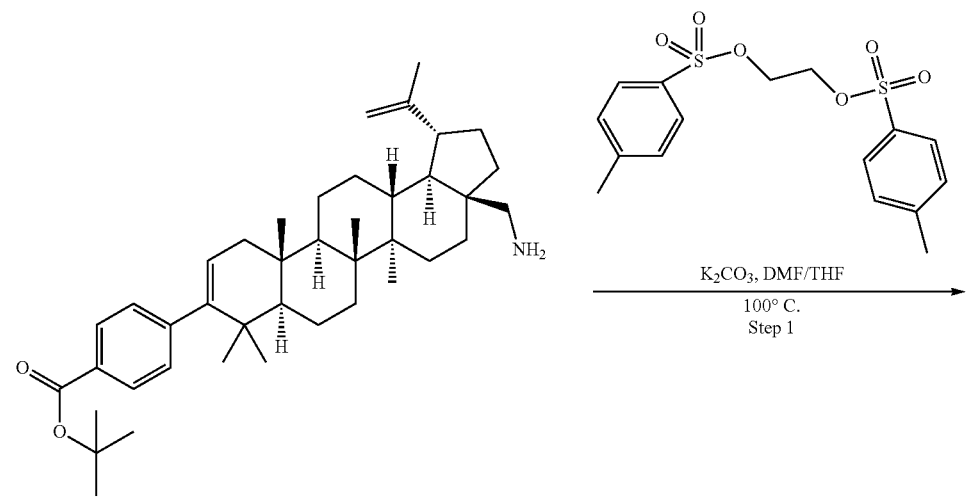

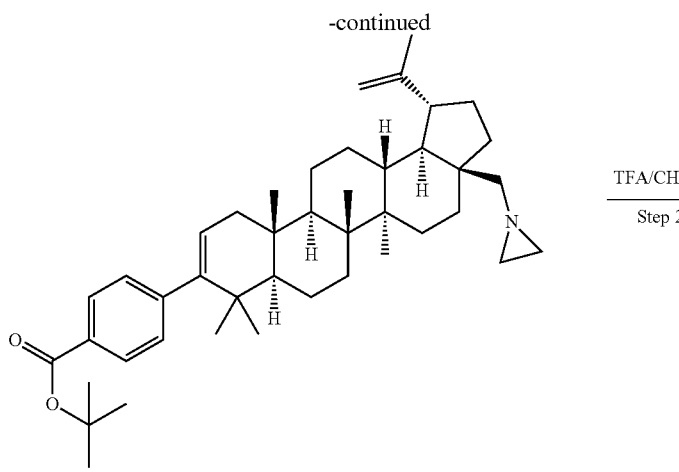

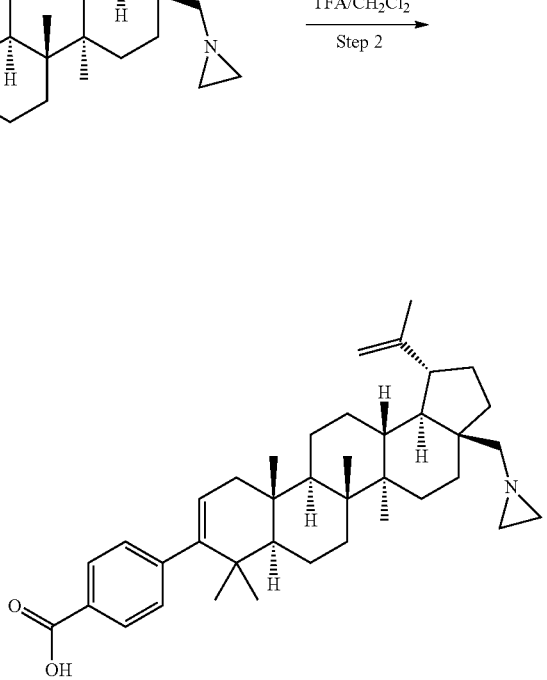

Step 1. Preparation of tert-butyl 4-((1R,3aS,5aR, 5bR,7aR,11aS,11bR,13aR,13bR)-3a-(aziridin-1-ylmethyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate tert-butyl 4-((1R,3aS,5aR,5bR,7aR,11aS,11bR,13aR, 13bR)-3a-(aminomethyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (200 mg, 0.667 mmol) was dissolved in DMF (10.00 mL) and THF (10.00 mL), ethane-1,2-diylbis(4-methylbenzenesulfonate) (247 mg, 0.667 mmol) was added, followed by $K_2CO_3$ (184 mg, 1.333 mmol) and the mixture was stirred at 100° C. until no starting material was detected by LCMS. An M+1=626.7 was observed by LC-MS. The reaction mixture was redissolved in $CH_2Cl_2$ (100 mL), washed by water (2×50 mL) and the organic layer was dried over sodium sulfate. The solvent was removed in vacuo and the resultant residue was purified by silica gel chromatography using a mixture of ethyl acetate/hexanes. A white foam was obtained (130 mg, 65%) LCMS: m/e 426.7 ($MH^+$), 4.393 min (method 8). $^1H$ NMR (400 MHz, CHLOROFORM-d) δ 7.90 (d, J=8.3 Hz, 2H), 7.24-7.11 (m, 2H), 5.30 (d, J=1.8 Hz, 1H), 4.70 (d, J=2.0 Hz, 1H), 4.60 (dd, J=2.3, 1.3 Hz, 1H), 2.56 (d, J=21.1 Hz, 1H), 2.44-2.33 (m, 1H), 2.26-2.05 (m, 3H), 2.04-1.89 (m, 1H), 1.86 (d, J=12.0 Hz, 1H), 1.82-1.58 (m, 18H), 1.56-1.37 (m, 7H), 1.35-1.21 (m, 6H), 1.19-1.06 (m, 6H), 1.03 (s, 3H), 0.99 (s, 3H), 0.93 (m, 6H)

Step 2. Preparation of 4-((1R,3aS,5aR,5bR,7aR, 11aS,11bR,13aR,13bR)-3a-(aziridin-1-ylmethyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid To a solution of tert-butyl 4-((1R,3aS,5aR,5bR,7aR,11aS, 11bR,13aR,13bR)-3a-(aziridin-1-ylmethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate (62 mg, 0.099 mmol) in DCM (4 mL) was added TFA (0.4 ml, 5.19 mmol). The mixture was stirred at rt for 6 h. The solvents were removed in vacuo and the residue was purified by reverse phase prep. HPLC to afford the title compound as a white foam (15 mg, 26.6%) LCMS: m/e 570.36 ($MH^+$), 2.363 min (method 9). $^1H$ NMR (400 MHz, METHANOL-$d_4$) δ 8.02-7.84 (m, 2H), 7.24 (d, J=8.3 Hz, 2H), 5.33 (s, 1H), 4.78 (s, 1H), 4.66 (s, 1H), 3.28-3.14 (m, 1H), 2.93-2.72 (m, 1H), 2.59-2.41 (m, 1H), 2.24-1.95 (m, 2H), 1.92-1.68 (m, 12H), 1.56 (br. s., 8H), 1.31 (m, 5H), 1.19 (m, 5H) 1.10 (s, 3H), 1.06 (s, 3H), 0.99 (s, 3H), 0.97 (s, 3H).

Example 178

Preparation of 4-((1R,3aS,5aR,5bR,7aR,11aS,11bR, 13aR,13bR)-3a-((2-hydroxyethylamino)methyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

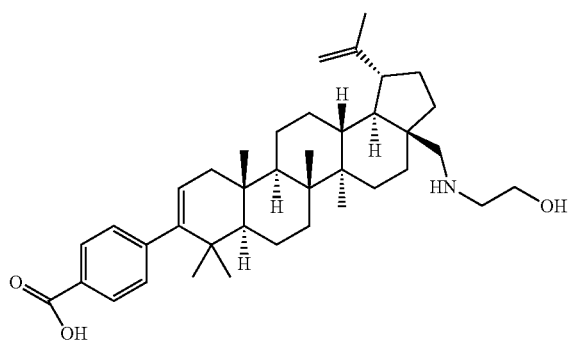

The title compound was prepared following the general procedures described above for the synthesis of 4-((1R,3aS, 5aR,5bR,7aR,11aS,11bR,13aR,13bR)-3a-(aziridin-1-ylmethyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoic acid using 2-bromoethanol as the alkylating reagent in step 1. The product was isolated as a white solid (21.9 mg, 79.9%). LCMS: m/e 588.9 (MH$^+$), 2.373 min (method 9). $^1$H NMR (500 MHz, DMSO-d$_6$) δ 7.88 (d, J=8.2 Hz, 2H), 7.23 (d, J=8.2 Hz, 2H), 5.25 (d, J=4.9 Hz, 1H), 4.72 (s, 1H), 4.61 (s, 1H), 3.74 (m, 2H), 3.14 (br. s., 1H), 3.08 (m, 2H), 2.80-2.68 (m, 1H), 2.45 (m, 1H), 2.12-1.94 (m, 2H), 1.93-1.79 (m, 2H), 1.74-1.58 (m, 8H), 1.57-1.29 (m, 8H), 1.28-1.13 (m, 4H), 1.08 (s, 4H) 1.00 (3H, s), 0.96 (3H, s), 0.91 (6H, s).

Example 179

Preparation of 4-((1R,3aS,5aR,5bR,7aR,11aS,11bR, 13aR,13bR)-5a,5b,8,8,11a-pentamethyl-3a-((2-(4-(methylsulfonyl)piperazin-1-yl)ethylamino)methyl)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

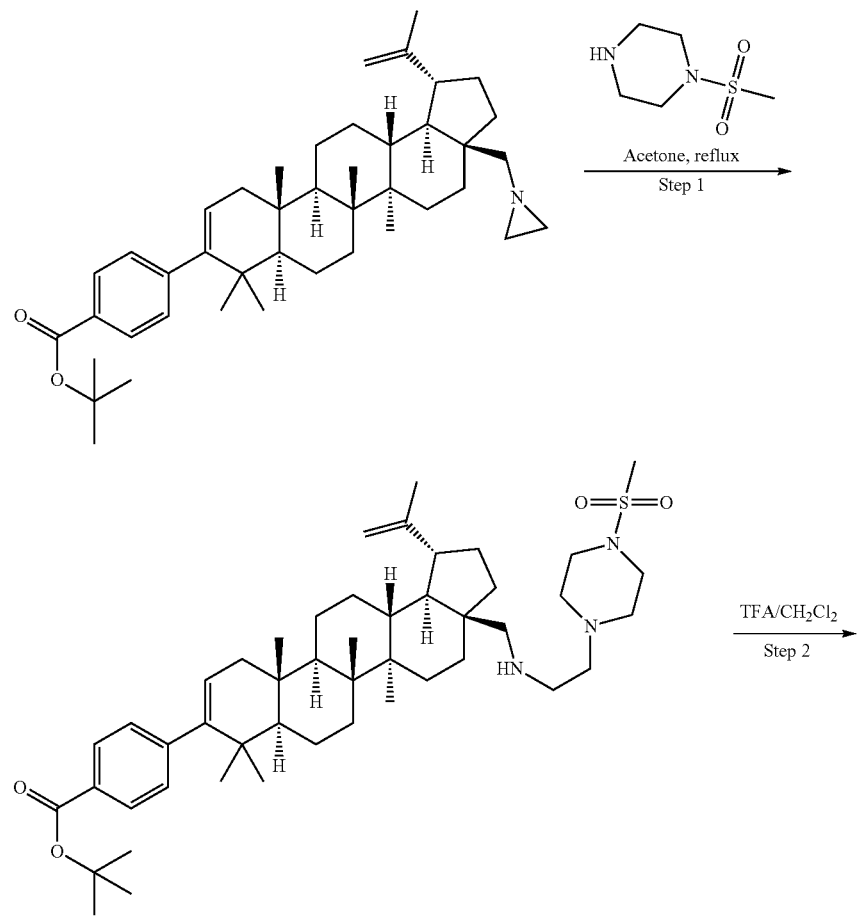

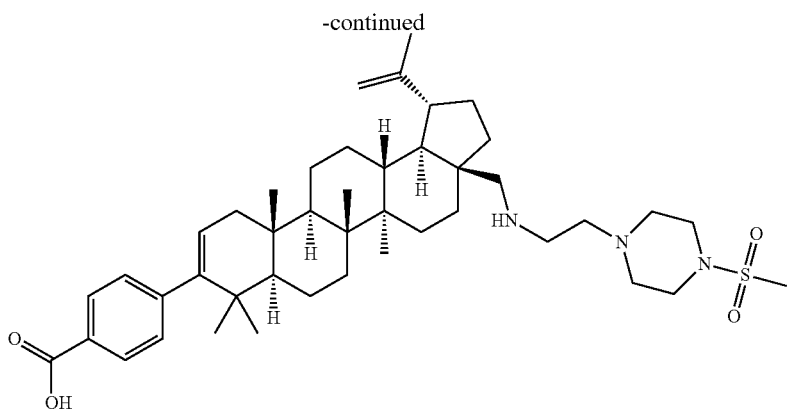

Step 1. Preparation of tert-butyl 4-((1R,3aS,5aR, 5bR,7aR,11aS,11bR,13aR,13bR)-5a,5b,8,8,11a-pentamethyl-3a-((2-(4-(methylsulfonyl)piperazin-1-yl)ethylamino)methyl)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoate A mixture of tert-butyl 4-((1R,3aS,5aR,5bR,7aR,11aS, 11bR,13aR,13bR)-3a-(aziridin-1-ylmethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate (30 mg, 0.048 mmol) and 1-(methylsulfonyl)piperazine (78.7 mg, 0.48 mmol) in acetone (5 mL) was heated at reflux in a sealed tube for 18 h. The desired compound was detected by LCMS (M+1=790.7, 2.96 min, method 9).

Step 2. Preparation of 4-((1R,3aS,5aR,5bR,7aR, 11aS,11bR,13aR,13bR)-5a,5b,8,8,11a-pentamethyl-3a-((2-(4-(methylsulfonyl)piperazin-1-yl)ethylamino)methyl)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)benzoic acid The title compound was prepared following the general procedures described above for the synthesis of 4-((1R,3aS, 5aR,5bR,7aR,11aS,11bR,13aR,13bR)-3a-(aziridin-1-ylmethyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoic acid, step 2. The product was isolated as a white solid (48 mg, 47.5%). LCMS: m/e 734.5 (MH$^+$), 2.35 min (method 9). $^1$H NMR (400 MHz, METHANOL-d$_4$) δ 7.95 (d, J=8.3 Hz, 2H), 7.24 (d, J=8.3 Hz, 2H), 5.36-5.27 (m, 1H), 4.78 (s, 1H), 4.67 (s, 1H), 3.56-3.42 (m, 6H), 3.30 (m, 3H), 3.24-3.09 (m, 4H), 3.06-2.87 (m, 4H), 2.58-2.50 (m, 1H), 2.23-1.99 (m, 2H), 1.94-1.68 (m, 10H), 1.65-1.46 (m, 8H), 1.42-1.24 (m, 4H) 1.19 (m, 4H) 1.10 (3H, s), 1.06 (3H, s), 0.99 (3H, s), 0.97 (3H, s).

Example 180

Preparation of 4-((1R,3aS,5aR,5bR,7aR,11aS,11bR, 13aR,13bR)-3a-((2-methoxyethylamino)methyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

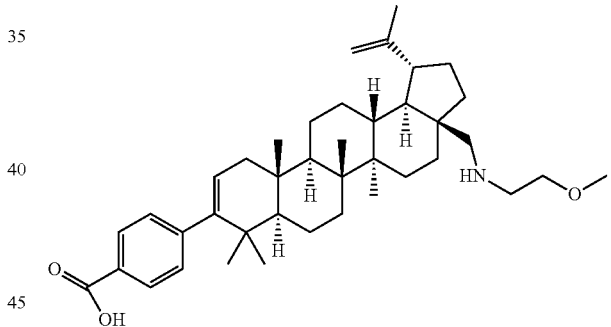

The title compound was prepared from tert-butyl 4-((1R, 3aS,5aR,5bR,7aR,11aS,11bR,13aR,13bR)-3a-(aziridin-1-ylmethyl)-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoate following the procedure described above for the synthesis of 4-((1R,3aS,5aR,5bR,7aR,11aS,11bR,13aR,13bR)-5a,5b,8, 8,11a-pentamethyl-3a-((2-(4-(methylsulfonyl)piperazin-1-yl)ethylamino)methyl)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)benzoic acid, using methanol as reagent in step 1. The product was isolated as a white solid (1.6 mg, 5.2%). LCMS: m/e 602.49 (MH$^+$), 2.40 min (method 9). $^1$H NMR (500 MHz, METHANOL-d$_4$) δ 7.85 (d, J=7.6 Hz, 2H), 7.12 (d, J=7.6 Hz, 2H), 5.29 (s, 1H), 4.79-4.76 (s, 1H), 4.66 (s, 1H), 3.67-3.64 (m, 2H), 3.43 (s, 3H), 3.21-3.15 (m, 3H), 2.69-2.62 (m, 1H), 2.52 (m, 1H), 2.19-2.10 (m, 1H), 2.07-2.00 (m, 1H), 1.79 (m, 8H), 1.57 (m, 8H), 1.40-1.24 (m, 7H), 1.18 (m, 4H), 1.09 (3H, s), 1.05 (3H, s), 0.97 (3H, s), 0.96 (3H, s).

Example 181

Preparation of 4-((1R,3aS,5aR,5bR,7aR,11aS,11bR,13aR,13bR)-3a-((2-(4-(hydroxymethyl)piperidin-1-yl)ethylamino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

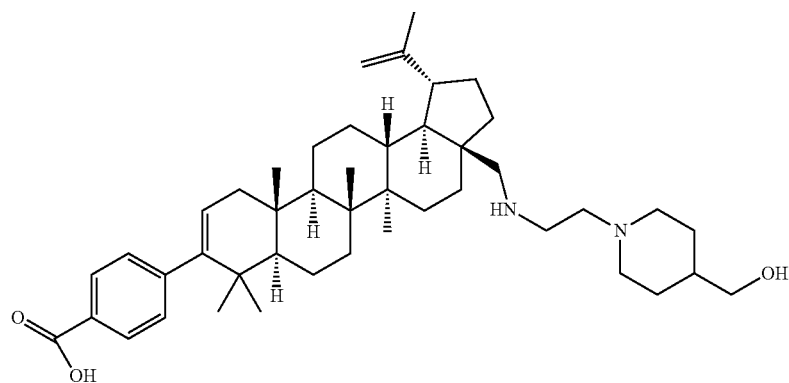

The title compound was prepared from tert-butyl 4-((1R,3aS,5aR,5bR,7aR,11aS,11bR,13aR,13bR)-3a-(aziridin-1-ylmethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the procedure described above for the synthesis of 4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethylamino)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, using piperidin-4-ylmethanol as reagent in step 1. The product was isolated as a white solid (5 mg, 16.7%). LCMS: m/e 685.5 (MH$^+$), 2.33 min (method 9). $^1$H NMR (400 MHz, METHANOL-d$_4$) δ 7.90 (d, J=8.0 Hz, 2H), 7.20 (d, J=8.0 Hz, 2H), 5.28 (d, J=4.5 Hz, 1H), 4.74 (br. s., 1H), 4.63 (br. s., 1H), 3.74-3.38 (m, 8H), 3.07 (br. s., 2H), 2.98-2.85 (m, 2H), 2.48 (br. s., 1H), 2.21-1.93 (m, 4H), 1.90-1.64 (m, 11H), 1.63-1.40 (m, 10H), 1.39-1.24 (m, 4H), 1.23-1.09 (m, 4H), 1.04 (m, 6H), 0.94 (m, 6H).

Example 182

Preparation of 4-((1R,3aS,5aR,5bR,7aR,11aS,11bR,13aR,13bR)-a,5b,8,8,11a-pentamethyl-3a-((2-oxooxazolidin-3-yl)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

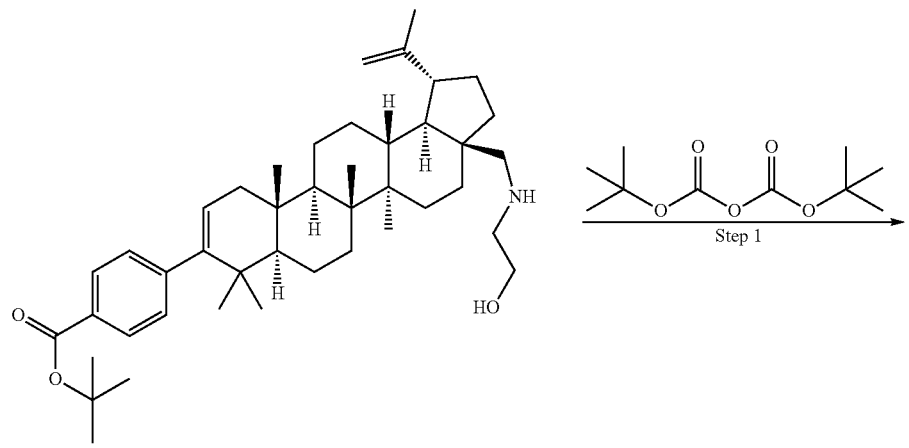

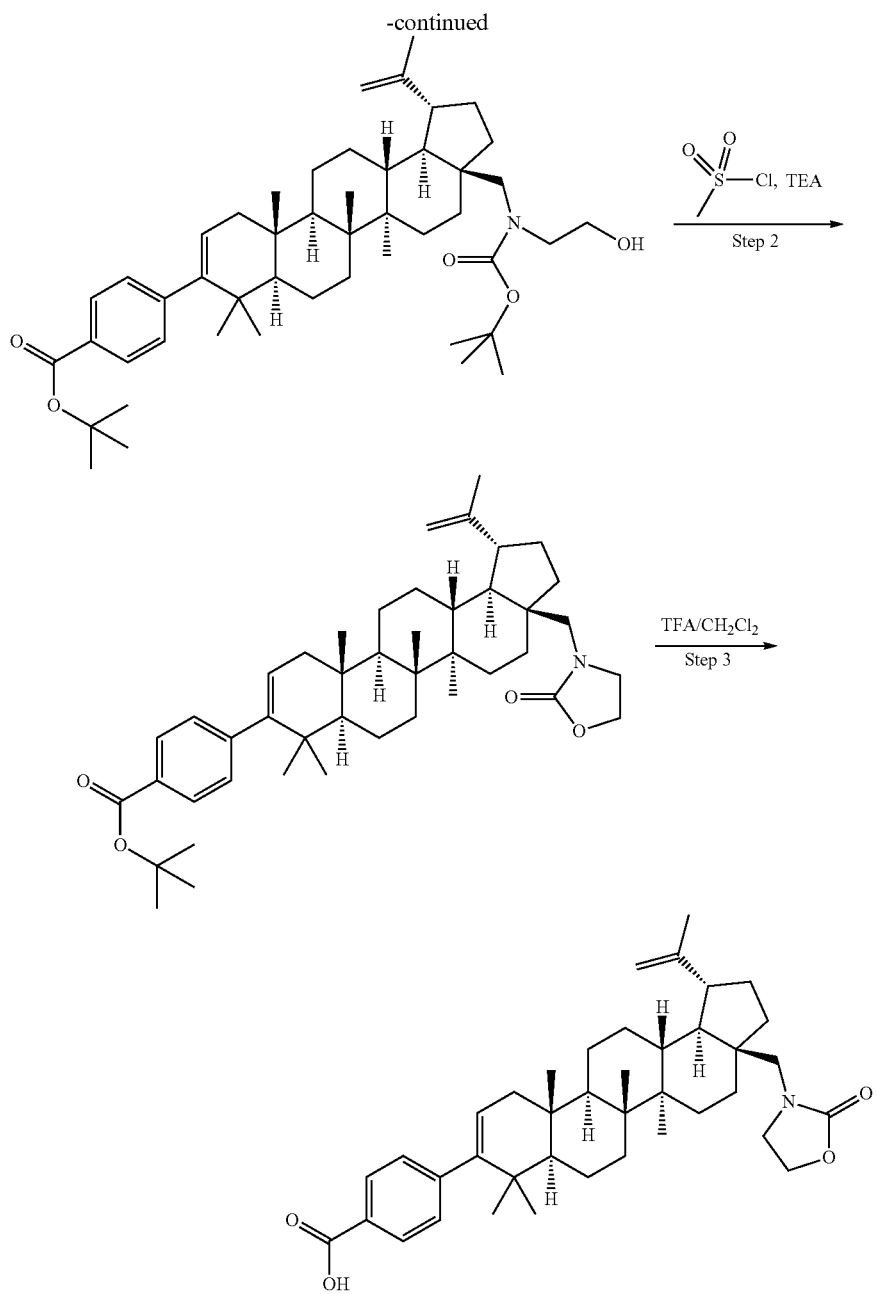

Step 1. Preparation of tert-butyl 4-((1R,3aS,5aR, 5bR,7aR,11aS,11bR,13aR,13bR)-3a-((tert-butoxy-carbonyl(2-hydroxyethyl)amino)methyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate tert-butyl 4-((1R,3aS,5aR,5bR,7aR,11aS,11bR,13aR, 13bR)-3a-((2-hydroxyethylamino)methyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate (600 mg, 0.932 mmol) was dissolved in CH$_2$Cl$_2$ (10 mL), BOC$_2$O (0.260 mL, 1.118 mmol) was added followed by Hunig's Base (0.163 mL, 0.932 mmol) to form a colorless solution that was stirred at 0° C. for 6 hrs. LCMS indicated formation of desired product (M+23=767). The solvent was removed in vacuo and the resultant white solid was used as is in the next step.

Step 2. Preparation of tert-butyl 4-((1R,3aS,5aR, 5bR,7aR,11aS,11bR,13aR,13bR)-3a-((tert-butoxy-carbonyl(2-hydroxyethyl)amino)methyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate tert-butyl 4-((1R,3aS,5aR,5bR,7aR,11aS,11bR,13aR, 13bR)-3a-(((tert-butoxycarbonyl)(2-hydroxyethyl)amino) methyl)-5a,5b,8,8,11a-pentamethyl-1-(prop-1-en-2-yl)-2,3, 3a,4,5,5a,5b,6,7,7a,8,11,11a,11b,12,13,13a,13b- octadecahydro-1H-cyclopenta[a]chrysen-9-yl)benzoate (133 mg, 0.179 mmol) was dissolved in $CH_2Cl_2$ (5 mL) and the solution was cooled at 0° C. Methanesulfonyl chloride (30.7 mg, 0.268 mmol) was added followed by TEA (0.050 mL, 0.357 mmol) and the mixture was stirred for 18 h. The solvent was removed and the resultant residue was purified by silica gel chromatography to afford the title compound as a white solid (100 mg, 83.3%). $^1$H NMR (400 MHz, CHLOROFORM-d) δ 7.95-7.86 (m, J=8.3 Hz, 2H), 7.24-7.10 (m, J=8.3 Hz, 2H), 5.36-5.24 (m, 1H), 4.82-4.68 (m, 1H), 4.62 (s, 1H), 4.39-4.26 (m, 2H), 3.75-3.59 (m, 2H), 3.46 (d, J=13.8 Hz, 1H), 3.10 (d, J=14.3 Hz, 1H), 2.58-2.39 (m, 1H), 2.24-2.04 (m, 2H), 1.98-1.69 (m, 8H), 1.69-1.58 (m, 12H), 1.57-1.39 (m, 8H), 1.36-1.22 (m, 4H), 1.21-1.07 (m, 5H), 1.07-0.97 (m, 6H), 0.97-0.80 (m, 6H).

Step 3. Preparation of 4-((1R,3aS,5aR,5bR,7aR,11aS,11bR,13aR,13bR)-5a,5b,8,8,11a-pentamethyl-3a-((2-oxooxazolidin-3-yl)methyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid The title compound was prepared following step 2 of the procedure described above for the synthesis of 4-((1R,3aS,5aR,5bR,7aR,11aS,11bR,13aR,13bR)-3a-(aziridin-1-ylmethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid. The product was isolated as a white solid (15 mg, 14.7%). LCMS: m/e 614.5 (MH$^+$), 2.47 min (method 8). $^1$H NMR (400 MHz, CHLOROFORM-d) δ 8.02 (d, J=8.3 Hz, 2H), 7.24 (d, J=8.3 Hz, 2H), 5.32 (d, J=4.5 Hz, 1H), 4.74 (s, 1H), 4.62 (s, 1H), 4.34 (t, J=7.9 Hz, 2H), 3.81-3.59 (m, 2H), 3.47 (m, 2H), 3.20-3.00 (m, 1H), 2.51 (td, J=11.2, 5.5 Hz, 1H), 2.26-2.06 (m, 2H), 1.97-1.66 (m, 10H), 1.50-1.22 (m, 10H), 1.15 (s, 4H), 1.06-0.83 (m, 13H)

BIOLOGY DATA FOR THE EXAMPLES

"µM" means micromolar;
"mL" means milliliter;
"µl" means microliter;
"mg" means milligram;
"µg" means microgram;

The materials and experimental procedures used to obtain the results reported in Tables 1-2 are described below.

HIV cell culture assay—MT-2 cells and 293T cells were obtained from the NIH AIDS Research and Reference Reagent Program. MT-2 cells were propagated in RPMI 1640 media supplemented with 10% heat inactivated fetal bovine serum, 100 µg/ml penicillin G and up to 100 units/ml streptomycin. The 293T cells were propagated in DMEM media supplemented with 10% heat inactivated fetal bovine serum (FBS), 100 units/ml penicillin G and 100 µg/ml streptomycin. The proviral DNA clone of $NL_{4-3}$ was obtained from the NIH AIDS Research and Reference Reagent Program. A recombinant $NL_{4-3}$ virus, in which a section of the nef gene from NL4-3 was replaced with the Renilla luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) µL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$ data for the compounds is shown in Table 2. Table 1 is the key for the data in Table 2.

Results

TABLE 1

Biological Data Key for $EC_{50}$

| Compounds with $EC_{50}$ > 0.1 µM | Compounds with $EC_{50}$ < 0.1 µM |
| --- | --- |
| Group "B" | Group "A" |

TABLE 2

| Example # | Structure | $EC_{50}$ |
| --- | --- | --- |
| 1 | 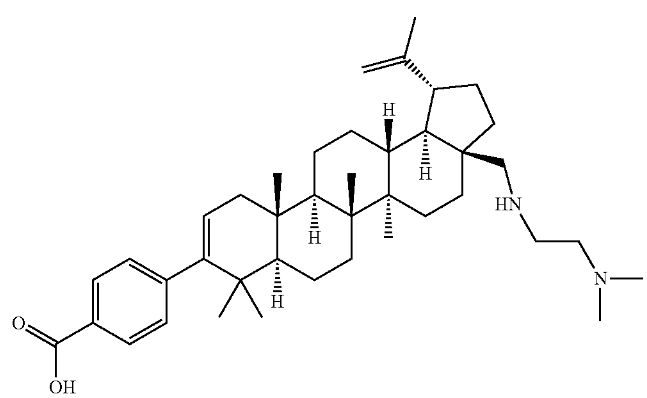 | A |

TABLE 2-continued
| Example # | Structure | $EC_{50}$ |
|---|---|---|
| 2 | 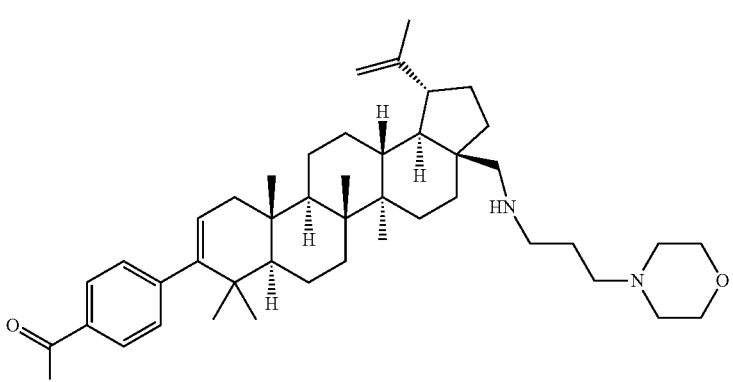 | A |
| 3 | 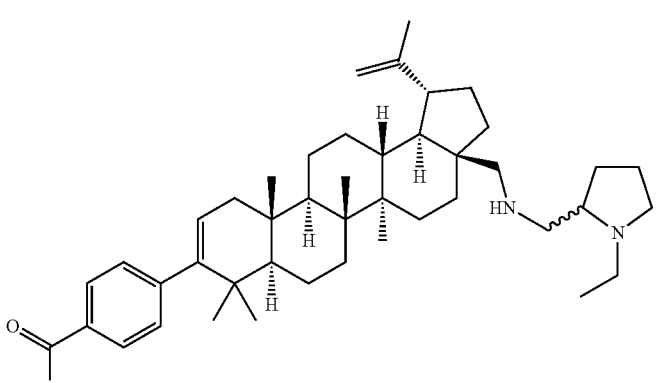  Diastereomer 1 | 0.03 |
| 4 | 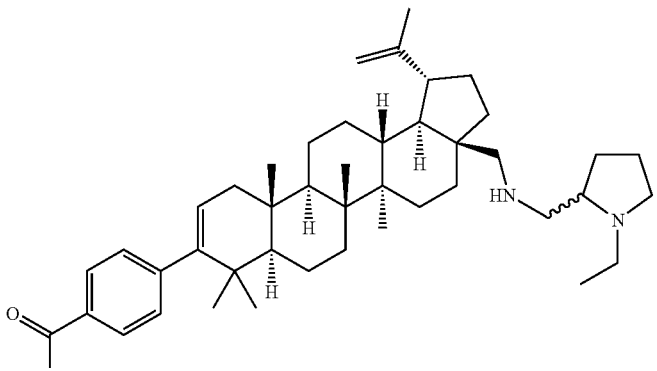  Diastereomer 2 | A |

TABLE 2-continued

| Example # | Structure | EC$_{50}$ |
|---|---|---|
| 5 | 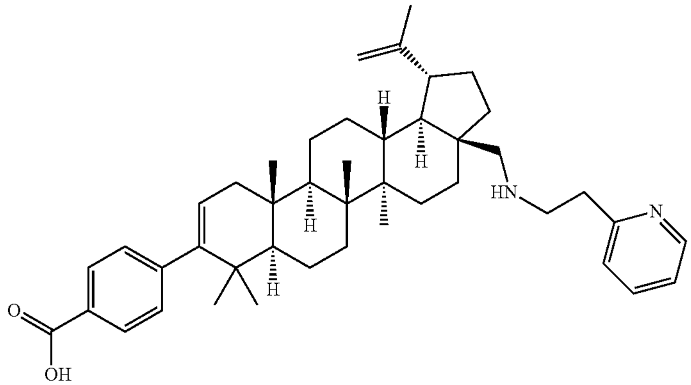 | 0.02 |
| 6 | 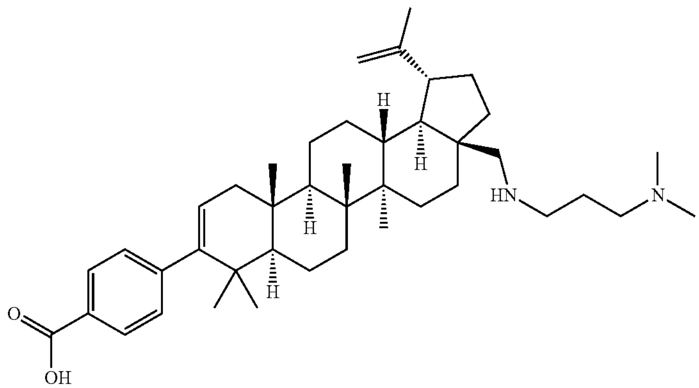 | 0.03 |
| 7 | 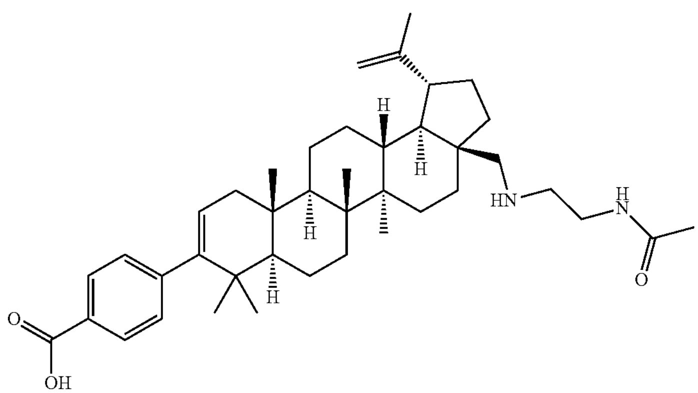 | A |
| 8 | 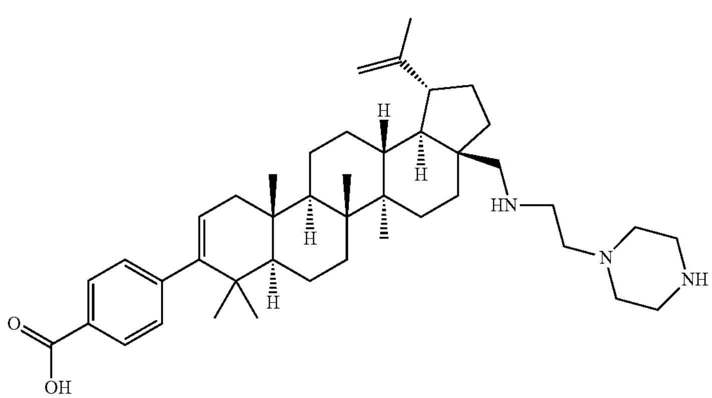 | A |

TABLE 2-continued
| Example # | Structure | EC$_{50}$ |
|---|---|---|
| 9 | 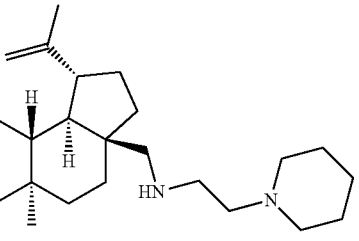 | A |
| 10 | 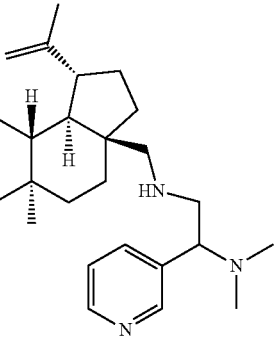 | 0.004 |
| 11 | 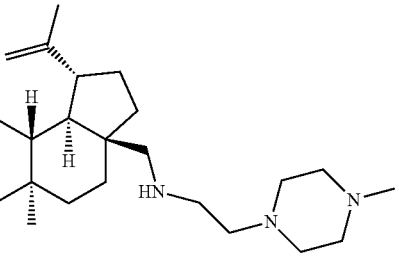 | A |
| 12 | 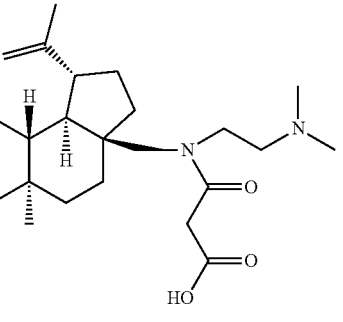 | A |

TABLE 2-continued

| Example # | Structure | EC$_{50}$ |
|---|---|---|
| 13 | 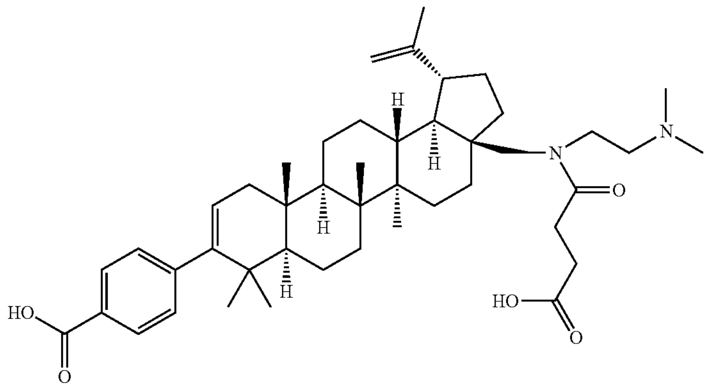 | A |
| 14 | 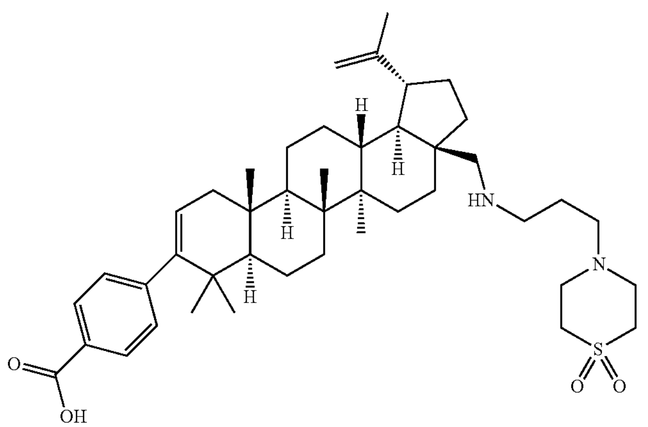 | A |
| 15 | 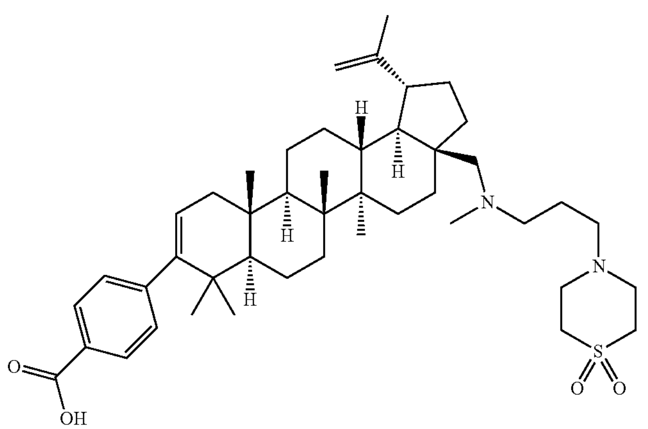 | A |

TABLE 2-continued
| Example # | Structure | EC$_{50}$ |
|---|---|---|
| 16 | 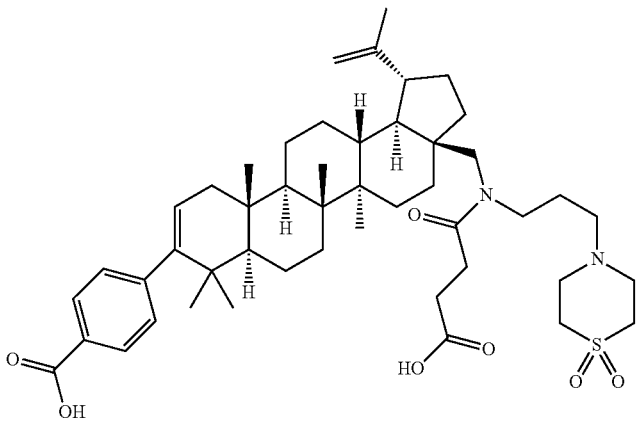 | A |
| 17 | 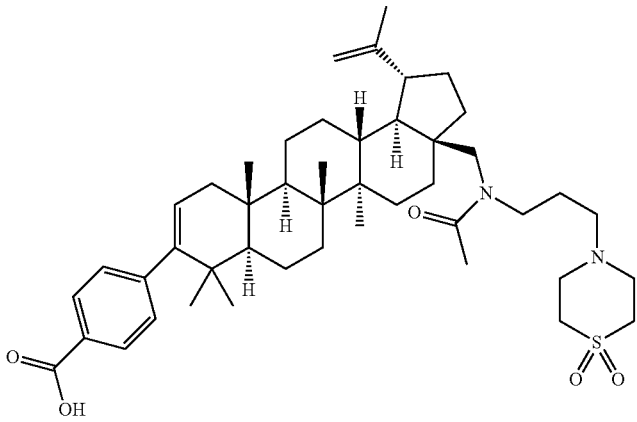 | A |
| 18 | 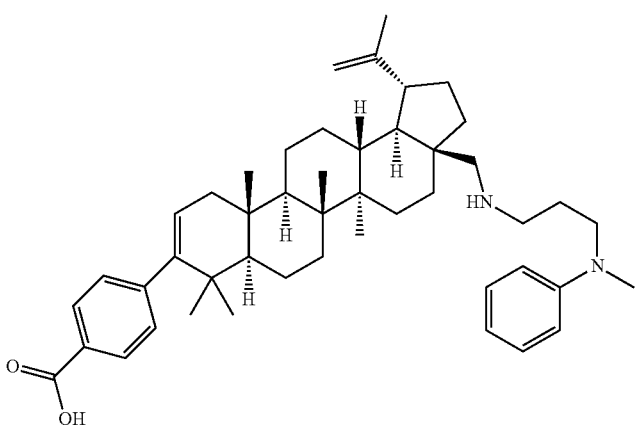 | A |

TABLE 2-continued
| Example # | Structure | EC$_{50}$ |
|---|---|---|
| 19 | 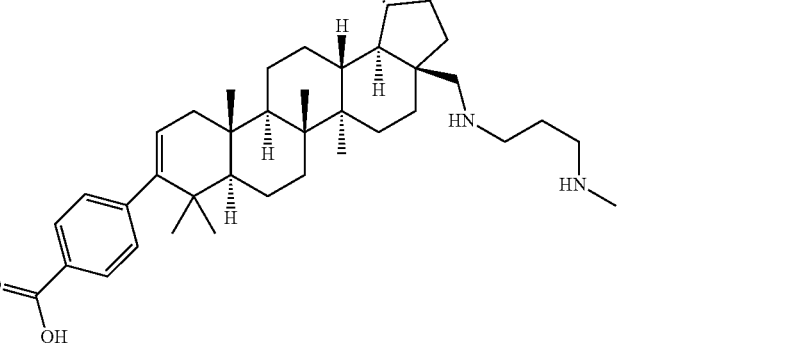 | A |
| 20 | 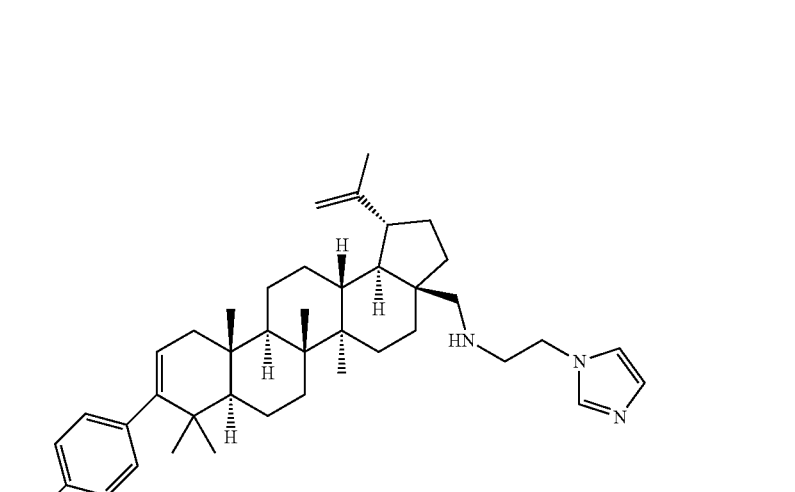 | A |
| 21 | 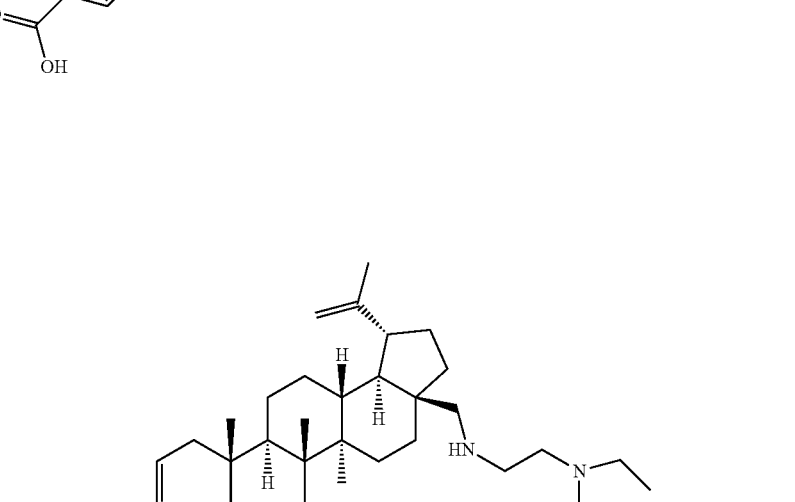 | A |

TABLE 2-continued
| Example # | Structure | EC$_{50}$ |
|---|---|---|
| 22 | 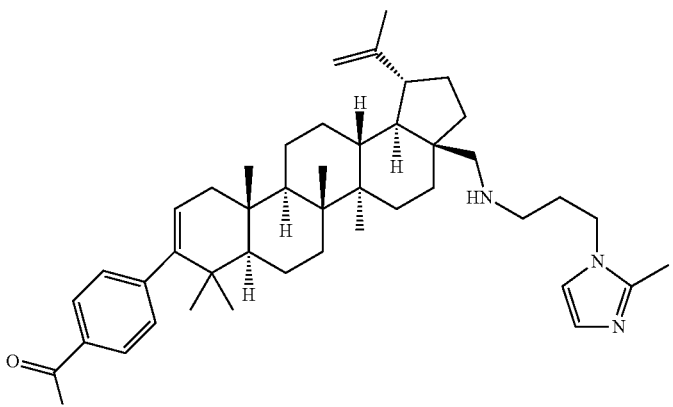 | A |
| 23 | 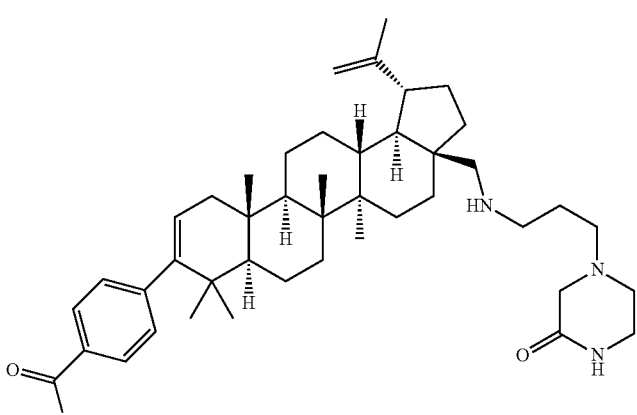 | A |
| 24 | 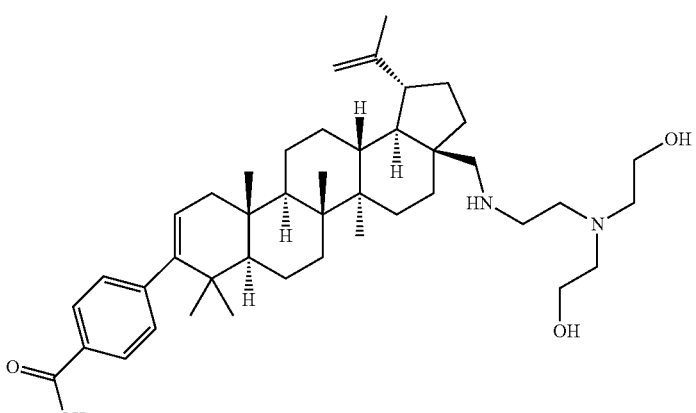 | A |

TABLE 2-continued
| Example # | Structure | EC$_{50}$ |
|---|---|---|
| 25 | 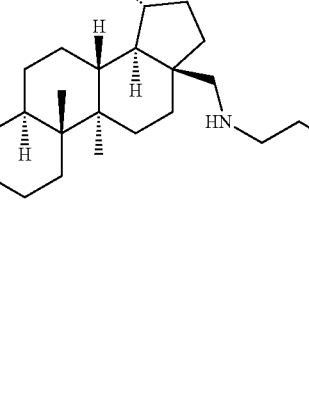 | A |
| 26 | 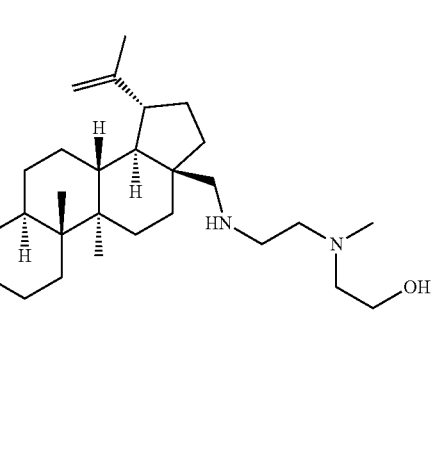 | A |
| 27 | 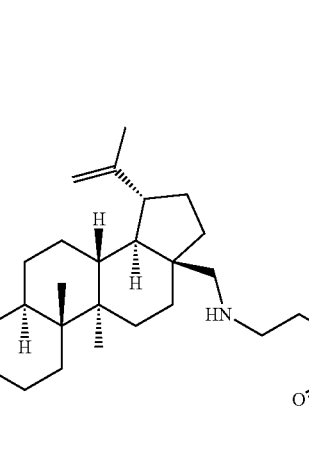 | A |

TABLE 2-continued

| Example # | Structure | EC$_{50}$ |
|---|---|---|
| 28 | 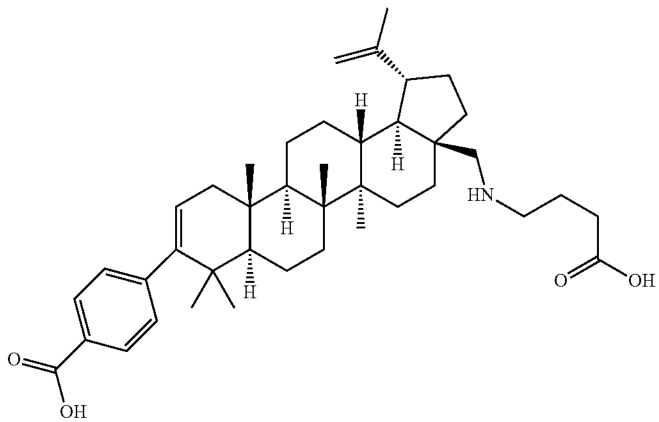 | 0.002 |
| 29 | 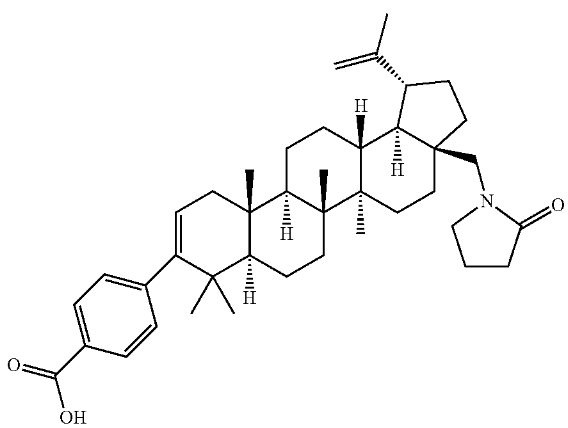 | 1.0 |
| 30 | 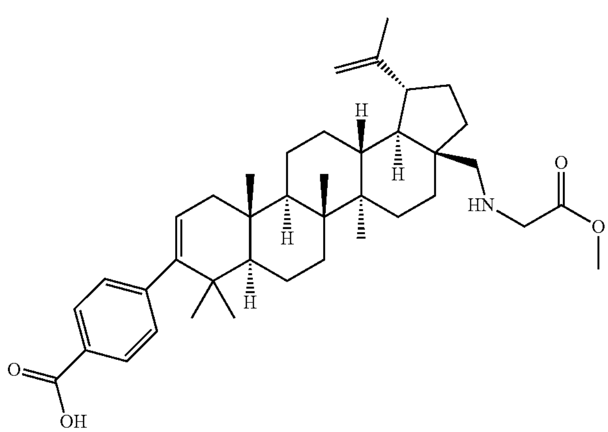 | A |

TABLE 2-continued

| Example # | Structure | EC₅₀ |
|---|---|---|
| 31 | 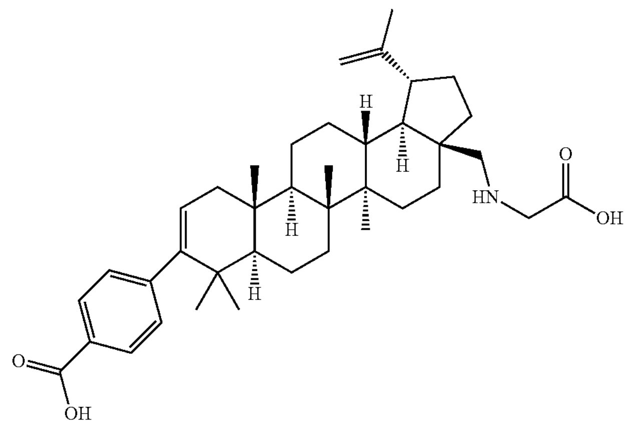 | A |
| 32 | 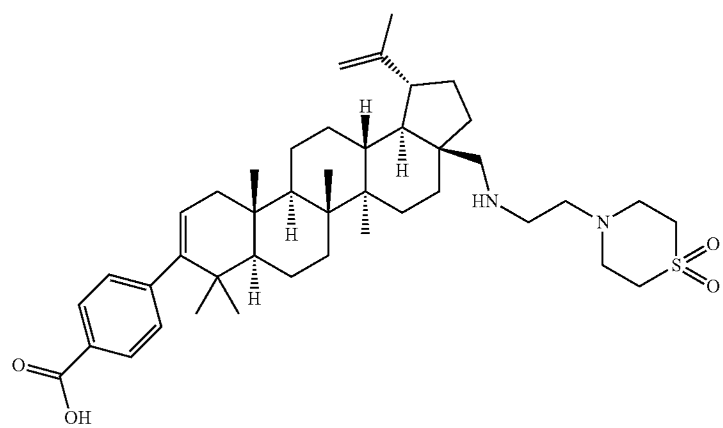 | A |
| 33 | 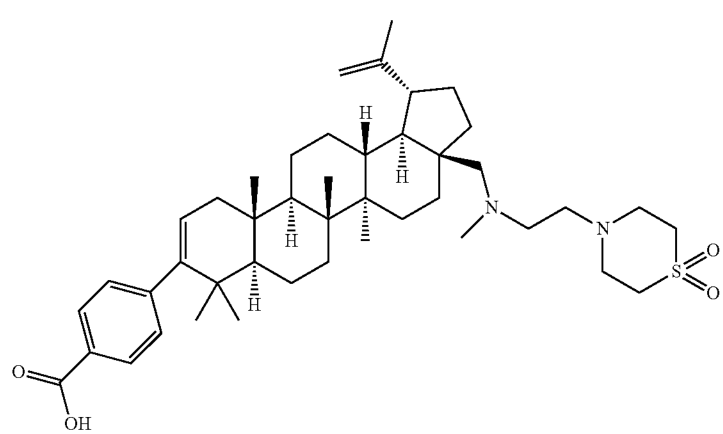 | A |

TABLE 2-continued

| Example # | Structure | EC$_{50}$ |
|---|---|---|
| 34 | 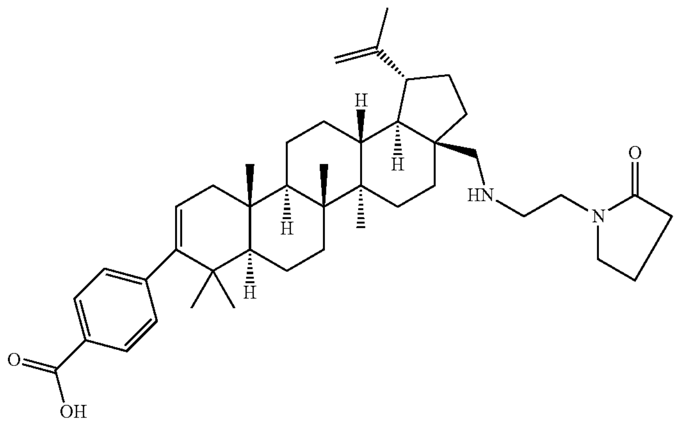 | A |
| 35 | 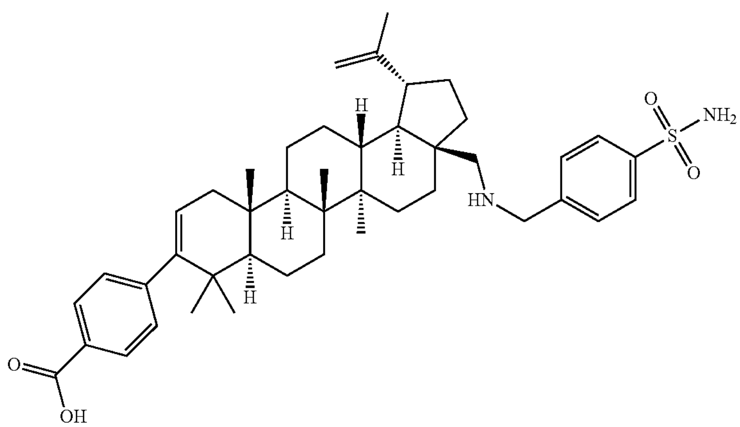 | A |
| 36 | 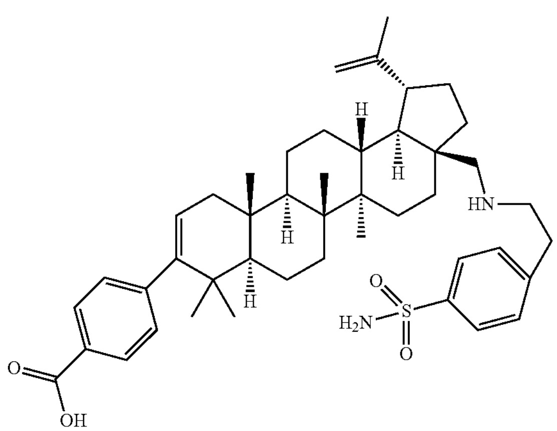 | A |

TABLE 2-continued
| Example # | Structure | EC$_{50}$ |
|---|---|---|
| 37 | 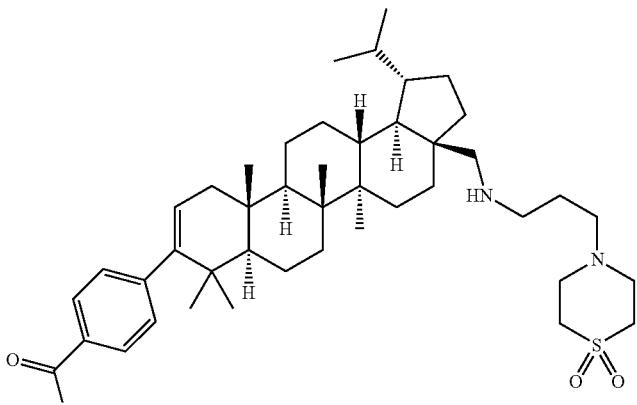 | A |
| 38 | 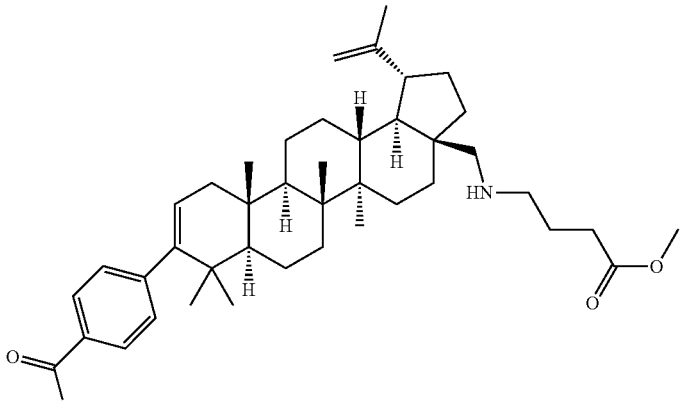 | A |
| 39 | 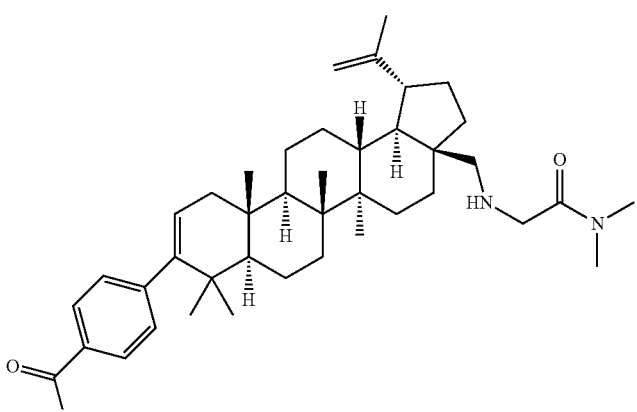 | A |

TABLE 2-continued

| Example # | Structure | EC$_{50}$ |
|---|---|---|
| 40 | 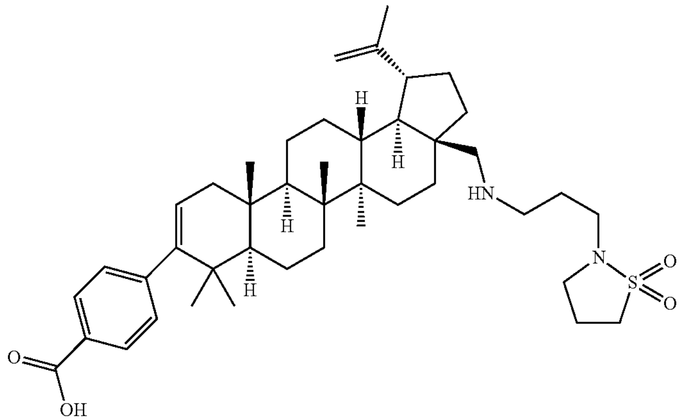 | A |
| 41 | 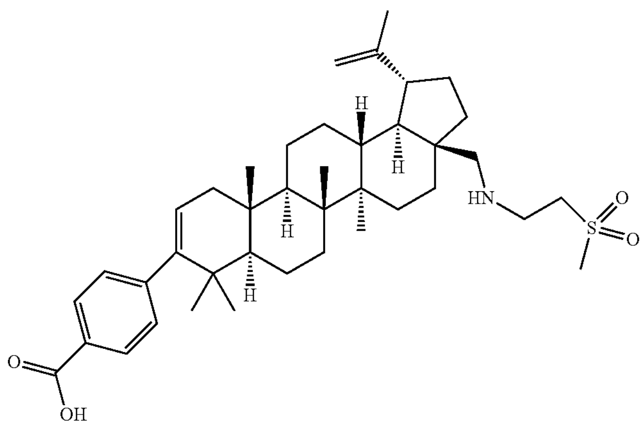 | A |
| 42 | 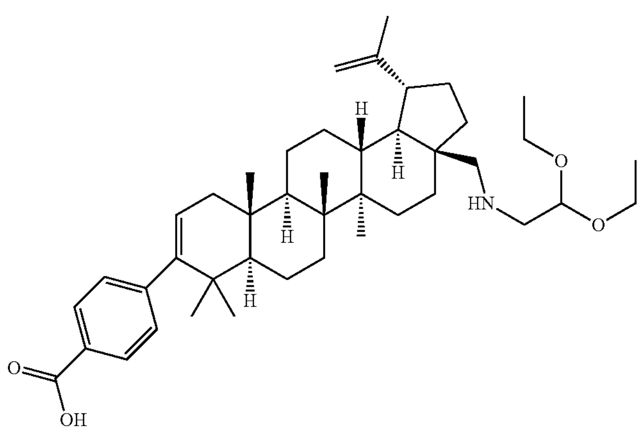 | A |

TABLE 2-continued

| Example # | Structure | EC$_{50}$ |
|---|---|---|
| 43 | 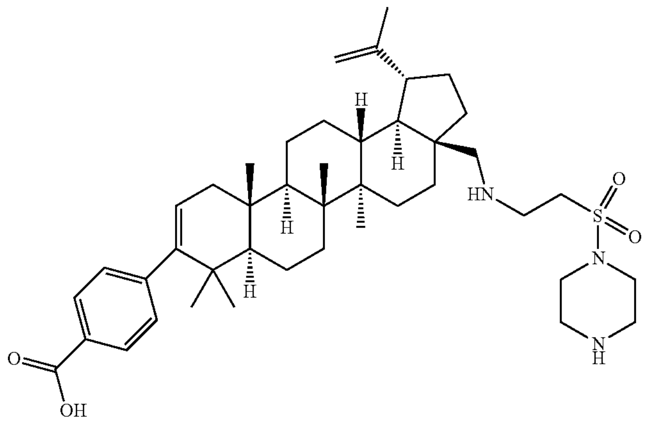 | A |
| 44 | 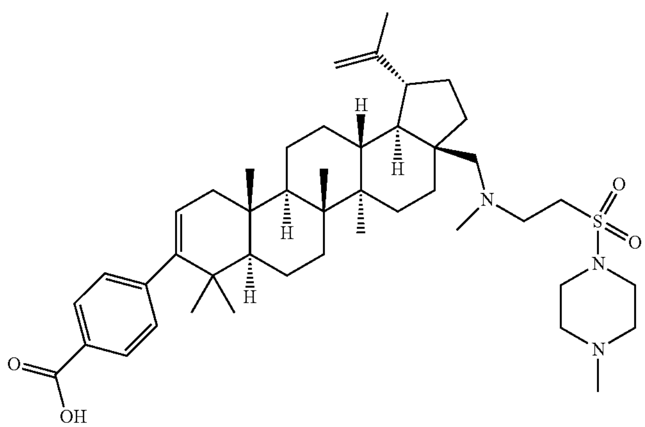 | 0.02 |
| 45 | 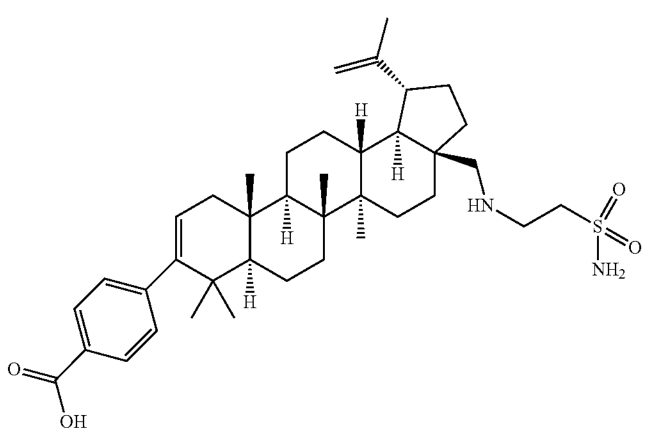 | A |

TABLE 2-continued
| Example # | Structure | EC$_{50}$ |
|---|---|---|
| 46 | 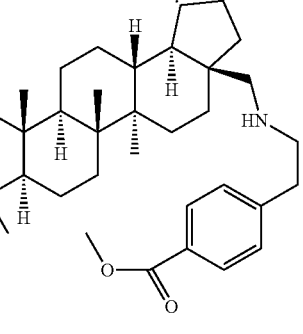 | A |
| 47 | 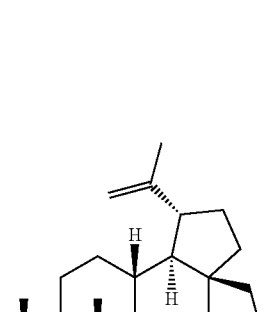 | A |
| 48 | 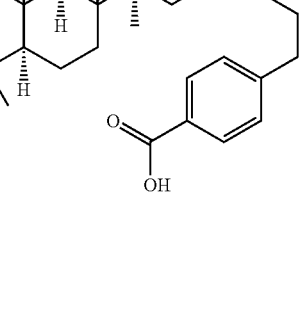 | A |

TABLE 2-continued

| Example # | Structure | EC$_{50}$ |
|---|---|---|
| 49 | 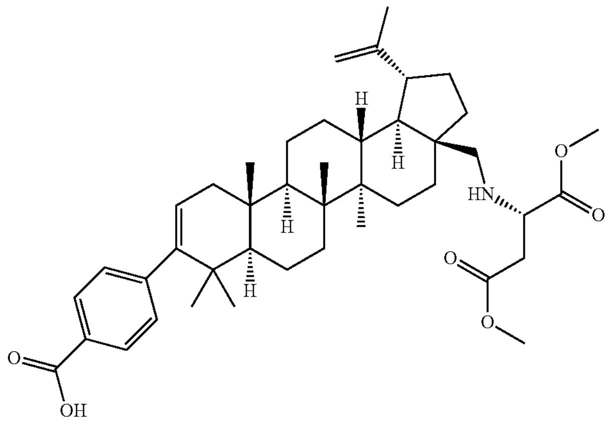 | A |
| 50 | 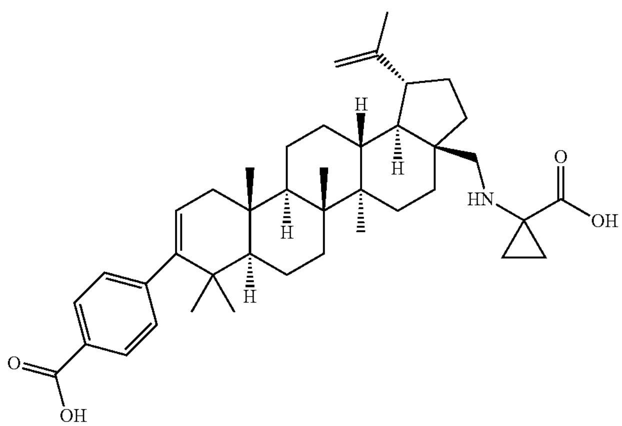 | A |
| 51 | 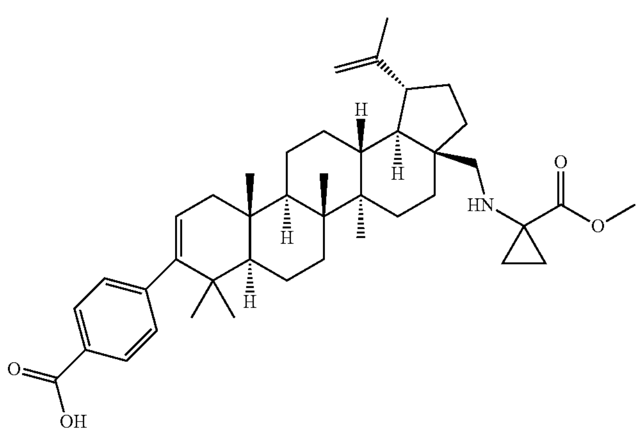 | A |

TABLE 2-continued
| Example # | Structure | EC$_{50}$ |
|---|---|---|
| 52 | 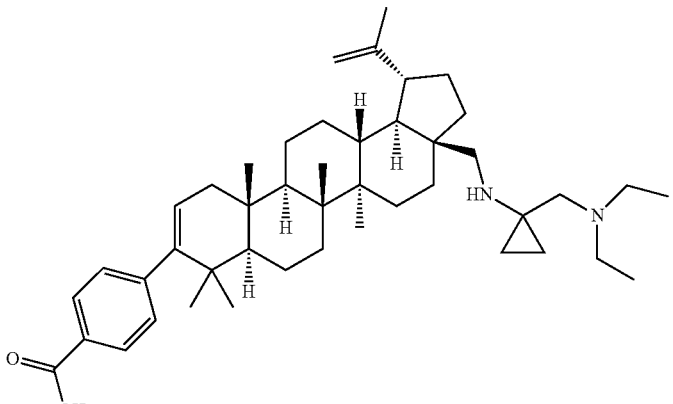 | A |
| 53 | 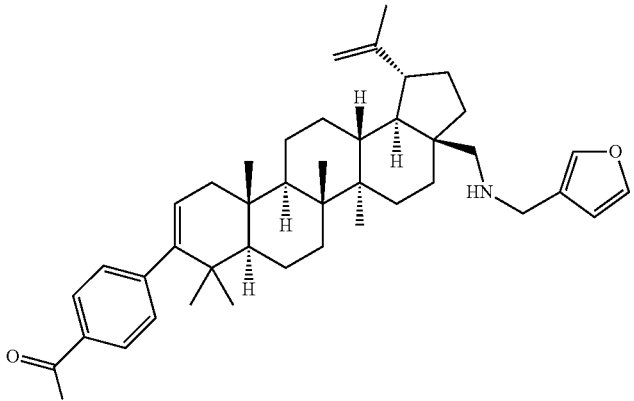 | A |
| 54 | 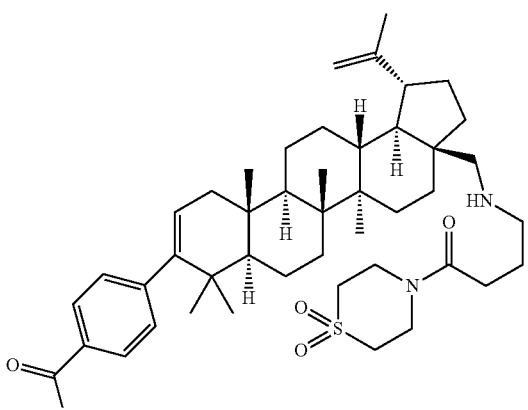 | A |

TABLE 2-continued
| Example # | Structure | EC$_{50}$ |
|---|---|---|
| 55 | 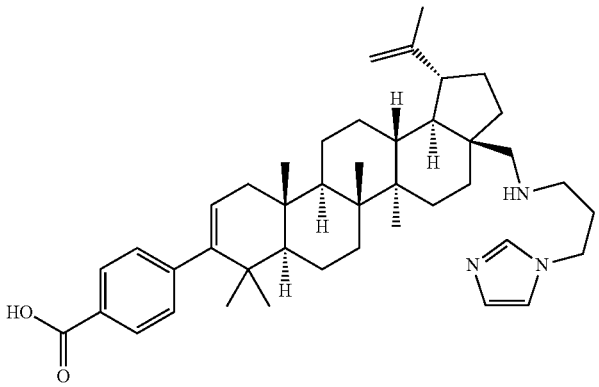 | A |
| 56 | 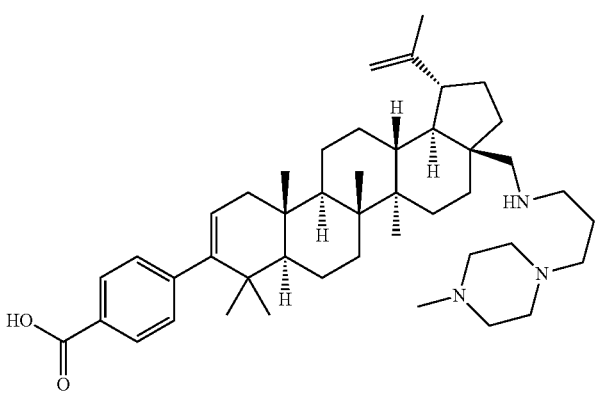 | A |
| 57 | 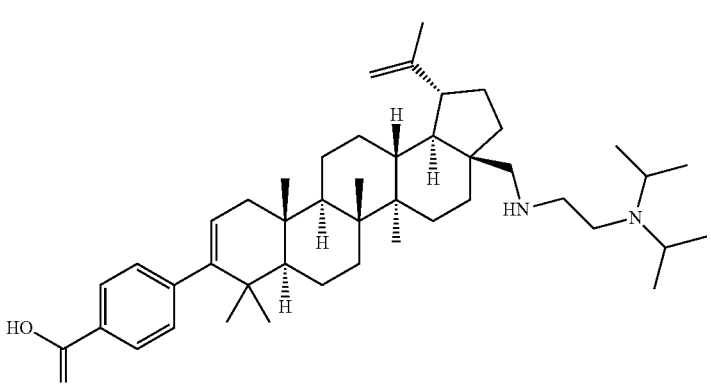 | A |
| 58 | 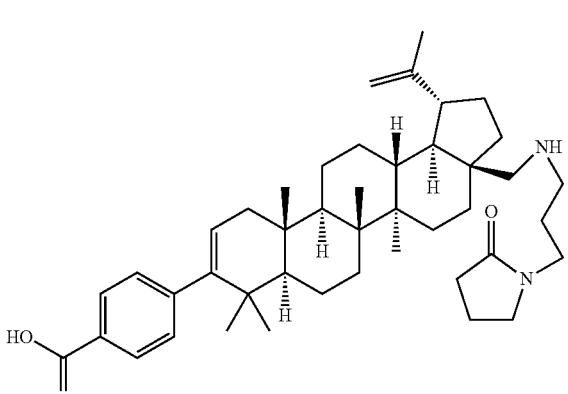 | A |

TABLE 2-continued
| Example # | Structure | EC$_{50}$ |
|---|---|---|
| 59 | 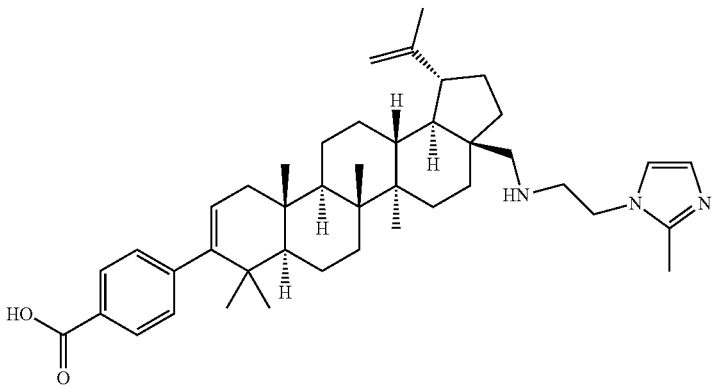 | A |
| 60 | 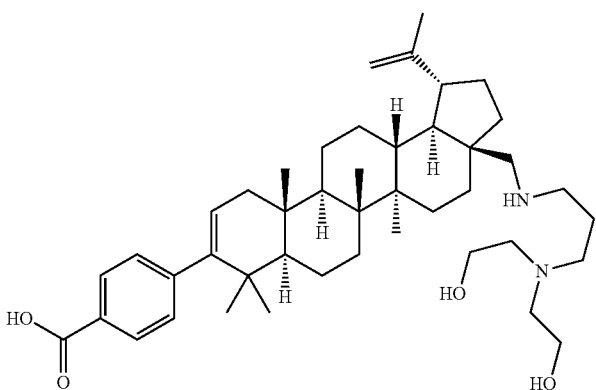 | A |
| 61 | 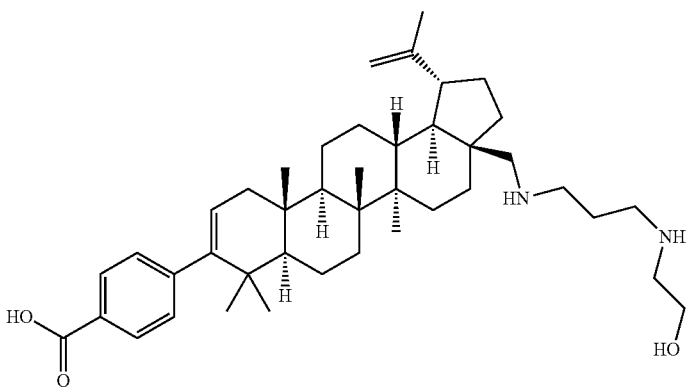 | A |
| 62 | 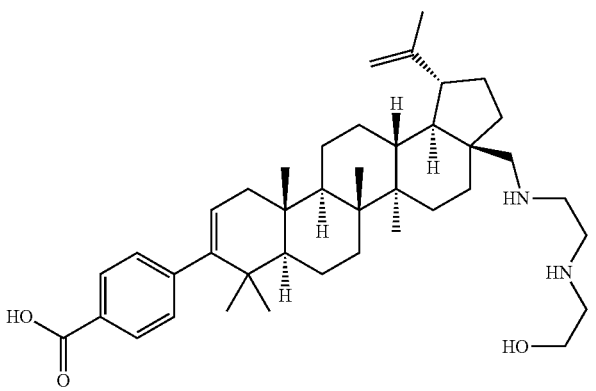 | A |

TABLE 2-continued

| Example # | Structure | EC$_{50}$ |
|---|---|---|
| 63 | 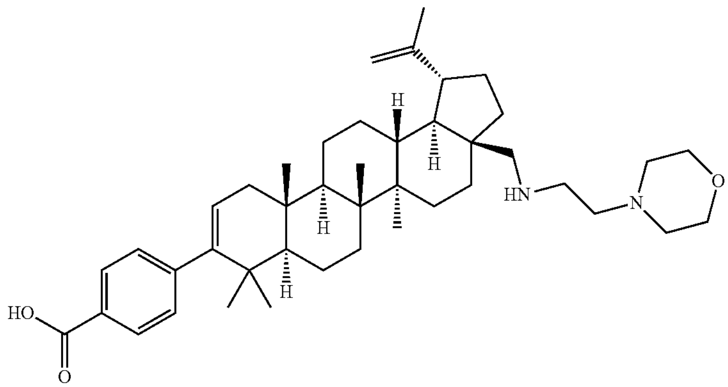 | A |
| 64 | 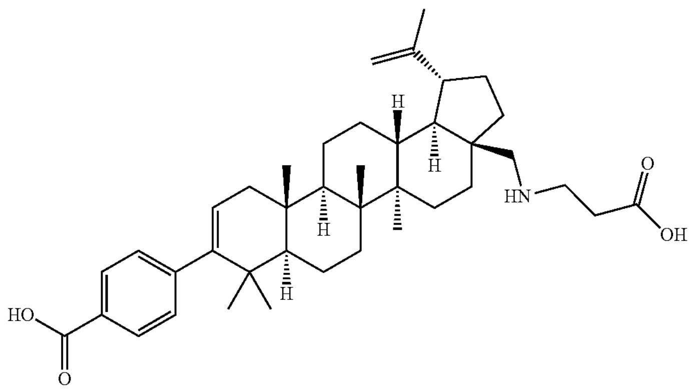 | A |
| 65 | 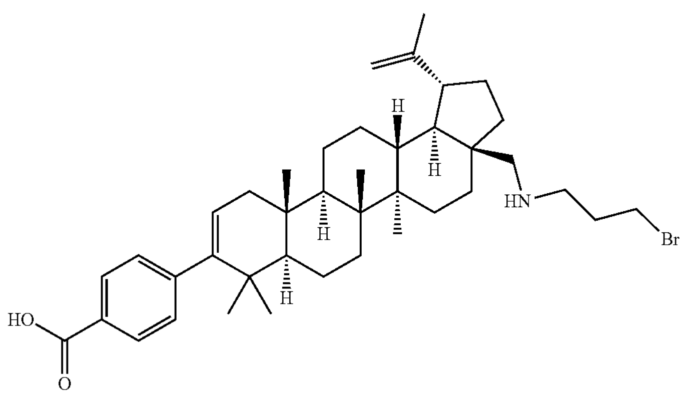 | 0.001 |
| 66 | 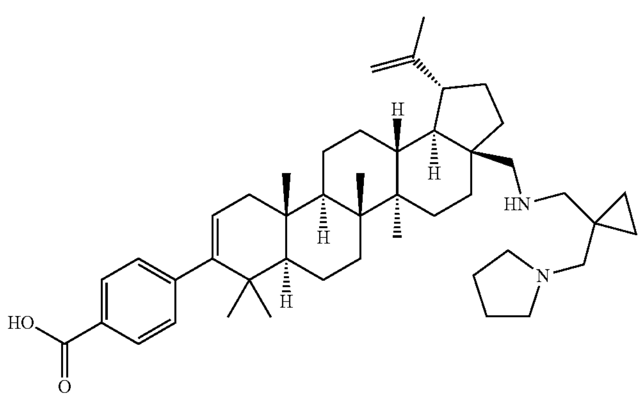 | A |

TABLE 2-continued
| Example # | Structure | EC$_{50}$ |
|---|---|---|
| 67 | 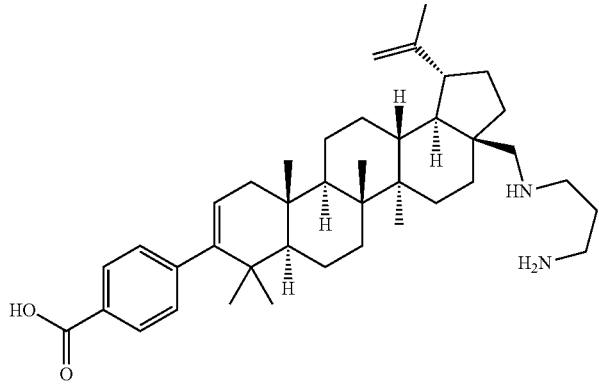 | A |
| 68 | 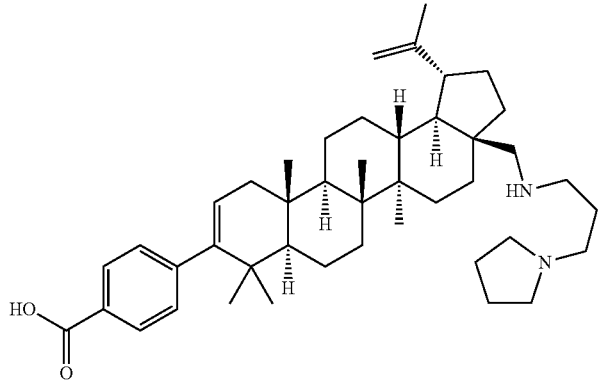 | A |
| 69 | 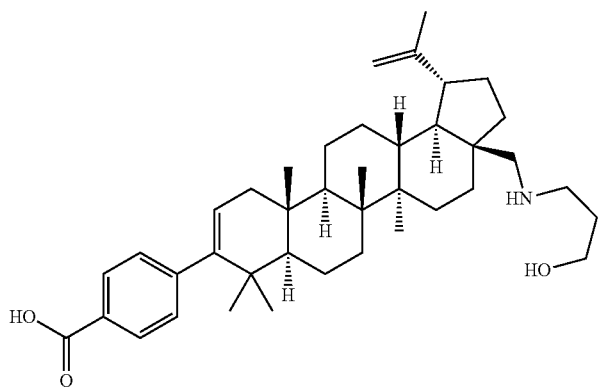 | A |
| 70 | 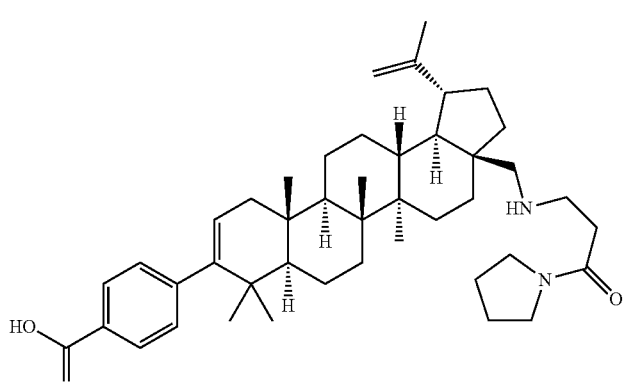 | A |

TABLE 2-continued

| Example # | Structure | EC$_{50}$ |
|---|---|---|
| 71 | 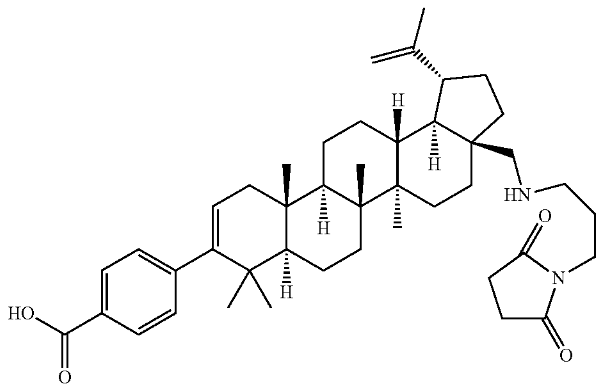 | A |
| 72 | 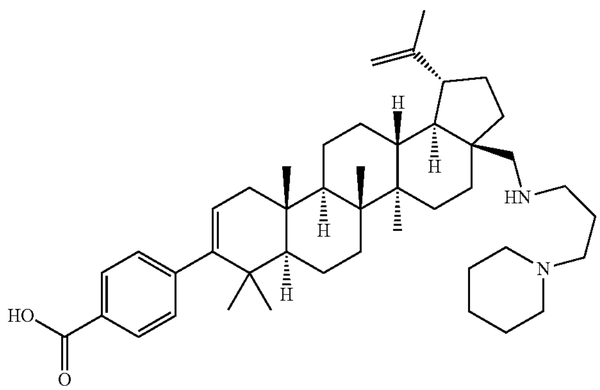 | A |
| 73 | 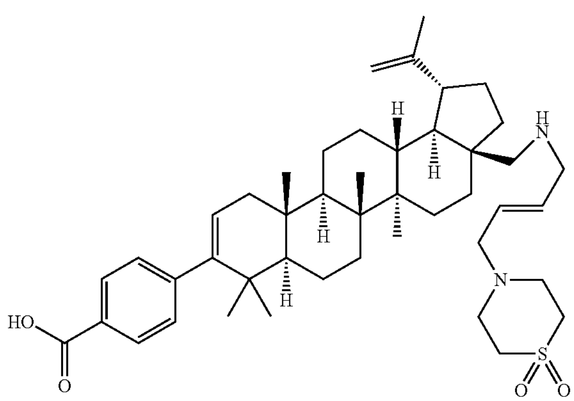 | A |
| 74 | 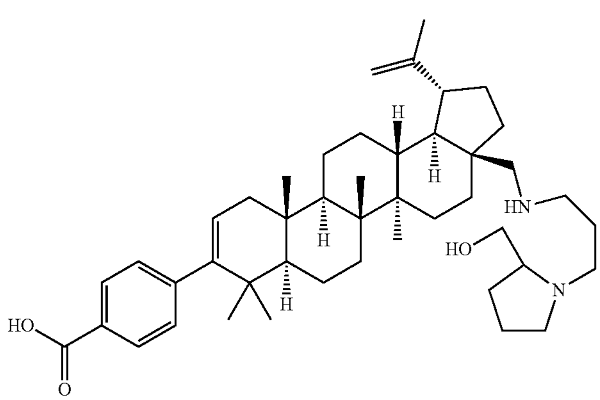 | A |

TABLE 2-continued
| Example # | Structure | EC$_{50}$ |
|---|---|---|
| 75 | 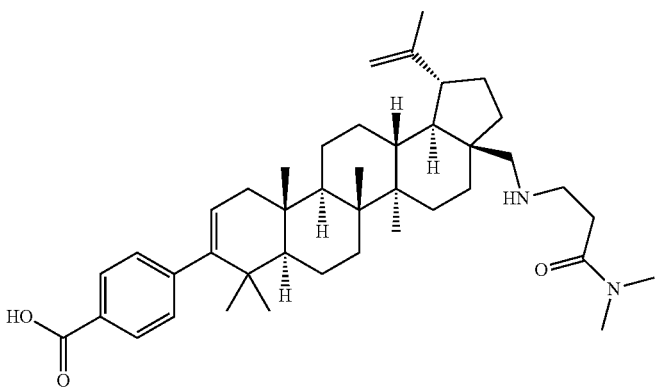 | A |
| 76 | 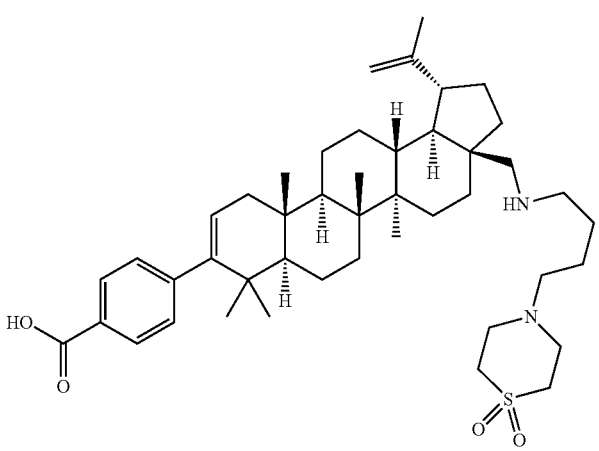 | A |
| 77 | 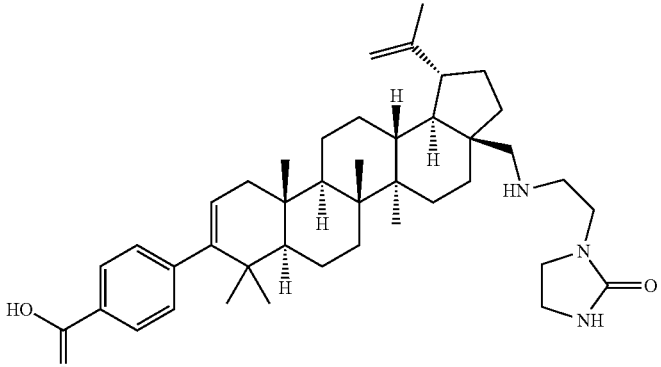 | A |

TABLE 2-continued
| Example # | Structure | EC$_{50}$ |
|---|---|---|
| 78 | 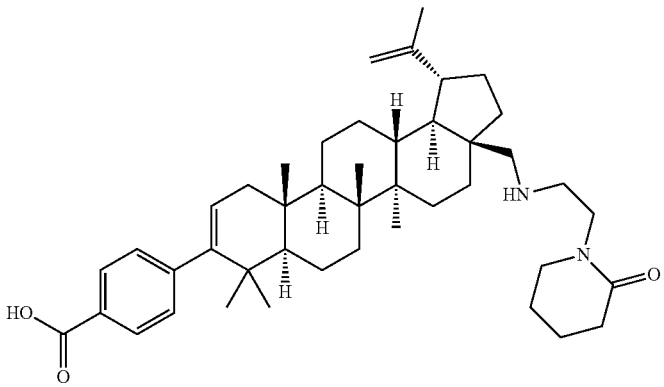 | A |
| 79 | 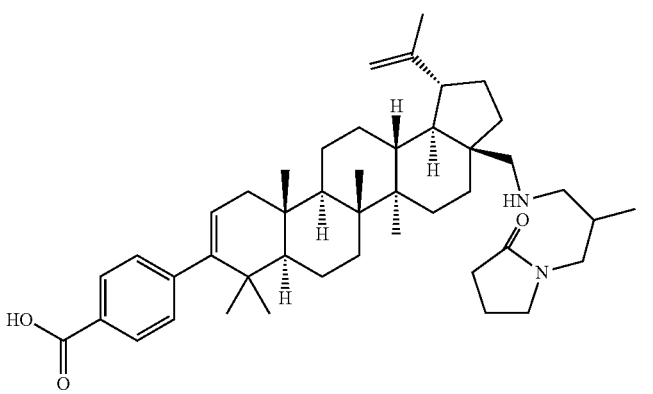 | A |
| 80 | 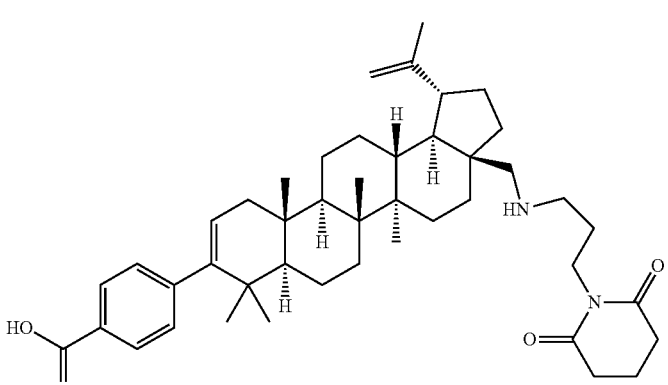 | A |
| 81 | 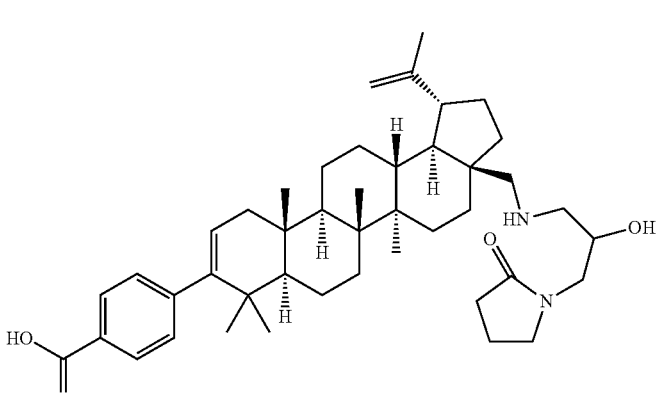 | A |

TABLE 2-continued

| Example # | Structure | EC$_{50}$ |
|---|---|---|
| 82 | 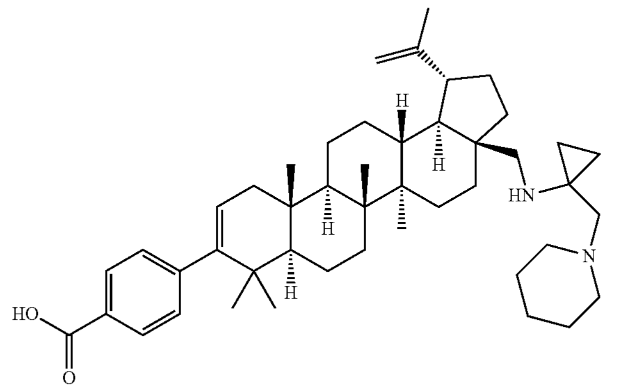 | A |
| 83 | 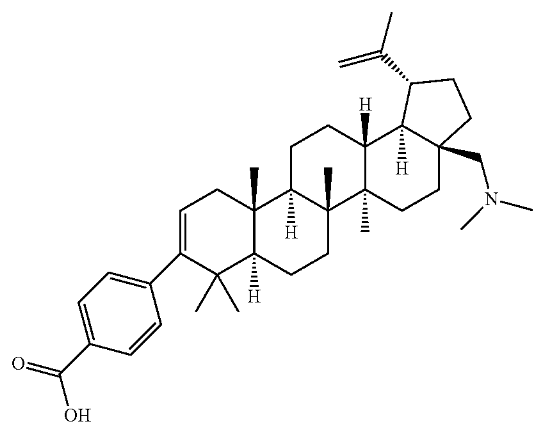 | A |
| 84 | 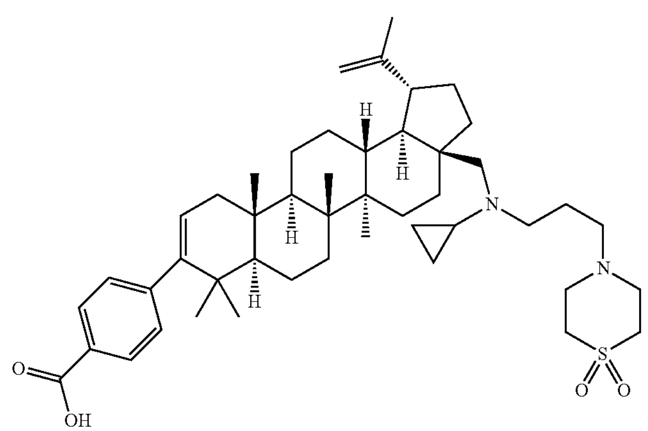 | A |

TABLE 2-continued
| Example # | Structure | EC$_{50}$ |
|---|---|---|
| 85 | 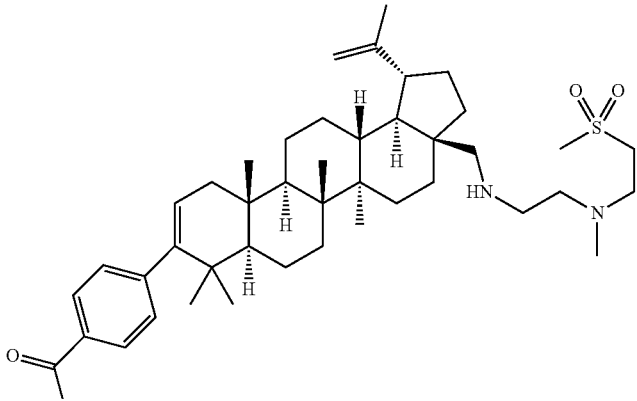 | A |
| 86 | 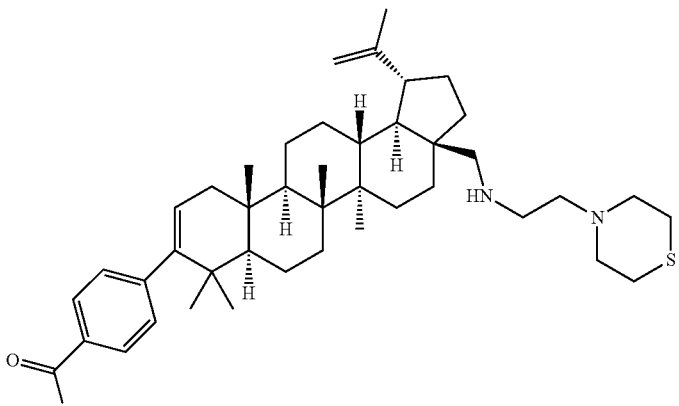 | A |
| 87 | 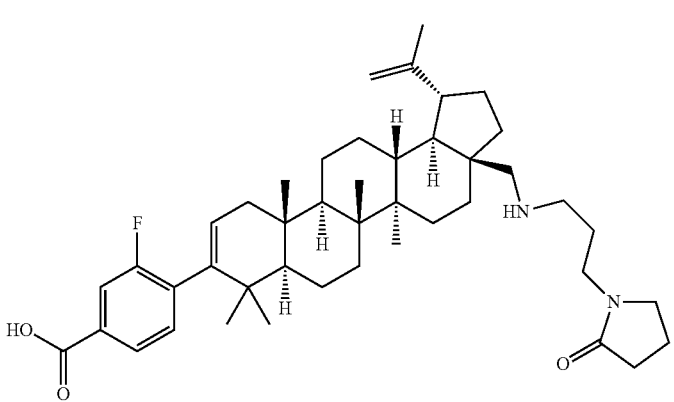 | A |

TABLE 2-continued

| Example # | Structure | EC$_{50}$ |
|---|---|---|
| 88 | 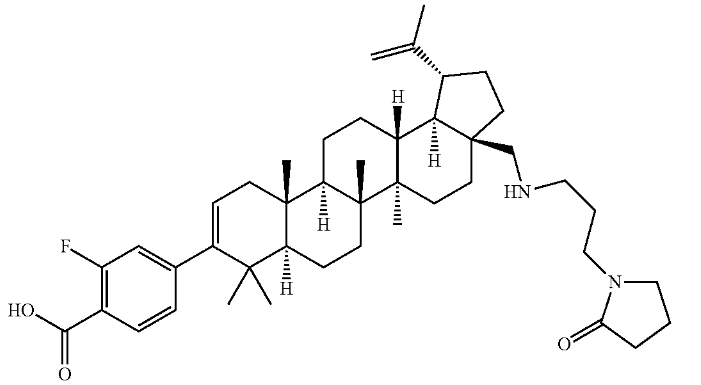 | A |
| 89 | 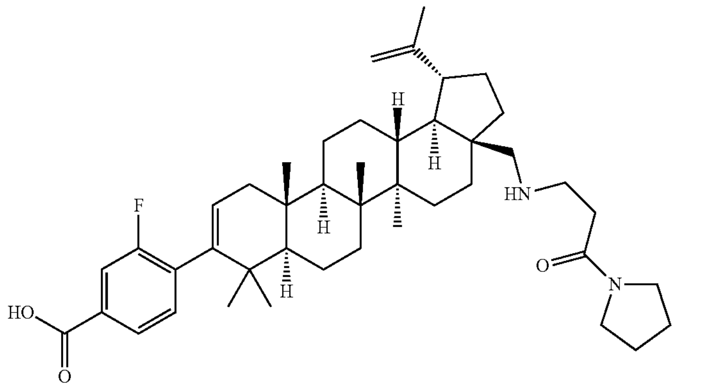 | A |
| 90 | 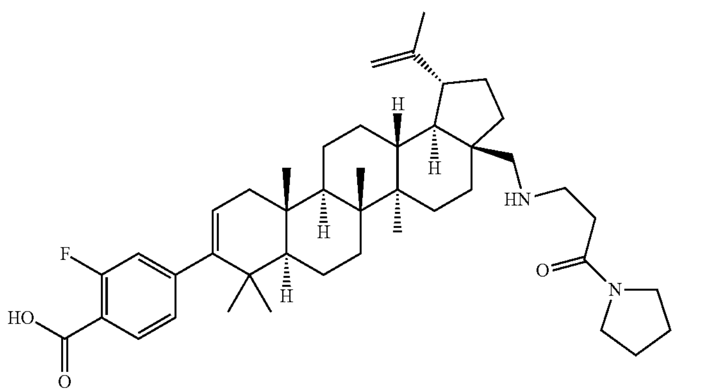 | A |
| 91 | 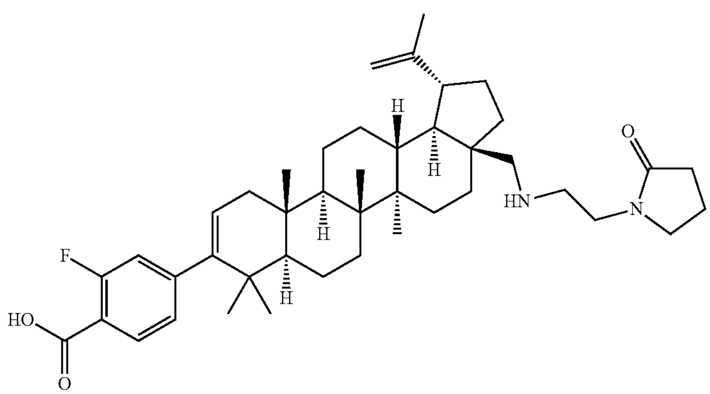 | A |

TABLE 2-continued
| Example # | Structure | EC$_{50}$ |
|---|---|---|
| 92 | 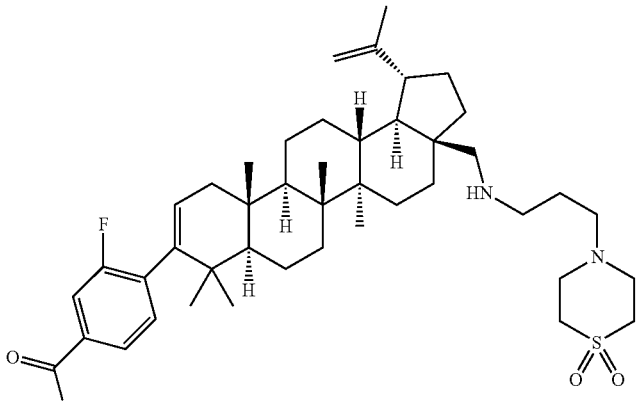 | A |
| 93 | 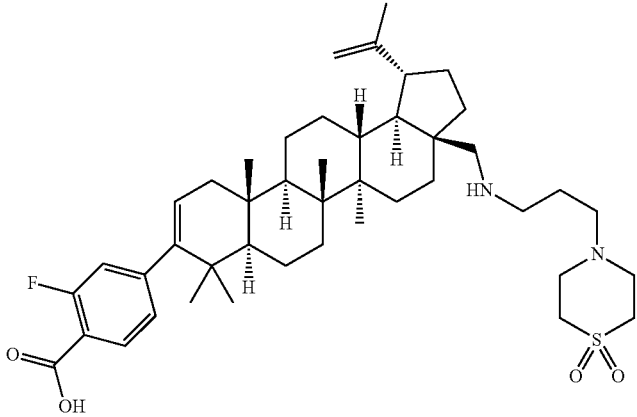 | A |
| 94 | 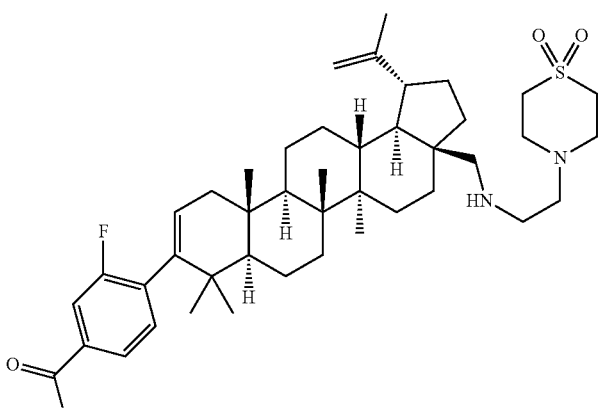 | A |

TABLE 2-continued
| Example # | Structure | EC$_{50}$ |
|---|---|---|
| 95 | 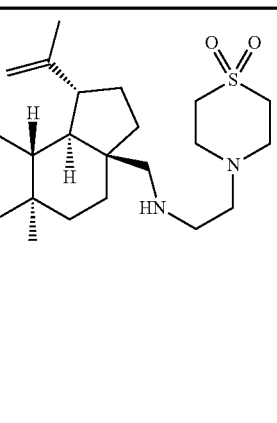 | A |
| 96 | 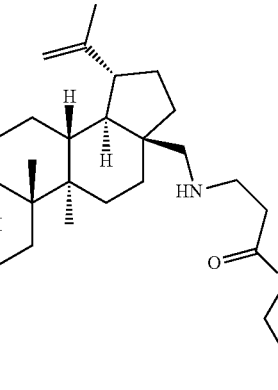 | A |
| 97 | 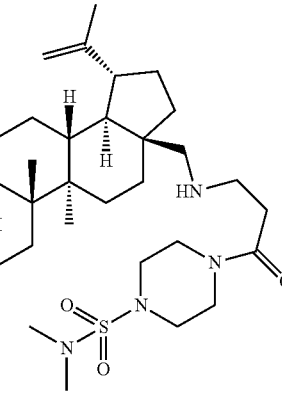 | A |
| 98 | 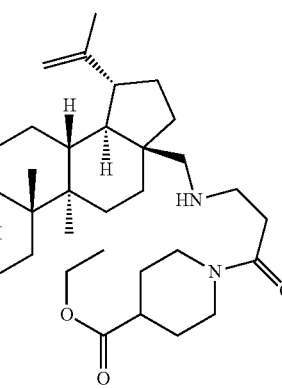 | A |

TABLE 2-continued

| Example # | Structure | EC$_{50}$ |
|---|---|---|
| 99 | 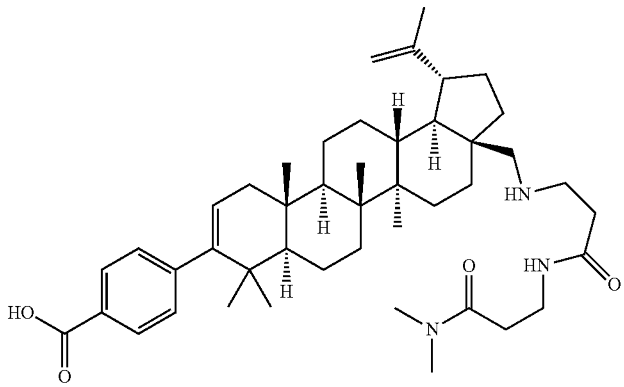 | A |
| 100 | 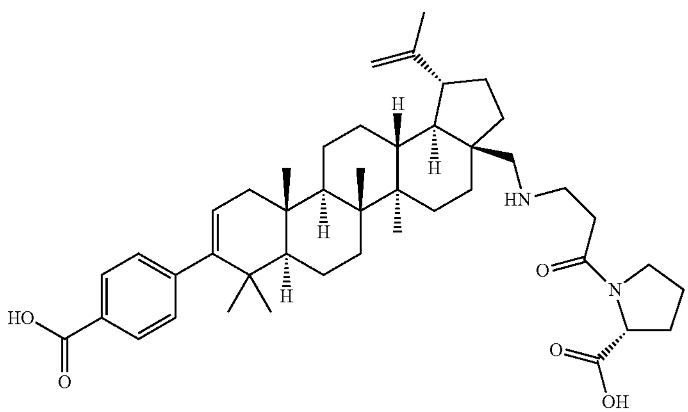 | A |
| 101 | 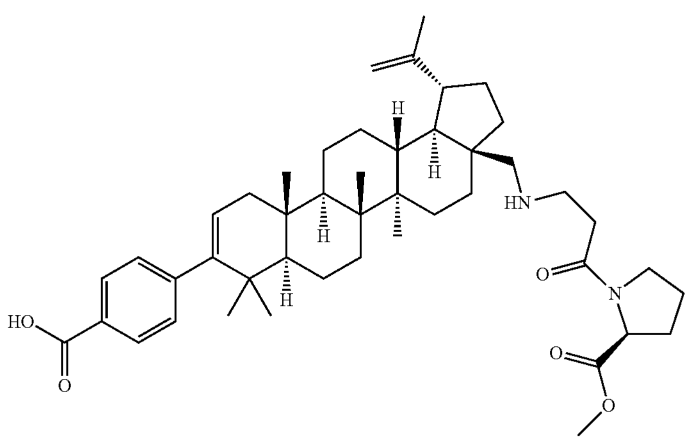 | A |

TABLE 2-continued

| Example # | Structure | EC$_{50}$ |
|---|---|---|
| 102 | 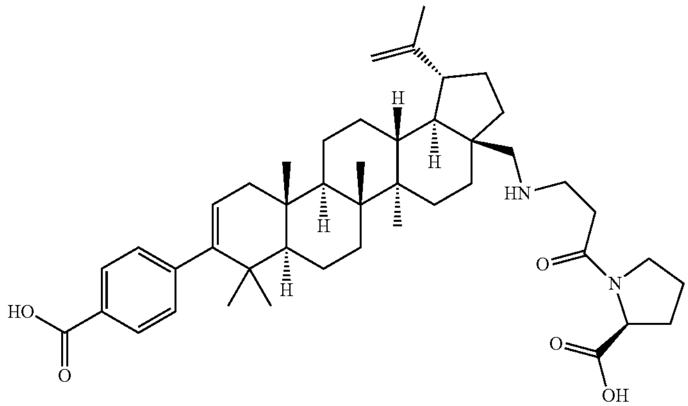 | A |
| 103 | 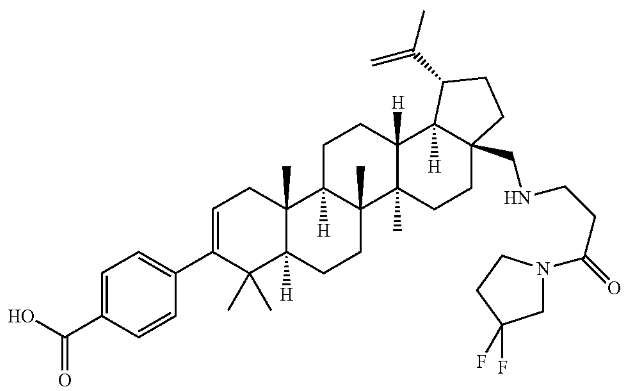 | A |
| 104 | 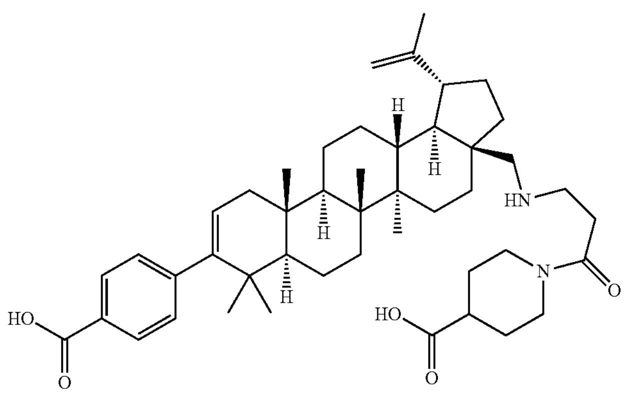 | A |
| 105 | 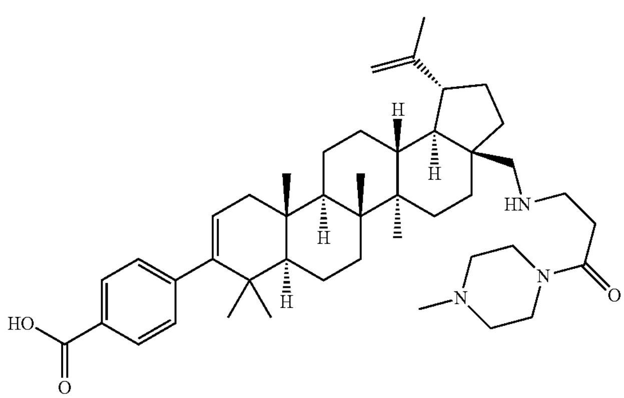 | A |

TABLE 2-continued
| Example # | Structure | EC$_{50}$ |
|---|---|---|
| 106 | 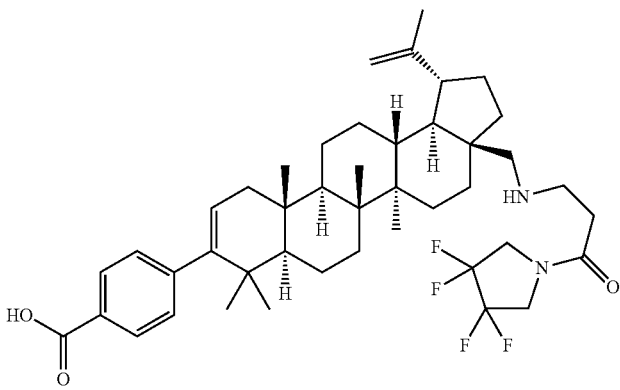 | A |
| 107 | 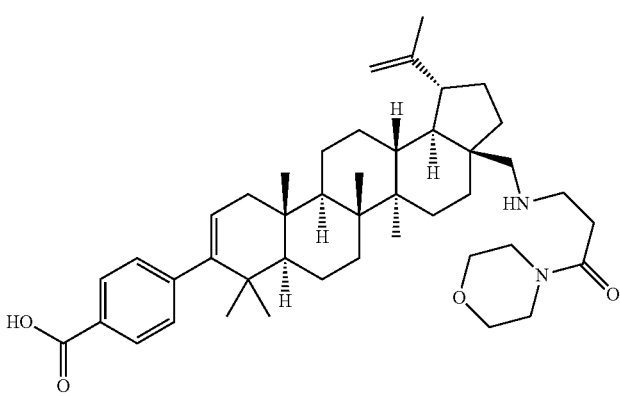 | A |
| 108 | 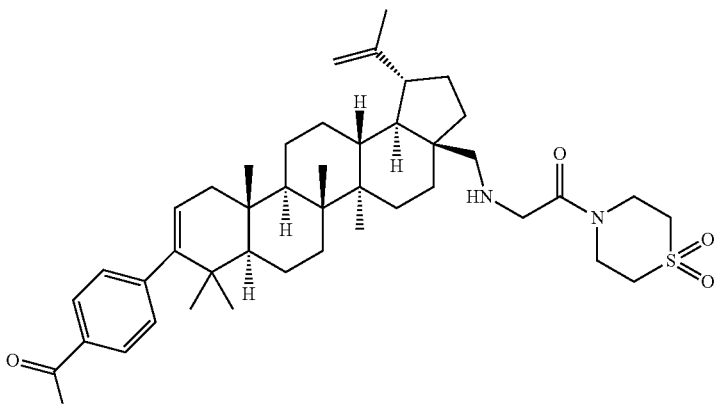 | A |

TABLE 2-continued

| Example # | Structure | EC$_{50}$ |
|---|---|---|
| 109 | 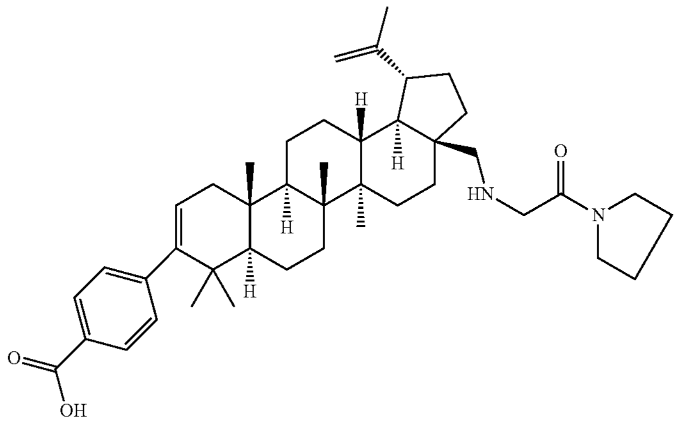 | A |
| 110 | 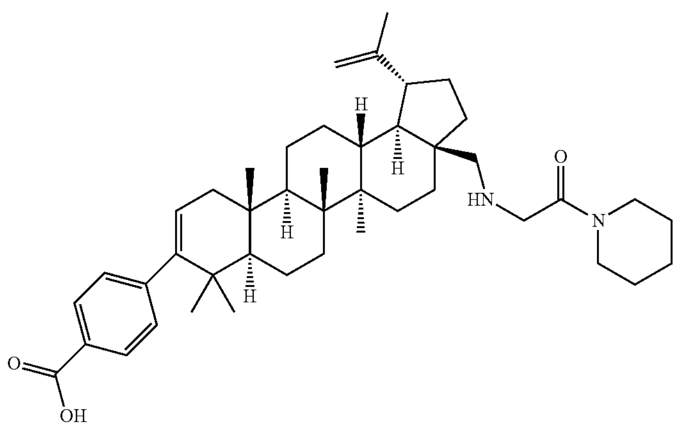 | A |
| 111 | 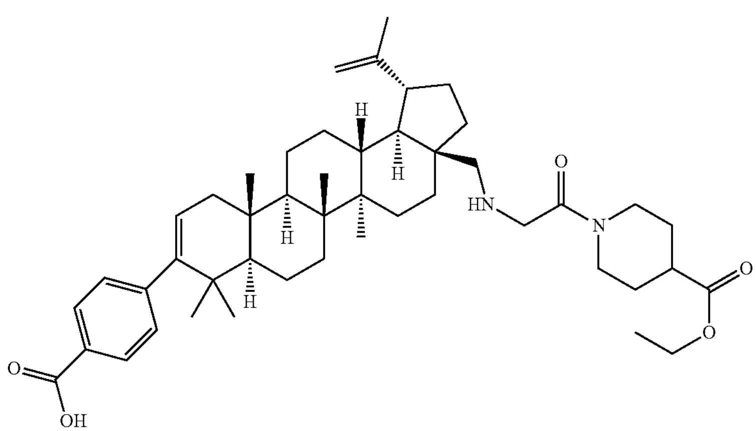 | A |

TABLE 2-continued

| Example # | Structure | EC$_{50}$ |
|---|---|---|
| 112 | 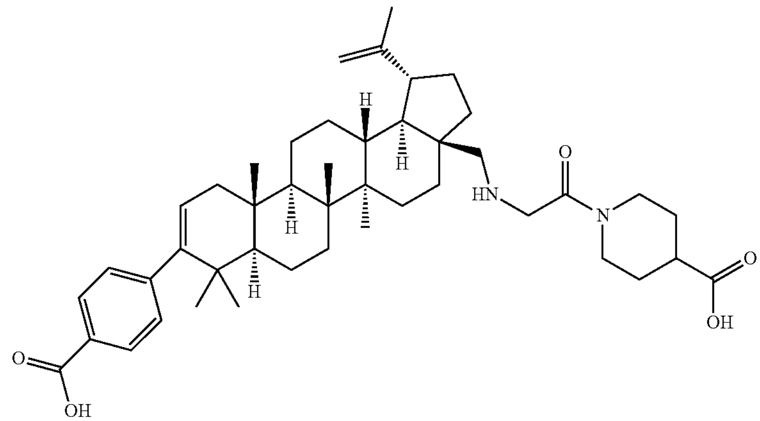 | A |
| 113 | 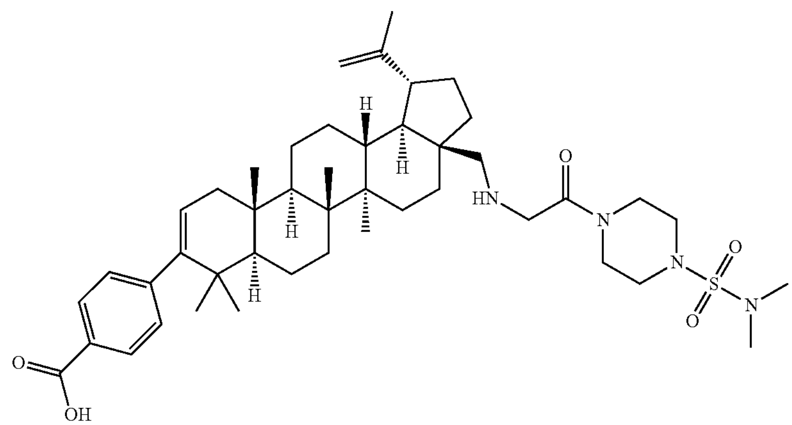 | A |
| 114 | 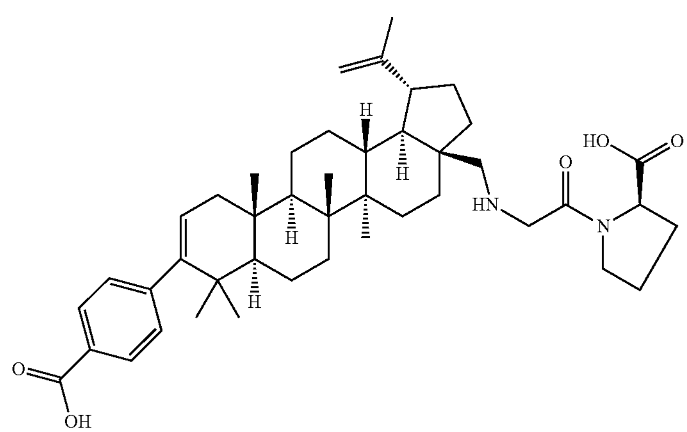 | A |

TABLE 2-continued

| Example # | Structure | EC50 |
|---|---|---|
| 115 | 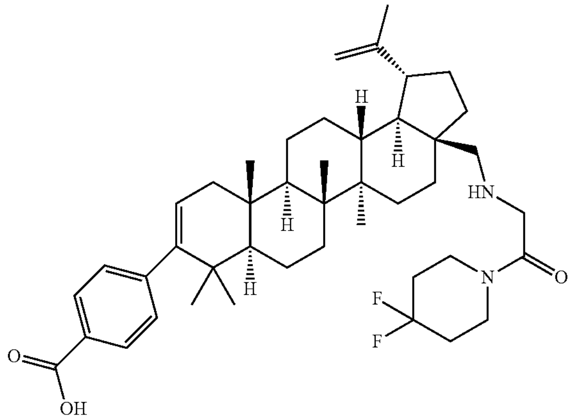 | 0.003 |
| 116 | 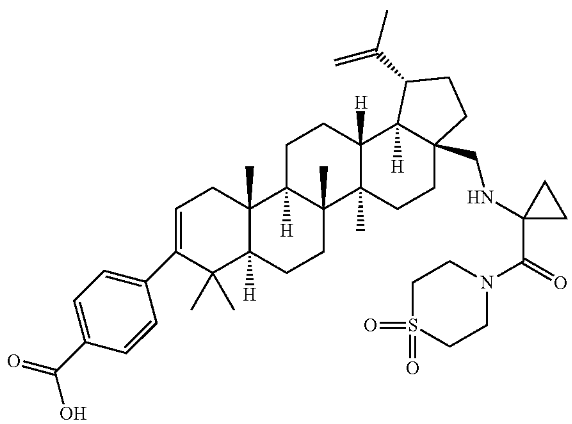 | A |
| 117 | 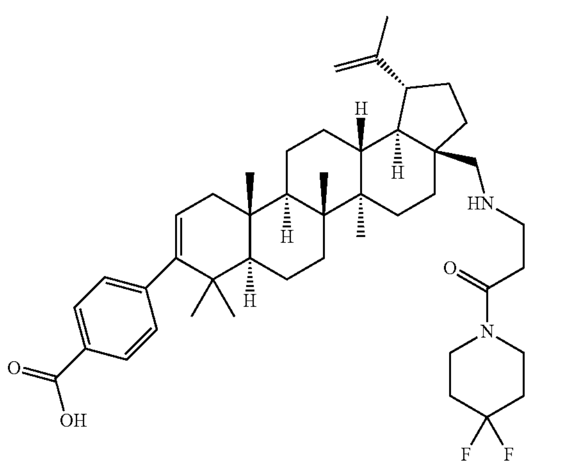 | A |

TABLE 2-continued

| Example # | Structure | EC$_{50}$ |
|---|---|---|
| 118 | 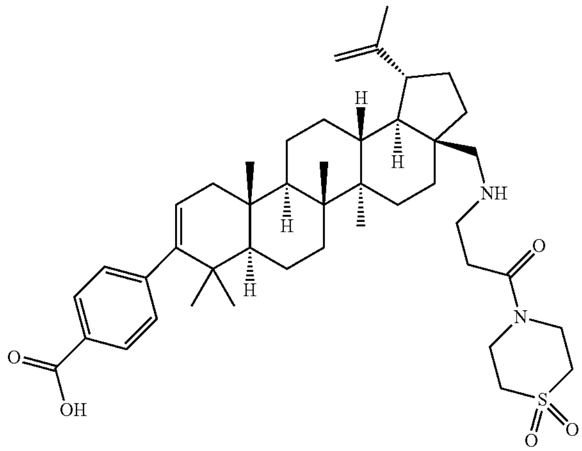 | A |
| 119 | 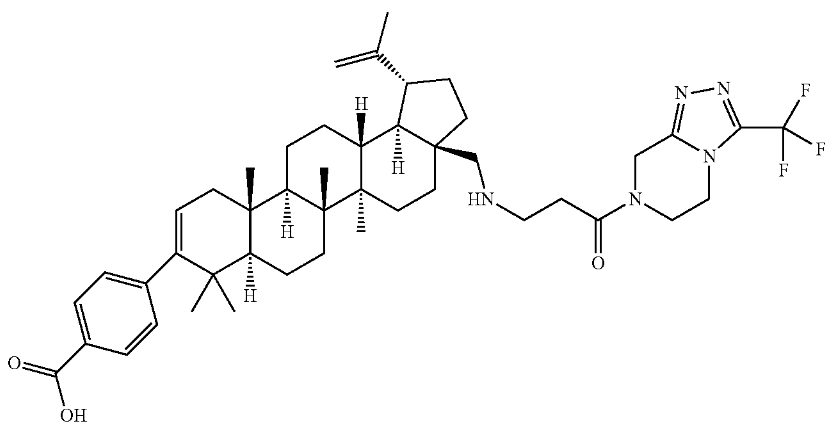 | A |
| 120 | 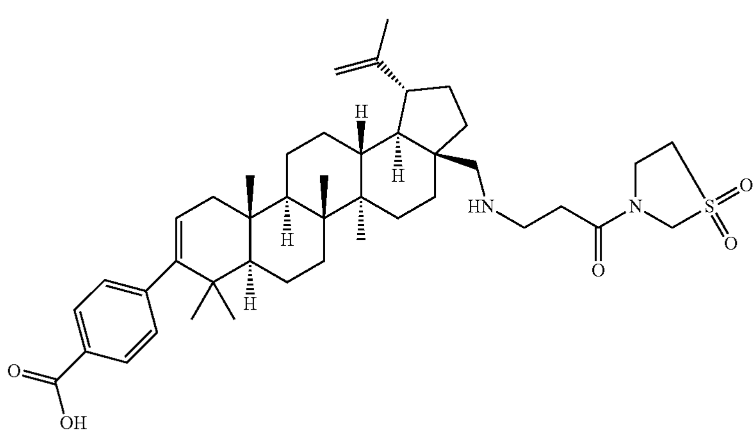 | A |

363 364
TABLE 2-continued
| Example # | Structure | EC$_{50}$ |
|---|---|---|
| 121 | 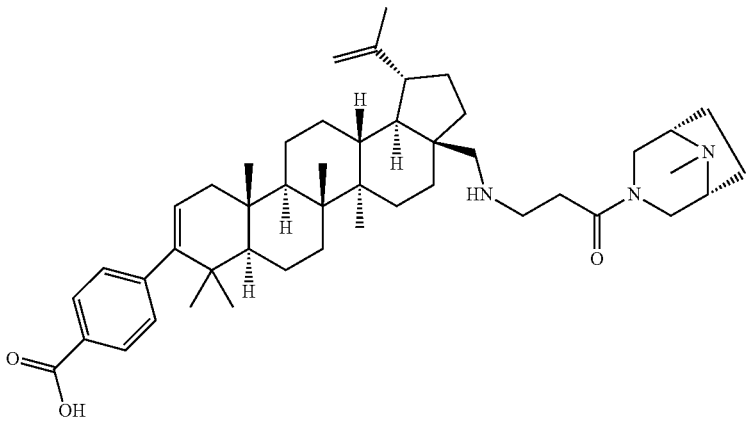 | A |
| 122 | 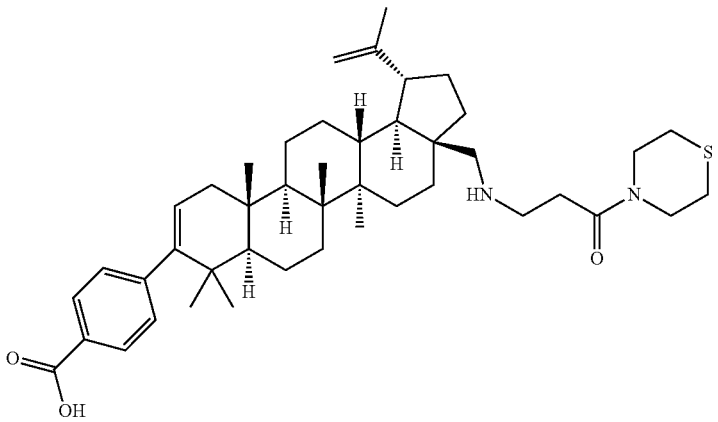 | A |
| 123 | 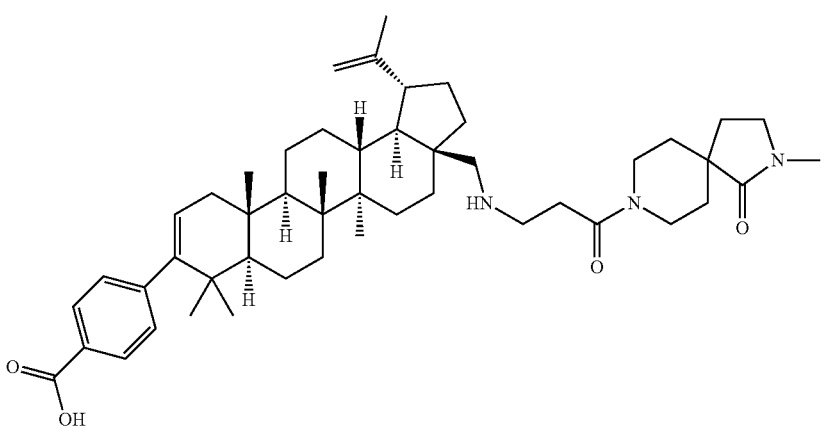 | A |

TABLE 2-continued
| Example # | Structure | EC$_{50}$ |
|---|---|---|
| 124 | 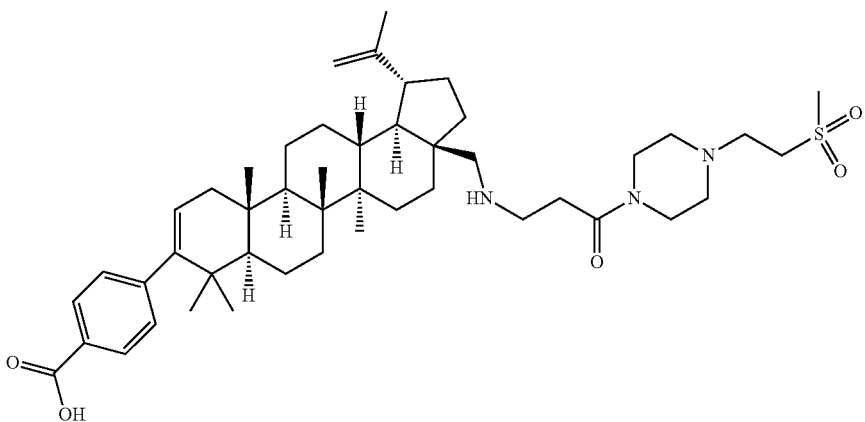 | A |
| 125 | 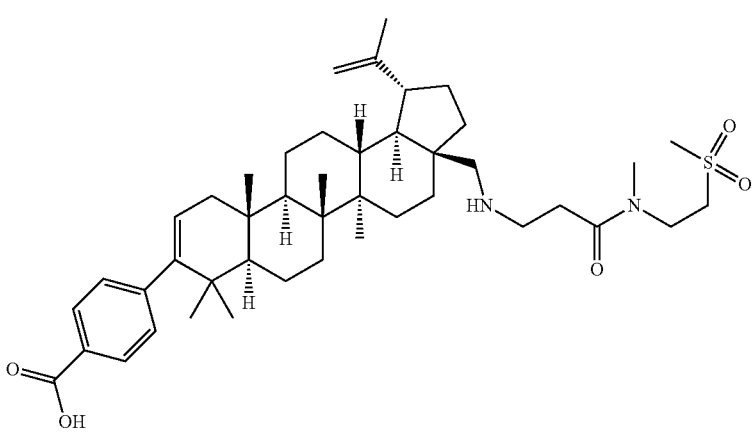 | A |
| 126 | 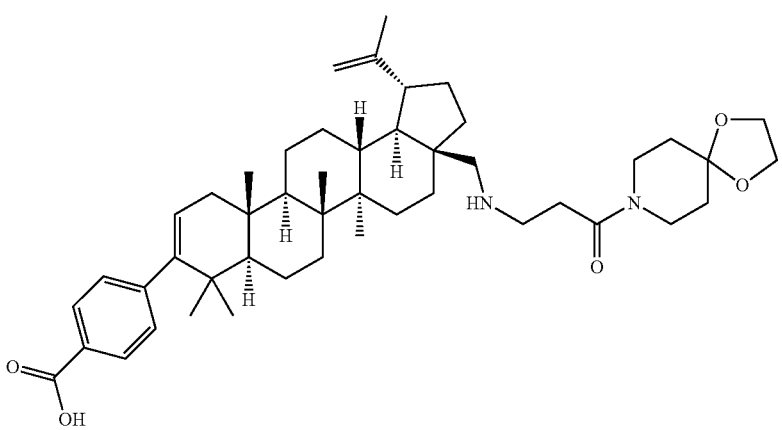 | 0.001 |

TABLE 2-continued

| Example # | Structure | EC$_{50}$ |
|---|---|---|
| 127 | 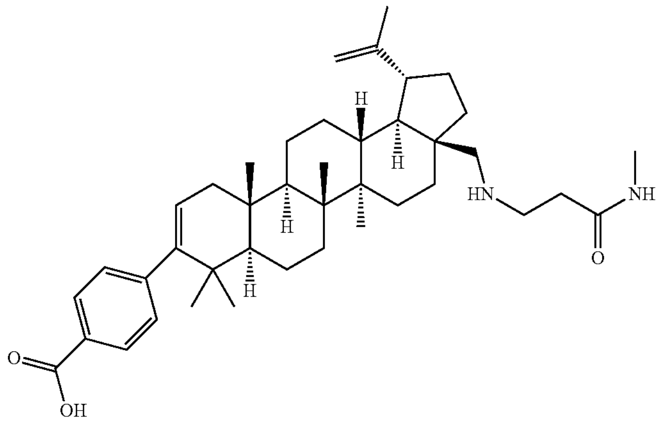 | A |
| 128 | 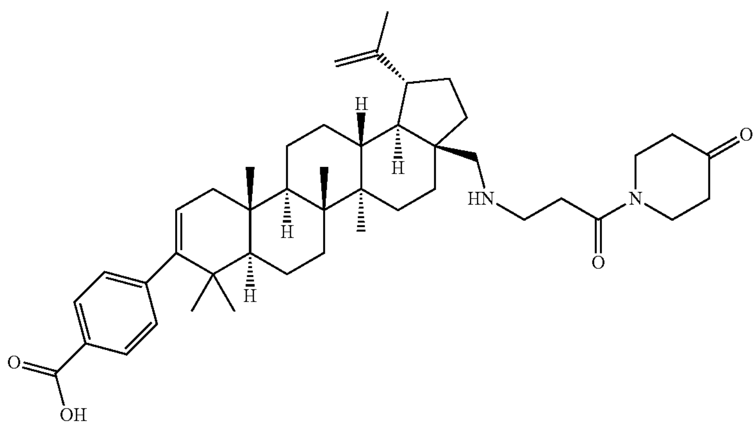 | A |
| 129 | 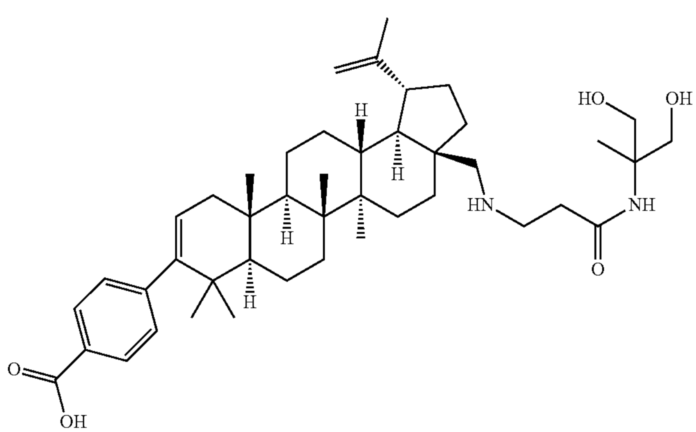 | A |

TABLE 2-continued
| Example # | Structure | EC₅₀ |
|---|---|---|
| 130 | 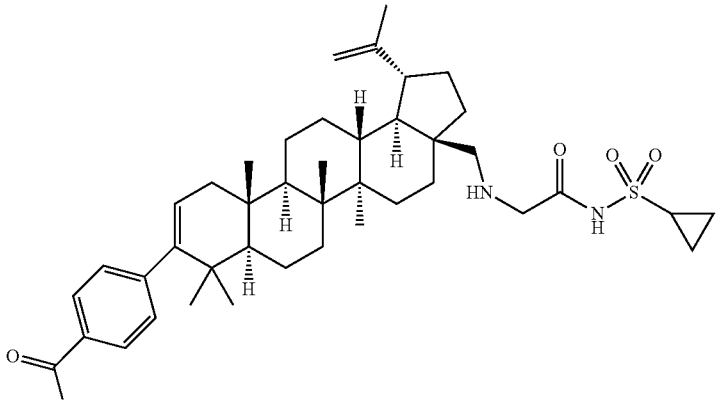 | A |
| 131 | 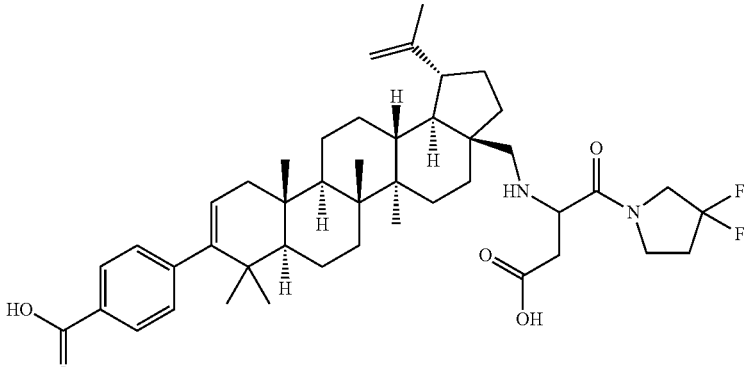 | A |
| 132 | 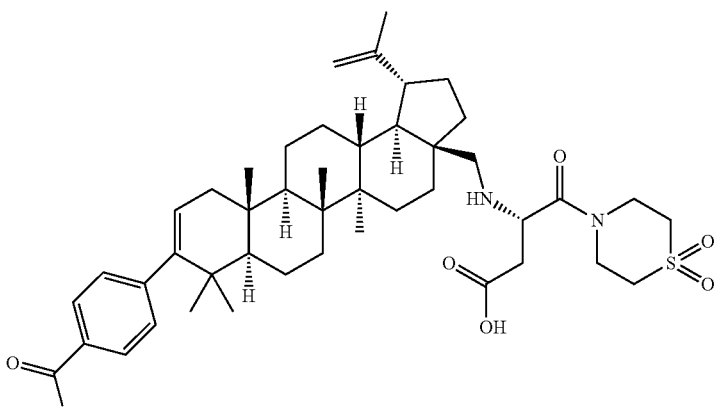 | A |

TABLE 2-continued
| Example # | Structure | EC$_{50}$ |
|---|---|---|
| 133 | 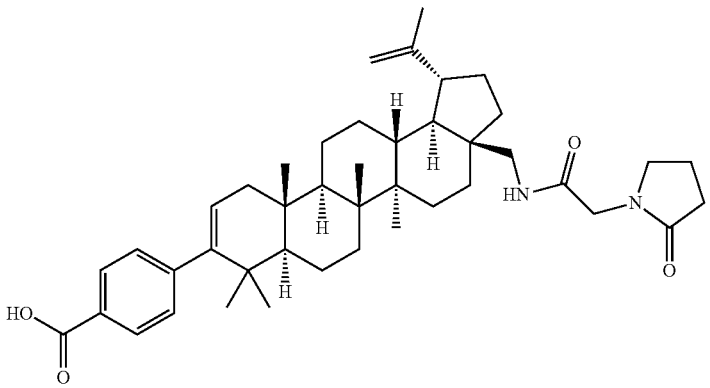 | A |
| 134 | 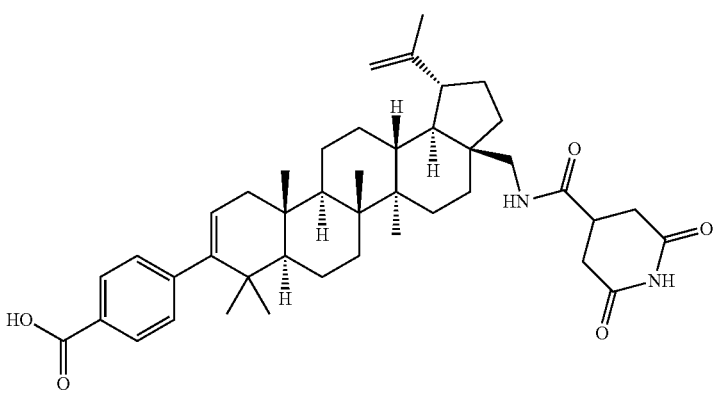 | A |
| 135 | 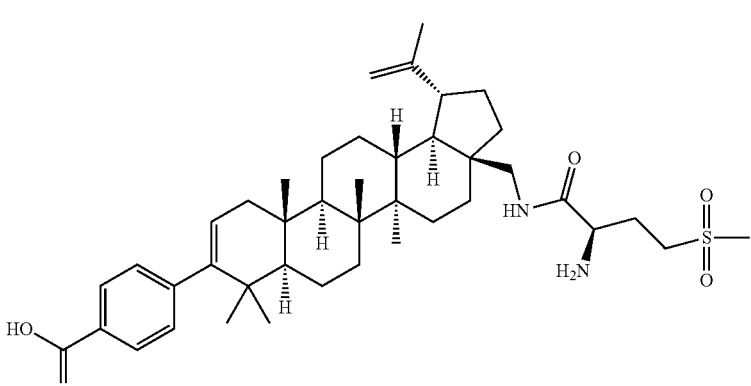 | A |
| 136 | 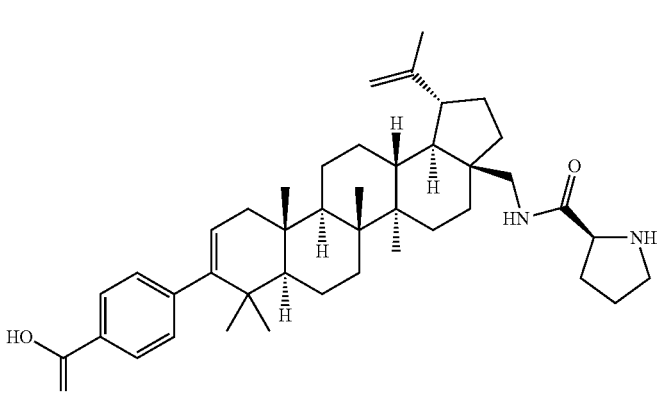 | A |

TABLE 2-continued

| Example # | Structure | EC$_{50}$ |
|---|---|---|
| 137 | 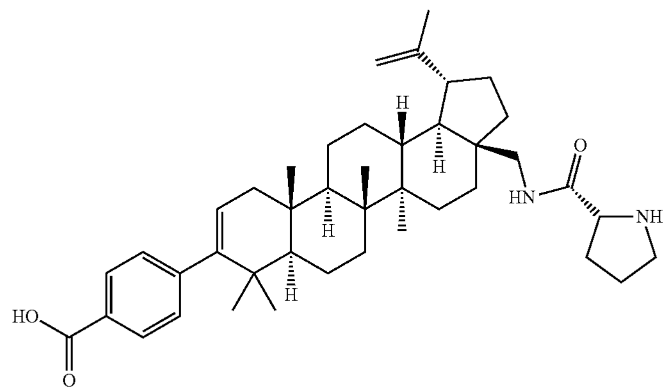 | A |
| 138 | 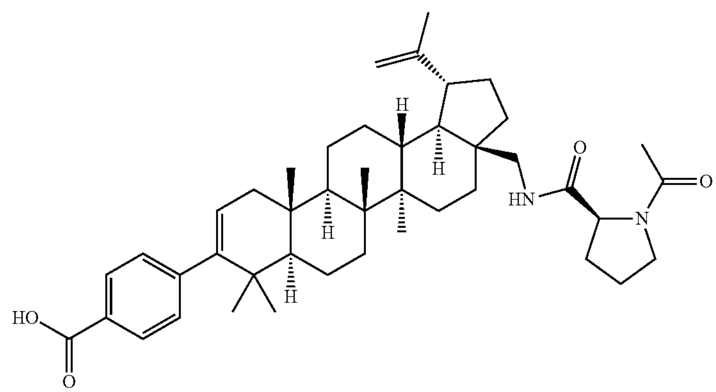 | A |
| 139 | 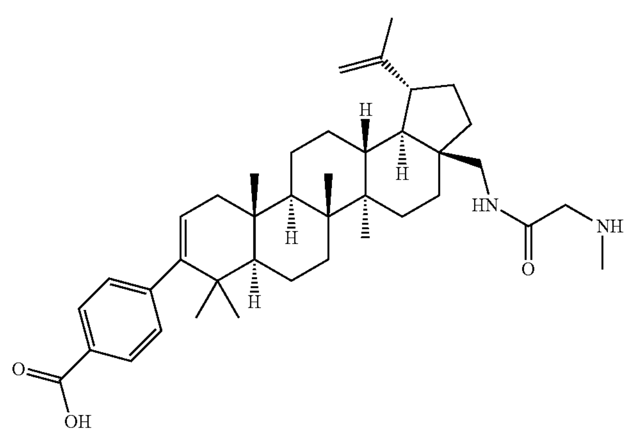 | A |

TABLE 2-continued
| Example # | Structure | EC$_{50}$ |
|---|---|---|
| 140 | 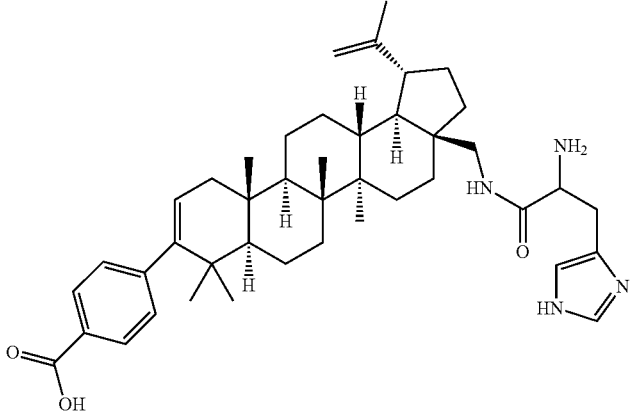 | A |
| 141 | 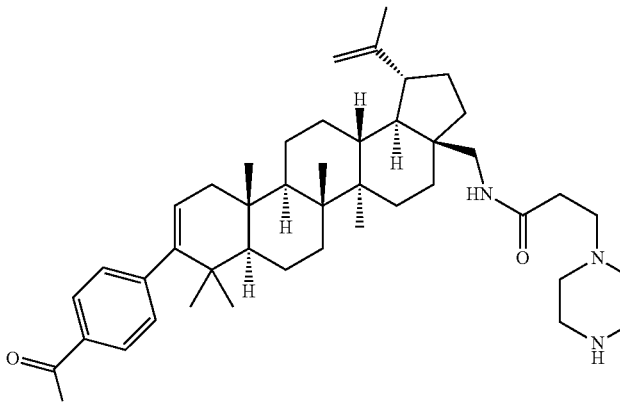 | A |
| 142 | 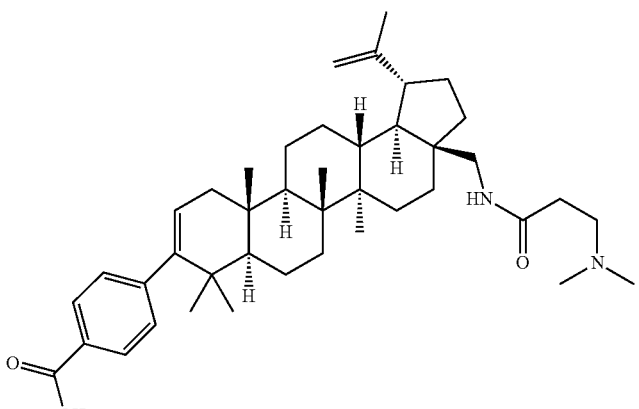 | A |

TABLE 2-continued

| Example # | Structure | EC$_{50}$ |
|---|---|---|
| 143 | 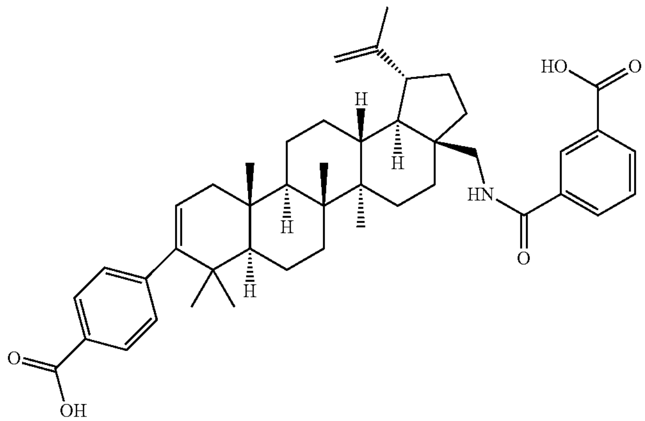 | A |
| 144 | 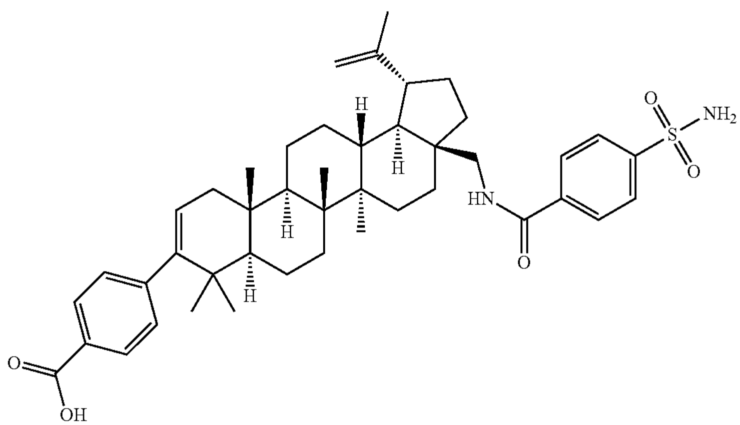 | A |
| 145 | 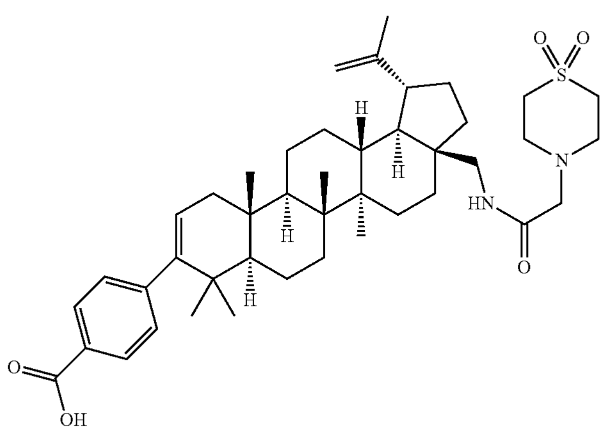 | A |

TABLE 2-continued
| Example # | Structure | EC$_{50}$ |
|---|---|---|
| 146 | 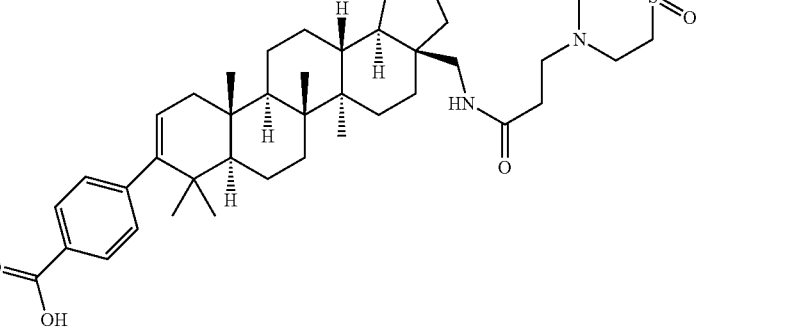 | A |
| 147 | 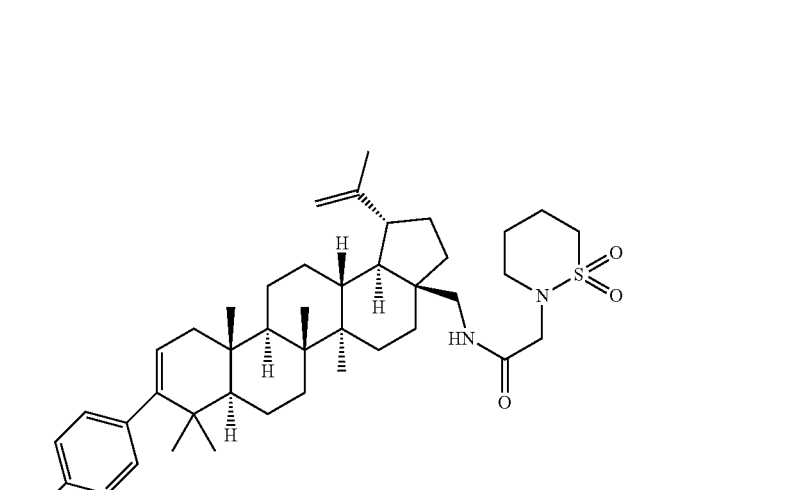 | A |
| 148 | 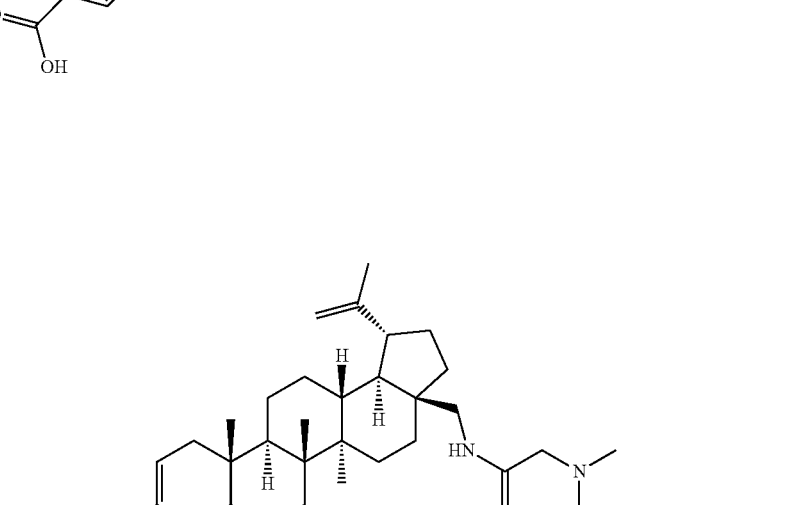 | A |

TABLE 2-continued

| Example # | Structure | EC$_{50}$ |
|---|---|---|
| 149 | 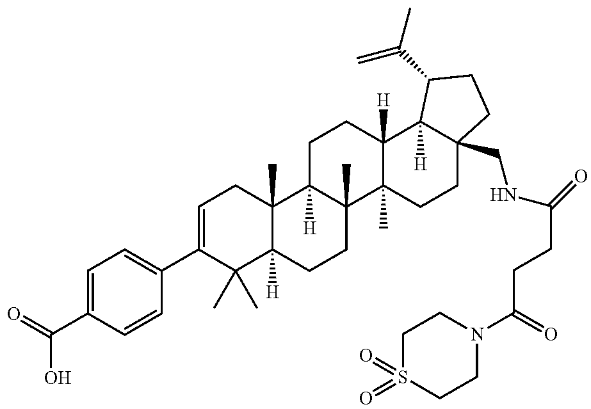 | A |
| 150 | 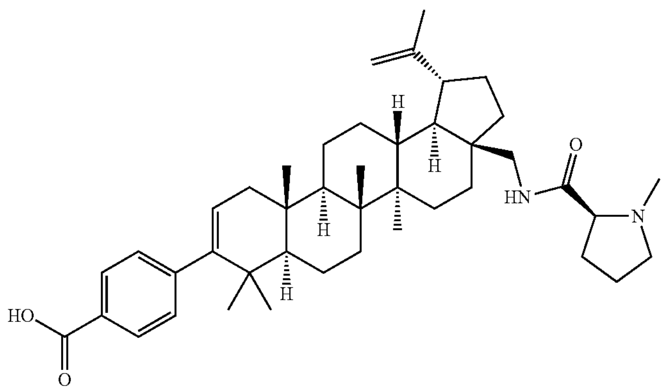 | A |
| 151 | 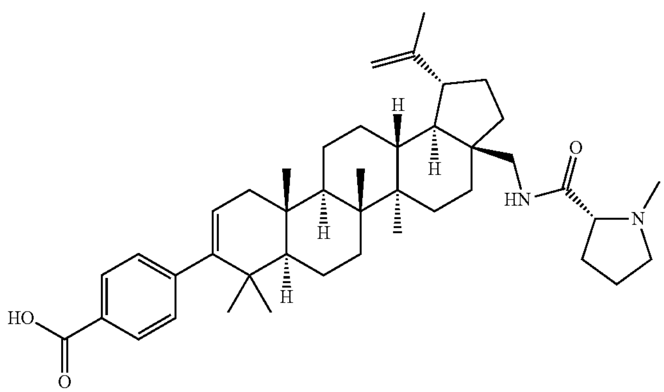 | A |
| 152 | 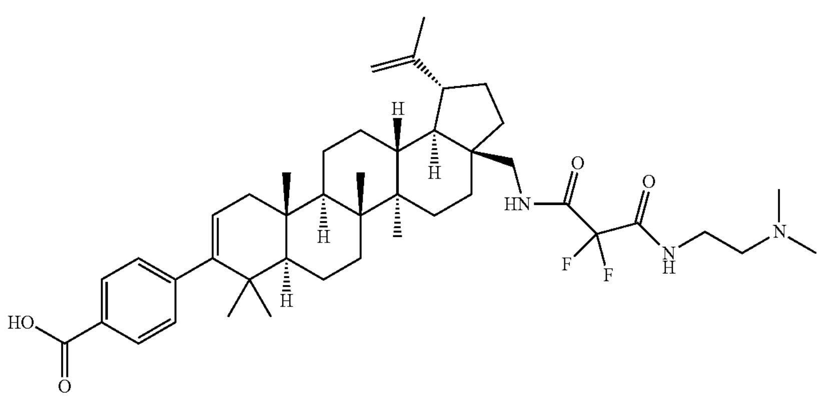 | A |

TABLE 2-continued
| Example # | Structure | EC$_{50}$ |
|---|---|---|
| 153 | 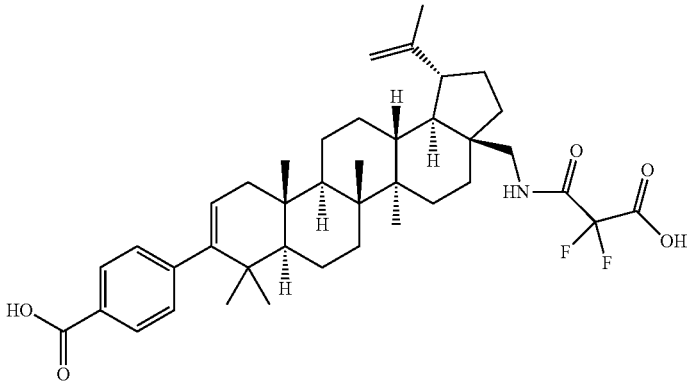 | B |
| 154 | 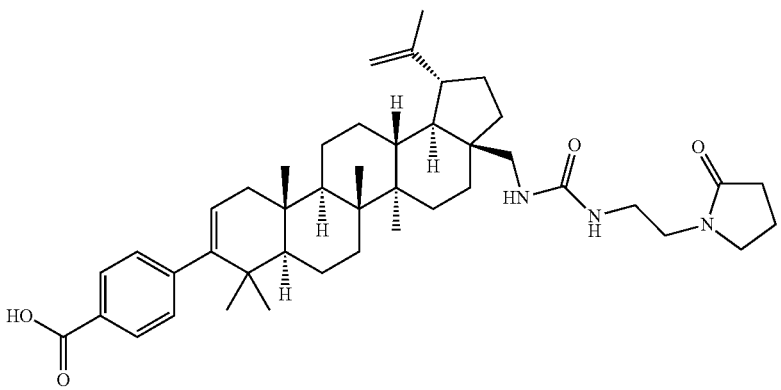 | A |
| 155 | 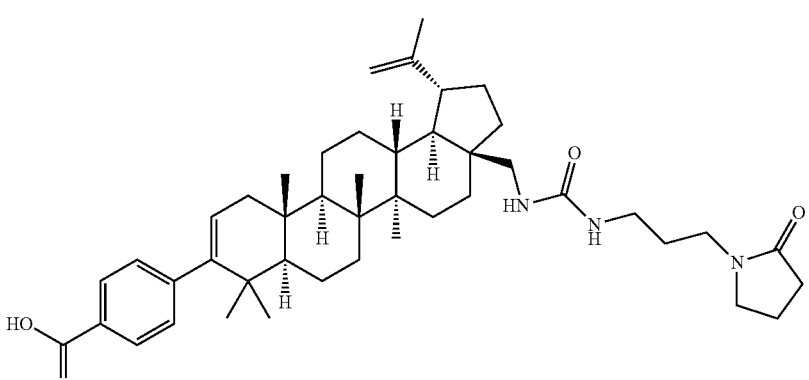 | A |
| 156 | 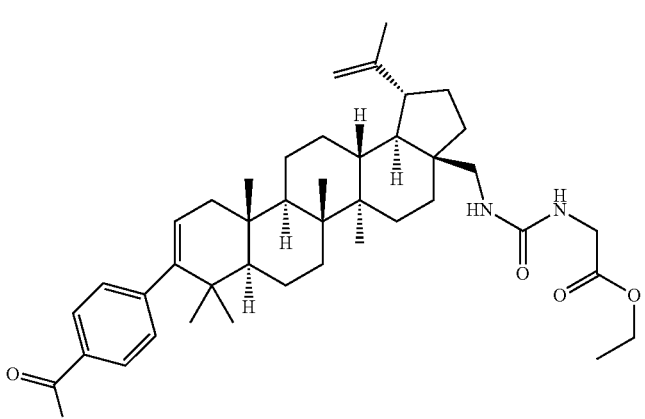 | A |

TABLE 2-continued

| Example # | Structure | EC$_{50}$ |
|---|---|---|
| 157 | 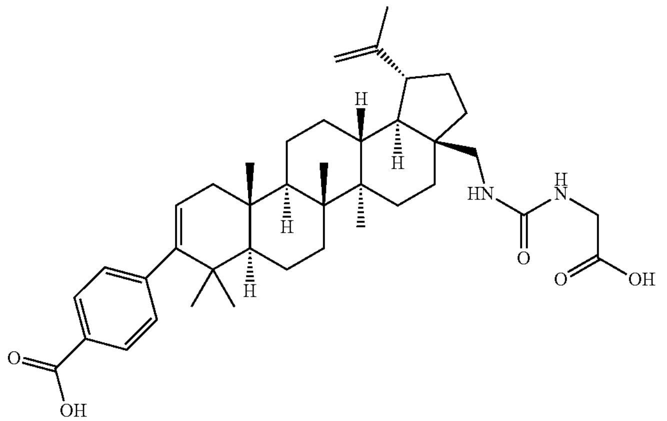 | 0.04 |
| 158 | 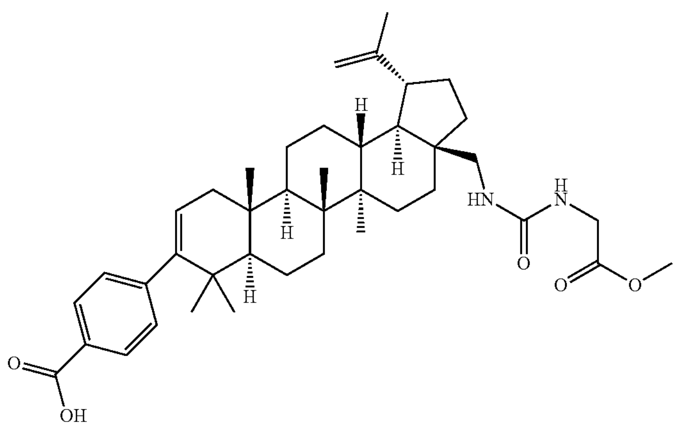 | A |
| 159 | 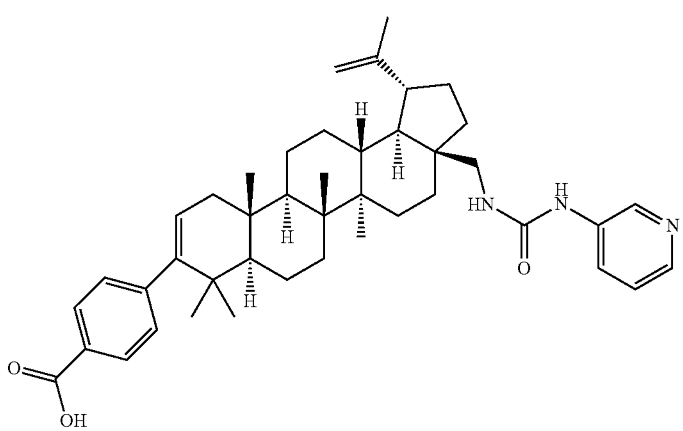 | 0.01 |

TABLE 2-continued
| Example # | Structure | EC$_{50}$ |
|---|---|---|
| 160 | 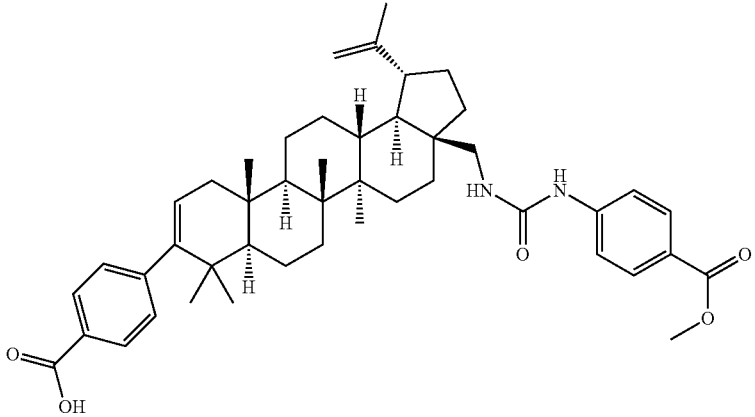 | 0.26 |
| 161 | 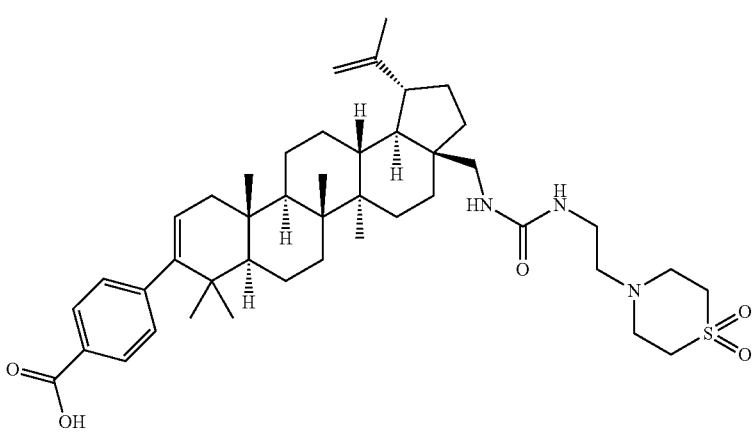 | A |
| 162 | 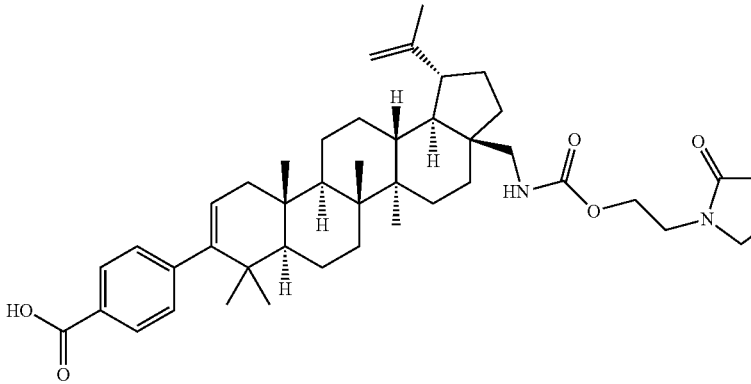 | A |

TABLE 2-continued
| Example # | Structure | EC$_{50}$ |
|---|---|---|
| 163 | 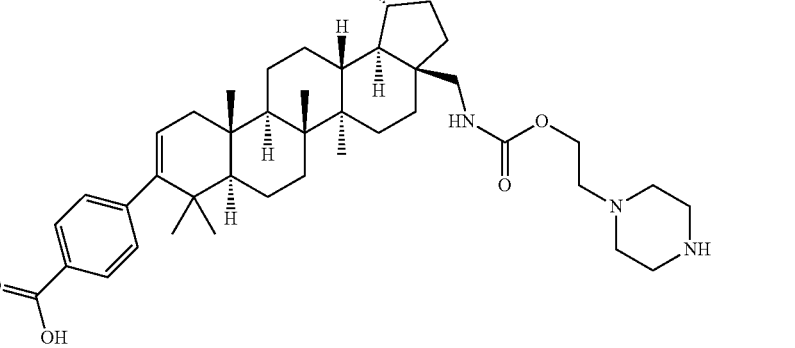 | A |
| 164 | 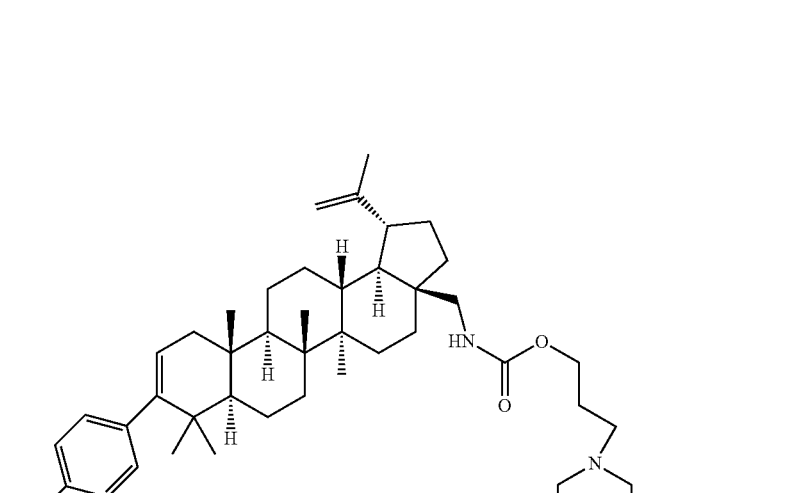 | A |
| 165 | 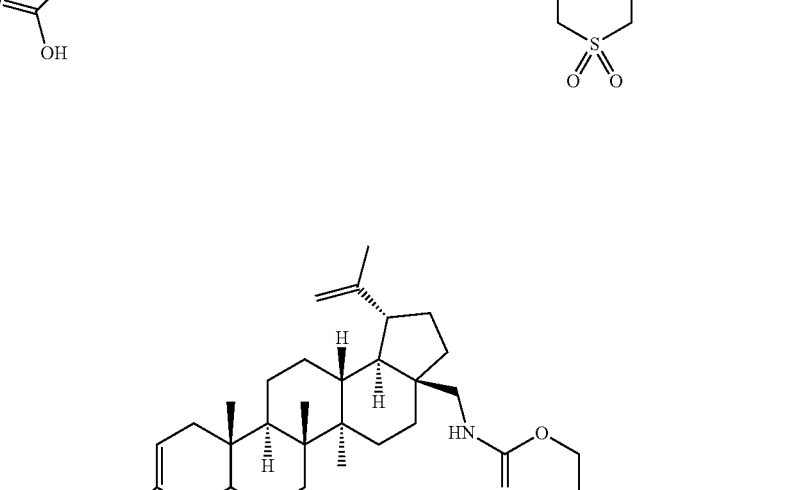 | A |

TABLE 2-continued

| Example # | Structure | EC$_{50}$ |
|---|---|---|
| 166 | 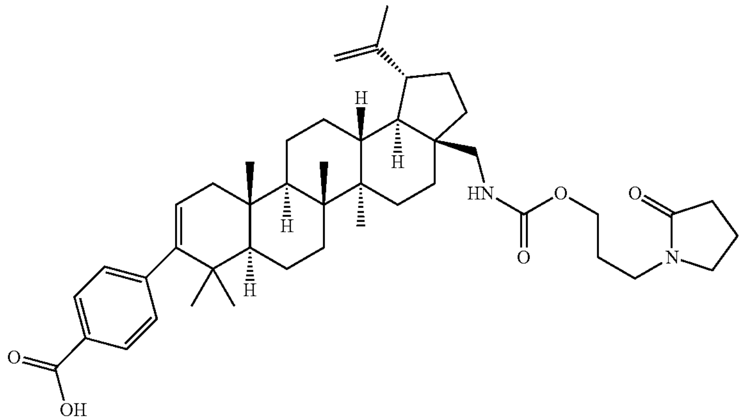 | A |
| 167 | 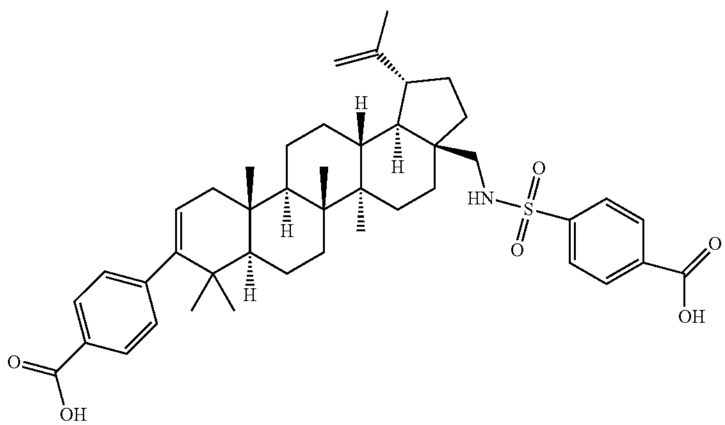 | A |
| 168 | 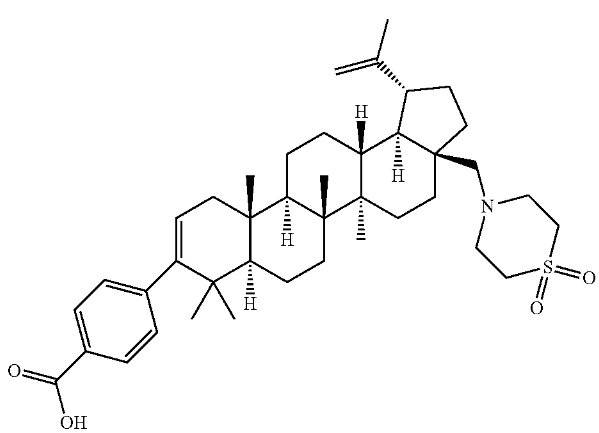 | A |

TABLE 2-continued
| Example # | Structure | EC₅₀ |
|---|---|---|
| 169 | 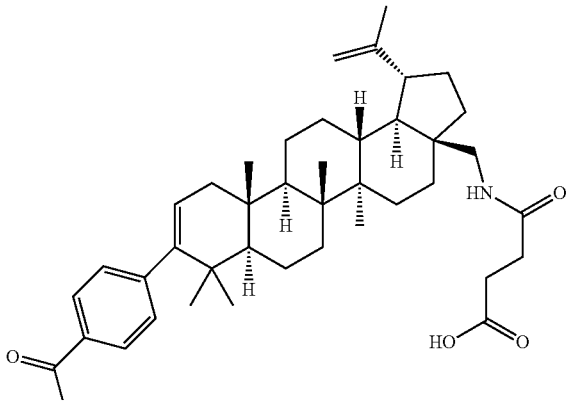 | A |
| 170 | 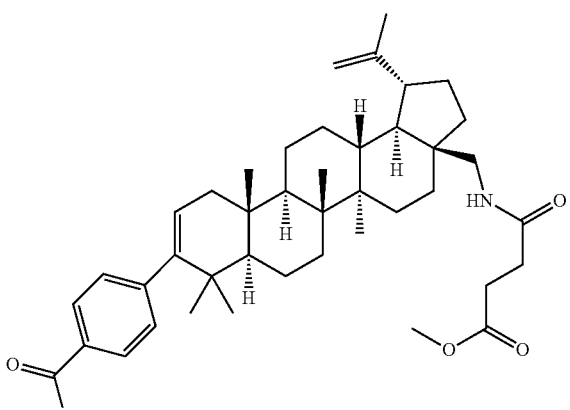 | A |
| 171 | 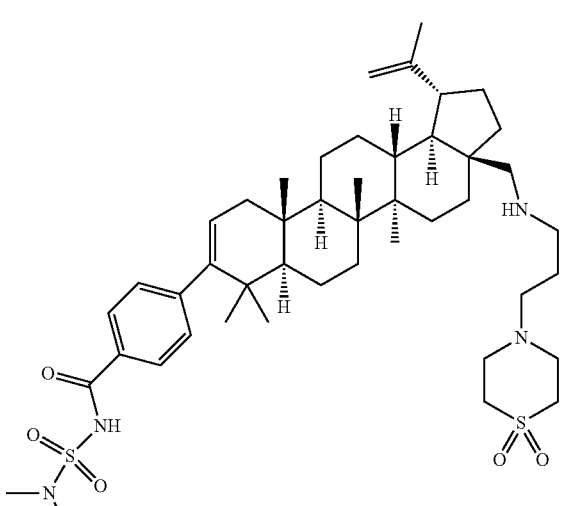 | A |

TABLE 2-continued
| Example # | Structure | EC$_{50}$ |
|---|---|---|
| 172 | 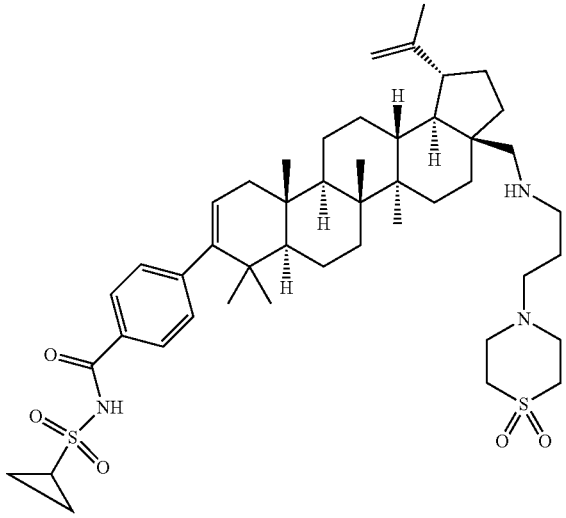 | A |
| 173 | 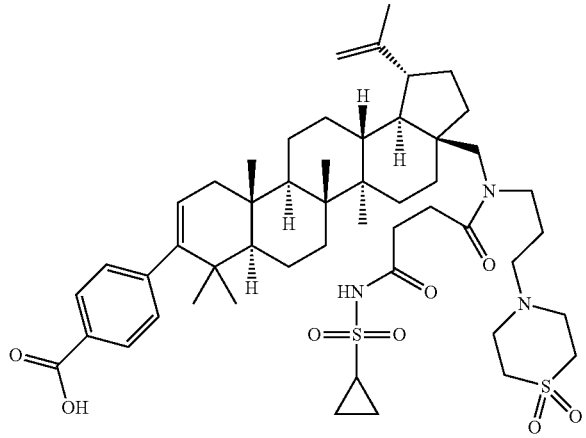 | A |
| 174 | 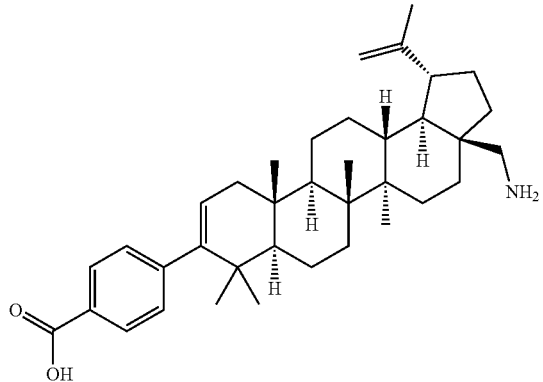 | A |

TABLE 2-continued
| Example # | Structure | EC$_{50}$ |
|---|---|---|
| 175 | 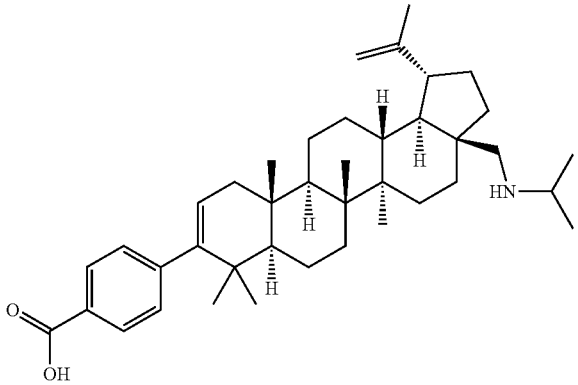 | A |
| 176 | 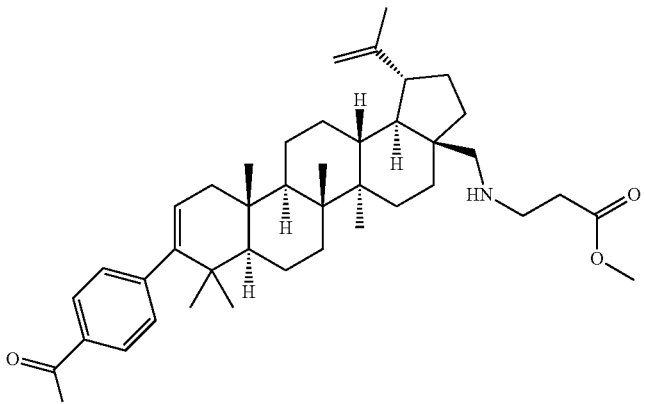 | 0.014 |
| 177 | 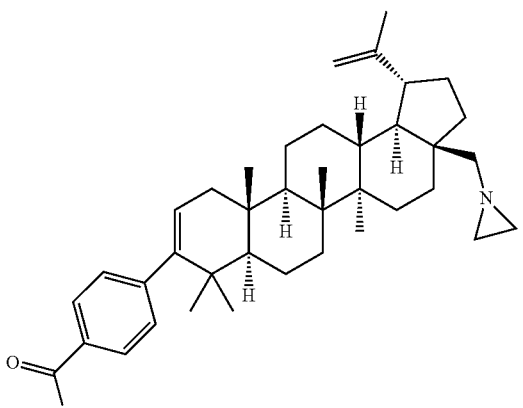 | A |

TABLE 2-continued

| Example # | Structure | EC$_{50}$ |
|---|---|---|
| 178 | 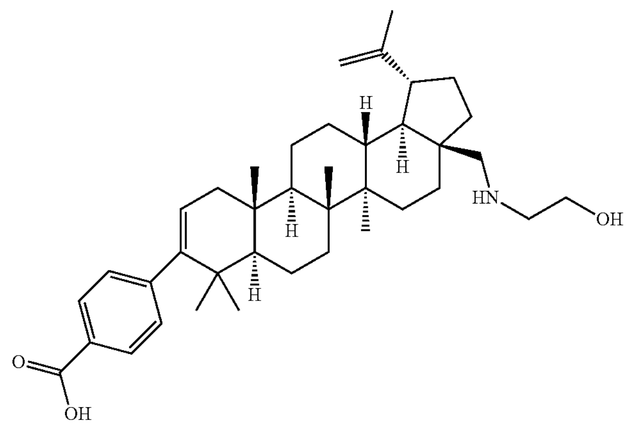 | A |
| 179 | 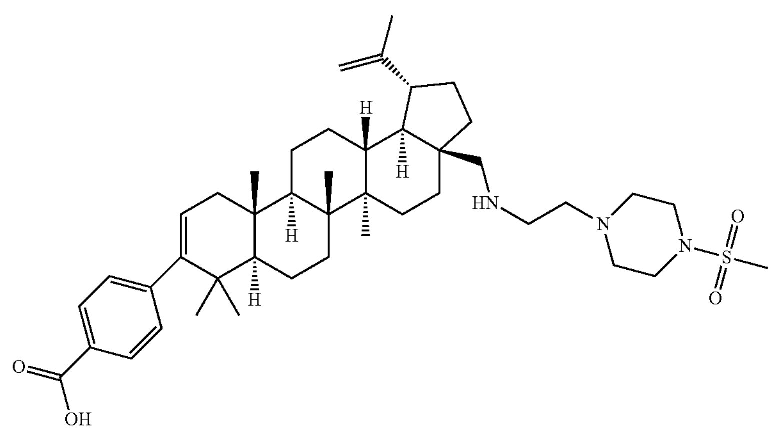 | A |
| 180 | 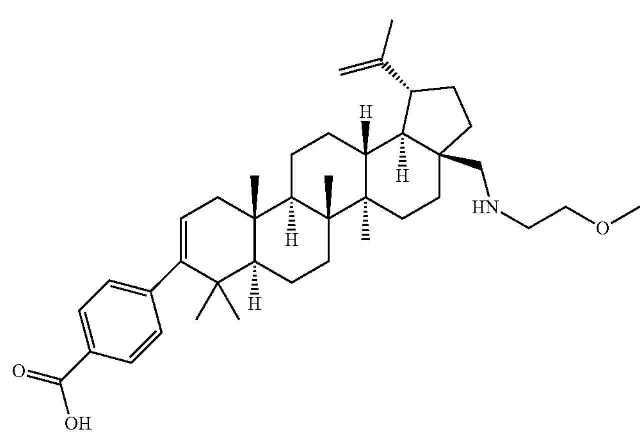 | A |

TABLE 2-continued

| Example # | Structure | EC$_{50}$ |
|---|---|---|
| 181 | 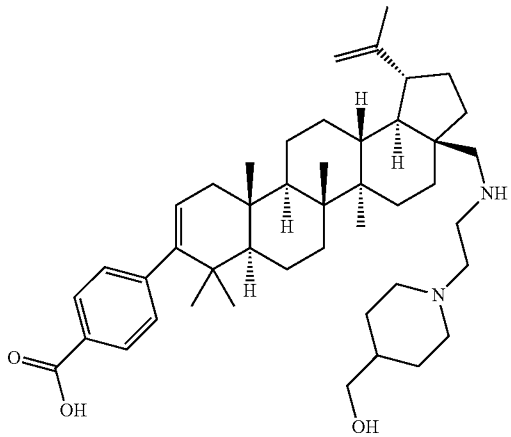 | 0.001 |
| 182 | 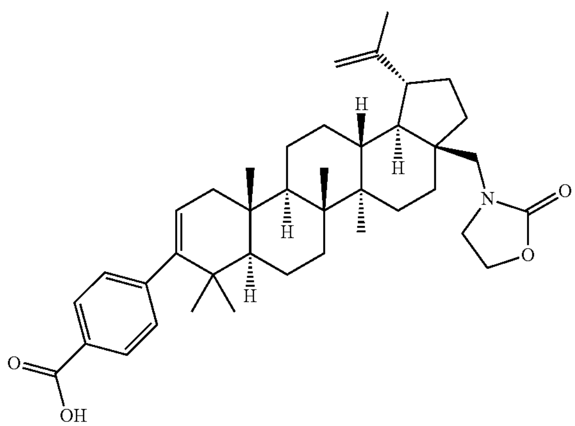 | A |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound, including pharmaceutically acceptable salts thereof, which is selected from the group of:

a compound of formula I

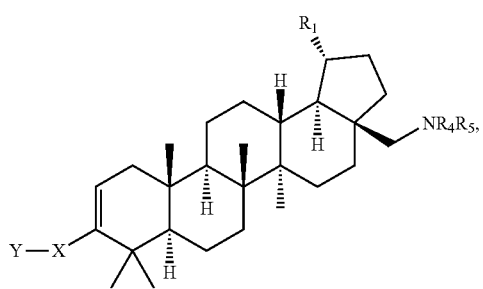

Formula I a compound of formula II

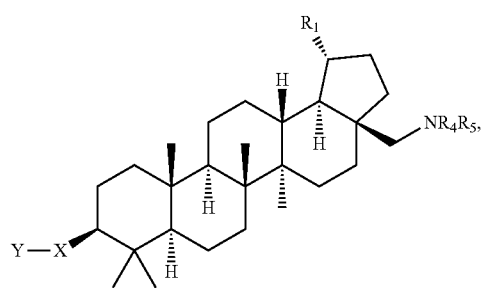

a compound of formula III

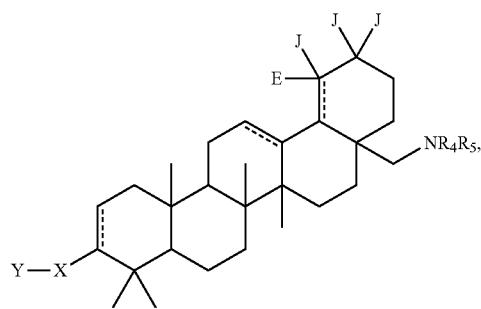

wherein $R_1$ is isopropenyl or isopropyl;

J and E are independently —H or —$CH_3$ and E is absent when the double bond is present;

X is a phenyl or heteroaryl ring substituted with A, wherein A is at least one member selected from the group of —H, -halo, -hydroxyl, —$C_{1-6}$ alkyl, —$C_{1-6}$ alkoxy, and —$COOR_2$;

$R_2$ is —H, —$C_{1-6}$ alkyl or -alkylsubstituted $C_{1-6}$ alkyl or -arylsubstituted $C_{1-6}$ alkyl;

Y is selected from the group of —$COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, —$C_{1-6}$ alkenyl-$COOR_2$, —$C_{1-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and —CONHOH, wherein n=1-6;

$R_3$ is —$C_{1-6}$ alkyl or alkylsubstituted $C_{1-6}$ alkyl;

$R_4$ is selected from the group of H, —$C_{1-6}$ alkyl, —$C_{3-6}$ cycloalkyl, —$C_{1-6}$ substituted alkyl, —$C_{1-6}$ alkyl-heteroaryl, alkyl-substitutedheteroaryl, alkyl-$NR_6R_7$, —$C_{1-6}$ alkyl-$CONR_8R_9$, —$C_{3-6}$ cycloalkyl-$CONR_8R_9$, cycloalkyl-$(CH_2)_{1-3}$—$NR_6R_7$, —$(CH_2)_{1-3}$—$C_{3-6}$ cycloalkyl-$NR_6R_7$, —$(CH_2)_{1-3}$—$C_{3-6}$ cycloalkyl-$(CH_2)_{1-3}$—$NR_6R_7$, —$C_{1-6}$ alkyl-$Q_1$, $C_{3-6}$ cycloalkyl-$Q_1$, —$COR_{10}$, —$SO_2R_3$ and —$SO_2NR_2R_2$;

$Q_1$=-hydroxy, —$COOR_2$, -halo, —$SO_2R_a$;

$R_a$=$C_{1-6}$ alkyl, $NR_2R_2$, $R_b$=—H, —$C_{1-6}$ alkyl, —$COR_3$, —$SO_2R_3$, —$SONR_3R_3$, $R_4$ can also be selected from the group of:

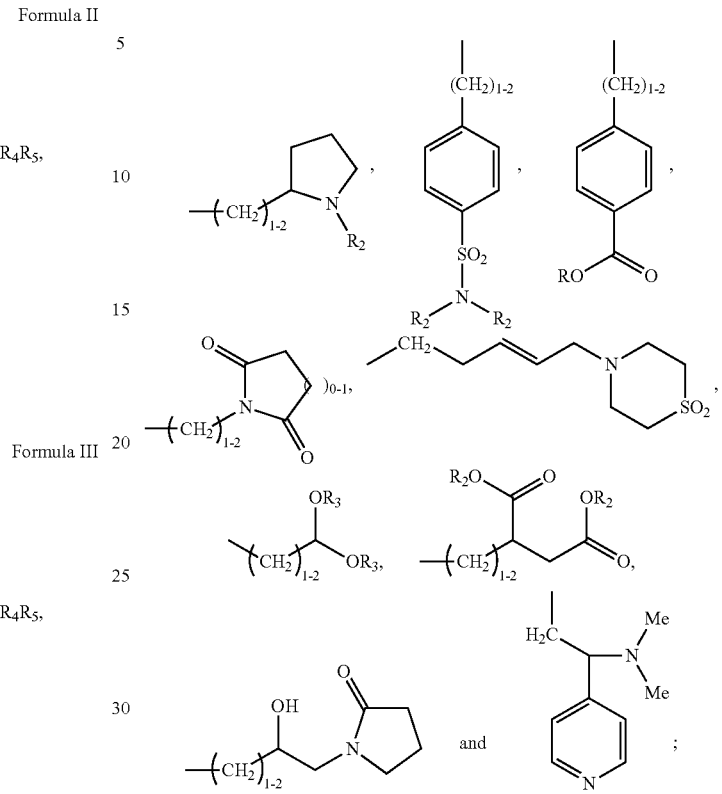

$R_5$ is selected from the group of —H, —$C_{1-6}$ alkyl, —$C_{3-6}$ cycloalkyl, —$C_{1-6}$ alkyl substitutedalkyl, —$COR_{10}$, —$SO_2R_3$ and —$SO_2NR_2R_2$;

with the proviso that only one of $R_4$ or $R_5$ can be selected from the group of —$COR_{10}$, —$SO_2R_3$ and —$SO_2NR_2R_2$;

or $R_4$ and $R_5$ are taken together with the adjacent N to form a cycle such as

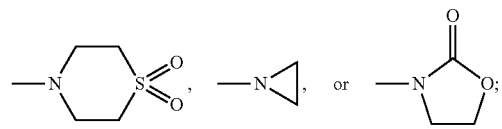

$R_{10}$ is selected from the group of —H, —$C_{1-6}$ alkyl, —$C_{1-6}$ alkyl-$NR_6R_7$, —$NR_{11}R_{12}$, —$OR_{13}$, —$C_{1-6}$ alkyl-$Q_2$, —$C_{3-6}$ cycloalkyl-$Q_2$, aryl-$Q_2$, wherein n=1-6, wherein $Q_2$=hydroxy, —$COOR_2$, -halo, $SO_2R_a$, —$CONHSO_2R_3$, —$CONHSO_2NR_2R_2$;

$R_{10}$ can also be selected from the group of:

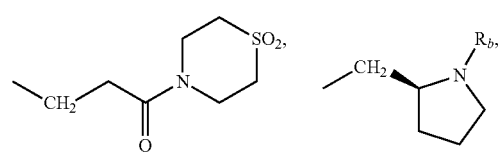

-continued

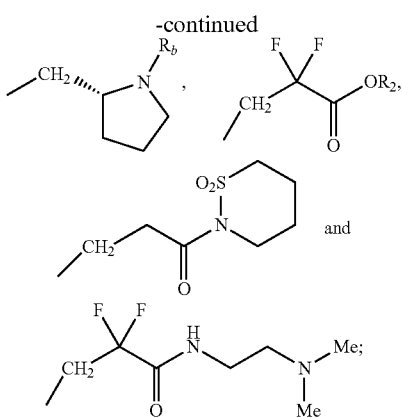

R$_6$ and R$_7$ are independently selected from the group of
—H, —C$_{1-6}$ alkyl, —C$_{1-6}$ substituted alkyl, aryl, heteroaryl, substituted aryl, substituted heteroaryl, and —C$_{1-6}$ alkyl-Q$_1$, or R$_6$ and R$_7$ are taken together with the adjacent N to form a cycle selected from the group of

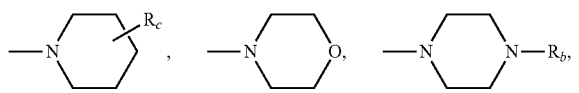

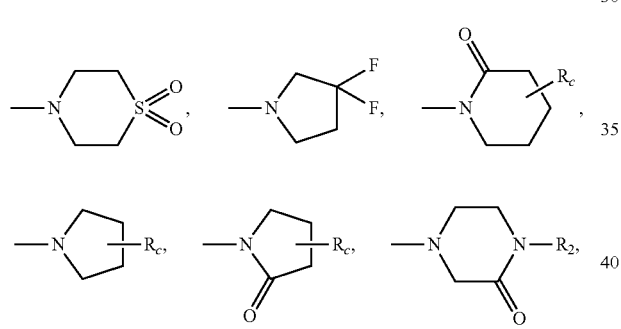

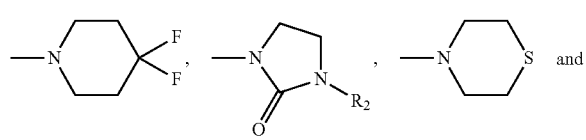

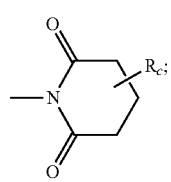

R$_c$=C$_{1-6}$ alkyl, NR$_2$R$_2$, —COOR$_3$;

R$_8$ and R$_9$ are independently selected from the group of —H, —C$_{1-6}$ alkyl, —C$_{3-6}$ cycloalkyl, —C$_{1-6}$ substituted alkyl, —C$_{1-6}$ alkyl-heteroaryl, —C$_{1-6}$ alkyl-substituted-heteroaryl, —C$_{1-6}$ alkyl-NR$_2$R$_2$, —C$_{1-6}$ alkyl-CONR$_2$R$_2$, —C$_{1-6}$ alkyl-Q$_1$, C$_{3-6}$ cycloalkyl-Q$_1$, or R$_8$ and R$_9$ can also be independently selected from the group of

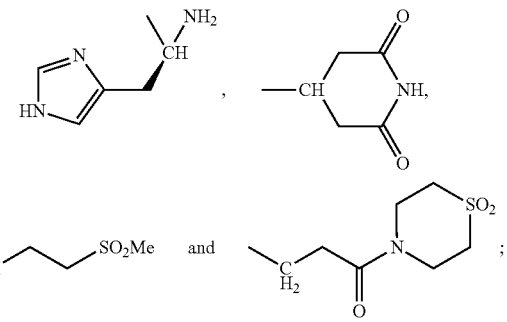

or R$_8$ and R$_9$ are taken together with the adjacent N to form a cycle selected from the group of:

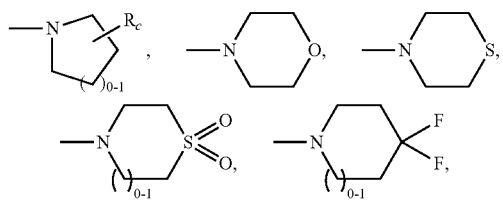

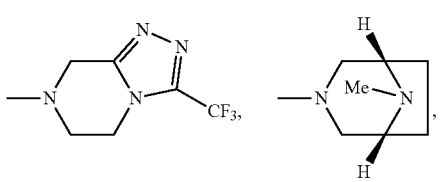

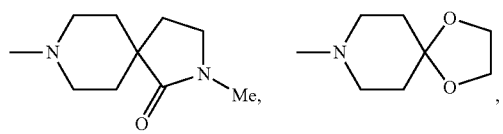

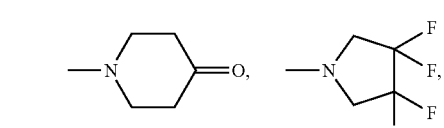

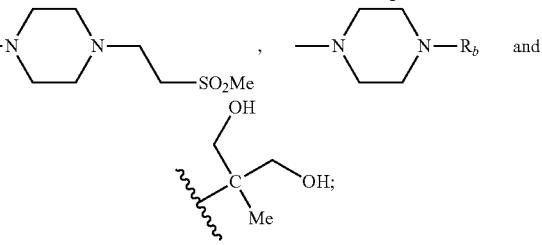

and R$_{11}$ and R$_{12}$ are independently selected from the group of —H, —C$_{1-6}$ alkyl, —C$_{3-6}$ cycloalkyl, and —C$_{1-6}$ alkylsubstituted alkyl;

or $R_{11}$ and $R_{12}$ are taken together with the adjacent N to form a cycle selected from the group of

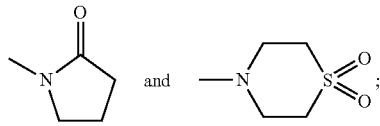

and $R_{13}$ is selected from the group of —H, $C_{1-6}$ alkyl, —$C_{1-6}$ alkyl substituted alkyl, and —$C_{1-6}$ alkyl $NR_{14}R_{15}$, wherein $R_{14}$ and $R_{15}$ are independently selected from the group of —H, —$C_{1-6}$ alkyl, and —$C_{1-6}$ alkylsubstituted alkyl, or $R_{14}$ and $R_{15}$ are taken together with the adjacent N to form a cycle selected from the group of

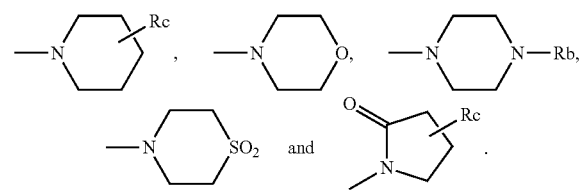

2. The compound as claimed in claim 1, wherein said compound has the Formula I.

3. The compound as claimed in claim 2, wherein X is a phenyl ring, and Y is in the para position.

4. The compound as claimed in claim 3, wherein X is a substituted phenyl ring.

5. The compound as claimed in 4, wherein said phenyl ring is substituted with A, and A is at least one member selected from the group of —OH and —F.

6. The compound as claimed in claim 5, wherein Y is —COOH.

7. The compound as claimed in claim 4, wherein X is a phenyl ring and Y is —COOH in the para position according to Formula Ia:

Formula Ia

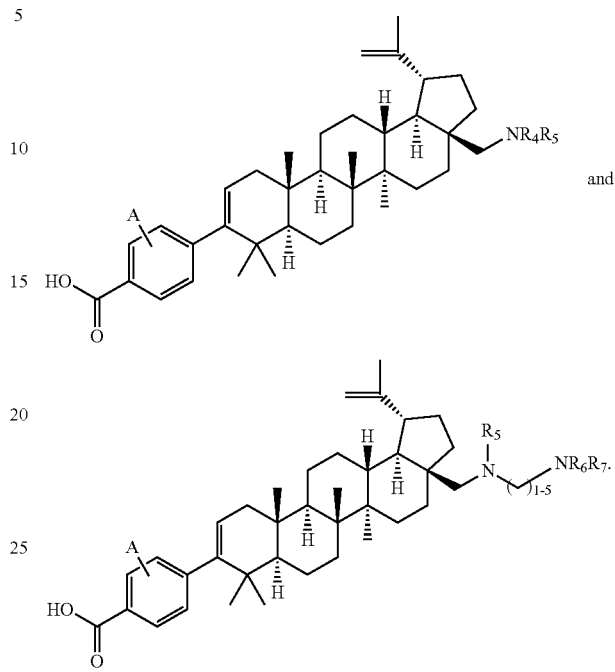

8. The compound as claimed in claim 7, wherein A is at least one member selected from the group of —H, —OH and —F.

9. The compound as claimed in claim 8, wherein A is —H or —F.

10. A compound, including pharmaceutically acceptable salts thereof, which is selected from the group consisting of:

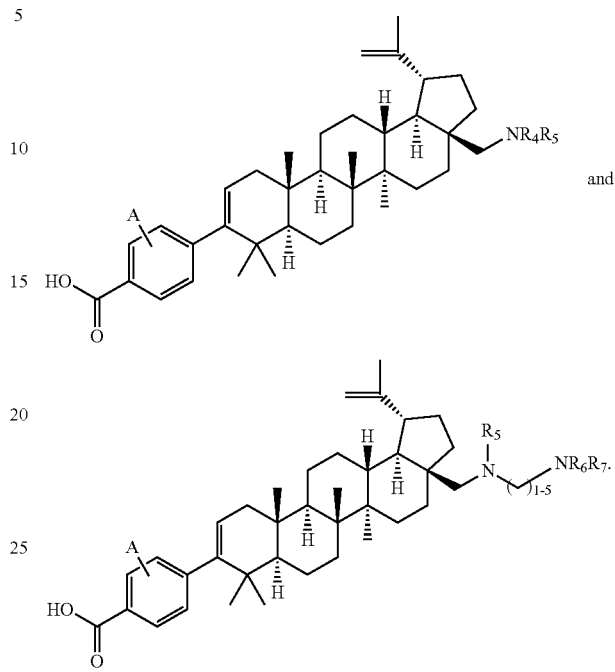

and

11. A compound which is selected from the group consisting of:

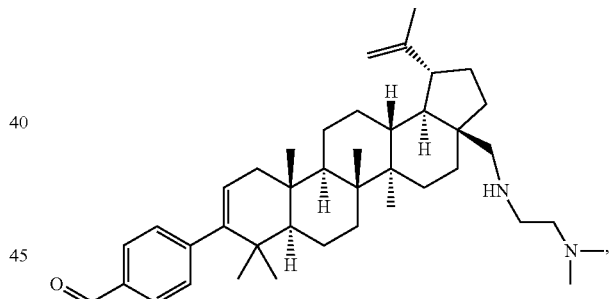

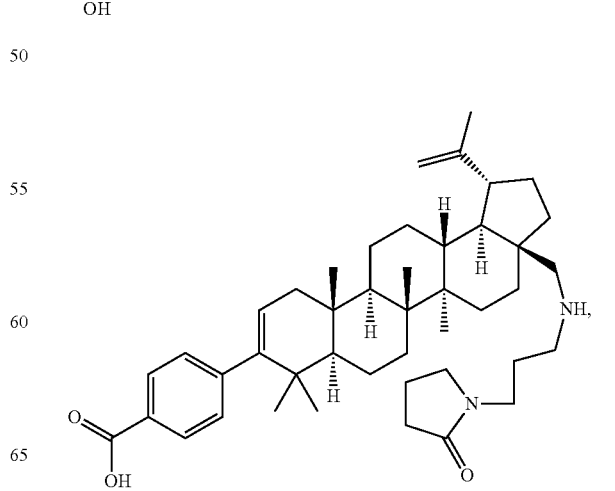

409 -continued
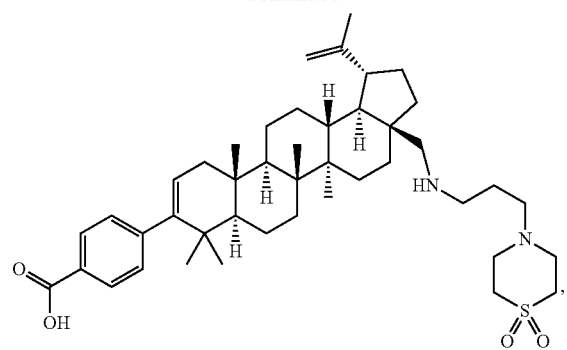
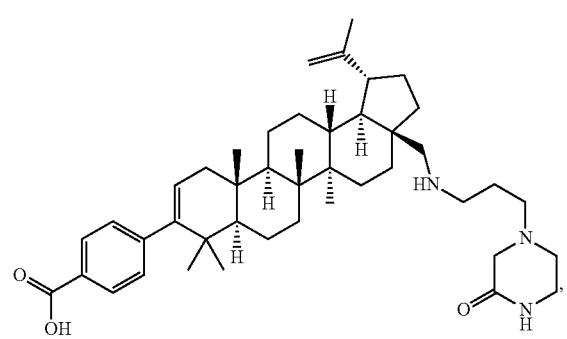
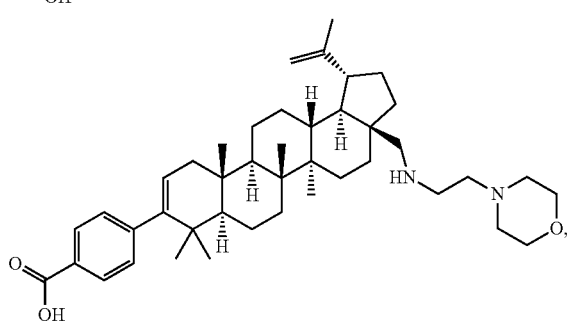
410 -continued
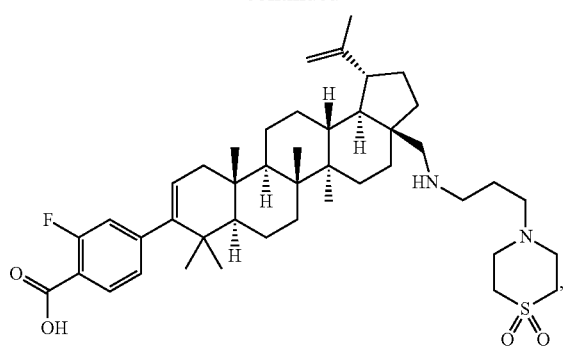
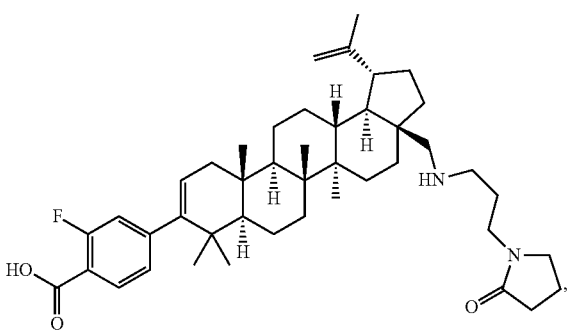
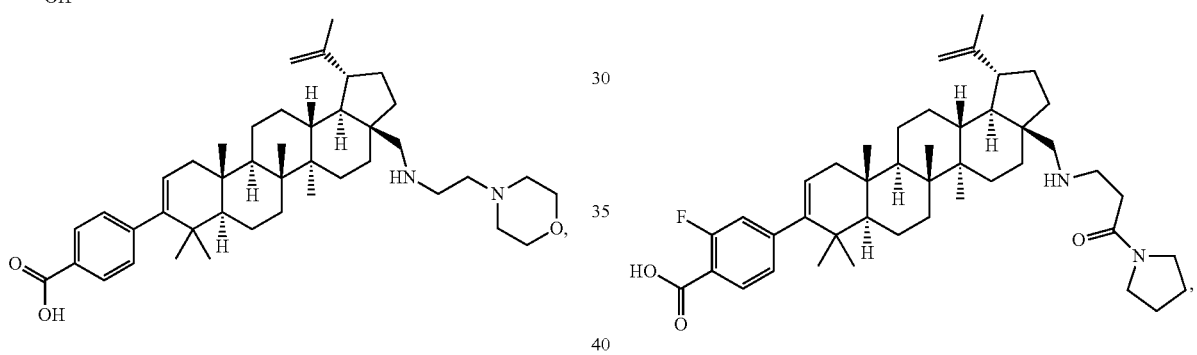
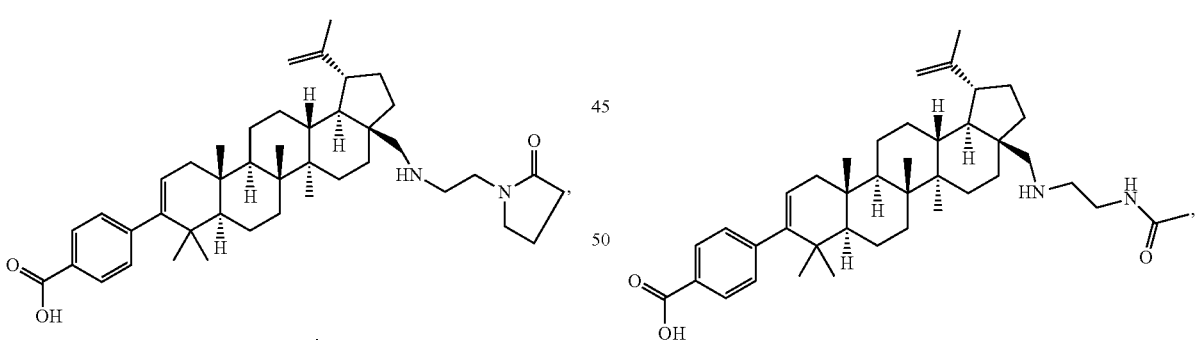
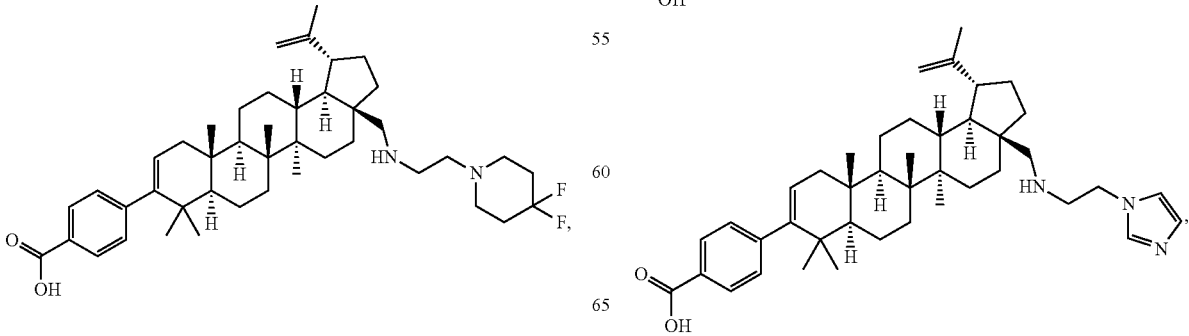

411
-continued
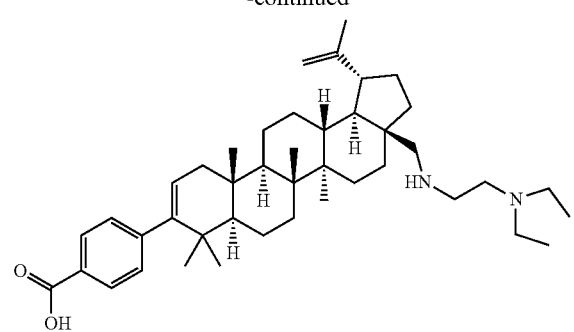
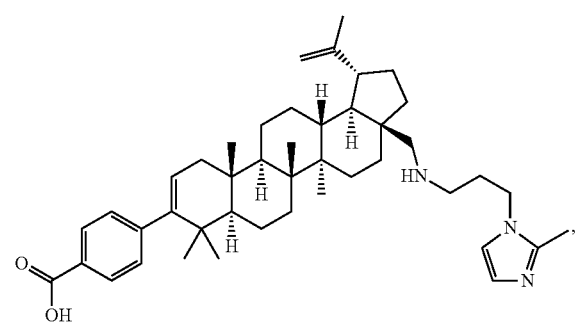
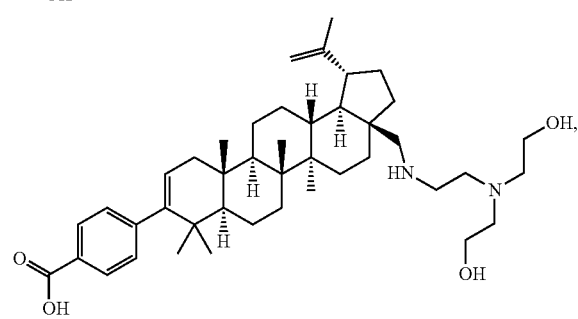
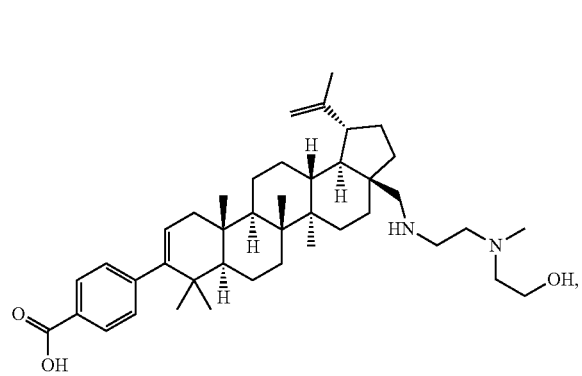
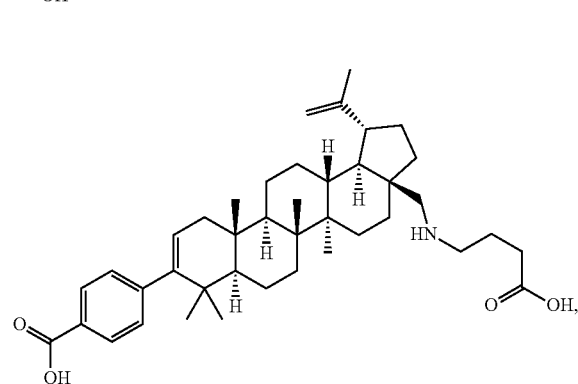
412
-continued
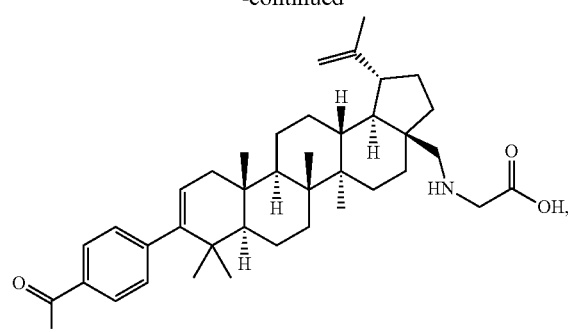
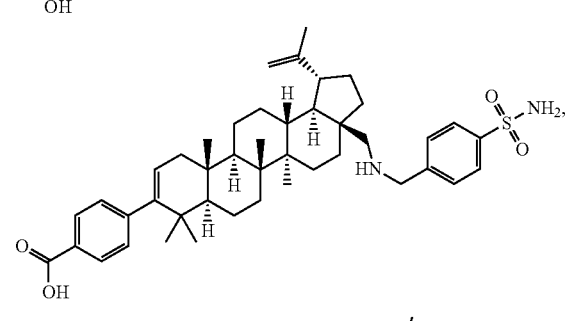
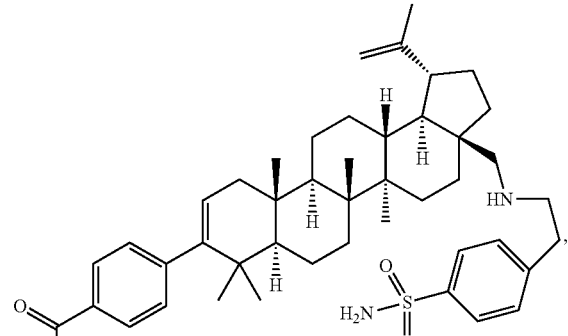
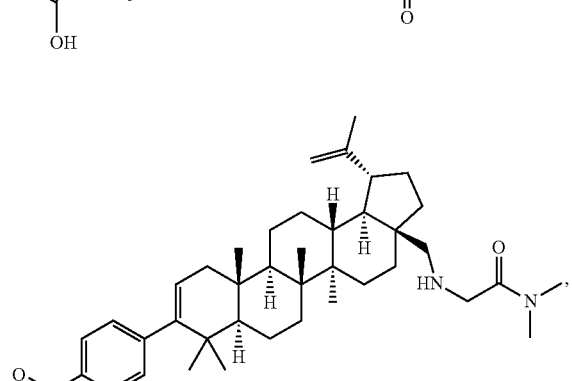
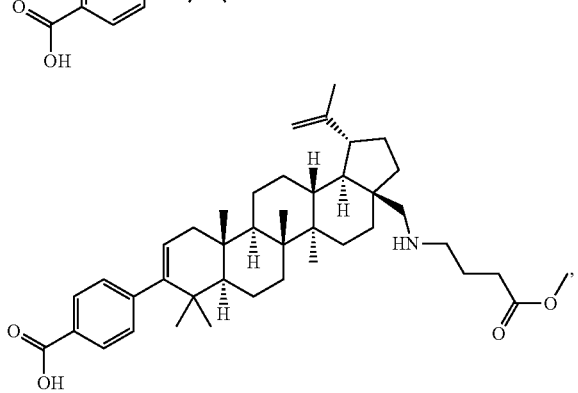

-continued

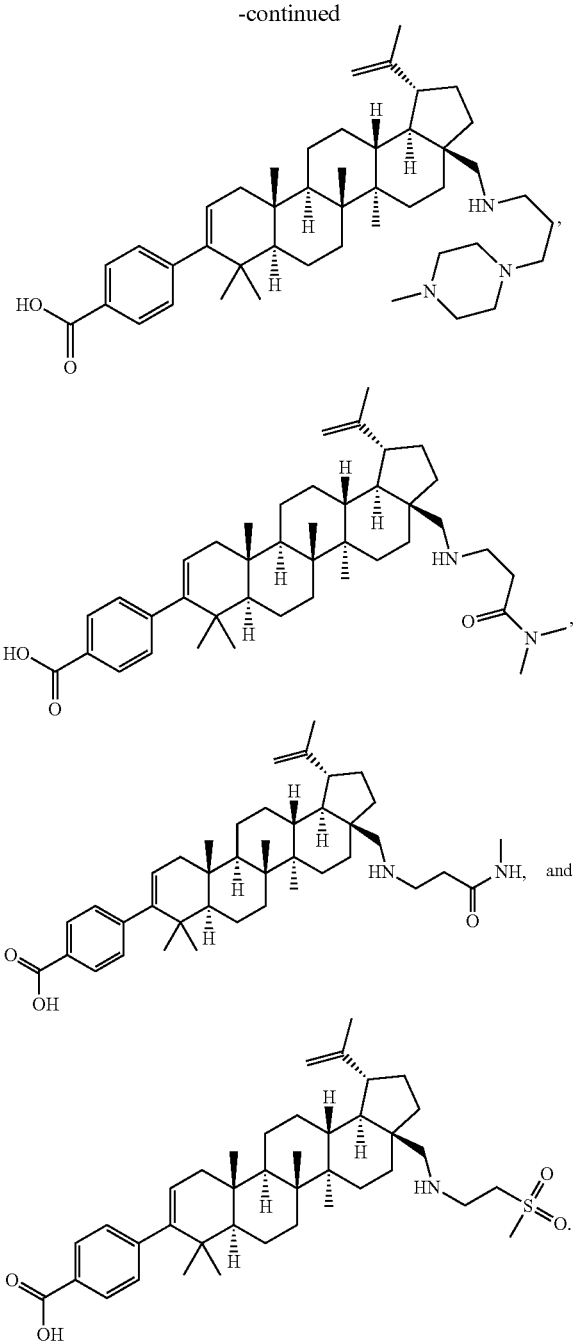

12. A pharmaceutical composition which comprises an antiviral effective amount of one or more of the compounds as claimed in claim 1, together with one or more pharmaceutically acceptable carriers, excipients or diluents.

13. The pharmaceutical composition of claim 12, useful for treating infection by HIV, which additionally comprises an antiviral effective amount of an AIDS treatment agent selected from the group consisting of:
(a) an AIDS antiviral agent;
(b) an anti-infective agent;
(c) an immunomodulator; and
(d) another HIV entry inhibitor.

14. A method for treating a mammal infected with the HIV virus comprising administering to said mammal an antiviral effective amount of a compound as claimed in claim 1, and one or more pharmaceutically acceptable carriers, excipients or diluents.

15. An intermediate compound which is selected from the group of:

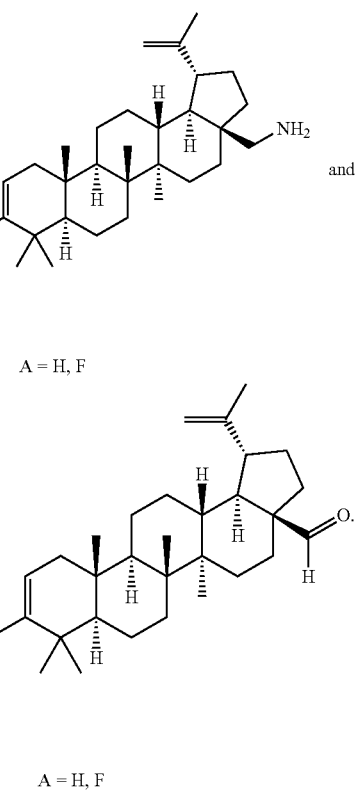

* * * * *